(12) United States Patent
Bollu et al.

(10) Patent No.: US 8,785,488 B2
(45) Date of Patent: Jul. 22, 2014

(54) TRIAZOLE AND IMIDAZOLE DERIVATIVES FOR USE AS TGR5 AGONISTS IN THE TREATMENT OF DIABETES AND OBESITY

(75) Inventors: Venkataiah Bollu, San Diego, CA (US); Brant Clayton Boren, San Diego, CA (US); Jackaline Dalgard Julien, Del Mar, CA (US); Brenton T. Flatt, Poway, CA (US); Nadia Haq, Waltham, MA (US); Sarah Hudson, San Diego, CA (US); Raju Mohan, Encinitas, CA (US); Michael Morrissey, Danville, CA (US); Benjamin Pratt, Encinitas, CA (US); Tie-Lin Wang, San Diego, CA (US); Richard Martin, San Diego, CA (US); Xiao-Hui Gu, Potomac, MD (US)

(73) Assignee: Exelixis Patent Company LLC, South San Francisco, CA (US)

( * ) Notice: Subject to any disclaimer, the term of this patent is extended or adjusted under 35 U.S.C. 154(b) by 225 days.

(21) Appl. No.: 13/148,811

(22) PCT Filed: Feb. 12, 2010

(86) PCT No.: PCT/US2010/023981
§ 371 (c)(1),
(2), (4) Date: Nov. 2, 2011

(87) PCT Pub. No.: WO2010/093845
PCT Pub. Date: Aug. 19, 2010

(65) Prior Publication Data
US 2012/0040985 A1    Feb. 16, 2012

Related U.S. Application Data

(60) Provisional application No. 61/152,163, filed on Feb. 12, 2009, provisional application No. 61/284,139, filed on Dec. 11, 2009.

(51) Int. Cl.
| | | |
|---|---|---|
| *A61K 31/4174* | (2006.01) | |
| *A61K 31/4178* | (2006.01) | |
| *C07D 233/56* | (2006.01) | |
| *C07D 233/64* | (2006.01) | |

(52) U.S. Cl.
USPC .................... 514/397; 548/311.1; 548/343.5; 548/345.1; 514/385

(58) Field of Classification Search
USPC ......... 548/311, 311.1, 343.5, 345.1; 514/397, 514/398, 385
See application file for complete search history.

(56) References Cited

U.S. PATENT DOCUMENTS

| | | |
|---|---|---|
| 5,910,506 A | 6/1999 | Sugimoto et al. |
| 2005/0154039 A1 | 7/2005 | Contour et al. |
| 2007/0270424 A1 | 11/2007 | Li et al. |

FOREIGN PATENT DOCUMENTS

| | | | | |
|---|---|---|---|---|
| EP | 1 988 083 A1 | 5/2008 | | |
| GB | 00970480 | 9/1964 | | |
| JP | 61-148176 A | 7/1986 | | |
| JP | 2005-170939 A | 6/2005 | | |
| JP | 2006-063064 A | 3/2006 | | |
| JP | 2007-210974 A | 8/2007 | | |
| WO | 03/104208 A1 | 12/2003 | | |
| WO | 03104207 A2 | 12/2003 | | |
| WO | WO-03/104207 A2 | * 12/2003 | ........... | C07D 249/00 |
| WO | 2004/089367 A1 | 10/2004 | | |
| WO | 2005044192 A2 | 5/2005 | | |
| WO | WO 2005-044192 | * 5/2005 | ............. | A61K 31/44 |
| WO | 2005/087750 A1 | 9/2005 | | |
| WO | 2006068199 A1 | 6/2006 | | |
| WO | 2006/080533 A1 | 8/2006 | | |
| WO | 2006/084186 A2 | 8/2006 | | |
| WO | 2007/021941 A2 | 2/2007 | | |

OTHER PUBLICATIONS

Ohta et al., "Introduction of Carbogenic Substituent into the 4-Position of 1-Methyl-1H-imidazole," Chem. Pharm. Bull. (1994): vol. 42, No. 4; pp. 821-825.
Patel et al., "Synthesis and antimicrobial activity of 1,2,4-triazoles," J. Indian Chem. Soc. (Dec. 2002): vol. 79, pp. 964-965.
Kawasaki et al., "New access to 1,3-dialkyl-2,3-dihydro-2-imino-1H-imidazoles and their application to the first total synthesis of naamine B, a marine 2,3-dihydro-2-imino-1,3-dimethyl-1H-imidazole alkaloid," J. Chem. Soc. (2001): Perkin Trans. 1; pp. 3095-3099.

(Continued)

*Primary Examiner* — Kamal Saeed
*Assistant Examiner* — Janet L Coppins
(74) *Attorney, Agent, or Firm* — McDonnell Boehnen Hulbert & Berghoff LLP

(57) ABSTRACT

The present invention comprises TGR5 agonists of structural formula I,

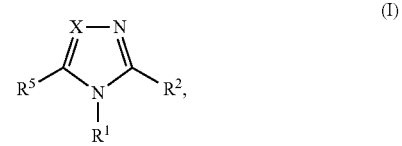

(I)

wherein X, $R^1$, $R^2$, and $R^5$ are defined herein, as well as N-oxides of them and pharmaceutically acceptable salts thereof. The invention further comprises composition comprising the compounds, N-oxides, and/or pharmaceutically acceptable salts thereof. The invention also comprises use of the compounds and compositions for treating diseases in which TGR5 is a mediator or is implicated. The invention also comprises use of the compounds in and for the manufacture of medicaments, particularly for treating diseases in which TGR5 is a mediator or is implicated.

14 Claims, 2 Drawing Sheets

(56) References Cited

OTHER PUBLICATIONS

Dilanyan et al., "Synthesis of Some Substituted 1,2,4-Triazole and 1,3,4-Thiadiazole Derivatives", Chemistry of Heterocyclic Compounds, 2008, 44(11), 1395-1397.

Theoclitou et al., "Rapid Parallel Synthesis of Combinatorial Libraries of Substituted 3-Thio-1,2,4-triazoles and 2-Thioimidazoles", Journal of Combinatorial Chemistry, 2002, 4(4), 315-319.

Zhu et al., 4-Methyl-5-phenyl triazoles as selective inhibitors of 11 Beta-hydroxysteroid dehydrogenase type I, Bioorganic & Medicinal Chemistry Letter, 2008, 18(11), 3405-3411.

Ivanova et al., "Parallel solution-phase synthesis of substituted 2-(1,2,4-triazol-3-yl)benxinnidazoles", Tetrahedron Letters, 2006, 47(46), 8025-8027.

Hamad, M.M., "Synthesis and Reactions of 2(5)-[Benzyl or Cyanomethyl]-1,3,4-oxadiazoles", Archiv der Pharmazie, 1990, 323(9), 595-599.

* cited by examiner

TRIAZOLE AND IMIDAZOLE DERIVATIVES FOR USE AS TGR5 AGONISTS IN THE TREATMENT OF DIABETES AND OBESITY

CROSS REFERENCE TO RELATED APPLICATIONS

This application is the 35 U.S.C. §371 National Phase Application of International Application Serial No. PCT/US2010/023981, filed Feb. 12, 2010, which claims priority to U.S. Provisional Patent Application Nos. 61/152,163, filed Feb. 12, 2009 and 61/284,139, filed Dec. 11, 2009, the disclosure of which are hereby incorporated by reference.

BACKGROUND OF THE INVENTION

1. Field of the Invention

The invention relates to agonists of the G protein-coupled receptor TGR5, compositions comprising them, methods of making the compounds and compositions and using them for the treatment of diseases TGR5 mediates or is implicated in.

2. Summary of the Related Art

Bile acids play essential roles in the absorption of dietary lipids and in the regulation of bile acid biosynthesis. While bile acids have long been known to be essential in dietary lipid absorption and cholesterol catabolism, in recent years an important role for bile acids as signaling molecules has emerged. Bile acids activate mitogen-activated protein kinase pathways, are ligands for the G-protein-coupled receptor (GPCR) TGR5, and activate nuclear hormone receptors such as farnesoid X receptor a (FXR-α). Through activation of these diverse signaling pathways, bile acids can regulate their own enterohepatic circulation, but also triglyceride, cholesterol, energy, and glucose homeostasis. Thus, bile acid (BA) controlled signaling pathways are promising novel drug targets to treat common metabolic diseases, such as obesity, type II diabetes, hyperlipidemia, and atherosclerosis. Houten et al., *The EMBO Journal* (2006) 25, 1419-1425).

Watanabe et al., *Nature* 2006, 439 (7075) 484-489 showed that the administration of bile acids to mice increases energy expenditure in brown adipose tissue, preventing obesity and resistance to insulin. This novel metabolic effect of bile acids is critically dependent on induction of the cyclic-AMP-dependent thyroid hormone activating enzyme type 2 iodothyronine deiodinase (D2) because it is lost in D2−/− mice. Treatment of brown adipocytes and human skeletal myocytes with bile acids increases D2 activity and oxygen consumption. These effects are independent of FXR-a, and instead are mediated by increased cAMP production that stems from the binding of bile acids with TGR5. In both rodents and humans, the most thermogenically important tissues are specifically targeted by this mechanism because they coexpress D2 and TGR5. The BA-TGR5-cAMP-D2 signaling pathway is therefore a crucial mechanism for fine-tuning energy homeostasis that can be targeted to improve metabolic control.

Glucagon-like peptide-1 (GLP-1) is produced by L-cells in the distal digestive tract and affects multiple metabolic parameters, including enhanced insulin secretion, glucagon suppression, and lowering of blood glucose. TGR5 expression in L-cells is linked to increased GLP-1 secretion. Katsuma, et al., *Biochem. Biophys. Res. Commun.* 2005, 329 (1), 386-390) showed that bile acids promote glucagon-like peptide-1 (GLP-1) secretion through TGR5 in a murine enteroendocrine cell line STC-1. RNA interference experiments showed that reduced expression of TGR5 resulted in reduced secretion of GLP-1. Furthermore, transient transfection of STC-1 cells with an expression plasmid containing TGR5 significantly enhanced GLP-1 secretion.

TGR5 and modulators of it have been the subject of a several patent applications:

WO/2008/097976—Heterocyclic Modulators of TGR5 for Treatment of Disease

WO/2008/091540—Substituted Bile Acids as TGR5 Modulators and Methods of Use

WO/2008/067219—Quinazolinone Modulators of TGR5

WO/2008/067222—Heterocyclic Modulators of TGR5

WO/2004/067008—Receptor Agonists

WO/2004/043468—Screening Method

US 2006/0199795—Receptor Agonists

US 2008/0031968—Methods for Increasing Cellular Energy Expenditure

SUMMARY OF THE INVENTION

The present invention comprises TGR5 agonists of structural formula I,

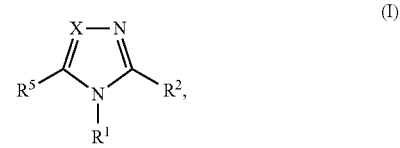

wherein X, $R^1$, $R^2$, and $R^5$ are defined hereinbelow, as well as N-oxides of them and pharmaceutically acceptable salts thereof. The invention further comprises compositions comprising the compounds, N-oxides, and/or pharmaceutically acceptable salts thereof. The invention also comprises use of the compounds and compositions for treating diseases in which TGR5 is a mediator or is implicated. The invention also comprises use of the compounds in and for the manufacture of medicaments, particularly for treating diseases in which TGR5 is a mediator or is implicated.

All of the compounds of Formula I or Formula VIII, and all embodiments thereof, are not considered to include quaternary ammonium moieties. The compounds of Formula I or Formula VIII, and all embodiments thereof, do include pharmaceutically acceptable salts thereof, which are not quaternary ammonium moieties.

DETAILED DESCRIPTION OF THE INVENTION

Figure 1:
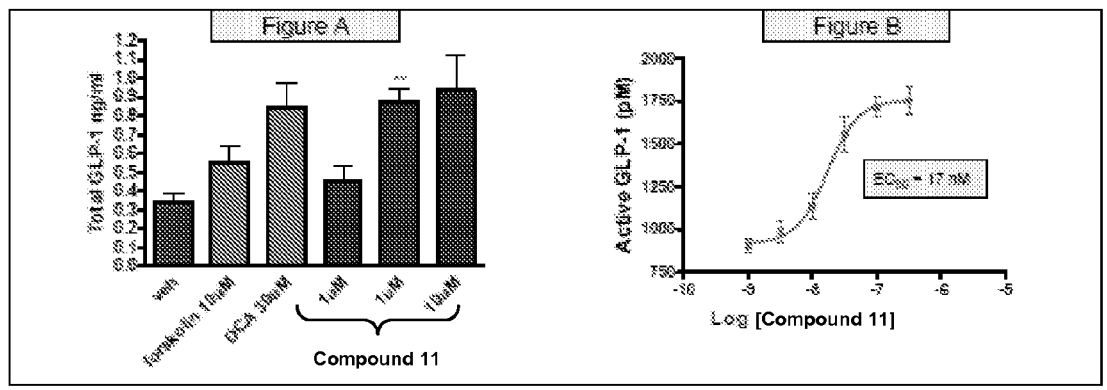
FIG. 1 is a graph illustrating GLP-1 levels in treated mouse enteroendocrine STC-1 cells.

In a first aspect, the invention comprises TGR5 agonists. As embodiment (1), the invention comprises a TGR5 agonist of structural formula (I),

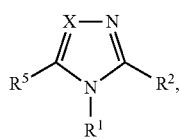

(I)

an N-oxide thereof, or pharmaceutically acceptable salt thereof, wherein

X is $=C(R^4)—$ or $=N—$, wherein $R^4$ is $R^A$, $R^C$, $R^D$, or $R^{10}$;

$R^1$ is $R^C$, $R^D$, or $R^{10}$;

$R^2$ is $R^A$, $R^D$, or $R^{10}$; and $R^5$ is $R^A$, $R^C$, $R^D$, or $R^{10}$, provided that one and only one of each of $R^A$, $R^C$, and $R^D$ are present, wherein $R^A$ is $—[C(R^8)_2]$-aryl or $—[C(R^8)_2]$-heteroaryl, wherein the aryl and heteroaryl are substituted with one, two, or three $R^{410}$ groups, wherein each $R^{410}$ is independently $—R^{411}$, $C_1$-$C_4$alkyl, $C_1$-$C_4$haloalkyl, $C_3$-$C_8$ cycloalkyl, heterocyclyl, aryl, heteroaryl, or $—OC_1$-$C_4$alkyl-$R^{411}$, wherein the alkyl, cycloalkyl, heterocyclyl, aryl, and heteroaryl groups are each optionally substituted by one, two, or three $R^{411}$ groups, wherein each $R^{411}$ is independently halogen cyano, nitro, $C_1$-$C_4$alkyl, $—N(R^{412})_2$, $—OR^{412}$, $—SR^{412}$, $—N(OR^{412})(R^{412})$, $—C(O)R^{412}$, $C(O)OR^{412}$, $—C(O)N(R^{412})_2$, $—N(R^{412})C(O)R^{412}$, $—N(R^{412})S(O)R^{412}$, $—N(R^{412})S(O)_2R^{412}$, $—S(O)N(R^{412})_2$, $—S(O)_2N(R^{412})_2$, $—S(O)_2R^{412}$, $—OC(O)R^{412}$, $—OC(O)N(R^{412})_2$, $—N(R^{412})C(O)R^{412}$, $—N(R^{412})S(O)_2R^{412}$, $—N(R^{412})C(O)OR^{412}$, $—N(R^{412})C(O)N(R^{412})_2$, $—N(R^{412})C(=NR^{412})N(R^{412})_2$, heterocyclyl, or heteroaryl, wherein each $R^{412}$ is independently hydrogen, $C_1$-$C_4$alkyl, or $C_1$-$C_4$haloalkyl;

or two $R^{410}$ are attached to adjacent carbon atoms and are (i) taken together to form $—O(CH_2)_x—O—$, wherein x is 1, 2, or 3; or (ii) taken together with the carbon atoms to which they are attached to form a fused phenyl or 5 or 6 membered heteroaryl ring, wherein the fused phenyl or heteroaryl ring are each optionally substituted with one, two, or three $R^{420}$ groups, wherein each $R^{420}$ is independently $—R^{421}$, $C_1$-$C_4$alkyl, $C_1$-$C_4$haloalkyl, $C_3$-$C_8$ cycloalkyl, heterocyclyl, aryl, heteroaryl, or $—OC_1$-$C_4$alkyl-$R^{421}$, wherein the alkyl, cycloalkyl, heterocyclyl, aryl, and heteroaryl groups are each optionally substituted by one, two, or three $R^{421}$ groups, wherein each $R^{421}$ is independently halogen cyano, nitro, $—N(R^{422})_2$, $—OR^{422}$, $—SR^{422}$, $—C(O)R^{422}$, $—C(O)OR^{422}$, $—C(O)N(R^{422})_2$, $—S(O)N(R^{422})_2$, $—S(O)_2N(R^{422})_2$, $—S(O)_2R^{422}$, $—OC(O)R^{422}$, $—OC(O)OR^{422}$, $—OC(O)N(R^{422})_2$, $—N(R^{422})C(O)R^{422}$, $—N(R^{422})S(O)_2R^{422}$, $—N(R^{422})C(O)OR^{422}$, $—N(R^{422})C(O)N(R^{422})_2$, $—N(R^{422})C(=NR^{422})N(R^{422})_2$, heterocyclyl, or heteroaryl, wherein each $R^{422}$ is independently hydrogen, $C_1$-$C_4$alkyl, or $C_1$-$C_4$haloalkyl;

and each $R^8$ is independently hydrogen, halogen, or methyl or both $R^8$ taken together with the carbon atom to which they are both attached form a $C_3$-$C_8$ cycloalkyl;

$R^C$ is (i) aryl, heteroaryl, or aryl($C_1$-$C_2$)alkyl, each optionally substituted with one, two, or three $R^{C10}$ groups, wherein each $R^{C10}$ is independently halogen, $C_1$-$C_4$alkyl, $C_1$-$C_4$halo alkyl, $C_3$-$C_8$cycloalkyl, heterocyclyl, $—R^{C11}$, $C_1$-$C_4$alkyl-$R^{C11}$, or $—OC_1$-$C_4$alkyl-$R^{C11}$ wherein $R^{C11}$ is cyano, nitro, $—N(R^{C12})_2$, $—OR^{C12}$, $—SR^{C12}$, $—C(O)R^{C12}$, $—C(O)OR^{C12}$, $—C(O)N(R^{C12})_2$, or $S(O)N(R^{C12})_2$, $—S(O)_2N(R^{C12})_2$, $—S(O)_2R^{C12}$, $—OC(O)R^{C12}$, $OC(O)OR^{C12}$, $—OC(O)N(R^{C12})_2$, $—N(R^{C12})C(O)R^{C12}$, $—N(R^{C12})C(O)OR^{C12}$, $—N(R^{C12})C(O)N(R^{C12})_2$, or $—N(R^{C12})C(NR^{C12})N(R^{C12})_2$, wherein each $R^{C12}$ is independently hydrogen, $C_1$-$C_4$alkyl, or $C_1$-$C_4$halo alkyl;

or (ii) $C_1$-$C_4$alkyl, $—C_1$-$C_4$alkyl-$N(R^{C13})_2$, $—C_1$-$C_4$alkyl-$OR^{C13}$, $—C_1$-$C_4$alkyl-$SR^{C13}$, $C_3$-$C_8$cycloalkyl, or heterocyclyl, wherein the cycloalkyl and heterocyclyl are each optionally substituted with 1 to 6 groups which are each independently $—R^{C15}$ or $—C_1$-$C_4$alkyl-$R^{C15}$, wherein each $R^{C15}$ is independently cyano, nitro, $—N(R^{C14})_2$, $—OR^{C14}$, $—SR^{C14}$, $—C(O)R^{C14}$, $—C(O)OR^{C14}$, $—C(O)N(R^{C14})_2$, $—S(O)N(R^{C14})_2$, $—S(O)_2N(R^{C14})_2$, or $—S(O)_2R^{C14}$, $—OC(O)R^{C14}$, $—OC(O)OR^{C14}$, $—OC(O)N(R^{C14})_2$, $—N(R^{C14})C(O)R^{C14}$, $—N(R^{C14})C(O)OR^{C14}$, $—N(R^{C14})C(O)N(R^{C14})_2$, or $—N(R^{C14})C(=NR^{C14})N(R^{C14})_2$, wherein each $R^{C14}$ is independently hydrogen, $C_1$-$C_4$alkyl, or $C_1$-$C_4$haloalkyl;

and each $R^{C13}$ is independently hydrogen, $C_1$-$C_4$alkyl, or $C_1$-$C_4$haloalkyl;

$R^D$ is (a) -$L^D$-$R^{D1}$, wherein $L^D$ is a bond, $—[C(R)_2]_p—Y—[C(R)_2]_q—$, $—Y^1—$, $—C(H)=C(H)—$, or $—CH_2CH_2—$, wherein each R is independently hydrogen, fluoro, chloro, methyl, ethyl, or hydroxymethyl;

p is 0, 1, or 2;

q is an integer selected from 0 to (2-p);

Y is $—(CQ_2)-$, $—C(H)(OH)—$, $—N(R^Y)—$, $—O—$, $—S—$, $—S(O)—$, $—S(O)_2—$, $—C(O)—$ or $Y^1$, wherein; each Q is independently halogen; and $Y^1$ is $—C(O)O—$, $—OC(O)—$, $—C(O)N(R^Y)—$, $—N(R^Y)C(O)—$, $—S(O)N(R^Y)—$, $—S(O)_2N(R^Y)—$, $—N(R^Y)S(O)—$, $—N(R^Y)S(O)_2—$, $—N(R^Y)C(O)N(R^Y)—$, $—OC(O)O—$, $—OC(O)N(R^Y)—$, or $—N(R^Y)C(O)O—$, wherein each $R^Y$ is independently hydrogen, $C_1$-$C_4$alkyl, or hydroxy($C_1$-$C_4$)alkyl; and $R^{D1}$ is (i) aryl or heteroaryl, each optionally substituted with one, two, or three $R^{D10}$ groups, wherein each $R^{D10}$ is independently $—R^{D12}$, $C_1$-$C_4$haloalkyl, $C_3$-$C_8$ cycloalkyl, heterocyclyl, aryl, heteroaryl, or $—OC_1$-$C_4$alkyl-$R^{D12}$, wherein the alkyl, cycloalkyl, heterocyclyl, aryl, and heteroaryl groups are each optionally substituted by one, two, or three $R^{D12}$ groups, wherein
each $R^{D12}$ is independently halogen, cyano, nitro, $C_1$-$C_4$alkyl, —$OR^{D11}$, —$SR^{D11}$, —$N(R^{D11})_2$, —$C(O)R^{D11}$, —$C(O)OR^{D11}$, —$C(O)N(H)C_1$-$C_4$alkyl-$R^{D13}$, —$C(O)N(R^{D11})_2$, —$C(O)N(R^{D11})OR^{D11}$, —$C(=NR^{D11})N(R^{D11})_2$, —$S(O)N(R^{D11})_2$, —$S(O)_2N(R^{D11})_2$, —$S(O)_2R^{D11}$, —$OC(O)R^{D11}$, —$OC(O)OR^{D11}$, —$OC(O)N(R^{D11})_2$, —$N(R^{D11})C(O)R^{D11}$, —$N(R^{D11})C(O)OR^{D11}$, —$N(R^{D11})C(O)N(R^{D11})_2$, —$N(R^{D11})C(NR^{D11})N(R^{D11})_2$, —$C(O)N(R^{D11})S(O)_2R^{D11}$, —$S(O)_2N(R^{D11})C(O)R^{D11}$, —$S(O)_2N(R^{D11})C(O)N(R^{D11})_2$, or —$S(O)_2N(R^{D11})C(O)N(R^{D11})(NR^{D11}_2)$, wherein
each $R^{D11}$ is independently hydrogen, $C_1$-$C_4$alkyl, $C_1$-$C_4$haloalkyl, $C_3$-$C_8$ cycloalkyl, heterocyclyl, aryl, or heteroaryl, wherein the alkyl, cycloalkyl, heterocyclyl, aryl, and heteroaryl are optionally substituted with one, two, or three groups which are each independently halogen, cyano, nitro, —$OR^{D15}$, —$N(R^{D15})_2$, —$SR^{D15}$, —$C(O)R^{D15}$, —$C(O)OR^{D15}$, —$C(O)N(R^{D15})_2$, —$S(O)R^{D15}$, —$S(O)_2R^{D15}$, —$S(O)OR^{D15}$, —$S(O)_2OR^{D15}$, —$S(O)N(R^{D15})_2$, —$S(O)_2N(R^{D15})_2$, —$OC(O)R^{D15}$, —$OC(O)O(R^{D15})$, —$OC(O)N(R^{D15})_2$, —$N(R^{D15})C(O)R^{D15}$, —$N(R^{D15})S(O)_2R^{D15}$, —$N(R^{D15})C(O)OR^{D15}$ or —$N(R^{D15})C(O)N(R^{D15})_2$, wherein each $R^{D15}$ is hydrogen or $C_1$-$C_4$alkyl; and
$R^{D13}$ is —$OR^{D14}$, —$N(R^{D14})_2$, —$C(O)OR^{D14}$, —$C(O)N(R^{D14})_2$, —$S(O)_2OR^{D14}$, heterocyclyl, or heteroaryl, wherein each $R^{D14}$ is hydrogen or $C_1$-$C_4$alkyl;

or (ii) a 5 or 6 membered cycloalkyl or heterocyclyl each optionally fused to a phenyl ring and each optionally substituted with one, two, or three $R^{D20}$, wherein
each $R^{D20}$ is independently —$R^{D21}$, —$C_1$-$C_4$ alkyl, aryl, heteroaryl, $C_3$-$C_8$ cycloalkyl, or heterocyclyl, wherein the alkyl, aryl, heteroaryl, cycloalkyl, and heterocyclyl groups are each optionally substituted with one, two, or three $R^{D21}$ groups, wherein
each $R^{D21}$ is independently halogen, cyano, nitro, —$C_1$-$C_4$ alkyl, aryl, heteroaryl, $C_3$-$C_8$ cycloalkyl, heterocyclyl, —$OR^{D22}$, —$N(R^{D22})_2$, —$SR^{D22}$, —$C(O)R^{D22}$, —$C(O)OR^{D22}$, —$C(O)N(R^{D22})_2$, —$S(O)R^{D22}$, —$S(O)_2R^{D22}$, —$S(O)OR^{D22}$, —$S(O)_2OR^{D22}$, —$S(O)N(R^{D22})^2$, —$S(O)_2N(R^{D22})_2$, —$OC(O)R^{D22}$, —$OC(O)O(R^{D22})$, —$OC(O)N(R^{D22})_2$, —$N(R^{D22})C(O)R^{D22}$, —$N(R^{D22})S(O)_2R^{D22}$, —$N(R^{D22})C(O)OR^{D22}$, —$N(R^{D22})C(O)N(R^{D22})_2$) or —$C(O)N(R^{D22})S(O)_2R^{D22}$, wherein
each $R^{D22}$ is independently hydrogen, $C_1$-$C_4$ alkyl, $C_1$-$C_4$ haloalkyl, aryl, heteroaryl, $C_3$-$C_8$ cycloalkyl, or heterocyclyl, wherein the alkyl, aryl, heteroaryl, cycloalkyl, and heterocyclyl groups are each optionally substituted by one, two, or three $R^{D23}$ groups, wherein
each $R^{D23}$ is independently halogen, cyano, nitro, —$C_1$-$C_4$ alkyl, aryl, heteroaryl, $C_3$-$C_8$ cycloalkyl, heterocyclyl, —$OR^{D24}$, —$N(R^{D24})_2$, —$SR^{D24}$, —$C(O)R^{D24}$, —$C(O)OR^{D24}$, —$C(O)N(R^{D24})_2$, $S(O)R^{D24}$, —$S(O)_2R^{D24}$, —$S(O)OR^{D24}$, —$S(O)_2OR^{D24}$, —$S(O)N(R^{D24})_2$, —$S(O)_2N(R^{D24})_2$, —$OC(O)R^{D24}$, —$OC(O)O(R^{D24})$, —$OC(O)N(R^{D24})_2$, —$N(R^{D24})C(O)R^{D24}$, —$N(R^{D24})S(O)_2R^{D24}$, —$N(R^{D24})C(O)OR^{D24}$, or —$N(R^{D24})C(O)N(R^{D24})_2$, wherein each $R^{D24}$ is hydrogen, $C_1$-$C_4$ alkyl, or $C_1$-$C_4$ haloalkyl;

or
(b) —$CH_2N(R^{D2})_2$, —$C(O)N(R^{D2})_2$, —$S(O)N(R^{D2})_2$, or —$S(O)_2N(R^{D2})_2$, wherein
one $R^{D2}$ is hydrogen or methyl and the other $R^{D2}$ is $C_1$-$C_4$alkyl or $C_3$-$C_8$cycloalkyl, wherein
the cycloalkyl is optionally fused to a phenyl ring, and the alkyl and cycloalkyl are each optionally substituted by one or two groups which are independently halogen, —$OR^{D30}$, —$N(R^{D30})_2$, or heterocyclyl groups, wherein
each $R^{D30}$ is independently hydrogen, $C_1$-$C_4$alkyl, or $C_1$-$C_4$haloalkyl; and
each heterocyclyl is independently optionally substituted by one or two $C_1$-$C_4$alkyl groups,
or both $R^{D2}$ taken together with the nitrogen to which they are both attached form a 5-8 membered heterocyclyl optionally substituted by
(i) one aryl or heteroaryl, each optionally substituted with one, two, or three $R^{D31}$ groups, wherein
each $R^{D31}$ is independently halogen, cyano, nitro, $C_1$-$C_4$alkyl, $C_1$-$C_4$haloalkyl, —$OR^{D32}$, —$SR^{D32}$, —$N(R^{D32})_2$, —$C(O)R^{D32}$, —$C(O)OR^{D32}$, —$C(O)N(R^{D32})_2$, —$C(NR^{D32})N(R^{D32})_2$, —$S(O)N(R^{D32})_2$, —$S(O)_2N(R^{D32})_2$, —$S(O)_2R^{D32}$, —$S(O)_2N(R^{D32})C(O)R^{D32}$, —$S(O)_2N(R^{D32})C(O)N(R^{D32})_2$, or —$S(O)_2N(R^{D32})C(O)N(R^{D32})(NR^{D32}_2)$, wherein each $R^{D32}$ is independently hydrogen, $C_1$-$C_4$alkyl, or $C_1$-$C_4$haloalkyl;
(ii) or one or two groups independently selected from the group consisting of halogen, hydroxy, —$C(O)OH$, $C_1$-$C_4$alkyl, $C_1$-$C_4$haloalkyl, hydroxy($C_1$-$C_4$)alkyl, and heterocyclyl($C_1$-$C_4$)alkyl,
wherein each heterocyclyl group in $R^{D2}$ is independently optionally fused to a phenyl ring, wherein the phenyl ring is optionally substituted by one, two, or three groups, each independently, halogen, cyano, nitro, hydroxy, $C_1$-$C_4$ alkoxy, —$C(O)OH$, $C_1$-$C_4$ alkoxycarbonyl, —$C(O)NH_2$, $C_1$-$C_4$ alkylaminocarbonyl, di($C_1$-$C_4$alkyl)aminocarbonyl, amino, $C_1$-$C_4$ alkylamino, or di($C_1$-$C_4$alkyl)amino;

and
$R^{10}$ is hydrogen, halogen, $C_1$-$C_4$alkyl, $C_1$-$C_4$haloalkyl, phenyl, or —$C(O)OH$, wherein the alkyl is optionally substituted with $R^{100}$, wherein
$R^{100}$ is $C_1$-$C_4$ alkyl, $C_1$-$C_4$ haloalkyl, cyano, nitro, heterocyclyl, —$OR^{101}$, —$N(R^{101})_2$, —$SR^{101}$, —$C(O)OR^{101}$, —$C(O)N(R^{101})_2$, —$S(O)OR^{101}$, —$S(O)_2OR^{101}$, —$S(O)N(R^{101})_2$, —$S(O)_2N(R^{101})_2$, —$OC(O)R^{101}$, —$OC(O)O(R^{101})$, —$OC(O)N(R^{101})_2$, —$N(R^{101})C(O)R^{101}$, —$N(R^{101})S(O)_2R^{101}$, —$N(R^{101})C(O)OR^{101}$, or —$N(R^{101})C(O)N(R^{101})_2$, wherein each $R^{101}$ is independently hydrogen, $C_1$-$C_4$ alkyl, or $C_1$-$C_4$ haloalkyl;

provided that i) when, simultaneously, $R^1$ is $R^C$, $R^2$ is $R^D$, X is CH or N, and $R^5$ is $R^A$, and $R^1$ is methyl, cyclohexyl, 4-chlorophenyl, 4-methylphenyl, 4-chlorobenzyl, or 6-methyl-pyrid-3-yl, $R^D$ is —S—$(CR_2)_q$—$R^{D1}$, and $R^{D1}$ is 3-phenyl-1,2,4-triazol-5-yl, morpholin-4-yl, 4-methylpiperazin-1-yl, pyrrolidin-1-yl, piperidin-1-yl, benzimidazol-2-yl, 1-methylbenzimidazol-2-yl, benzothiazol-2-yl, 4-methoxyphenyl, imidazol-2-yl, 2-methylthiazol-5-yl, thiazol-2-yl, or pyridyl, then at least one $R^8$ is not hydrogen;

and (ii) the compound is not 1-(4-chlorophenyl)-2-(4-fluorobenzyl)-1H-imidazol-4-ylmethyl]-(4-fluorophenyl)methylamine;

3-[1-methyl-1-(4-methylphenyl)ethyl]-5-phenyl-4-(2-phenylethyl)-4H-1,2,4-triazole;

3-(3-chlorophenyl)-4-[2-(4-fluorophenyl)ethyl]-5-[1-methyl-1-(4-methylphenyl)ethyl]-4H-1,2,4-triazole;

3-[1-(2-chlorophenyl)-1-methylethyl]-5-phenyl-4-(2-phenylethyl)-4H-1,2,4-triazole;

3-[1-(3-chlorophenyl)-1-methylethyl]-5-phenyl-4-(2-phenylethyl)-4H-1,2,4-triazole; and 3-[1-(4-chlorophenyl)-1-methylethyl]-5-phenyl-4-(2-phenylethyl)-4H-1,2,4-triazole.

The invention further comprises subgenera of embodiment (1) in which the substituents are selected as any and all combinations of the following definitions of structural formula I, $R^C$, $R^{C10}$, $R^D$, $R^{D1}$, $R^{D10}$, $L^D$, Y, $Y^1$, $R^A$, $R^{A10}$, and $R^{10}$;

Structural Formula (I)

$R^C$ aryl, heteroaryl, or aryl($C_1$-$C_2$)alkyl, each optionally substituted with one, two, or three $R^{C10}$ groups, aryl or heteroaryl, each optionally substituted with one, two, or three $R^{C10}$ groups, phenyl substituted with one, two, or three $R^{C10}$ groups, phenyl substituted with one or two halogen groups, 4-fluorophenyl, wherein $R^{C21}$ is halogen (e.g., fluoro) and $R^{C20}$ is —$OR^{C12}$ or —$OC_1$-$C_4$alkyl-$R^{C11}$, heteroaryl optionally substituted with one, two, or three $R^{C10}$ groups, pyridyl optionally substituted with one, two, or three $R^{C10}$ groups, $C_1$-$C_4$alkyl, $C_3$-$C_8$cycloalkyl, —$C_1$-$C_4$alkyl-$N(R^{C13})_2$, —$C_1$-$C_4$alkyl-$OR^{C13}$, or —$C_1$-$C_4$alkyl-$SR^{C13}$, wherein each $R^{C13}$ is independently hydrogen, $C_1$-$C_4$alkyl, or $C_1$-$C_4$halo alkyl, or —$C_1$-$C_4$alkyl-$N(R^{C13})_2$ or —$C_1$-$C_4$alkyl-$OR^{C13}$, wherein each $R^{C13}$ is independently hydrogen, $C_1$-$C_4$alkyl, or $C_1$-$C_4$halo alkyl;

$C_3$-$C_8$cycloalkyl, or heterocyclyl, wherein the cycloalkyl and 2heterocyclyl are each optionally substituted with 1 to 6 groups which are each independently —$R^{C15}$ or —$C_1$-$C_4$alkyl-$R^{C15}$, $R^{C10}$ each $R^{C10}$ is independently halogen, heterocyclyl, cyano, $C_1$-$C_4$ alkyl, $C_1$-$C_4$ haloalkyl, —$OR^{C12}$, —$C_1$-$C_4$alkyl-$R^{C11}$ or —$OC_1$-$C_4$alkyl-$R^{C11}$, each $R^{C10}$ is independently halogen, one $R^{C10}$ is —$C_1$-$C_4$alkyl-$R^{C11}$ or —$OC_1$-$C_4$alkyl-$R^{C11}$, one $R^{C10}$ is —$C_1$-$C_4$alkyl-$R^{C11}$ or —$OC_1$-$C_4$alkyl-$R^{C11}$ and one $R^{C10}$ is halogen, or one $R^{C10}$ is —$C_1$-$C_4$alkyl-$R^{C11}$ or —$OC_1$-$C_4$alkyl-$R^{C11}$ wherein $R^{C11}$ is —$N(R^{C12})_2$, —$OR^{C12}$, or —$C(O)OR^{C12}$;

$R^D$

-$L^D$-$R^{D1}$,

—$[C(R)_2]_p$—Y—$R^{D1}$,

—Y—$[C(R)_2]_q$—$R^{D1}$,

—$CH_2N(R^{D2})_2$, —$C(O)N(R^{D2})_2$, —$S(O)N(R^{D2})_2$, or —$S(O)_2N(R^{D2})_2$,

—$C(O)N(R^{D2})_2$ or —$S(O)_2N(R^{D2})_2$,

—$C(O)N(R^{D2})_2$ or —$S(O)_2N(R^{D2})_2$, wherein both $R^{D2}$ taken together with the nitrogen to which they are both attached form a 5-8 membered heterocyclyl optionally substituted by (i) one aryl or heteroaryl, each optionally substituted with one, two, or three $R^{D31}$ groups, wherein each $R^{D31}$ is independently halogen, cyano, nitro, $C_1$-$C_4$alkyl, $C_1$-$C_4$haloalkyl, —$OR^{D32}$, —$SR^{D32}$, —$N(R^{D32})_2$, —$C(O)R^{D32}$, —$C(O)N(R^{D32})_2$, —$C(NR^{D32})N(R^{D32})_2$, —$S(O)N(R^{D32})_2$, —$S(O)_2N(R^{D32})_2$, or —$S(O)_2R^{D32}$, wherein each $R^{D32}$ is independently hydrogen, $C_1$-$C_4$alkyl, or $C_1$-$C_4$haloalkyl; or (ii) one or two groups independently selected from the group consisting of halogen, hydroxy, —$C(O)OH$, $C_1$-$C_4$alkyl, $C_1$-$C_4$haloalkyl, hydroxy($C_1$-$C_4$)alkyl, and heterocyclyl($C_1$-$C_4$)alkyl, wherein each heterocyclyl group is independently optionally fused to a phenyl ring, wherein the phenyl ring is optionally substituted by one, two, or three groups, each independently, halogen, cyano, nitro, hydroxy, $C_1$-$C_4$ alkoxy, —C(O)OH, $C_1$-$C_4$ alkoxycarbonyl, —C(O)NH$_2$, $C_1$-$C_4$ alkylaminocarbonyl, di($C_1$-$C_4$alkyl)aminocarbonyl, amino, $C_1$-$C_4$ alkylamino, or di($C_1$-$C_4$alkyl)amino, —C(O)N($R^{D2}$)$_2$ or —S(O)$_2$N($R^{D2}$)$_2$, wherein both $R^{D2}$ taken together with the nitrogen to which they are both attached form a 5-8 membered heterocyclyl optionally substituted by one or two groups independently selected from the group consisting of halogen, hydroxy, —C(O)OH, $C_1$-$C_4$alkyl, $C_1$-$C_4$haloalkyl, hydroxy($C_1$-$C_4$)alkyl, and heterocyclyl($C_1$-$C_4$)alkyl, wherein each heterocyclyl group is independently optionally fused to a phenyl ring, wherein the phenyl ring is optionally substituted by one, two, or three groups, each independently, halogen, cyano, nitro, hydroxy, $C_1$-$C_4$ alkoxy, —C(O)OH, $C_1$-$C_4$ alkoxycarbonyl, —C(O)NH$_2$, $C_1$-$C_4$ alkylaminocarbonyl, di($C_1$-$C_4$alkyl)aminocarbonyl, amino, $C_1$-$C_4$ alkylamino, or di($C_1$-$C_4$alkyl)amino, —S(O)$_2$N($R^{D2}$)$_2$, wherein one $R^{D2}$ is hydrogen or methyl and the other $R^{D2}$ is $C_1$-$C_4$alkyl optionally substituted by one or two groups which are independently halogen, —O$R^{D30}$, —N($R^{D30}$)$_2$, or heterocyclyl, wherein each $R^{D30}$ is independently hydrogen, $C_1$-$C_4$alkyl, or $C_1$-$C_4$haloalkyl; and each heterocyclyl is independently optionally substituted by one or two $C_1$-$C_4$alkyl groups, —S(O)$_2$N($R^{D2}$)$_2$, wherein one $R^{D2}$ is hydrogen or methyl and the other $R^{D2}$ is $C_1$-$C_4$alkyl substituted by one —O$R^{D30}$, —N($R^{D30}$)$_2$, or heterocyclyl group, wherein each $R^{D30}$ is independently hydrogen, $C_1$-$C_4$alkyl, or $C_1$-$C_4$haloalkyl; and the heterocyclyl is independently optionally substituted by one or two $C_1$-$C_4$alkyl groups, -$L^D$-$R^{D1}$, wherein $R^{D1}$ is a 5 or 6 membered cycloalkyl or heterocyclyl optionally fused to a phenyl ring and optionally substituted with one, two, or three $R^{D20}$, or

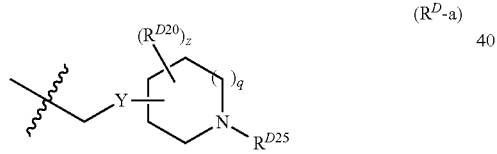
($R^D$-a)

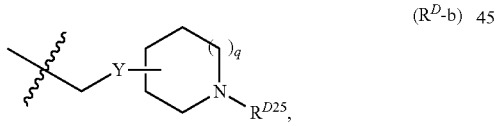
($R^D$-b)

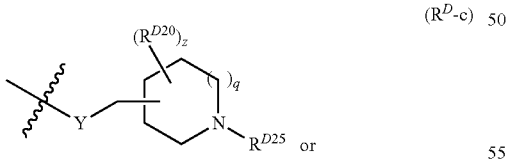
($R^D$-c) or

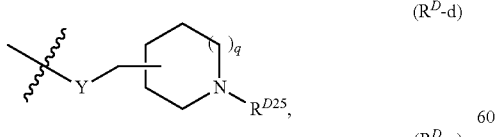
($R^D$-d)

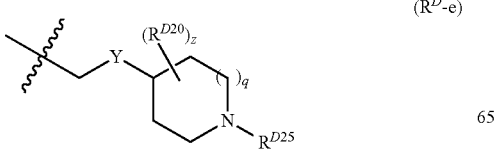
($R^D$-e)

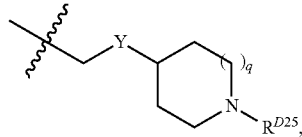
($R^D$-f)

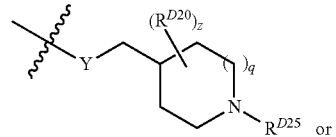
($R^D$-g)

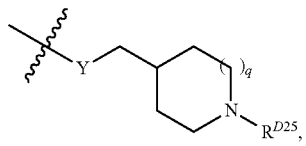
($R^D$-h)

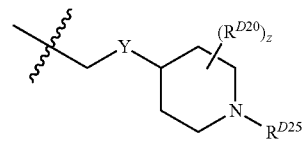
($R^D$-i)

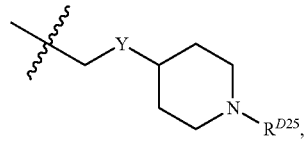
($R^D$-j)

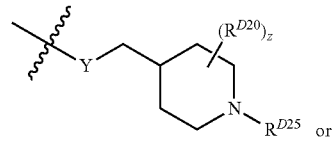
($R^D$-k) or

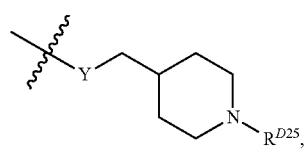
($R^D$-l)

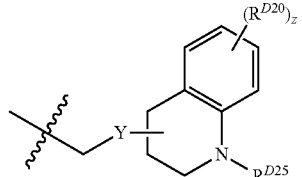
($R^D$-m)

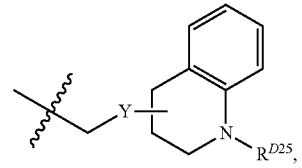
($R^D$-n)

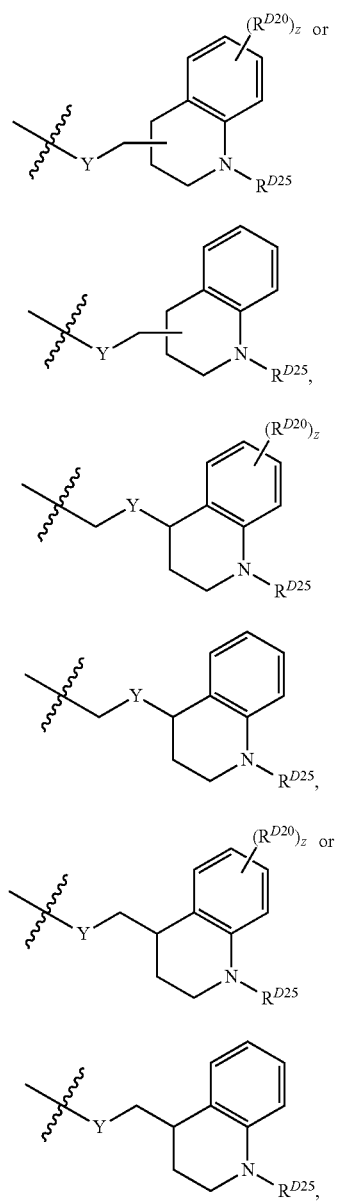

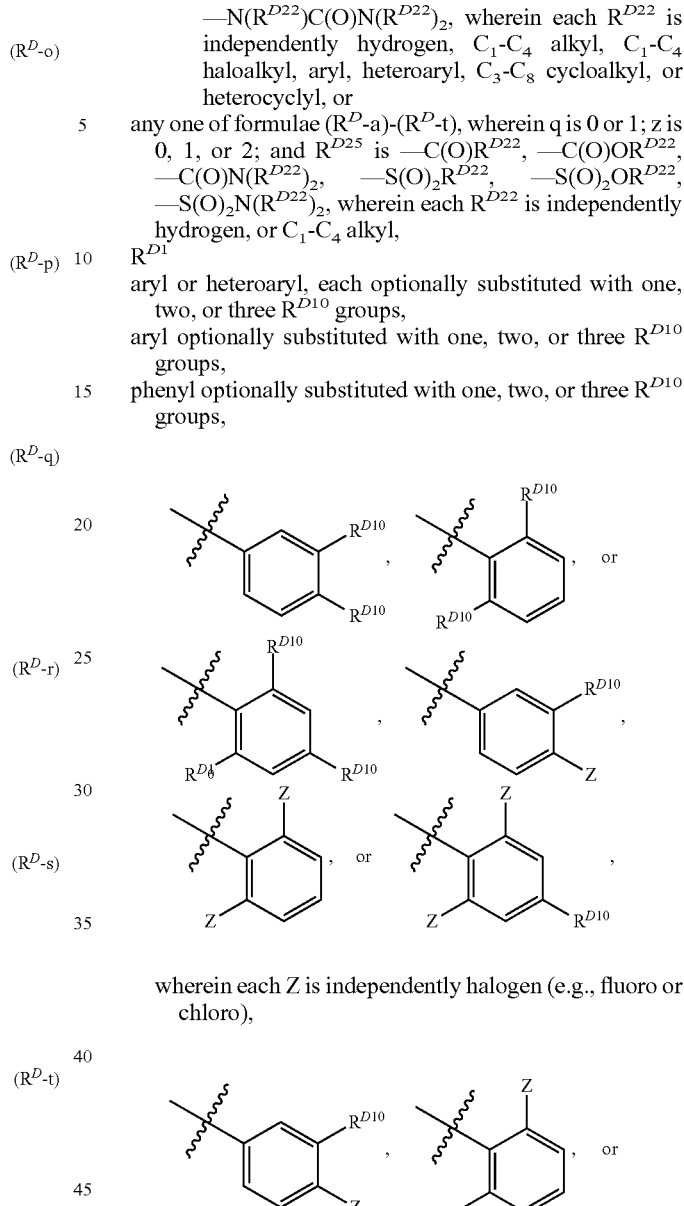

wherein $R^{D20}$ is as defined for formula (I); q is 0 or 1; z is 0, 1, or 2; and $R^{D25}$ is —C(O)$R^{D22}$, —C(O)O$R^{D22}$, —C(O)N($R^{D22}$)$_2$, —S(O)$R^{D22}$, —S(O)$_2$$R^{D22}$, —S(O)O$R^{D22}$, —S(O)$_2$O$R^{D22}$, —S(O)N($R^{D22}$)$_2$, —S(O)$_2$N($R^{D22}$)$_2$, —C$_1$-C$_4$ alkyl, aryl, heteroaryl, C$_3$-C$_8$ cycloalkyl, or heterocyclyl, wherein the alkyl, aryl, heteroaryl, cycloalkyl, and heterocyclyl groups are each optionally substituted with one, two, or three $R^{D21}$ groups, wherein each $R^{D21}$ is independently halogen, cyano, nitro, —C$_1$-C$_4$ alkyl, aryl, heteroaryl, C$_3$-C$_8$ cycloalkyl, heterocyclyl, —O$R^{D22}$, —N($R^{D22}$)$_2$, —S$R^{D22}$, —C(O)$R^{D22}$, —C(O)O$R^{D22}$, —C(O)N($R^{D22}$)$_2$, —S(O)$R^{D22}$, —S(O)$_2$$R^{D22}$, —S(O)O$R^{D22}$, —S(O)$_2$O$R^{D22}$, —S(O)N($R^{D22}$)$_2$, —S(O)$_2$N ($R^{D22}$)$_2$, —N($R^{D22}$)C(O)$R^{D22}$, —N(R$D^{22}$) S(O)$_2$$R^{D22}$, —OC(O)$R^{D22}$, —OC(O)N($R^{D22}$)$_2$, —OC(O)O($R^{D22}$), —N($R^{D22}$)C(O)O$R^{D22}$, or —N($R^{D22}$)C(O)N($R^{D22}$)$_2$, wherein each $R^{D22}$ is independently hydrogen, C$_1$-C$_4$ alkyl, C$_1$-C$_4$ haloalkyl, aryl, heteroaryl, C$_3$-C$_8$ cycloalkyl, or heterocyclyl, or any one of formulae ($R^D$-a)-($R^D$-t), wherein q is 0 or 1; z is 0, 1, or 2; and $R^{D25}$ is —C(O)$R^{D22}$, —C(O)O$R^{D22}$, —C(O)N($R^{D22}$)$_2$, —S(O)$_2$$R^{D22}$, —S(O)$_2$O$R^{D22}$, —S(O)$_2$N($R^{D22}$)$_2$, wherein each $R^{D22}$ is independently hydrogen, or C$_1$-C$_4$ alkyl, $R^{D1}$ aryl or heteroaryl, each optionally substituted with one, two, or three $R^{D10}$ groups, aryl optionally substituted with one, two, or three $R^{D10}$ groups, phenyl optionally substituted with one, two, or three $R^{D10}$ groups, wherein each Z is independently halogen (e.g., fluoro or chloro),

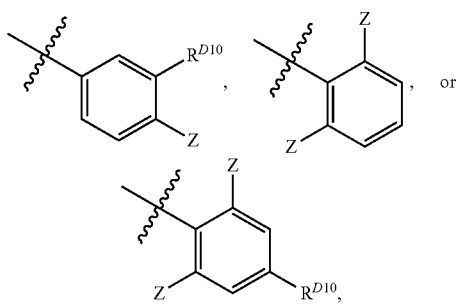

wherein each Z is independently halogen (e.g., fluoro or chloro), and $R^{D10}$ is —C(O)O$R^{D11}$, —C(O)N ($R^{D11}$)$_2$, —S(O)$_2$N($R^{D11}$)$_2$, —S(O)$_2$$R^{D11}$, —C$_1$-C$_{11}$alkyl-O$R^{D11}$, or tetrazolyl, heteroaryl optionally substituted with one, two, or three $R^{D10}$ groups, pyridyl, pyrimidinyl, indolyl, or imidazopyridyl, each optionally substituted with one, two, or three $R^{D10}$ groups, a 5 or 6 membered cycloalkyl or heterocyclyl, each optionally fused to a phenyl ring and each optionally substituted with one, two, or three $R^{D20}$, piperidinyl, piperazinyl, or pyrroylidinyl, each optionally substituted with one, two, or three $R^{D20}$ groups, piperidinyl or pyrroylidinyl, each optionally substituted with one, two, or three $R^{D20}$ groups, piperidinyl optionally substituted with one, two, or three $R^{D20}$ groups, pyrroylidinyl optionally substituted with one, two, or three $R^{D20}$ groups, cyclohexyl optionally substituted with one, two, or three $R^{D20}$ groups,

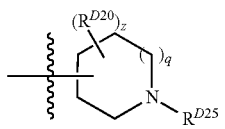
($R^{D1}$-a)

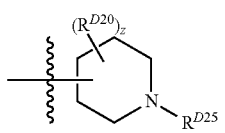
($R^{D1}$-b)

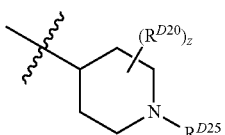
($R^{D1}$-c)

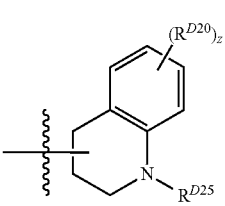
($R^{D1}$-d)

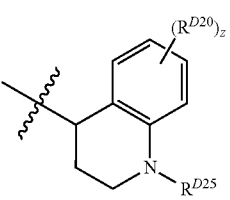
($R^{D1}$-e)

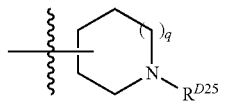
($R^{D1}$-f)

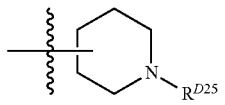
($R^{D1}$-g)

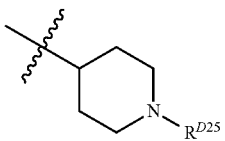
($R^{D1}$-h)

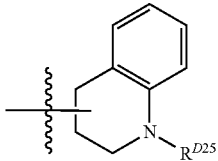
($R^{D1}$-i)

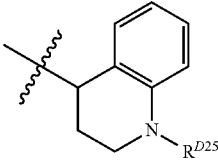
($R^{D1}$-j)

wherein q is 0 or 1; z is 0, 1, or 2; and $R^{D25}$ is —C(O)$R^{D22}$, —C(O)O$R^{D22}$, —C(O)N($R^{D22}$)$_2$, —S(O)$R^{D22}$, —S(O)$_2$$R^{D22}$, —S(O)O$R^{D22}$, —S(O)$_2$O$R^{D22}$, —S(O)N($R^{D22}$)$_2$, —S(O)$_2$N($R^{D22}$)$_2$, —C$_1$-C$_4$ alkyl, aryl, heteroaryl, C$_3$-C$_8$ cycloalkyl, or heterocyclyl, wherein the alkyl, aryl, heteroaryl, cycloalkyl, and heterocyclyl groups are each optionally substituted with one, two, or three $R^{D21}$ groups, wherein each $R^{D21}$ is independently halogen, cyano, nitro, —C$_1$-C$_4$ alkyl, aryl, heteroaryl, C$_3$-C$_8$ cycloalkyl, heterocyclyl, —O$R^{D22}$, —N($R^{D22}$)$_2$, —S$R^{D22}$, —C(O)$R^{D22}$, —C(O)O$R^{D22}$, —C(O)N($R^{D22}$)$_2$, —S(O)$R^{D22}$, —S(O)$_2$$R^{D22}$, —S(O)O$R^{D22}$, —S(O)$_2$O$R^{D22}$, —S(O)N($R^{D22}$)$_2$, —S(O)$_2$N($R^{D22}$)$_2$, —N($R^{D22}$)C(O)$R^{D22}$, —N(R$D^{22}$)S(O)$_2$$R^{D22}$, —OC(O)$R^{D22}$, —OC(O)N($R^{D22}$)$_2$, —OC(O)O($R^{D22}$), —N($R^{D22}$)C(O)O$R^{D22}$, or —N($R^{D22}$)C(O)N($R^{D22}$)$_2$, wherein each $R^{D22}$ is independently hydrogen, C$_1$-C$_4$ alkyl, C$_1$-C$_4$ haloalkyl, aryl, heteroaryl, C$_3$-C$_8$ cycloalkyl, or heterocyclyl, or any one of formulae ($R^{D1}$-a)-($R^{D1}$-j), wherein q is 0 or 1; z is 0, 1, or 2; and $R^{D25}$ is —C(O)$R^{D22}$, —C(O)O$R^{D22}$, —C(O)N($R^{D22}$)$_2$, —S(O)$_2$$R^{D22}$, —S(O)$_2$O$R^{D22}$, —S(O)$_2$N($R^{D22}$)$_2$, wherein each $R^{D22}$ is independently hydrogen, or C$_1$-C$_4$ alkyl;

$R^{D10}$ at least one $R^{D10}$ is halogen, one $R^{D10}$ is —C(O)N(H)C$_1$-C$_4$alkyl-$R^{D13}$, one $R^{D10}$ is halogen, C$_1$-C$_4$ alkyl, C$_1$-C$_4$ haloalkyl, cyano, nitro, —O$R^{11}$, —C(O)O$R^{D11}$, —C(O)N($R^{D11}$)$_2$, —C(=N$R^{D11}$)N($R^{D11}$)$_2$, —N($R^{D11}$)C(N$R^{D11}$)N($R^{D11}$)$_2$, —S(O)$_2$N($R^{D11}$)$_2$, —S(O)$_2$$R^{D11}$, —OC$_1$-C$_4$alkyl-$R^{D12}$, —C$_1$-C$_4$alkyl-O$R^{D11}$, —C(O)N(H)C$_1$-C$_4$alkyl-$R^{D13}$, a 5 or 6-membered heterocyclyl (e.g., piperazinyl), or a 5 or 6-membered heteroaryl (e.g., tetrazolyl), wherein the heterocyclyl and heteroaryl are optionally substituted with one, two, or three $R^{D12}$ groups, at least one $R^{D10}$ is halogen and one $R^{D10}$ is halogen, C$_1$-C$_4$ alkyl, C$_1$-C$_4$ haloalkyl, cyano, nitro, —O$R^{D11}$, —C(O)O$R^{D11}$, —C(O)N($R^{D11}$)$_2$, —C(=N$R^{D11}$)N($R^{D11}$)$_2$, —N($R^{D11}$)C(N$R^{D11}$)N($R^{D11}$)$_2$, —S(O)$_2$N($R^{D11}$)$_2$, —S(O)$_2$$R^{D11}$, —OC$_1$-C$_4$alkyl-$R^{D12}$, —C$_1$-C$_4$alkyl-O$R^{D11}$, —C(O)N(H)C$_1$-C$_4$alkyl-$R^{D13}$, a 5 or 6-membered heterocyclyl (e.g., piperazinyl), or a 5 or 6-membered heteroaryl (e.g., tetrazolyl), wherein the heterocyclyl and heteroaryl are optionally substituted with one, two, or three $R^{D12}$ groups, one $R^{D10}$ is —S(O)$_2$N($R^{D11}$)C(O)$R^{D11}$, —S(O)$_2$N($R^{D11}$)C(O)N($R^{D11}$)$_2$, or —S(O)$_2$N($R^{D11}$)C(O)N($R^{D11}$)(N$R^{D11}_2$), or one $R^{D10}$ is —S(O)$_2$N($R^{D11}$)C(O)N($R^{D11}$)($R^{110}$), wherein $R^{D110}$ is $C_1$-$C_4$alkyl, $C_1$-$C_4$haloalkyl, $C_3$-$C_8$ cycloalkyl, or heterocyclyl;

$L^D$

—[C(R)$_2$]$_p$—Y—[C(R)$_2$]$_q$—, wherein p is 0, 1, or 2; and q is an integer selected from 0 to (2-p), provided that either p or q is not 0;

—(CH$_2$)$_p$—Y—(CH$_2$)$_q$—,
—Y—(CH$_2$)$_q$— or —(CH$_2$)$_p$—Y—,
—Y—CH$_2$— or —CH$_2$—Y,
—S—(CH$_2$)$_q$— or —(CH$_2$)$_p$—S—,
—S—CH$_2$— or —CH$_2$—S—,
—O—(CH$_2$)$_q$— or —(CH$_2$)$_p$—O—,
—O—CH$_2$— or —CH$_2$—O—,
—N($R^Y$)—(CH$_2$)$_q$— or —(CH$_2$)$_p$—N($R^Y$)—,
—N($R^Y$)—CH$_2$— or —CH$_2$—N($R^Y$)—,
—CH$_2$CH$_2$— or —C(H)=C(H)—,
—S(O)$_2$N(H)—[C(R)$_2$]$_q$—, wherein q is 1 or 2,
—S(O)$_2$N(H)—(CH$_2$)$_q$—, wherein q is 1 or 2,
—C(O)N($R^Y$)—, —N($R^Y$)C(O)—, —S(O)$_2$N($R^Y$)— or —N($R^Y$)S(O)$_2$—, $Y^1$, or
a bond;

Y
—N($R^Y$)—, —O—, or —S—, or
—S(O)$_2$— or —C(O)—;

$Y^1$
—C(O)N($R^Y$)— or —N($R^Y$)C(O)—,
—S(O)$_2$N(H)—, or —N(H)S(O)$_2$—,
—C(O)N(H)— or —S(O)$_2$N(H)—, or
—S(O)$_2$N(H)—;

$R^A$
—[C($R^8$)$_2$]-aryl, wherein the aryl group is substituted with one, two, or three $R^{410}$ groups,
—[C($R^8$)$_2$]-phenyl, wherein the phenyl group is substituted with one, two, or three $R^{410}$ groups,
—[C($R^8$)$_2$]-heteroaryl, wherein the heteroaryl group is substituted with one, two, or three $R^{410}$ groups,
—[C(CH$_3$)$_2$]-phenyl, wherein the phenyl is substituted with one, two, or three $R^{410}$ groups,
—[C($R^8$)$_2$]-phenyl, wherein the phenyl is substituted with two $R^{410}$ groups,

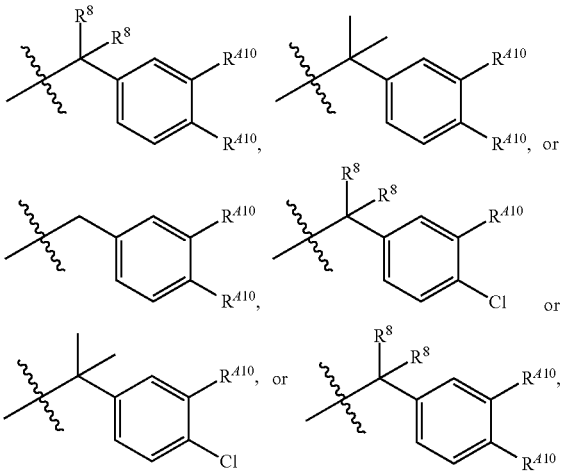

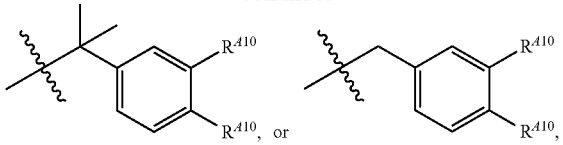

wherein both $R^{410}$ are taken together with the carbon atoms to which they are attached to form a fused phenyl or 5 or 6 membered heteroaryl ring (e.g., pyridyl), wherein the fused phenyl or heteroaryl ring are each optionally substituted with one, two, or three $R^{420}$ groups;

$R^{410}$
halogen, hydroxy, or methoxy,
at least one $R^{410}$ is halogen,
halogen, —O$R^{412}$, —C(O)O$R^{412}$, —C(O)N($R^{412}$)$_2$, —S(O)$_2$N($R^{412}$)$_2$, —S(O)$_2$$R^{412}$, cyano, nitro, pyrrolyl, tetrazolyl, —$C_1$-$C_4$alkyl-$R^{411}$ (e.g., —$C_1$-$C_4$ alkyl-OH), or —O$C_1$-$C_4$alkyl-$R^{411}$ (e.g., —O$C_1$-$C_4$alkyl-OH, —O$C_1$-$C_4$alkyl-COOH, —O$C_1$-$C_4$alkyl-morpholinyl, or —O$C_1$-$C_4$alkyl-imidazolyl), one $R^{410}$ is —O$R^{412}$, —C(O)O$R^{412}$, —C(O)N($R^{412}$)$_2$, —S(O)$_2$N($R^{412}$)$_2$, —S(O)$_2$$R^{412}$, cyano, nitro, pyrrolyl, tetrazolyl, —$C_1$-$C_4$alkyl-$R^{411}$ (e.g., —$C_1$-$C_4$ alkyl-OH), or —O$C_1$-$C_4$alkyl-$R^{411}$ (e.g., —O$C_1$-$C_4$alkyl-OH, —O$C_1$-$C_4$alkyl-COOH, —O$C_1$-$C_4$alkyl-morpholinyl, or —O$C_1$-$C_4$alkyl-imidazolyl), or one $R^{410}$ is halogen and one $R^{410}$ is —O$R^{412}$, —C(O)O$R^{412}$, —C(O)N($R^{412}$)$_2$, —S(O)$_2$N($R^{412}$)$_2$, —S(O)$_2$$R^{412}$, cyano, nitro, pyrrolyl, tetrazolyl, —$C_1$-$C_4$alkyl-$R^{411}$ (e.g., —$C_1$-$C_4$ alkyl-OH), or —O$C_1$-$C_4$alkyl-$R^{411}$ (e.g., —O$C_1$-$C_4$alkyl-OH, —O$C_1$-$C_4$alkyl-COOH, —O$C_1$-$C_4$alkyl-morpholinyl, or —O$C_1$-$C_4$alkyl-imidazolyl);

$R^{10}$
hydrogen, halogen, $C_1$-$C_4$alkyl, $C_1$-$C_4$haloalkyl, —$C_1$-$C_4$alkyl-$R^{100}$, or —C(O)OH,
hydroxy($C_1$-$C_2$)alkyl or —C(O)OH,
hydrogen or halogen,
—$C_1$-$C_4$alkyl-$R^{100}$, or
hydrogen.

$R^{D11B}$ is selected from —C(=NH)—NH$_2$, —N(H)C(=NH)NH$_2$, C(H)=NN(H)C(=NH)NH$_2$, and —N(H)C(=NH)—N(H)C(=NH)NH$_2$ Another aspect of the invention relates to a compound of Formula VIII:

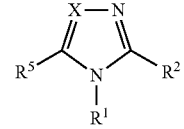

VIII or pharmaceutically acceptable salt thereof, wherein:
X is =N— or =C($R^4$)—;
$R^1$ is $R^C$;
or X can be =C($R^C$)— only when $R^1$ is phenyl optionally substituted with one, two, or three $R^{C10}$ groups;
$R^C$ is selected from phenyl, —($C_5$-$C_6$)-cycloalkyl, —CH$_2$-phenyl, heteroaryl, and —($C_1$-$C_4$)alkyl optionally substituted with —O$R^{C13}$, —N($R^{C13}$)$_2$ or —S($R^{C13}$), wherein the cyclic group of $R^C$ can be optionally substituted with 1, 2, 3, 4 or 5

$R^{C10}$ groups, wherein the 1, 2, 3, 4, or 5 $R^{C10}$ groups are independently selected from $R^{C10A}$ and $R^{C10B}$, provided that $R^C$ cannot be substituted with more than 2 $R^{C10B}$ groups, and provided that substitution of $R^C$ with $R^{C10}$ can only occur by replacing a hydrogen that is covalently bound to either a carbon or a nitrogen of $R^C$, wherein each $R^{10A}$ is independently selected from halo, cyano and —$(C_1$-$C_4)$alkyl optionally substituted with 1-3 groups selected from —OH and halo;

each $R^{C10B}$ is independently selected from —C(O)NH$_2$, (5-6 membered)heterocycloalkyl, —O—$(C_1$-$C_4)$alkyl-$R^{C11}$, —C(O)OR$^{C12}$, —OC(O)OR$^{C12}$ and —O—$(C_1$-$C_4)$alkyl optionally substituted with —OH or —C(O)OH;

$R^{C11}$ is cyano, nitro, —N(R$^{C12}$)$_2$, —OR$^{C12}$, —SR$^{C12}$, —C(O)R$^{C12}$, —C(O)OR$^{C12}$, —C(O)N(R$^{C12}$)$_2$, —S(O)N(R$^{C12}$)$_2$, —S(O)$_2$N(R$^{C12}$)$_2$, —S(O)$_2$R$^{C12}$, —OC(O)R$^{C12}$, —OC(O)OR$^{C12}$, —OC(O)N(R$^{C12}$)$_2$, —N(R$^{C12}$)C(O)R$^{C12}$, —N(R$^{C12}$)C(O)OR$^{C12}$, —(R$^{C12}$)C(O)N(R$^{C12}$)$_2$, or N(R$^{C12}$)C(=NR$^{C12}$)N(R$^{C12}$)$_2$;

each $R^{C12}$ is independently selected from hydrogen, —$(C_1$-$C_4)$alkyl, and —$(C_1$-$C_4)$haloalkyl;

each $R^{C13}$ is independently selected from hydrogen, —$(C_1$-$C_4)$alkyl, and —$(C_1$-$C_4)$haloalkyl;

$R^2$ is -L$^D$-R$^{D1}$;

$L^D$ is —$[C(R)_2]_p$—Y—$[C(R)_2]_q$—;

p is 0 or 1:

q is 0 or 1;

each R is independently selected from H, —$(C_1$-$C_3)$alkyl, halo, —OH, and —CH$_2$OH;

Y is a bond, —S—, —S(O)$_2$—, —CH(OH)—, —O—, —C(H)=C(H)—, —C(O)—$(C_1$-$C_4)$alkyl-, —$(C_1$-$C_4)$alkyl-S—$(C_1$-$C_4)$alkyl-, —$(C_1$-$C_4)$alkyl-N(R$^Y$)—$(C_1$-$C_4)$alkyl-, —C(H)(halo)-, —$(C_1$-$C_4)$alkyl-S(O)$_2$—, —S(O)$_2$—N(R$^Y$)—, —$(C_1$-$C_4)$alkyl-O—, or —C(O)—N(R$^Y$)—, wherein R$^Y$ is H, —$(C_1$-$C_4)$alkyl, hydroxyl$(C_1$-$C_4)$alkyl or —C≡C—$(C_1$-$C_3)$alkyl-;

$R^{D1}$ is selected from —$(C_6$-$C_{10})$aryl, —N(H)-phenyl, cycloalkyl, heterocycloalkyl, and heteroaryl, wherein $R^{D1}$ can be optionally substituted with 1, 2, 3, 4 or 5 $R^{D10}$, provided that substitution of $R^{D1}$ with $R^{D10}$ can only occur by replacing a hydrogen that is covalently bound to either a carbon or a nitrogen of $R^{D1}$, wherein the 1-5 $R^{D10}$ groups are independently selected from A groups and B groups, provided that $R^{D1}$ cannot be substituted with more than 2 B groups;

each A group, when they occur, is independently selected from halo, —CF$_3$, —CN, —NO$_2$, —OH, —O—$(C_1$-$C_4)$alkyl optionally substituted at the alkyl group with 1-3 substituents independently selected from —OH and halo, and —$(C_1$-$C_4)$alkyl optionally substituted with 1-3 substituents independently selected from —OH and halo;

each B group, when they occur, is independently selected from —$(C_1$-$C_4)$alkylN(R$^{D11}$)$_2$, —C(O)—NH$_2$, —C(O)—N(H)—OH, —C(O)—N(H)—R$^{D11C}$, —C(O)—$(C_1$-$C_4)$alkyl optionally substituted with R$^{D11B}$, —C(O)OH, —S(O)$_2$—$(C_1$-$C_4)$alkyl-N(R$^{D11}$)$_2$, —S(O)$_2$—N(R$^{D11}$)R$^{D11C}$, —S(O)$_2$—N(H)C(O)—N(R$^{D11}$)R$^{D11B}$, —C(=NH)—NH$_2$, —C(O)O—$(C_1$-$C_4)$alkyl optionally substituted with R$^{D11B}$, —O—$(C_1$-$C_4)$alkyl optionally substituted at the alkyl group with 1 or 2 R$^{D11B}$, —C(O)-heterocycloalkyl, wherein the —C(O)-heterocycloalkyl can be optionally substituted with R$^{D11B}$, provided that substitution of —C(O)-heterocycloalkyl with R$^{D11B}$ can only occur by replacing a hydrogen that is covalently bound to either a carbon or a nitrogen of —C(O)-heterocycloalkyl, —C(O)—N(H)—$(C_1$-$C_6)$alkyl optionally substituted at the alkyl group with 1 or 2 R$^{D11B}$, heterocycloalkyl optionally substituted with oxo or R$^{D11}$, provided that substitution of the heterocycloalkyl with R$^{D11}$ can only occur by replacing a hydrogen that is covalently bound to either a carbon or a nitrogen of the heterocycloalkyl, heterocycloalkenyl optionally substituted with oxo or R$^{D11}$, provided that substitution of the heterocycloalkenyl with R$^{D11}$ can only occur by replacing a hydrogen that is covalently bound to either a carbon or a nitrogen of the heterocycloalkenyl, heteroaryl optionally substituted with R$^{D11}$, provided that substitution of the heteroaryl with R$^{D11}$ can only occur by replacing a hydrogen that is covalently bound to either a carbon or a nitrogen of the heteroaryl, —S(O)$_2$-(4-6 membered)heterocycloalkyl optionally substituted with R$^{D11C}$, provided that substitution of the —S(O)$_2$-(4-6 membered)heterocycloalkyl with R$^{D11C}$ can only occur by replacing a hydrogen that is covalently bound to either a carbon or a nitrogen of the —S(O)$_2$-(4-6 membered)heterocycloalkyl, —S(O)$_2$—N(H)C(O)—$(C_1$-$C_4)$alkyl optionally substituted with R$^{D11B}$, —S(O)$_2$—N(H)C(O)O—$(C_1$-$C_4)$alkyl optionally substituted with R$^{D11B}$, —S(O)$_2$—$(C_1$-$C_4)$alkyl optionally substituted with R$^{D11B}$, —N(H)—C(O)—$(C_1$-$C_4)$alkyl optionally substituted at the alkyl group with 1 or 2 R$^{D11B}$, —N(H)—C(O)—N(H)—$(C_1$-$C_3)$alkyl optionally substituted at the alkyl group with R$^{D11B}$, —$(C_1$-$C_6)$alkyl optionally substituted with 1 or 2 R$^{D11B}$, and —C≡C—$(C_1$-$C_3)$alkyl optionally substituted with R$^{D11B}$;

each R$^{D11}$ is independently selected from H, —$(C_3$-$C_6)$cycloalkyl, —OH, —$(C_1$-$C_4)$haloalkyl, —$(C_1$-$C_4)$alkyl optionally substituted with halo, —OH, —C(O)OH, —S(O)$_2$OH, C(O)OH, —NH$_2$, or —N(H)C(=NH)NH$_2$, and —$(C_1$-$C_3)$alkyl-phenyl optionally substituted at the phenyl group with 1-3 substituents selected from methoxy, hydroxyl and halo;

R$^{D11B}$ is selected from H, —OH, —CF$_3$, a PEG polymer, —N(R$^{D11}$)$_2$, —C(O)OH, —O—$(C_1$-$C_4)$alkyl, —S(O)$_2$OH, —C(=NH)—NH$_2$, —N(H)C(=NH)NH$_2$, —C(H)=NC(=NH)NH$_2$, —C(H)=NN(H)C(=NH)NH$_2$, —N(H)C(=NH)—N(H)C(=NH)NH$_2$, —C(O)—$(C_1$-$C_3)$alkyl, —O—$(C_1$-$C_4)$alkyl-C(O)OH, (5-6 membered)heteroaryl, —$(C_1$-$C_4)$alkyl optionally substituted with 1-3 groups independently selected from halo, —OH, —S(O)$_2$OH, C(O)OH, —NH$_2$, and —N(H)C(=NH)NH$_2$, —$(C_0$-$C_3)$alkyl-(5-8 membered)heterocycloalkyl, optionally substituted with 1, 2 or 3 R$^{D11}$, provided that substitution of —$(C_0$-$C_3)$alkyl-(5-8 membered)heterocycloalkyl with R$^{D11}$ can only occur by replacing a hydrogen that is covalently bound to either a carbon or a nitrogen of —$(C_0$-$C_3)$alkyl-(5-8 membered)heterocycloalkyl, —$(C_0$-$C_3)$alkyl-$(C_3$-$C_6)$cycloalkyl optionally substituted with R$^{D11}$, and aryl optionally substituted with 1-5 halo;

or R$^{D11}$ and R$^{D11B}$, when they both exist and are each attached to nitrogen, can join together with the nitrogen to which they are attached to form a (5-6 membered) heterocycloalkyl optionally substituted with a group selected from —$(C_3$-$C_6)$cycloalkyl, —$(C_1$-$C_4)$haloalkyl, —OH, —S(O)$_2$OH, C(O)OH, —NH$_2$, —N(H)C(=NH)NH$_2$, —$(C_1$-$C_4)$alkyl optionally substituted with halo, —OH or —C(O)OH, and —$(C_1$-$C_3)$alkyl-phenyl optionally substituted at the phenyl group with 1-3 substituents selected from methoxy, hydroxyl and halo, provided that substitution of the (5-6 membered) heterocycloalkyl can only occur by replacing a hydrogen that is covalently bound to either a carbon or a nitrogen of the (5-6 membered) heterocycloalkyl;

R$^{D11C}$ is selected from H, —OH, —CF$_3$, —O—$(C_1$-$C_4)$alkyl, —$(C_1$-$C_4)$alkyl-N(H)C(=NH)—NH$_2$, —$(C_0$-$C_3)$alkyl-(5-6 membered)heteroaryl, —$(C_1$-$C_4)$alkyl optionally substituted with 1-3 groups independently selected from halo, —OH, —S(O)$_2$OH, C(O)OH, —NH$_2$, and —N(H)C (=NH)NH$_2$, —(C$_0$-C$_3$)alkyl-(5-6 membered)heterocycloalkyl optionally substituted with one (5-6 membered)heteroaryl, provided that substitution of the —(C$_0$-C$_3$)alkyl-(5-6 membered)heterocycloalkyl with (5-6 membered)heteroaryl can only occur by replacing a hydrogen that is covalently bound to either a carbon or a nitrogen of the —(C$_0$-C$_3$)alkyl-(5-6 membered)heterocycloalkyl, —(C$_0$-C$_3$)alkyl-(5-6 membered)heterocycloalkyl substituted with 1, 2 or 3 groups selected from —OH and —(C$_1$-C$_3$)alkyl, provided that substitution of the —(C$_0$-C$_3$)alkyl-(5-6 membered)heterocycloalkyl can only occur by replacing a hydrogen that is covalently bound to either a carbon or a nitrogen of the —(C$_0$-C$_3$)alkyl-(5-6 membered)heterocycloalkyl, and —(C$_0$-C$_3$)alkyl-aryl optionally substituted at the aryl group with 1-3 halo;

R$^4$ is H, —(C$_1$-C$_3$)alkyl or halo;

R$^5$ is —[C(R$^8$)$_2$]-phenyl, —[C(R$^8$)$_2$]-naphthalenyl, or —[C(R$^8$)$_2$]-(5-10 membered) heteroaryl, wherein the heteroaryl is selected from (benzo[d][1,3]dioxolyl, benzo[d]isoxazole, quinoxalinyl, quinolinyl and 2,3,4a,8a-tetrahydrobenzo[b][1,4]dioxinyl, wherein the cyclic group of R$^5$ is optionally substituted with 1, 2, 3, 4 or 5 R$^{A10}$, provided that substitution of R$^5$ with R$^{A10}$ can only occur by replacing a hydrogen that is covalently bound to either a carbon or a nitrogen of R$^5$, wherein the 1-5 R$^{A10}$ groups are independently selected from R$^{A10A}$ groups and R$^{A10B}$ groups, provided that R$^5$ cannot be substituted with more than 2 R$^{A10B}$ groups;

each R$^{A10A}$, when they occur, is independently selected from halo, alkoxyl, hydroxyl, —CN, —OCF$_3$, —(C$_1$-C$_4$)alkyl and —NH$_2$, each R$^{A10B}$, when they occur, is selected from —O—(C$_1$-C$_4$)alkyl-R$^{A11}$, —S(O)$_2$—NH$_2$, —S(O)$_2$CH$_3$, —N(H)—S(O)$_2$CH$_3$, —S(O)$_2$N(H)—CH$_3$, —C(O)OH, —(C$_1$-C$_4$)alkyl-OH, —C(O)NH$_2$, and —(C$_1$-C$_4$)alkyl substituted with 1-3 groups selected from —OH and halo;

R$^{A11}$ is selected from —C(O)OH, (5-6 membered)heterocycloalkyl, halogen, cyano, nitro, —(C$_1$-C$_4$)alkyl, —N(R$^{A12}$)$_2$, —OR$^{A12}$, —SR$^{A12}$, —N(OR$^{A12}$)R$^{A12}$, —C(O)R$^{A12}$, —C(O)OR$^{A12}$, —C(O)N(R$^{A12}$)$_2$, —N(R$^{A12}$)S(O)R$^{A12}$, —N(R$^{A12}$)S(O)$_2$R$^{A12}$, —S(O)N(R$^{A12}$)$_2$, —S(O)$_2$N(R$^{A12}$)$_2$, —S(O)$_2$R$^{A12}$, —OC(O)R$^{A12}$, —OC(O)OR$^{A12}$, —OC(O)N(R$^{A12}$)$_2$, —N(R$^{A12}$)C(O)R$^{A12}$, —N(R$^{A12}$)S(O)$_2$R$^{A12}$, —N(R$^{A12}$)C(O)OR$^{A12}$, —N(R$^{A12}$)C(O)N(R$^{A12}$)$_2$, —N(R$^{A12}$)C(=NR$^{A12}$)N(R$^{A12}$)$_2$, and heteroaryl, wherein each R$^{A12}$ is independently hydrogen, —(C$_1$-C$_4$)alkyl, or —(C$_1$-C$_4$)halo alkyl; and each R$^8$ is independently hydrogen, halogen, or methyl, or both R$^8$ taken together with the carbon to which they are both attached form either a (C$_3$-C$_6$)cycloalkyl or a (3-6 membered) heterocycloalkyl. In another embodiment of the compound of Formula VIII, R$^C$ is substituted with 1, 2, 3, 4 or 5 R$^{C10A}$ groups.

In another embodiment of the compound of Formula VIII, R$^C$ is substituted with 0, 1, 2, 3 or 4 R$^{C10A}$ groups and 1 R$^{C10B}$ group.

In another embodiment of the compound of Formula VIII, R$^C$ is substituted with 0, 1, 2 or 3 R$^{C10A}$ groups and 1 or 2 R$^{C10B}$ groups.

In another embodiment of the compound of Formula VIII, R$^{D1}$ is substituted with 0-4 A groups and 1 B group.

In another embodiment of the compound of Formula VIII, R$^{D1}$ is substituted with 0-3 A groups and 1-2 B groups.

In another embodiment of the compound of Formula VIII, R$^5$ is optionally substituted with 1-5 R$^{A10A}$ groups.

In another embodiment of the compound of Formula VIII, R$^5$ is optionally substituted with 0-4 R$^{A10A}$ groups and 1 R$^{A10B}$ group.

In another embodiment of the compound of Formula VIII, R$^5$ is optionally substituted with 0-3 R$^{A10A}$ groups and 1-2 R$^{A10B}$ groups.

Another embodiment of the compound VIII relates to structural formulae (VI) or (VII):

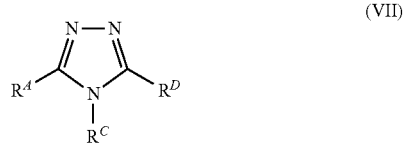

or pharmaceutically acceptable salt thereof, wherein:

R$^A$ is —[C(CH$_3$)$_2$]-phenyl, —[C(CH$_3$)$_2$]-naphthalenyl, or —[C(CH$_3$)$_2$]-(5-10 membered)heteroaryl, wherein the heteroaryl is selected from (benzo[d][1,3]dioxolyl, benzo[d]isoxazole, quinoxalinyl, quinolinyl and 2,3,4a,8a-tetrahydrobenzo[b][1,4]dioxinyl, wherein the cyclic group of R$^A$ is optionally substituted with 1, 2 or 3 R$^{A10}$;

each R$^{A10}$ is independently selected from halo, alkoxyl, hydroxyl, —NH$_2$, —S(O)$_2$—NH$_2$, —S(O)$_2$CH$_3$, —N(H)—S(O)$_2$CH$_3$, —SO$_2$N(H)—CH$_3$, —CN, —C(O)OH, —(C$_1$-C$_4$)alkyl-OH, —OCF$_3$, —C(O)NH$_2$, and —(C$_1$-C$_4$)alkyl optionally substituted with 1-3 groups independently selected from —OH and halo;

R$^C$ is phenyl, —CH$_2$-phenyl, —(C$_5$-C$_6$)-cycloalkyl, —CH$_2$-phenyl, or pyridinyl, wherein the cyclic group of R$^C$ can be optionally substituted with 1, 2 or 3 R$^{C10}$, wherein the 1, 2, or 3 R$^{C10}$ groups are independently selected from R$^{C10A}$ and R$^{C10B}$, provided that R$^C$ cannot be substituted with more than 1 R$^{C10B}$ group;

each R$^{C10A}$ is independently selected from halo, and —(C$_1$-C$_3$)alkyl optionally substituted with 1-3 groups selected from —OH, methoxy, —CF$_3$ and halo;

R$^{C10B}$ is selected from —C(O)NH$_2$, (5-6 membered)heterocycloalkyl, —C(O)OH, or —N[—(C$_1$-C$_4$)alkyl]$_2$, —O—(C$_1$-C$_4$)alkyl optionally substituted with —OH, and —(C$_1$-C$_4$)alkyl substituted with —N[—(C$_1$-C$_4$)alkyl]$_2$;

R$^D$ is -L$^D$-R$^{D1}$;

L$^D$ is —[C(R)$_2$]$_p$—Y—[C(R)$_2$]$_q$—;

p is 0 or 1;

q is 0 or 1;

each R is independently selected from H, —(C$_1$-C$_3$)alkyl, halo, —OH, and —CH$_2$OH;

Y is a bond, —S—, —S(O)$_2$—, —CH(OH)—, —O—, —C(H)=C(H)—, —C(O)—(C$_1$-C$_4$)alkyl-, —(C$_1$-C$_4$)alkyl-S—(C$_1$-C$_4$)alkyl-, —(C$_1$-C$_4$)alkyl-N(R$^Y$)—(C$_1$-C$_4$)alkyl-, —C(H)(halo)-, —(C$_1$-C$_4$)alkyl-S(O)$_2$—, —S(O)$_2$—N(R$^Y$)—, —(C$_1$-C$_4$)alkyl-O—, or —C(O)—N(R$^Y$)—, wherein R$^Y$ is H, —(C$_1$-C$_4$)alkyl, hydroxyl(C$_1$-C$_4$)alkyl or —C≡C—(C$_1$-C$_3$)alkyl-;

R$^{D1}$ is selected from phenyl —(C$_6$-C$_{10}$)aryl, —N(H)-phenyl, —(C$_5$-C$_6$)cycloalkyl, heterocycloalkyl, or heteroaryl, wherein R$^{D1}$ can be optionally substituted with 1, 2, 3 or 4

$R^{D10}$, provided that substitution of $R^{D1}$ with $R^{D10}$ can only occur by replacing a hydrogen that is covalently bound to either a carbon or a nitrogen of $R^{D1}$, wherein the 1-4 $R^{D10}$ groups are independently selected from A groups and B groups, provided that $R^{D1}$ cannot be substituted with more than 2 B groups;

each A group, when they occur, is independently selected from halo, —$CF_3$, —CN, —$NO_2$, —OH, —O—($C_1$-$C_4$)alkyl optionally substituted at the alkyl group with 1-3 substituents independently selected from —OH and halo, and —($C_1$-$C_4$)alkyl optionally substituted with 1-3 substituents independently selected from —OH and halo;

each B group, when they occur, is independently selected from —($C_1$-$C_4$)alkylN($R^{D11}$)$_2$, —C(O)—$NH_2$, —C(O)—N(H)—OH, —C(O)—N(H)—$R^{D11C}$, —C(O)—($C_1$-$C_4$)alkyl, —C(O)OH, —C(O)O—($C_1$-$C_4$)alkyl, —S(O)$_2$—($C_1$-$C_4$)alkyl-N($R^{D11}$)$_2$, —S(O)$_2$—N($R^{D11}$)$R^{D11C}$, S(O)$_2$—N(H)C(O)—($C_1$-$C_4$)alkyl, —S(O)$_2$—N(H)C(O)O—($C_1$-$C_4$)alkyl, —S(O)$_2$—N(H)C(O)—N($R^{D11}$)$R^{D11B}$, S(O)$_2$—($C_1$-$C_4$)alkyl, —C(O)-heterocycloalkyl optionally substituted with $R^{D11B}$, provided that substitution of the —C(O)-heterocycloalkyl with $R^{D11B}$ can only occur by replacing a hydrogen that is covalently bound to either a carbon or a nitrogen of the —C(O)-heterocycloalkyl with $R^{D11B}$, —C(O)—N(H)—($C_1$-$C_6$)alkyl optionally substituted at the alkyl group with 1 or 2 $R^{D11B}$, heterocycloalkyl optionally substituted with oxo or $R^{D11}$, provided that substitution of the heterocycloalkyl with $R^{D11}$ can only occur by replacing a hydrogen that is covalently bound to either a carbon or a nitrogen of the heterocycloalkyl, heterocycloalkenyl optionally substituted with oxo or $R^{D11}$, provided that substitution of the heterocycloalkenyl with $R^{D11}$ can only occur by replacing a hydrogen that is covalently bound to either a carbon or a nitrogen of the heterocycloalkenyl, heteroaryl optionally substituted with $R^{D11}$, provided that substitution of the heteroaryl with $R^{D11}$ can only occur by replacing a hydrogen that is covalently bound to either a carbon or a nitrogen of the heteroaryl, —O—($C_1$-$C_4$)alkyl optionally substituted at the alkyl group with 1 or 2 $R^{D11B}$, —S(O)$_2$-(4-6 membered)heterocycloalkyl optionally substituted with $R^{D11C}$, provided that substitution of the —S(O)$_2$-(4-6 membered)heterocycloalkyl with $R^{D11C}$ can only occur by replacing a hydrogen that is covalently bound to either a carbon or a nitrogen of the —S(O)$_2$-(4-6 membered)heterocycloalkyl, —N(H)—C(O)—($C_1$-$C_4$)alkyl optionally substituted at the alkyl group with 1 or 2 $R^{D11B}$, —N(H)—C(O)—N(H)—($C_1$-$C_3$)alkyl optionally substituted at the alkyl group with $R^{D11B}$, —($C_1$-$C_6$)alkyl optionally substituted with 1 or 2 $R^{D11B}$, —C(=NH)—$NH_2$, and —C≡C—($C_1$-$C_3$)alkyl optionally substituted with $R^{D11B}$;

each $R^{D11}$ is independently selected from H, —($C_3$-$C_6$)cycloalkyl, —($C_1$-$C_4$)haloalkyl; —OH, —S(O)$_2$OH, C(O)OH, —$NH_2$, —N(H)C(=NH)$NH_2$, —($C_1$-$C_4$)alkyl optionally substituted with halo, —OH or —C(O)OH, —($C_1$-$C_3$)alkyl-phenyl optionally substituted at the phenyl group with 1-3 substituents selected from methoxy, hydroxyl and halo;

$R^{D11B}$ is selected from H, —OH, —$CF_3$, —N($R^{D11}$)$_2$, —C(O)OH, —O—($C_1$-$C_4$)alkyl, —S(O)$_2$OH, —C(=NH)—$NH_2$, —N(H)C(=NH)$NH_2$, —C(H)=NN(H)C(=NH)$NH_2$, —O—($C_1$-$C_4$)alkyl-C(O)OH, —N(H)C(=NH)—N(H)C(=NH)$NH_2$, (5-6 membered)heteroaryl, —C(O)—($C_1$-$C_3$)alkyl, —($C_1$-$C_4$)alkyl optionally substituted with 1-3 groups independently selected from halo and —OH, —($C_1$-$C_4$)alkyl optionally substituted with 1-3 groups independently selected from halo, —OH, —S(O)$_2$OH, —C(O)OH, —$NH_2$, and —N(H)C(=NH)$NH_2$, —($C_0$-$C_3$)alkyl-(5-8 membered)heterocycloalkyl optionally substituted with 1, 2 or 3 $R^{D11}$, provided that substitution of —($C_0$-$C_3$)alkyl-(5-8 membered)heterocycloalkyl with $R^{D11}$ can only occur by replacing a hydrogen that is covalently bound to either a carbon or a nitrogen of —($C_0$-$C_3$)alkyl-(5-8 membered)heterocycloalkyl, —($C_0$-$C_3$)alkyl-($C_3$-$C_6$)cycloalkyl optionally substituted with $R^{D11}$, and —($C_6$-$C_{10}$)aryl optionally substituted with 1-3 halo;

or $R^{D11}$ and $R^{D11B}$, when they both exist and are each attached to nitrogen, can join together with the nitrogen to which they are attached to form a (5-6 membered) heterocycloalkyl optionally substituted with a group selected from —OH, —($C_1$-$C_4$)haloalkyl, —S(O)$_2$OH, C(O)OH, —$NH_2$, —N(H)C(=NH)$NH_2$, —($C_3$-$C_6$)cycloalkyl, —($C_1$-$C_4$)alkyl optionally substituted with halo, —OH or —C(O)OH, and —($C_1$-$C_3$)alkyl-phenyl optionally substituted at the phenyl group with 1-3 substituents selected from methoxy, hydroxyl and halo, provided that substitution of the (5-6 membered) heterocycloalkyl can only occur by replacing a hydrogen that is covalently bound to either a carbon or a nitrogen of the (5-6 membered) heterocycloalkyl; and $R^{D11C}$ is selected from H, —OH, —$CF_3$, —O—($C_1$-$C_4$)alkyl, —($C_1$-$C_4$)alkyl-N(H)C(=NH)—$NH_2$, —($C_0$-$C_3$)alkyl-(5-6 membered)heteroaryl, —($C_1$-$C_4$)alkyl optionally substituted with 1-3 groups independently selected from halo, —OH, —S(O)$_2$OH, C(O)OH, —$NH_2$, and —N(H)C(=NH)$NH_2$, —($C_0$-$C_3$)alkyl-(5-6 membered)heterocycloalkyl optionally substituted with a -(5-6 membered)heteroaryl, provided that substitution of the —($C_0$-$C_3$)alkyl-(5-6 membered)heterocycloalkyl can only occur by replacing a hydrogen that is covalently bound to either a carbon or a nitrogen of the —($C_0$-$C_3$)alkyl-(5-6 membered)heterocycloalkyl, —($C_0$-$C_3$)alkyl-(5-6 membered)heterocycloalkyl substituted 1, 2 or 3 groups selected from selected from —OH and —($C_1$-$C_3$)alkyl, provided that substitution of the —($C_0$-$C_3$)alkyl-(5-6 membered)heterocycloalkyl can only occur by replacing a hydrogen that is covalently bound to either a carbon or a nitrogen of the —($C_0$-$C_3$)alkyl-(5-6 membered) heterocycloalkyl, and —($C_0$-$C_3$)alkyl-aryl optionally substituted at the aryl group with 1-3 halo.

In another embodiment of the compound of Formula VIII, $R^C$ is substituted with 1, 2, 3, 4 or 5 $R^{C10A}$ groups.

In another embodiment of the compound of Formula VI, $R^C$ is substituted with 0, 1, 2, 3 or 4 $R^{C10A}$ groups and 1 $R^{C10B}$ group.

In another embodiment of the compound of Formula VI, $R^C$ is substituted with 0, 1, 2 or 3 $R^{C10A}$ groups and 1 or 2 $R^{C10B}$ groups.

In another embodiment of the compound of Formula VI, $R^{D1}$ is substituted with 0-4 A groups and 0-1 B groups.

In another embodiment of the compound of Formula VI, $R^{D1}$ is substituted with 0-3 A groups and 0-1 B groups.

In another embodiment of the compound of Formula VI, $R^5$ is optionally substituted with 1-5 $R^{A10A}$ groups.

In another embodiment of the compound of Formula VI, $R^5$ is optionally substituted with 0-4 $R^{A10A}$ groups and 1 $R^{A10B}$ group.

In another embodiment of the compound of Formula VI, $R^5$ is optionally substituted with 0-3 $R^{A10A}$ groups and 1-2 $R^{A10B}$ groups.

In another embodiment of the compound of Formula VII, $R^C$ is substituted with 1, 2, 3, 4 or 5 $R^{C10A}$ groups.

In another embodiment of the compound of Formula VII, $R^C$ is substituted with 0, 1, 2, 3 or 4 $R^{C10A}$ groups and 1 $R^{C10B}$ group.

In another embodiment of the compound of Formula VII, $R^C$ is substituted with 0, 1, 2 or 3 $R^{C10A}$ groups and 1 or 2 $R^{C10B}$ groups.

In another embodiment of the compound of Formula VII, $R^{D1}$ is substituted with 0-4 A groups and 1 B group.

In another embodiment of the compound of Formula VII, $R^{D1}$ is substituted with 0-3 A groups and 1-2 B groups.

In another embodiment of the compound of Formula VII, $R^5$ is optionally substituted with 1-5 $R^{410A}$ groups.

In another embodiment of the compound of Formula VII, $R^5$ is optionally substituted with 0-4 $R^{410A}$ groups and 1 $R^{410B}$ group.

In another embodiment of the compound of Formula VII, $R^5$ is optionally substituted with 0-3 $R^{410A}$ groups and 1-2 $R^{410B}$ groups.

In another embodiment of the compound of formula VIII, X is =C($R^4$)—;

each R is independently selected from H, —($C_1$-$C_3$)alkyl, —OH, and —$CH_2$OH;

Y is —S—, —S(O)$_2$—, —CH(OH)—, —C(H)=C(H)—, —C(O)—, —($C_1$-$C_4$)alkyl-S—, —($C_1$-$C_4$)alkyl-N($R^Y$)—, —C(H)(halo)-, —($C_1$-$C_4$)alkyl-S(O)$_2$—, —S(O)$_2$—N($R^Y$)—, —($C_1$-$C_4$)alkyl-O—, or —C(O)—N($R^Y$)—, wherein $R^Y$ is H, —($C_1$-$C_4$)alkyl or hydroxyl($C_1$-$C_4$)alkyl;

$R^{D1}$ is selected from phenyl —($C_6$-$C_{10}$)aryl, —N(H)-phenyl, —($C_5$-$C_6$)cycloalkyl, heterocycloalkyl, or heteroaryl, wherein $R^{D1}$ can be optionally substituted with 1, 2, 3 or 4 $R^{D10}$, provided that substitution of $R^{D1}$ with $R^{D10}$ can only occur by replacing a hydrogen that is covalently bound to either a carbon or a nitrogen of $R^{D1}$, wherein the 1-4 $R^{D10}$ groups are independently selected from A groups and B groups, provided that $R^{D1}$ cannot be substituted with more than 2 B groups;

each A group, when they occur, is independently selected from halo, —$CF_3$, —CN, —$NO_2$, —OH, —O—($C_1$-$C_4$)alkyl optionally substituted at the alkyl group with 1-3 substituents independently selected from —OH and halo, and —($C_1$-$C_4$)alkyl optionally substituted with 1-3 substituents independently selected from —OH and halo;

each B group, when they occur, is independently selected from —($C_1$-$C_4$)alkylN($R^{D11}$)$_2$, —C(O)—$NH_2$, —C(O)—N(H)—OH, —C(O)—N(H)—$R^{D11C}$, —C(O)—($C_1$-$C_4$)alkyl, —C(O)OH, —C(O)O—($C_1$-$C_4$)alkyl, —S(O)$_2$—($C_1$-$C_4$)alkyl-N($R^{D11}$)$_2$, —S(O)$_2$—N($R^{D11}$)$R^{D11C}$, S(O)$_2$—N(H)C(O)—($C_1$-$C_4$)alkyl, —S(O)$_2$—N(H)C(O)O—($C_1$-$C_4$)alkyl, —S(O)$_2$—N(H)C(O)—N($R^{D11}$) $R^{D11B}$, —S(O)$_2$—($C_1$-$C_4$)alkyl, —C(O)-heterocycloalkyl optionally substituted with $R^{D11B}$, provided that substitution of the —C(O)-heterocycloalkyl with $R^{D11B}$ can only occur by replacing a hydrogen that is covalently bound to either a carbon or a nitrogen of the —C(O)-heterocycloalkyl with $R^{D11B}$, —C(O)—N(H)—($C_1$-$C_6$)alkyl optionally substituted at the alkyl group with 1 or 2 $R^{D11B}$, heterocycloalkyl optionally substituted with oxo or $R^{D11}$ provided that substitution of the heterocycloalkyl with $R^{D11}$ can only occur by replacing a hydrogen that is covalently bound to either a carbon or a nitrogen of the heterocycloalkyl, heterocycloalkenyl optionally substituted with oxo or $R^{D11}$, provided that substitution of the heterocycloalkenyl with $R^{D11}$ can only occur by replacing a hydrogen that is covalently bound to either a carbon or a nitrogen of the heterocycloalkenyl, heteroaryl optionally substituted with $R^{D11}$, provided that substitution of the heteroaryl with $R^{D11}$ can only occur by replacing a hydrogen that is covalently bound to either a carbon or a nitrogen of the heteroaryl, —O—($C_1$-$C_4$)alkyl optionally substituted at the alkyl group with 1 or 2 $R^{D11B}$, —S(O)$_2$-(4-6 membered)heterocycloalkyl optionally substituted with $R^{D11C}$, provided that substitution of the —S(O)$_2$-(4-6 membered)heterocycloalkyl with $R^{D11C}$ can only occur by replacing a hydrogen that is covalently bound to either a carbon or a nitrogen of the —S(O)$_2$-(4-6 membered)heterocycloalkyl, —N(H)—C(O)—($C_1$-$C_4$)alkyl optionally substituted at the alkyl group with 1 or 2 $R^{D11B}$, —N(H)—C(O)—N(H)—($C_1$-$C_3$)alkyl optionally substituted at the alkyl group with $R^{D11B}$, —($C_1$-$C_6$)alkyl optionally substituted with 1 or 2 $R^{D11B}$, —C(=NH)—$NH_2$, and —C≡C—($C_1$-$C_3$)alkyl optionally substituted with $R^{D11B}$;

each $R^{D11}$ is independently selected from H, —($C_3$-$C_6$)cycloalkyl, —($C_1$-$C_4$)haloalkyl; —OH, —S(O)$_2$OH, C(O)OH, —$NH_2$, —N(H)C(=NH)$NH_2$, —($C_1$-$C_4$)alkyl optionally substituted with halo, —OH or —C(O)OH, —($C_1$-$C_3$)alkyl-phenyl optionally substituted at the phenyl group with 1-3 substituents selected from methoxy, hydroxyl and halo;

$R^{D11B}$ is selected from H, —OH, —$CF_3$, —N($R^{D11}$)$_2$, —C(O)OH, —O—($C_1$-$C_4$)alkyl, —S(O)$_2$OH, —C(=NH)—$NH_2$, —N(H)C(=NH)$NH_2$, —C(H)=NN(H)C(=NH)$NH_2$, —O—($C_1$-$C_4$)alkyl-C(O)OH, —N(H)C(=NH)—N(H)C(=NH)$NH_2$, (5-6 membered)heteroaryl, —C(O)—($C_1$-$C_3$)alkyl, —($C_1$-$C_4$)alkyl optionally substituted with 1-3 groups independently selected from halo, —OH, —S(O)$_2$OH, —C(O)OH, —$NH_2$, and —N(H)C(=NH)$NH_2$, —($C_0$-$C_3$)alkyl-(5-8 membered)heterocycloalkyl optionally substituted with 1, 2 or 3 $R^{D11}$, provided that substitution of —($C_0$-$C_3$)alkyl-(5-8 membered)heterocycloalkyl with $R^{D11}$ can only occur by replacing a hydrogen that is covalently bound to either a carbon or a nitrogen of —($C_0$-$C_3$)alkyl-(5-8 membered)heterocycloalkyl, —($C_0$-$C_3$)alkyl-($C_3$-$C_6$)cycloalkyl optionally substituted with $R^{D11}$, and —($C_6$-$C_{10}$)aryl optionally substituted with 1-3 halo;

or $R^{D11}$ and $R^{D11B}$, when they both exist and are each attached to nitrogen, can join together with the nitrogen to which they are attached to form a (5-6 membered) heterocycloalkyl optionally substituted with a group selected from —OH, —($C_1$-$C_4$)haloalkyl, —S(O)$_2$OH, C(O)OH, —$NH_2$, —N(H)C(=NH)$NH_2$, —($C_3$-$C_6$)cycloalkyl, —($C_1$-$C_4$)alkyl optionally substituted with halo, —OH or —C(O)OH, and —($C_1$-$C_3$)alkyl-phenyl optionally substituted at the phenyl group with 1-3 substituents selected from methoxy, hydroxyl and halo, provided that substitution of the (5-6 membered) heterocycloalkyl can only occur by replacing a hydrogen that is covalently bound to either a carbon or a nitrogen of the (5-6 membered) heterocycloalkyl; and $R^{D11C}$ is selected from H, —OH, —$CF_3$, —O—($C_1$-$C_4$)alkyl, —($C_1$-$C_4$)alkyl-N(H)C(=NH)—$NH_2$, —($C_0$-$C_3$)alkyl-(5-6 membered)heteroaryl, —($C_1$-$C_4$)alkyl optionally substituted with 1-3 groups independently selected from halo, —OH, —S(O)$_2$OH, C(O)OH, —$NH_2$, and —N(H)C(=NH)$NH_2$, —($C_0$-$C_3$)alkyl-(5-6 membered)heterocycloalkyl optionally substituted with a -(5-6 membered)heteroaryl, provided that substitution of the —($C_0$-$C_3$)alkyl-(5-6 membered)heterocycloalkyl can only occur by replacing a hydrogen that is covalently bound to either a carbon or a nitrogen of the —($C_0$-$C_3$)alkyl-(5-6 membered)heterocycloalkyl, —($C_0$-$C_3$)alkyl-(5-6 membered)heterocycloalkyl substituted 1, 2 or 3 groups selected from selected from —OH and —($C_1$-$C_3$)alkyl, provided that substitution of the —($C_0$-$C_3$)alkyl-(5-6 membered)heterocycloalkyl can only occur by replacing a hydrogen that is covalently bound to either a carbon or a nitrogen of the —($C_0$-$C_3$)alkyl-(5-6 membered) heterocycloalkyl, and —($C_0$-$C_3$)alkyl-aryl optionally substituted at the aryl group with 1-3 halo.

In another embodiment of the compound of formulae VI, VII or VIII, or a pharmaceutically acceptable salt thereof, wherein:

X is =C($R^4$)—;

Y is a bond, —S—, —S(O)$_2$—, —CH($CH_3$)—S(O)$_2$—, —CH($CH_3$)—S—, —CH(OH)—, —CH($CH_3$)—O—, —C(O)—, —($CH_2$)—S—, —$CH_2$—N($R^Y$)—, —CH(halo)-, —CH$_2$—S(O)$_2$—, —S(O)$_2$—N(R$^Y$)—, —(CH$_2$)—O—, or —C(O)—N(R$^Y$)—, wherein R$^Y$ is H, —(C$_1$-C$_3$)alkyl or hydroxyl(C$_1$-C$_3$)alkyl, each R is independently selected from H, —CH$_3$, —OH, F and —CH$_2$OH;

R$^{D1}$ is selected from phenyl, —N(H)-phenyl, —(C$_3$-C$_6$)cycloalkyl, -(5-6 membered)heterocycloalkyl, -(5-6 membered)heteroaryl-(5-6 membered)heterocycloalkyl, and -(5-6 membered)heteroaryl, wherein R$^{D1}$ is optionally substituted with 1, 2, or 3 R$^{D10}$, provided that substitution of R$^{D1}$ with R$^{D10}$ can only occur by replacing a hydrogen that is covalently bound to either a carbon or a nitrogen of R$^{D1}$, wherein the 1-3 R$^{D10}$ groups are independently selected from A groups and B groups, provided that R$^{D1}$ cannot be substituted with more than 1 B groups;

each A group, when they occur, is independently selected from halo, —CF$_3$, —CN, —NO$_2$, —OH, —O—(C$_1$-C$_4$)alkyl optionally substituted with 1-3 substituents independently selected from —OH and halo, and —(C$_1$-C$_4$)alkyl optionally substituted with 1-3 substituents independently selected from —OH and halo;

the B group is selected from —O—(C$_1$-C$_4$)alkyl-C(O)OH, —O—(C$_1$-C$_4$)alkyl, —O—(C$_1$-C$_4$)alkyl-C(O)—(C$_1$-C$_3$)alkyl, —O—(C$_1$-C$_4$)alkylN(R$^{D11}$)$_2$, —(C$_1$-C$_4$)alkyl-C(O)OH, -(5-6 membered)heteroaryl, —C(=NH)—NH$_2$, —S(O)$_2$—N(H)C(O)—(C$_1$-C$_4$)alkyl, —S(O)$_2$—N(H)C(O)—(C$_1$-C$_4$)alkyl, —S(O)$_2$—N(H)C(O)—N(H)—(C$_1$-C$_4$)alkyl, —S(O)$_2$—N(H)C(O)—N(H)-(5-6 membered)heterocycloalkyl, —S(O)$_2$—(C$_1$-C$_3$)alkyl, —O—(C$_1$-C$_4$)alkyl-N(H)—C(=NH)—NH$_2$, —O—(C$_1$-C$_4$)alkyl-(5-6 membered)heteroaryl, —(C$_1$-C$_4$)alkylN(R$^{D11}$)$_2$, —C(O)—NH$_2$, —C(O)—N(H)—OH, —C(O)—N(H)—R$^{D11C}$, —C(O)—(C$_1$-C$_3$)alkyl, —C(O)OH, —C(O)O—(C$_1$-C$_4$)alkyl, —S(O)$_2$—NH$_2$, —O—(C$_1$-C$_4$)alkyl-(5-6 membered)heterocycloalkyl optionally substituted with oxo or methyl, provided that substitution of the —O—(C$_1$-C$_4$)alkyl-(5-6 membered)heterocycloalkyl can only occur by replacing a hydrogen that is covalently bound to either a carbon or a nitrogen of the —O—(C$_1$-C$_4$)alkyl-(5-6 membered)heterocycloalkyl, —C(O)-(5-6 membered)heterocycloalkyl optionally substituted with —S(O)$_2$OH, —C(O)OH, —NH$_2$, or —C(O)—N(H)—(C$_1$-C$_4$)alkyl optionally substituted at the alkyl group with 1 or 2 groups selected from —S(O)$_2$OH, —C(O)OH, —NH$_2$, and —N(H)C(=NH)NH$_2$, provided that substitution of the —C(O)-(5-6 membered)heterocycloalkyl can only occur by replacing a hydrogen that is covalently bound to either a carbon or a nitrogen of the —C(O)-(5-6 membered)heterocycloalkyl, -(5-6 membered)heterocycloalkyl optionally substituted with oxo or R$^{D11}$, provided that substitution of the -(5-6 membered)heterocycloalkyl can only occur by replacing a hydrogen that is covalently bound to either a carbon or a nitrogen of the -(5-6 membered)heterocycloalkyl, —S(O)$_2$—N(H)—(C$_1$-C$_4$)alkyl optionally substituted at the alkyl group with 1 or 2 groups selected from —S(O)$_2$OH, C(O)OH, —NH$_2$, and —N(H)C(=NH)NH$_2$, —S(O)$_2$—N(C$_1$-C$_3$)alkyl-(C$_1$-C$_4$)alkyl optionally substituted at the (C$_1$-C$_4$)alkyl group with 1 or 2 groups selected from —S(O)$_2$OH, C(O)OH, —NH$_2$, and —N(H)C(=NH)NH$_2$, —S(O)$_2$-(4-6 membered)heterocycloalkyl optionally substituted with —S(O)$_2$OH, C(O)OH, —NH$_2$, or —N(H)C(=NH)NH$_2$, provided that substitution of the —S(O)$_2$-(4-6 membered)heterocycloalkyl can only occur by replacing a hydrogen that is covalently bound to either a carbon or a nitrogen of the —S(O)$_2$-(4-6 membered)heterocycloalkyl, —N(H)—C(O)(C$_1$-C$_4$)alkyl optionally substituted at the alkyl group with 1 or 2 groups selected from —S(O)$_2$OH, C(O)OH, —NH$_2$ and —N(H)C(=NH)NH$_2$, —N(H)—C(O)—N(H)—(C$_1$-C$_3$)alkyl optionally substituted at the alkyl group with —S(O)$_2$OH, C(O)OH, —NH$_2$, or —N(H)C(=NH)NH$_2$, —(C$_1$-C$_6$)alkyl optionally substituted with 1 or 2 groups selected from —S(O)$_2$OH, C(O)OH, —NH$_2$, and —N(H)C(=NH)NH$_2$, and —C≡C—(C$_1$-C$_3$)alkyl optionally substituted with 1 or 2 groups selected from —S(O)$_2$OH, C(O)OH, —NH$_2$, and —N(H)C(=NH)NH$_2$;

each R$^{D11}$ is independently selected from H, —(C$_3$-C$_6$)cycloalkyl, —OH, —S(O)$_2$OH, C(O)OH, —NH$_2$, —N(H)C(=NH)NH$_2$, —(C$_1$-C$_4$)haloalkyl, —(C$_1$-C$_3$)alkyl-phenyl optionally substituted at the phenyl group with 1-3 substituents selected from methoxy, hydroxyl and halo, and —(C$_1$-C$_4$)alkyl optionally substituted with halo, —OH or —C(O)OH;

R$^{D11B}$ is selected from H, —OH, —CF$_3$, —N(R$^{D11}$)$_2$, —C(O)OH, —O—(C$_1$-C$_4$)alkyl, —S(O)$_2$OH, —C(=NH)—NH$_2$, —N(H)C(=NH)NH$_2$, —C(H)=NN(H)C(=NH)NH$_2$, (5-6 membered)heteroaryl, —N(H)C(=NH)—N(H)C(=NH)NH$_2$, —O—(C$_1$-C$_4$)alkyl-C(O)OH, —(C$_0$-C$_3$)alkyl-(5-8 membered)heterocycloalkyl, —C(O)—(C$_1$-C$_3$)alkyl, —(C$_1$-C$_4$)alkyl optionally substituted with 1 or 2 groups independently selected from halo, —OH, —S(O)$_2$OH, C(O)OH, —NH$_2$, and —N(H)C(=NH)NH$_2$, —(C$_0$-C$_3$)alkyl-(C$_3$-C$_6$)cycloalkyl optionally substituted with R$^{D11}$, and phenyl optionally substituted with 1-3 halo; and R$^{D11C}$ is selected from H, —OH, —CF$_3$, —O—(C$_1$-C$_4$)alkyl, —(C$_1$-C$_4$)alkyl optionally substituted with 1-2 groups independently selected from halo, —OH, —S(O)$_2$OH, C(O)OH, —NH$_2$, and —N(H)C(=NH)NH$_2$, —(C$_0$-C$_3$)alkyl-(5-6 membered)heterocycloalkyl, —C(O)-(5-6 membered)heterocycloalkyl optionally substituted with a (5-6 membered)heteroaryl, provided that substitution of the —C(O)-(5-6 membered)heterocycloalkyl can only occur by replacing a hydrogen that is covalently bound to either a carbon or a nitrogen of the —C(O)-(5-6 membered)heterocycloalkyl, —(C$_0$-C$_3$)alkyl-(5-6 membered)heterocycloalkyl substituted with 1-3 groups selected from —OH and —(C$_1$-C$_3$)alkyl, —(C$_1$-C$_4$)alkyl-N(H)C(=NH)—NH$_2$, —(C$_0$-C$_3$)alkyl-(5-6 membered)heteroaryl, and —(C$_0$-C$_3$)alkyl-phenyl optionally substituted at the phenyl group with 1-3 halo.

In other embodiments of the compounds of formulae VI, VII and VIII, or any embodiments of the compounds of formulae VI, VII and VIII described herein as it may apply, or a pharmaceutically acceptable salt of any of these compounds, p is 0;

Y is a bond, —S—, —S(O)$_2$—, —CH(CH$_3$)—S(O)$_2$—, —CH(CH$_3$)—S—, —CH(OH)—, —CH(CH$_3$)—O—, —C(H)=C(H)—, —C(O)—, —(CH$_2$)—S—, —CH$_2$—N(R$^Y$)—, —CH(halo)-, —CH$_2$—S(O)$_2$—, —S(O)$_2$—N(H)—, —S(O)$_2$—N(R$^Y$)—, —(CH$_2$)—O—, or —C(O)—N(R$^Y$)—, wherein R$^Y$ is H, —(C$_1$-C$_4$)alkyl or hydroxyl(C$_1$-C$_4$)alkyl;

each R is independently selected from H, —(C$_1$-C$_2$)alkyl, fluoro, —OH and —CH$_2$OH;

R$^{D1}$ is selected from phenyl, —N(H)-phenyl, cyclohexyl, cyclopentyl, piperidinyl, piperazinyl, pyrrolidinyl, morpholinyl, 1,2,3,6-tetrahydropyridine, heteroarylheterocycloalkyl, pyridinyl, oxazolyl, pyrazinyl, quinolinyl, 1,2,4-oxadiazolyl, 1,2,3,4-tetrahydroquinolinyl, and pyrazolyl, wherein R$^{D1}$ can be optionally substituted 1, 2 or 3 R$^{D10}$, provided that substitution of R$^{D1}$ with R$^{D10}$ can only occur by replacing a hydrogen that is covalently bound to either a carbon or a nitrogen of R$^{D1}$, wherein the 1-3 R$^{D10}$ groups are independently selected from A groups and B groups, provided that R$^{D1}$ cannot be substituted with more than 1 B group;

each A group, when they occur, is independently selected from halo, —$CF_3$, —CN, —$NO_2$, —OH, —O—($C_1$-$C_4$)alkyl optionally substituted with 1-3 substituents independently selected from —OH and halo, and —($C_1$-$C_4$)alkyl optionally substituted with 1-3 substituents independently selected from —OH and halo;

the B group is selected from —O—($C_1$-$C_4$)alkyl-C(O)OH, —O—($C_1$-$C_4$)alkyl, —O—($C_1$-$C_4$)alkyl-C(O)—($C_1$-$C_3$) alkyl, —O—($C_1$-$C_4$)alkylN($R^{D11}$)$_2$, —O—($C_1$-$C_4$)alkyl-N (H)—C(=NH)—$NH_2$, —O—($C_1$-$C_4$)alkyl-(5-6 membered) heteroaryl, —($C_1$-$C_4$)alkylN($R^{D11}$)$_2$, —C(O)—$NH_2$, —C(O)—N(H)—OH, —C(O)—N(H)—$R^{D11C}$, —C(O)—($C_1$-$C_4$)alkyl, —($C_1$-$C_4$)alkyl-C(O)OH, —C(O)OH, —C(O)O—($C_1$-$C_4$)alkyl, —S(O)$_2$—($C_1$-$C_4$)alkyl-N($R^{D11}$)$_2$, —S(O)$_2$—$NH_2$, —S(O)$_2$—N(H)C(O)—($C_1$-$C_4$)alkyl, —S(O)$_2$—N(H)C(O)O—($C_1$-$C_4$)alkyl, —S(O)$_2$—N(H)C(O)—N(H)—($C_1$-$C_4$)alkyl, —S(O)$_2$—N(H)C(O)—N(H)-morpholinyl, —S(O)$_2$—N(H)C(O)—N(H)-pyrrolidinyl, —S(O)$_2$—N(H)C(O)—N(H)-piperidinyl, —S(O)$_2$—$CH_3$, —C(=NH)—$NH_2$, 2,3-dihydro-1H-tetrazolyl, —O—($C_1$-$C_4$)alkyl optionally substituted at the alkyl group with 1 or 2 $R^{D11B}$, —O—($C_1$-$C_4$)alkyl-(5-6 membered)heterocycloalkyl optionally substituted with oxo or methyl, provided that substitution of the —O—($C_1$-$C_4$)alkyl-(5-6 membered) heterocycloalkyl can only occur by replacing a hydrogen that is covalently bound to either a carbon or a nitrogen of the —O—($C_1$-$C_4$)alkyl-(5-6 membered)heterocycloalkyl, —C(O)-heterocycloalkyl optionally substituted with —S(O)$_2$OH, C(O)OH or —$NH_2$, provided that substitution of the —C(O)-heterocycloalkyl can only occur by replacing a hydrogen that is covalently bound to either a carbon or a nitrogen of the —C(O)-heterocycloalkyl, —C(O)—N(H)—($C_1$-$C_4$)alkyl optionally substituted at the alkyl group with 1 or 2 groups selected from —S(O)$_2$OH, C(O)OH, —$NH_2$ and —N(H)C(=NH)$NH_2$, heterocycloalkyl selected from 1H-tetrazolyl, piperizinyl, 2,3-dihydro-1,3,4-oxadiazole and 4,5-dihydro-1,2,4-oxadiazole optionally substituted with oxo or —($C_1$-$C_4$)alkyl, provided that substitution of the heterocycloalkyl can only occur by replacing a hydrogen that is covalently bound to either a carbon or a nitrogen of the heterocycloalkyl, —S(O)$_2$—N(H)—($C_1$-$C_4$)alkyl optionally substituted at the alkyl group with 1 or 2 groups selected from —S(O)$_2$OH, C(O)OH, —$NH_2$, and —N(H)C(=NH)$NH_2$, —S(O)$_2$—N($C_1$-$C_3$)alkyl-($C_1$-$C_4$)alkyl optionally substituted at the ($C_1$-$C_4$)alkyl group with 1 or 2 groups selected from —S(O)$_2$OH, C(O)OH, —$NH_2$, and —N(H)C(=NH) $NH_2$, —S(O)$_2$-(4-6 membered)heterocycloalkyl optionally substituted with —S(O)$_2$OH, C(O)OH, provided that substitution of the —S(O)$_2$-(4-6 membered)heterocycloalkyl can only occur by replacing a hydrogen that is covalently bound to either a carbon or a nitrogen of the —S(O)$_2$-(4-6 membered)heterocycloalkyl, —$NH_2$, or —N(H)C(=NH)$NH_2$, —N(H)—C(O)—($C_1$-$C_4$)alkyl optionally substituted at the alkyl group with 1 or 2 groups selected from —S(O)$_2$OH, C(O)OH, —$NH_2$, and —N(H)C(=NH)$NH_2$, —N(H)—C(O)—N(H)—($C_1$-$C_3$)alkyl optionally substituted at the alkyl group with a group selected from —S(O)$_2$OH, C(O)OH, —$NH_2$ and —N(H)C(=NH)$NH_2$, ($C_1$-$C_6$)alkyl optionally substituted with 1 group selected from —S(O)$_2$OH, C(O)OH, —$NH_2$ and —N(H)C(=NH)$NH_2$, and —C≡C—($C_1$-$C_3$) alkyl optionally substituted at the alkyl group with 1 group selected from —S(O)$_2$OH, C(O)OH, —$NH_2$, and —N(H)C(=NH)$NH_2$;

each $R^{D11}$ is independently selected from H, —($C_3$-$C_6$) cycloalkyl, —($C_1$-$C_4$)alkyl optionally substituted with halo, —OH or —C(O)OH, —OH, —S(O)$_2$OH, C(O)OH, —$NH_2$ or —N(H)C(=NH)$NH_2$, —($C_1$-$C_3$)alkyl-phenyl optionally substituted at the phenyl group with 1-3 substituents selected from methoxy, hydroxyl and halo, and —($C_1$-$C_4$)haloalkyl;

$R^{D11B}$ is selected from H, —OH, —$CF_3$, —$NH_2$, —C(O)OH, —O—($C_1$-$C_4$)alkyl, —S(O)$_2$OH, —C(=NH)—$NH_2$, —N(H)C(=NH)$NH_2$, —C(H)=NN(H)C(=NH)$NH_2$, —N(H)C(=NH)—N(H)C(=NH)$NH_2$, —C(O)—($C_1$-$C_3$) alkyl, —($C_1$-$C_4$)alkyl optionally substituted with 1-3 groups independently selected from halo and —OH, —($CH_2$)$_{1-4}$—C(O)OH, —($C_1$-$C_4$)alkyl optionally substituted with 1-2 groups independently selected from halo, —OH, —S(O)$_2$OH, C(O)OH, —$NH_2$, and —N(H)C(=NH)$NH_2$, —O—($C_1$-$C_4$)alkyl-C(O)OH, a heterocycloalkyl selected from morpholinyl, pyrrolidinyl, piperazinyl, and piperidinyl, wherein the heterocycloalkyl can be optionally substituted with 1, 2 or 3 $R^{D11}$, provided that substitution of the heterocycloalkyl can only occur by replacing a hydrogen that is covalently bound to either a carbon or a nitrogen of the heterocycloalkyl, cyclopropane, cyclopentyl, imidazole, pyridinyl, thiazolyl, 1(H)-tetrazolyl, and phenyl optionally substituted with 1-3 halo, or $R^{D11}$ and $R^{D11B}$, when they both exist and are each attached to nitrogen, can join to form a (5-6 membered) heterocycloalkyl optionally substituted with $R^{11}$; and $R^{D11C}$ is selected from H, —OH, —$CF_3$, —O—($C_1$-$C_4$)alkyl, —($C_1$-$C_4$)alkyl optionally substituted with 1-2 groups independently selected from halo, —OH, —S(O)$_2$OH, C(O)OH, —$NH_2$ and —N(H)C(=NH)$NH_2$, a heterocycloalkyl selected from morpholinyl, pyrrolidinyl, piperidinyl and piperazinyl, wherein the heterocycloalkyl is optionally substituted with a (5-6 membered)heteroaryl, —$C_0$-$C_3$alkyl-(5-6 membered)heterocycloalkyl, wherein the (5-6 membered) heterocycloalkyl group of —$C_0$-$C_3$alkyl-(5-6 membered)heterocycloalkyl is selected from morpholinyl, pyrrolidinyl, piperidinyl and piperazinyl and wherein the —$C_0$-$C_3$alkyl-(5-6 membered)heterocycloalkyl group is substituted with 1, 2 or 3 substituents selected from —OH and —($C_1$-$C_3$)alkyl, provided that substitution of the —$C_0$-$C_3$alkyl-(5-6 membered) heterocycloalkyl can only occur by replacing a hydrogen that is covalently bound to either a carbon or a nitrogen of the —$C_0$-$C_3$alkyl-(5-6 membered)heterocycloalkyl, —($C_1$-$C_4$) alkyl-N(H)C(=NH)—$NH_2$, —$C_0$-$C_3$alkyl-imidazole, —$C_0$-$C_3$alkyl-pyridinyl, and —$C_0$-$C_3$alkyl-phenyl optionally substituted at the phenyl group with 1-3 halo.

In other embodiments of the compounds of formulae VI, VII and VIII, or any embodiments of the compounds of formulae VI, VII and VIII described herein as it may apply, or a pharmaceutically acceptable salt of any of these compounds, X is =C(H)—;

p is 0;

Y is a bond, —S—, —S(O)$_2$—, —CH($CH_3$)—S(O)$_2$—, —CH($CH_3$)—S—, —CH(OH)—, —CH($CH_3$)—O—, —C(H)=C(H)—, —C(O)—, —($CH_2$)—S—, —$CH_2$—N ($R^Y$)—, —CH(halo)-, —$CH_2$—S(O)$_2$—, —S(O)$_2$—N(H)—, —S(O)$_2$—N($R^Y$)—, —($CH_2$)—O—, or —C(O)—N($R^Y$)—, wherein $R^Y$ is H, —($C_1$-$C_4$)alkyl or hydroxyl($C_1$-$C_4$)alkyl;

each R is independently selected from H, —($C_1$-$C_2$)alkyl, fluoro, —OH and —$CH_2$OH;

$R^{D1}$ is selected from phenyl, —N(H)-phenyl, cyclohexyl, cyclopentyl, piperidinyl, piperazinyl, pyrrolidinyl, morpholinyl, 1,2,3,6-tetrahydropyridine, heteroarylheterocycloalkyl, pyridinyl, oxazolyl, pyrazinyl, quinolinyl, 1,2,4-oxadiazolyl, 1,2,3,4-tetrahydroquinolinyl, and pyrazolyl, wherein $R^{D1}$ is substituted with 1, 2 or 3 $R^{D10}$, provided that substitution of the $R^{D1}$ can only occur by replacing a hydrogen that is covalently bound to either a carbon or a nitrogen of $R^{D1}$, wherein the 1-3 $R^{D10}$ groups are 0-2 A groups and 0-1 B group;

each A group, when they occur, is independently selected from halo, —CF$_3$, —CN, —NO$_2$, —OH, —O—(C$_1$-C$_4$)alkyl optionally substituted with 1-3 substituents independently selected from —OH and halo, and —(C$_1$-C$_4$)alkyl optionally substituted with 1-3 substituents independently selected from —OH and halo;

the B group, when it occurs, is selected from —O—(C$_1$-C$_4$)alkyl optionally substituted at the alkyl group with 1 or 2 R$^{D11B}$, —O—(C$_1$-C$_4$)alkyl-C(O)OH, —O—(C$_1$-C$_4$)alkyl, —O—(C$_1$-C$_4$)alkyl-C(O)—(C$_1$-C$_3$)alkyl, —O—(C$_1$-C$_4$)alkylN(R$^{D11}$)$_2$, —O—(C$_1$-C$_4$)alkyl-N(H)—C(=NH)—NH$_2$, —O—(C$_1$-C$_4$)alkyl-(5-6 membered)heteroaryl, —O—(C$_1$-C$_4$)alkyl-(5-6 membered)heterocycloalkyl optionally substituted with oxo or methyl, provided that substitution of the —O—(C$_1$-C$_4$)alkyl-(5-6 membered)heterocycloalkyl can only occur by replacing a hydrogen that is covalently bound to either a carbon or a nitrogen of the —O—(C$_1$-C$_4$)alkyl-(5-6 membered)heterocycloalkyl, —(C$_1$-C$_4$)alkylN(R$^{D11}$)$_2$, —C(O)—NH$_2$, —C(O)—N(H)—OH, —C(O)—N(H)—R$^{D11C}$, —C(O)—(C$_1$-C$_4$)alkyl, —C(O)OH, —C(O)O—(C$_1$-C$_4$)alkyl, —C(O)-heterocycloalkyl optionally substituted with —S(O)$_2$OH, provided that substitution of the —C(O)-heterocycloalkyl can only occur by replacing a hydrogen that is covalently bound to either a carbon or a nitrogen of the —C(O)-heterocycloalkyl, C(O)OH, —NH$_2$, —C(O)—N(H)—(C$_1$-C$_4$)alkyl optionally substituted at the alkyl group with 1 or 2 groups selected from —S(O)$_2$OH, C(O)OH, —NH$_2$, and —N(H)C(=NH)NH$_2$, —(C$_1$-C$_4$)alkyl-C(O)OH, 2,3-dihydro-1H-tetrazolyl, heterocycloalkyl selected from 1H-tetrazolyl, piperizinyl, 2,3-dihydro-1,3,4-oxadiazole and 4,5-dihydro-1,2,4-oxadiazole wherein the heterocycloalkyl is optionally substituted with oxo or —(C$_1$-C$_4$)alkyl, provided that substitution of the heterocycloalkyl can only occur by replacing a hydrogen that is covalently bound to either a carbon or a nitrogen of the heterocycloalkyl, —S(O)$_2$—(C$_1$-C$_4$)alkyl-N(R$^{D11}$)$_2$, —S(O)$_2$—NH$_2$, —S(O)$_2$—N(H)—(C$_1$-C$_4$)alkyl optionally substituted at the alkyl group with 1 or 2 groups selected from —S(O)$_2$OH, C(O)OH, —NH$_2$ and —N(H)C(=NH)NH$_2$), —S(O)$_2$—N(C$_1$-C$_3$)alkyl-(C$_1$-C$_4$)alkyl optionally substituted at the (C$_1$-C$_4$)alkyl group with 1 or 2 groups selected from —S(O)$_2$OH, C(O)OH, —NH$_2$, and —N(H)C(=NH)NH$_2$, —S(O)$_2$-(4-6 membered)heterocycloalkyl optionally substituted with —S(O)$_2$OH, C(O)OH, —NH$_2$ or —N(H)C(=NH)NH$_2$, provided that substitution of the —S(O)$_2$-(4-6 membered)heterocycloalkyl can only occur by replacing a hydrogen that is covalently bound to either a carbon or a nitrogen of the —S(O)$_2$-(4-6 membered)heterocycloalkyl, —S(O)$_2$—N(H)C(O)—(C$_1$-C$_4$)alkyl, —S(O)$_2$—N(H)C(O)O—(C$_1$-C$_4$)alkyl, —S(O)$_2$—N(H)C(O)—N(H)—(C$_1$-C$_4$)alkyl, —S(O)$_2$—N(H)C(O)—N(H)-morpholinyl, —S(O)$_2$—N(H)C(O)—N(H)-pyrrolidinyl, —S(O)$_2$—N(H)C(O)—N(H)-piperidinyl, —S(O)$_2$—CH$_3$, —N(H)—C(O)—(C$_1$-C$_4$)alkyl optionally substituted at the alkyl group with 1 or 2 groups selected from —S(O)$_2$OH, C(O)OH, —NH$_2$, and —N(H)C(=NH)NH$_2$, —N(H)—C(O)—N(H)—(C$_1$-C$_3$)alkyl optionally substituted at the alkyl group with a group selected from —S(O)$_2$OH, C(O)OH, —NH$_2$, and —N(H)C(=NH)NH$_2$, —(C$_1$-C$_6$)alkyl optionally substituted with 1 group selected from —S(O)$_2$OH, C(O)OH, —NH$_2$ and —N(H)C(=NH)NH$_2$, —C(=NH)—NH$_2$, and —C≡C—(C$_1$-C$_3$)alkyl optionally substituted at the alkyl group with 1 group selected from —S(O)$_2$OH, C(O)OH, —NH$_2$, and —N(H)C(=NH)NH$_2$;

each R$^{D11}$ is independently selected from H, —(C$_3$-C$_6$)cycloalkyl, —OH, —S(O)$_2$OH, C(O)OH, —NH$_2$, —N(H)C(=NH)NH$_2$, —(C$_1$-C$_4$)alkyl optionally substituted with halo, —OH or —C(O)OH, —(C$_1$-C$_3$)alkyl-phenyl optionally substituted at the phenyl group with 1-3 substituents selected from methoxy, hydroxyl and halo, and —(C$_1$-C$_4$)haloalkyl;

R$^{D11B}$ is selected from H, —OH, —CF$_3$, —NH$_2$, —C(O)OH, —O—(C$_1$-C$_4$)alkyl, —S(O)$_2$OH, —C(=NH)—NH$_2$, —N(H)C(=NH)NH$_2$, —C(H)=NN(H)C(=NH)NH$_2$, —O—(C$_1$-C$_4$)alkyl-C(O)OH, —N(H)C(=NH)—N(H)C(=NH)NH$_2$, —C(O)—(C$_1$-C$_3$)alkyl, —(CH$_2$)$_{1-4}$—C(O)OH, cyclopropane, cyclopentyl, imidazole, pyridinyl, thiazolyl, 1(H)-tetrazolyl, —(C$_1$-C$_4$)alkyl optionally substituted with 1-2 groups independently selected from halo, —OH, —S(O)$_2$OH, C(O)OH, —NH$_2$, and —N(H)C(=NH)NH$_2$, a heterocycloalkyl selected from morpholinyl, pyrrolidinyl, piperazinyl, and piperidinyl, wherein the heterocycloalkyl is optionally substituted with 1, 2 or 3 R$^{D11}$, provided that substitution of the heterocycloalkyl can only occur by replacing a hydrogen that is covalently bound to either a carbon or a nitrogen of the heterocycloalkyl, and phenyl optionally substituted with 1-3 halo, or R$^{D11}$ and R$^{D11B}$, when they both exist and are each attached to nitrogen, can join to form a (5-6 membered)heterocycloalkyl optionally substituted with R$^{11}$; and R$^{D11C}$ is selected from H, —OH, —CF$_3$, —O—(C$_1$-C$_4$)alkyl, —(C$_1$-C$_4$)alkyl optionally substituted with 1-2 groups independently selected from halo, —OH, —S(O)$_2$OH, C(O)OH, —NH$_2$, and —N(H)C(=NH)NH$_2$, —(C$_1$-C$_4$)alkyl-N(H)C(=NH)—NH$_2$, —C$_0$-C$_3$alkyl-imidazole, —C$_0$-C$_3$alkyl-pyridinyl, a heterocycloalkyl selected from morpholinyl, pyrrolidinyl, piperidinyl and piperazinyl, wherein the heterocycloalkyl is optionally substituted with a (5-6 membered)heteroaryl, provided that substitution of the heterocycloalkyl can only occur by replacing a hydrogen that is covalently bound to either a carbon or a nitrogen of the heterocycloalkyl, —C$_0$-C$_3$alkyl-(5-6 membered)heterocycloalkyl, wherein the (5-6 membered)heterocycloalkyl group of —C$_0$-C$_3$alkyl-(5-6 membered)heterocycloalkyl is selected from morpholinyl, pyrrolidinyl, piperidinyl and piperazinyl, and wherein the -(5-6 membered)heterocycloalkyl group is substituted with a 1, 2 or 3 groups selected from —OH and —(C$_1$-C$_3$)alkyl, provided that substitution of the -(5-6 membered)heterocycloalkyl can only occur by replacing a hydrogen that is covalently bound to either a carbon or a nitrogen of the -(5-6 membered)heterocycloalkyl, and —C$_0$-C$_3$alkyl-phenyl optionally substituted at the phenyl group with 1-3 halo.

In other embodiments of the compounds of formulae VI, VII and VIII, or any embodiments of the compounds of formulae VI, VII and VIII described herein as it may apply, or a pharmaceutically acceptable salt of any of these compounds, X is =C(R$^4$)—;

p is 0;

Y is a bond, —S—, —S(O)$_2$—, —CH(CH$_3$)—S(O)$_2$—, —CH(CH$_3$)—S—, —CH(OH)—, —CH(CH$_3$)—O—, —C(H)=C(H)—, —C(O)—, —(CH$_2$)—S—, —CH$_2$—N(R$^Y$)—, —CH(halo)-, —CH$_2$—S(O)$_2$—, —S(O)$_2$—N(R$^Y$)—, —(CH$_2$)—O—, or —C(O)—N(R$^Y$)—, wherein R$^Y$ is H, —(C$_1$-C$_4$)alkyl or hydroxyl(C$_1$-C$_4$)alkyl;

each R is independently selected from H, —(C$_1$-C$_2$)alkyl, fluoro, —OH and —CH$_2$OH;

R$^{D1}$ is selected from phenyl, —N(H)-phenyl, cyclohexyl, cyclopentyl, piperidinyl, piperazinyl, pyrrolidinyl, morpholinyl, 1,2,3,6-tetrahydropyridine, heteroarylheterocycloalkyl, pyridinyl, oxazolyl, pyrazinyl, quinolinyl, 1,2,4-oxadiazolyl, 1,2,3,4-tetrahydroquinolinyl, and pyrazolyl, wherein R$^{D1}$ is substituted with 1, 2 or 3 R$^{D10}$, provided that substitution of the R$^{D10}$ can only occur by replacing a hydrogen that is covalently bound to either a carbon or a nitrogen of the R$^{D10}$, wherein the 1-3 R$^{D10}$ groups are 0-2 A groups and 1 B group;

each A group, when they occur, is independently selected from halo, —CF$_3$, —CN, —NO$_2$, —OH, —O—(C$_1$-C$_4$)alkyl optionally substituted with 1-3 substituents independently selected from —OH and halo, and —(C$_1$-C$_4$)alkyl optionally substituted with 1-3 substituents independently selected from —OH and halo;

the B group is selected from —O—(C$_1$-C$_4$)alkyl-C(O)OH, —O—(C$_1$-C$_4$)alkyl, —O—(C$_1$-C$_4$)alkyl-C(O)—(C$_1$-C$_3$)alkyl, —C(O)OH, —NH$_2$, —(C$_1$-C$_4$)alkyl-C(O)OH, 2,3-dihydro-1H-tetrazolyl, —O—(C$_1$-C$_4$)alkylN(R$^{D11}$)$_2$, —O—(C$_1$-C$_4$)alkyl-N(H)—C(=NH)—NH$_2$, —O—(C$_1$-C$_4$)alkyl-(5-6 membered)heteroaryl, —(C$_1$-C$_4$)alkylN(R$^{D11}$)$_2$, —C(O)—NH$_2$, —C(O)—N(H)—OH, —C(O)—N(H)—R$^{D11C}$, —C(O)—(C$_1$-C$_4$)alkyl, —C(O)OH, —C(O)O—(C$_1$-C$_4$)alkyl, —S(O)$_2$—(C$_1$-C$_4$)alkyl-N(R$^{D11}$)$_2$—S(O)$_2$—NH$_2$, —S(O)$_2$—N(H)C(O)—(C$_1$-C$_4$)alkyl, —S(O)$_2$—N(H)C(O)O—(C$_1$-C$_4$)alkyl, —S(O)$_2$—N(H)C(O)—N(H)—(C$_1$-C$_4$)alkyl, —S(O)$_2$—N(H)C(O)—N(H)-morpholinyl, —S(O)$_2$—N(H)C(O)—N(H)-pyrrolidinyl, —S(O)$_2$—N(H)C(O)—N(H)-piperidinyl, —S(O)$_2$—CH$_3$, —C(=NH)—NH$_2$, —O—(C$_1$-C$_4$)alkyl optionally substituted at the alkyl group with 1 or 2 R$^{D11B}$, —O—(C$_1$-C$_4$)alkyl-(5-6 membered)heterocycloalkyl optionally substituted with oxo or methyl, provided that substitution of the —O—(C$_1$-C$_4$)alkyl-(5-6 membered) heterocycloalkyl can only occur by replacing a hydrogen that is covalently bound to either a carbon or a nitrogen of the —O—(C$_1$-C$_4$)alkyl-(5-6 membered)heterocycloalkyl, —C(O)-heterocycloalkyl optionally substituted with —S(O)$_2$OH, —C(O)—N(H)—(C$_1$-C$_4$)alkyl optionally substituted at the alkyl group with 1 or 2 groups selected from —S(O)$_2$OH, C(O)OH, —NH$_2$ and —N(H)C(=NH)NH$_2$, heterocycloalkyl selected from 1H-tetrazolyl, piperizinyl, 2,3-dihydro-1,3,4-oxadiazole and 4,5-dihydro-1,2,4-oxadiazole, wherein the heterocycloalkyl can be optionally substituted with oxo or —(C$_1$-C$_4$)alkyl, provided that substitution of the heterocycloalkyl can only occur by replacing a hydrogen that is covalently bound to either a carbon or a nitrogen of the heterocycloalkyl, —S(O)$_2$—N(H)—(C$_1$-C$_4$)alkyl optionally substituted at the alkyl group with 1 or 2 groups selected from —S(O)$_2$OH, C(O)OH, —NH$_2$, and —N(H)C(=NH)NH$_2$, —S(O)$_2$—N(C$_1$-C$_3$)alkyl-(C$_1$-C$_4$)alkyl optionally substituted at the (C$_1$-C$_4$)alkyl group with 1 or 2 groups selected from —S(O)$_2$OH, —C(O)OH, —NH$_2$, and —N(H)C(=NH)NH$_2$, —S(O)$_2$-(4-6 membered)heterocycloalkyl optionally substituted with —S(O)$_2$OH, C(O)OH, —NH$_2$, or —N(H)C(=NH)NH$_2$, provided that substitution of the —S(O)$_2$-(4-6 membered)heterocycloalkyl can only occur by replacing a hydrogen that is covalently bound to either a carbon or a nitrogen of the —S(O)$_2$-(4-6 membered)heterocycloalkyl, —N(H)—C(O)—(C$_1$-C$_4$)alkyl optionally substituted at the alkyl group with 1 or 2 groups selected from —S(O)$_2$OH, C(O)OH, —NH$_2$, and —N(H)C(=NH)NH$_2$, —N(H)—C(O)—N(H)—(C$_1$-C$_3$)alkyl optionally substituted at the alkyl group with a group selected from —S(O)$_2$OH, C(O)OH, —NH$_2$ and —N(H)C(=NH)NH$_2$, —(C$_1$-C$_6$)alkyl optionally substituted with 1 group selected from —S(O)$_2$OH, C(O)OH, —NH$_2$ and —N(H)C(=NH)NH$_2$, and —C≡C—(C$_1$-C$_3$)alkyl optionally substituted at the alkyl group with 1 group selected from —S(O)$_2$OH, C(O)OH, —NH$_2$ and —N(H)C(=NH)NH$_2$;

each R$^{D11}$ is independently selected from H, —(C$_3$-C$_6$)cycloalkyl, —OH, —(C$_1$-C$_4$)haloalkyl, —S(O)$_2$OH, C(O)OH, —NH$_2$, —N(H)C(=NH)NH$_2$, —(C$_1$-C$_4$)alkyl optionally substituted with halo, —OH or —C(O)OH, and —(C$_1$-C$_3$)alkyl-phenyl optionally substituted at the phenyl group with 1-3 substituents selected from methoxy, hydroxyl and halo;

R$^{D11B}$ is selected from H, —OH, —CF$_3$, —NH$_2$, —C(O)OH, —O—(C$_1$-C$_4$)alkyl, —S(O)$_2$OH, —C(=NH)—NH$_2$, —N(H)C(=NH)NH$_2$, —C(H)=NN(H)C(=NH)NH$_2$, —N(H)C(=NH)—N(H)C(=NH)NH$_2$, —C(O)—(C$_1$-C$_3$)alkyl, —O—(C$_1$-C$_4$)alkyl-C(O)OH, —(CH$_2$)$_{1-4}$—C(O)OH, cyclopropane, cyclopentyl, imidazole, pyridinyl, thiazolyl, 1(H)-tetrazolyl, —(C$_1$-C$_4$)alkyl optionally substituted with 1-2 groups independently selected from halo, —OH, —S(O)$_2$OH, C(O)OH, —NH$_2$, and —N(H)C(=NH)NH$_2$, a heterocycloalkyl selected from morpholinyl, pyrrolidinyl, piperazinyl, and piperidinyl, wherein the heterocycloalkyl is optionally substituted with 1, 2 or 3 R$^{D11}$, provided that substitution of the heterocycloalkyl can only occur by replacing a hydrogen that is covalently bound to either a carbon or a nitrogen of the heterocycloalkyl, and phenyl optionally substituted with 1-3 halo;

or R$^{D11}$ and R$^{D11B}$, when they both exist and are each attached to nitrogen, can join to form a (5-6 membered) heterocycloalkyl optionally substituted with R$^{11}$; and R$^{D11C}$ is selected from H, —OH, —CF$_3$, —O—(C$_1$-C$_4$)alkyl, —(C$_1$-C$_4$)alkyl-N(H)C(=NH)—NH$_2$, —C$_0$-C$_3$alkyl-imidazole, —C$_0$-C$_3$alkyl-pyridinyl, —(C$_1$-C$_4$)alkyl optionally substituted with 1-2 groups independently selected from halo, —OH, —S(O)$_2$OH, C(O)OH, —NH$_2$, and a heterocycloalkyl selected from morpholinyl, pyrrolidinyl, piperidinyl and piperazinyl, wherein the heterocycloalkyl is optionally substituted with a (5-6 membered)heteroaryl, provided that substitution of the heterocycloalkyl can only occur by replacing a hydrogen that is covalently bound to either a carbon or a nitrogen of the heterocycloalkyl, —C$_0$-C$_3$alkyl-(5-6 membered)heterocycloalkyl, wherein the (5-6 membered)heterocycloalkyl group of —C$_0$-C$_3$alkyl-(5-6 membered)heterocycloalkyl is selected from morpholinyl, pyrrolidinyl, piperidinyl and piperazinyl, and wherein the —C$_0$-C$_3$alkyl-(5-6 membered)heterocycloalkyl group is substituted with a group selected from 1, 2, or 3 groups selected from —OH and —(C$_1$-C$_3$)alkyl, provided that substitution of the —C$_0$-C$_3$alkyl-(5-6 membered)heterocycloalkyl can only occur by replacing a hydrogen that is covalently bound to either a carbon or a nitrogen of the —C$_0$-C$_3$alkyl-(5-6 membered) heterocycloalkyl, and —C$_0$-C$_3$alkyl-phenyl optionally substituted at the phenyl group with 1-3 halo.

In other embodiments of the compounds of formulae VI, VII and VIII, or any embodiments of the compounds of formulae VI, VII and VIII described herein as it may apply, or a pharmaceutically acceptable salt of any of these compounds, L$^D$ is selected from —(C$_1$-C$_3$)alkyl-O—, —(C$_0$-C$_3$)alkyl-NR$^Y$—(C$_0$-C$_3$)alkyl-, —(C$_0$-C$_3$)alkyl-S—(C$_0$-C$_3$)alkyl-, —(C$_0$-C$_3$)alkyl-S(O)$_2$—(C$_0$-C$_3$)alkyl-; —C(O)N(R$^Y$)—(C$_0$-C$_3$)alkyl-, —S(O)$_2$—N(R$^Y$)—(C$_0$-C$_3$)alkyl-, —C(O)—(C$_0$-C$_3$)alkyl-, —(C$_1$-C$_4$)alkyl- optionally substituted with halo or —OH, —C≡C—(C$_0$-C$_3$)alkyl- and —(C$_0$-C$_3$)alkyl-.

In other embodiments of the compounds of formulae VI, VII and VIII, or any embodiments of the compounds of formulae VI, VII and VIII described herein as it may apply, or a pharmaceutically acceptable salt of any of these compounds, L$^D$ is selected from: —(CH$_2$)$_{1-3}$—O—, —(CH$_2$)$_{1-3}$—NR$^Y$—, —(C$_0$-C$_3$)alkyl-S—(C$_0$-C$_3$)alkyl-; —(CH$_2$)$_{1-3}$—S—, —S—(CH$_2$)$_{1-3}$—, —S(O)$_2$—(CH$_2$)$_{1-3}$—, —S(O)$_2$—, —C(O)N(H)—(CH$_2$)$_{1-3}$—, —S(O)$_2$—N(H)—(CH$_2$)$_{1-3}$—, —C(O)—(CH$_2$)$_{1-2}$—, —(C$_1$-C$_4$)alkyl- optionally substituted with halo or —OH, —C≡C—(C$_0$-C$_3$)alkyl- and a bond.

In other embodiments of the compounds of formulae VI, VII and VIII, or any embodiments of the compounds of formulae VI, VII and VIII described herein as it may apply, or a pharmaceutically acceptable salt of any of these compounds, $L^D$ is selected from —(CH$_2$)—O—, —(CH$_2$)—NR$^Y$—, —(CH$_2$)—S—, —S—(CH$_2$)—, —S(O)$_2$—, —S(O)$_2$—(CH$_2$)—, —C(O)N(R$^Y$)—(C$_0$-C$_3$)alkyl-; —S(O)$_2$—N(H)—(CH$_2$)$_{1-3}$—, —C(O)—(CH$_2$)$_{1-2}$—, —(C$_1$-C$_4$)alkyl-optionally substituted with halo or —OH, and —C≡C—(C$_2$-C$_3$)alkyl-.

In other embodiments of the compounds of formulae VI, VII and VIII, or any embodiments of the compounds of formulae VI, VII and VIII described herein as it may apply, or a pharmaceutically acceptable salt of any of these compounds, $L^D$ is selected from —(CH$_2$)—O—, —(CH$_2$)—NR$^Y$—, —(CH$_2$)—S—, —S—(CH$_2$)—, —S(O)$_2$—, —S(O)$_2$—(CH$_2$)—, —C(O)N(R$^Y$)—(C$_0$-C$_3$)alkyl-, —S(O)$_2$—N(H)—(CH$_2$)$_{1-3}$—, —C(O)—(CH$_2$)$_{1-2}$—, —(C$_1$-C$_4$)alkyl-optionally substituted with halo or —OH, and —C≡C—(C$_2$-C$_3$)alkyl-.

In other embodiments of the compounds of formulae VI, VII and VIII, or any embodiments of the compounds of formulae VI, VII and VIII described herein as it may apply, or a pharmaceutically acceptable salt of any of these compounds, $L^D$ is selected from —(CH$_2$)—O—, —(CH$_2$)—NH—, —(CH$_2$)—S—, —S—(CH$_2$)—, —S(O)$_2$—, —S(O)$_2$—(CH$_2$)—, —C(O)N(H)—(CH$_2$)$_{1-3}$—, —S(O)$_2$—N(H)—(CH$_2$)$_{1-3}$—, —C(O)—(CH$_2$)$_{1-2}$—, —(C$_1$-C$_4$)alkyl- optionally substituted with halo or —OH, and —C≡C—(C$_2$-C$_3$)alkyl-.

Another aspect of the invention relates to a compound of Formula VIII:

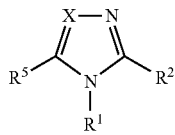

VIII or pharmaceutically acceptable salt thereof, wherein:

X is =N— or =C(R$^4$)—;

R$^1$ is R$^C$;

or X can be =C(R$^C$)— only when R$^1$ is phenyl optionally substituted with one, two, or three R$^{C10}$ groups;

R$^C$ is selected from phenyl, —(C$_5$-C$_6$)-cycloalkyl, —CH$_2$-phenyl, heteroaryl, and —(C$_1$-C$_4$)alkyl optionally substituted with —OR$^{C13}$, —N(R$^{C13}$)$_2$ or —S(R$^{C13}$), wherein the cyclic group of R$^C$ can be optionally substituted with 1, 2, 3, 4 or 5 R$^{C10}$ groups, wherein the 1, 2, 3, 4, or 5 R$^{C10}$ groups are independently selected from R$^{C10A}$ and R$^{C10B}$ provided that R$^C$ cannot be substituted with more than 2 R$^{C10B}$ groups, and provided that substitution of R$^C$ with R$^{C10}$ can only occur by replacing a hydrogen that is covalently bound to either a carbon or a nitrogen of R$^C$, wherein each R$^{C10A}$ is independently selected from halo, cyano and —(C$_1$-C$_4$)alkyl optionally substituted with 1-3 groups selected from —OH and halo;

each R$^{C10B}$ is independently selected from —C(O)NH$_2$, (5-6 membered)heterocycloalkyl, —O—(C$_1$-C$_4$)alkyl-R$^{C11}$, —C(O)OR$^{C12}$, —OC(O)OR$^{C12}$ and —O—(C$_1$-C$_4$)alkyl optionally substituted with —OH or —C(O)OH;

R$^{C11}$ is cyano, nitro, —N(R$^{C12}$)$_2$, —OR$^{C12}$, —SR$^{C12}$, —C(O)R$^{C12}$, —C(O)OR$^{C12}$, —C(O)N(R$^{C12}$)$_2$, —S(O)N(R$^{C12}$)$_2$, —S(O)$_2$N(R$^{C12}$)$_2$, —S(O)$_2$R$^{C12}$, —OC(O)R$^{C12}$, —OC(O)OR$^{C12}$, —OC(O)N(R$^{C12}$)$_2$, —N(R$^{C12}$)C(O)R$^{C12}$, —N(R$^{C12}$)C(O)OR$^{C12}$, —N(R$^{C12}$)C(O)N(R$^{C12}$)$_2$, or —N(R$^{C12}$)C(=NR$^{C12}$)N(R$^{C12}$)$_2$;

each R$^{C12}$ is independently selected from hydrogen, —(C$_1$-C$_4$)alkyl, and —(C$_1$-C$_4$)haloalkyl;

each R$^{C13}$ is independently selected from hydrogen, —(C$_1$-C$_4$)alkyl, and —C$_1$-C$_4$)haloalkyl;

R$^2$ is -L$^D$-R$^{D1}$;

$L^D$ is —[C(R)$_2$]$_p$—Y—[C(R)$_2$]$_q$—;

p is 0 or 1;

q is 0 or 1;

each R is independently selected from H, —(C$_1$-C$_3$)alkyl, halo, —OH, and —CH$_2$OH;

Y is a bond, —S—, —S(O)$_2$—, —CH(OH)—, —O—, —C(H)=C(H)—, —C(O)—(C$_1$-C$_4$)alkyl-, —(C$_1$-C$_4$)alkyl-S—(C$_1$-C$_4$)alkyl-, —(C$_1$-C$_4$)alkyl-N(R$^Y$)—(C$_1$-C$_4$)alkyl-, —C(H)(halo)-, —(C$_1$-C$_4$)alkyl-S(O)$_2$—, —S(O)$_2$—N(R$^Y$)—, —(C$_1$-C$_4$)alkyl-O—, or —C(O)—N(R$^Y$)—, wherein R$^Y$ is H, —(C$_1$-C$_4$)alkyl, hydroxyl(C$_1$-C$_4$)alkyl or —C≡C—(C$_1$-C$_3$)alkyl-;

R$^{D1}$ is selected from —(C$_6$-C$_{10}$)aryl, —N(H)-phenyl, cycloalkyl, heterocycloalkyl, and heteroaryl, wherein R$^{D1}$ is substituted with 0-3 A groups and 1-2 B groups, each A group, when they occur, is independently selected from halo, —CF$_3$, —CN, —NO$_2$, —OH, —O—(C$_1$-C$_4$)alkyl optionally substituted at the alkyl group with 1-3 substituents independently selected from —OH and halo, and —(C$_1$-C$_4$) alkyl optionally substituted with 1-3 substituents independently selected from —OH and halo;

each B group is independently selected from —C(O)—N(H)—R$^{D11C}$, —C(O)—(C$_1$-C$_4$)alkyl substituted with R$^{D11B}$, —S(O)$_2$—N(R$^{D11}$)R$^{D11C}$, —S(O)$_2$—N(H)C(O)—N(R$^{D11}$)R$^{D11B}$, —C(=NH)—NH$_2$, —C(O)O—(C$_1$-C$_4$)alkyl substituted with R$^{D11B}$, —O—(C$_1$-C$_4$)alkyl substituted at the alkyl group with 1 or 2 R$^{D11B}$, —C(O)-heterocycloalkyl, wherein the —C(O)-heterocycloalkyl is substituted with R$^{D11B}$, provided that substitution of —C(O)-heterocycloalkyl with R$^{D11B}$ can only occur by replacing a hydrogen that is covalently bound to either a carbon or a nitrogen of —C(O)-heterocycloalkyl, —C(O)—N(H)—(C$_1$-C$_6$)alkyl substituted at the alkyl group with 1 or 2 R$^{D11B}$, —S(O)$_2$-(4-6 membered)heterocycloalkyl substituted with R$^{D11C}$, provided that substitution of the —S(O)$_2$-(4-6 membered)heterocycloalkyl with R$^{D11C}$ can only occur by replacing a hydrogen that is covalently bound to either a carbon or a nitrogen of the —S(O)$_2$-(4-6 membered)heterocycloalkyl, —S(O)$_2$—N(H)C(O)—(C$_1$-C$_4$)alkyl substituted with R$^{D11B}$, —S(O)$_2$—N(H)C(O)O—(C$_1$-C$_4$)alkyl substituted with R$^{D11B}$, —S(O)$_2$—(C$_1$-C$_4$)alkyl substituted with R$^{D11B}$, —N(H)—C(O)—(C$_1$-C$_4$)alkyl substituted at the alkyl group with 1 or 2 R$^{D11B}$, —N(H)—C(O)—N(H)—(C$_1$-C$_3$)alkyl substituted at the alkyl group with R$^{D11B}$, —(C$_1$-C$_6$)alkyl substituted with 1 or 2 R$^{D11B}$, and —C≡C—(C$_1$-C$_3$)alkyl substituted with R$^{D11B}$;

R$^{D11B}$ is selected from —C(=NH)—NH$_2$, —N(H)C(=NH)NH$_2$, —C(H)=NN(H)C(=NH)NH$_2$, and —N(H)C(=NH)—N(H)C(=NH)NH$_2$;

R$^{D11C}$ is selected from —(C$_1$-C$_4$)alkyl-N(H)C(=NH)—NH$_2$, and —(C$_1$-C$_4$)alkyl substituted with 1 —N(H)C(=NH)NH$_2$;

R$^4$ is H, —(C$_1$-C$_3$)alkyl or halo;

R$^5$ is —[C(R$^8$)$_2$]-phenyl, —[C(R$^8$)$_2$]-naphthalenyl, or —[C(R$^8$)$_2$]-(5-10 membered) heteroaryl, wherein the heteroaryl is selected from (benzo[d][1,3]dioxolyl, benzo[d]isoxazole, quinoxalinyl, quinolinyl and 2,3,4a,8a-tetrahydrobenzo[b][1,4]dioxinyl, wherein the cyclic group of R$^5$ is optionally substituted with 1, 2, 3, 4 or 5 R$^{410}$, provided that substitution of R$^5$ with R$^{410}$ can only occur by replacing a hydrogen that is covalently bound to either a carbon or a nitrogen of R$^5$, wherein the 1-5 R$^{410}$ groups are independently selected from $R^{A10A}$ groups and $R^{A10B}$ groups, provided that $R^5$ cannot be substituted with more than 2 $R^{A10B}$ groups;

each $R^{A10A}$, when they occur, is independently selected from halo, alkoxyl, hydroxyl, —CN, —OCF$_3$, —(C$_1$-C$_4$) alkyl and —NH$_2$, each $R^{A10B}$, when they occur, is selected from —O—(C$_1$-C$_4$)alkyl-$R^{A11}$, —S(O)$_2$—NH$_2$, —S(O)$_2$CH$_3$, —N(H)—S(O)$_2$CH$_3$, —S(O)$_2$N(H)—CH$_3$, —C(O)OH, —(C$_1$-C$_4$)alkyl-OH, —C(O)NH$_2$, and —(C$_1$-C$_4$)alkyl substituted with 1-3 groups selected from —OH and halo;

$R^{A11}$ is selected from —C(O)OH, (5-6 membered)heterocycloalkyl, halogen, cyano, nitro, —(C$_1$-C$_4$)alkyl, —N(R$^{A12}$)$_2$, —OR$^{A12}$, —SR$^{A12}$, —N(OR$^{A12}$)R$^{A12}$, C(O)R$^{A12}$, —C(O)OR$^{A12}$, C(O)N(R$^{A12}$)$_2$, —N(R$^{A12}$)S(O)R$^{A12}$, —N(R$^{A12}$)S(O)$_2$R$^{A12}$, —S(O)N(R$^{A12}$)$_2$, —S(O)$_2$N(R$^{A12}$)$_2$, —S(O)$_2$R$^{A12}$, —OC(O)R$^{A12}$, —OC(O)OR$^{A12}$, —OC(O)N(R$^{A12}$)$_2$, —N(R$^{A12}$)C(O)R$^{A12}$, —N(R$^{A12}$)S(O)$_2$R$^{A12}$, —N(R$^{A12}$)C(O)OR$^{A12}$, —N(R$^{A12}$)C(O)N(R$^{A12}$)$_2$, —N(R$^{A12}$)C(=NR$^{A12}$)N(R$^{A12}$)$_2$, and heteroaryl, wherein each $R^{A12}$ is independently hydrogen, —(C$_1$-C$_4$)alkyl, or —(C$_1$-C$_4$)halo alkyl; and each $R^8$ is independently hydrogen, halogen, or methyl, or both $R^8$ taken together with the carbon to which they are both attached form either a (C$_3$-C$_6$)cycloalkyl or a (3-6 membered) heterocycloalkyl.

In other embodiments of the compounds of formulae VI, VII and VIII, or any embodiments of the compounds of formulae VI, VII and VIII described herein as it may apply, or a pharmaceutically acceptable salt of any of these compounds, the B group of $R^{D1}$ is selected from:

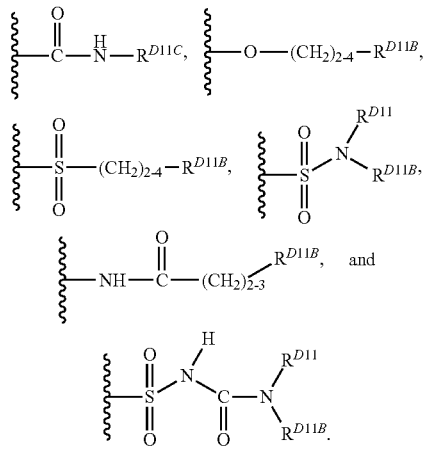

In other embodiments of the compounds of formulae VI, VII and VIII, or any embodiments of the compounds of formulae VI, VII and VIII described herein as it may apply, or a pharmaceutically acceptable salt of any of these compounds, $R^C$ is phenyl, —CH$_2$-phenyl, —(C$_5$-C$_6$)-cycloalkyl, or pyridinyl, wherein $R^C$ can be optionally substituted with 1, 2 or 3 $R^{C10}$, provided that substitution of $R^C$ can only occur by replacing a hydrogen that is covalently bound to either a carbon or a nitrogen of the $R^C$, and wherein the 1, 2 or 3 $R^{C10}$ groups are independently selected from $R^{C10A}$ and $R^{C10B}$, provided that $R^C$ cannot be substituted with more than 1 $R^{C10B}$ group;

each $R^{C10A}$, when they occur, is independently selected from halo, —(C$_1$-C$_3$)alkyl optionally substituted with 1-3 groups selected from halo and —OH, methoxy, —CF$_3$ and halo; and $R^{C10B}$ is selected from —C(O)NH$_2$, (5-6 membered)heterocycloalkyl, —O—(C$_1$-C$_4$)alkyl optionally substituted with —OH, —C(O)OH, or —N[(C$_1$-C$_4$)alkyl]$_2$, and —(C$_1$-C$_4$)alkyl substituted with —N[—(C$_1$-C$_4$)alkyl]$_2$.

In other embodiments of the compounds of formulae VI, VII and VIII, or any embodiments of the compounds of formulae VI, VII and VIII described herein as it may apply, or a pharmaceutically acceptable salt of any of these compounds, $R^C$ is phenyl, —CH$_2$-phenyl, —(C$_5$-C$_6$)-cycloalkyl, or pyridinyl, wherein the cyclic group of $R^C$ can be optionally substituted with one, two, or three $R^{C10}$ groups and, wherein the one, two, or three $R^{C10}$ groups are independently selected from $R^{C10A}$ and $R^{C10B}$, provided that $R^C$ cannot be substituted with more than 1 $R^{C10B}$ group;

each $R^{C10A}$, when they occur, is independently selected from methoxy, —CF$_3$, halo, and —(C$_1$-C$_3$)alkyl optionally substituted with 1-3 groups selected from halo and —OH; and $R^{C10B}$ is selected from (5-6 membered)heterocycloalkyl, —(C$_1$-C$_4$)alkyl substituted with —N[—(C$_1$-C$_4$)alkyl]$_2$, —C(O)NH$_2$, and —O—(C$_1$-C$_4$)alkyl optionally substituted with —OH, —C(O)OH, or —N[—(C$_1$-C$_4$)alkyl]$_2$.

In other embodiments of the compounds of formulae VI, VII and VIII, or any embodiments of the compounds of formulae VI, VII and VIII described herein as it may apply, or a pharmaceutically acceptable salt of any of these compounds, $R^C$ is phenyl, —CH$_2$-phenyl or pyridinyl, wherein the cyclic group of $R^C$ can be optionally substituted with 1, 2 or 3 $R^{C10}$, provided that substitution of $R^C$ can only occur by replacing a hydrogen that is covalently bound to either a carbon or a nitrogen of $R^C$, and wherein the 1, 2 or 3 $R^{C10}$ groups are independently selected from $R^{C10A}$ and $R^{C10B}$, provided that $R^C$ cannot be substituted with more than 1 $R^{C10B}$ group;

each $R^{C10A}$, when they occur, is independently selected from —(C$_1$-C$_3$)alkyl optionally substituted with 1-3 groups selected from —OH, methoxy, —CF$_3$ and halo;

$R^{C10B}$ is selected from —C(O)NH$_2$, (5-6 membered)heterocycloalkyl, —(C$_1$-C$_4$)alkyl substituted with —N[—(C$_1$-C$_4$)alkyl]$_2$, and —O—(C$_1$-C$_4$)alkyl optionally substituted with —OH, —C(O)OH, or —N[—(C$_1$-C$_4$)alkyl]$_2$.

In other embodiments of the compounds of formulae VI, VII and VIII, or any embodiments of the compounds of formulae VI, VII and VIII described herein as it may apply, or a pharmaceutically acceptable salt of any of these compounds, $R^C$ is phenyl or pyridinyl, wherein the cyclic group of $R^C$ can be optionally substituted with 1, 2 or 3 $R^{C10}$, provided that substitution of $R^C$ can only occur by replacing a hydrogen that is covalently bound to either a carbon or a nitrogen of $R^C$, and wherein the 1, 2 or 3 $R^{C10}$ groups are independently selected from $R^{C10A}$ and $R^{C10B}$, provided that $R^C$ cannot be substituted with more than 1 $R^{C10B}$ group;

each $R^{C10A}$, when they occur, is independently selected from methoxy and halo; and $R^{C10B}$ is selected from —C(O)NH$_2$, (5-6 membered)heterocycloalkyl, —(C$_1$-C$_4$)alkyl substituted with —N[—(C$_1$-C$_4$)alkyl]$_2$, and —O—(C$_1$-C$_4$)alkyl optionally substituted with —OH, —C(O)OH, or —N[—(C$_1$-C$_4$)alkyl]$_2$.

In other embodiments of the compounds of formulae VI, VII and VIII, or any embodiments of the compounds of formulae VI, VII and VIII described herein as it may apply, or a pharmaceutically acceptable salt of any of these compounds, $R^C$ is phenyl or pyridinyl, wherein the cyclic group of $R^C$ can be optionally substituted with 1 or 2 groups selected from methoxy, methyl and halo, provided that substitution of $R^C$ can only occur by replacing a hydrogen that is covalently bound to either a carbon or a nitrogen of $R^C$.

In other embodiments of the compounds of formulae VI, VII and VIII, or any embodiments of the compounds of formulae VI, VII and VIII described herein as it may apply, or a pharmaceutically acceptable salt of any of these compounds, $R^C$ is phenyl or pyridinyl, wherein the cyclic group of $R^C$ can be optionally substituted 1 or 2 groups selected from methoxy, methyl, fluoro and chloro, provided that substitution of $R^C$ can only occur by replacing a hydrogen that is covalently bound to either a carbon or a nitrogen of $R^C$.

In other embodiments of the compounds of formulae VI, VII and VIII, or any embodiments of the compounds of formulae VI, VII and VIII described herein as it may apply, or a pharmaceutically acceptable salt of any of these compounds, $R^C$ is phenyl substituted with one or two groups selected from methoxy, fluoro or chloro.

In other embodiments of the compounds of formulae VI, VII and VIII, or any embodiments of the compounds of formulae VI, VII and VIII described herein as it may apply, or a pharmaceutically acceptable salt of any of these compounds, the compound is one of formula IX, X, XI, XII, XIII, XIV or XV:

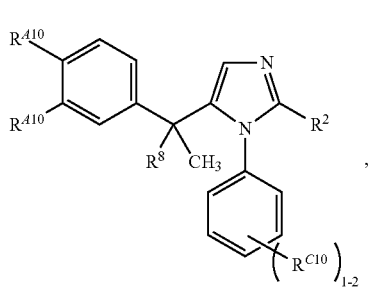

IX

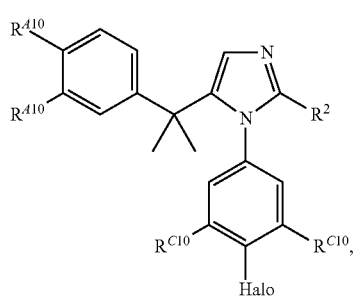

X

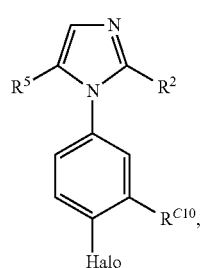

XI

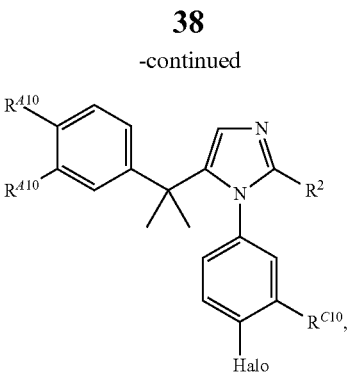

XII

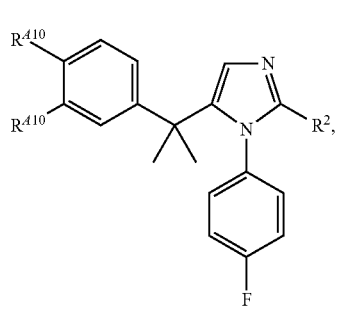

XIII

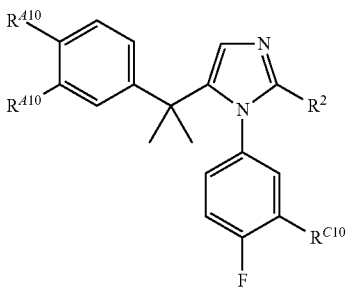

XIV

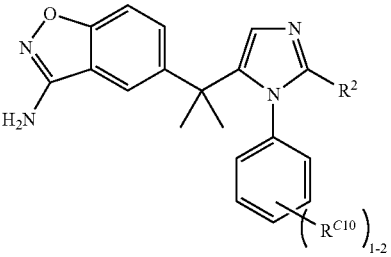

XV

In other embodiments of the compounds of formula IX, X, XI, XII, XIII, XIV or XV:

each $R^{410}$ is selected from fluoro, chloro and methoxy;
each $R^{C10}$ is selected from fluoro, chloro and methoxy;
$R^2$ is $-L^D-R^{D1}$, wherein:
$L^D$ is selected from $—(CH_2)—O—$, $—(CH_2)—NH—$, $—(CH_2)—S—$, $—S—(CH_2)—$, $—S(O)_2—$, $—S(O)_2—(CH_2)—$, $—C(O)N(H)—(CH_2)_{1-3}—$, $—S(O)_2—N(H)—(CH_2)_{1-3}—$, $—C(O)—(CH_2)_{1-2}—$, $—(C_1-C_3)alkyl-$ optionally substituted with halo or $—OH$, and $—C\equiv C—(C_2-C_3)$alkyl; and $R^{D1}$ is one of:

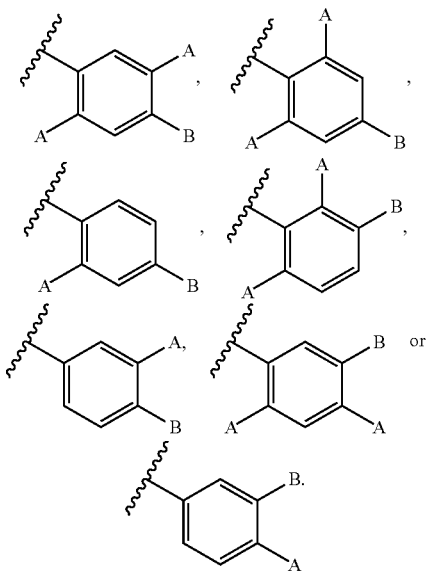

wherein each A is chloro or fluoro, and B is selected from:

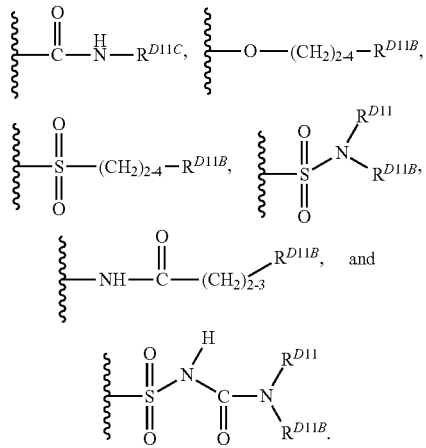

In other embodiments of the compounds of formulae VI, VII, VIII, IX, X, XI, XII, XIII, XIV or XV, or any embodiments of the compounds of formulae VI, VII, VIII, IX, X, XI, XII, XIII, XIV or XV described herein as it may apply, or a pharmaceutically acceptable salt of any of these compounds, $L^D$ is selected from —(CH$_2$)—O—, —(CH$_2$)—NH—, —(CH$_2$)—S—, —S—(CH$_2$)—, —S(O)$_2$—, —S(O)$_2$—(CH$_2$)—, —C(O)N(H)—(C$_0$-C$_3$)alkyl-; —C(O)N(H)—(CH$_2$)$_{1-3}$—, and —S(O)$_2$—N(H)—(CH$_2$)$_{1-3}$—.

In other embodiments of the compounds of formulae VI, VII, VIII, IX, X, XI, XII, XIII, XIV or XV, or any embodiments of the compounds of formulae VI, VII, VIII, IX, X, XI, XII, XIII, XIV or XV described herein as it may apply, or a pharmaceutically acceptable salt of any of these compounds, $L^D$ is selected from —S—(C$_1$-C$_3$)alkyl-, —(CH$_2$)$_2$— and —(C$_1$-C$_3$)alkyl-O—.

In other embodiments of the compounds of formulae VI, VII and VIII, or in any of the above embodiments of the compounds of formulae VI, VII, and VIII, IX described herein as it may apply, or a pharmaceutically acceptable salt of any of these compounds, $R^{D11B}$ is H.

In other embodiments of the compounds of formulae VI, VII and VIII, or in any of the above embodiments of the compounds of formulae VI, VII, and VIII, IX described herein as it may apply, or a pharmaceutically acceptable salt of any of these compounds, $R^{D11B}$ is —OH.

In other embodiments of the compounds of formulae VI, VII and VIII, or in any of the above embodiments of the compounds of formulae VI, VII, and VIII, IX described herein as it may apply, or a pharmaceutically acceptable salt of any of these compounds, $R^{D11B}$ is —CF$_3$.

In other embodiments of the compounds of formulae VI, VII and VIII, or in any of the above embodiments of the compounds of formulae VI, VII, and VIII, IX described herein as it may apply, or a pharmaceutically acceptable salt of any of these compounds, $R^{D11B}$ is —C(O)OH.

In other embodiments of the compounds of formulae VI, VII and VIII, or in any of the above embodiments of the compounds of formulae VI, VII, and VIII, IX described herein as it may apply, or a pharmaceutically acceptable salt of any of these compounds, $R^{D11B}$ is —O—(C$_1$-C$_4$)alkyl.

In other embodiments of the compounds of formulae VI, VII and VIII, or in any of the above embodiments of the compounds of formulae VI, VII, and VIII, IX described herein as it may apply, or a pharmaceutically acceptable salt of any of these compounds, $R^{D11B}$ is —S(O)$_2$OH.

In other embodiments of the compounds of formulae VI, VII and VIII, or in any of the above embodiments of the compounds of formulae VI, VII, and VIII, IX described herein as it may apply, or a pharmaceutically acceptable salt of any of these compounds, $R^{D11B}$ is —C(O)—(C$_1$-C$_3$)alkyl.

In other embodiments of the compounds of formulae VI, VII and VIII, or in any of the above embodiments of the compounds of formulae VI, VII, and VIII, IX described herein as it may apply, or a pharmaceutically acceptable salt of any of these compounds, $R^{D11B}$ is —O—(C$_1$-C$_4$)alkyl-C(O)OH.

In other embodiments of the compounds of formulae VI, VII, and VIII, or in any of the above embodiments of the compounds of formulae VI, VII, and VIII described herein as it may apply, or a pharmaceutically acceptable salt of any of these compounds, $R^{D11B}$ is (5-6 membered)heteroaryl.

In other embodiments of the compounds of formulae VI, VII and VIII, or in any of the above embodiments of the compounds of formulae VI, VII, and VIII described herein as it may apply, or a pharmaceutically acceptable salt of any of these compounds, $R^{D11B}$ is —(C$_1$-C$_4$)alkyl optionally substituted with 1-3 groups independently selected from halo and —OH.

In other embodiments of the compounds of formulae VI, VII and VIII, or in any of the above embodiments of the compounds of formulae VI, VII, and VIII described herein as it may apply, or a pharmaceutically acceptable salt of any of these compounds, $R^{D11B}$ is —C$_1$-C$_4$)alkyl optionally substituted with 1-3 groups independently selected from halo, —OH, —S(O)$_2$OH, C(O)OH, —NH$_2$ and —N(H)C(=NH)NH$_2$.

In other embodiments of the compounds of formulae VI, VII and VIII, or in any of the above embodiments of the compounds of formulae VI, VII, and VIII described herein as it may apply, or a pharmaceutically acceptable salt of any of these compounds, $R^{D11B}$ is —(C$_0$-C$_3$)alkyl-(5-8 membered) heterocycloalkyl optionally substituted at the heterocycloalkyl group with 1 to 3 $R^{D11}$.

In other embodiments of the compounds of formulae VI, VII and VIII, or in any of the above embodiments of the compounds of formulae VI, VII, and VIII described herein as it may apply, or a pharmaceutically acceptable salt of any of these compounds, $R^{D11B}$ is —$(C_0$-$C_3)$alkyl-$(C_3$-$C_6)$cycloalkyl optionally substituted with $R^{D11}$.

In other embodiments of the compounds of formulae VI, VII and VIII, or in any of the above embodiments of the compounds of formulae VI, VII, and VIII described herein as it may apply, or a pharmaceutically acceptable salt of any of these compounds, $R^{D11B}$ is aryl optionally substituted with 1-3 halo.

In other embodiments of the compounds of formulae VI, VII, VIII, IX, X, XI, XII, XIII, XIV or XV, or any embodiments of the compounds of formulae VI, VII, VIII, IX, X, XI, XII, XIII, XIV or XV described herein as it may apply, or a pharmaceutically acceptable salt of any of these compounds, $R^{D11B}$ is selected from —C(=NH)—NH$_2$, —N(H)C(=NH)NH$_2$, —C(H)=NN(H)C(=NH)NH$_2$, and —N(H)C(=NH)—N(H)C(=NH)NH$_2$.

In other embodiments of the compounds of formulae VI, VII, VIII, IX, X, XI, XII, XIII, XIV or XV, or any embodiments of the compounds of formulae VI, VII, VIII, IX, X, XI, XII, XIII, XIV or XV described herein as it may apply, or a pharmaceutically acceptable salt of any of these compounds, $R^{D11B}$ is selected from —C(O)—$(C_1$-$C_3)$alkyl, —O—$(C_1$-$C_4)$alkyl-C(O)OH, and —$(CH_2)_{1-4}$—C(O)OH.

In other embodiments of the compounds of formulae VI, VII, VIII, IX, X, XI, XII, XIII, XIV or XV, or any embodiments of the compounds of formulae VI, VII, VIII, IX, X, XI, XII, XIII, XIV or XV described herein as it may apply, or a pharmaceutically acceptable salt of any of these compounds, $R^{D11B}$ is a heterocycloalkyl selected from morpholinyl, pyrrolidinyl, piperazinyl, and piperidinyl, wherein the heterocycloalkyl is optionally substituted with 1, 2 or 3 $R^{D11}$, provided that substitution of the heterocycloalkyl can only occur by replacing a hydrogen that is covalently bound to either a carbon or a nitrogen of the heterocycloalkyl.

In other embodiments of the compounds of formulae VI, VII, VIII, IX, X, XI, XII, XIII, XIV or XV, or any embodiments of the compounds of formulae VI, VII, VIII, IX, X, XI, XII, XIII, XIV or XV described herein as it may apply, or a pharmaceutically acceptable salt of any of these compounds, $R^{D11B}$ is —C(=NH)—NH$_2$.

In other embodiments of the compounds of formulae VI, VII, VIII, IX, X, XI, XII, XIII, XIV or XV, or any embodiments of the compounds of formulae VI, VII, VIII, IX, X, XI, XII, XIII, XIV or XV described herein as it may apply, or a pharmaceutically acceptable salt of any of these compounds, $R^{D11B}$ is —N(H)C(=NH)NH$_2$.

In other embodiments of the compounds of formulae VI, VII, VIII, IX, X, XI, XII, XIII, XIV or XV, or any embodiments of the compounds of formulae VI, VII, VIII, IX, X, XI, XII, XIII, XIV or XV described herein as it may apply, or a pharmaceutically acceptable salt of any of these compounds, $R^{D11B}$ is —C(H)=NN(H)C(=NH)NH$_2$.

In other embodiments of the compounds of formulae VI, VII, VIII, IX, X, XI, XII, XIII, XIV or XV, or any embodiments of the compounds of formulae VI, VII, VIII, IX, X, XI, XII, XIII, XIV or XV described herein as it may apply, or a pharmaceutically acceptable salt of any of these compounds, $R^{D11B}$ is —N(H)C(=NH)—N(H)C(=NH)NH$_2$.

In other embodiments of the compounds of formulae VI, VII, VIII, IX, X, XI, XII, XIII, XIV or XV, or any embodiments of the compounds of formulae VI, VII, VIII, IX, X, XI, XII, XIII, XIV or XV described herein as it may apply, or a pharmaceutically acceptable salt of any of these compounds, $R^{D11B}$ is —C(O)—$(C_1$-$C_3)$alkyl.

In other embodiments of the compounds of formulae VI, VII, VIII, IX, X, XI, XII, XIII, XIV or XV, or any embodiments of the compounds of formulae VI, VII, VIII, IX, X, XI, XII, XIII, XIV or XV described herein as it may apply, or a pharmaceutically acceptable salt of any of these compounds, RD11B is —O—(C1-C4)alkyl-C(O)OH.

In other embodiments of the compounds of formulae VI, VII, VIII, IX, X, XI, XII, XIII, XIV or XV, or any embodiments of the compounds of formulae VI, VII, VIII, IX, X, XI, XII, XIII, XIV or XV described herein as it may apply, or a pharmaceutically acceptable salt of any of these compounds, $R^{D11B}$ is —$(CH_2)_{1-4}$—C(O)OH.

The invention also comprises as another embodiment, a composition comprising a TGR agonist compound according to any one of the preceding embodiments together with a pharmaceutically acceptable diluent, excipient, and/or carrier. Such compositions are substantially free of non-pharmaceutically acceptable components, i.e., contain amounts of non-pharmaceutically acceptable components lower than permitted by US regulatory requirements at the time of filing this application. In some embodiments of this aspect, if the compound is dissolved or suspended in water, the composition further optionally comprises an additional pharmaceutically acceptable carrier, diluent, or excipient.

The invention also comprises as another embodiment a method for treating or preventing a metabolic disease in a subject in need of such treatment comprising administering to the subject an effective amount of a TGR agonist compound according to any one of the preceding embodiments. Metabolic diseases that may be treated or prevented include, without limitation, metabolic syndrome, insulin resistance, and Type 1 and Type 2 diabetes.

The invention also comprises as another embodiment a method for treating obesity or type II diabetes in a subject in need of such treatment comprising administering to the subject an effective amount of a TGR agonist compound or pharmaceutical composition according to any one of the preceding embodiments.

The invention also comprises as another embodiment a method for treating hyperlipidemia in a subject in need of such treatment comprising administering to the subject an effective amount of a TGR agonist compound or pharmaceutical composition according to any one of the preceding embodiments.

The invention also comprises as another embodiment a method for treating athersclerosis in a subject in need of such treatment comprising administering to the subject an effective amount of a TGR agonist compound or pharmaceutical composition according to any one of the preceding embodiments.

The invention also comprises as another embodiment a method for lowering blood glucose in a subject in need of such treatment comprising administering to the subject an effective amount of a TGR agonist compound or pharmaceutical composition according to any one of the preceding embodiments.

The invention also comprises as another embodiment a method for enhancing insulin secretion in a subject in need of such treatment comprising administering to the subject an effective amount of a TGR agonist compound or pharmaceutical composition according to any one of the preceding embodiments.

The invention also comprises as another embodiment a method for treating a disease associated with perturbed bile acid metabolism in a subject in need of such treatment comprising administering to the subject an effective amount of a TGR agonist compound or pharmaceutical composition according to any one of the preceding embodiments. Such diseases include, but are not limited to, gall bladder stones, cholecystitis, cholangitis, choledocholithiasis, jaundice, and obstetric cholestasis and the itch associated with it.

The invention also comprises as another embodiment a method for treating obesity or type II diabetes in a subject in need of such treatment comprising co-administering to the subject, simultaneously or sequentially, an effective amount of a TGR agonist compound according to any one of the preceding embodiments and a second anti-diabetic drug or pharmaceutical composition comprising an effective amount of a TGR agonist compound according to any one of the preceding embodiments and a second anti-diabetic drug. Non-limiting examples of anti-diabetic drugs include:

- Sulfonylureas (e.g., tolbutamide(3-butyl-1-(4-methylphenyl)sulfonylurea), acetohexamide(4-acetyl-N-(cyclohexylcarbamoyl)benzenesulfonamide), tolazamide (3-azepan-1-yl-1-(4-methylphenyl)sulfonyl-urea), chlorpropamide(N-(4-chlorophenyl)sulfonylmethanamide), glipizide (N-[2-[4-(cyclohexylcarbamoylsulfamoyl)phenyl]ethyl]-5-methyl-pyrazine-2-carboxamide), glyburide (5-chloro-N-[2-[4-(cyclohexylcarbamoylsulfamoyl)phenyl]ethyl]-2-methoxy-benzamide), glimepiride (3-ethyl-N,N-bis(3-ethyl-4-methyl-2-oxo-5H-pyrrol-2-yl)-4-methyl-2-oxo-5H-pyrrole-1-carboxamide), gliclazide (3-(7-azabicyclo[3.3.0]oct-7-yl)-1-(4-methylphenyl) sulfonyl-urea), and gliquidone (3-cyclohexyl-1-[4-[2-(7-methoxy-4,4-dimethyl-1,3-dioxo-isoquinolin-2-yl) ethyl]phenyl]sulfonyl-urea))
- Meglitinides (e.g., repaglinide (S(+)-2-ethoxy-4(2((3-methyl-1-(2-(1-piperidinyl)phenyl)-butyl)amino)-2-oxoethyl)benzoic acid), nateglinide (3-phenyl-2-(4-propan-2-ylcyclohexyl)carbonylamino-propanoic acid), and mitiglinide ((2S)-2-benzyl-4-(3aR,7aS)-octahydro-2H-isoindol-2-yl]-4-oxobutanoic acid))
- Biguanides (e.g., metformin (N,N-dimethylimidodicarbonimidic diamide), phenformin (2-(N-phenethylcarbamimidoyl)guanidine), and buformin (2-butyl-1-(diaminomethylidene)guanidine))
- Alpha-glucosidase inhibitors (e.g., miglitol ((2R,3R,4R,5S)-1-(2-hydroxyethyl)-2-(hydroxymethyl)piperidine-3,4,5-triol), acarbose ((2R,3R,4R,5S,6R)-5-{[(2R,3R,4R,5S,6R)-5-{[(2R,3R,4S,5S,6R)-3,4-dihydroxy-6-methyl-5-{[1S,4R,5S,6S)-4,5,6-trihydroxy-3-(hydroxymethyl)cyclohex-2-en-1-yl] amino}tetrahydro-2H-pyran-2-yl]oxy}-3,4-dihydroxy-6-(hydroxymethyl)tetrahydro-2H-pyran-2-yl]oxy}-6-(hydroxymethyl)tetrahydro-2H-pyran-2,3,4-triol), and voglibose ((1S,2S,3R,4S,5S)-5-(1,3-dihydroxypropan-2-ylamino)-1-(hydroxymethyl)cyclohexane-1,2,3,4-tetrol))
- Glucagon-like peptide (GLP) analogs and agonists (e.g., exenatide and liraglutide)
- Amylin analogues (e.g., pramlintide acetate (Symlin))
- Dipeptidyl peptidase-4 (DPP-4) inhibitors (e.g., vildagliptin, (2S)-1-{2-[(3-hydroxy-1-adamantyl)amino] acetyl}pyrrolidine-2-carbonitrile and sitagliptin ((3R)-3-amino-1-[9-(trifluoromethyl)-1,4,7,8-tetrazabicyclo [4.3.0]nona-6,8-dien-4-yl]-4-(2,4,5-trifluorophenyl) butan-1-one)), and
- Thiazolidinediones (e.g., rosiglitazone, 5-((4-(2-(methyl-2-pyridinylamino)ethoxy)phenyl)methyl)-2,4-thiazolidinedione, pioglitazone (5-((4-(2-(5-ethyl-2-pyridinyl)ethoxy)phenyl)methyl)-, (+−)-2,4-thiazolidinedione), and troglitazone (5-(4-((6-hydroxy-2,5,7,8-tetramethylchroman-2-yl-methoxy)benzyl)-2,4-thiazolidinedione))

The invention also comprises as another embodiment, a method for inducing increased GLP-1 secretion in cell, in vitro, comprising contacting the cell with an inducing effective amount of a TGR agonist compound according to any one of the preceding embodiments.

The invention also comprises as another embodiment the use of an effective amount of a TGR agonist compound according to any one of the preceding embodiments for the preparation of a medicament for treating a metabolic disease in a subject in need of such treatment.

The invention also comprises as another embodiment, the use of an effective amount of a TGR agonist compound according to any one of the preceding embodiments for the preparation of a medicament for treating obesity or type II diabetes in a subject in need of such treatment.

The invention also comprises as another embodiment, the use of an effective amount of a TGR agonist compound according to any one of the preceding embodiments for the preparation of a medicament for treating hyperlipidemia in a subject in need of such treatment.

The invention also comprises as another embodiment, the use of an effective amount of a TGR agonist compound according to any one of the preceding embodiments for the preparation of a medicament for treating athersclerosis in a subject in need of such treatment.

The invention also comprises as another embodiment, the use of an effective amount of a TGR agonist compound according to any one of the preceding embodiments for the preparation of a medicament for lowering blood glucose in a subject in need of such treatment.

The invention also comprises as another embodiment, the use of an effective amount of a TGR agonist compound according to any one of the preceding embodiments for the preparation of a medicament for enhancing insulin secretion in a subject in need of such treatment.

The invention also comprises as another embodiment, the use of an effective amount of a TGR agonist compound according to any one of the preceding embodiments for the preparation of a medicament for treating a disease associated with perturbed bile acid metabolism in a subject in need of such treatment.

The invention also comprises as another embodiment, the use of an effective amount of a TGR agonist compound according to any one of the preceding embodiments and a second anti-diabetic drug for the preparation of a medicament for treating obesity or type II diabetes in a subject in need of such treatment.

Pharmaceutical Formulations and Dosage Forms

Administration of the compounds of this disclosure, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracistemally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages.

The compositions will include a conventional pharmaceutical carrier, excipient, and/or diluent and a compound of this disclosure as the/an active agent, and, in addition, can include carriers and adjuvants, etc.

Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It can also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the compounds in this disclosure can also contain minor amounts of auxiliary substances such as wetting or emulsifying agents, pH buffering agents, antioxidants, and the like, such as, for example, citric acid, sorbitan monolaurate, triethanolamine oleate, butylalted hydroxytoluene, etc.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

Compositions suitable for parenteral injection can comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One preferable route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms can also comprise buffering agents.

Solid dosage forms, as described above, can be prepared with coatings and shells, such as enteric coatings and others well known in the art. They can contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of this disclosure, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, can contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of this disclosure with, for example, suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this disclosure include ointments, powders, sprays, and inhalants. The active component is admixed under sterile conditions with a physiologically acceptable carrier and any preservatives, buffers, or propellants as can be required. Ophthalmic formulations, eye ointments, powders, and solutions are also contemplated for the compounds in this disclosure.

Compressed gases can be used to disperse a compound of this disclosure in aerosol form. Inert gases suitable for this purpose are nitrogen, carbon dioxide, etc.

Generally, depending on the intended mode of administration, the pharmaceutically acceptable compositions will contain about 1% to about 99% by weight of a compound(s) of this disclosure, or a pharmaceutically acceptable salt thereof, and 99% to 1% by weight of a suitable pharmaceutical excipient. In one example, the composition will be between about 5% and about 75% by weight of a compound(s) of this disclosure, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of this disclosure, or a pharmaceutically acceptable salt thereof, for treatment of a disease-state in accordance with the teachings of this disclosure.

The compounds of this disclosure, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of this disclosure can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

The compositions will include a conventional pharmaceutical carrier or excipient and a compound of this disclosure as the/an active agent, and, in addition, can include other medicinal agents and pharmaceutical agents. Compositions of the compounds in this disclosure can be used in combination with anticancer and/or other agents that are generally administered to a patient being treated for cancer, e.g. surgery, radiation and/or chemotherapeutic agent(s). Chemotherapeutic agents that can be useful for administration in combination with compounds of Formula I in treating cancer include alkylating agents, platinum containing agents.

If formulated as a fixed dose, such combination products employ the compounds of this disclosure within the dosage range described above and the other pharmaceutically active agent(s) within its approved dosage range. Compounds of this disclosure can alternatively be used sequentially with known pharmaceutically acceptable agent(s) when a combination formulation is inappropriate.

The compounds described herein, as well as their pharmaceutically acceptable salts, or other derivatives thereof, can exist in isotopically-labeled form, in which one or more atoms of the compounds are replaced by an atom having the same atomic number but an atomic mass different from the atomic mass usually found in nature. Examples of isotopes that can be incorporated into compounds of the invention include isotopes of hydrogen, carbon, nitrogen, oxygen, phosphorous, sulfur, fluorine and chloride, such as $^2$H (deuterium), $^3$H (tritium), $^{13}$C, $^{14}$C, $^{15}$N, $^{18}$O, $^{17}$O, $^{31}$P, $^{35}$S, $^{18}$F and $^{36}$Cl, respectively. Isotopically labeled compounds of the present invention, as well as pharmaceutically acceptable salts, esters, prodrugs, solvates, hydrates or other derivatives thereof, generally can be prepared by carrying out the procedures disclosed in the Schemes and/or in the Examples and Preparations below, by substituting a readily available isotopically labeled reagent for a non-isotopically labeled reagent.

In the compounds of the invention, unless otherwise stated, any atom not specifically designated as a particular isotope is meant to represent any stable isotope of that atom at its natural abundance. When a position is designated as "H" or "hydrogen", the position is to be understood to have hydrogen at its natural abundance isotopic composition, with the understanding that some variation of natural isotopic abundance occurs in a synthesized compound depending upon the origin of chemical materials used in the synthesis. When a particular position is designated as "D" or "deuterium", it is to be understood that the abundance of deuterium at that position is substantially greater than the natural abundance of deuterium, which is 0.015%, and typically has at least 50% deuterium incorporation at that position.

The methods disclosed herein also include methods of treating diseases by administering deuterated compounds of the invention or other isotopically-labeled compounds of the invention alone or as pharmaceutical compositions. In some of these situations, substitution of hydrogen atoms with heavier isotopes such as deuterium can afford certain therapeutic advantages resulting from greater metabolic stability (for example, increased in vivo half-life or reduced dosage requirements).

Moreover, certain isotopically-labeled compounds, for example those into which radioactive isotopes such as $^3$H and $^{14}$C are incorporated, are useful in drug and/or substrate tissue distribution assays such as positron emission tomography (PET). Tritiated, ($^3$H) and carbon-14 ($^{14}$C) isotopes are useful for these embodiments because of their detectability.

Definitions

Terms used herein may be preceded and/or followed by a single dash, "—", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)OC$_1$-C$_6$alkyl indicate the same functionality. Also, for instance, when variable X of formula VIII(Q) is defined as =N— or =C(R$^4$)—, the bonds are only to indicate attachment points and the bonds are not meant to add additional bonds to the parent structure. So, for instance, when variable X of formula VIII(Q) is defined as =N—, this would mean the same thing as X being defined as N.

Certain variables used herein are indicated as divalent linking moieties, for example, when R$^D$ is -L$^D$-R$^{D1}$, L$^D$ is a divalent moiety linking R$^{D1}$ to the parent structure. For such divalent variables, particular members defining L$^D$ may be written, for example, in the form —X—Y— or —Y—X—. Such members are intended to replace the term being defined, in this case L$^D$, as written, such that when L$^D$ is —X—Y—, then R$^D$ is —X—Y—R$^{D1}$; further, when L$^D$ is —Y—X—, then R$^D$ is —Y—X—R$^{D1}$.

"Administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., surgery, radiation, chemotherapy, and the like), "administration" and its variants are each understood to include concurrent and sequential introduction of the compound or prodrug thereof and other agents.

"Alkoxy" means the group —OR wherein R is alkyl, as defined herein. Representative examples include methoxy, ethoxy, propoxy, butoxy, pentyloxy, hexyloxy, 4-methylhexyloxy, 4-methylheptyloxy, 4,7-dimethyloctyloxy, and the like.

"Alkoxycarbonyl" means an alkoxy group, as defined herein, appended to a parent moiety via a carbonyl group (i.e., a group of the form, —C(O)OR$^0$, wherein R$^0$ is alkyl, as defined herein). Examples of alkoxycarbonyl groups include, but are not limited to, methoxycarbonyl, ethoxycarbonyl, isopropoxycarbonyl, t-butoxycarbonyl, and n-hexylcarbonyl.

"Alkyl" means a linear or branched hydrocarbon group having from 1 to 10 carbon atoms unless otherwise defined. Representative examples for alkyl groups include methyl, ethyl, propyl, butyl, pentyl, hexyl, 4-methylhexyl, 4-methylheptyl, 4,7-dimethyloctyl, and the like. ($C_{1-4}$)alkyl means a groups selected from methyl, ethyl, propyl, isopropyl, butyl, sec-butyl, isobutyl and tert-butyl.

"Alkylamino" means an alkyl group, as defined herein, appended to a parent moiety through an —NH— group (i.e., substituents of the form —N(H)$R^O$, where $R^O$ is an alkyl group). Examples of alkylamino groups include, but are not limited to, methylamino, ethylamino, isopropylamino, hexylamino, and the like.

"Alkylaminocarbonyl" means an alkylamino group, as defined herein, appended to a parent moiety via a carbonyl group (i.e., a group of the form, —C(O)N(H)$R^O$, wherein $R^O$ is alkyl, as defined herein). Examples of alkylaminocarbonyl groups include, but are not limited to, methylaminocarbonyl, ethylaminocarbonyl, isopropylaminocarbonyl, t-butylaminocarbonyl, and n-hexylaminocarbonyl.

"Amino" means a —$NH_2$ group.

"Aryl" means a monovalent, monocyclic, or polycyclic radical having 6 to 14 ring carbon atoms. The monocyclic aryl radical is aromatic and whereas the polycyclic aryl radical may be partially saturated, at least one of the rings comprising a polycyclic radical is aromatic. The polycyclic aryl radical includes fused, bridged, and spiro ring systems. Any 1 or 2 ring carbon atoms of any nonaromatic rings comprising a polycyclic aryl radical may be replaced by a —C(O)—, —C(S)—, or —C(=NH)— group. Unless stated otherwise, the valency may be located on any atom of any ring of the aryl group, valency rules permitting. Representative examples include phenyl, naphthyl, indanyl, and the like.

"Carbonyl" means a —C(O)— group.

"Cycloalkyl" means a monocyclic or polycyclic hydrocarbon radical having 3 to 13 carbon ring atoms. The cycloalkyl radical may be saturated or partially unsaturated, but cannot contain an aromatic ring. The cycloalkyl radical includes fused, bridged and spiro ring systems. Examples of such radicals include cyclopropyl, cyclobutyl, cyclopentyl and cyclohexyl.

"Dialkylamino" means two alkyl groups, each independently as defined herein, appended to a parent moiety through a nitrogen atom (i.e., substituents of the form —N($R^O$)$_2$, where each $R^O$ is an alkyl group). Examples of dialkylamino groups include, but are not limited to N,N-dimethylamino, N,N-diethylamino, N-isopropyl-N-methylamino, N-ethyl-N-hexylamino, and the like.

"Di($C_1$-$C_4$alkyl)aminocarbonyl" means a dialkylamino group, as defined herein, appended to a parent moiety via a carbonyl group (i.e., a group of the form, —C(O)N($R^O$)$_2$, wherein each $R^O$ is alkyl, as defined herein). Examples of dialkylamino groups include, but are not limited to N,N-dimethylaminocarbonyl, N,N-diethylaminocarbonyl, N-isopropyl-N-methylaminocarbonyl, N-ethyl-N-hexylaminocarbonyl, and the like.

"Fused ring system" and "fused ring" refer to a polycyclic ring system that contains bridged or fused rings; that is, where two rings have more than one shared atom in their ring structures. In this application, fused-polycyclics and fused ring systems are not necessarily all aromatic ring systems. Typically, but not necessarily, fused-polycyclics share a vicinal set of atoms, for example naphthalene or 1,2,3,4-tetrahydronaphthalene. A spiro ring system is not a fused-polycyclic by this definition, but fused polycyclic ring systems of the invention may themselves have spiro rings attached thereto via a single ring atom of the fused-polycyclic. In some examples, as appreciated by one of ordinary skill in the art, two adjacent groups on an aromatic system may be fused together to form a ring structure. The fused ring structure may contain heteroatoms and may be optionally substituted with one or more groups. It should additionally be noted that saturated carbons of such fused groups (i.e., saturated ring structures) can contain two substitution groups.

"Halo" and "halogen" mean a fluoro, chloro, bromo or iodo group.

"Haloalkyl" means an alkyl radical, as defined herein, substituted with one or more halo atoms. For example, halo-substituted ($C_{1-4}$)alkyl includes trifluoromethyl, 2,2-dichloroethyl, 2,2,2-trifluoroethyl, perchloroethyl, 2-bromopropyl, and the like.

"Heteroaryl" means a monovalent monocyclic or polycyclic radical having 5 to 14 ring atoms of which one or more of the ring atoms, for example one, two, three, or four ring atoms, are heteroatoms independently selected from —O—, —S(O)$_n$— (n is 0, 1, or 2), —N—, —N($R^x$)—, and the remaining ring atoms are carbon atoms, where $R^x$ is hydrogen, alkyl, hydroxy, alkoxy, —C(O)$R^O$ or —S(O)$_2R^O$, where $R^O$ is alkyl. The monocyclic heteroaryl radical is aromatic and whereas the polycyclic heteroaryl radical may be partially saturated, at least one of the rings comprising a polycyclic radical is aromatic. The polycyclic heteoaryl radical includes fused, bridged and spiro ring systems. Any 1 or 2 ring carbon atoms of any nonaromatic rings comprising a polycyclic heteroaryl radical may be replaced by a —C(O)—, —C(S)—, or —C(=NH)— group. Unless stated otherwise, the valency may be located on any atom of any ring of the heteroaryl group, valency rules permitting. In particular, when the point of valency is located on the nitrogen, then $R^x$ is absent. More specifically, the term heteroaryl includes, but is not limited to, 1,2,4-triazolyl, 1,3,5-triazolyl, phthalimidyl, pyridinyl, pyrrolyl, imidazolyl, thienyl, furanyl, indolyl, 2,3-dihydro-1H-indolyl (including, for example, 2,3-dihydro-1H-indol-2-yl, 2,3-dihydro-1H-indol-5-yl, and the like), isoindolyl, indolinyl, isoindolinyl, benzimidazolyl, benzodioxol-4-yl, benzofuranyl, cinnolinyl, indolizinyl, naphthyridin-3-yl, phthalazin-3-yl, phthalazin-4-yl, pteridinyl, purinyl, quinoxalinyl, quinoxalinyl, tetrazoyl, pyrazolyl, pyrazinyl, pyrimidinyl, pyridazinyl, oxazolyl, isoxazolyl, oxadiazolyl, benzoxazolyl, quinolinyl, isoquinolinyl, tetrahydroisoquinolinyl (including, for example, tetrahydroisoquinolin-4-yl, tetrahydroisoquinolin-6-yl, and the like), 2,3,3a,7a-tetrahydro-1H-isoindolyl, pyrrolo[3,2-c]pyridinyl (including, for example, pyrrolo[3,2-c]pyridin-2-yl, pyrrolo[3,2-c]pyridin-7-yl, and the like), benzopyranyl, thiazolyl, isothiazolyl, thiadiazolyl, benzothiazolyl, benzothienyl, and the N-oxide derivatives thereof.

"Heterocyclyl" means a monovalent, monocyclic or polycyclic hydrocarbon radical having 3 to 13 ring atoms of which one or more of the ring atoms, for example 1, 2, 3 or 4 ring atoms, are heteroatoms independently selected from —O—, —S(O)$_n$— (n is 0, 1, or 2), —N= and —N($R^y$)— (where $R^y$ is hydrogen, alkyl, hydroxy, alkoxy, —C(O)$R^O$ or —S(O)$_2R^O$, where $R^O$ is alkyl, as defined herein), and the remaining ring atoms are carbon. The heterocycloalkyl radical may be saturated or partially unsaturated, but cannot contain an aromatic ring. The heteocycloalkyl radical includes fused, bridged and spiro ring systems. Any 1 or 2 ring carbon atoms independently may be replaced by a —C(O)—, —C(S)—, or —C(=NH)— group. Unless otherwise stated, the valency of the group may be located on any atom of any ring within the radical, valency rules permitting. In particular, when the point of valency is located on a nitrogen atom, $R^y$ is absent. More specifically the term heterocycloalkyl includes, but is not limited to, azetidinyl, pyrrolidinyl, 2-oxopyrrolidinyl, 2,5-dihydro-1H-pyrrolyl, piperidinyl, 4-piperidonyl, morpholinyl, piperazinyl, 2-oxopiperazinyl, tetrahydropyranyl, 2-oxopiperidinyl, thiomorpholinyl, thiamorpholinyl, perhydroazepinyl, pyrazolidinyl, imidazolinyl, imidazolidinyl, dihydropyridinyl, tetrahydropyridinyl, oxazolinyl, oxazolidinyl, isoxazolidinyl, thiazolinyl, thiazolidinyl, quinuclidinyl, isothiazolidinyl, octahydroindolyl, octahydroisoindolyl, decahydroisoquinolyl, tetrahydrofuryl, 1,4-dioxa-8-azaspiro[4.5]decan-8-yl and tetrahydropyranyl, and the N-oxide derivatives thereof.

"Heterocyclylalkyl" means a heterocyclyl group appended to a parent moiety via an alkyl group, as defined herein. Examples of heterocyclylalkyl groups include, but are not limited to, morpholin-4-ylmethyl, 2-(morpholin-4-yl)ethyl, morpholin-2-ylmethyl, 2-(morpholin-2-yl)ethyl, morpholin-3-ylmethyl, 2-(morpholin-3-yl)ethyl, piperazin-1-ylmethyl, 2-(piperazin-1-yl)ethyl, piperidin-1-ylmethyl, 2-(piperidin-1-yl)ethyl, piperidin-2-ylmethyl, 2-(piperidin-2-yl)ethyl, piperidin-4-ylmethyl, 2-(piperidin-4-yl)ethyl, pyrrolidin-1-ylmethyl, 2-(pyrrolidin-1-yl)ethyl, pyrrolidin-2-ylmethyl, 2-(pyrrolidin-2-yl)ethyl.

"Hydroxyalkyl" means an alkyl group, as defined herein, substituted with at least one, for example one, two, or three, hydroxy group(s), provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylbutyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl, 2-(hydroxymethyl)-3-hydroxypropyl, 2-hydroxyethylene, 2,3-dihydroxypropyl, 1-(hydroxymethyl)-2-hydroxyethyl, and the like.

The term "optionally substituted" means the substitution may or may not occur and includes instances where said substitution occurs and instances in which it does not. One of ordinary skill in the art would understand that with respect to any molecule described as containing one or more substituents, only sterically practical and/or synthetically feasible compounds are meant to be included. Unless otherwise specified in this specification, when a variable is said to optionally substituted or substituted with a substituent(s), this is to be understood that this substitution occurs by replacing a hydrogen that is covalently bound to the variable with one these substituent(s). This meaning shall apply to all variables that are stated to be substituted or optionally substituted in the specification. For instance, when it is stated that variable $R^C$ can be optionally substituted with $R^{C10}$, this means that this substitution, when it occurs, takes place by replacing a hydrogen that is covalently bound to $R^C$ with $R^{C10}$. Other non-limiting examples of variables that are described in certain instances in the specification as being optionally substituted or substituted with various substituents include, but are not limited to, $R^{D1}$, A groups, B groups, and $R^5$.

"Saturated bridged ring system" refers to a bicyclic or polycyclic ring system that is not aromatic. Such a system may contain isolated or conjugated unsaturation, but not aromatic or heteroaromatic rings in its core structure (but may have aromatic substitution thereon). For example, hexahydro-furo[3,2-b]furan, 2,3,3a,4,7,7a-hexahydro-1H-indene, 7-aza-bicyclo[2.2.1]heptane and 1,2,3,4,4a,5,8,8a-octahydro-naphthalene are all included in the class "saturated bridged ring system."

"Spiro ring" refers to a ring originating from a particular annular carbon of another ring. For example, as depicted below:

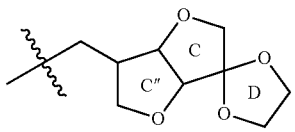

a ring atom of a saturated bridged ring system (rings C and C'), but not a bridgehead atom, can be a shared atom between the saturated bridged ring system and a spiro ring (ring D) attached thereto. A representative example of a spiro ring system is 2,3-dioxa-8-azaspiro[4.5]decan-8-yl.

"Isomers" means compounds having identical molecular formulae but differing in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are nonsuperimposable minor images are termed "enantiomers" or sometimes "optical isomers." A carbon atom bonded to four nonidentical substituents is termed a "chiral center." A compound with one chiral center has two enantiomeric forms of opposite chirality is termed a "racemic mixture." A compound that has more than one chiral center has $2^{n-1}$ enantiomeric pairs, where n is the number of chiral centers. Compounds with more than one chiral center may exist as ether an individual diastereomer or as a mixture of diastereomers, termed a "diastereomeric mixture." When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry," 3rd edition, March, Jerry, John Wiley & Sons, New York, 1985). The names and illustration used in this application to describe compounds of the invention, unless indicated otherwise, are meant to be encompassed all possible stereoisomers and any mixture, racemic or otherwise, thereof.

The present invention also includes N-oxide derivatives of the compounds of the invention. N-oxide derivatives mean derivatives of compounds of the invention in which nitrogens are in an oxidized state (i.e., N→O), e.g., pyridine N-oxide, and which possess the desired pharmacological activity.

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" 8.sup.th Ed., Pergamon Press, gilman et al. (eds), 1990 for a discussion of biotransformation). As used herein, the metabolite of a compound of the invention or its salt may be the biologically active form of the compound in the body. In one example, a prodrug may be used such that the biologically active form, a metabolite, is released in vivo. In another example, a biologically active metabolite is discovered serendipitously, that is, no prodrug design per se was under-taken. An assay for activity of a metabolite of a compound of the present invention is known to one of skill in the art in light of the present disclosure.

"Patient" and "subject" for the purposes of the present invention includes humans and other animals, particularly mammals, and other organisms. Thus the methods are applicable to both human therapy and veterinary applications. In another embodiment the patient is a mammal, and in another embodiment the patient is human.

Polyethylene glycol (PEG) are polymers of ethylene oxide. Polyethylene glycol refers to the polymer with molecular weight less than 50,000. A polymer is made by joining molecules of ethylene oxide and water together in a repeating pattern. Polyethylene glycol has the following structure: —(CH$_2$—CH$_2$—O)n—

A "pharmaceutically acceptable salt" of a compound means a salt that is pharmaceutically acceptable and that possesses the desired pharmacological activity of the parent compound. It is understood that the pharmaceutically acceptable salts are non-toxic. Additional information on suitable pharmaceutically acceptable salts can be found in *Remington's Pharmaceutical Sciences*, 17$^{th}$ ed., Mack Publishing Company, Easton, Pa., 1985, which is incorporated herein by reference or S. M. Berge, et al., "Pharmaceutical Salts," J. Pharm. Sci., 1977; 66:1-19 both of which are incorporated herein by reference. It is also understood that the compound can have one or more pharmaceutically acceptable salts associated with it.

Examples of pharmaceutically acceptable acid addition salts include those formed with inorganic acids such as hydrochloric acid, hydrobromic acid, sulfuric acid, nitric acid, phosphoric acid, and the like; as well as organic acids such as acetic acid, trifluoroacetic acid, propionic acid, hexanoic acid, cyclopentanepropionic acid, glycolic acid, pyruvic acid, lactic acid, oxalic acid, maleic acid, malonic acid, succinic acid, fumaric acid, tartaric acid, citric acid, benzoic acid, cinnamic acid, 3-(4-hydroxybenzoyl)benzoic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, p-toluenesulfonic acid, salicylic acid and the like.

Examples of a pharmaceutically acceptable base addition salts include those formed when an acidic proton present in the parent compound is replaced by a metal ion, such as sodium, potassium, lithium, ammonium, calcium, magnesium, iron, zinc, copper, manganese, aluminum salts and the like. Preferable salts are the ammonium, potassium, sodium, calcium and magnesium salts. Salts derived from pharmaceutically acceptable organic non-toxic bases include, but are not limited to, salts of primary, secondary and tertiary amines, substituted amines including naturally occurring substituted amines, cyclic amines and basic ion exchange resins. Examples of organic bases include isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, tromethamine, N-methylglucamine, polyamine resins, and the like. Exemplary organic bases are isopropylamine, diethylamine, ethanolamine, trimethylamine, dicyclohexylamine, choline, and caffeine.

Pharmaceutically acceptable salts, as defined above, do not include quaternary ammonium moieties. Pharmaceutically acceptable salts, as defined above, are acid addition or base addition salts, which are ionic in nature. The quaternary ammonium moieties, which are cations, in this disclosure are positively charged polyatomic ions of the structure $NR^4+$ with R being alkyl groups. Unlike the ammonium ion ($NH^4+$) and the primary, secondary, or tertiary ammonium cations, the quaternary ammonium cations are permanently charged, independent of the pH of their solution. The compounds of Formula I or Formula VIII, and all embodiments thereof, are quaternary ammonium moieties, and these are separate and distinct from pharmaceutically acceptable salts.

"Prodrug" refers to compounds that are transformed (typically rapidly) in vivo to yield the parent compound of the above formulae, for example, by hydrolysis in blood. Aommon examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides and secondary and tertiary alkyl amides (for example with between about one and about six carbons). Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Therapeutically effective amount" is an amount of a compound of the invention, that when administered to a patient, effectively treats the disease. The amount of a compound of the invention which constitutes a "therapeutically effective amount" will vary depending upon a sundry of factors including the activity, metabolic stability, rate of excretion and duration of action of the compound, the age, weight, general health, sex, diet and species of the patient, the mode and time of administration of the compound, the concurrent administration of adjuvants or additional therapies and the severity of the disease for which the therapeutic effect is sought. The therapeutically effective amount for a given circumstance can be determined without undue experimentation.

"Treating" or "treatment" of a disease, disorder, or syndrome, as used herein, includes (i) preventing the disease, disorder, or syndrome from occurring in a human, i.e., causing the clinical symptoms of the disease, disorder, or syndrome not to develop in an animal that may be exposed to or predisposed to the disease, disorder, or syndrome but does not yet experience or display symptoms of the disease, disorder, or syndrome; (ii) inhibiting the disease, disorder, or syndrome, i.e., arresting its development; and (iii) relieving the disease, disorder, or syndrome, i.e., causing regression of the disease, disorder, or syndrome. As is known in the art, adjustments for systemic versus localized delivery, the age, weight, general health, sex, diet and species of the patient, the mode and time of administration of the compound, the concurrent administration of adjuvants or additional therapeutically active ingredients and the severity of the disease for which the therapeutic effect is sought may be necessary, and will be ascertainable with routine experimentation.

The examples and scheme below depict the general synthetic procedure for the compounds disclosed herein. Synthesis of the compounds of Formulae I or VIII disclosed herein, and embodiments thereof, are not limited by these examples and schemes. One skilled in the art will know that other procedures can be used to synthesize the compounds of Formulae I or VIII disclosed herein, and that the procedures described in the examples and schemes is only one such procedure. In the descriptions below, one of ordinary skill in the art would recognize that specific reaction conditions, added reagents, solvents, and reaction temperatures can be modified for the synthesis of specific compounds that fall within the scope of this disclosure. All intermediate compounds described below, for which there is no description of how to synthesize such intermediates within these examples below, are commercially available compounds unless otherwise specified.

Synthesis

In the following general methods, $L^D$, X, $R^2$, $R^1$, $R^4$, $R^8$, $R^{410}$, $R^{D1}$, $R^{D10}$, $R^{D11}$, and $R^Y$ are as previously defined for a compound of formula (I) and VIII, and embodiments thereof, unless otherwise stated. The following abbreviations and acronyms are used herein, When $L^D$ represents —SCH$_2$— and X represents =C(H)—, then compounds of formula (I$^4$) may be prepared as depicted in Scheme 1.

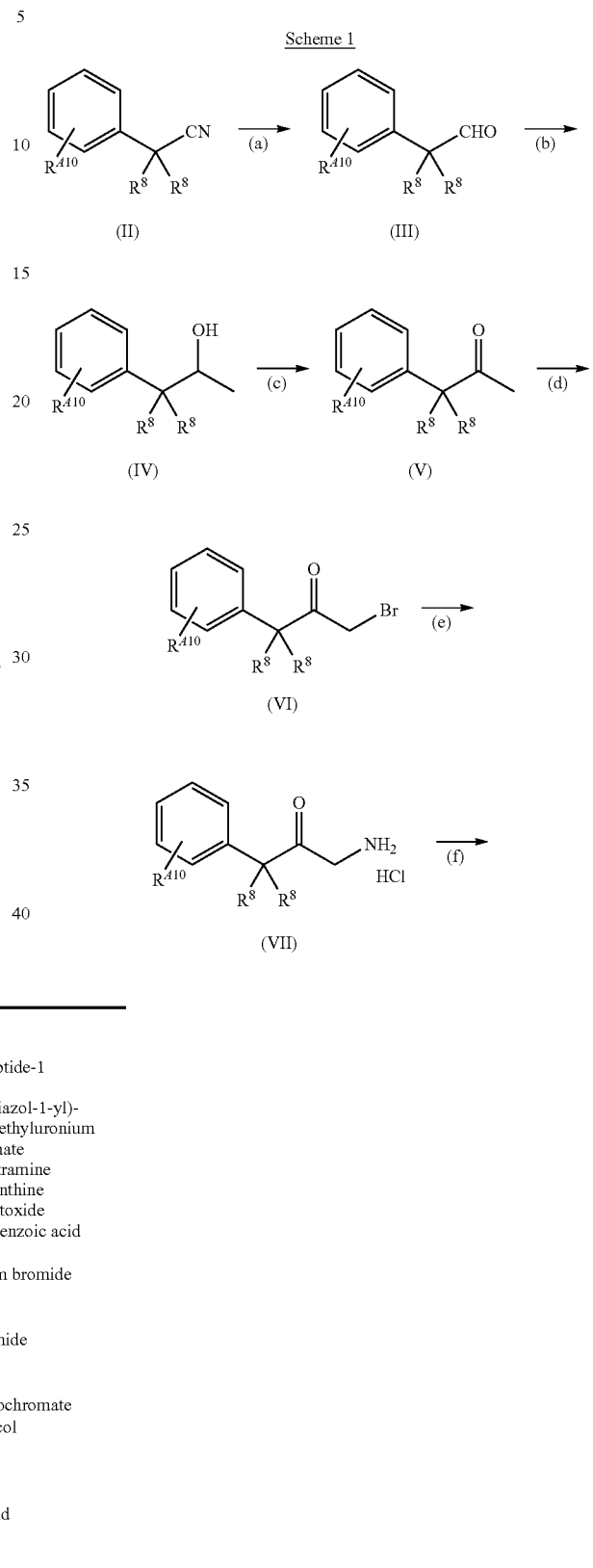

| AcOH or HOAc | acetic acid | Et$_3$N | triethylamine |
|---|---|---|---|
| AIBN | azobisisobutyronitrile | GLP-1 | glucagon-like peptide-1 |
| cAMP | cyclic adenosine monophosphate | Hex | hexane |
| CD-FBS | charcoal-dextran-treated fetal bovine serum | HATU | O-(7-Azabenzotriazol-1-yl)-N,N,N',N'-tetramethyluronium hexafluorophosphate |
| CMC | carboxymethyl cellulose | HMTA | hexamethylenetetramine |
| conc. | concentrated | IBMX | isobutylmethylxanthine |
| DCM | dichloromethane | KOtBu | potassium tert-butoxide |
| DIBAH | diisobutylaluminum hydride | mCPBA | m-chloroperoxybenzoic acid |
| DIPEA | diisopropylethylamine | MeCN | acetonitrile |
| DMEM | Dulbecco's modified essential medium | MeMgBr | methylmagnesium bromide |
| DMF | N,N-dimethylformamide | MeOH | methanol |
| DMSO | dimethylsulfoxide | NBS | N-bromosuccinimide |
| DPBS | Dulbecco's Phosphate Buffered Saline | OAc | acetate |
| DPP-IV | dipeptidyl peptidase IV | PCC | pyridinium chlorochromate |
| EDTA | ethylenediaminetetraacetic acid | PEG | polyethylene glycol |
| Et$_2$O | diethyl ether | PG | protecting group |
| EtOAc | ethyl acetate | satd | saturated |
| EtOH | ethanol | STC-1 | stanniocalcin 1 |
| FAF-BSA | Fatty acid-free bovine serum albumin | TFA | trifluoroacetic acid |
| FBS | fetal bovine serum | THF | tetrahydrofuran |

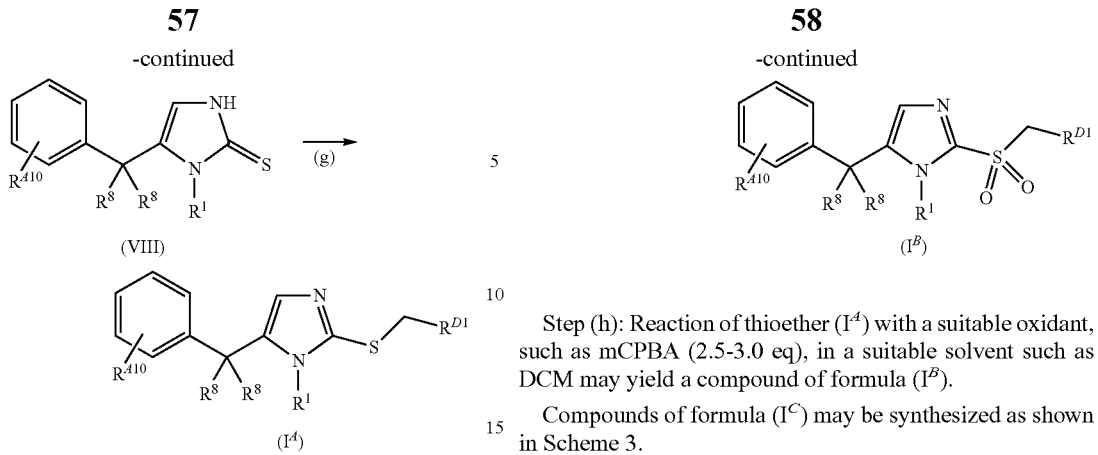

Compounds of formula (II) are commercially available or may be prepared from known compounds using standard methodologies as exemplified in the preparations below.

Step (a): An aldehyde of formula (III) may be prepared by reaction of nitrile (II) with diisobutylaluminum hydride in a suitable solvent, such as THF.

Step (b): Formation of carbinol (IV) may be achieved by treatment of aldehyde (III) with methylmagnesium bromide in a suitable solvent, such as diethyl ether or THF.

Step (c): Conversion of carbinol (IV) to ketone (V) may occur under standard conditions, such as the Swern oxidation—known to one trained in the art of chemistry.

Step (d): Bromoketone (VI) may be prepared by bromination of ketone (V) under typical conditions, such as with tetrabutylammonium tribromide in 1:2 mixture of MeOH-DCM.

Step (e): Reaction of bromoketone (VI) with sodium azide in a suitable solvent, such as DMF, followed by reduction of the resulting azido-ketone under standard conditions, such as with zinc dust and hydrochloric acid in THF, may afford amino-ketone hydrochloride (VII).

Step (f): Isothiocyanate $R^1$NCS may react with amino-ketone hydrochloride (VII) in a suitable solvent, such as DCM or toluene, and in the presence of a base, such as triethylamine, at elevated temperature to yield the corresponding thiourea, which may condense upon treatment with HOAc at elevated temperature to give a compound of formula (VIII).

Step (g): Alkylation of imidazol-2-thione (VIII) with an electrophile $R^{D1}CH_2Br$ in a suitable solvent, such as acetone or MeCN, and in the presence of a base, such as potassium carbonate, may afford a compound of formula ($I^A$).

Compounds of formula ($I^B$) may be prepared as shown in Scheme 2.

Step (h): Reaction of thioether ($I^A$) with a suitable oxidant, such as mCPBA (2.5-3.0 eq), in a suitable solvent such as DCM may yield a compound of formula ($I^B$).

Compounds of formula ($I^C$) may be synthesized as shown in Scheme 3.

Scheme 3

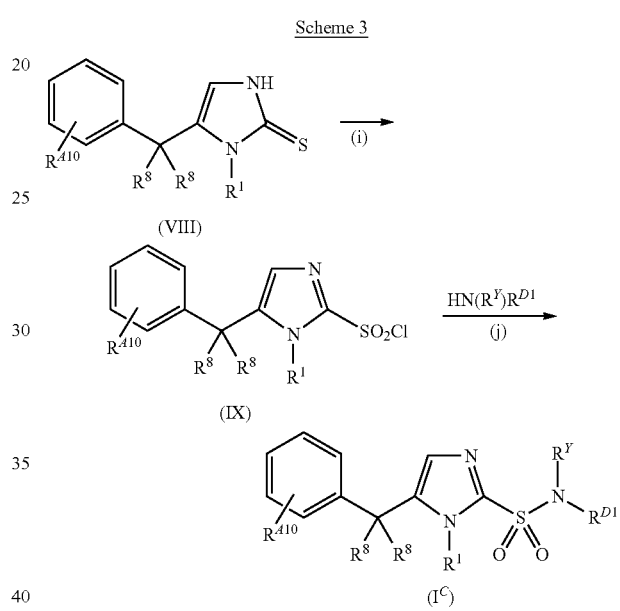

Step (i): Thione ($I^A$) may be converted to the corresponding sulfonyl chloride (IX) under standard conditions, such as adding NaOCl (3 eq) to thione ($I^A$) in a 1:1 mixture of DCM and 1N HCl at reduced temperature, preferably below 0° C.

Step (j): Compounds of formula ($I^C$) may be prepared by reaction of amine $HN(R^Y)R^{D1}$ with sulfonyl chloride (IX) in a suitable solvent, such as DCM, and in the presence of a base, such as triethylamine.

Compounds of formula ($I^D$) may be synthesized as depicted in Scheme 4.

Scheme 2

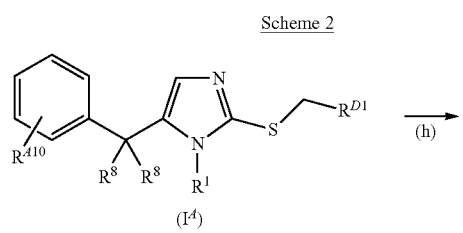

Scheme 4

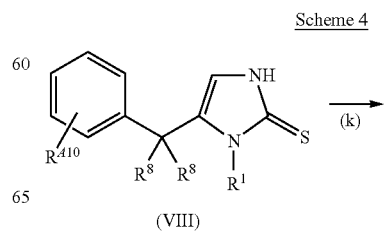

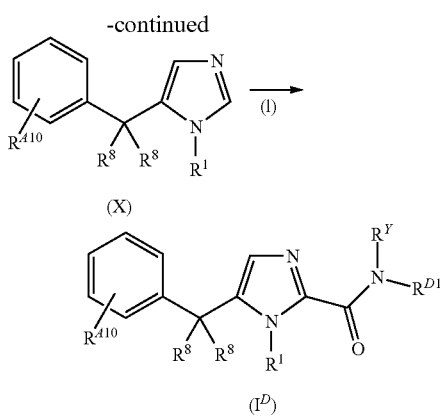

Step (k): Thione (VIII) may undergo desulfurization under standard conditions, such as with $H_2O_2$ in a mixture of HOAc-DCM, to afford imidazole (X).

Step (l): Reaction of imidazole (X) with butyllithium in a suitable solvent (e.g. THF) at reduced temperature, preferably at −78° C. for 30-40 minutes, may yield the corresponding organolithium, which may react with a suitable electrophile (e.g. isocyanate or carbamoyl chloride) at the same temperature to afford a compound of formula ($I^D$).

Compounds of formulae ($I^E$) and ($I^F$) may be prepared as shown in Scheme 5.

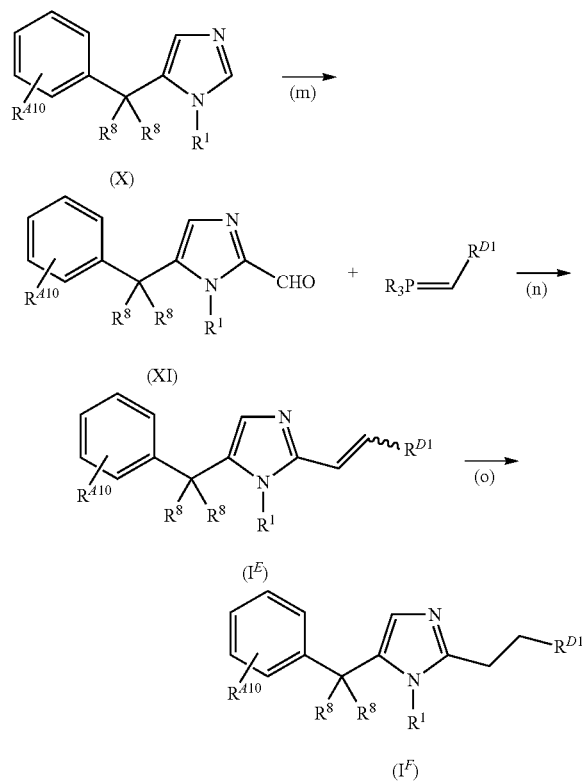

Step (m): Imidazole (X) may be converted to the corresponding organolithium, as described previously, and then treated with DMF, preferably at −78° C. for 30-40 minutes, to yield aldehyde (XI).

Step (n): Compounds of formula ($I^E$) may be prepared by reaction of aldehyde (XI) with a phosphorus ylide under Wittig or Horner-Emmons conditions—both known to one skilled in the art of chemistry.

Step (o): Compounds of formula ($I^F$) may be prepared by catalytic hydrogenolysis of alkene ($I^E$) under standard conditions, such as in MeOH under 50-60 psi of hydrogen and over $PtO_2$ (10-20 mole %).

Compounds of formula ($I^G$), wherein Y is chosen from $NR^Y$, O or S, may be prepared as depicted in Scheme 6.

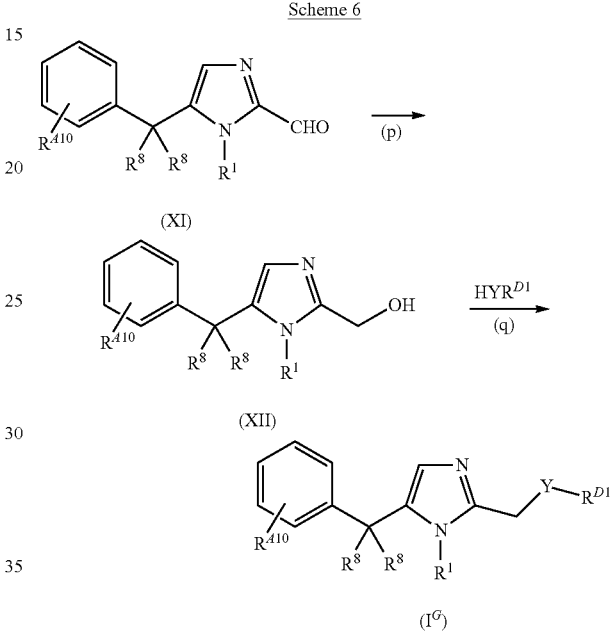

Step (p): Reduction of aldehyde (XI) using standard conditions, such as $NaBH_4$ in EtOH at ambient temperature, may afford the corresponding carbinol (XII).

Step (q): Compounds of formula ($I^G$) may be prepared from carbinol (XII) and a suitable nucleophile $HYR^{D1}$, such as a phenol or thiophenol wherein Y represents O or S, respectively, and $R^{D1}$ is aryl, under Mitsunobu conditions—known to one skilled in the art. Alternatively carbinol (XII) may be converted to the corresponding chloride, for example, by treatment with thionyl chloride (2 eq) in chloroform, followed by reaction with a suitable nucleophile $HYR^{D1}$ in MeCN (or acetone) and in the presence of a base (e.g. $K_2CO_3$) to yield compounds of formula ($I^G$).

Compounds of formula ($I^H$), wherein $R^4$ is chosen from Br, Cl or F, may be prepared as shown in Scheme 7.

Scheme 7

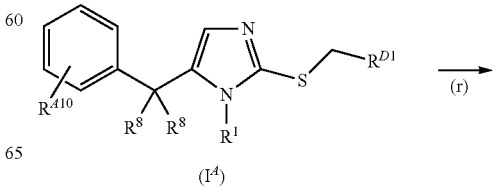

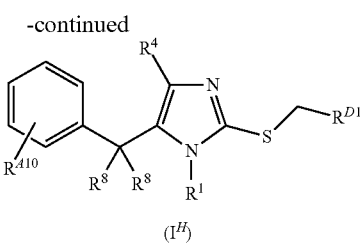

(I^H)

Step (r): Compounds of the formula (I^H) may be prepared from imidazole (I^A) by treatment with a suitable halogen source such as, for example, N-bromosuccinimide in DCM. N-chlorosuccinimide and Selectfluor™ in a suitable solvent, such as DCM or MeCN, may be used to generate the corresponding chloro- and fluoro-substituted compounds (I^H), respectively.

When $L^D$ represents —SCH$_2$— and X is N, then compounds of formula (I^J) may be synthesized as depicted in Scheme 8.

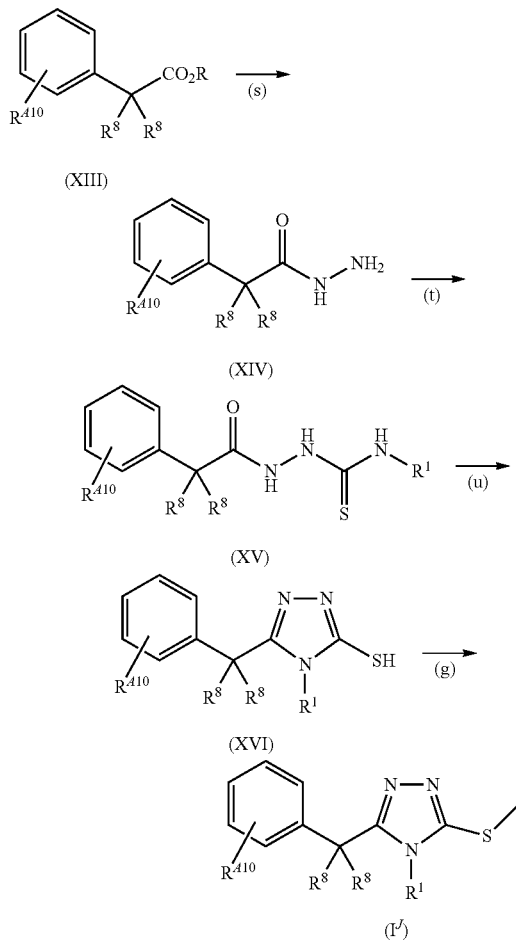

Compounds of formula (XIII) are commercially available or may be prepared from known compounds using standard methodologies.

Step (s): Ester (XIII), wherein R represents alkyl (e.g. methyl), may react with hydrazine in a suitable solvent, such as MeOH, at elevated temperature and in a sealed vessel to yield hydrazide (XIV). Alternatively acid (XIII), wherein R is H, may be converted to its hydrazide (XIV) under standard conditions—known to one skilled in the art.

Step (t): Hydrazide (XIV) may react with isothiocyanate R$^1$NCS in a suitable solvent, such as EtOH, at elevated temperature, preferably at reflux, to generate thiourea (XV).

Step (u): Reaction of thiourea (XV) under basic conditions, such as in 5-10% aqueous NaOH at elevated temperature, preferably at reflux, may condense to yield thiol (XVI).

Next compounds of formula (I^J) may be prepared from thiol (XVI) under conditions previously described in step (g).

Compounds of formula (I^K) may be prepared as depicted in Scheme 9.

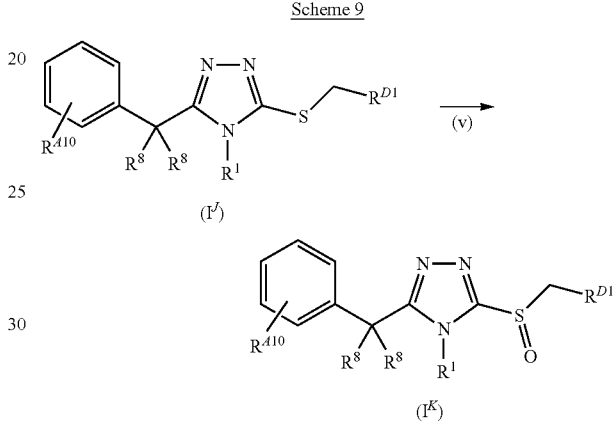

Step (v): Reaction of thioether (I^J) with a suitable oxidant, such as mCPBA (1-1.1 equiv) in DCM, may yield compounds of formula (I^K).

Compounds of formula (I^L), wherein R$^8$ is H, may be prepared as depicted in Scheme 10.

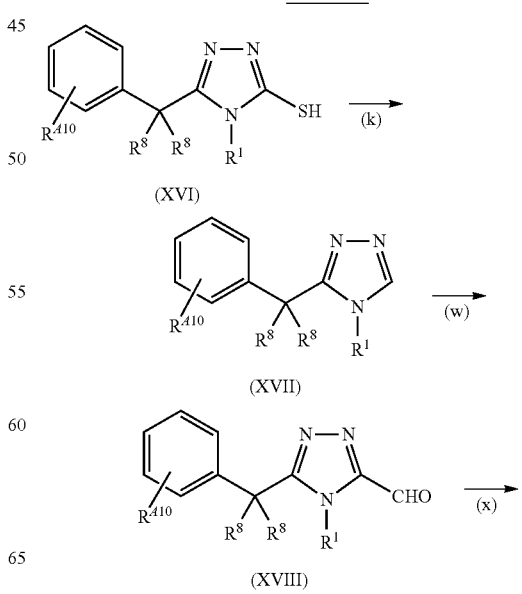

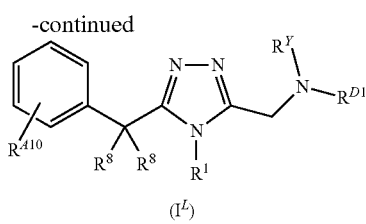

(I$^L$)

Under conditions previously described in step (k), thiol (XVI) may undergo de-sulfurization to afford triazole (XVII).

Step (w): Hydroxymethylation of triazole (XVII) may proceed under standard conditions, such as with paraformaldehyde in toluene heated at reflux, to afford the corresponding hydroxymethyltriazole, which may undergo oxidation upon treatment with a suitable oxidant, such as $MnO_2$, in THF to yield the corresponding aldehyde (XVIII).

Step (x): Reaction of aldehyde (XVIII) with amine $HN(R^Y)R^{D1}$ under typical reductive amination conditions, such as with $NaB(OAc)_3H$ in a suitable solvent, may give compounds of formula (I$^L$).

Compounds of formula (I$^M$), wherein Y is chosen from $NR^Y$, O or S, may be prepared as depicted in Scheme 11.

Scheme 11

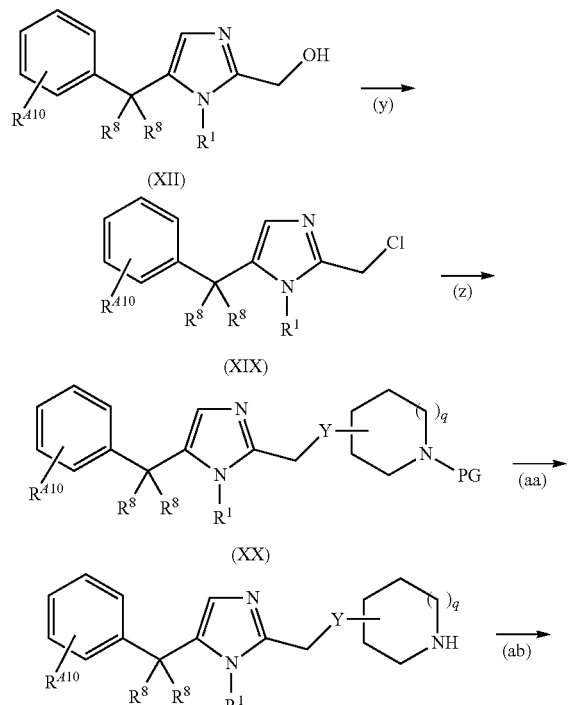

Step (y): Chlorination of carbinol (XII) using standard conditions, such as thionyl chloride in chloroform, may afford the corresponding intermediate (XIX).

Step (z): Treatment of intermediate (XIX) with an appropriately protected amino-alcohol (Y=O) or diamine (Y=NR$^Y$) under standard conditions may yield the corresponding amine (XX).

Step (aa): Deprotection of amine (XX) under typical conditions, such as using trifluoroacetic acid in DCM to remove a tert-butyl carbamate group (PG), may afford the free amine (XXI).

Step (ab): Reaction of amine (XXI) with a sulfonyl chloride in a suitable solvent and with a base (e.g. $Et_3N$) may give compounds of formula (I$^M$).

Compounds of formula (I$^N$), wherein Y is chosen from $NR^Y$, O or S, may be prepared as depicted in Scheme 12.

Scheme 12

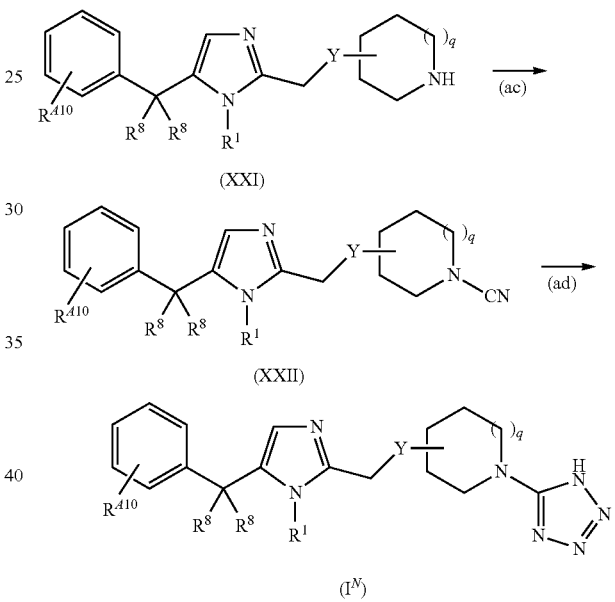

Step (ac): Reaction of amine (XXI) with cyanogen bromide in a suitable solvent and with a base (e.g. $Et_3N$) may yield the corresponding N-cyanoamine (XXII).

Step (ad): Treatment of cyanoamine (XXII) with sodium azide and ammonium chloride in a suitable solvent, such as DMF, may give compounds of formula (I$^N$).

Compounds of formula (I$^O$) may be prepared as shown in Scheme 13.

Scheme 13

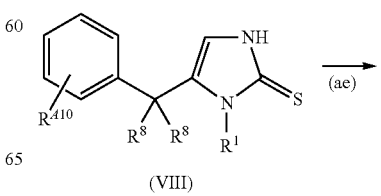

(VIII)

-continued

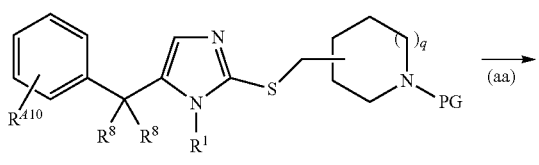

(XXIII)

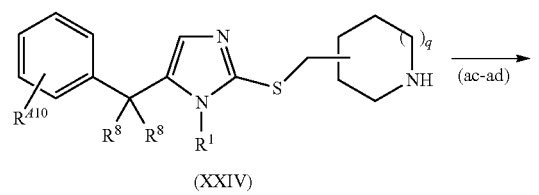

(XXIV)

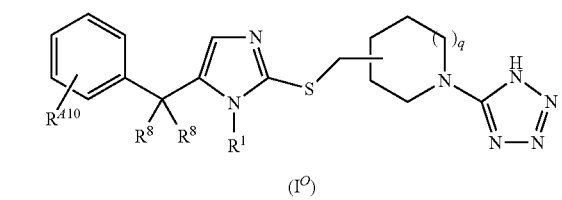

(I$^O$)

Step (ae): Alkylation of imidazol-2-thione (VIII) with an electrophile R$^{D1}$CH$_2$Br, wherein R$^{D1}$ is a protected cyclic amine, in a suitable solvent (e.g. acetone) and with a base (e.g. potassium carbonate) may afford the corresponding intermediate (XXIII).

Step (aa): Deprotection of intermediate (XXIII) under conditions previously described in step (aa) may give amine (XXIV).

Steps (ac) to (ad): Under conditions previously described in steps (ac) and (ad), amine (XXIV) may undergo sequential transformation to yield compounds of formula (I$^O$).

Compounds of formula (I$^P$) may be prepared as shown in Scheme 14.

Scheme 14

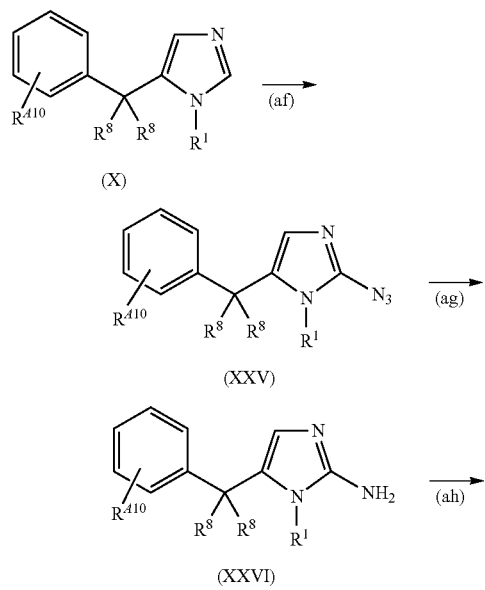

-continued

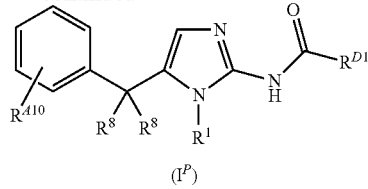

(I$^P$)

Step (af): Imidazole (X) may be converted to the corresponding organolithium, as described previously, and then treated with tosyl azide in a suitable solvent (e.g. THF), preferably at −78° C. for 30 minutes, to yield azide (XXV).

Step (ag): Azide (XXV) may undergo catalytic hydrogenation under standard conditions, such as with a suitable palladium catalyst, preferably Lindlar catalyst, under hydrogen at ambient pressure, to give amine (XXVI).

Step (ah): Reaction of amine (XXVI)2 with an acid chloride in a suitable solvent (e.g. DCM) and with a base (e.g. pyridine) may afford compounds of formula (I$^P$).

Compounds of formula (I$^Q$), for example, wherein R$^4$ is chosen from aryl or heteroaryl, may be prepared as shown in Scheme 15.

Scheme 15

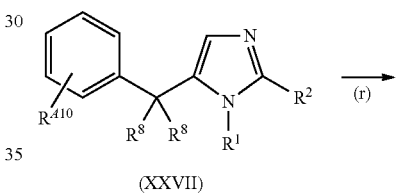

(XXVII)

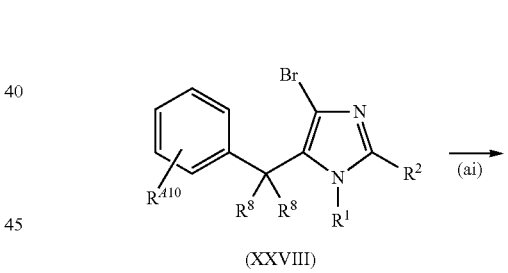

(XXVIII)

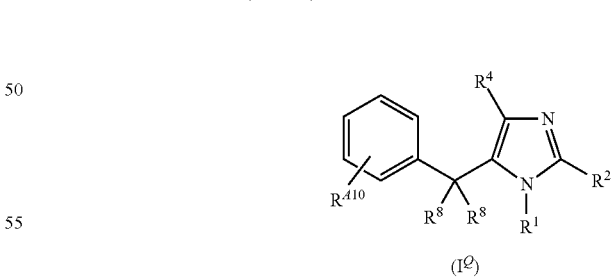

(I$^Q$)

Step (r): Under conditions previously described in step (r), imidazole (XXVII) may be brominated to give bromoimidazole (XXVIII).

Step (ai): Compounds of the formula (I$^Q$) may be prepared from bromoimidazole (XXVIII) using standard cross-coupling conditions, such as with suitable boronic acids under Suzuki conditions known to one skilled in the art of chemistry.

Compounds of formula ($I^R$) may be prepared as depicted in Scheme 16.

Scheme 16

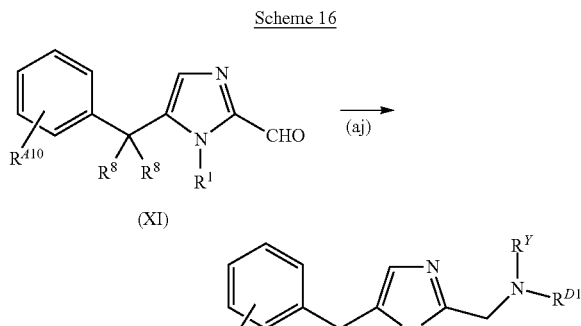

Step (aj): Reaction of aldehyde (XI) and a suitable amine $HN(R^Y)R^{D1}$ under standard reductive amination conditions, such as with toluene sulfonic acid followed by sodium borohydride in EtOH at ambient temperature, may afford compounds of formula ($I^R$).

Compounds of formula ($I^S$) may be prepared as depicted in Scheme 17.

Scheme 17

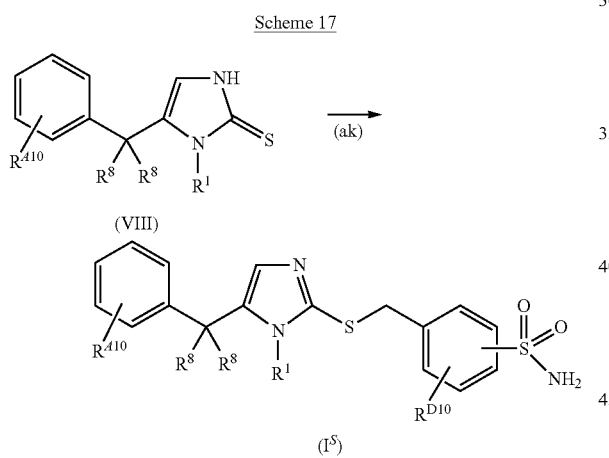

Step (ak): Alkylation of imidazol-2-thione (VIII) with an electrophile $R^{D1}CH_2Br$, wherein $R^{D1}$ is a benzenesulfonamide, in a suitable solvent (e.g. acetone) and with a base (e.g. potassium carbonate) may afford compounds of formula ($I^S$).

Compounds of formula ($I^T$) may be prepared as depicted in Scheme 18.

Scheme 18

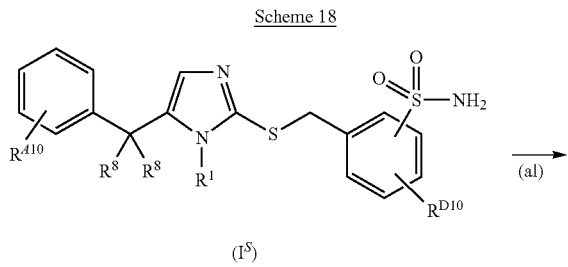

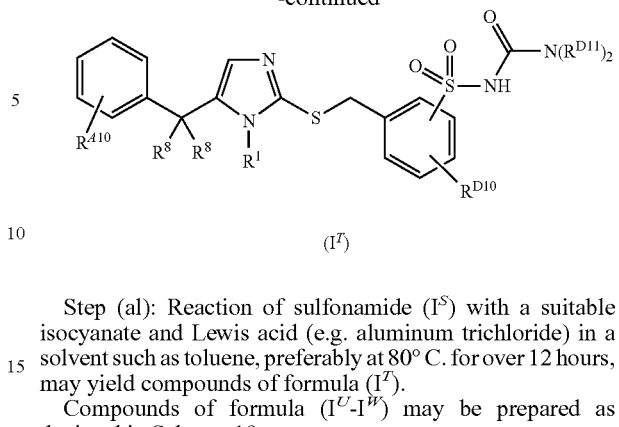

Step (al): Reaction of sulfonamide ($I^S$) with a suitable isocyanate and Lewis acid (e.g. aluminum trichloride) in a solvent such as toluene, preferably at 80° C. for over 12 hours, may yield compounds of formula ($I^T$).

Compounds of formula ($I^U$-$I^W$) may be prepared as depicted in Scheme 19.

Scheme 19

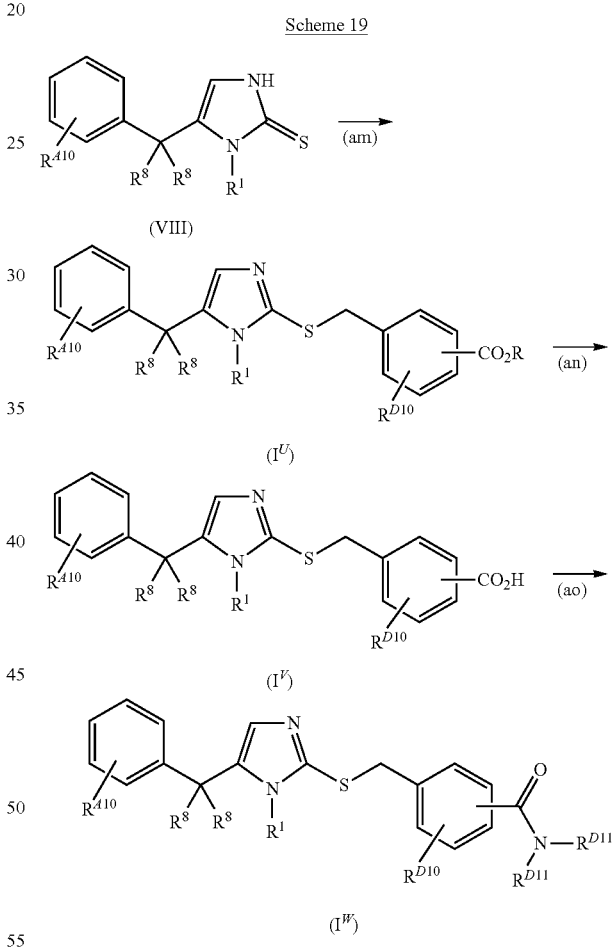

Step (am): Alkylation of imidazol-2-thione (VIII) with an electrophile $R^{D1}CH_2Br$, wherein $R^{D1}$ is a benzoate ester, in a suitable solvent (e.g. acetone) and with a base (e.g. potassium carbonate) may afford compounds of formula ($I^U$).

Step (an): Hydrolysis of ester ($I^U$) may proceed under standard conditions, e.g. NaOH in aqueous methanol, to afford compounds of formula ($I^V$).

Step (ao): Conversion of acid ($I^V$) to compounds of formula ($I^W$) may occur under standard peptide coupling conditions, e.g. upon addition of an amine $HN(R^{D11})_2$ and coupling agent HATU in a suitable solvent, such as DCM or DMF.

Compounds of formula (I^X-I^Y) may be prepared as depicted in Scheme 20.

Scheme 20

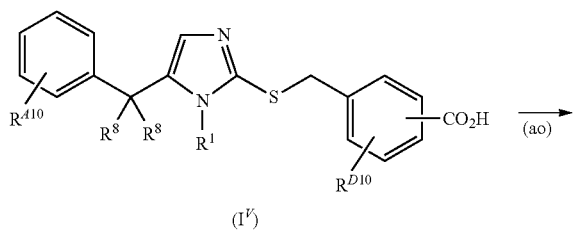

(I^V)

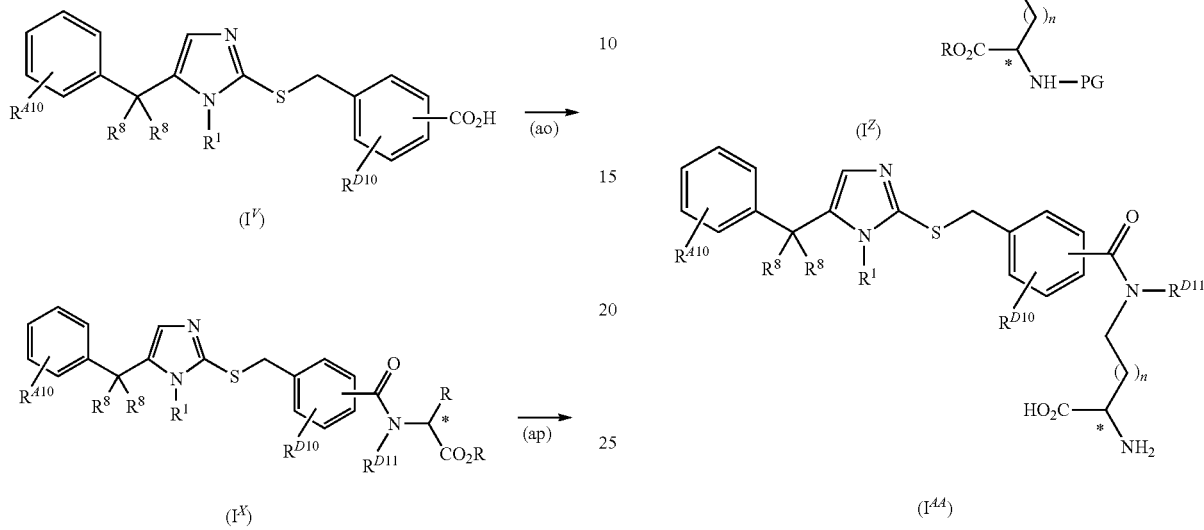

Under conditions previously described in step (ao), acid (I^V) may be treated with a suitably protected amino ester (e.g. Alanine methyl ester) and HATU in DCM to afford compounds of formula (I^Y).

Step (ap): Hydrolysis of ester (I^X) may proceed under standard conditions, e.g. LiOH in a THF-water mixture, to afford compounds of formula (I^Y).

Compounds of formula (I^Z-I^AA) may be synthesized as shown in Scheme 21.

Scheme 21

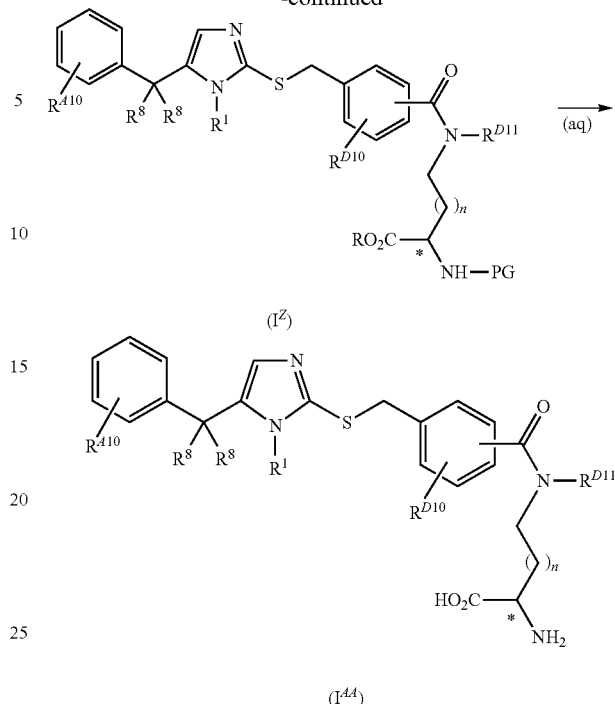

Under conditions previously described in step (ao), acid (I^V) may be treated with a suitably protected amino ester, such as one derived from Ornithine (wherein n=2), and HATU in DCM to afford compounds of formula (I^Z).

Step (aq): Hydrolysis of ester (I^X) and deprotection of the amine moiety may proceed under standard conditions, e.g. HCl in dioxane (wherein R=tert-butyl and PG=BOC), to afford compounds of formula (I^AA).

Compounds of formula (I^AB) may be synthesized as shown in Scheme 22.

Scheme 22

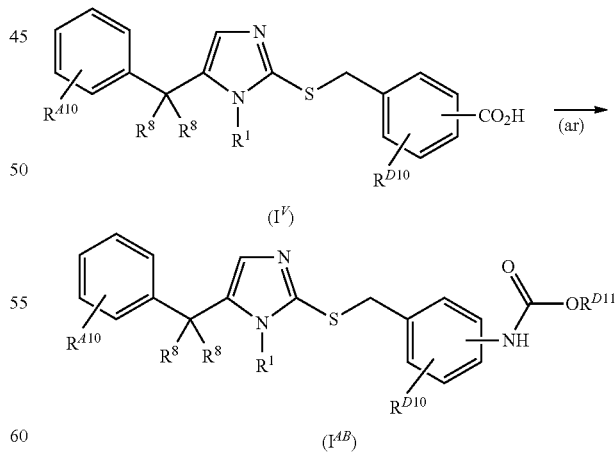

Step (ar): Under typical Curtius rearrangement conditions, acid (I^V) may react with diphenylphosphoryl azide, a suitable alcohol (e.g. tert-butanol), an organic base (e.g. Et_3N) and toluene at elevated temperature, preferably 80 to 100° C., to yield compounds of formula (I^AB).

Compounds of formula (I$^{AC}$-I$^{AD}$) may be synthesized as shown in Scheme 23.

Scheme 23

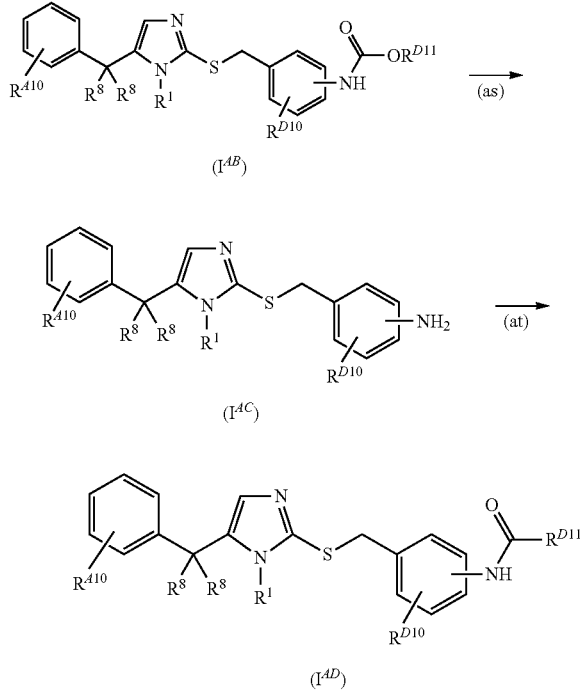

(I$^{AB}$)

(I$^{AC}$)

(I$^{AD}$)

Step (as): Deprotection of carbamate (I$^{AB}$), wherein R$^{D11}$ is tert-butyl, may occur under standard conditions, such as with 1:1 TFA-DCM, to give compounds of formula (I$^{AC}$).

Step (at): Amine (I$^{AC}$) may react with acid chlorides in the presence of a base, such as Et$_3$N, to afford compounds of formula (I$^{AD}$).

Compounds of formula (I$^{AE}$-I$^{AF}$) may be synthesized as shown in Scheme 24.

Scheme 24

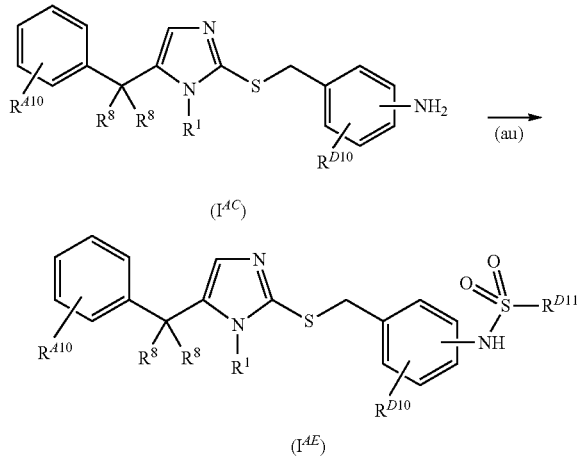

(I$^{AC}$)

(I$^{AE}$)

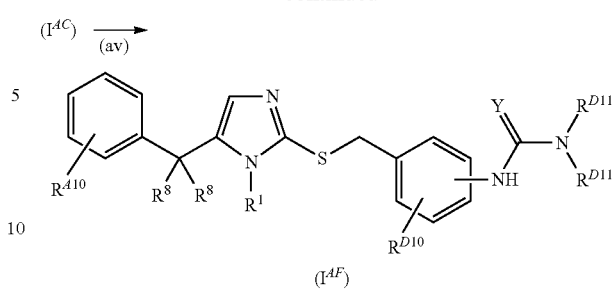

(I$^{AF}$)

Step (au): Amine (I$^{AC}$) may react with sulfonyl chlorides in the presence of a base, such as Et$_3$N, to afford compounds of formula (I$^{AE}$).

Step (au): Amine (I$^{AC}$) may react with isocyanates or isothiocyanates in the presence of a base, such as Et$_3$N, to afford compounds of formula (I$^{AF}$), wherein Y is O or S, respectively.

Compounds of formula (I$^{AG}$) may be synthesized as shown in Scheme 25.

Scheme 25

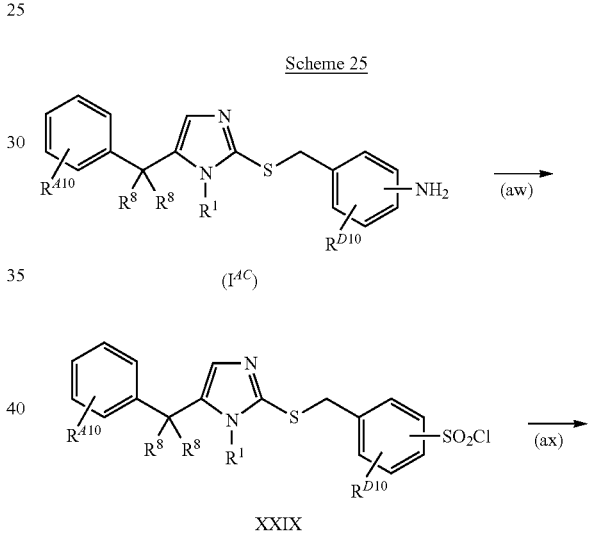

(I$^{AC}$)

XXIX (I$^{AG}$)

Step (aw): Amine (I$^{AC}$) may undergo diazotization under typical conditions, such as with aqueous sodium nitrite, and then may be converted to the corresponding sulfonyl chloride (XXIX) upon reaction with a mixture of copper (II) chloride, sulfur dioxide, HCl and HOAc.

Step (ax): Sulfonyl chloride (XXIX)$_2$ may react with an amine HN(R$^{D11}$)$_2$ in the presence of a base, such as K$_2$CO$_3$, to afford compounds of formula (I$^{AG}$). In addition, ammonia may react with sulfonyl chloride (XXIX) to yield a sulfonamide (I$^{AG}$), wherein both R$^{D11}$ are H.

Compounds of formula (I^AQ) may be prepared as depicted in Scheme 26.

Scheme 26

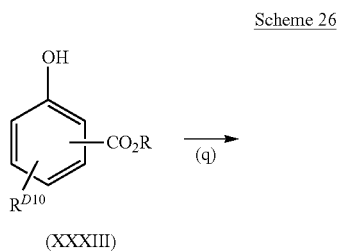

(XXXIII)

Under conditions previously described in step (q), phenol (XXXIII) may react with carbinol (XII) to afford compounds of formula (I^AQ).

Compounds of formula (I^AR) may be prepared as depicted in Scheme 27.

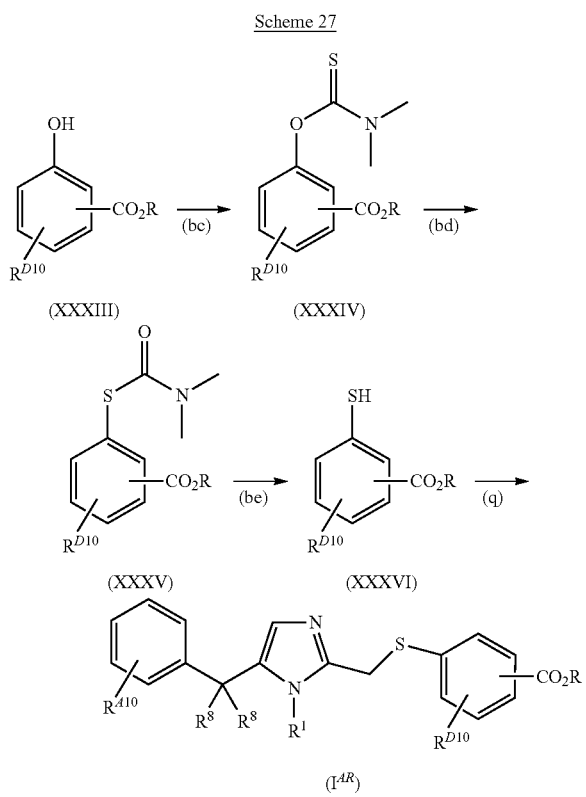

Step (bc): Phenol (XXXIII) may react under standard conditions, for example, with dimethylthiocarbamoyl chloride (1 eq) and DABCO (1.25 eq) in NMP at 50° C., to yield the respective O-aryl-thiocarbamate (XXXIV).

Step (bd): Upon heating, such as at 240° C. for 20 min in a microwave apparatus, thiocarbamate (XXXIV) may undergo a Newmann-Kwart rearrangement to give S-aryl-thiocarbamate (XXXV).

Step (be): Hydrolysis of thiocarbamate (XXXV), for example, with sodium hydroxide in methanol, may afford the corresponding thiophenol (XXXVI).

Under conditions previously described in step (q), thiophenol (XXXVI) may react with carbinol (XII) to afford compounds of formula (I^AR).

Compounds of formula (I^AS-I^AT) may be prepared as depicted in Scheme 28.

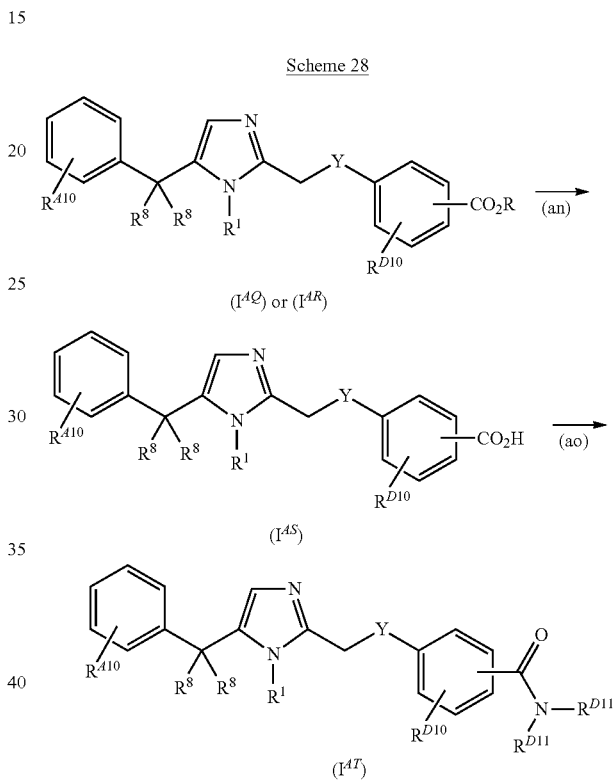

Under conditions previously described in step (an), ester (I^AQ or I^AR) may be hydrolyzed to yield compounds of formula (IAS), wherein Y is O or S, respectively.

Under conditions previously described in step (ao), acid (I^AS) may react with an amine to afford compounds of formula (I^AT), wherein Y is O or S.

Compounds of formula (I^AU-I^AV) may be prepared as depicted in Scheme 29.

Scheme 29

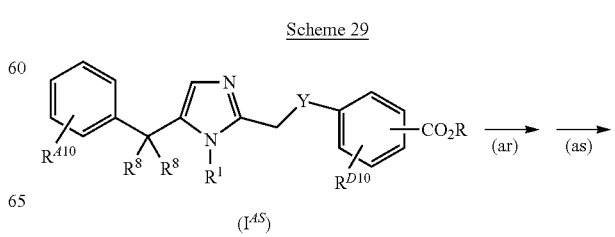

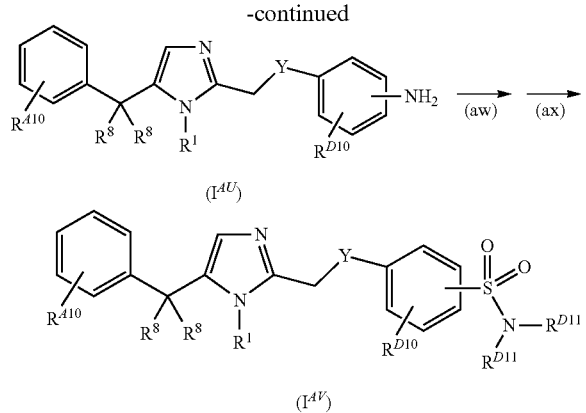

Under conditions previously described in steps (ar) to (as), acid ($I^{AS}$) may be converted to compounds of formula ($I^{AU}$), wherein Y is O or S.

Under conditions previously described in steps (aw) to (ax), amine ($I^{AU}$) may be converted to compounds of formula ($I^{AV}$), wherein Y is O or S.

Compounds of formula ($I^{AW}$-$I^{AX}$) may be prepared as depicted in Scheme 30.

Step (bf): Aryl bromide (XXXVII) may react with an alkynyl-carbinol (XXXVIII), such as propargyl alcohol, under standard Sonogashira conditions—known to one trained in the art of chemistry—to afford compounds of formula ($I^{AW}$).

Step (bg): Carbinol ($I^{AW}$) may react with a protected guanidine, such as 1,3-bis-BOC-guanidine, under standard Mitsunobu conditions to yield an alkyl guanidine (XXXIX).

Under conditions previously described in step (aa), guanidine (XXXIX) may be deprotected to give compounds of formula ($I^{AX}$).

Compounds of formula ($I^{BC}$-$I^{BD}$) may be prepared as depicted in Scheme 31.

Scheme 31

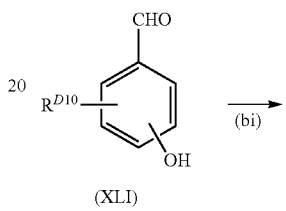

Scheme 30

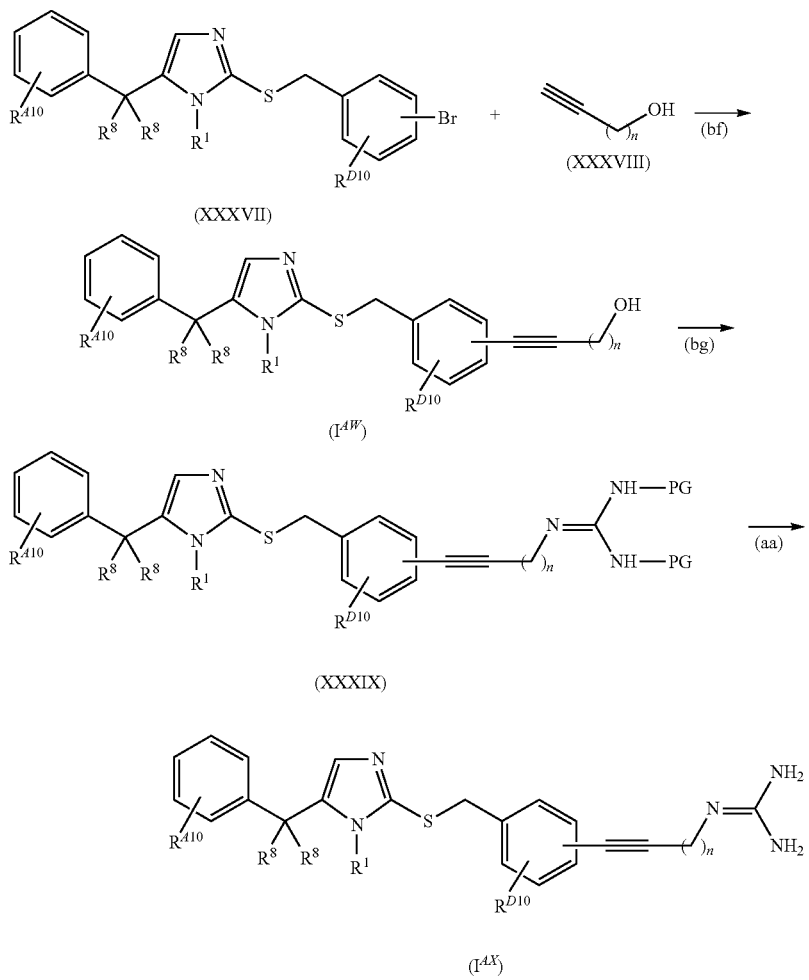

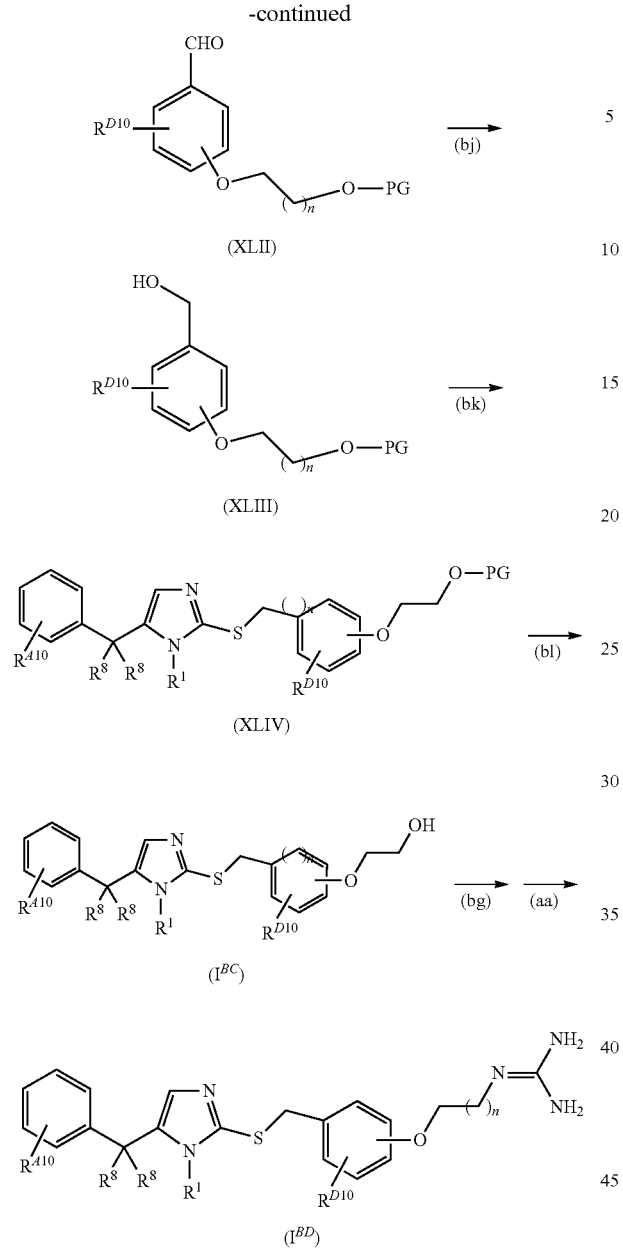

Step (bi): Aldehyde (XLI) may be alkylated with a mono-protected diol under standard Mitsunobu conditions to afford the corresponding intermediate (XLII).

Step (bj): Reduction of aldehyde (XLII) under typical conditions, such as with sodium borohydride in ethanol, may provide the respective alcohol (XLIII).

Step (bk): Alcohol (XLIII) may react with thione (VIII) under standard Mitsunobu conditions to yield the corresponding intermediate (XLIV).

Step (bl): Deprotection of intermediate (XLIV), for example, wherein PG is tert-butyl-dimethylsilyl, may occur under typical conditions, such as with HF in MeCN, to give compounds of formula ($I^{BC}$).

Under conditions previously described for steps (bg) and (aa), alcohol ($I^{BC}$) may be converted to compounds of formula ($I^{BD}$).

EXAMPLES

Example 1

2-(2-chloro-4-fluorobenzylthio)-5-(2-(3,4-dimethoxyphenyl)propan-2-yl)-1-(4-fluorophenyl)-1H-imidazole

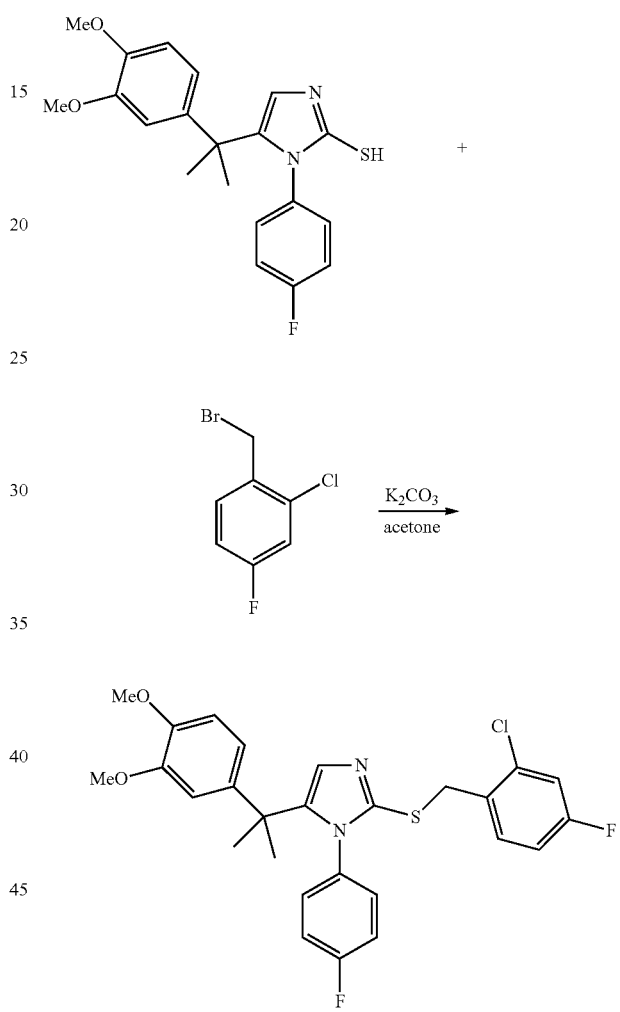

A mixture of 5-(2-(3,4-dimethoxyphenyl)propan-2-yl)-1-(4-fluorophenyl)-1H-imidazole-2(3H)-thione (170 mg, 0.46 mmol) and $K_2CO_3$ (95 mg, 0.69 mmol) in acetone (5 mL) was stirred for 30 min at room temperature. The resulting mixture was charged with 2-chloro-1-(chloromethyl)-4-fluorobenzene (98 mg, 0.55 mmol) and then heated at reflux overnight. The reaction mixture was cooled to room temperature and filtered through a Celite™ pad. The filtrate was evaporated in vacuo to give a crude product, which was purified by flash chromatography to afford the title product (208 mg, 89%). $^1$H NMR (400 MHz, $CDCl_3$) δ 7.24 (m, 1H), 7.20 (s, 1H), 7.04 (dd, 1H), 6.86 (td, 1H), 6.74 (m, 2H), 6.64 (d, 1H), 6.45-6.43 (m, 2H), 6.21 (m, 2H), 4.25 (s, 2H), 3.86 (s, 3H), 3.71 (s, 3H), 1.47 (s, 6H); MS (EI) m/z 515 (MH$^+$).

2-(2-chloro-6-fluorobenzylthio)-5-(2-(3,4-dimethoxyphenyl)propan-2-yl)-1-(4-fluorophenyl)-1H-imidazole

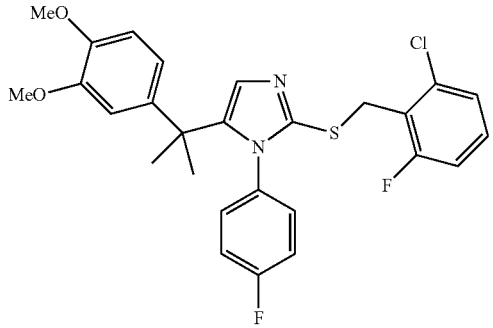 [SMILES: COc1ccc(C(C)(C)c2cnc(SCc3c(F)cccc3Cl)n2-c2ccc(F)cc2)cc1OC]

In a manner similar to that described for Example 1, the title compound was prepared from 2-chloro-6-fluorobenzyl bromide and 5-(2-(3,4-dimethoxyphenyl)propan-2-yl)-1-(4-fluorophenyl)-1H-imidazole-2(3H)-thione. $^1$H NMR (400 MHz, CDCl$_3$) δ 7.22 (s, 1H), 7.17-7.10 (m, 2H), 6.92-6.88 (m, 1H), 6.75-6.71 (m, 2H), 6.65 (d, 1H), 6.52 (d, 1H), 6.47 (dd, 1H), 6.34 (m, 2H), 4.24 (s, 2H), 3.87 (s, 3H), 3.77 (s, 3H), 1.49 (s, 6H); MS (EI) m/z 515 (MH$^+$).

2-(2-chloro-6-fluorobenzylthio)-5-(2-(3,4-dichlorophenyl)propan-2-yl)-1-(4-fluorophenyl)-1H-imidazole

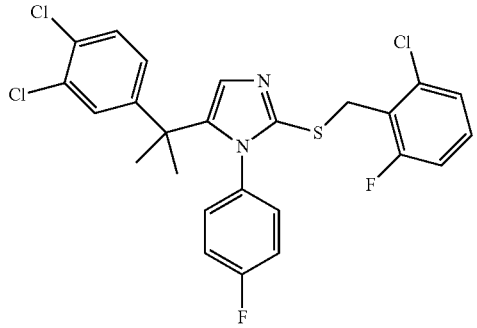 [SMILES: CC(C)(c1ccc(Cl)c(Cl)c1)c1cnc(SCc2c(F)cccc2Cl)n1-c1ccc(F)cc1]

To a mixture of 5-(2-(3,4-dichlorophenyl)propan-2-yl)-1-(4-fluorophenyl)-1H-imidazole-2(3H)-thione (138 mg, 0.362 mmol) and K$_2$CO$_3$ (76 mg, 0.543 mmol) in acetone (6 mL) was added 2-chloro-6-fluorobenzyl chloride (79 mg, 0.434 mmol). After stirring 2 h, the reaction mixture was filtered, concentrated and purified by flash chromatography to provide the title product (77 mg, 33%). $^1$H NMR (400 MHz, CDCl$_3$) δ 7.25 (m, 1H), 7.22 (s, 1H), 7.16-7.11 (m, 2H), 7.03 (d, 1H), 6.91 (m, 1H), 6.83 (dd, 1H), 6.78 (t, 2H), 6.34 (m, 2H), 4.25 (s, 2H), 1.49 (s, 6H); MS (EI) m/z 523, 525 (MH$^+$).

3-(2,6-difluorobenzylthio)-5-(3,4-dimethoxybenzyl)-4-(4-fluorophenyl)-4H-1,2,4-triazole

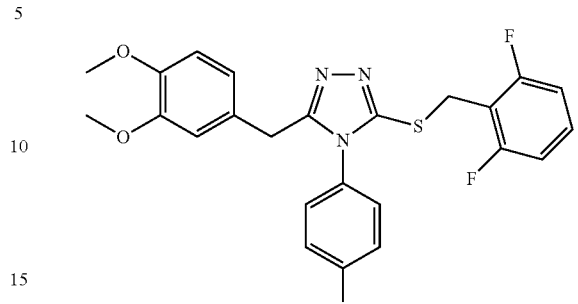

To a solution of 5-(3,4-dimethoxybenzyl)-4-(4-fluorophenyl)-4H-1,2,4-triazole-3-thiol (119 mg, 0.345 mmol) and Et$_3$N (53 μL, 0.379 mmol) in CH$_2$Cl$_2$ (1.8 mL) was added 2,6-difluorobenzyl bromide (88 mg, 0.414 mmol). After stirring 2 h, the reaction mixture was concentrated and purified by flash chromatography (30% EtOAc/hexanes) to yield the title product (107 mg, 66%) as a white foam. $^1$H NMR (400 MHz, (CD$_3$)$_2$CO) δ 7.25 (m, 1H), 7.10 (m, 2H), 6.98 (m, 2H), 6.84 (m, 2H), 6.63 (d, J=8.2 Hz, 1H), 6.4 (d, J=2.0 Hz, 1H), 6.31 (m, 1H), 4.45 (s, 2H), 3.82 (s, 2H), 3.61 (s, 3H), 3.54 (s, 3H); MS (EI) m/z 472.3 (MH$^+$).

3-(2-Chloro-6-fluorobenzylthio)-5-(2-(3,4-dimethoxyphenyl)propan-2-yl)-4-(4-fluorophenyl)-4H-1,2,4-triazole

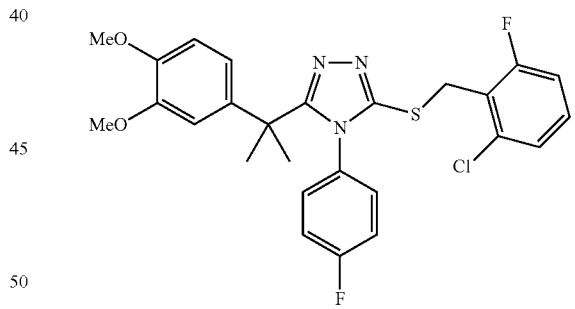

A mixture of 3-(2-(3,4-dimethoxyphenyl)propan-2-yl)-4-(4-fluorophenyl)-1H-1,2,4-triazole-5(4H)-thione (200 mg, 0.54 mmol) and K$_2$CO$_3$ (111 mg, 0.80 mmol) in acetone (15 mL) was stirred for 30 min at room temperature. 2-Chloro-6-fluorobenzyl chloride (206 μL, 1.61 mmol) was added to the reaction mixture, and the resulting mixture was refluxed for 2 h. The reaction mixture was cooled to room temperature, filtered through Celite, and concentrated. Purification by flash chromatography [Hex/EtOAc, 1:4 to 1:1] afforded the title product (230 mg, 0.45 mmol, 83%). $^1$H NMR (400 MHz, CDCl$_3$) δ 7.20-7.12 (m, 2H), 6.95-6.91 (m, 1H), 6.84-6.80 (m, 2H), 6.68 (d, 1H), 6.54 (d, 1H), 6.50 (dd, 1H), 6.45-6.40 (m, 2H), 4.45 (s, 2H), 3.87 (s, 3H), 3.77 (s, 3H), 1.65 (s, 6H); MS (EI) m/z 516 (MH$^+$).

2-(4-bromo-2,6-difluorobenzylthi)-5-(2-(4-chloro-3-methoxyphenyl)propan-2-yl)-1-(4-fluorophenyl)-1H-imidazole

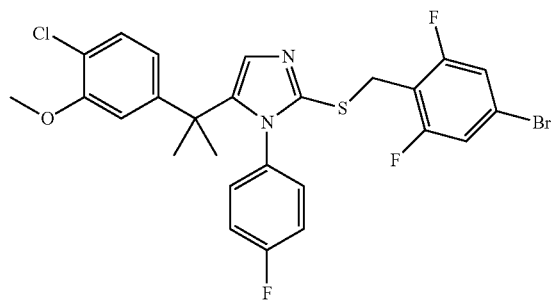 [SMILES: COc1cc(C(C)(C)c2cnc(SCc3c(F)cc(Br)cc3F)n2-c2ccc(F)cc2)ccc1Cl]

To a mixture of 5-(2-(4-chloro-3-methoxyphenyl)propan-2-yl)-1-(4-fluorophenyl)-1H-imidazole-2-thiol (1.00 g, 2.65 mmol) and $K_2CO_3$ (0.51 g, 3.70 mmol) in acetone (13 mL) was added 5-bromo-2-(bromomethyl)-1,3-difluorobenzene (0.91 g, 3.18 mmol). The reaction mixture was stirred 1 h and then filtered. The filtrate was concentrated under reduced pressure and purified by chromatography (10% MeOH/DCM) to yield the title compound as a tan solid (1.34 g, 87%). MS (EI) m/z 581 (MH+).

Methyl 2-bromo-5-((5-(2-(3,4-dichlorophenyl)propan-2-yl)-1-(4-fluoro-3-methoxyphenyl)-1H-imidazol-2-ylthio)methyl)benzoate

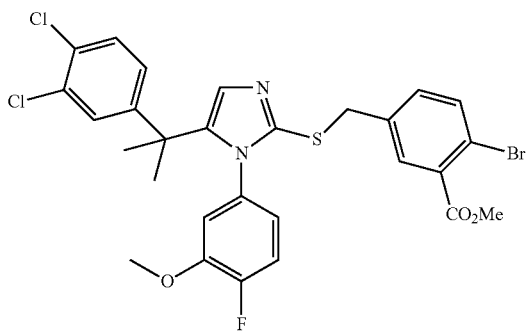 [SMILES: COC(=O)c1cc(CSc2ncc(C(C)(C)c3ccc(Cl)c(Cl)c3)n2-c2ccc(F)c(OC)c2)ccc1Br]

A mixture of 5-(2-(3,4-dichlorophenyl)propan-2-yl)-1-(4-fluoro-3-methoxyphenyl)-1H-imidazole-2-thiol (700 mg, 1.7 mmol, 1.0 eq), methyl 2-bromo-5-(bromomethyl)benzoate (630 mg, 2.0 mmol, 1.2 eq) and potassium carbonate (350 mg, 2.6 mmol, 1.5 eq) in acetone (9 mL) was stirred at room temperature 1 h. The solids were filtered and the organics were concentrated and purified (silica, 0 to 60% EtOAc/Hex) to afford the title compound (900 mg, 83%). MS (EI) m/z 638.9 (MH+).

Example 2

5-((5-(2-(3,4-Dichlorophenyl)propan-2-yl)-1-(4-fluorophenyl)-1H-imidazol-2-ylthio)methyl)-2-fluorobenzonitrile

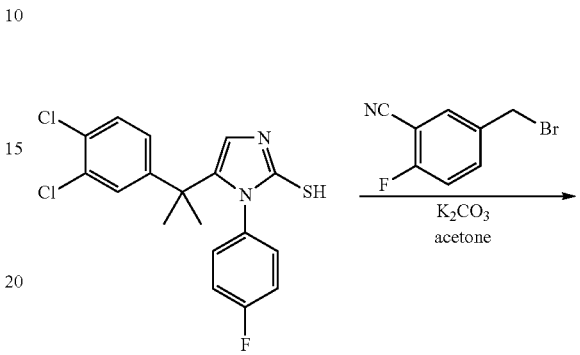

A solution of 2-fluoro-5-methylbenzonitrile (3.00 g, 22 mmol), N-bromosuccinimide (4.12 g, 23 mmol) and benzoyl peroxide (1.07 g, 4.4 mmol) in $CCl_4$ (100 mL) was heated at reflux 6 h. The reaction mixture was cooled to room temperature and then combined with water. The separated organic phase was dried over $MgSO_4$, filtered through a Celite™ pad, and evaporated under reduced pressure. Purification by flash chromatography (Hex/EtOAc, 20:1) gave 5-(bromomethyl)-2-fluorobenzonitrile (1.58 g, 33% yield) as an oil. $^1$H NMR ($CDCl_3$, 400 MHz): δ 4.45 (s, 2H), 7.21 (m, 1H), 7.65 (m, 2H).

To a pre-stirred mixture of 5-(2-(3,4-dichlorophenyl)propan-2-yl)-1-(4-fluorophenyl)-1H-imidazole-2(3H)-thione (1.50 g, 3.93 mmol) and $K_2CO_3$ (0.82 g, 5.90 mmol) in acetone (60 mL) was added 5-(bromomethyl)-2-fluorobenzonitrile (1.09 g, 5.11 mmol), and the reaction mixture was heated at reflux 2 h. After cooling, the reaction mixture was filtered through Celite™ and concentrated. Purification by flash chromatography (Hex/EtOAc, 2:1) afforded the title product (1.74 g, 3.38 mmol, 86%) as a white solid. $^1$H NMR ($CDCl_3$, 400 MHz): δ 1.53 (s, 6H) 4.21 (s, 2H), 6.36 (m, 2H), 6.84 (m, 3H), 6.96 (s, 1H), 7.11 (t, 1H), 7.18 (s, 1H), 7.26 (d, 1H), 7.52 (m, 2H); MS (EI) m/z 514 (MH+).

2-Chloro-5-((5-(2-(3-chloro-4-methoxyphenyl)propan-2-yl)-1-(4-fluorophenyl)-1H-imidazol-2-ylthio)methyl)benzonitrile

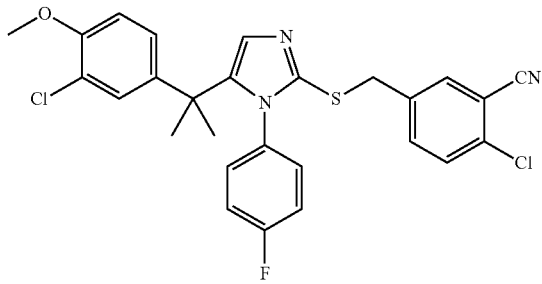 [SMILES: COc1ccc(C(C)(C)c2cnc(SCc3ccc(Cl)c(C#N)c3)n2-c2ccc(F)cc2)cc1Cl]

To a solution of 5-(2-(3-chloro-4-methoxyphenyl)propan-2-yl)-1-(4-fluorophenyl)-1H-imidazole-2(3H)-thione (125 mg, 0.33 mmol) in acetone (2 mL) were added K$_2$CO3 (70, mg, 0.50 mmol) and 5-(bromomethyl)-2-chlorobenzonitrile (92 mg, 0.40 mmol). The mixture was stirred at room temperature for 2 h and filtered. The mother liquor was concentrated and purified by column chromatography (silica, 0 to 30% EtOAc/Hex) to afford the title compound (105 mg, 60%) as a white solid. MS (EI) m/z 526 (MH$^+$).

4-((5-(2-(3,4-dichlorophenyl)propan-2-yl)-1-(4-fluorophenyl)-1H-imidazol-2-ylthio)methyl)-3,5-difluorobenzonitrile

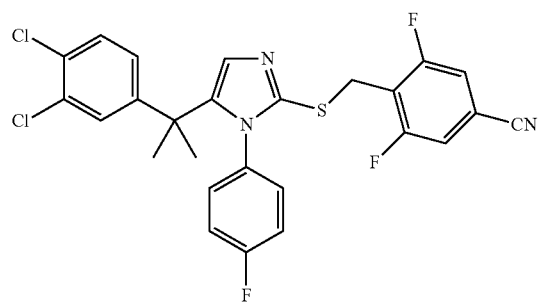 [SMILES: CC(C)(c1ccc(Cl)c(Cl)c1)c1cnc(SCc2c(F)cc(C#N)cc2F)n1-c1ccc(F)cc1]

A mixture of 5-(2-(3,4-dichlorophenyl)propan-2-yl)-1-(4-fluorophenyl)-1H-imidazole-2(3H)-thione (760 mg, 2 mmol), 4-(bromomethyl)-3,5-difluorobenzonitrile (464 mg, 2 mmol) and K$_2$CO$_3$ (414 mg, 3 mmol) in acetone (10 mL) was stirred at 56° C. for 4 h. After cooling, the solids were removed by filtration and rinsed with acetone. The combined filtrates were concentrated and purified by flash chromatography, eluting with EtOAc-Hexane (1:1) to afford the title compound (89 mg). $^1$H NMR (400 MHz, CDCl$_3$) δ 7.26 (t, J=4.2, 2H), 7.17 (d, J=6.5, 2H), 7.03 (d, J=2.2, 1H), 6.88-6.79 (m, 3H), 6.50-6.44 (m, 2H), 4.08 (d, J=9.1, 2H), 2.04 (s, 1H), 1.49 (s, 7H); MS (EI) m/z 432 (MH$^+$).

Example 3

5-((5-(2-(3,4-Dichlorophenyl)propan-2-yl)-1-(4-fluorophenyl)-1H-imidazol-2-ylthio)methyl)-2-fluorobenzamide

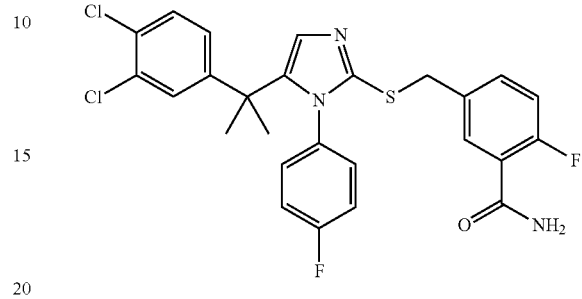

A solution of 5-((5-(2-(3,4-dichlorophenyl)propan-2-yl)-1-(4-fluorophenyl)-1H-imidazol-2-ylthio)methyl)-2-fluorobenzonitrile (270 mg, 0.527 mmol) in TFA/H$_2$SO$_4$ (6 mL, 4:1, v/v) was heated at 65° C. for 8 h. The reaction mixture was cooled to room temperature, and the residue was partitioned into DCM and water. The separated organic layer was washed with satd NaHCO$_3$, dried over MgSO$_4$, filtered through Celite™, and concentrated. Purification by flash chromatography (DCM/EtOAc, 1:1) gave the title product (217 mg, 77%) as a white foam. $^1$H NMR (CDCl$_3$, 400 MHz): δ 1.47 (s, 6H) 4.13 (s, 2H), 6.04 (br s, 1H), 6.36 (m, 2H), 6.65 (br s, 1H), 6.81 (m, 3H), 6.96 (s, 1H), 7.06 (m, 1H), 7.27 (m, 2H), 7.40 (m, 1H), 7.91 (m, 1H); MS (EI) m/z 532 (MH$^+$).

Example 4

5-(2-Chloro-5-((5-(2-(3-chloro-4-methoxyphenyl)propan-2-yl)-1-(4-fluorophenyl)-1H-imidazol-2-ylthio)methyl)phenyl)-1H-tetrazole

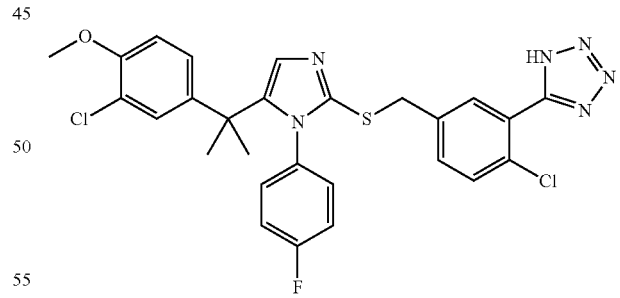

A mixture of 2-chloro-5-((5-(2-(3-chloro-4-methoxyphenyl)propan-2-yl)-1-(4-fluorophenyl)-1H-imidazol-2-ylthio)methyl)benzonitrile (104 mg, 0.20 mmol), sodium azide (130 mg, 2.0 mmol, 10.0 eq) and NH$_4$Cl (110 mg, 2.0 mmol) in DMF (2 mL, anhyd) was stirred at 110° C. for 16 h. The reaction mixture was cooled to room temperature and partitioned between water and ethyl acetate. The combined extracts were washed with water and brine, then dried over MgSO$_4$ and concentrated. Purification by column chromatography (silica, 0 to 20% MeOH/DCM) provided the title compound (85 mg, 76%) as a white solid. ¹H NMR (DMSO-d₆, 400 MHz): δ 7.59 (d, J=1.7 Hz, 1H), 7.47 (d, J=8.3 Hz, 1H), 7.18-7.14 (m, 2H), 6.95-6.89 (m, 3H), 6.78-6.74 (m, 2H), 6.37-6.31 (m, 2H), 4.17 (s, 2H), 3.81 (s, 3H), 1.39 (s, 6H); MS (EI) m/z 569 (MH⁺).

Example 5

4-((5-(2-(3,4-dichlorophenyl)propan-2-yl)-1-(4-fluorophenyl)-1H-imidazol-2-ylthio)methyl)-3,5-difluorobenzoic acid

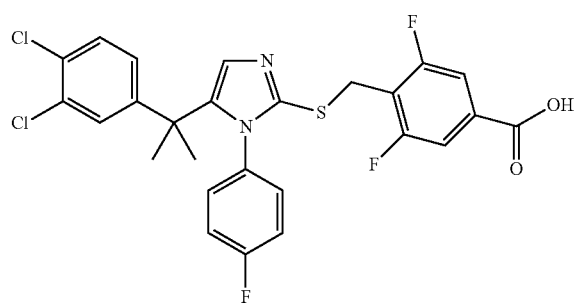 [SMILES: CC(C)(c1ccc(Cl)c(Cl)c1)c1cnc(SCc2c(F)cc(C(=O)O)cc2F)n1-c1ccc(F)cc1]

A solution of 4-((5-(2-(3,4-dichlorophenyl)propan-2-yl)-1-(4-fluorophenyl)-1H-imidazol-2-ylthio)methyl)-3,5-difluorobenzonitrile (800 mg, 1.5 mmol) in H₂O/conc H₂SO₄ (7 mL, 3:4, v/v) was heated at 110° C. for 8 h. After cooling, the reaction mixture was diluted with water. Solids were collected by filtration, rinsed with water and then dissolved in MeOH. Water was added and precipitated solids were collected by filtration, rinsed with water and dried under high-vacuum to afford the title compound (778 mg). ¹H NMR (400 MHz, CD₃OD) δ 7.52 (d, J=7.7, 2H), 7.38 (d, J=8.4, 1H), 7.31 (s, 1H), 7.01 (d, J=2.2, 1H), 6.91 (dd, J=8.4, 2.2, 1H), 6.84 (t, J=8.6, 2H), 6.31 (dd, J=8.9, 4.8, 2H), 3.97 (s, 2H), 1.52 (s, 6H); MS (EI) m/z 551 (MH⁺).

Example 6

4-((5-(2-(4-chloro-3-methoxyphenyl)propan-2-yl)-1-(4-fluorophenyl)-1H-imidazol-2-ylthio)methyl)-3,5-difluorobenzoic acid

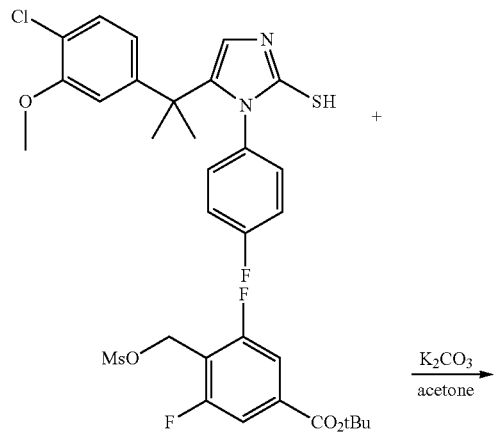

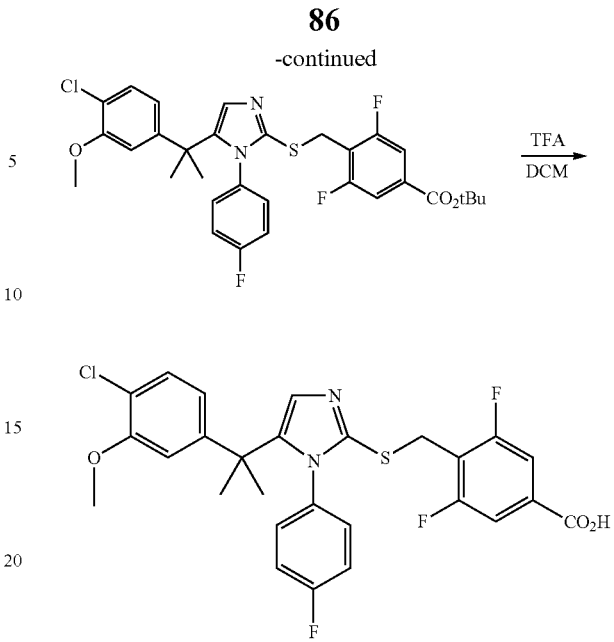

A mixture of 5-(2-(4-chloro-3-methoxyphenyl)propan-2-yl)-1-(4-fluorophenyl)-1H-imidazole-2-thiol (60 g, 0.16 mmol), tert-butyl 3,5-difluoro-4-((methylsulfonyloxy)methyl)benzoate (51 g, 0.16 mol, 1.0 eq.) and Cs₂CO₃ (62 g, 0.19 mol, 1.2 eq.) in MeCN (680 mL) was stirred for 2 h and evaporated to give a residue. The residue was diluted with water (1.5 L) and extracted with CH₂Cl₂ (1 L). The organic layer was washed with brine, dried over MgSO₄, filtered and concentrated in vacuo to give tert-butyl 4-((5-(2-(4-chloro-3-methoxyphenyl)propan-2-yl)-1-(4-fluorophenyl)-1H-imidazol-2-ylthio)methyl)-3,5-difluorobenzoate (95 g, quant). ¹H NMR (400 MHz, CDCl₃) δ 7.40-7.42 (d, 2H), 7.19 (s, 1H), 7.14-7.16 (d, 1H), 6.76-6.80 (t, 2H), 6.51 (s, 1H), 6.41-6.49 (m, 3H), 4.07 (s, 2H), 3.75 (s, 3H), 1.58 (s, 9H), 1.47 (s, 6H).

To a solution of tert-butyl 4-((5-(2-(4-chloro-3-methoxyphenyl)propan-2-yl)-1-(4-fluorophenyl)-1H-imidazol-2-ylthio)methyl)-3,5-difluorobenzoate (95 g, 0.16 mmol) in CH₂Cl₂ (500 mL) at 0° C. was added TFA (500 mL) and then was stirred at room temperature. After 3 h, the reaction mixture was evaporated and the residue was diluted with CH₂Cl₂ (1.5 L), washed with water (600 mL×2). To the organic layers more water (600 mL) was added, it was neutralized with slow addition of aq. NaHCO₃ solution and organic layer was separated. Water (600 mL) was added to the organic layer and adjusted aqueous layer to pH 3-4 with 1N HCl. The organic layer was separated, dried over MgSO₄, filtered and concentrated under reduced pressure to give a residue. Toluene (600 mL) was added to the residue and the solution was evaporated and same process was repeated one more time to give the title compound as a white solid (88 g, quant). ¹H NMR (400 MHz, CDCl₃) δ 7.55 (s, 1H), 7.46-7.49 (d, 2H), 7.16-7.19 (m, 1H), 6.92-6.97 (t, 2H), 6.69-6.71 (t, 2H), 6.62 (s, 1H), 6.49-6.51 (d, 1H), 3.84 (s, 3H), 3.53 (s, 2H), 1.58 (s, 6H); MS (EI) m/z 547 (MH⁺).

87 tert-Butyl 4-((5-(2-(3,4-dichlorophenyl)propan-2-yl)-1-(4-fluoro-3-methoxyphenyl)-1H-imidazol-2-ylthio)methyl)-3,5-difluorobenzoate

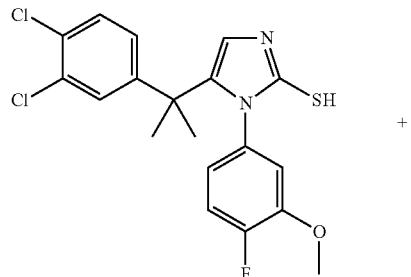

+

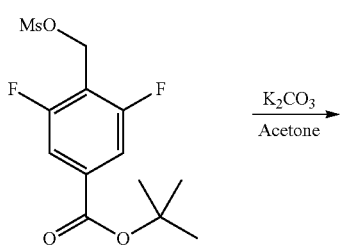

K₂CO₃ / Acetone

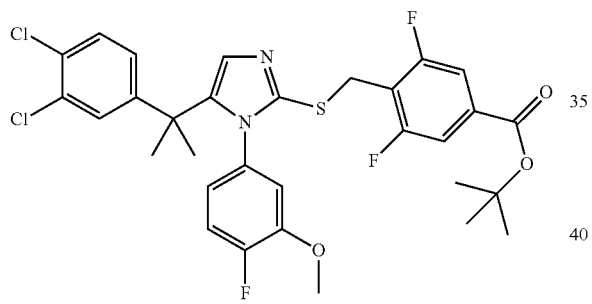

A mixture of tert-butyl 3,5-difluoro-4-((methylsulfonyloxy)methyl)benzoate (355 mg, 1.10 mmol) and 5-(2-(3,4-dichlorophenyl)propan-2-yl)-1-(4-fluoro-3-methoxyphenyl)-1H-imidazole-2-thiol (402 mg, 0.98 mmol)—prepared in a manner similar to that described for Example 3 from commercially available reagents—was suspended in acetone (4 mL) and treated with K₂CO₃ (223 mg, 1.6 mmol). The resulting white suspension was stirred at ambient temperature. The reaction mixture rapidly became a thick slurry, and acetone (5 mL) was added to facilitate stirring. After 75 min, the reaction was diluted with EtOAc and water. The aqueous layer was extracted with EtOAc. The combined extracts were washed with brine, dried over Na₂SO₄ and concentrated under reduced pressure to afford crude product that was purified by flash chromatography (silica gel, EtOAc/Hex, 0:100 to 80:20) to afford the title compound (541 mg, 87% yield) as a white solid. $^1$H NMR (400 MHz, CDCl₃) δ 7.49-7.40 (m, 2H), 7.30-7.24 (m, 1H), 7.19 (s, 1H), 7.10 (d, J=2.2 Hz, 1H), 6.87 (ddd, J=10.7, 9.5, 5.4 Hz, 2H), 6.28 (ddd, J=8.5, 3.8, 2.5 Hz, 1H), 5.85 (dd, J=7.5, 2.4 Hz, 1H), 4.20-4.07 (m, 2H), 3.46 (s, 3H), 1.57 (s, 9H), 1.54 (s, 3H), 1.46 (s, 3H); MS (EI) m/z 637 (MH⁺).

88

4-((5-(2-(3,4-dichlorophenyl)propan-2-yl)-1-(4-fluoro-3-methoxyphenyl)-1H-imidazol-2-ylthio)methyl)-3,5-difluorobenzoic acid

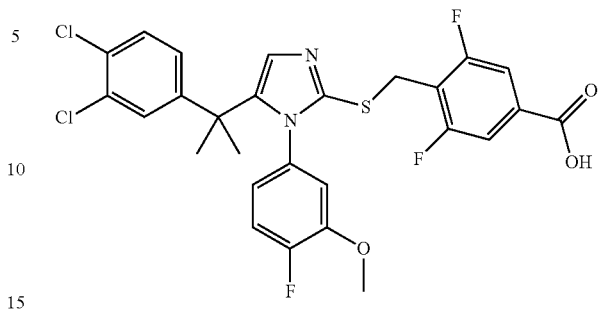

A solution of tert-butyl 4-((5-(2-(3,4-dichlorophenyl)propan-2-yl)-1-(4-fluoro-3-methoxyphenyl)-1H-imidazol-2-ylthio)methyl)-3,5-difluorobenzoate (540 mg, 0.85 mmol) in DCM (2 mL) was treated with TFA (2.0 mL) at ambient temperature. After 40 min, the reaction mixture was concentrated under reduced pressure to afford a colorless oil. This oil was taken up in DCM and toluene and again concentrated under reduced pressure to remove any residual TFA and to provide the title compound. MS (EI) m/z 581 (MH⁺).

4-((5-(2-(3-Chloro-4-sulfamoylphenyl)propan-2-yl)-1-(4-fluoro-3-methoxyphenyl)-1H-imidazol-2-ylthio)methyl)-3,5-difluorobenzoic acid

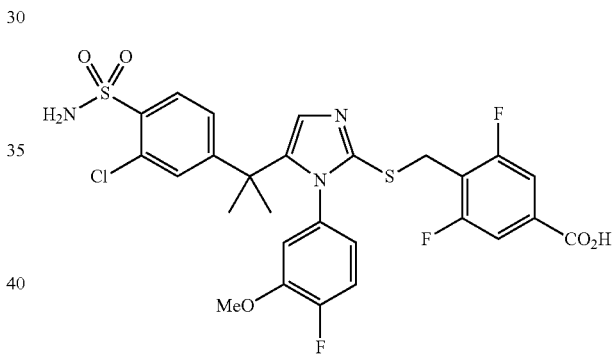

$^1$H NMR (400 MHz, CDCl₃+MeOD) δ 7.95 (d, J=8.4 Hz, 1H), 7.46 (d, J=7.6 Hz, 2H), 7.33 (s, 1H), 7.12 (d, J=2.0 Hz, 1H), 7.05 (d, J=8.4 Hz, 1H), 6.81 (m, 1H), 5.89 (m, 1H), 5.81 (dd, J=7.2 Hz, 1H), 4.04 (s, 2H), 3.40 (s, 3H), 1.51 (d, J=13.6 Hz, 6H); MS (EI) m/z 626 (MH⁺).

3,5-difluoro-4-((1-(4-fluorophenyl)-5-(2-(4-(methylsulfonyl)phenyl)propan-2-yl)-1H-imidazol-2-ylthio)methyl)benzoic acid

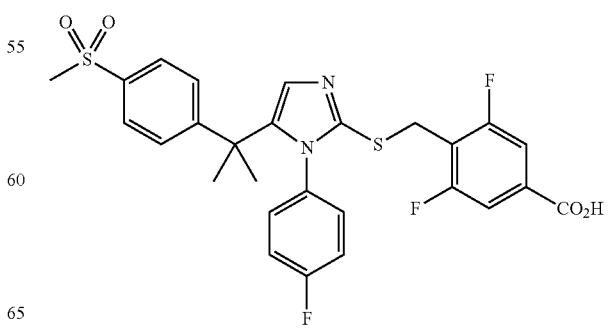

¹H NMR (400 MHz, CDCl₃+MeOD) δ 7.94 (d, J=8.4, 1H), 7.46 (d, J=7.6, 2H), 7.33 (s, 1H), 7.12 (d, J=2.0, 1H), 7.04 (dd, J=8.4, 1H), 6.81 (m, 1H), 5.89 (m, 1H), 5.80 (dd, J=7.2, 1H), 4.04 (s, 2H), 3.40 (s, 3H), 1.52 (d, J=13.6, 6H); MS (EI) m/z 626 (MH⁺).

3-Chloro-4-((5-(2-(4-chloro-3-methoxyphenyl)propan-2-yl)-1-(4-fluorophenyl)-1H-imidazol-2-ylthio)methyl)-5-fluorobenzoic acid

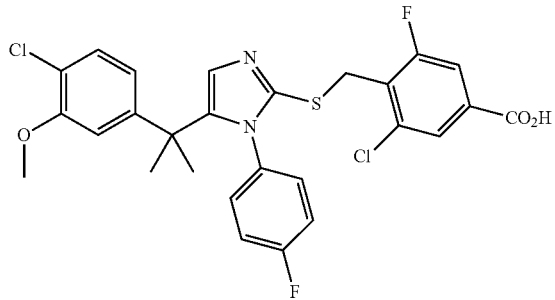 [SMILES: COc1cc(C(C)(C)c2cnc(SCc3c(F)cc(C(=O)O)cc3Cl)n2-c2ccc(F)cc2)ccc1Cl]

¹H NMR (400 MHz, DMSO) δ 13.63 (s, 1H), 7.72 (s, 1H), 7.59 (dd, J=9.6, 1.5 Hz, 1H), 7.22 (d, J=8.3 Hz, 1H), 7.19 (s, 1H), 6.94 (d, J=8.4 Hz, 1H), 6.92 (d, J=8.2 Hz, 1H), 6.54 (d, J=2.0 Hz, 1H), 6.51-6.45 (m, 3H), 4.08 (s, 2H), 3.67 (s, 3H), 1.46 (s, 6H); MS EI m/z 563.3 (MH⁺).

4-((5-(2-(3-cyano-4-fluorophenyl)propan-2-yl)-1-(4-fluoro-3-methoxyphenyl)-1H-imidazol-2-ylthio)methyl)-3,5-difluorobenzoic acid

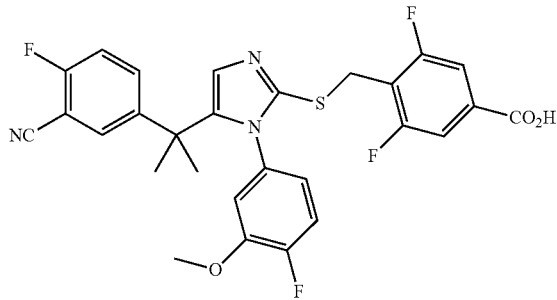 [SMILES: COc1cc(-n2c(C(C)(C)c3ccc(F)c(C#N)c3)cnc2SCc2c(F)cc(C(=O)O)cc2F)ccc1F]

¹H NMR (400 MHz, CDCl₃) δ 7.52 (d, J=7.6 Hz, 2H), 7.31-7.12 (m, 4H), 6.87 (t, J=2.0 Hz, 1H), 6.05-5.98 (m, 2H), 4.01 (dd, J=7.8, 4.4 Hz, 2H), 3.61 (s, 3H), 1.59 (s, 6H); MS (EI) m/z 556 (MH⁺).

4-((5-(2-(3-aminobenzo[d]isoxazol-5-yl)propan-2-yl)-1-(4-fluoro-3-methoxyphenyl)-1H-imidazol-2-ylthio)methyl)-3,5-difluorobenzoic acid

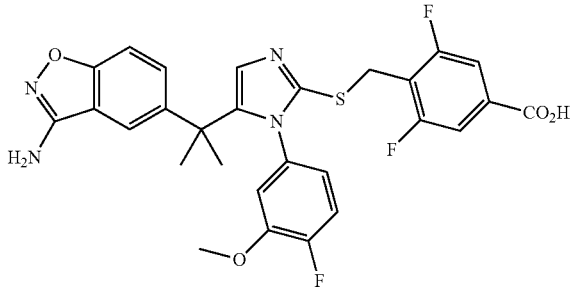 [SMILES: COc1cc(-n2c(C(C)(C)c3ccc4onc(N)c4c3)cnc2SCc2c(F)cc(C(=O)O)cc2F)ccc1F]

¹H NMR (400 MHz, CDCl₃) δ 7.52 (d, J=7.2 Hz, 2H), 7.32-7.26 (m, 2H), 7.15 (d, J=8.0 Hz, 1H), 6.83 (t, J=9.6 Hz, 1H), 6.05 (bs, 1H), 5.74 (d, J=5.6 Hz, 1H), 4.16 (s, 2H), 3.25 (s, 3H), 1.52 (d, J=24 Hz, 6H); MS (EI) m/z 569 (MH⁺).

Example 7

3-(4-((5-(2-(3,4-Dichlorophenyl)propan-2-yl)-1-(4-fluoro-3-methoxyphenyl)-1H-imidazol-2-ylthio)methyl)-3,5-difluorobenzamido)propanoic acid

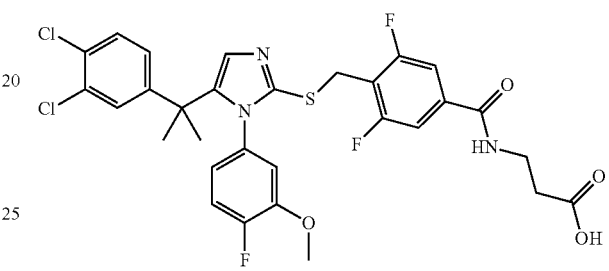

A mixture of 4-((5-(2-(3,4-dichlorophenyl)propan-2-yl)-1-(4-fluoro-3-methoxyphenyl)-1H-imidazol-2-ylthio)methyl)-3,5-difluorobenzoic acid (0.85 mmol from previous step) and β-alanine methyl ester hydrochloride (139 mg, 1.0 mmol) in DCM (10 mL) was treated with Et₃N (0.36 mL, 2.6 mmol) and HATU (390 mg, 1.0 mmol) at ambient temperature. After stirring for 16 h at ambient temperature the reaction mixture was quenched by the addition of H₂O, 1N HCl, and DCM. The aqueous layer was extracted with DCM. The combined extracts were washed with satd NaHCO₃, dried over Na₂SO₄ and concentrated under reduced pressure to afford crude product. This material was purified by flash chromatography (silica gel, EtOAc/Hex, 0:100 to 100:0) to give methyl 3-(4-((5-(2-(3,4-dichlorophenyl)propan-2-yl)-1-(4-fluoro-3-methoxyphenyl)-1H-imidazol-2-ylthio)methyl)-3,5-difluorobenzamido)propanoate as a clear syrup, that was carried on to the next step directly. ¹H NMR (400 MHz, CDCl₃) δ 7.31-7.23 (m, 2H), 7.19 (s, 1H), 7.09 (d, J=2.2 Hz, 1H), 6.99 (t, J=5.5 Hz, 1H), 6.88 (ddd, J=10.7, 9.6, 5.4 Hz, 2H), 6.26 (ddd, J=8.5, 3.8, 2.5 Hz, 1H), 5.91 (dd, J=7.5, 2.4 Hz, 1H), 4.16-4.08 (m, 2H), 3.76-3.66 (m, 5H), 3.50 (s, 3H), 2.66 (t, J=5.9 Hz, 2H), 1.89 (s, 1H), 1.54 (s, 3H), 1.47 (s, 3H); MS (EI) m/z 666 (MH⁺).

A solution of methyl 3-(4-((5-(2-(3,4-dichlorophenyl)propan-2-yl)-1-(4-fluoro-3-methoxyphenyl)-1H-imidazol-2-ylthio)methyl)-3,5-difluorobenzamido)propanoate (0.85 mmol from previous step) in MeOH (10 mL) was treated with a solution of NaOH (0.6 mL of a 5M aqueous solution, 3 mmol) at ambient temperature. After stirring for 100 min, the reaction mixture was added dropwise to 1N HCl. The addition afforded a thick, white oil that separated from the aqueous acid. The aqueous mixture was extracted with EtOAc.

The combined extracts were washed with brine, dried over Na₂SO₄ and concentrated under reduced pressure to afford crude product. This material was purified by flash chromatography (silica gel, MeOH/DCM, 0:100 to 10:90) to afford the title compound (220 mg, 40% yield over three steps) as a white powder. ¹H NMR (400 MHz, CDCl₃) δ 7.29 (dt, J=9.4, 6.0 Hz, 5H), 7.07 (d, J=2.2 Hz, 1H), 6.95 (dd, J=10.5, 8.6 Hz, 1H), 6.82 (dd, J=8.4, 2.2 Hz, 1H), 6.34-6.25 (m, 1H), 5.94 (dd, J=7.4, 2.4 Hz, 1H), 3.96 (s, 2H), 3.76-3.67 (m, 2H), 3.53 (s, 3H), 2.65 (s, 2H), 1.54 (s, 3H), 1.48 (s, 3H); MS (EI) m/z 652 (MH⁺).

Example 8

2-(4-((5-(2-(3,4-Dichlorophenyl)propan-2-yl)-1-(4-fluoro-3-methoxyphenyl)-1H-imidazol-2-ylthio)methyl)-3,5-difluorobenzamido)ethanesulfonic acid

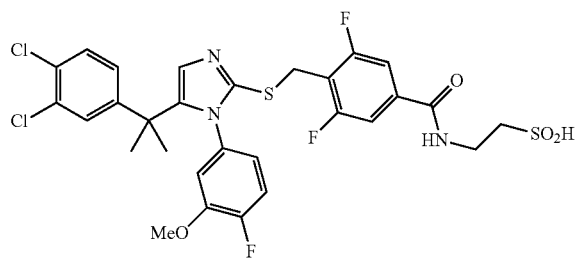

To a solution of 4-((5-(2-(3,4-dichlorophenyl)propan-2-yl)-1-(4-fluoro-3-methoxyphenyl)-1H-imidazol-2-ylthio)methyl)-3,5-difluorobenzoic acid (735 mg, 1.27 mmol) in DCM was added 2M solution of oxalyl chloride in DCM (2.53 mmol, 2 eq) followed by DMF (3 drops) at 0° C. After stirring at ambient temperature for 1 h, the reaction mixture was concentrated under reduced pressure and kept under high vacuum for 20 min.

A solution of the resulting acid chloride in DCM at 0° C. was charged with taurine (613 mg, 4.9 mmol) and Et₃N (9.78 mmol, 1.4 mL). After stirring at ambient temperature for 16 h, the reaction mixture was concentrated under reduced pressure and then diluted with EtOAc. White solids (NEt₃.HCl) were filtered off, and the filtrate was concentrated and purified on column chromatography (silica, 20% MeOH/DCM). Product fractions were combined and concentrated to yield a white solid, which was suspended in aq NH₄Cl (10 mL) and washed with Et₂O (3×15 mL) to remove starting acid. The desired product was extracted into EtOAc (3×20 mL). Combined extracts were washed with aq NH₄Cl, dried (MgSO₄) and concentrated to afford the title compound. ¹H NMR (400 MHz, MeOD) δ 7.46-7.36 (m, 3H), 7.27 (s, 1H), 7.08 (d, J=2.0 Hz, 1H), 6.99-6.89 (m, 2H), 6.14 (d, J=8.5 Hz, 1H), 5.96 (d, J=7.3 Hz, 1H), 4.00 (s, 2H), 3.80 (t, J=6.2 Hz, 2H), 3.49 (s, 3H), 3.11 (t, J=6.9 Hz, 2H), 1.57 (s, 3H), 1.51 (s, 3H); MS (EI) m/z 688.3 (MH⁺).

Sodium 2-(4-((5-(2-(4-chloro-3-methoxyphenyl)propan-2-yl)-1-(4-fluorophenyl)-1H-imidazol-2-ylthio)methyl)-3-fluorobenzamido)ethanesulfonate

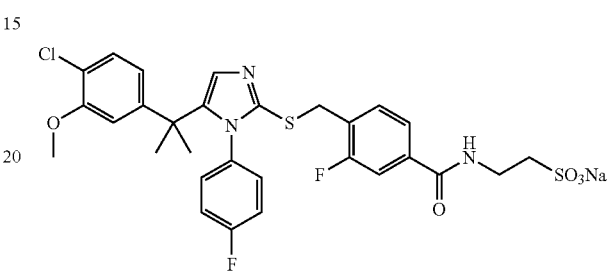

To a solution of 4-((5-(2-(4-chloro-3-methoxyphenyl)propan-2-yl)-1-(4-fluorophenyl)-1H-imidazol-2-ylthio)methyl)-3-fluorobenzoic acid (50 mg, 0.095 mmol) in DCM (3 mL) was added thionyl chloride (14 μL, 0.19 mmol) at 0° C. After refluxing for 13 h, the reaction mixture was cooled to room temperature and concentrated in vacuo. The crude material was dissolved in DCM (3 mL). To this solution were added taurine (12.4 mg, 0.099 mmol) and Et₃N (26 μL, 0.19 mmol). The mixture was stirred for 5 h at room temperature and concentrated in vacuo. The crude residue was triturated with EtOAc (10 mL), and filtered through Celite™. The filtrate was concentrated in vacuo and was purified by chromatography (silica, DCM-MeOH=10:1) to afford triethylammonium 2-(4-((5-(2-(4-chloro-3-methoxyphenyl)propan-2-yl)-1-(4-fluorophenyl)-1H-imidazol-2-ylthio)methyl)-3-fluorobenzamido)ethanesulfonate (45 mg, 65%) as a white solid. ¹H NMR (400 MHz, CD₃OD): δ 7.54-7.47 (m, 2H), 7.27 (s, 1H), 7.15 (d, 1H), 7.06 (t, 1H) 6.81-6.77 (m, 2H), 6.48-6.45 (m, 2H), 6.06-6.03 (m, 2H), 4.04 (s, 2H), 3.85 (t, 2H), 3.69 (s, 3H), 3.24 (q, 6H), 3.13 (t, 2H), 1.50 (s, 6H), 1.33 (t, 9H); MS (EI) m/z 637 (MH⁺).

To a solution of triethylammonium 2-(4-((5-(2-(4-chloro-3-methoxyphenyl)propan-2-yl)-1-(4-fluorophenyl)-1H-imidazol-2-ylthio)methyl)-3-fluorobenzamido)ethanesulfonate (45 mg, 0.061 mmol) in water (3 mL) was added NaHCO₃ (5.1 mg, 0.061 mmol). After stirring 4 h, the aqueous mixture was washed with Et₂O (5 mL). The aqueous layer was concentrated in vacuo, and the residue was triturated with DCM-MeOH (2:1=v/v, 6 mL). The mixture was filtered through Celite™ and the filtrate was concentrated in vacuo to give the title compound (25 mg, 63%) as white solid. ¹H NMR (400 MHz, CD₃OD): δ 7.53-7.48 (m, 2H), 7.27 (s, 1H), 7.15 (d, 1H), 7.06 (t, 1H) 6.79 (t, 2H), 6.48-6.45 (m, 2H), 6.07-6.03 (m, 2H), 4.05 (s, 2H), 3.84 (t, 2H), 3.66 (s, 3H), 3.12 (t, 2H), 1.50 (s, 6H).

Example 9

(S)-2-(3-chloro-4-((5-(2-(4-chloro-3-methoxyphenyl)propan-2-yl)-1-(4-fluorophenyl)-1H-imidazol-2-ylthio)methyl)-5-fluorobenzamido)-5-guanidinopentanoic acid

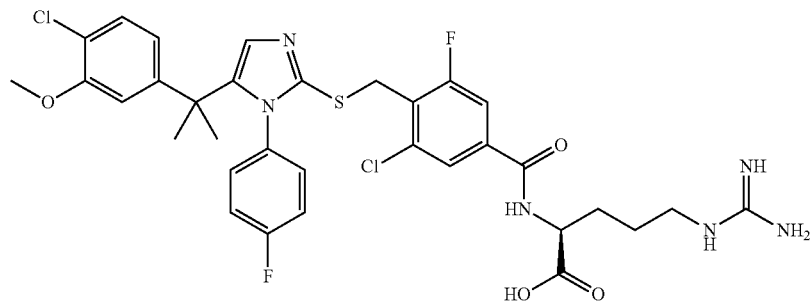 [SMILES: COc1cc(C(C)(C)c2cnc(SCc3c(F)cc(C(=O)N[C@@H](CCCNC(=N)N)C(=O)O)cc3Cl)n2-c2ccc(F)cc2)ccc1Cl]

To a solution of 3-chloro-4-((5-(2-(4-chloro-3-methoxyphenyl)propan-2-yl)-1-(4-fluorophenyl)-1H-imidazol-2-ylthio)methyl)-5-fluorobenzoic acid (0.96 g, 1.70 mmol) and (S)-tert-butyl 2-amino-5-guanidinopentanoate (0.54 g, 1.79 mmol) in DMF (4 mL) at 0° C. was added HATU (0.69 g, 1.79 mmol) and DIPEA (0.82 mL, 5.27 mmol). The reaction was stirred at room temperature for 1 h, quenched with satd NaHCO$_3$ and diluted with EtOAc. The mixture was washed with water (10 mL), brine (10 mL) and dried with Na$_2$SO$_4$. The residue was purified by column chromatography (silica, MeOH/DCM) to afford (S)-tert-butyl 2-(3-chloro-4-((5-(2-(4-chloro-3-methoxyphenyl)propan-2-yl)-1-(4-fluorophenyl)-1H-imidazol-2-ylthio)methyl)-5-fluorobenzamido)-5-guanidinopentanoate (1.2 g) as a white solid. The solids were dissolved in 4N HCl in dioxane (8 mL) and stirred for 3 h. The reaction was concentrated and purified by chromatography (silica, MeOH/DCM) to yield the title compound (380 mg) as a white solid. $^1$H-NMR (DMSO-d$_6$, 400 MHz) δ 8.84 (d, J=7.6 Hz, 1H), 7.81 (s, 1H), 7.64-7.61 (m, 1H), 7.46-7.43 (m, 1H), 7.21 (d, J=8.30 Hz, 1H), 7.18 (s, 1H), 7.01-6.93 (m, 2H), 6.61-6.57 (m, 1H), 6.54-6.49 (m, 3H), 4.37-4.31 (m, 1H), 4.07 (s, 2H), 3.68 (s, 3H), 3.15-3.11 (m, 2H), 1.88-1.70 (m, 2H), 1.61-1.54 (m, 2H), 1.47-1.46 (m, 6H), 1.42 (s, 9H); MS (EI) m/z 719 [MH]$^+$.

(R)-2-(3-chloro-5-fluoro-4-((5-(2-(4-fluoro-3-methoxyphenyl)propan-2-yl)-1-(4-fluorophenyl)-1H-imidazol-2-ylthio)methyl)benzamido)-5-guanidinopentanoic acid

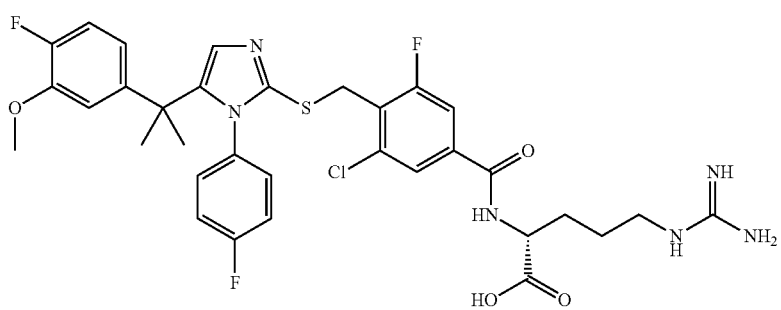 [SMILES: COc1cc(C(C)(C)c2cnc(SCc3c(F)cc(C(=O)N[C@H](CCCNC(=N)N)C(=O)O)cc3Cl)n2-c2ccc(F)cc2)ccc1F]

¹H NMR (400 MHz, CD₃OD) δ 7.66 (s, 1H), 7.51-7.43 (m, 1H), 6.90 (dd, J=11.11, 8.54 Hz, 1H), 6.81 (td, J=8.34, 6.29 Hz, 2H), 6.57 (dd, J=8.07, 2.08 Hz, 1H), 6.47 (ddd, J=8.47, 3.98, 2.28 Hz, 1H), 6.35-6.18 (m, 2H), 4.50 (dd, J=8.54, 4.91 Hz, 1H), 4.00 (d, J=2.93 Hz, 2H), 3.70 (d, J=4.92 Hz, 3H), 3.48 (d, J=7.01 Hz, 1H), 3.29-3.12 (m, 4H), 1.99 (s, 1H), 1.88 (s, 1H), 1.77-1.63 (m, 2H), 1.50 (d, J=4.50 Hz, 7H), 1.33-1.24 (m, 1H); MS (EI) m/z 703 [MH]⁺.

(R)-2-(3-chloro-4-((5-(2-(3-chloro-4-sulfamoylphenyl)propan-2-yl)-1-(4-fluoro-3-methoxyphenyl)-1H-imidazol-2-ylthio)methyl)-5-fluorobenzamido)-5-guanidinopentanoic acid

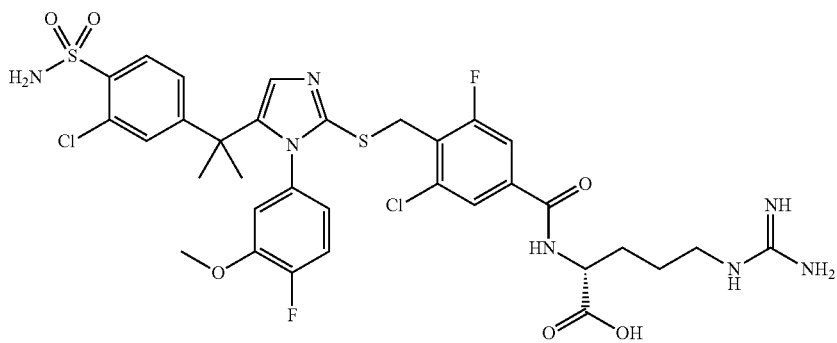 [SMILES: COc1cc(-n2c(C(C)(C)c3ccc(S(N)(=O)=O)c(Cl)c3)cnc2SCc2c(F)cc(C(=O)N[C@H](CCCNC(=N)N)C(=O)O)cc2Cl)ccc1F]

¹H NMR (400 MHz, CD₃OD) δ 7.94-7.86 (m, 1H), 7.71 (s, 1H), 7.55-7.49 (m, 1H), 7.28 (d, J=0.98 Hz, 1H), 7.15 (d, J=1.84 Hz, 1H), 7.13-7.07 (m, 1H), 6.91-6.78 (m, 1H), 6.00-5.91 (m, 2H), 4.56-4.38 (m, 1H), 4.07 (s, 2H), 3.40 (d, J=5.52 Hz, 3H), 3.23 (dd, J=7.22, 4.30 Hz, 7H), 2.06-1.89 (m, 1H), 1.89-1.76 (m, 1H), 1.67 (s, 3H), 1.59-1.46 (m, 9H), 1.25 (d, J=6.40 Hz, 6H); MS (EI) m/z 798 [MH]⁺.

(R)-2-(4-((5-(2-(3-aminobenzo[d]isoxazol-5-yl)propan-2-yl)-1-(4-fluoro-3-methoxyphenyl)-1H-imidazol-2-ylthio)methyl)-3-chloro-5-fluorobenzamido)-5-guanidinopentanoic acid

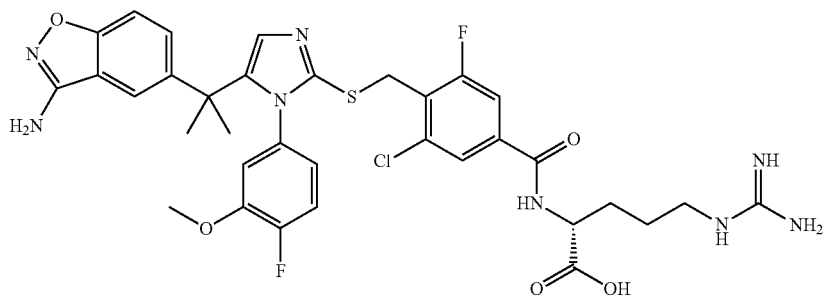 [SMILES: COc1cc(-n2c(C(C)(C)c3ccc4onc(N)c4c3)cnc2SCc2c(F)cc(C(=O)N[C@H](CCCNC(=N)N)C(=O)O)cc2Cl)ccc1F]

¹H NMR (400 MHz, CD₃OD) δ 7.82-7.67 (m, 1H), 7.63-7.49 (m, 1H), 7.37 (d, J=1.46 Hz, 1H), 7.32-7.18 (m, 3H), 6.87-6.74 (m, 1H), 6.10-6.01 (m, 1H), 5.73-5.59 (m, 1H), 4.55-4.42 (m, 1H), 4.09 (d, J=0.71 Hz, 2H), 3.16-3.08 (m, 2H), 2.08-1.92 (m, 1H), 1.92-1.79 (m, 1H), 1.65 (d, J=3.38 Hz, 4H), 1.58 (s, 4H), 3.22 (s, 2H); MS (EI) m/z 741 [MH]⁺.

Example 10

(S)-5-amino-2-(3-chloro-4-((5-(2-(4-chloro-3-methoxyphenyl)propan-2-yl)-1-(4-fluorophenyl)-1H-imidazol-2-ylthio)methyl)-5-fluorobenzamido)pentanoic acid hydrochloride

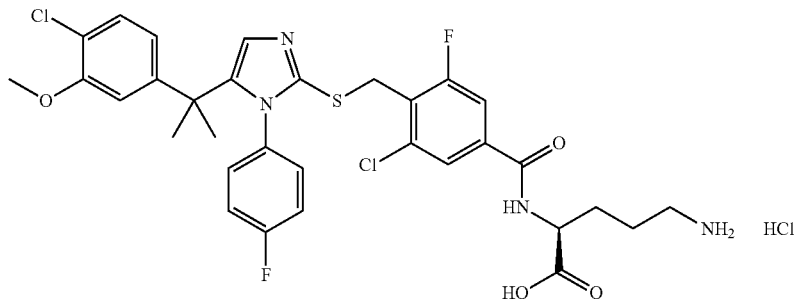 [SMILES: COc1cc(C(C)(C)c2cnc(SCc3c(F)cc(C(=O)N[C@@H](CCCN)C(=O)O)cc3Cl)n2-c2ccc(F)cc2)ccc1Cl ; Cl]

To a 0° C. solution of 3-chloro-4-((5-(2-(4-chloro-3-methoxyphenyl)propan-2-yl)-1-(4-fluoro-phenyl)-1H-imidazol-2-ylthio)methyl)-5-fluorobenzoic acid (0.94 g, 0.17 mmol), (S)-tert-butyl 2-amino-5-(tert-butoxycarbonylamino)pentanoate (0.050 g, 0.18 mmol) and HATU (0.067 g, 0.18 mmol) in DMF (4 mL) was added DIPEA (0.058 mL, 0.33 mmol). The ice bath was removed and the reaction was stirred for 2 h at room temperature. The reaction was quenched with satd NaHCO$_3$ and diluted with EtOAc. The organic layer was washed with H$_2$O (2×5 mL), brine, and dried with Na$_2$SO$_4$. The solvent was removed in vacuo and the residue was purified by column chromatography to afford 114 mg of (S)-tert-butyl 5-(tert-butoxycarbonylamino)-2-(3-chloro-4-((5-(2-(4-chloro-3-methoxyphenyl)propan-2-yl)-1-(4-fluorophenyl)-1H-imidazol-2-ylthio)methyl)-5-fluorobenzamido)pentanoate. The compound was then dissolved in 4N solution of HCl in dioxane and stirred for 2 h, when the reaction was determined to be complete by LCMS. Ether was added to the reaction mixture. Then the solids were collected by filtration and dried under vacuum to afford the title compound (75 mg). $^1$H-NMR (DMSO$_6$, 400 MHz) δ 9.00 (d, J=8.3 Hz, 1H), 8.01 (s, 3H), 7.93 (s, 1H), 7.82-7.75 (m, 2H), 7.23 (d, J=8.5 Hz, 1H), 7.06-6.99 (m, 2H), 6.67-6.64 (m, 1H), 6.61-6.57 (m, 1H), 6.53-6.52 (m, 1H), 6.50-6.47 (m, 1H), 4.43-4.38 (m, 1H), 4.19 (s, 2H), 3.70 (s, 3H), 2.84-2.80 (m, 2H), 1.97-1.80 (m, 2H), 1.75-1.66 (m, 2H), 1.51 (m, 6H); MS (ES): 677 [M]$^+$.

(S)-2-Amino-5-(3-chloro-4-((5-(2-(4-chloro-3-methoxyphenyl)propan-2-yl)-1-(4-fluorophenyl)-1H-imidazol-2-ylthio)methyl)-5-fluorobenzamido)pentanoic acid

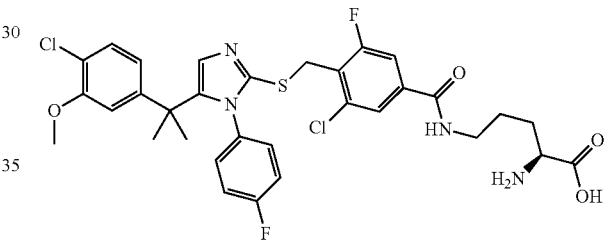

$^1$H NMR (400 MHz, MeOD) δ 8.27 (s, 1H), 8.04 (s, 1H), 7.86 (d, J=9.9 Hz, 1H), 7.86 (d, J=9.9 Hz, 1H), 7.52 (d, J=8.4 1H), 7.24-7.16 (m, 2H), 6.84-6.72 (m, 2H), 6.69-6.60 (m, 2H), 4.52 (s, 2H), 4.35 (t, J=6.2 Hz, 1H), 3.96 (s, 3H), 3.74 (dd, J=11.6, 6.6 Hz, 2H), 2.38-1.92 (m, 4H), 1.87 (s, 6H). LC-MS: 677.1 [M+1]$^+$.

Example 11

(S)-5-(3-Chloro-4-((5-(2-(4-chloro-3-methoxyphenyl)propan-2-yl)-1-(4-fluorophenyl)-1H-imidazol-2-ylthio)methyl)-5-fluorobenzamido)-2-guanidinopentanoic acid

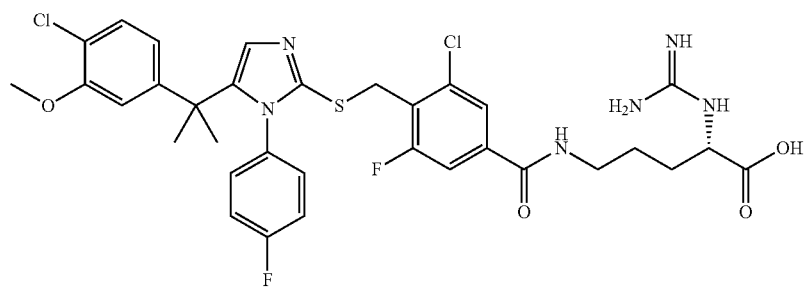 [SMILES: COc1cc(C(C)(C)c2cnc(SCc3c(F)cc(C(=O)NCCC[C@H](NC(=N)N)C(=O)O)cc3Cl)n2-c2ccc(F)cc2)ccc1Cl]

A solution of (S)-2-amino-5-(3-chloro-4-((5-(2-(4-chloro-3-methoxyphenyl)propan-2-yl)-1-(4-fluorophenyl)-1H-imidazol-2-ylthio)methyl)-5-fluorobenzamido)pentanoic acid (268 mg, 0.40 mmol), N,N'-di-Boc-1H-pyrazole-1-carboxamidine (135 mg, 0.44 mmol) and triethylamine (175 µL, 1.19 mmol) in MeOH (10 mL) was stirred at 25° C. for 18 h. The reaction mixture was concentrated and reconstituted in EtOAc. The organic layer was washed with 1N HCl (3×5 mL), sat. aq. NaHCO₃ (5 mL), dried over Na₂SO₄ and concentrated to a colorless oil. To the oil was added 4N HCl in Dioxane (10 mL) at 25° C. and stirred for 18 h. Upon completion, the reaction mixture was concentrated and purified by flash chromatography (MeOH/DCM, 0-20%) to give the title product (64 mg, 28% yield) as a white solid. ¹H NMR (400 MHz, DMSO-d₆) δ 8.91 (t, J=5.2 Hz, 1H), 7.76 (s, 1H), 7.61 (dd, J=10.1, 1.0 Hz, 1H), 7.50-7.10 (br s, 4H), 7.45 (d, J=6.6 Hz, 2H), 7.21 (d, J=8.3 Hz, 1H), 7.17 (s, 1H), 6.95 (t, J=8.4 Hz, 2H), 6.58-6.43 (m, 4H), 4.06 (s, 2H), 3.77 (d, J=4.6 Hz, 1H), 3.67 (s, 3H), 3.23 (s, 2H), 1.71-1.59 (m, 2H), 1.58-1.46 (m, 2H), 1.46 (s, 6H). MS (EI) m/z 719 (MH⁺).

Example 12

3-Chloro-4-((5-(2-(4-chloro-3-methoxyphenyl)propan-2-yl)-1-(4-fluorophenyl)-1H-imidazol-2-ylthio)methyl)-5-fluoroaniline

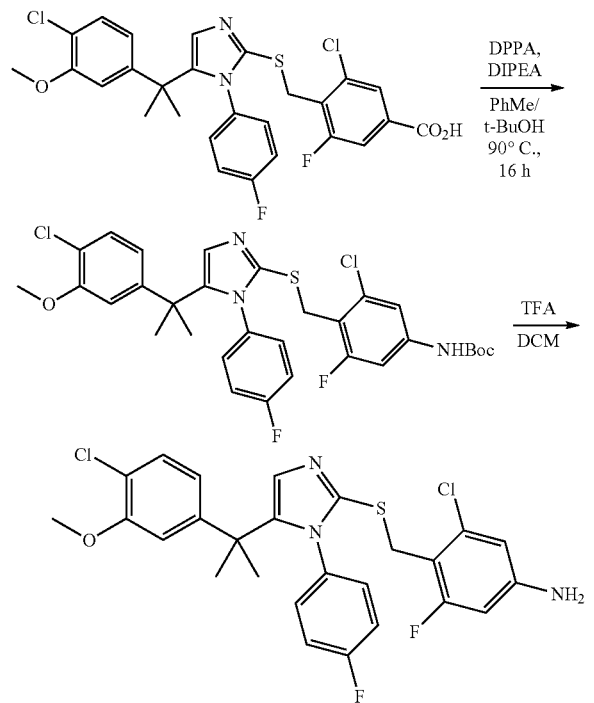

To a suspension of 3-chloro-4-((5-(2-(4-chloro-3-methoxyphenyl)propan-2-yl)-1-(4-fluorophenyl)-1H-imidazol-2-ylthio)methyl)-5-fluorobenzoic acid (540 mg) in a mixture of toluene (5 mL) and t-BuOH (1.5 mL) cooled to 0° C. was added diphenyl phosphoryl azide (DPPA) (302 mg, 1.1 eq) followed by DIPEA (1.3 eq, 0.23 mL). During addition of base, white slurry became clear solution. Reaction mixture was heated at 80° C. overnight. LC-MS showed complete conversion. After cooling to ambient temperature, the reaction mixture was diluted with EtOAc and washed with satd NaHCO₃. The organic layer was dried, concentrated and purified by chromatography (silica, EtOAc/Hex, 10-60%) to yield tert-butyl 3-chloro-4-((5-(2-(4-chloro-3-methoxyphenyl)propan-2-yl)-1-(4-fluorophenyl)-1H-imidazol-2-ylthio)methyl)-5-fluorophenylcarbamate (230 mg). MS (EI) m/z 634 (MH⁺).

A solution of tert-butyl 3-chloro-4-((5-(2-(4-chloro-3-methoxyphenyl)propan-2-yl)-1-(4-fluorophenyl)-1H-imidazol-2-ylthio)methyl)-5-fluorophenylcarbamate (200 mg) in DCM (1 mL) was treated with TFA (1 mL) with stirring. After 1 h, the solution was concentrated under reduced pressure, diluted with DCE (5 mL). The organic layer was washed with water, satd NaHCO₃ and brine, then dried (MgSO₄) and concentrated to afford the title compound (152 mg, 90%). ¹H NMR (400 MHz, MeOD) δ 7.40 (s, 1H), 7.36 (d, J=9.1 Hz, 1H), 6.93 (d, J=8.4, 1H), 6.87 (d, J=8.4 Hz, 1H), 6.68-6.61 (m, 2H), 6.53 (s, 1H), 6.40-6.27 (m, 3H), 4.01 (s, 2H), 3.76 (s, 3H), 1.58 (s, 6H); MS (EI) m/z 534 (MH⁺).

Example 13

(S)-3-Amino-4-(3-chloro-4-((5-(2-(4-chloro-3-methoxyphenyl)propan-2-yl)-1-(4-fluorophenyl)-1H-imidazol-2-ylthio)methyl)-5-fluorophenylamino)-4-oxobutanoic acid

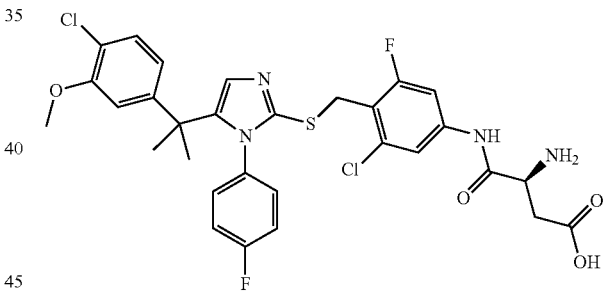

To a solution of 3-chloro-4-((5-(2-(4-chloro-3-methoxyphenyl)propan-2-yl)-1-(4-fluorophenyl)-1H-imidazol-2-ylthio)methyl)-5-fluoroaniline (50 mg, 93.6 µmol) and (S)-4-t-butoxy-2-(t-butoxycarbonylamino)-4-oxobutanoic acid (2.4 equiv, 66 mg, 0.244 mmol) in DCM (3 mL) was added HATU (2.2 equiv, 80 mg, 0.204 mmol) followed by DIPEA (3.0 equiv, 49 mL, 0.281 mmol). The mixture was stirred at room temperature overnight. Purification by column chromatography provided the protected product. Deprotection was performed by stirring with TFA (1 mL) and DCM (1 mL) for 1 h. Purification by HPLC using NH₄CO₃ as a modifier afforded the title compound as a white solid (11 mg, 18%). ¹H NMR (400 MHz, MeOD) δ 7.43 (s, 1H), 7.37 (d, J=11.6 Hz, 1H), 7.25 (s, 1H), 7.18 (d, J=8.4 Hz, 1H), 6.80 (m, 2H), 6.56-6.49 (m, 2H), 6.38-6.30 (m, 1H), 6.22 (m, 1H), 4.19 (t, J=7.6, 1H), 4.00 (dd, J=13.5, 7.4 Hz, 2H), 3.71 (s, 3H), 2.89-2.78 (m, 1H), 2.67 (dd, J=17.0, 8.1 Hz, 1H), 1.54 (s, 3H), 1.53 (s, 3H); MS (EI) m/z 649 (MH⁺).

Example 14

(S)-2-(3-(3-Chloro-4-((5-(2-(4-chloro-3-methoxyphenyl)propan-2-yl)-1-(4-fluorophenyl)-1H-imidazol-2-ylthio)methyl)-5-fluorophenyl)ureido)-5-guanidinopentanoic acid

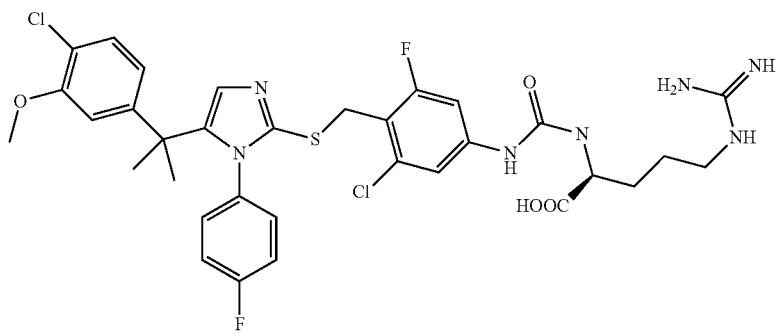 [SMILES: COc1cc(C(C)(C)c2cnc(SCc3c(F)cc(NC(=O)N[C@@H](CCCNC(=N)N)C(=O)O)cc3Cl)n2-c2ccc(F)cc2)ccc1Cl]

To a solution of 3-chloro-4-((5-(2-(4-chloro-3-methoxyphenyl)propan-2-yl)-1-(4-fluorophenyl)-1H-imidazol-2-ylthio)methyl)-5-fluoroaniline (175 mg, 0.322 mmol) in CHCl$_3$ (10 mL) was added triphosgene (97 mg, 0.322 mmol) followed by Et$_3$N (227.6 mg, 2.254 mmol) at 0° C. The mixture was stirred at room temperature 20 min. PMC protected L-arginine was added to the reaction mixture and allowed to stir at the same temperature overnight. Purification by column chromatography provided the protected product. Deprotection was performed by stirring with TFA (2 mL) and DCM (2 mL) for 1 h. Purification on HPLC yielded the title compound (52 mg). $^1$H NMR (400 MHz, MeOD) δ 7.24 (s, 1H), 7.26-7.12 (m, 3H), 6.81 (d, J=8.7 Hz, H), 6.79 (d, J=8.7 Hz, 1H), 6.54-6.48 (m, 2H), 6.25-6.14 (m, 2H), 4.22 (t, J=5.7 Hz, 1H), 3.97 (s, 2H), 3.68 (s, 3H), 3.23 (dt, J=13.6, 6.7 Hz, 2H), 2.08-1.77 (m, 4H), 1.53 (s, 6H); MS (EI) m/z 734 (MH$^+$).

Example 15

4-((5-(2-(4-chloro-3-methoxyphenyl)propan-2-yl)-1-(4-fluorophenyl)-1H-imidazol-2-ylthio)methyl)-3,5-difluorobenzenesulfonamide

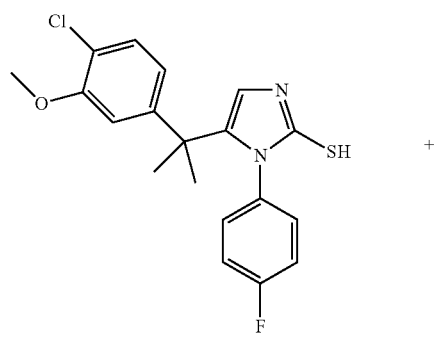

+

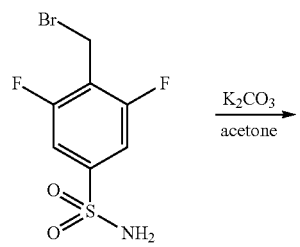

→ (K$_2$CO$_3$, acetone)

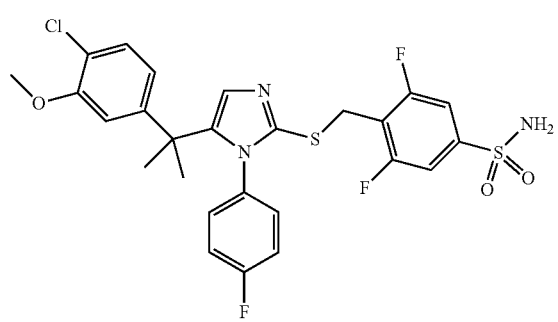

A mixture of 5-(2-(4-chloro-3-methoxyphenyl)propan-2-yl)-1-(4-fluorophenyl)-1H-imidazole-2-thiol (170 mg, 0.45 mmol, 1.0 eq), 4-(bromomethyl)-3,5-difluorobenzenesulfonamide (155 mg, 0.54 mmol, 1.2 eq) and K$_2$CO$_3$ (94 mg, 0.68 mmol, 1.5 eq) in acetone (2.3 mL) was stirred for 30 min. The reaction mixture was filtered, and the filtrate was concentrated and purified (silica, 0-75% EtOAc/Hex) to afford the title compound (252 mg, 96%) as a white solid. MS (EI) m/z 584 (MH$^+$).

3-Chloro-4-((5-(2-(3,4-dichlorophenyl)propan-2-yl)-1-(4-fluorophenyl)-1H-imidazol-2-ylthio)methyl)benzenesulfonamide

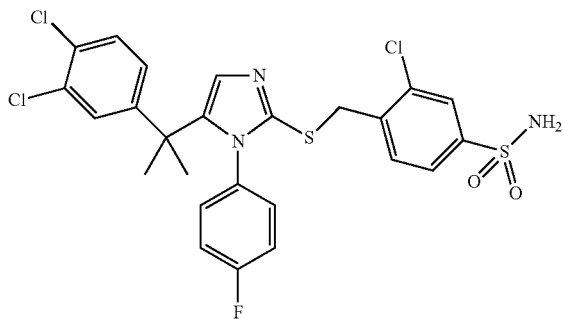 [SMILES: CC(C)(c1ccc(Cl)c(Cl)c1)c1cnc(SCc2ccc(S(N)(=O)=O)cc2Cl)n1-c1ccc(F)cc1]

Similarly the title compound was prepared from 5-(2-(3,4-dichlorophenyl)propan-2-yl)-1-(4-fluorophenyl)-1H-imidazole-2(3H)-thione and 4-(bromomethyl)-3-chlorobenzenesulfonamide. MS (EI) m/z 584 (MH)⁺.

4-Chloro-5-((5-(2-(4-chloro-3-methoxyphenyl)propan-2-yl)-1-(4-fluorophenyl)-1H-imidazol-2-ylthio)methyl)-2-fluorobenzenesulfonamide

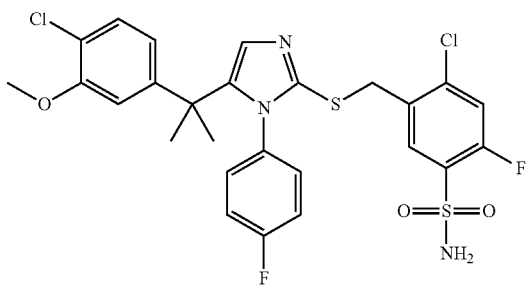 [SMILES: COc1cc(C(C)(C)c2cnc(SCc3cc(S(N)(=O)=O)c(F)cc3Cl)n2-c2ccc(F)cc2)ccc1Cl]

To a solution of 2-chloro-4-fluoro-5-sulfamoylbenzoic acid (3.2 g, 12.65 mmol) in THF (10 mL) was added 1M BH₃·THF (38 mL, 38.0 mmol). After stirring 12 h, the reaction mixture was quenched with MeOH and concentrated in vacuo. The residue was purified by chromatography (silica, EtOAc-Hex) to afford 4-chloro-2-fluoro-5-(hydroxymethyl)benzenesulfonamide (1.9 g). To a suspension of 4-chloro-2-fluoro-5-(hydroxymethyl)benzenesulfonamide (1.78 g, 7.43 mmol) in DCM (10 mL) was added PBr₃ (2.21 g, 8.17 mmol). The reaction was stirred for 24 h when it was determined to be complete by GCMS. The reaction was carefully quenched with H₂O and then partitioned between THF and brine. The organic layer was dried over Na₂SO₄ and concentrated in vacuo to afford 5-(bromomethyl)-4-chloro-2-fluorobenzenesulfonamide (1.98 g) as an off-white solid. ¹H-NMR (DMSO-d₆, 400 MHz) δ 8.08 (d, J=7.8 Hz, 1H), 7.84 (s, 2H), 7.80 (d, J=9.9 Hz, 1H), 4.83 (s, 2H).

To a mixture of 5-(2-(4-chloro-3-methoxyphenyl)propan-2-yl)-1-(4-fluorophenyl)-1H-imidazole-2-thiol (0.94 g, 2.49 mmol) and K₂CO₃ in acetone (5 mL) was added 5-(bromomethyl)-4-chloro-2-fluorobenzenesulfonamide (0.83 g, 2.73 mmol). After stirring 3 h, the reaction mixture was filtered. The filtrate was concentrated and purified by chromatography (silica, EtOAc-Hex) to afford the title compound (1.21 g). ¹H-NMR (DMSO-d₆, 400 MHz) δ 7.81 (d, J=7.8 Hz, 1H), 7.77 (s, 2H), 7.70 (d, J=9.7 Hz, 1H), 7.22-7.19 (m, 1H), 7.16 (s, 1H), 7.01-6.97 (m, 2H), 6.56-6.49 (m, 4H), 4.26 (s, 2H), 3.64 (s, 3H), 1.46 (s, 6H); MS (EI) m/z 598 [M]⁺.

3-((5-(2-(4-Chloro-3-methoxyphenyl)propan-2-yl)-1-(4-fluorophenyl)-1H-imidazol-2-ylthio)methyl)-2,4-difluorobenzenesulfonamide

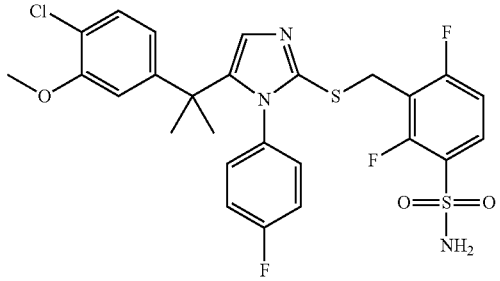 [SMILES: COc1cc(C(C)(C)c2cnc(SCc3c(F)ccc(S(N)(=O)=O)c3F)n2-c2ccc(F)cc2)ccc1Cl]

¹H NMR (400 MHz, DMSO-d₆) δ 7.80-7.68 (m, 3H), 7.27-7.12 (m, 3H), 7.03-6.92 (m, 2H), 6.61-6.46 (m, 4H), 4.06 (s, 2H), 3.67 (s, 3H), 1.46 (s, 6H); MS (EI) m/z 582 [M]⁺.

3-chloro-4-((5-(2-(3,4-difluoro-5-methoxyphenyl)propan-2-yl)-1-(4-fluorophenyl)-1H-imidazol-2-ylthio)methyl)-5-fluorobenzenesulfonamide

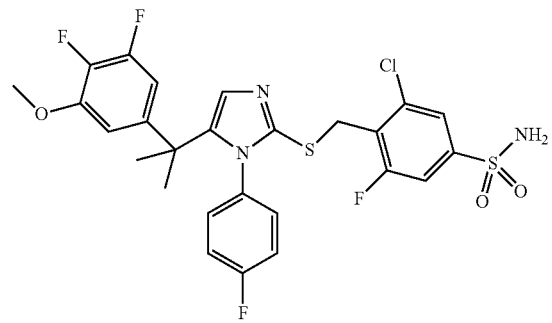 [SMILES: COc1cc(C(C)(C)c2cnc(SCc3c(F)cc(S(N)(=O)=O)cc3Cl)n2-c2ccc(F)cc2)cc(F)c1F]

¹H NMR (400 MHz, CD₃OD) δ 7.68 (s, 1H), 7.44-7.46 (d, 2H), 7.25 (s, 1H), 6.87-6.90 (t, 2H), 6.40-6.43 (d, 2H), 6.36-6.38 (m, 2H), 4.02 (s, 2H), 3.75 (s, 3H), 1.49 (s, 6H); MS (EI) m/z 600 [M]⁺.

Example 16

3-Chloro-4-((5-(2-(3,4-dichlorophenyl)propan-2-yl)-1-(4-fluorophenyl)-1H-imidazol-2-ylthio)methyl)-N-(isopropylcarbamoyl)benzenesulfonamide

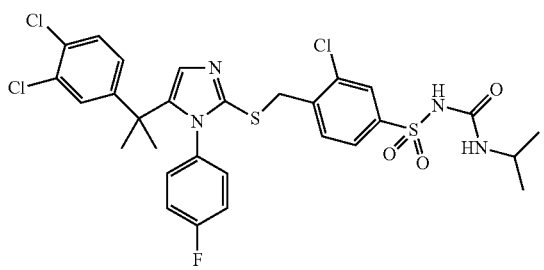 [SMILES: CC(C)NC(=O)NS(=O)(=O)c1ccc(CSc2ncc(C(C)(C)c3ccc(Cl)c(Cl)c3)n2-c2ccc(F)cc2)c(Cl)c1]

To a stirred solution of aluminum trichloride (75 mg, 513 μmol, 3.0 eq) in toluene (1 mL, anhyd) was added isopropylisocyanate (17 μL, 170 μmol, 1.0 eq). After 3 min of stirring at room temperature, 3-chloro-4-((5-(2-(3,4-dichlorophenyl)propan-2-yl)-1-(4-fluorophenyl)-1H-imidazol-2-ylthio)methyl)benzenesulfonamide (100 mg, 170 μmol, 1.0 eq) was added neat. The reaction mixture was heated at 80° C. for 16 h, then partitioned between ethyl acetate and water. The aqueous layer was extracted with ethyl acetate (3×), washed with water, brine, then dried and concentrated. Purification (silica gel chromatography, 20% methanol/ethyl acetate) provided the title compound (50 mg) as an off-white foam. $^1$H NMR (DMSO-d$_6$, 400 MHz): δ 8.33 (s, 1H), 7.78 (s, 1H), 7.63 (d, J=7.8 Hz, 1H), 7.43 (d, J=8.2 Hz, 1H), 7.31 (d, J=8.2 Hz, 1H), 7.22 (s, 1H), 6.98-6.87 (m, 4H), 6.41-6.35 (m, 2H), 6.05 (br s, 1H), 4.22 (s, 2H), 3.61-3.50 (m, 1H), 1.44 (s, 6H), 0.97 (d, J=6.6 Hz, 6H); MS (EI) m/z 671 (MH)$^+$.

Example 17

3-Chloro-4-((5-(2-(3,4-dichlorophenyl)propan-2-yl)-1-(4-fluorophenyl)-1H-imidazol-2-ylthio)methyl)-N-(pyrrolidin-1-ylcarbamoyl)benzenesulfonamide To a stirred solution of 3-chloro-4-((5-(2-(3,4-dichlorophenyl)propan-2-yl)-1-(4-fluorophenyl)-1H-imidazol-2-ylthio)methyl)benzenesulfonamide (76 mg, 0.13 mmol, 1.0 eq) in MeOH (0.5 mL) was added sodium hydroxide (5 mg, 0.13 mmol, 1.0 eq, dissolved in 0.5 mL MeOH). The mixture was stirred at room temperature for 16 h then concentrated in vacuo. The residue was diluted with anhydrous DMF (0.5 mL) and then charged with a solution of phenyl pyrrolidin-1-ylcarbamate (30 mg, 0.14 mmol, 1.1 eq) in 0.5 mL of DMF. Phenyl pyrrolidin-1-ylcarbamate was prepared by treatment of phenychloroformate with 1-aminopyrrolidine. The reaction mixture was then heated at 50° C. overnight. The mixture was cooled, acidified with 1M HCl and extracted with ethyl acetate (3×). The organic layers were washed with brine, dried (magnesium sulfate) and concentrated. Purification by column chromatography (30% methanol/ethyl acetate) provided the title compound (15 mg) as a white foam. $^1$H NMR (CD$_2$Cl$_2$, 400 MHz): δ 8.98 (br s, 1H), 8.00 (s, 1H), 7.82 (dd, J=8.3, 2.2 Hz, 1H), 7.51 (d, J=8.3 Hz, 1H), 7.27 (d, J=8.3 Hz, 1H), 7.18 (s, 1H), 7.00 (d, J=2.2 Hz, 1H), 6.85-6.78 (m, 4H), 6.32-6.27 (m, 2H), 4.33 (s, 2H), 3.22-3.13 (2H), 2.48-2.38 (m, 2H), 1.86-1.78 (m, 4H), 1.47 (s, 6H); MS (EI) m/z 695 (MH)$^+$.

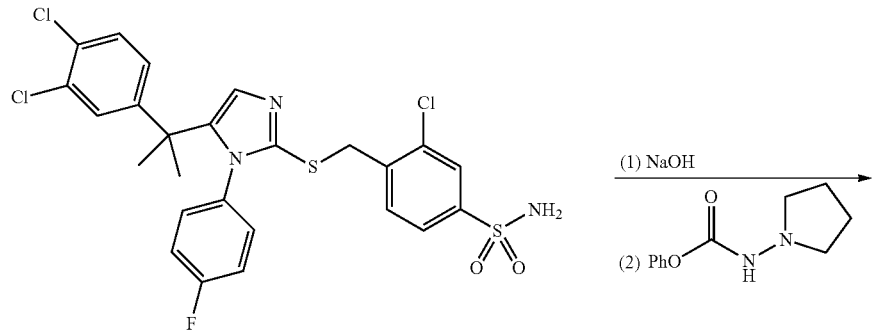

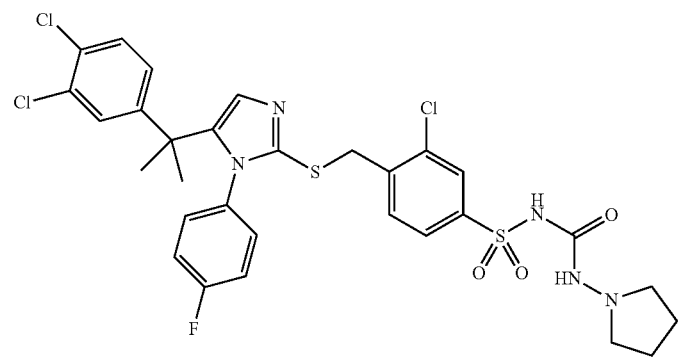

Example 18

Ethyl 4-((5-(2-(4-chloro-3-methoxyphenyl)propan-2-yl)-1-(4-fluorophenyl)-1H-imidazol-2-ylthio)methyl)-3,5-difluorophenylsulfonylcarbamate

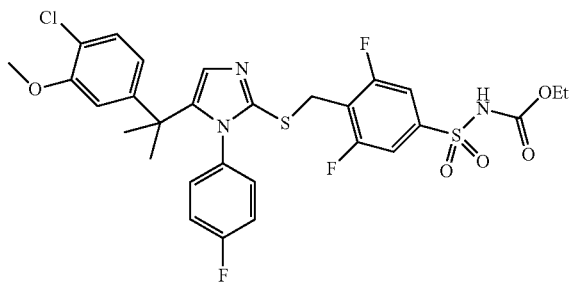 [SMILES: CCOC(=O)NS(=O)(=O)c1cc(F)c(CSc2ncc(C(C)(C)c3ccc(Cl)c(OC)c3)n2-c2ccc(F)cc2)c(F)c1]

To a mixture of 4-((5-(2-(4-chloro-3-methoxyphenyl)propan-2-yl)-1-(4-fluorophenyl)-1H-imidazol-2-ylthio)methyl)-3,5-difluorobenzenesulfonamide (100 mg, 0.17 mmol, 1.0 eq) and ethyl chloroformate (0.022 mL, 0.21 mmol, 1.2 eq) in DCM was added Et$_3$N (0.05 mL, 0.34 mmol, 2.0 eq). After stirring 3 h, the reaction mixture was diluted with EtOAc, washed with water and brine, and purified by chromatography (silica, 0 to 80% EtOAc/Hex, then 10% MeOH/DCM) to provide the title compound (76 mg, 68%). MS (EI) m/z 655 (MH$^+$).

Example 19

4-((5-(2-(4-Chloro-3-methoxyphenyl)propan-2-yl)-1-(4-fluorophenyl)-1H-imidazol-2-ylthio)methyl)-3,5-difluoro-N-(morpholinocarbamoyl)benzenesulfonamide

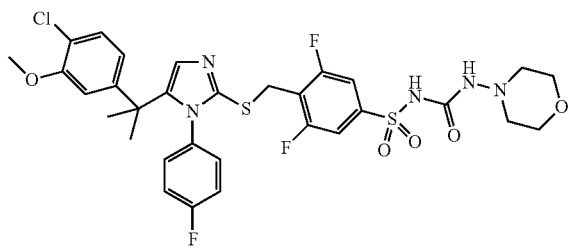 [SMILES: COc1cc(C(C)(C)c2cnc(SCc3c(F)cc(S(=O)(=O)NC(=O)NN4CCOCC4)cc3F)n2-c2ccc(F)cc2)ccc1Cl]

Ethyl 4-((5-(2-(4-chloro-3-methoxyphenyl)propan-2-yl)-1-(4-fluorophenyl)-1H-imidazol-2-ylthio)methyl)-3,5-difluorophenylsulfonylcarbamate (76 mg, 0.12 mmol, 1.0 eq) and 4-aminomorpholine (0.045 mL, 0.46 mmol, 4.0 eq) in toluene (2.5 mL, anhyd) were heated at reflux for 2.5 h. The reaction mixture was cooled to room temperature, diluted with EtOAc and washed with water, followed by brine. After drying (MgSO$_4$), the organics were concentrated and purified by chromatography (silica, 0 to 80% EtOAc/Hex, then 10% MeOH/DCM) to provide the title compound (40 mg). $^1$H NMR (400 MHz, DMSO-d$_6$) δ 8.33 (s, 1H), 7.41-7.16 (m, 4H), 7.03-6.90 (m, 3H), 6.57-6.43 (m, 4H), 4.02-3.98 (m, 2H), 3.71-3.65 (m, 3H), 3.57-3.50 (m, 3H), 3.48-3.38 (m, 1H), 3.31-3.25 (m, 1H), 2.69-2.58 (m, 3H), 1.46 (s, 6H); MS (EI) m/z 710.1 (MH$^+$).

Example 20

4-((5-(2-(4-Chloro-3-methoxyphenyl)propan-2-yl)-1-(4-fluorophenyl)-1H-imidazol-2-ylthio)methyl)-3,5-difluoro-N-(3-guanidinopropyl)benzenesulfonamide

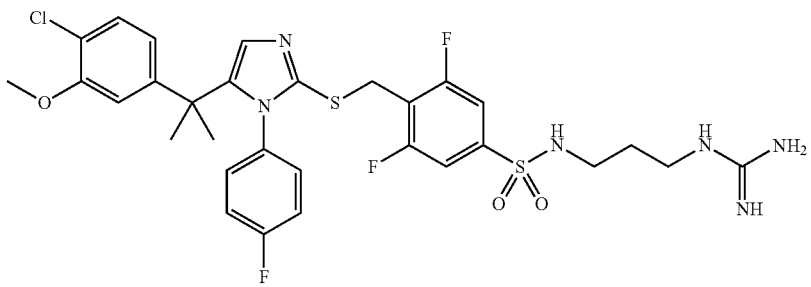 [SMILES: COc1cc(C(C)(C)c2cnc(SCc3c(F)cc(S(=O)(=O)NCCCNC(=N)N)cc3F)n2-c2ccc(F)cc2)ccc1Cl]

A solution of N-(3-aminopropyl)-4-((5-(2-(4-chloro-3-methoxyphenyl)propan-2-yl)-1-(4-fluorophenyl)-1H-imidazol-2-ylthio)methyl)-3,5-difluorobenzenesulfonamide (172 mg, 0.27 mmol), N,N'-di-Boc-1H-pyrazole-1-carboxamidine (100 mg, 0.32 mmol) and Et$_3$N (190 μL, 1.35 mmol) in MeOH (10 mL) was stirred at 25° C. for 18 h. The reaction mixture was concentrated and reconstituted in EtOAc. The organic layer was washed with 1N HCl (3×5 mL), satd NaHCO$_3$ (5 mL), dried over Na$_2$SO$_4$ and concentrated to a colorless oil. To the oil was added 4N HCl in dioxane (10 mL) at 25° C. and stirred for 18 h. Upon completion, the reaction mixture was concentrated and purified by preparatory HPLC (MeCN/H$_2$O with 0.1% TFA, 10-99%) to give the title product (54 mg, 28% yield) as white solid. $^1$H NMR (400 MHz, MeOD) δ 7.99 (s, 1H), 7.51 (s, 2H), 7.37 (s, 1H), 7.28 (d, J=5.7 Hz, 1H), 6.98 (s, 2H), 6.62 (s, 2H), 6.56 (s, 2H), 4.14 (s, 2H), 3.73 (s, 3H), 3.70-3.54 (m, 3H), 3.30-3.21 (m, 2H), 3.00 (s, 2H), 1.80 (s, 2H), 1.63 (s, 6H); MS (EI) m/z 681 (MH$^+$).

Example 21

3-Chloro-4-((5-(2-(4-chloro-3-methoxyphenyl)propan-2-yl)-1-(4-fluorophenyl)-1H-imidazol-2-ylthio)methyl)-5-fluorobenzenesulfonic acid

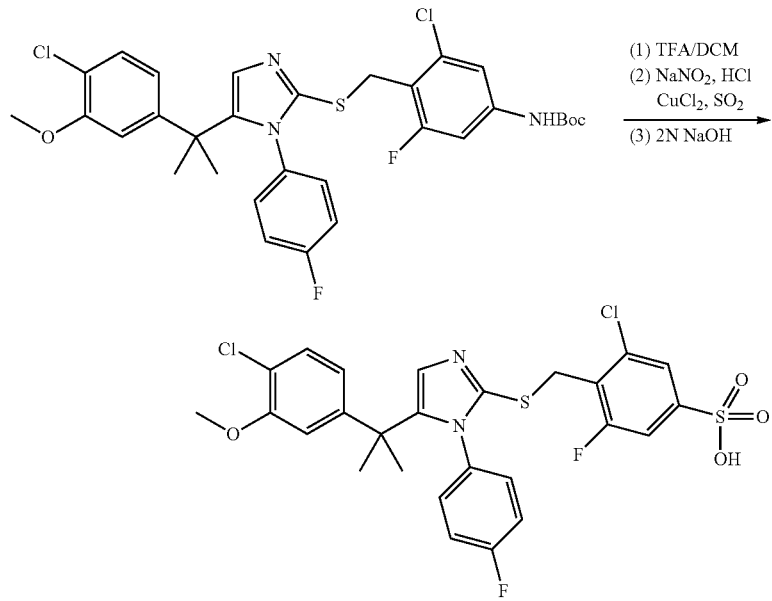

To a solution of tert-butyl 3-chloro-4-((5-(2-(4-chloro-3-methoxyphenyl)propan-2-yl)-1-(4-fluorophenyl)-1H-imidazol-2-ylthio)methyl)-5-fluorophenylcarbamate (12.0 g, 19 mmol) in DCM (anhyd, 30 mL) at 5° C. was added slowly TFA (30 mL). The flask was removed from the ice bath and stirred at ambient temperature. After 60 min, the deprotection was complete by LCMS and TLC. The mixture was concentrated to a minimum volume and then diluted with HOAc (64 mL). Added slowly mixture of conc HCl (21 mL) and water (12 mL), then submerged flask in ice bath to attain temperature of 5° C. While maintaining a temperature of 4-6° C., added dropwise a solution of sodium nitrite (3.1 g, 1.24 eq, 44.9 mmol) in water (4 mL).

In a 1000 mL 3-neck flask added CuCl$_2$ (0.509 g, 0.2 eq, 3.8 mmol), acetic acid (61 mL) and water (1.0 mL). Bubbled sulfur dioxide through the mixture at a slow rate for 10 min, then submerged flask in ice bath at 5° C. Continued bubbling sulfur dioxide through mixture with stirring. After diazotization reaction has stirred 30-40 min at 5° C., transfer mixture in small portions via cannula into other flask at 5° C. Addition of diazonium salt took 20 min and temperature held steady at 5° C. After stirring 60 min, an aliquot from the mixture showed 90-95% sulfonyl chloride present by LCMS. Diluted with water (400 mL), sulfonyl chloride was extracted into DCM (2×400 mL) and concentrated under reduced pressure to remove DCM. This material was dissolved in THF (200 mL), chilled to 5° C. with an ice bath, and then treated with 2N NaOH dropwise until slightly basic (pH 8). After stirring 10 min, the mixture was concentrated under reduced pressure, diluted with water (100 mL) and acidified with 1N HCl. The aqueous layer was extracted with DCM (4×150 mL). Combined extracts were washed with brine, dried (Na$_2$SO$_4$) and concentrated. The residue was purified by column chromatography (silica, DCM/MeOH, 0-20%) to afford the title compound (8.05 g, 70.9%). $^1$H NMR (400 MHz, MeOD) δ 7.63 (s, 1H), 7.48 (s, 1H), 7.40 (dd, J=9.1, 1.4 Hz, 1H), 7.22-7.16 (m, 1H), 6.90 (d, J=8.7, 1H), 6.88 (d, J=8.7, 1H), 6.56-6.50 (m, 2H), 6.44-6.36 (m, 2H), 4.10 (s, 2H), 3.71 (s, 3H), 1.57 (s, 6H); MS (EI) m/z 599 (MH$^+$).

4-((5-(2-(4-Chloro-3-methoxyphenyl)propan-2-yl)-1-(4-fluorophenyl)-1H-imidazol-2-ylthio)methyl)-3,5-difluorobenzenesulfonic acid

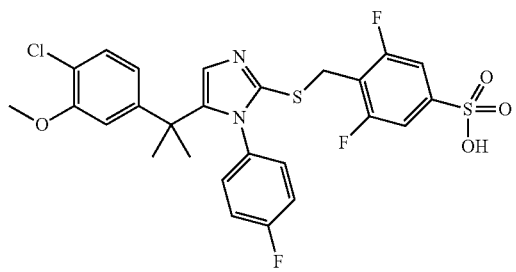 [SMILES: COc1cc(C(C)(C)c2cnc(SCc3c(F)cc(S(=O)(=O)O)cc3F)n2-c2ccc(F)cc2)ccc1Cl]

To a solution of 4-((5-(2-(4-chloro-3-methoxyphenyl)propan-2-yl)-1-(4-fluorophenyl)-1H-imidazol-2-ylthio)methyl)-3,5-difluorobenzoic acid (88 g, 0.16 mmol) in toluene (590 mL) and tert-butanol (200 mL) were added DPPA (49 g, 0.178 mol) and DIPEA (272 g, 0.21 mol) at 0° C. The reaction mixture was warmed to room temperature, stirred 30 min and heated at 80° C. overnight. After cooling, the reaction mixture was diluted with EtOAc (800 mL) and washed with 10% citric acid (1.5 L), satd NaHCO$_3$ (1.5 L) and brine (1.5 L), dried over MgSO$_4$, filtered and concentrated under reduced pressure to give a residue. The resulting residue was purified by column chromatography (Hex/EtOAc=3:1 to 2:1, v/v) to afford tert-butyl 4-((5-(2-(4-chloro-3-methoxyphenyl)propan-2-yl)-1-(4-fluorophenyl)-1H-imidazol-2-ylthio)methyl)-3,5-difluorophenylcarbamate (75 g, 74%) as a light-pink foam. ¹H NMR (400 MHz, CDCl₃): δ 7.22 (s, 1H), 7.14-7.16 (d, 1H), 6.88-6.92 (d, 2H), 6.85 (s, 1H), 6.75-6.80 (t, 2H), 6.48-6.53 (m, 2H), 6.33-6.37 (m, 2H), 3.99 (s, 2H), 3.76 (s, 3H), 1.52 (s, 9H), 1.49 (s, 6H).

To a solution of tert-butyl 4-((5-(2-(4-chloro-3-methoxyphenyl)propan-2-yl)-1-(4-fluorophenyl)-1H-imidazol-2-ylthio)methyl)-3,5-difluorophenylcarbamate (75 g, 0.12 mmol) in DCM (300 mL) was added TFA (300 mL) at 0° C. The reaction mixture was warmed to room temperature, stirred for 2 h and evaporated to give 4-((5-(2-(4-chloro-3-methoxyphenyl)propan-2-yl)-1-(4-fluorophenyl)-1H-imidazol-2-ylthio)methyl)-3,5-difluorobenzenamine as a light-pink foam (62 g, quant). ¹H NMR (400 MHz, CDCl₃): δ 7.65 (s, 1H), 7.20-7.23 (d, 1H), 6.92-6.96 (t, 2H), 6.41-6.50 (m, 6H), 3.91 (s, 2H), 3.79 (s, 3H), 1.58 (s, 6H).

To a solution of 4-((5-(2-(4-chloro-3-methoxyphenyl)propan-2-yl)-1-(4-fluorophenyl)-1H-imidazol-2-ylthio)methyl)-3,5-difluorobenzenamine (62 g, 0.12 mol) in AcOH (330 mL) was added slowly conc HCl (104 mL) and water (40 mL), and then the flask was submerged in ice-bath to attain constant temperature of 5° C. A solution of NaNO₂ (9.52 g, 0.14 mol) in water (20 mL) was added dropwise to the reaction mixture, while maintaining a temperature at 4-6° C. In a flask containing CuCl₂ (3.22 g, 0.02 mol), AcOH (288 mL) and water (12 mL) was bubbled sulfur dioxide through at a slow rate for 10 min, then the mixture was submerged in ice-bath at 5° C. Bubbling of sulfur dioxide through mixture was continued with stirring for 30 min at 5° C. The prepared diazonium salt was transferred to the mixture in small portions via cannula at 5° C. Addition of diazonium salt took 20 min and temperature held steady at 5° C. After 30 min at same temperature, the reaction mixture was then poured into a ice-water and stirred 30 min. After filtration, the resulting solid was dissolved in THF (250 mL), and then the solution was chilled to 5° C. with an ice bath. 2N NaOH solution was added dropwise until the mixture was basic. The solution was stirred for 10 min and evaporated to give a residue. The residue was diluted with water, acidified with 1N HCl, stirred 30 min and filtered give a residue which was purified by column chromatography (MC/MeOH=20:1, 10:1 to 5:1, v/v) to afford the title compound (23 g, 33%) as a light beige solid. ¹H NMR (400 MHz, DMSO-d₆): δ 7.55 (s, 1H), 7.16-7.24 (d, 1H), 7.14-7.16 (d, 2H), 7.00-7.04 (t, 2H), 6.63-6.66 (t, 2H), 6.55 (s, 1H), 6.46-6.48 (d, 1H), 3.96 (s, 2H), 3.70 (s, 3H), 1.48 (s, 6H); MS (EI) m/z 581.0 (M⁺).

Example 22

(R)-Methyl 2-(4-((5-(2-(4-chloro-3-methoxyphenyl)propan-2-yl)-1-(4-fluorophenyl)-1H-imidazol-2-ylthio)methyl)-3,5-difluorophenylsulfonamido)propanoate

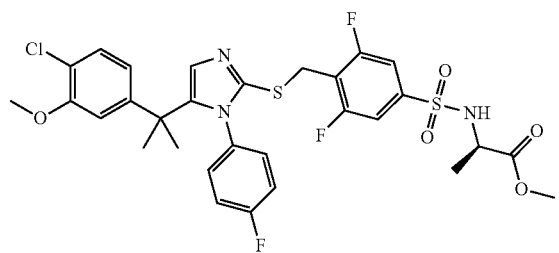

To a solution of 4-((5-(2-(4-chloro-3-methoxyphenyl)propan-2-yl)-1-(4-fluorophenyl)-1H-imidazol-2-ylthio)methyl)-3,5-difluorobenzenesulfonic acid (3.0 g, 5.1 mmol) in DCM (15 mL) was added thionyl chloride (7.5 mL) and DMF (0.1 mL). The mixture was heated at 65° C. for 1 h then concentrated in vacuo and azeotroped with toluene (10 mL) and DCM (10 mL). The pale yellow foam was dissolved in DCM (15 mL) and was added dropwise to a solution of D-alanine methyl ester (2.9 g, 20.6 mmol) in 2M Na₂CO₃ (30 mL) with vigorous stirring. Upon complete addition the layers were separated and the organics were dried over Na₂SO₄, filtered and concentrated in vacuo. The residue was purified by flash chromatography eluting with 0-70% ethyl acetate/hexane to afford a white foam (2.4 g, 77%). MS (EI) m/z 601.3 (M⁺).

Example 23

3-(4-((5-(2-(4-chloro-3-methoxyphenyl)propan-2-yl)-1-(4-fluorophenyl)-1H-imidazol-2-ylthio)methyl)-3,5-difluorophenyl)prop-2-yn-1-ol

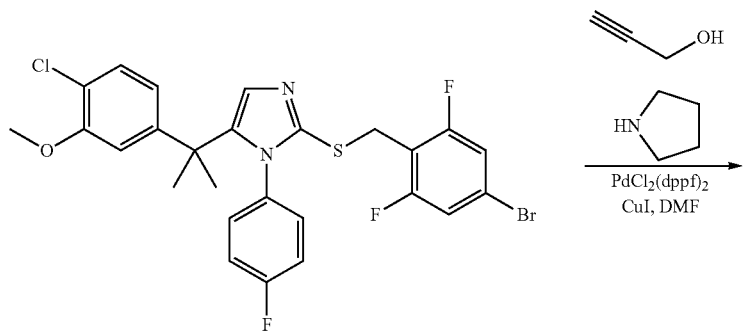

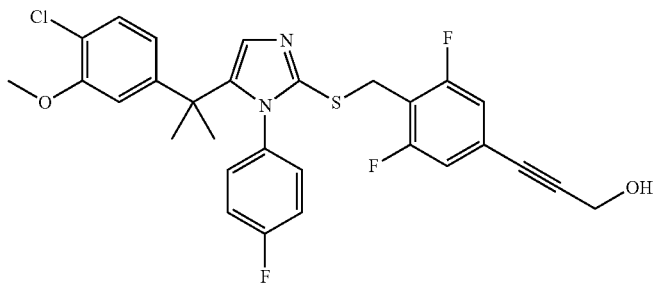

A mixture of 2-(4-bromo-2,6-difluorobenzylthio)-5-(2-(4-chloro-3-methoxyphenyl)propan-2-yl)-1-(4-fluorophenyl)-1H-imidazole (0.79 g, 1.35 mmol), propargyl alcohol (122 µL, 2.03 mmol), pyrrolidine (169 µL, 2.03 mmol), CuI (26 mg, 0.13 mmol) and PdCl$_2$(dppf)$_2$ (50 mg, 0.07 mmol) in DMF (6.80 mL) was purged with argon and then heated to 80° C. for 3 h. The reaction mixture was filtered through Celite™ to remove solids. The filter agent was rinsed with EtOAc (3×75 mL). The filtrate was washed with water and brine, dried over anhyd Na$_2$SO$_4$, concentrated and purified by flash chromatography (80% EtOAc/Hex) to give the title compound (714 mg, 94%) as a yellow solid. MS (EI) m/z 557 (MH$^+$).

Example 24

3-(4-((5-(2-(4-chloro-3-methoxyphenyl)propan-2-yl)-1-(4-fluorophenyl)-1H-imidazol-2-ylthio)methyl)-3,5-difluorophenyl)propan-1-ol

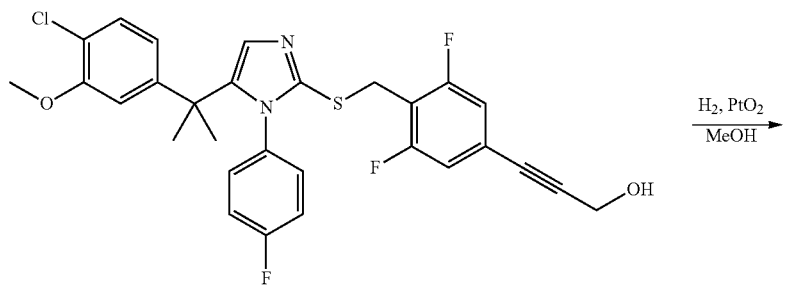

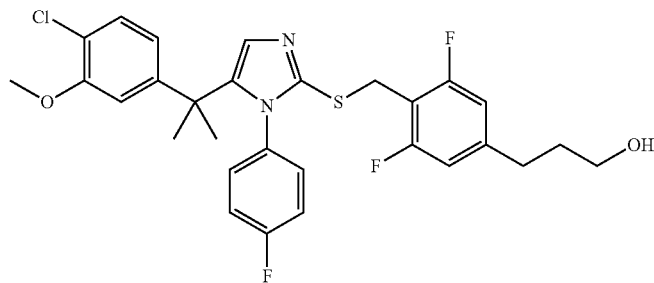

A solution of 3-(4-((5-(2-(4-chloro-3-methoxyphenyl)propan-2-yl)-1-(4-fluorophenyl)-1H-imidazol-2-ylthio)methyl)-3,5-difluorophenyl)prop-2-yn-1-ol (714 mg, 1.28 mmol) in MeOH (75 mL) was sparged with argon, charged with PtO$_2$ (30 wt %, 214 mg) and then pressurized to 65 psi under hydrogen atmosphere in a Parr shaker for 36 h. The reaction was monitored by LCMS and upon completion the mixture was filtered through Celite™ to remove the catalyst. The filtrate was concentrated and purified by flash chromatography (80% EtOAc/Hex) to yield the title compound (560 mg, 0.99 mmol). MS (EI) m/z 561 (MH$^+$).

Example 25

Methyl 5-((5-(2-(3,4-dichlorophenyl)propan-2-yl)-1-(4-fluoro-3-methoxyphenyl)-1H-imidazol-2-ylthio)methyl)-2-(3-hydroxypropyl)benzoate

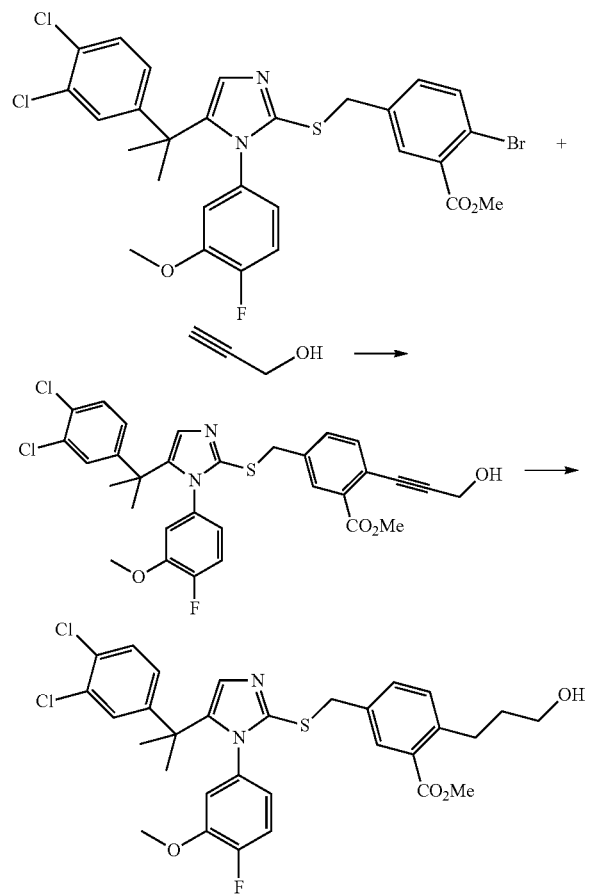

To a stirred solution of methyl 2-bromo-5-((5-(2-(3,4-dichlorophenyl)propan-2-yl)-1-(4-fluoro-3-methoxyphenyl)-1H-imidazol-2-ylthio)methyl)benzoate (506 mg, 0.79 mmol, 1.0 eq), propargyl alcohol (0.07 mL, 1.2 mmol, 1.5 eq) and pyrrolidine (0.1 mL, 1.2 mmol, 1.5 eq) in dry, degassed DMF (4 mL) was added PdCl$_2$(dppf)$_2$ (30 mg, 0.04 mmol, 5 mol %) and CuI (15 mg, 0.08 mmol, 10 mol %). The reaction mixture was heated at 80° C. for 5 h at which time LCMS showed 85% conversion. The mixture was diluted with EtOAc, washed with brine, dried and concentrated. Purification by column chromatography (0 to 75% EtOAc/Hexanes) provided 378 mg (78% yield) of methyl 5-((5-(2-(3,4-dichlorophenyl)propan-2-yl)-1-(4-fluoro-3-methoxyphenyl)-1H-imidazol-2-ylthio)methyl)-2-(3-hydroxyprop-1-ynyl)benzoate. MS (EI) m/z 615 (MH$^+$).

To a Parr bottle charged with methyl 5-((5-(2-(3,4-dichlorophenyl)propan-2-yl)-1-(4-fluoro-3-methoxyphenyl)-1H-imidazol-2-ylthio)methyl)-2-(3-hydroxyprop-1-ynyl)benzoate (140 mg, 0.23 mmol) in degassed ethanol (10 mL) was added PtO$_2$ (100 mg). The reaction vessel was pressurized to 60 psi with hydrogen gas and agitated at room temperature for 16 h. After LCMS analysis showed complete conversion, the reaction mixture was filtered through Celite™ and concentrated in vacuo to give the title compound (120 mg, 85%). MS (EI) m/z 619 (MH$^+$).

Example 26

2-(4-((5-(2-(4-chloro-3-methoxyphenyl)propan-2-yl)-1-(4-fluorophenyl)-1H-imidazol-2-ylthio)methyl)-3,5-difluorophenoxy)ethanol

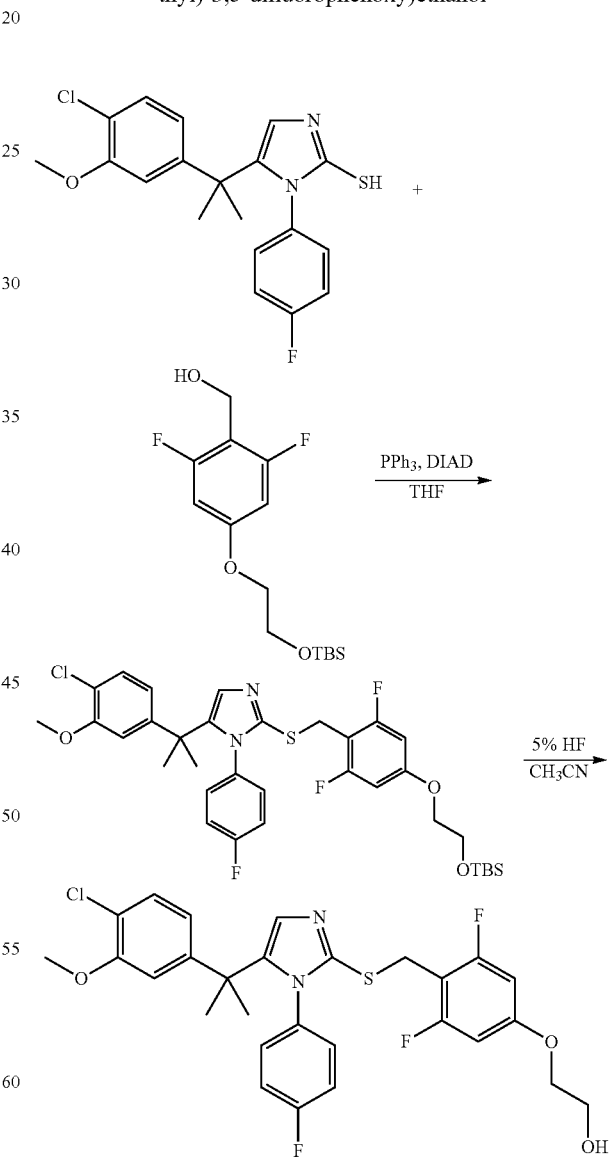

To a solution of 5-(2-(4-chloro-3-methoxyphenyl)propan-2-yl)-1-(4-fluorophenyl)-1H-imidazole-2-thiol (400 mg, 1.06 mmol) in anhyd THF (1.2 mL) were added PPh$_3$ (347 mg, 1.32 mmol), (4-(2-(tert-butyldimethylsilyloxy)ethoxy)-2,6-difluorophenyl)methanol (458 mg, 1.37 mmol) and DIAD (275 μL, 1.32 mmol). The reaction was stirred for 24 h and monitored by LCMS. The reaction mixture was partitioned in EtOAc and $H_2O$. The organic layer was washed with brine, concentrated under reduced pressure, and purified by flash chromatography (45% EtOAc/Hex) to give 2-(4-(2-(tert-butyldimethylsilyloxy)ethoxy)-2,6-difluorobenzylthio)-5-(2-(4-chloro-3-methoxyphenyl)propan-2-yl)-1-(4-fluorophenyl)-1H-imidazole (620 mg, 87%). MS (EI) m/z 677.40 (MH$^+$).

To a solution of 2-(4-(2-(tert-butyldimethylsilyloxy)ethoxy)-2,6-difluorobenzylthio)-5-(2-(4-chloro-3-methoxyphenyl)propan-2-yl)-1-(4-fluorophenyl)-1H-imidazole in $CH_3CN$ (1 mL) was added a 5% solution of aqueous HF in $CH_3CN$ (3 mL). The reaction was complete in 1 h and the crude product was extracted with EtOAc (3×75 mL). The combined extracts were washed with $H_2O$ and brine, and dried over anhyd $Na_2SO_4$, concentrated and purified by flash chromatography (20% MeOH/DCM) to yield the title compound (493 mg, 95%) as a white solid. MS (EI) m/z 563.30 (MH$^+$).

3-(4-((5-(2-(4-chloro-3-methoxyphenyl)propan-2-yl)-1-(4-fluorophenyl)-1H-imidazol-2-ylthio)methyl)-3,5-difluorophenoxy)propan-1-ol

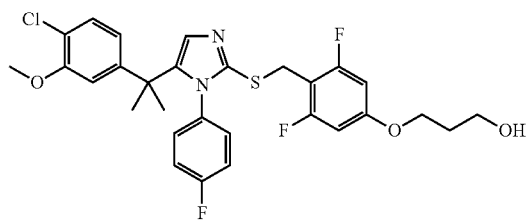 [SMILES: COc1cc(C(C)(C)c2cnc(SCc3c(F)cc(OCCCO)cc3F)n2-c2ccc(F)cc2)ccc1Cl]

In a manner similar to that described previously, a mixture of 5-(2-(4-chloro-3-methoxyphenyl)propan-2-yl)-1-(4-fluorophenyl)-1H-imidazole-2-thiol (580 mg, 1.53 mmol), (4-(3-(tert-butyldimethylsilyloxy)propoxy)-2,6-difluoro)benzylalcohol (919 mg, 2.76 mmol), $PPh_3$ (604 mg, 2.30 mmol) and DIAD (477 μL, 2.30 mmol) in THF (2 mL) was stirred 24 h, processed and purified by chromatography (80% EtOAc/Hex) to give 2-(4-(3-(tert-butyldimethylsilyloxy)propoxy)-2,6-difluorobenzylthio)-5-(2-(4-chloro-3-methoxyphenyl)-propan-2-yl)-1-(4-fluorophenyl)-1H-imidazole (785 mg, 74%). MS (EI) m/z 691.5 (MH$^+$).

A solution of 2-(4-(3-(tert-butyldimethylsilyloxy)propoxy)-2,6-difluorobenzylthio)-5-(2-(4-chloro-3-methoxyphenyl)-propan-2-yl)-1-(4-fluorophenyl)-1H-imidazole (785 mg, 1.13 mmol) in $CH_3CN$ was treated with 5% HF in $CH_3CN/H_2O$ (8:2) and purified by chromatography to afford the title compound (330 mg, 50%) as a white solid. MS (EI) m/z 577.4 (MH$^+$).

3-(3-chloro-5-fluoro-4-((5-(2-(4-fluoro-3-methoxyphenyl)propan-2-yl)-1-(4-fluorophenyl)-1H-imidazol-2-ylthio)methyl)phenoxy)propan-1-ol

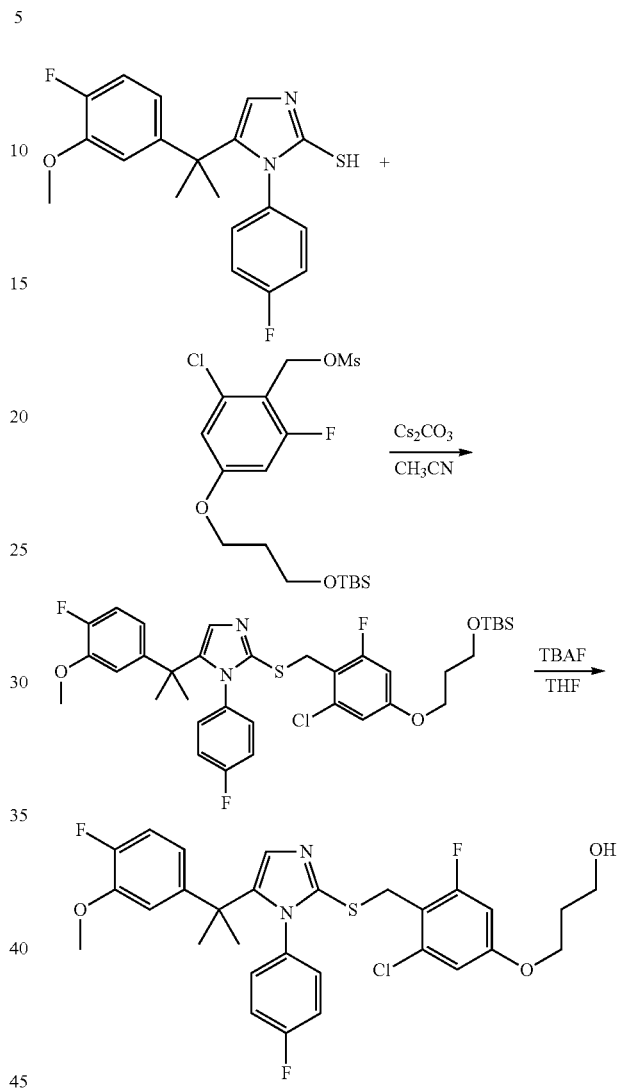

To a stirred solution of 5-(2-(4-fluoro-3-methoxyphenyl)propan-2-yl)-1-(4-fluorophenyl)-1H-imidazole-2-thiol (548 mg, 1.52 mmol) and 4-(3-(tert-butyldimethylsilyloxy)propoxy)-2-chloro-6-fluorobenzyl methanesulfonate (681 mg, 1.60 mmol) in $CH_3CN$ (5 mL) was added $Cs_2CO_3$ (743 mg, 2.28 mmol, 1.5 eq). The reaction mixture was stirred for 2 h, filtered and evaporated in vacuo to give a residue, which was purified by flash column chromatography (EtOAc/Hex=1:4) to afford 2-(4-(3-(tert-Butyldimethylsilyloxy)propoxy)-2-chloro-6-fluorobenzylthio)-5-(2-(4-fluoro-3-methoxyphenyl)propan-2-yl)-1-(4-fluorophenyl)-1H-imidazole (756 mg, 72%). $^1$H NMR (400 MHz, CDCl$_3$) δ 7.20 (s, 1H), 6.85 (dd, J=11.04, 8.48 Hz, 1H), 6.80-6.72 (m, 2H), 6.66 (dd, J=2.37, 1.50 Hz, 1H), 6.56 (dd, J=8.11, 2.19 Hz, 1H), 6.48 (ddd, J=8.41, 4.28, 2.19 Hz, 2H), 6.44 (d, J=2.45 Hz, 1H), 6.39-6.32 (m, 2H), 4.19 (d, J=1.41 Hz, 2H), 3.99 (t, J=6.19 Hz, 2H), 3.83-3.72 (m, 5H), 1.95 (dd, J=12.08, 6.05 Hz, 2H), 1.48 (s, 6H), 0.96-0.84 (m, 10H), 0.03 (t, J=4.73 Hz, 6H).

To a solution of 2-(4-(3-(tert-Butyldimethylsilyloxy)propoxy)-2-chloro-6-fluorobenzylthio)-5-(2-(4-fluoro-3-methoxyphenyl)propan-2-yl)-1-(4-fluorophenyl)-1H-imidazole (750 mg, 1.08 mmol) in THF (10 mL) was added dropwise TBAF (1.0M in THF, 0.54 mL, 0.54 mmol). After the reaction was complete, it was quenched by addition of AcOH (0.5 mL). The mixture was evaporated in vacuo and the residue was purified by flash chromatography (EtOAc/Hex=1:2) to give the title compound (592 mg, 95%). $^1$H NMR (400 MHz, CDCl$_3$) δ 7.29-7.26 (m, 1H), 7.21 (d, J=0.96 Hz, 1H), 6.91-6.84 (m, 1H), 6.76 (dt, J=8.18, 0.81 Hz, 3H), 6.70-6.65 (m, 1H), 6.58 (d, J=8.03 Hz, 1H), 6.52-6.43 (m, 2H), 6.38-6.30 (m, 2H), 4.15 (s, 3H), 4.06 (t, J=5.98 Hz, 3H), 3.84 (t, J=5.89 Hz, 2H), 3.79 (t, J=10.73 Hz, 4H), 2.13-1.97 (m, 4H), 1.48 (s, 8H).

Example 27

1-(3-(4-((5-(2-(4-chloro-3-methoxyphenyl)propan-2-yl)-1-(4-fluorophenyl)-1H-imidazol-2-ylthio)methyl)-3,5-difluorophenyl)propyl)guanidine To a solution of 3-(4-((5-(2-(4-chloro-3-methoxyphenyl)propan-2-yl)-1-(4-fluorophenyl)-1H-imidazol-2-ylthio)methyl)-3,5-difluorophenyl)propan-1-ol (407 mg, 0.73 mmol) in anhyd THF (0.97 mL) were added PPh$_3$ (285 mg, 1.08 mmol), 1,3-bis(tert-butoxycarbonyl)guanidine (384 mg, 1.45 mmol) and diisopropyl azodicarboxylate (DIAD) (225 μL, 1.08 mmol) sequentially. After stirring overnight, the reaction mixture was diluted with EtOAc, washed with H$_2$O and brine, dried over Na$_2$SO$_4$ and concentrated. The crude material was purified by flash chromatography (80% EtOAc/hexanes) to yield tert-butyl(tert-butoxycarbonylamino)(3-(4-((5-(2-(4-chloro-3-methoxyphenyl)propan-2-yl)-1-(4-fluorophenyl)-1H-imidazol-2-ylthio)methyl)-3,5-difluorophenyl)propylamino)methylenecarbamate (740 mg), which was taken to the next step without further purification. MS (EI) m/z 802.50 (MH$^+$).

To a solution of tert-butyl(tert-butoxycarbonylamino) (3-(4-((5-(2-(4-chloro-3-methoxyphenyl)propan-2-yl)-1-(4-fluorophenyl)-1H-imidazol-2-ylthio)methyl)-3,5-difluorophenyl)propylamino)methylenecarbamate (740 mg) in DCM (1 mL) was added dropwise TFA (2 mL) at ambient temperature. After 1 h the reaction was diluted with EtOAc,

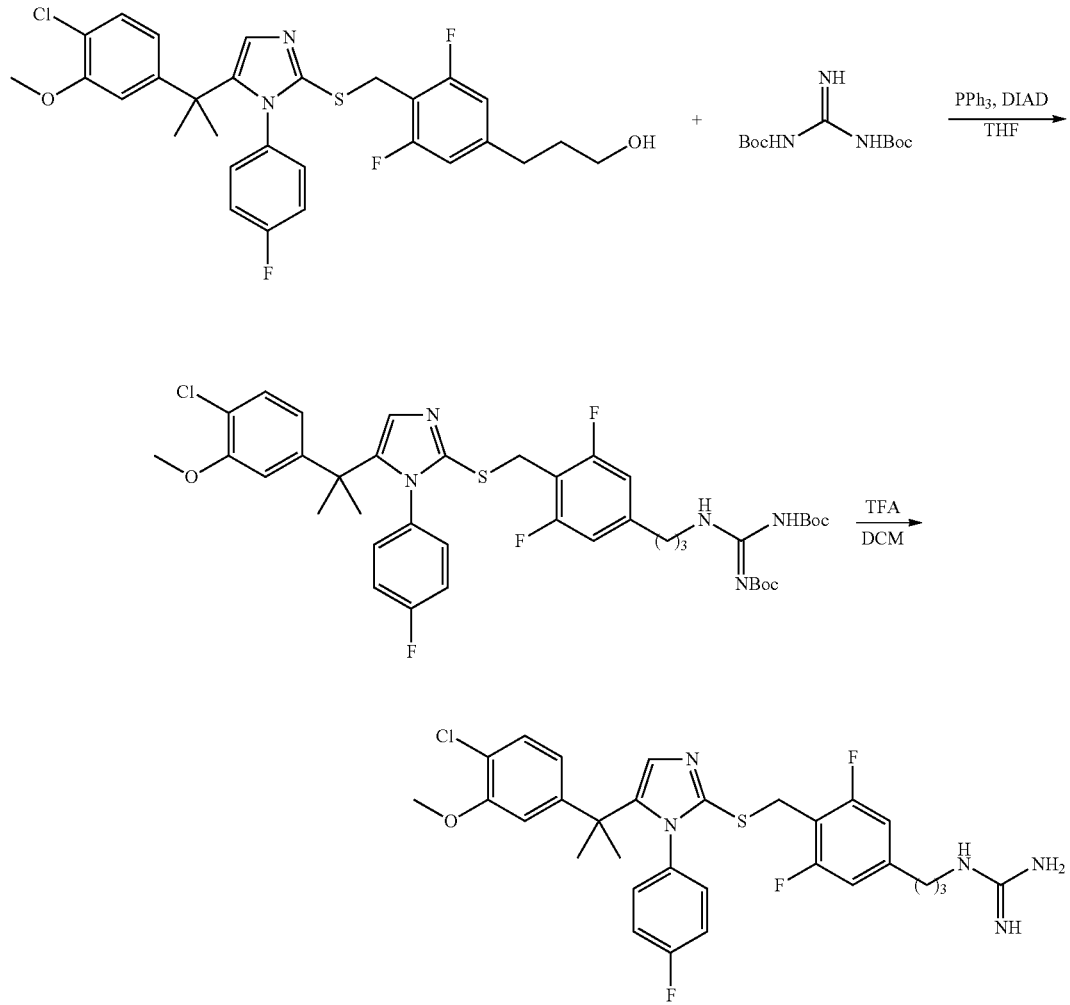

washed with H$_2$O, satd NaHCO$_3$ and brine. The combined organic layers were concentrated and purified by preparative HPLC (30% to 100% CH$_3$CN/H$_2$O) to yield the title compound (280 mg, 64%, 2 steps). $^1$HNMR (400 MHz, DMSO-d$_6$) δ 7.40-7.10 (m, 4H), 6.91 (m, 4H), 6.54 (d, J=2.0 Hz, 1H), 6.48 (dd, J=8.3, 2.0 Hz, 1H), 6.38 (m, 2H), 3.97 (s, 2H), 3.68 (s, 3H), 3.10 (t, J=6.8 Hz, 2H), 2.59 (t, J=7.3 Hz, 2H), 1.75 (m, 2H), 1.44 (s, 6H); MS (EI) m/z 602.40 (MH$^+$).

Amino(3-(2-carboxy-4-((5-(2-(3,4-dichlorophenyl)propan-2-yl)-1-(4-fluoro-3-methoxyphenyl)-1H-imidazol-2-ylthio)methyl)phenyl)propylamino)methaniminium 2,2,2-trifluoroacetate

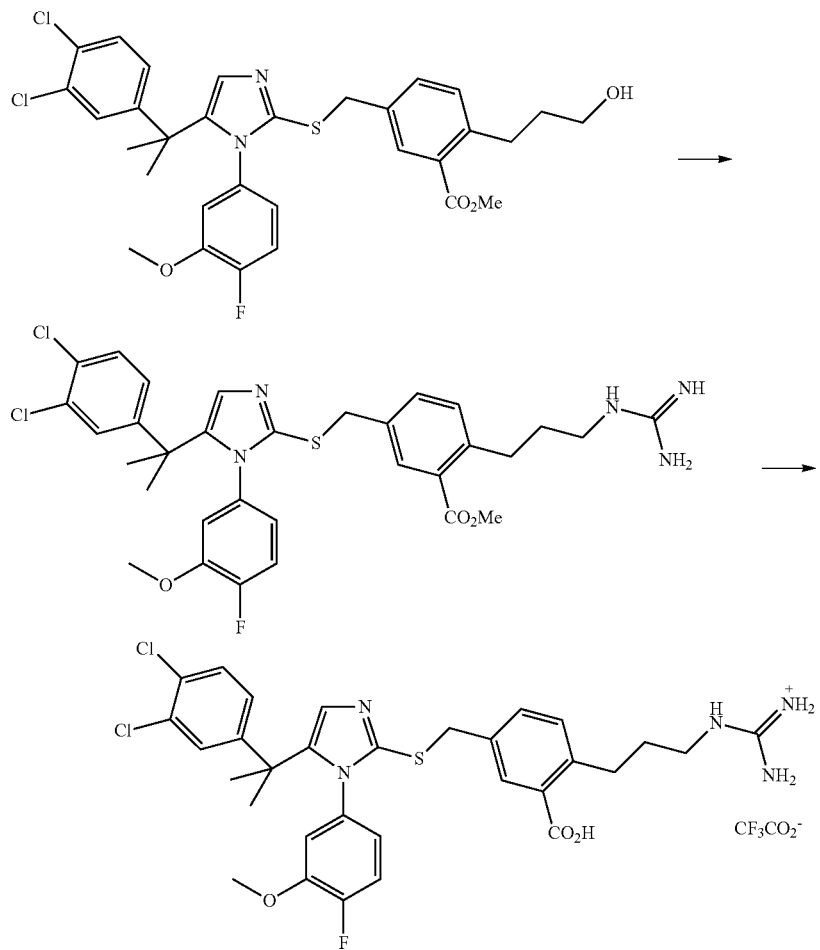

To a mixture of methyl 5-((5-(2-(3,4-dichlorophenyl)propan-2-yl)-1-(4-fluoro-3-methoxyphenyl)-1H-imidazol-2-ylthio)methyl)-2-(3-hydroxypropyl)benzoate (90 mg, 0.15 mmol, 1.0 eq), tert-butyl amino(tert-butoxycarbonylamino)methylenecarbamate (76 mg, 0.29 mmol, 2.0 eq) and triphenylphosphine (59 mg, 0.22 mmol, 1.5 eq) in tetrahydrofuran (0.7 mL) was added diisopropylazodicarboxylate (0.04 mL, 0.22 mmol, 1.5 eq). After stirring for 16 h, the reaction mixture was directly poured onto silica gel and purified (0 to 75% ethyl acetate/hexanes). This product was treated with 1:2 trifluoroacetic acid/dichloromethane (2 mL) at room temperature for 16 h. The reaction mixture was concentrated to provide 77 mg (70%) of methyl 5-((5-(2-(3,4-dichlorophenyl)propan-2-yl)-1-(4-fluoro-3-methoxyphenyl)-1H-imidazol-2-ylthio)methyl)-2-(3-guanidinopropyl)benzoate: MS (EI) m/z 759 [(M-Boc)H$^+$].

A solution of methyl 5-((5-(2-(3,4-dichlorophenyl)propan-2-yl)-1-(4-fluoro-3-methoxyphenyl)-1H-imidazol-2-ylthio)methyl)-2-(3-guanidinopropyl)benzoate (77 mg, 0.1 mmol, 1.0 eq) in MeOH (2.5 mL) was treated with Ba(OH)$_2$ (77 mg, 4.1 mmol, 4.0 eq, in 1 mL of water). Additional MeOH (1 mL) was added to make the solution homogeneous. The reaction mixture was heated at 50° C. for 2.5 h, at which time complete consumption of starting material was observed by LCMS. Satd ammonium chloride was added and the mixture was extracted with EtOAc (3×). The combined extracts were concentrated and purified by preparative HPLC (30-70% MeCN/H$_2$O, 0.1% TFA) provided the title compound (20 mg, 27%) as a white solid: $^1$H NMR (400 MHz, CD$_2$Cl$_2$) δ 11.32 (br s, 4H), 7.79 (s, 1H), 7.59 (s, 1H), 7.34 (d, J=8.4 Hz, 1H), 7.30-7.16 (m, 2H), 7.11-6.92 (m, 2H), 6.83 (dd, J=8.5, 2.1 Hz, 1H), 6.70 (br s, 2H), 6.39-6.08 (m, 1H), 5.91 (dd, J=7.2, 2.4 Hz, 1H), 4.61-4.14 (m, 2H), 3.57 (s, 3H), 3.26-3.16

(m, 2H), 2.98-2.90 (m, 2H), 1.88-1.74 (m, 2H), 1.59 (d, J=24.9 Hz, 6H); MS (EI) m/z 659 (M⁺).

Amino(2-(4-((5-(2-(4-chloro-3-methoxyphenyl)propan-2-yl)-1-(4-fluorophenyl)-1H-imidazol-2-ylthio)methyl)-3,5-difluorophenoxy)ethylamino)methaniminium 2,2,2-trifluoroacetate

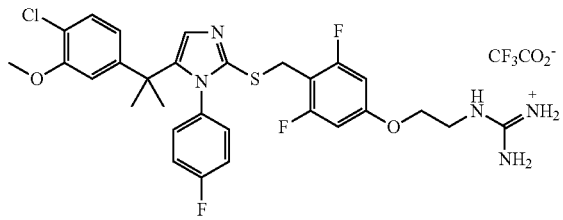 [SMILES: COc1cc(C(C)(C)c2cnc(SCc3c(F)cc(OCCNC(=N)N)cc3F)n2-c2ccc(F)cc2)ccc1Cl ; "CF3CO2-"]

To a solution of 2-(4-((5-(2-(4-chloro-3-methoxyphenyl)propan-2-yl)-1-(4-fluorophenyl)-1H-imidazol-2-ylthio)methyl)-3,5-difluorophenoxy)ethanol (153 mg, 0.27 mmol) in THF (0.39 mL) were added PPh₃ (107 mg, 0.41 mmol), 1,3-bis(tert-butoxycarbonyl)guanidine (144 mg, 0.55 mmol) and DIAD (85 µL, 0.41 mmol). After stirring overnight, the reaction mixture was diluted with EtOAc, washed with H₂O and brine, dried over Na₂SO₄ and concentrated. The crude material was purified by flash chromatography (80% EtOAc/hexanes) to afford tert-butyl(tert-butoxycarbonylamino)(2-(4-((5-(2-(4-chloro-3-methoxyphenyl)propan-2-yl)-1-(4-fluorophenyl)-1H-imidazol-2-ylthio)methyl)-3,5-difluorophenoxy)ethylamino)methylenecarbamate (279 mg), which was taken to the final step without further purification. MS (EI) m/z 804.5 (MH⁺).

To a solution of tert-butyl(tert-butoxycarbonylamino)(2-(4-((5-(2-(4-chloro-3-methoxyphenyl)propan-2-yl)-1-(4-fluorophenyl)-1H-imidazol-2-ylthio)methyl)-3,5-difluorophenoxy)ethylamino)methylenecarbamate (273 mg) in DCM (1 mL) was added TFA (5 mL). After 1 h the reaction mixture was diluted with EtOAc, washed with H₂O, satd NaHCO₃ and brine. The combined organic layers were concentrated and purified by preparative HPLC (30-100%, CH₃CN/H₂O with 0.05% TFA) to yield the title compound as a white solid (112 mg, 68%, 2 steps). ¹HNMR (400 MHz, CD₃CN) δ 8.01 (m, 1H), 7.20-7.13 (m, 2H), 6.99-6.94 (m, 2H), 6.88-6.78 (m, 2H), 6.57 (d, J=2.1 Hz, 1H), 6.55-6.48 (m, 3H), 6.44-6.38 (m, 2H), 4.08 (t, J=5.0 Hz, 2H), 3.92 (s, 2H), 3.71 (s, 3H), 3.52 (dd, J=10.6, 5.4 Hz, 2H), 1.49 (s, 6H); MS (EI) m/z 604.4 (MH⁺).

Amino(3-(4-((5-(2-(4-chloro-3-methoxyphenyl)propan-2-yl)-1-(4-fluorophenyl)-1H-imidazol-2-ylthio)methyl)-3,5-difluorophenoxy)propylamino)methaniminium 2,2,2-trifluoroacetate

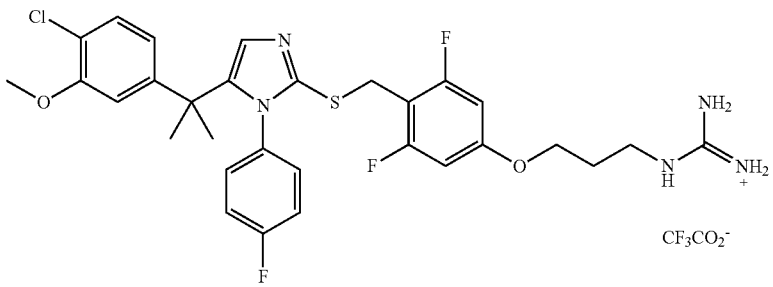

In a manner described previously, a mixture of 3-(4-((5-(2-(4-chloro-3-methoxyphenyl)propan-2-yl)-1-(4-fluorophenyl)-1H-imidazol-2-ylthio)methyl)-3,5-difluorophenoxy)propan-1-ol (330 mg, 0.57 mmol), 1,3-bis(tert-butoxycarbonyl)guanidine (266 mg, 1.02 mmol), PPh₃ (225 mg, 0.85 mmol) and DIAD (177 µL, 0.85 mmol) was reacted in THF, processed and purified by flash chromatography (80% EtOAc/Hex) to give tert-butyl(tert-butoxycarbonylamino)(3-(4-((5-(2-(4-chloro-3-methoxyphenyl)propan-2-yl)-1-(4-fluorophenyl)-1H-imidazol-2-ylthio)methyl)-3,5-difluorophenoxy)propylamino)methylenecarbamate. MS (EI) m/z 818.6 (MH⁺).

A solution of TFA (5 mL) and tert-butyl(tert-butoxycarbonylamino)(3-(4-((5-(2-(4-chloro-3-methoxyphenyl)propan-2-yl)-1-(4-fluorophenyl)-1H-imidazol-2-ylthio)methyl)-3,5-difluorophenoxy)propylamino)methylenecarbamate (559 mg, 0.57 mmol) in DCM (1 mL) was stirred 1 h and purified by preparative HPLC (30-100%, CH₃CN/H₂O with 0.05% TFA) to yield the title compound as a white solid (157 mg, 45%, 2 steps). ¹HNMR (400 MHz, CD₃CN) δ 7.25-7.10 (m, 2H), 6.88-6.78 (m, 2H), 6.56 (d, J=2.0 Hz, 1H), 6.50 (m, 3H), 6.46-6.30 (m, 2H), 4.04 (t, J=6.1 Hz, 2H), 3.90 (s, 2H), 3.71 (s, 3H), 3.28 (t, J=6.7 Hz, 2H), 2.06-1.98 (m, 2H), 1.48 (s, 6H); MS (EI) m/z 618.4 (MH⁺).

Example 28

2-(4-((5-(2-(4-Chloro-3-methoxyphenyl)propan-2-yl)-1-(4-fluorophenyl)-1H-imidazol-2-ylthio)methyl)-3,5-difluorophenoxy)ethanamine hydrochloride

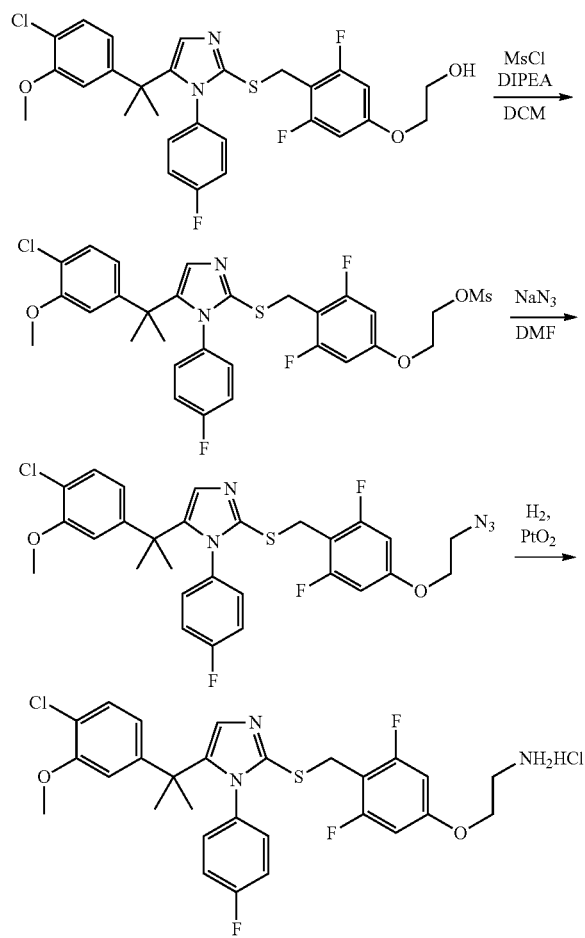

To a stirred solution of 2-(4-((5-(2-(4-chloro-3-methoxyphenyl)propan-2-yl)-1-(4-fluorophenyl)-1H-imidazol-2-ylthio)methyl)-3,5-difluorophenoxy)ethanol (3.8 g, 6.75 mmol) and DIPEA (3.52 mL, 20.3 mmol) in DCM (100 mL) at 0° C. was added methanesulfonyl chloride (603 μL, 7.8 mmol). After the reaction was slowly warmed to ambient temperature over 30 min, it was partitioned in DCM (100 mL) and water (100 mL). Organic layer was dried over MgSO₄ and evaporated in vacuo. The residue was purified by column chromatography (Hex/EtOAc=1:3) to give 2-(4-((5-(2-(4-chloro-3-methoxyphenyl)propan-2-yl)-1-(4-fluorophenyl)-1H-imidazol-2-ylthio)methyl)-3,5-difluorophenoxy)ethyl methanesulfonate (4.1 g, 95% yield) as a white solid. $^1$H NMR (400 MHz, CDCl₃) δ 7.16 (d, J=8.25 Hz, 1H), 7.22 (s, 1H), 6.82-6.72 (m, 2H), 6.58-6.47 (m, 2H), 6.42-6.32 (m, 4H), 4.55 (dd, J=5.27, 3.62 Hz, 2H), 4.18 (dd, J=5.26, 3.64 Hz, 2H), 4.04 (s, 2H), 3.78 (s, 3H), 3.09 (s, 3H), 1.50 (d, J=10.49 Hz, 6H).

To a solution of 2-(4-((5-(2-(4-chloro-3-methoxyphenyl)propan-2-yl)-1-(4-fluorophenyl)-1H-imidazol-2-ylthio)methyl)-3,5-difluorophenoxy)ethyl methanesulfonate (400 mg, 0.624 mmol) in DMF (6 mL) at 0° C. was added NaN₃ (60 mg, 0.922 mmol). After stirring 1 h, the residue was partitioned in EtOAc (20 mL) and water (20 mL). The organic layer was washed with 1M HCl (10 mL) and water (10 mL) successively, dried over MgSO₄, filtered and evaporated. The residue was purified by column chromatography (CH₂Cl₂/MeOH=20:1) to give 2-(4-(2-azidoethoxy)-2,6-difluorobenzylthio)-5-(2-(4-chloro-3-methoxyphenyl)propan-2-yl)-1-(4-fluorophenyl)-1H-imidazole (320 mg, 87% yield) as a white foam. $^1$H NMR (400 MHz, CDCl₃) δ 7.22 (s, 1H), 7.16 (d, J=8.24 Hz, 1H), 6.77 (t, 2H), 6.55 (d, J=2.09 Hz, 1H), 6.51 (dd, J=8.25 Hz, 1H), 6.39-6.32 (m, 4H), 4.05 (m, 4H), 3.78 (s, 3H), 3.60 (t, 2H), 1.49 (s, 6H).

A pressure bottle was charged with a solution of 2-(4-(2-azidoethoxy)-2,6-difluorobenzylthio)-5-(2-(4-chloro-3-methoxyphenyl)propan-2-yl)-1-(4-fluorophenyl)-1H-imidazole (340 mg, 0.56 mmol) in EtOH (10 mL), conc HCl (0.5 mL) and PtO₂ (170 mg). The bottle was purged with hydrogen (2×40 psi), pressurized with hydrogen (45 psi) and was agitated for 5 h. The reaction mixture was filtered through Celite™ and the filtrate was evaporated to give a residue. The residue was triturated with ether, and the solids were collected by filtration and dried to give the title compound (290 mg, 99%). $^1$H NMR (400 MHz, CD₃OD) δ 7.21 (s, 1H), 7.17 (d, J=8.24 Hz, 1H), 6.76 (t, 2H), 6.55 (m, 1H), 6.51 (m, 3H), 6.29 (m, 2H), 4.07 (t, 2H), 3.83 (s, 2H), 3.68 (s, 3H), 3.62 (t, 2H), 1.49 (s, 6H).

3-(3-Chloro-5-fluoro-4-((5-(2-(4-fluoro-3-methoxyphenyl)propan-2-yl)-1-(4-fluorophenyl)-1H-imidazol-2-ylthio)methyl)phenoxy)propan-1-amine hydrochloride

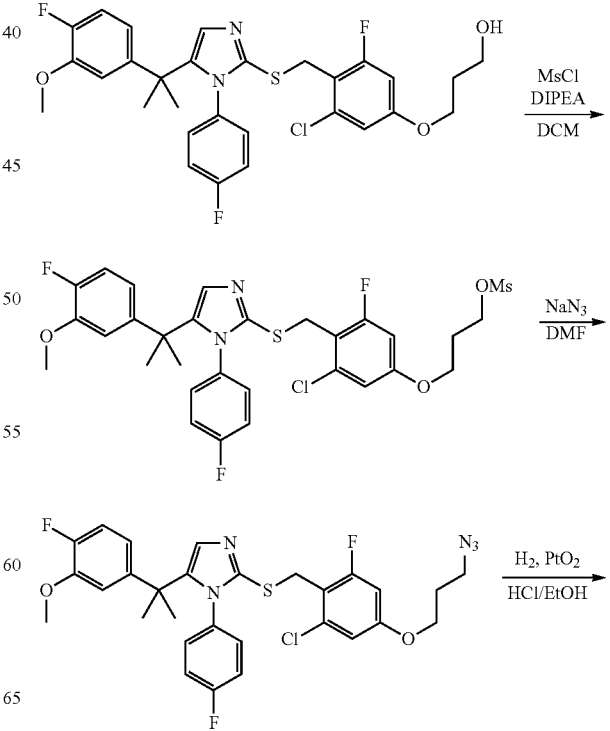

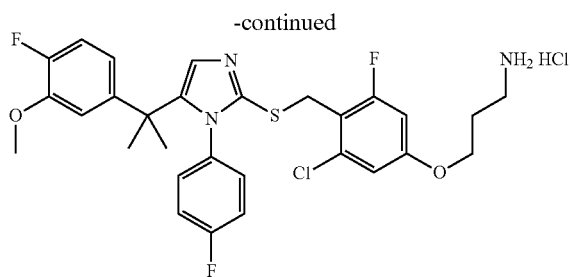

To a stirred solution of 3-(3-chloro-5-fluoro-4-((5-(2-(4-fluoro-3-methoxyphenyl)propan-2-yl)-1-(4-fluorophenyl)-1H-imidazol-2-ylthio)methyl)phenoxy)propan-1-ol (420 mg, 0.73 mmol) and DIPEA (0.32 mL, 1.83 mmol) in DCM (10 mL) at 0° C. was added dropwise methanesulfonylchloride (113 μL, 1.45 mmol). After stirring 30 min, the reaction mixture was partitioned in DCM (20 mL) and water (20 mL). The aqueous layer was re-extracted with DCM (20 mL×2). The combined organic layers were dried over MgSO$_4$, concentrated and purified by column chromatography (EtOAc/Hex=1:2) to give 3-(3-chloro-5-fluoro-4-((5-(2-(4-fluoro-3-methoxyphenyl)propan-2-yl)-1-(4-fluorophenyl)-1H-imidazol-2-ylthio)methyl)phenoxy)propyl methanesulfonate (470 mg, 99% yield) as a white solid. $^1$H NMR (400 MHz, CDCl$_3$) δ 7.25 (d, J=8.65 Hz, 1H), 6.87 (dd, J=11.04, 8.48 Hz, 1H), 6.81-6.73 (m, 2H), 6.69-6.66 (m, 1H), 6.58 (dd, J=8.13, 2.23 Hz, 1H), 6.50-6.43 (m, 2H), 6.38-6.31 (m, 1H), 4.42 (t, J=6.04 Hz, 2H), 4.18 (s, 2H), 4.03 (t, J=5.88 Hz, 2H), 3.77 (d, J=5.83 Hz, 2H), 3.68 (s, 4H), 3.10-2.98 (m, 3H), 2.22 (p, J=5.94 Hz, 2H), 1.51 (t, J=4.73 Hz, 5H).

To a solution of 3-(3-chloro-5-fluoro-4-((5-(2-(4-fluoro-3-methoxyphenyl)propan-2-yl)-1-(4-fluorophenyl)-1H-imidazol-2-ylthio)methyl)phenoxy)propyl methanesulfonate (470 mg, 0.72 mmol) in DMF (3 mL) at 0° C. was added NaN$_3$ (186 mg, 2.87 mmol). After stirring for 16 h, the mixture was partitioned in EtOAc (20 mL) and water (20 mL). The separated organic layer was washed with 1M HCl (10 mL) and water (10 mL) successively, dried over MgSO$_4$, filtered and evaporated. The mixture was purified by column chromatography (EtOAc/Hex=1:3) to provide 2-(4-(3-azidopropoxy)-2-chloro-6-fluorobenzylthio)-5-(2-(4-fluoro-3-methoxyphenyl)-propan-2-yl)-1-(4-fluorophenyl)-1H-imidazole (344 mg, 80% yield) as a white foam. $^1$H NMR (400 MHz, CDCl$_3$) δ 7.21 (s, 1H), 6.87 (dd, J=10.99, 8.49 Hz, 1H), 6.76 (t, J=8.49 Hz, 2H), 6.67 (s, 1H), 6.58 (dd, J=8.15, 2.15 Hz, 1H), 6.52-6.42 (m, 2H), 6.38-6.29 (m, 2H), 4.16 (t, J=4.34 Hz, 2H), 3.98 (t, J=5.89 Hz, 2H), 3.77 (d, J=5.67 Hz, 3H), 3.50 (t, J=6.51 Hz, 2H), 2.17 (s, 1H), 2.13-1.97 (m, 3H), 1.60 (s, 2H), 1.49 (s, 6H).

A pressure bottle was charged with a solution of 2-(4-(3-azidopropoxy)-2-chloro-6-fluorobenzylthio)-5-(2-(4-fluoro-3-methoxyphenyl)propan-2-yl)-1-(4-fluorophenyl)-1H-imidazole (340 mg, 0.56 mmol) in EtOH (10 mL), conc HCl (1 mL) and PtO$_2$ (170 mg). The bottle was purged with hydrogen (3×40 psi), pressurized with hydrogen (45 psi) and then agitated for 5 h. The reaction mixture was filtered through Celite™ and the filtrate was evaporated. The residue was triturated with ether, and the solids collected by filtration and dried to give the title compound (344 mg, 99% yield). $^1$H NMR (400 MHz, CD$_3$OD) δ 7.21 (s, 1H), 6.87 (dd, J=10.99, 8.49 Hz, 1H), 6.76 (t, J=8.49 Hz, 2H), 6.67 (s, 1H), 6.58 (dd, J=8.15, 2.15 Hz, 1H), 6.52-6.42 (m, 2H), 6.38-6.29 (m, 2H), 4.16 (t, J=4.34 Hz, 2H), 3.98 (t, J=5.89 Hz, 2H), 3.77 (d, J=5.67 Hz, 3H), 3.50 (t, J=6.51 Hz, 2H), 2.65 (s, 2H), 2.17 (s, 1H), 2.43-2.15 (m, 3H), 1.49 (s, 6H).

Example 29

(E)-1-(2-(4-((5-(2-(4-chloro-3-methoxyphenyl)propan-2-yl)-1-(4-fluorophenyl)-1H-imidazol-2-ylthio)methyl)-3,5-difluorophenoxy)ethyl)-2-cyanoguanidine

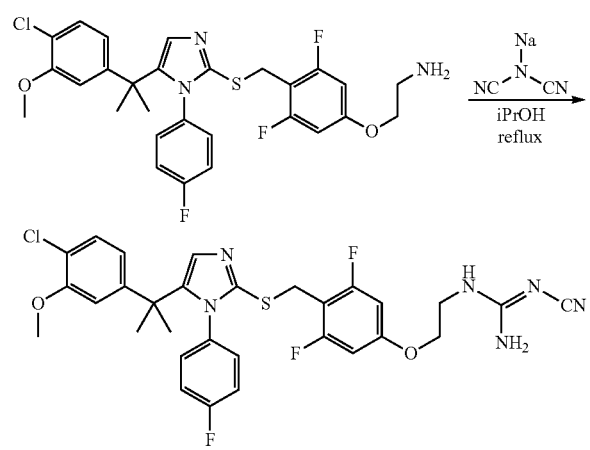

To a solution of 2-(4-((5-(2-(4-chloro-3-methoxyphenyl)propan-2-yl)-1-(4-fluorophenyl)-1H-imidazol-2-ylthio)methyl)-3,5-difluorophenoxy)ethanamine hydrochloride (100 mg, 0.167 mmol) in isopropylalcohol (5 mL) was added dicyanamide (19.3 mg, 0.217 mmol) and the reaction mixture was heated at reflux for 24 h. Solvent was evaporated in vacuo and the residue was purified by column chromatography (CH$_2$Cl$_2$/MeOH=20:1) to give the title compound (60 mg, 57%) as an ivory solid. $^1$H NMR (400 MHz, CD$_3$OD) δ 7.22 (s, 1H), 7.17 (d, J=8.2 Hz, 1H), 6.77 (t, J=8.43 Hz, 2H), 6.60-6.42 (m, 5H), 6.25 (dd, J=7.8, 4.7 Hz, 2H), 4.02 (t, J=4.54 Hz, 2H), 3.83 (s, 2H), 3.71 (s, 3H), 3.56 (t, J=4.65 Hz, 2H), 3.51-3.41 (m, 1H), 1.49 (s, 6H), 1.20 (d, J=44.2 Hz, 3H), 0.93-0.80 (m, 1H); MS (EI) m/z 629 (MH$^+$).

Example 30

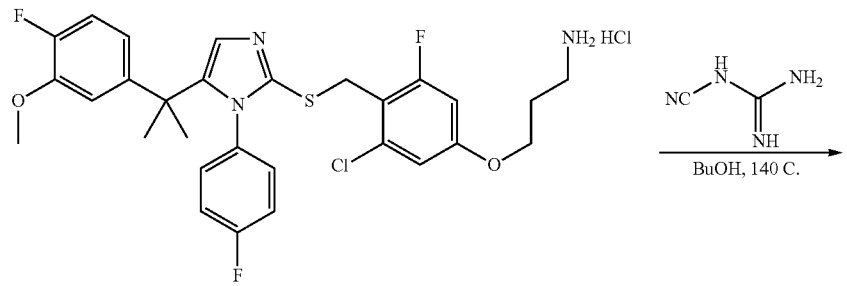

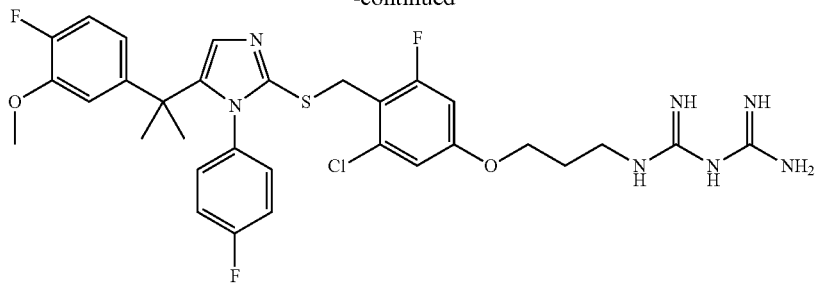

To a solution of 3-(3-chloro-5-fluoro-4-((5-(2-(4-fluoro-3-methoxyphenyl)propan-2-yl)-1-(4-fluorophenyl)-1H-imidazol-2-ylthio)methyl)phen oxy)propan-1-amine hydrochloride (140 mg, 0.23 mmol) in 1-butanol (0.5 mL) was added N-cyanoguanidine (100 mg, 1.19 mmol). The reaction mixture was irradiated in microwave at 140° C. for 1 h. After evaporation of volatiles, the residue was purified by column chromatography (DCM/MeOH=10:1) to give the title product (28 mg, 18%) as a white solid. $^1$H NMR (400 MHz, CD$_3$OD) δ 7.21 (s, 1H), 6.90 (dd, J=11.17, 8.49 Hz, 1H), 6.78 (dd, J=11.98, 5.11 Hz, 3H), 6.70-6.56 (m, 2H), 6.48 (s, 1H), 6.35-6.19 (m, 1H), 4.01 (dd, J=11.15, 5.29 Hz, 2H), 3.95 (d, J=11.18 Hz, 2H), 3.70 (d, J=13.62 Hz, 3H), 3.40 (t, J=6.74 Hz, 2H), 2.00 (dd, J=12.53, 6.07 Hz, 2H), 1.48 (s, 6H); MS (EI) m/z 660 (MH$^+$).

Example 31

5-((4-((5-(2-(4-chloro-3-methoxyphenyl)propan-2-yl)-1-(4-fluorophenyl)-1H-imidazol-2-ylthio)methyl)-3,5-difluorophenoxy)methyl)-1H-tetrazole

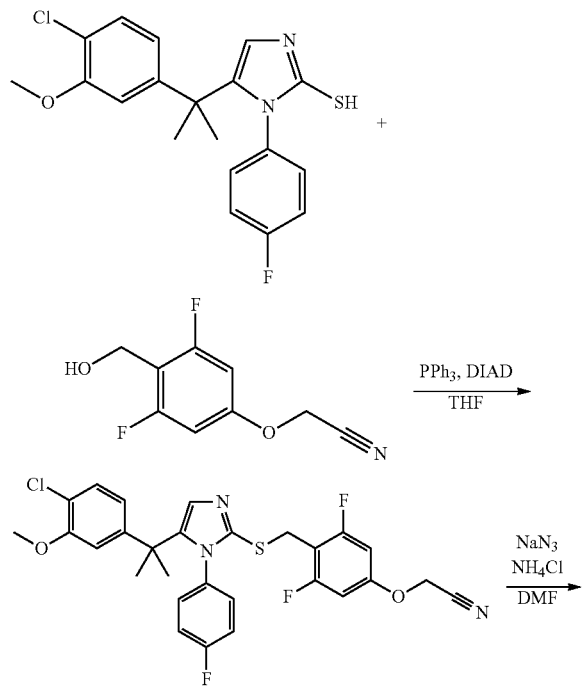

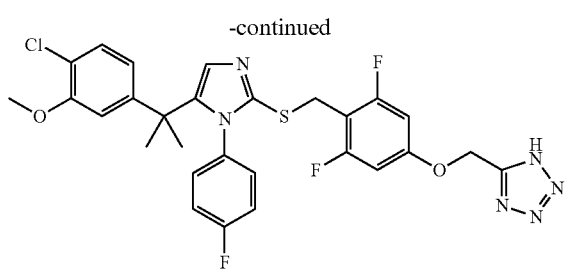

In a similar manner 5-(2-(4-chloro-3-methoxyphenyl)propan-2-yl)-1-(4-fluorophenyl)-1H-imidazole-2-thiol (227 mg, 0.60 mmol), 2-(3,5-difluoro-4-(hydroxymethyl)phenoxy)acetonitrile (156 mg, 0.78 mmol), PPh$_3$ (173 mg, 0.66 mmol) and DIAD (137 μL, 0.66 mmol) in THF (0.8 mL) were reacted, processed and purified by flash chromatography (80% EtOAc/Hex) to provide 2-(4-((5-(2-(4-chloro-3-methoxyphenyl)propan-2-yl)-1-(4-fluorophenyl)-1H-imidazol-2-ylthio)methyl)-3,5-difluorophenoxy)acetonitrile (129 mg, 39%). MS (EI) m/z 558.3 (MH$^+$).

A mixture of 2-(4-((5-(2-(4-chloro-3-methoxyphenyl)propan-2-yl)-1-(4-fluorophenyl)-1H-imidazol-2-ylthio)methyl)-3,5-difluorophenoxy)acetonitrile (129 mg, 0.23 mmol), NH$_4$Cl (124 mg, 2.3 mmol) and NaN$_3$ (16.60 mg, 0.25 mmol) in DMF (1.5 mL) was heated 17 h at 90° C. The reaction mixture was partitioned in EtOAc and H$_2$O. The organic layer was washed with H$_2$O and brine, dried over Na$_2$SO$_4$ and purified by flash chromatography (20% MeOH/DCM) to give the title compound (93 mg, 67%). $^1$HNMR (400 MHz, DMSO-d$_6$) δ7.23 (d, J=8.3 Hz, 1H), 7.18 (s, 1H), 6.96 (m, 2H), 6.82 (m, 2H), 6.57-6.45 (m, 4H), 5.30 (s, 2H), 3.95 (s, 2H), 3.68 (s, 3H), 1.46 (s, 6H); MS (EI) m/z 601.3 (MH$^+$).

Example 32

Tert-butyl-4-((5-(2-(4-chloro-3-methoxyphenyl)propan-2-yl)-1-(4-fluorophenyl)-1H-imidazol-2-ylthio)methyl)piperidine-1-carboxylate

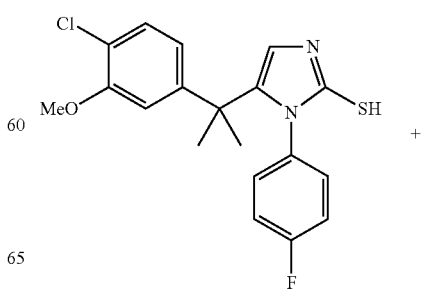

-continued

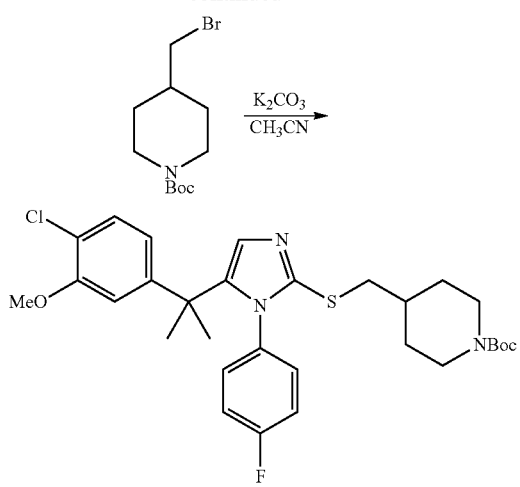

To a suspension of 5-(2-(4-chloro-3-methoxyphenyl)propan-2-yl)-1-(4-fluorophenyl)-1H-imidazole-2-thiol (0.557 g, 1.48 mmol) and $K_2CO_3$ (0.306 g, 2.22 mmol) in acetone (4 mL) was added tert-butyl 4-(bromomethyl)piperidine-1-carboxylate (0.431 g, 1.55 mmol). The reaction was heated at reflux. After 4 h, the reaction was concentrated and purified by column chromatography using Hex:EtOAc as eluents to afford the title compound (0.765 g) as a white solid. MS (EI) m/z 574 $[M+H]^+$.

Example 33

4-((5-(2-(4-Chloro-3-methoxyphenyl)propan-2-yl)-1-(4-fluorophenyl)-1H-imidazol-2-ylthio)methyl)-1-(methylsulfonyl)piperidine

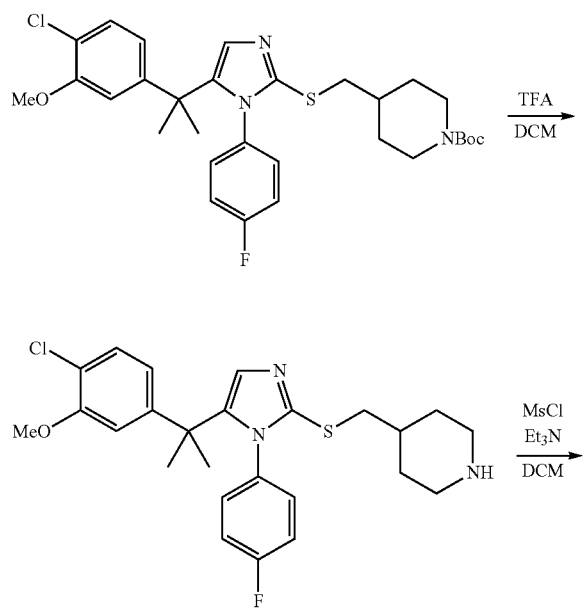

-continued

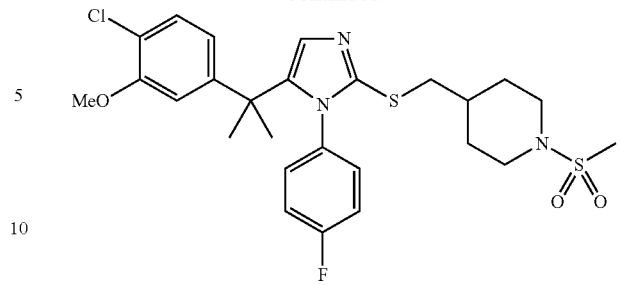

To a 0° C. solution of tert-butyl-4-((5-(2-(4-chloro-3-methoxyphenyl)propan-2-yl)-1-(4-fluorophenyl)-1H-imidazol-2-ylthio)methyl)piperidine-1-carboxylate (0.755 g, 1.31 mmol) in DCM (4 mL) was added TFA (1 mL). After stirring at room temperature 2 h, when the reaction was determined to be complete by LCMS, the reaction was concentrated in vacuo. The residue was diluted with DCM, washed with satd $NaHCO_3$ and brine, dried over $MgSO_4$ and concentrated in vacuo to afford 4-((5-(2-(4-chloro-3-methoxyphenyl)propan-2-yl)-1-(4-fluorophenyl)-1H-imidazol-2-ylthio)methyl)piperidine (0.491 g) as a white solid. MS (ES): 474 $[M+H]^+$.

To a solution of 4-((5-(2-(4-chloro-3-methoxyphenyl)propan-2-yl)-1-(4-fluorophenyl)-1H-imidazol-2-ylthio)methyl)piperidine (0.154 g, 0.33 mmol) and triethylamine (0.089 mL, 0.65 mmol) in DCM (2 mL) was added mesyl chloride (0.027 mL, 0.34 mmol). After 2 h the reaction was concentrated in vacuo and purified by column chromatography, using Hex:EtOAc as eluents, to afford the title compound (0.136 g) as a white solid. MS (EI) m/z 552 $[M+H]^+$.

Example 34

4-((5-(2-(4-chloro-3-methoxyphenyl)propan-2-yl)-1-(4-fluorophenyl)-1H-imidazol-2-ylsulfonyl)methyl)-1-(methylsulfonyl)piperidine To a solution of 4-((5-(2-(4-Chloro-3-methoxyphenyl)propan-2-yl)-1-(4-fluorophenyl)-1H-imidazol-2-ylthio)methyl)-1-(methylsulfonyl)piperidine (0.130 g, 0.24 mmol) in DCM (2 mL) was added 3-chlorobenzoperoxoic acid (0.125 g, 0.72 mmol). After stirring 5 h, the reaction was concentrated in vacuo and the residue was purified by HPLC (10-

99%, CH$_3$CN/H$_2$O with 0.05% TFA) to afford the title compound (40 mg) as a white solid. MS (EI) m/z 584 [M+H]$^+$.

Example 35

3-chloro-4-((5-(2-(3,4-dichlorophenyl)propan-2-yl)-1-(4-fluorophenyl)-1H-imidazol-2-yl)methoxy)-5-fluorobenzoic acid

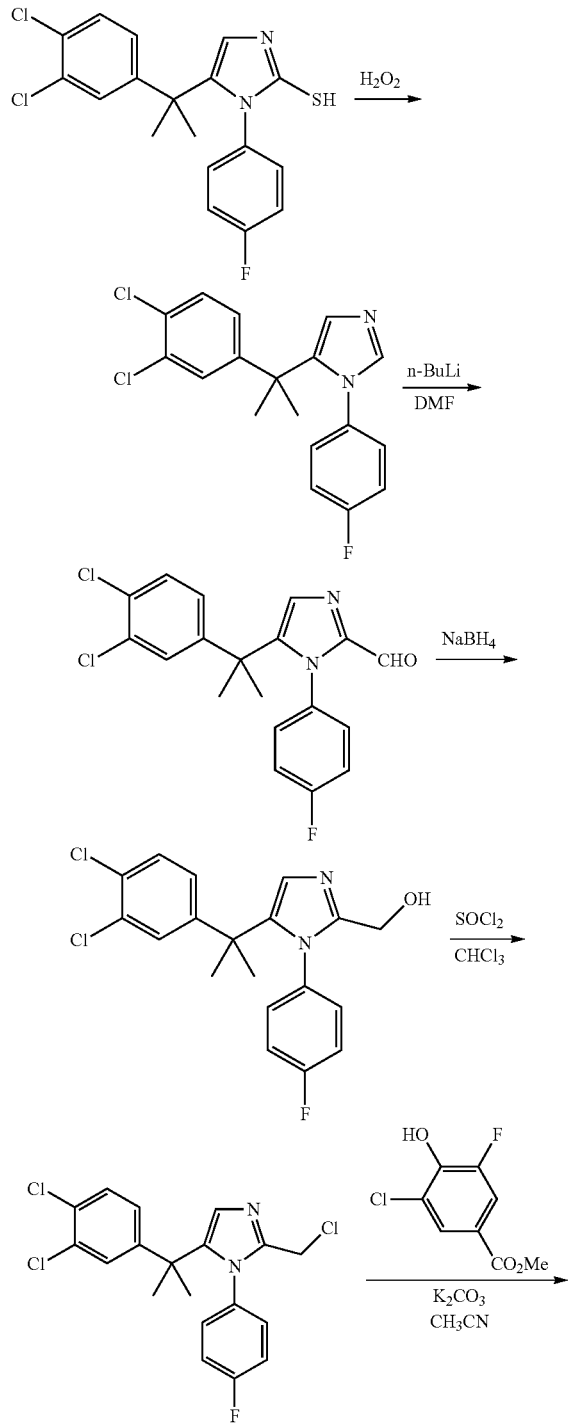

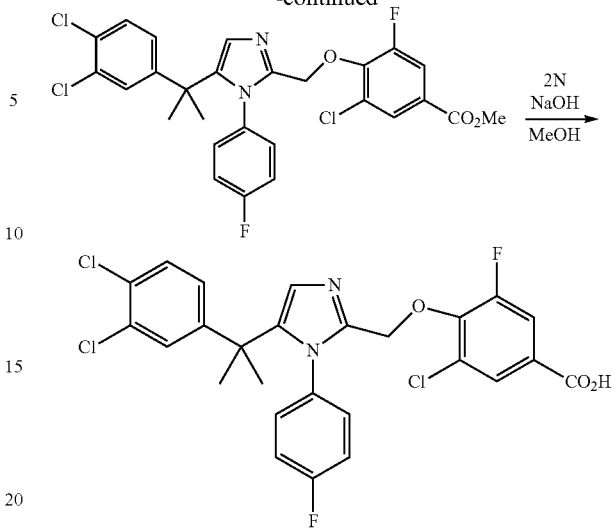

To a suspension of 5-(2-(3,4-dichlorophenyl)propan-2-yl)-1-(4-fluorophenyl)-1H-imidazole-2-thiol (737 mg, 1.9 mmol) in DCM (4 mL) at 0° C. was added a solution of 0.6 mL H$_2$O$_2$ (35% wt.) in HOAc (2 mL). After stirring 40 min, the mixture was allowed to warm to room temperature. After stirring 6 h, the reaction mixture was neutralized to pH 9 using 2N NaOH and was extracted with DCM. The combined extracts were washed with brine, dried over Na$_2$SO$_4$, and concentrated in vacuo. The crude material was purified by chromatography (silica, 0-95% EtOAc/Hex) to give 5-(2-(3,4-dichlorophenyl)propan-2-yl)-1-(4-fluorophenyl)-1H-imidazole as a white solid (455 mg, 69% yield).

To a solution of 5-(2-(3,4-dichlorophenyl)propan-2-yl)-1-(4-fluorophenyl)-1H-imidazole (770 mg, 2.2 mmol) in anhyd THF (10 mL) at −78° C. was added n-BuLi (1.4 mL, 2.0M in hexane, 2.8 mmol) dropwise. After stirring 1 h at −78° C., anhyd DMF (0.85 mL) was added in one portion. After stirring another 3 h at −78° C., the reaction was quenched with water. After warming to ambient temperature, the mixture was extracted with EtOAc. The combined extracts were washed with brine, dried over Na$_2$SO$_4$, and concentrated in vacuo. The crude material was purified by column chromatography (silica, 0-90% EtOAc/Hex) to give 5-(2-(3,4-dichlorophenyl)propan-2-yl)-1-(4-fluorophenyl)-1H-imidazole-2-carbaldehyde as a white solid (740 mg, 89% yield).

To a solution of 5-(2-(3,4-dichlorophenyl)propan-2-yl)-1-(4-fluorophenyl)-1H-imidazole-2-carbaldehyde (740 mg, 1.96 mmol) in anhyd ethanol (15 mL) was added NaBH$_4$ (91 mg, 2.4 mmol). After stirring 3 h, the mixture was poured into water, and extracted with EtOAc. The combined extracts were washed with brine, dried over Na$_2$SO$_4$, and concentrated in vacuo to give (5-(2-(3,4-dichlorophenyl)propan-2-yl)-1-(4-fluorophenyl)-1H-imidazol-2-yl)methanol as a white solid (670 mg, 88% yield).

To a solution of (5-(2-(3,4-dichlorophenyl)propan-2-yl)-1-(4-fluorophenyl)-1H-imidazol-2-yl)methanol (402 mg, 1.06 mmol) in CH$_3$CN (6 mL) at 0° C. was added thionyl chloride. After stirring 3 h, the solution was concentrated under reduced pressure, and azeotroped with DCM (3×) to give 2-(chloromethyl)-5-(2-(3,4-dichlorophenyl)propan-2-yl)-1-(4-fluorophenyl)-1H-imidazole as a yellow solid (420 mg) that was used directly for the next step without purification.

A mixture of 2-(chloromethyl)-5-(2-(3,4-dichlorophenyl)propan-2-yl)-1-(4-fluorophenyl)-1H-imidazole (154 mg, 0.39 mmol), methyl 3-chloro-5-fluoro-4-hydroxybenzoate (118 mg 0.57 mmol), potassium carbonate (79 mg, 0.57 mmol), and 18-crown-6 (11 mg, 0.04 mmol) in CH$_3$CN (4 mL) was heated 8 h at 60° C. After cooling, the reaction mixture was filtered, combined with water and DCM, and then extracted further with DCM. The combined extracts were washed with brine, dried over Na$_2$SO$_4$, and concentrated in vacuo. The material was purified by chromatography (silica, 0-70% EtOAc/Hex) to give methyl 3-chloro-4-((5-(2-(3,4-dichlorophenyl)propan-2-yl)-1-(4-fluorophenyl)-1H-imidazol-2-yl)methoxy)-5-fluorobenzoate as a white solid (150 mg, 68% yield). MS (EI) m/z 567.3 [M+H]$^+$.

A mixture of methyl 3-chloro-4-((5-(2-(3,4-dichlorophenyl)propan-2-yl)-1-(4-fluorophenyl)-1H-imidazol-2-yl)methoxy)-5-fluorobenzoate (120 mg, 0.21 mmol) and 2N NaOH (0.31 mL, 0.63 mmol) in MeOH (3 mL) was heated 3 h at 65° C. After cooling, the reaction was neutralized to pH 3 with 3N HCl, concentrated under reduced pressure, diluted with water, and then extracted with EtOAc. The combined extracts were washed with brine, dried over Na$_2$SO$_4$, and concentrated in vacuo. The crude material was purified by HPLC (MeCN/H$_2$O, 10-99%) to give the title compound as an off-white solid (45 mg, 39%). MS (EI) m/z 553.5 [M+H]$^+$.

3-chloro-4-((5-(2-(4-chloro-3-methoxyphenyl)propan-2-yl)-1-(4-fluorophenyl)-1H-imidazol-2-yl)methoxy)-5-fluorobenzoic acid

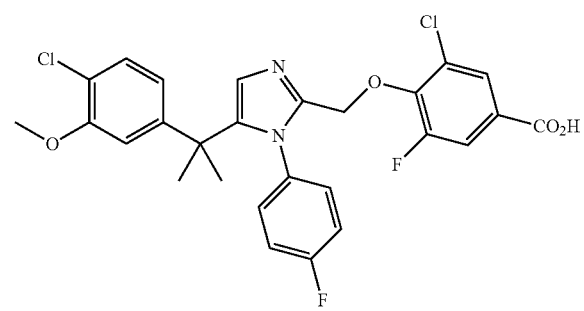 [SMILES: COc1cc(C(C)(C)c2cnc(COc3c(F)cc(C(=O)O)cc3Cl)n2-c2ccc(F)cc2)ccc1Cl]

The title compound was prepared from 5-(2-(4-chloro-3-methoxyphenyl)propan-2-yl)-1-(4-fluorophenyl)-1H-imidazole-2-thiol under similar conditions. $^1$H NMR (400 MHz, DMSO) δ 7.72 (t, J=1.6 Hz, 1H), 7.64 (dd, J=11.0, 1.9 Hz, 1H), 7.22 (d, J=8.3 Hz, 1H), 7.11 (s, 1H), 7.05 (d, J=8.1 Hz, 1H), 7.03 (d, J=8.7 Hz, 1H), 6.82-6.76 (m, 2H), 6.57 (d, J=2.0 Hz, 1H), 6.51 (dd, J=8.3, 2.0 Hz, 1H), 4.77 (s, 2H), 3.68 (s, 3H), 1.49 (s, 6H).

Example 36

3-chloro-4-((5-(2-(4-chloro-3-methoxyphenyl)propan-2-yl)-1-(4-fluorophenyl)-1H-imidazol-2-yl)methoxy)-5-fluorobenzenesulfonic acid

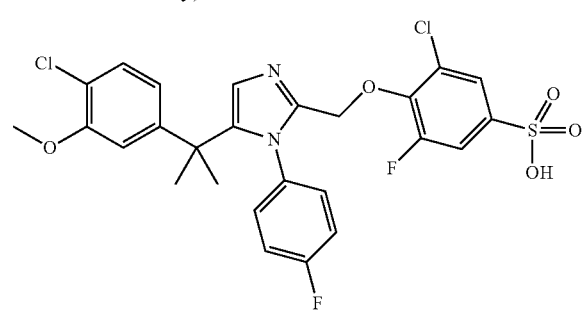

The title compound was prepared from 3-chloro-4-((5-(2-(4-chloro-3-methoxyphenyl)propan-2-yl)-1-(4-fluorophenyl)-1H-imidazol-2-yl)methoxy)-5-fluorobenzoic acid under conditions previously described. $^1$H NMR (400 MHz, DMSO) δ 7.87 (s, 1H), 7.42 (t, J=1.6 Hz, 1H), 7.34 (dd, J=10.1, 1.8 Hz, 1H), 7.25 (d, J=8.3 Hz, 1H), 7.16 (d, J=8.4 Hz, 1H), 7.214 (d, J=8.7 Hz, 1H), 6.97-6.92 (m, 2H), 6.58 (d, J=2.0 Hz, 1H), 6.52 (dd, J=8.3, 2.1 Hz, 1H), 4.84 (s, 2H), 3.71 (s, 3H), 1.56 (s, 6H); MS (EI) m/z 583.2 [M+1]$^+$.

Example 37

2-chloro-N-((5-(2-(3,4-dimethoxyphenyl)propan-2-yl)-1-(4-fluorophenyl)-1H-imidazol-2-yl)methyl)-6-fluoroaniline

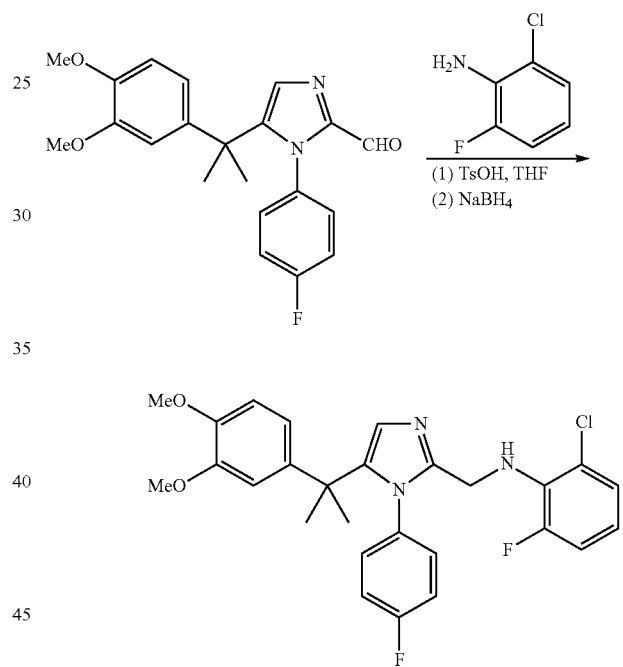

A solution of 5-(2-(3,4-dimethoxyphenyl)propan-2-yl)-1-(4-fluorophenyl)-1H-imidazole-2-carbaldehyde (280 mg, 0.76 mmol), 2-chloro-6-fluoroaniline (332 mg, 2.28 mmol), TsOH (72 mg, 0.38 mmol) in THF (8 mL) was heated at reflux for 15 h over molecular sieves (4A). The solution was cooled to 0° C., and NaBH$_4$ (57 mg, 1.5 2 mmol) was added in several portions. The resulting mixture was stirring for 1 h, and filtered through Celite™ to remove molecular sieves. The filtrate was quenched with H$_2$O (5 mL), 2N NaOH (5 mL) and extracted with DCM (2×10 mL). The organic layers were dried over MgSO$_4$ and concentrated to give a residue, which was purified by flash chromatography to provide the title compound as a white solid (157 mg, 0.315 mmol, 42%). $^1$H NMR (400 MHz, CDCl$_3$) δ1.49 (s, 6H), 3.72 (s, 3H), 3.85 (s, 3H), 4.13 (d, 2H), 4.65 (br, 1H), 6.45 (dd, 1H), 6.48 (m, 2H), 6.51 (d, 1H), 6.60 (m, 1H), 6.64 (d, 1H), 6.76 (dd, 1H), 6.80 (t, 2H), 7.00 (dt, 1H), 7.13 (s, 1H). MS (EI) m/z 498 [M+H]$^+$.

Example 38

4-((5-(2-(3,4-Dichlorophenyl)propan-2-yl)-1-(4-fluorophenyl)-1H-imidazol-2-yl)methoxy)-1-(1H-tetrazol-5-yl)piperidine

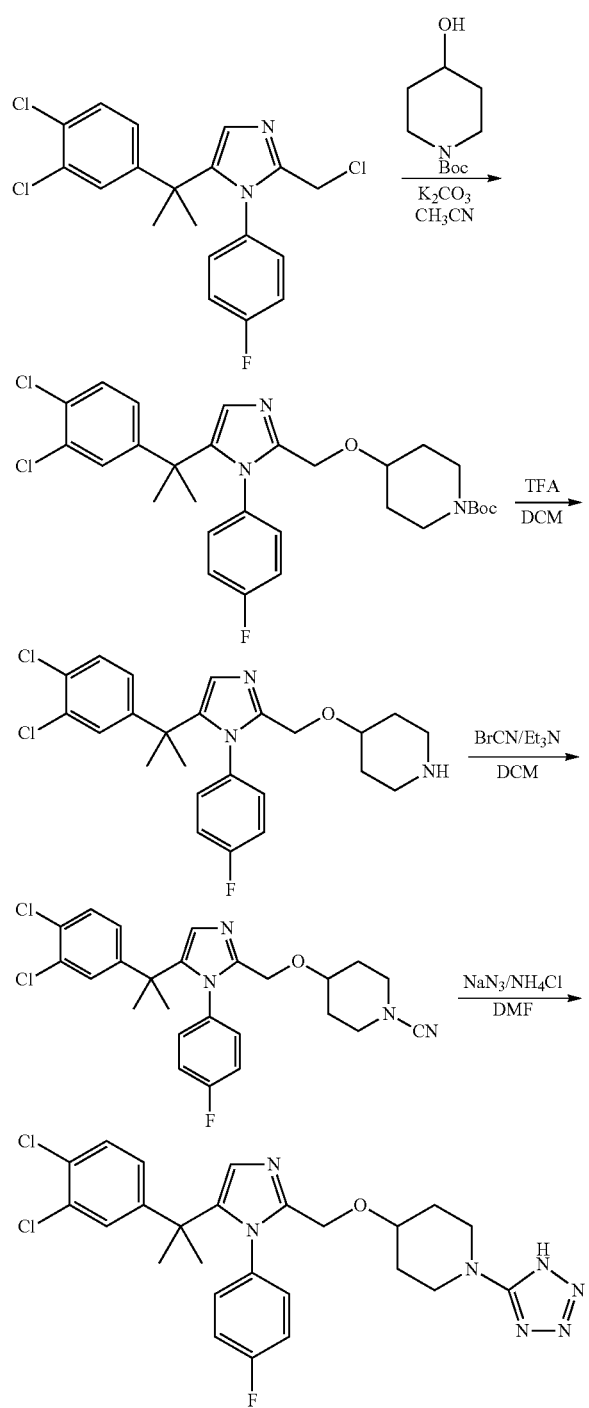

To a solution of tert-butyl 4-hydroxypiperidine-1-carboxylate (202 mg, 1 mmol) in anhyd THF (3 mL) was added NaH (60% in mineral oil, 53 mg, 1.32 mmol). The mixture stirred at room temperature for 30 min, then a solution of 2-(chloromethyl)-5-(2-(3,4-dichlorophenyl)propan-2-yl)-1-(4-fluorophenyl)-1H-imidazole (262 mg, 0.66 mmol) in THF (2 mL) was added. After stirring at ambient temperature overnight, the reaction was quenched by addition of MeOH and concentrated in vacuo. The residue was partitioned in water and EtOAc. The combined organic layers were washed with brine, dried over $Na_2SO_4$, concentrated in vacuo, and purified by column chromatography (silica, 0-90% EtOAc/Hex) to give tert-butyl 4-((5-(2-(3,4-dichlorophenyl)propan-2-yl)-1-(4-fluorophenyl)-1H-imidazol-2-yl)methoxy)piperidine-1-carboxylate as a white solid (215 mg, 60%).

To a solution of tert-butyl 4-((5-(2-(3,4-dichlorophenyl)propan-2-yl)-1-(4-fluorophenyl)-1H-imidazol-2-yl)methoxy)piperidine-1-carboxylate (101 mg, 0.18 mmol) in DCM (2 mL) at 0° C. was added TFA (0.2 mL). After stirring at room temperature for 2 h, the reaction mixture was diluted with DCM, washed with satd $NaHCO_3$ and brine, dried over $Na_2SO_4$, and concentrated in vacuo to give 4-((5-(2-(3,4-Dichlorophenyl)propan-2-yl)-1-(4-fluorophenyl)-1H-imidazol-2-yl)methoxy)piperidine as a white solid that was used directly for the next step.

To a solution of 4-((5-(2-(3,4-dichlorophenyl)propan-2-yl)-1-(4-fluorophenyl)-1H-imidazol-2-yl)methoxy)piperidine (prepared above) in anhyd DCM (2 mL) was added $Et_3N$ (37 uL, 0.27 mmol), followed by cyanic bromide (20 mg, 0.18 mmol). After stirring overnight, the reaction was diluted with DCM, washed with brine, dried over $Na_2SO_4$, and concentrated in vacuo to give 4-((5-(2-(3,4-dichlorophenyl)propan-2-yl)-1-(4-fluorophenyl)-1H-imidazol-2-yl)methoxy)piperidine-1-carbonitrile as a white solid that was used directly for the next step.

A mixture of 4-((5-(2-(3,4-dichlorophenyl)propan-2-yl)-1-(4-fluorophenyl)-1H-imidazol-2-yl)methoxy)piperidine-1-carbonitrile, $NaN_3$ (59 mg, 0.9 mmol), and $NH_4Cl$ (50 mg, 0.9 mmol) in DMF (2 mL) was heated at 100° C. overnight. The crude product was purified by HPLC (10-99%, MeCN/$H_2O$ with 0.05% TFA) to give the title product as a white solid (45 mg, 47%). MS (EI) m/z 530.3 $[M+H]^+$.

4-((5-(2-(3,4-Dichlorophenyl)propan-2-yl)-1-(4-fluorophenyl)-1H-imidazol-2-yl)methoxy)-1-(methylsulfonyl)piperidine

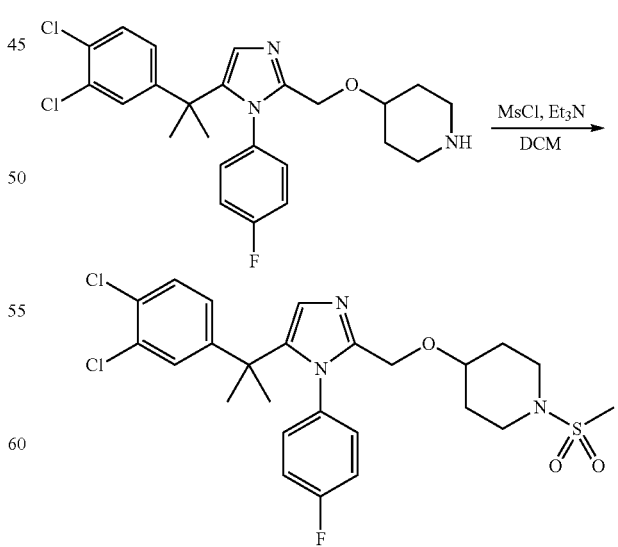

To a solution of 4-((5-(2-(3,4-dichlorophenyl)propan-2-yl)-1-(4-fluorophenyl)-1H-imidazol-2-yl)methoxy)-1-(methylsulfonyl)piperidine in anhyd DCM (2 mL) at 0° C. was added Et₃N (75 uL, 0.54 mmol) and MeSO₂Cl (31 mg, 0.27 mmol). The mixture was stirred then at room temperature for 3 h, diluted with DCM, washed with satd NaHCO₃ and brine, dried over Na₂SO₄, and concentrated in vacuum. The crude material was purified by HPLC (10-99%, MeCN/H₂O with 0.05% TFA) to give the title product as a white solid (50 mg, 52%). MS (EI) m/z 540.5 [M+H]⁺.

Example 39

3-chloro-4-(2-(5-(2-(4-chloro-3-methoxyphenyl) propan-2-yl)-1-(4-fluorophenyl)-1H-imidazol-2-yl) ethyl)-5-fluorobenzoic acid

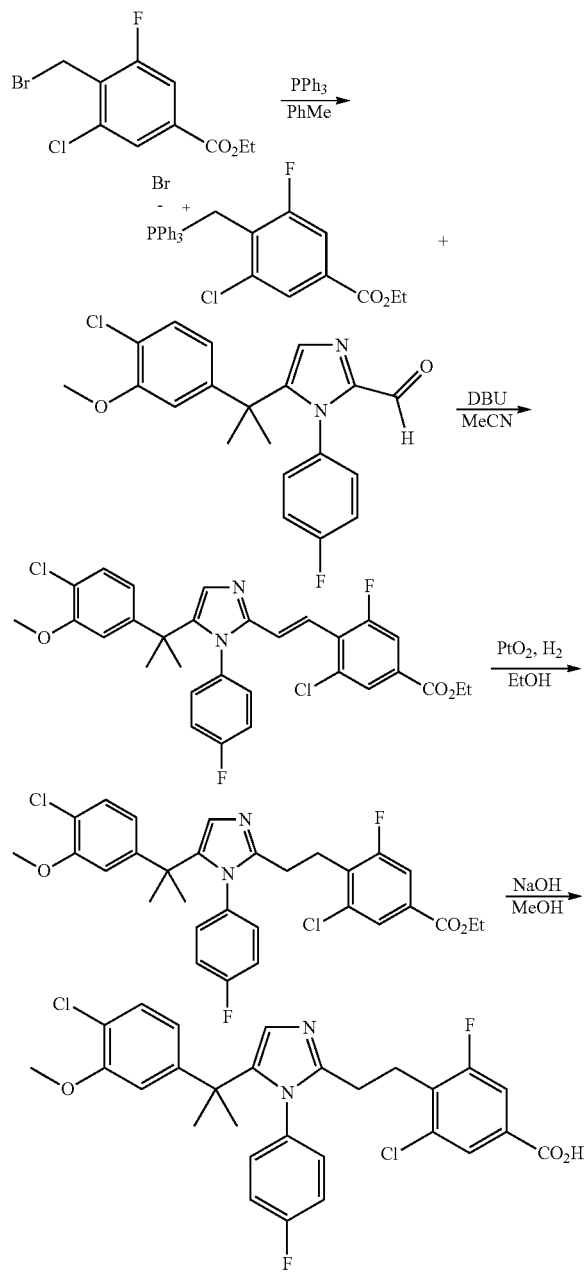

To a solution of ethyl 4-(bromomethyl)-3-chloro-5-fluorobenzoate (531 mg, 1.797 mmol) in toluene (10 mL) was added PPh₃ (471 mg, 1.797 mmol). The solution was refluxed at 90° C. overnight. Upon cooling a white precipitate formed. The mixture was diluted with hexanes, filtered and dried under vacuum to yield (2-chloro-4-(ethoxycarbonyl)-6-fluorobenzyl)triphenylphosphonium bromide (0.874 g, 86%) as a white solid. ¹H NMR (400 MHz, DMSO-d₆) δ 8.05-7.87 (m, 3H), 7.85-7.58 (m, 13H), 7.20 (tt, J=15.1, 7.1 Hz, 1H), 5.21 (d, J=15.0 Hz, 2H), 4.34 (dq, J=14.2, 7.1 Hz, 2H), 1.33 (dt, J=14.2, 7.1 Hz, 3H).

To a mixture of 5-(2-(4-chloro-3-methoxyphenyl)propan-2-yl)-1-(4-fluorophenyl)-1H-imidazole-2-carbaldehyde (304 mg, 0.815 mmol) and (2-chloro-4-(ethoxycarbonyl)-6-fluorobenzyl)triphenylphosphonium bromide (454 mg, 0.815 mmol) in MeCN (5 mL) was added dropwise DBU (136 mg, 0.896 mmol). After stirring at 50° C. overnight, the mixture was diluted with H₂O and extracted with DCM. The combined extracts were dried (MgSO₄), filtered, concentrated and purified by flash chromatography (20-90% EtOAc/hexanes) to yield ethyl 3-chloro-4-(2-(5-(2-(4-chloro-3-methoxyphenyl)propan-2-yl)-1-(4-fluorophenyl)-1H-imidazol-2-yl)vinyl)-5-fluorobenzoate (0.241 g, 51%) as a yellow oil. ¹H NMR (400 MHz, DMSO-d₆) δ 8.05-7.87 (m, 3H), 7.85-7.58 (m, 13H), 7.20 (tt, J=15.1, 7.1 Hz, 1H), 5.21 (d, J=15.0 Hz, 2H), 4.34 (dq, J=14.2, 7.1 Hz, 2H), 1.33 (dt, J=14.2, 7.1 Hz, 3H).

A solution of ethyl 3-chloro-4-(2-(5-(2-(4-chloro-3-methoxyphenyl)propan-2-yl)-1-(4-fluorophenyl)-1H-imidazol-2-yl)vinyl)-5-fluorobenzoate (224 mg, 0.392 mmol) in EtOH (10 mL) was degassed using N₂ for 5-10 minutes prior to the addition of PtO₂ (42 mg, 0.184 mmol). The resulting suspension was pressurized with 70 psi H₂ and agitated overnight. The catalyst was removed by filtration through Celite™ and eluting with more EtOH. The filtrate was concentrated in vacuo to provide ethyl 3-chloro-4-(2-(5-(2-(4-chloro-3-methoxyphenyl)propan-2-yl)-1-(4-fluorophenyl)-1H-imidazol-2-yl)ethyl)-5-fluorobenzoate (153 mg, 68%) as a gray oil. ¹H NMR (400 MHz, CDCl₃) δ 7.87-7.61 (m, 1H), 7.50 (td, J=9.4, 1.4 Hz, 1H), 7.15 (d, J=8.4 Hz, 1H), 7.11-6.98 (m, 1H), 6.98-6.65 (m, 2H), 6.65-6.32 (m, 4H), 4.38 (dq, J=21.4, 7.1 Hz, 2H), 3.74 (d, J=3.3 Hz, 3H), 3.25-2.83 (m, 2H), 2.52 (dd, J=16.6, 8.9 Hz, 2H), 1.50 (s, 6H), 1.39 (dt, J=14.3, 7.2 Hz, 3H).

To a solution of ethyl 3-chloro-4-(2-(5-(2-(4-chloro-3-methoxyphenyl)propan-2-yl)-1-(4-fluorophenyl)-1H-imidazol-2-yl)ethyl)-5-fluorobenzoate (151 mg, 0.263 mmol) in MeOH (1.0 mL) was added dropwise a 2N solution of NaOH in H₂O (0.5 mL). After stirring 1 h, the reaction mixture was concentrated under reduced pressure, diluted with H₂O (1.5 mL), neutralized with 1N HCl and then extracted with DCM (10 mL×2). The combined extracts were dried (MgSO₄), filtered and concentrated to give the title compound (116 mg, 81%) as gray solid. ¹H NMR (400 MHz, DMSO) δ 7.69 (s, 1H), 7.57 (d, J=9.6 Hz, 1H), 7.27-7.17 (m, 2H), 7.05 (d, J=8.6 Hz, 1H), 7.03 (d, J=8.6 Hz, 1H), 6.69 (dd, J=8.6, 4.8 Hz, 2H), 6.54 (s, 1H), 6.53-6.48 (m, 1H), 3.69 (s, 3H), 2.94 (t, J=7.2 Hz, 2H), 2.57 (t, J=7.2 Hz, 2H), 1.48 (s, 6H).

Example 40

3-chloro-4-(2-(5-(2-(4-chloro-3-methoxyphenyl)propan-2-yl)-1-(4-fluorophenyl)-1H-imidazol-2-yl)ethyl)-5-fluorobenzenesulfonic acid

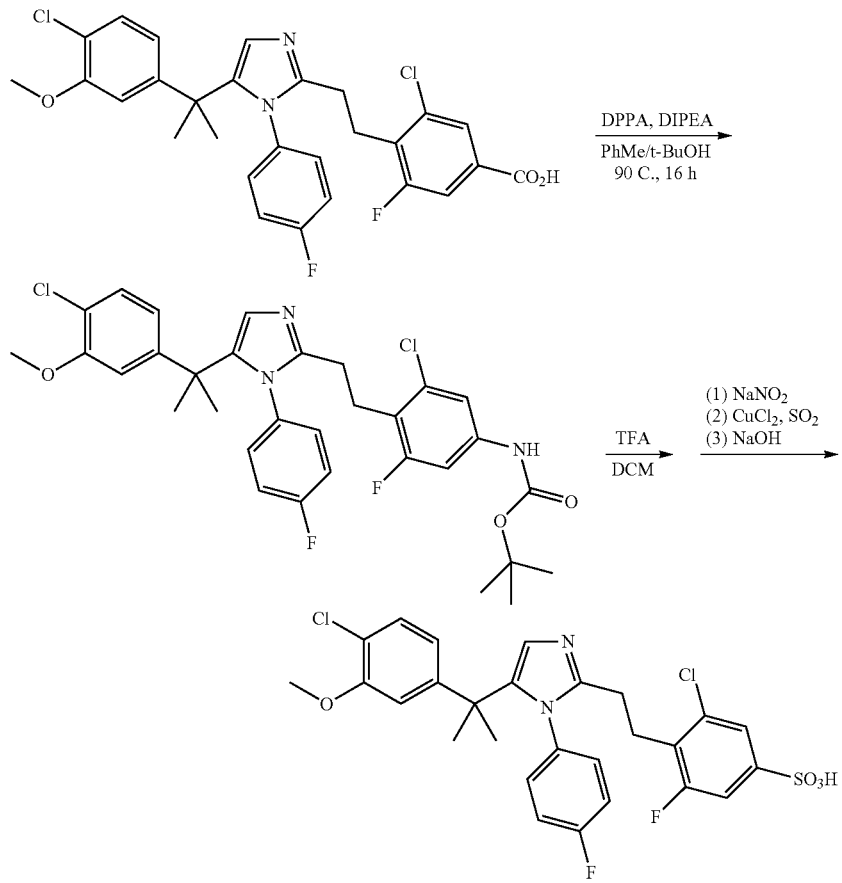

To solution of 3-chloro-4-(2-(5-(2-(4-chloro-3-methoxyphenyl)propan-2-yl)-1-(4-fluorophenyl)-1H-imidazol-2-yl)ethyl)-5-fluorobenzoic acid (540 mg) in a mixture of toluene (5 mL) and tert-butanol (1.5 mL) cooled to 0° C. was added diphenyl phosphoryl azide (DPPA) (1.1 eq, 302 mg) followed by DIPEA (1.3 eq, 226 μL). During addition of base, the white slurry became a clear solution, which was heated at 80° C. After 16 h, complete conversion was observed by LC-MS. The reaction was diluted with EtOAc, washed with satd NaHCO$_3$, dried (Na$_2$SO$_4$), concentrated and purified by chromatography (silica, EtOAc/Hex, 10-60%) to yield tert-butyl 3-chloro-4-(2-(5-(2-(4-chloro-3-methoxyphenyl)propan-2-yl)-1-(4-fluorophenyl)-1H-imidazol-2-yl)ethyl)-5-fluorophenylcarbamate (230 mg). MS (EI) m/z 616 (MH$^+$).

To a solution of tert-butyl 3-chloro-4-(2-(5-(2-(4-chloro-3-methoxyphenyl)propan-2-yl)-1-(4-fluorophenyl)-1H-imidazol-2-yl)ethyl)-5-fluorophenylcarbamate (230 mg, 0.373 mmol) in DCM (anhyd, 3 mL) at 5° C. was added slowly TFA (3 mL). The flask was removed from the ice bath and stirred at ambient temperature. After 30 min, the deprotection was complete by LCMS and TLC. The mixture was concentrated to minimum volume and diluted with HOAc (1.34 mL). To this flask was added slowly conc HCl (387 μL) and water (231 μL). Then submerged flask in ice bath to attain constant temperature of 5° C. To this acidic mixture added dropwise a solution of sodium nitrite (31.7 mg, 0.458 mmol) in minimum water, while maintaining a temperature of 4-6° C. In another flask a mixture of CuCl$_2$ (10 mg, 0.0746 mmol), HOAc (1 mL) and H$_2$O (4 drops) was sparged with sulfur dioxide at a slow rate for 10 min, then submerged flask in ice bath at 5° C. After diazotization reaction has stirred 30-40 min at 5° C., this mixture was transferred to the second flask in small portions. After stirring 1 h, an aliquot from the mixture showed 90-95% sulfonyl chloride present by LCMS. The mixture was diluted with H$_2$O (5 mL) and extracted with DCM (2×5 mL). Combined extracts were concentrated under reduced pressure and then dissolved in THF (3 mL). To this solution chilled to 5° C. was added dropwise 2N NaOH until the mixture attained pH 8. After stirring 10 min, the reaction mixture was concentrated under reduced pressure, diluted with H$_2$O (3 mL) and acidified with 1N HCl. The aqueous mixture was extracted with DCM (4×5 mL). Combined extracts were washed with brine, dried (Na$_2$SO$_4$) and concentrated. The residue was purified by chromatography (silica, MeOH/DCM, 0-20%) to afford 3-chloro-4-(2-(5-(2-(4-chloro-3-methoxyphenyl)propan-2-yl)-1-(4-fluorophenyl)-1H-imidazol-2-yl)ethyl)-5-fluorobenzenesulfonic acid (201 mg). $^1$H NMR (400 MHz, DMSO) δ 7.68 (s, 1H), 7.37 (s, 1H), 7.26-7.19 (m, 2H), 7.11 (d, J=8.4 Hz, 1H), 7.09 (d, J=8.7 Hz, 1H), 6.87-6.81 (m, 2H), 6.55 (d, J=2.0 Hz, 1H), 6.50 (dd, J=8.3, 2.1 Hz, 1H), 3.70 (d, J=8.1 Hz, 3H), 2.84 (t, J=7.2 Hz, 2H), 2.68 (t, J=7.3 Hz, 2H), 1.51 (s, 6H).

Example 41

2-chloro-N-(5-(2-(4-chloro-3-methoxyphenyl)propan-2-yl)-1-(4-fluorophenyl)-1H-imidazol-2-yl)-6-fluorobenzamide

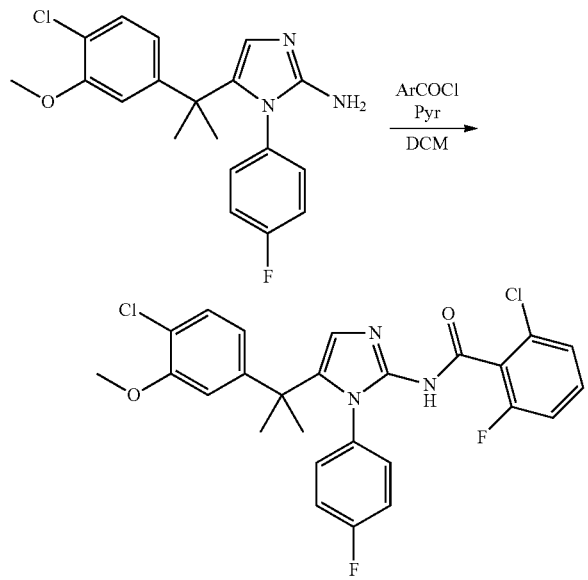

To a 0° C. solution of 5-(2-(4-chloro-3-methoxyphenyl)propan-2-yl)-1-(4-fluorophenyl)-1H-imidazol-2-amine (93 mg, 0.26 mmol) and pyridine (0.05 mL, 0.52 mmol) in DCM (1.5 mL) was added 2-chloro-6-fluorobenzoyl chloride (0.050 g, 0.26 mmol) in DCM (0.5 mL). After stirring 2 h at ambient temperature, the reaction was quenched with water. The mixture was extracted with DCM (3×5 mL) and dried with MgSO$_4$. The residue was purified by HPLC (10-99%, MeCN/H$_2$O with 0.05% TFA) to afford the title compound (9 mg) as a white solid. MS (EI) m/z 516 [M+H]$^+$.

Example 42

4-Bromo-2-(2-chloro-6-fluorobenzylthio)-5-(2-(3,4-dichlorophenyl)propan-2-yl)-1-(4-fluorophenyl)-1H-imidazole

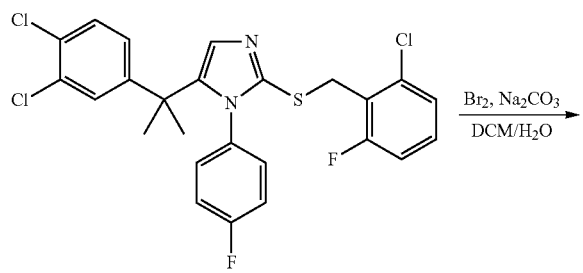

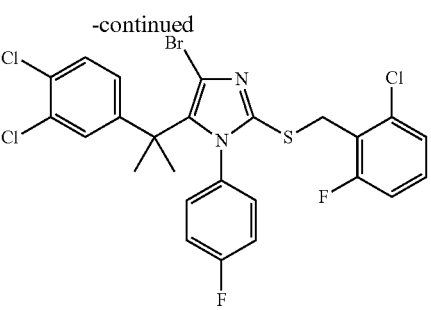

To a solution of 2-(2-chloro-6-fluorobenzylthio)-5-(2-(3,4-dichlorophenyl)propan-2-yl)-1-(4-fluorophenyl)-1H-imidazole (950 mg, 1.81 mmol) and sodium carbonate (634 mg, 5.98 mmol) in DCM:H$_2$O (5 mL:5 mL) was added bromine (0.1 mL, 2.00 mmol) dropwise at 0° C. The resulting mixture was stirred for 3 h and diluted with DCM (15 mL). The organic layer was washed with H$_2$O and brine, dried over MgSO$_4$, and concentrated in vacuo. The crude material was purified with flash chromatography to afford the title compound (970 mg, 89%) as a white solid. $^1$H NMR (400 MHz, CDCl$_3$) δ 1.62 (s, 6H), 4.35 (s, 2H), 6.43 (m, 2H), 6.80 (t, 2H), 6.84 (dd, 1H), 6.95 (t, 1H), 6.99 (dd, 1H), 7.16 (m, 2H), 7.25 (t, 1H); MS (EI) m/z 602 [M+H]$^+$.

Example 43

2-(2-chloro-6-fluorobenzylthio)-5-(2-(3,4-dichlorophenyl)propan-2-yl)-1-(4-fluorophenyl)-4-phenyl-1H-imidazole A mixture of 4-bromo-2-(2-chloro-6-fluorobenzylthio)-5-(2-(3,4-dichlorophenyl)propan-2-yl)-1-(4-fluorophenyl)-1H-imidazole (100 mg, 0.166 mmol), phenylboronic acid (40.5 mg, 0.332 mmol), Pd(OAc)$_2$ (2 mg, 0.008 mmol), tris (2-methoxyphenyl)phosphine (6 mg, 0.017 mmol), and K$_3$PO$_4$ (106 mg, 0.498 mmol) in EtOH—H$_2$O (3 mL, 10:1 v/v) was refluxed overnight. The reaction mixture was filtered through Celite™. The filtrate was concentrated in vacuo, dissolved in DCM (5 mL) and washed with H$_2$O (5 mL). The organic layer was dried over MgSO₄ and concentrated in vacuo. The crude material was purified by flash chromatography (Hex/EtOAc=9:1) to give the title product (17 mg, 17%) as a white solid. ¹H NMR (400 MHz, CDCl₃) δ 1.23 (s, 6H), 4.57 (s, 2H), 6.10 (m, 2H), 6.30 (t, 2H), 6.50 (dd, 1H), 6.75 (m, 1H), 6.80 (d, 1H), 6.85 (dd, 1H), 7.19 (m, 1H), 7.25 (t, 2H), 7.70 (s, 1H), 7.71 (s, 1H); MS (EI) m/z 601 [M+H]⁺.

Intermediates

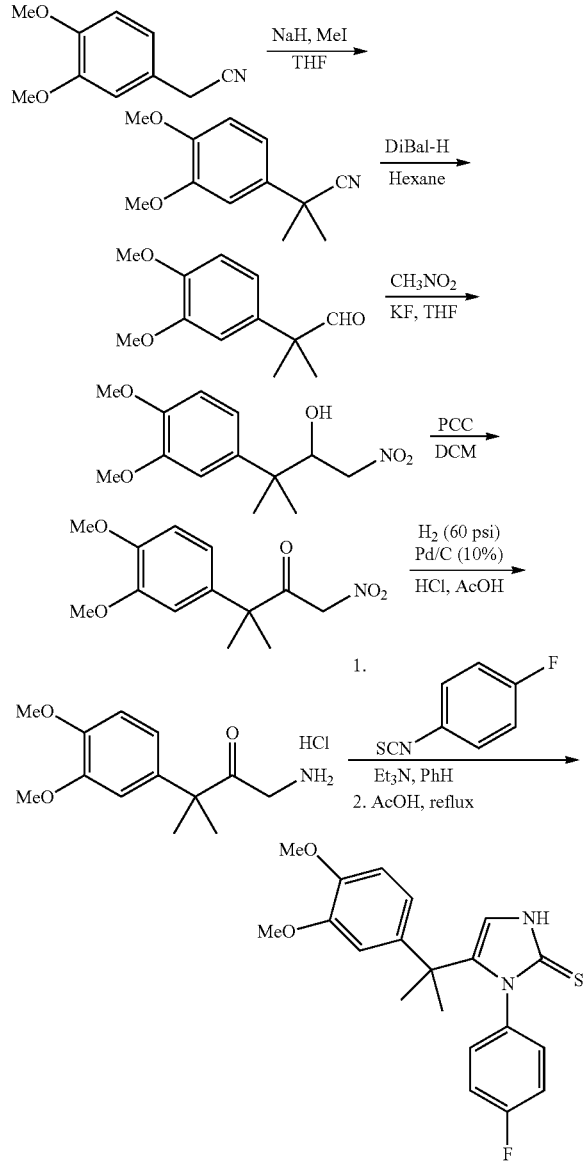

To a dispersion of NaH (3.60 g, 90.0 mmol) in THF (50 mL, anhyd) at 0° C. was added 2-(3,4-dimethoxyphenyl)acetonitrile (5.32 g, 30.0 mmol). The mixture was stirred for 30 min, and CH₃I (9.4 mL, 150 mmol) was added to the reaction mixture. After stirring 12 h, the reaction mixture was quenched with satd NH₄Cl (100 mL) and extracted with EtOAc (150 mL). The combined extracts were washed with brine, dried over MgSO₄, filtered, and concentrated to give 2-(3,4-dimethoxyphenyl)-2-methylpropanenitrile (5.77 g, 94%). ¹H NMR (400 MHz, CDCl₃) δ 7.01-6.97 (m, 2H), 6.86 (d, 1H), 3.92 (s, 3H), 3.89 (s, 3H), 1.72 (s, 6H).

To a solution of 2-(3,4-dimethoxyphenyl)-2-methylpropanenitrile (1.0 g, 4.87 mmol) in hexane (50 mL) at −78° C. was added a 1.5M solution of DIBAH (6.5 mL, 9.74 mmol) in toluene. After stirring for 1 h at −78° C., the mixture was warmed to room temperature, quenched with satd NH₄Cl (10 mL) and extracted with EtOAc (50 mL). The organic layer was washed with brine, dried over MgSO₄, filtered, concentrated to give 2-(3,4-dimethoxyphenyl)-2-methylpropanal (680 mg, 67%). ¹H NMR (400 MHz, CDCl₃) δ 9.45 (s, 1H), 6.89-6.85 (m, 2H), 6.73 (s, 1H), 3.88 (s, 6H), 1.45 (s, 6H).

To a solution of 2-(3,4-dimethoxyphenyl)-2-methylpropanal (1.0 g, 4.8 mmol) in EtOH (30 mL) were added KF (335 mg, 5.8 mmol) and CH₃NO₂ (1.56 mL, 28.8 mmol). The resulting mixture was stirred overnight at room temperature. The solution was concentrated, diluted with EtOAc, and washed with brine. The organic layer was dried over MgSO₄, filtered and concentrated to give 3-(3,4-dimethoxyphenyl)-3-methyl-1-nitrobutan-2-ol (1.25 g, 97%). ¹H NMR (400 MHz, CDCl₃) δ 6.91-6.84 (m, 3H), 4.44 (m, 1H), 4.24 (d, 2H), 3.90 (s, 3H), 3.88 (s, 3H), 2.38 (d, 1H), 1.40 (s, 3H), 1.38 (s, 3H).

To a solution of 3-(3,4-dimethoxyphenyl)-3-methyl-1-nitrobutan-2-ol (700 mg, 2.60 mmol) in DCM (30 mL) were added PCC (3.36 g, 15.60 mmol) and Celite (3.36 g). After stirring 48 h, additional PCC (3.36 g, 15.60 mmol) and Celite (3.36 g) were added. After stirring further for 24 h, the mixture was diluted with Et₂O and filtered. The filtrate was concentrated and purified by flash chromatography to afford 3-(3,4-dimethoxyphenyl)-3-methyl-1-nitrobutan-2-one (502 mg, 72%). ¹H NMR (400 MHz, CDCl₃) δ 6.91-6.84 (m, 2H), 6.69 (s, 1H), 5.13 (s, 2H), 3.90 (s, 3H), 3.89 (s, 3H), 1.56 (s, 6H).

To a solution of 3-(3,4-dimethoxyphenyl)-3-methyl-1-nitrobutan-2-one (400 mg, 1.50 mmol) in acetic acid (6 mL) and conc HCl (2 mL) was added 10% Pd/C (400 mg) in a pressure vessel. The mixture was hydrogenated under 60 psi hydrogen for 48 h and then filtered. The residue was concentrated and triturated with Et₂O to give 1-amino-3-(3,4-dimethoxyphenyl)-3-methylbutan-2-one hydrochloride (306 mg, 75%). ¹H NMR (400 MHz, DMSO-d₆) δ 8.22 (brs, 2H), 6.90 (d, 1H), 6.80 (dd, 1H), 6.72 (d, 1H), 3.73 (s, 3H), 3.70 (s, 3H), 3.68 (s, 2H), 1.42 (s, 6H).

A mixture of 1-amino-3-(3,4-dimethoxyphenyl)-3-methylbutan-2-one hydrochloride (210 mg, 0.77 mmol), 4-fluorophenyl isothiocyanate (141 mg, 0.92 mmol), and Et₃N (0.16 mL, 1.15 mmol) in benzene (7 mL, anhyd) was refluxed for 8 h. The volatiles were removed under reduced pressure. The residue was combined with acetic acid (5 mL) and heated at reflux 4 h. After concentration, the crude product was purified by flash chromatography to provide 5-(2-(3,4-dimethoxyphenyl)propan-2-yl)-1-(4-fluorophenyl)-1H-imidazole-2(3H)-thione (260 mg, 91%). ¹H NMR (400 MHz, CDCl₃) δ 10.35 (s, 1H), 6.87 (t, 2H), 6.80 (d, 1H), 6.67 (d, 1H), 6.62-6.59 (m, 2H), 6.48 (d, 1H), 6.46 (s, 1H), 3.87 (s, 3H), 3.75 (s, 3H), 1.44 (s, 6H).

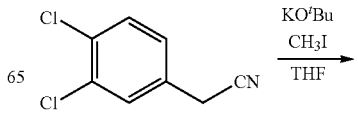

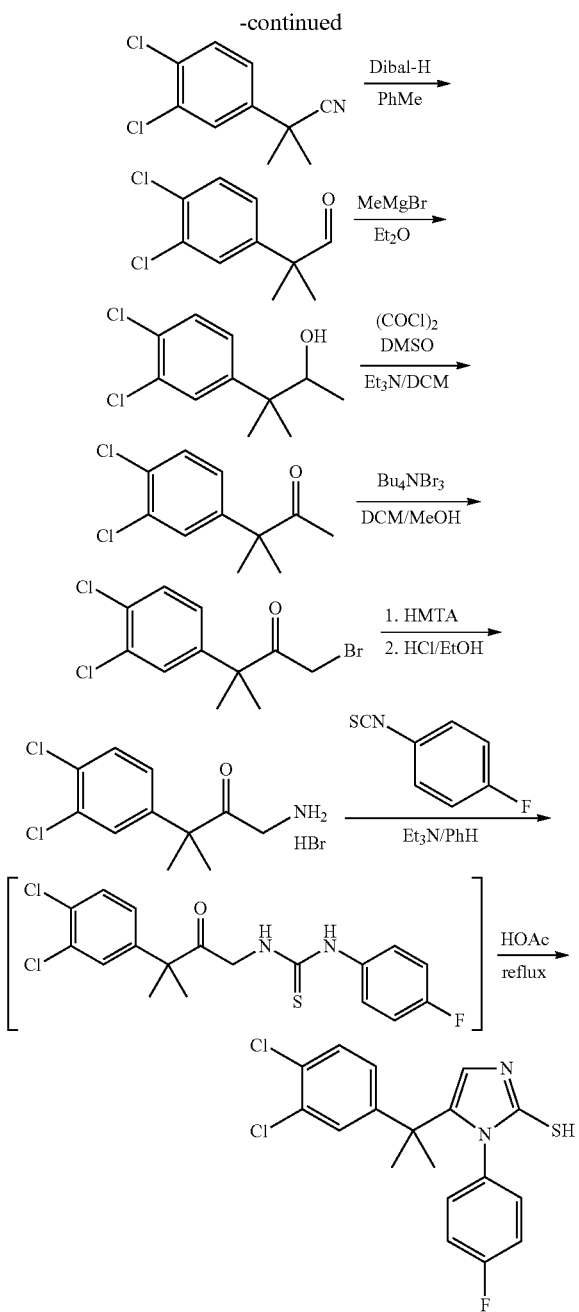

A solution of CH$_3$I (50 mL, 0.806 mol) and 3,4-dichlorophenylacetonitrile (50 g, 0.268 mol) in THF (200 mL) was added dropwise to a suspension of KO$^t$Bu (95 g, 0.806 mol) in THF (800 mL) at 0° C. under argon. After stirring 1.5 h, the reaction mixture was quenched with satd NH$_4$Cl solution (250 mL), diluted with H$_2$O (300 mL) and extracted with EtOAc (3×200 mL). The organic layers were washed with brine, dried over Na$_2$SO$_4$, filtered, and concentrated to give a residue, which was purified by column chromatography to afford 2-(3,4-dichlorophenyl)-2-methylpropanenitrile (56 g, 97%). $^1$H NMR (400 MHz, CDCl$_3$) δ 7.55 (d, 1H), 7.48 (d, 1H), 7.32 (dd, 1H), 1.72 (s, 6H).

A 1.0M solution of DIBAH (340 mL, 0.340 mol) in toluene was added dropwise to a solution of 2-(3,4-dichlorophenyl)-2-methylpropanenitrile (56 g, 0.261 mol) in toluene (650 mL) at −78° C. After stirring for 2 h, the mixture was quenched at −78° C. with 6N HCl solution (500 mL). The mixture was warmed to room temperature, stirred further for 1 h, and extracted with EtOAc (2×250 mL). To the combined extracts was added a satd solution of Rochelle's salt (300 mL) and the mixture was stirred until the organic layer was clear. The organic layer was separated, washed with brine, dried over Na$_2$SO$_4$, filtered, and concentrated. The crude product was purified by column chromatography to yield 2-(3,4-dichlorophenyl)-2-methylpropanal (47.1 g, 83%). $^1$H NMR (400 MHz, CDCl$_3$) δ 9.47 (s, 1H), 7.44 (d, 1H), 7.36 (m, 1H), 7.10 (d, 1H), 1.46 (s, 6H).

To a solution of 2-(3,4-dichlorophenyl)-2-methylpropanal (47.13 g, 0.217 mol) in Et$_2$O (223 mL) at 0° C. was added a 3.0M solution of MeMgBr (217 mL, 0.651 mol) in Et$_2$O. After stirring 2 h at 0° C., the reaction mixture was warmed to room temperature over 1 h. Then the reaction mixture was cooled to 0° C., quenched with H$_2$O (100 mL) and 3N HCl (200 mL), extracted with EtOAc and washed with brine. The organic layer was dried over Na$_2$SO$_4$ and concentrated to afford the crude product, which was purified by column chromatography to yield 3-(3,4-dichlorophenyl)-3-methylbutan-2-ol (45.9 g, 90%). $^1$H NMR (400 MHz, CDCl$_3$) δ 7.46 (d, 1H), 7.37 (d, 1H), 7.21 (dd, 1H), 3.83 (m, 1H), 1.31 (s, 3H), 1.29 (s, 3H), 1.05 (d, 3H).

DMSO (14.7 mL, 205 mmol) was added dropwise to a solution of oxalyl chloride (9.0 mL, 103 mmol) in CH$_2$Cl$_2$ (200 mL) at −78° C. The reaction mixture was stirred for 30 min and a solution of 3-(3,4-dichlorophenyl)-3-methylbutan-2-ol (12 g, 51.4 mmol) in CH$_2$Cl$_2$ (50 mL) was added by cannula over 15 min. After stirring 30 min, Et$_3$N (43 mL, 308 mmol) was added, and the reaction mixture was allowed to warm to room temperature over 1 h. Water (200 mL) was added, and the organic layer was separated. The aqueous layer was further extracted with CH$_2$Cl$_2$ (3×50 mL). The combined organic layers were washed with brine, dried over Na$_2$SO$_4$, filtered, and concentrated. The crude product was purified by column chromatography to give 3-(3,4-dichlorophenyl)-3-methylbutan-2-one (10.7 g, 89%). $^1$H NMR (400 MHz, CDCl$_3$) δ 7.41 (d, 1H), 7.37 (m, 1H), 7.08 (d, 1H), 1.95 (s, 3H), 1.59 (s, 6H).

Tetrabutylammonium tribromide (20.4 g, 41.5 mmol) was added to a solution of 3-(3,4-dichlorophenyl)-3-methylbutan-2-one (9.60 g, 41.5 mmol) in MeOH-DCM (160 mL, 1:2, v/v). After stirring 24 h, the reaction mixture was concentrated under reduced pressure and then combined with EtOAc (80 mL). The organic layer was washed with H$_2$O (50 mL), 1N HCl (50 mL), and H$_2$O (20 mL) successively. The organic layer was washed with brine, dried over Na$_2$SO$_4$, and concentrated. Purification by column chromatography afforded 1-bromo-3-(3,4-dichlorophenyl)-3-methylbutan-2-one (11.8 g, 91%). $^1$H NMR (400 MHz, CDCl$_3$) δ 7.45 (d, 1H), 7.38 (d, 1H), 7.08 (d, 1H), 3.86 (s, 2H), 1.56 (s, 6H).

A mixture of 1-bromo-3-(3,4-dichlorophenyl)-3-methylbutan-2-one (4.0 g, 13 mmol) and HMTA (hexamethylenetetramine, 2.0 g, 14 mmol) in DCM (25 mL) was stirred 48 h at room temperature. The volatiles were evaporated in vacuo. The crude material was dissolved in EtOH (80 mL) and combined with conc HCl (40 mL). The resulting mixture was heated at reflux 2 h, cooled to room temperature, and concentrated in vacuo to give 1-amino-3-(3,4-dichlorophenyl)-3-methylbutan-2-one hydrobromide (6.75 g), which was used in the next reaction without purification. $^1$H NMR (400 MHz, DMSO-d$_6$) δ 8.00 (bs, 3H), 7.61 (d, 1H), 7.52 (d, 1H), 7.29 (dd, 1H), 3.94 (m, 2H), 1.47 (s, 6H).

A mixture of 1-amino-3-(3,4-dichlorophenyl)-3-methylbutan-2-one hydrobromide (900 mg, 2.75 mmol), 4-fluorophenyl isothiocyanate (464 mg, 3.029 mmol), and Et$_3$N (570 uL, 4.13 mmol) in dry benzene (20 mL) was heated at reflux 6 h. The reaction mixture was concentrated under reduced pressure, diluted with acetic acid (9 mL) and then heated at reflux 5 h. After cooling to room temperature and concentrating, the crude product was purified by flash column chromatography to afford 5-(2-(3,4-dichlorophenyl)propan-2-yl)-1-(4-fluorophenyl)-1H-imidazole-2-thiol (370 mg). $^1$H NMR (400 MHz, CDCl$_3$) δ 7.15 (m, 2H), 6.91 (m, 2H), 6.80 (m, 2H), 6.62 (m, 2H), 1.61 (s, 6H).

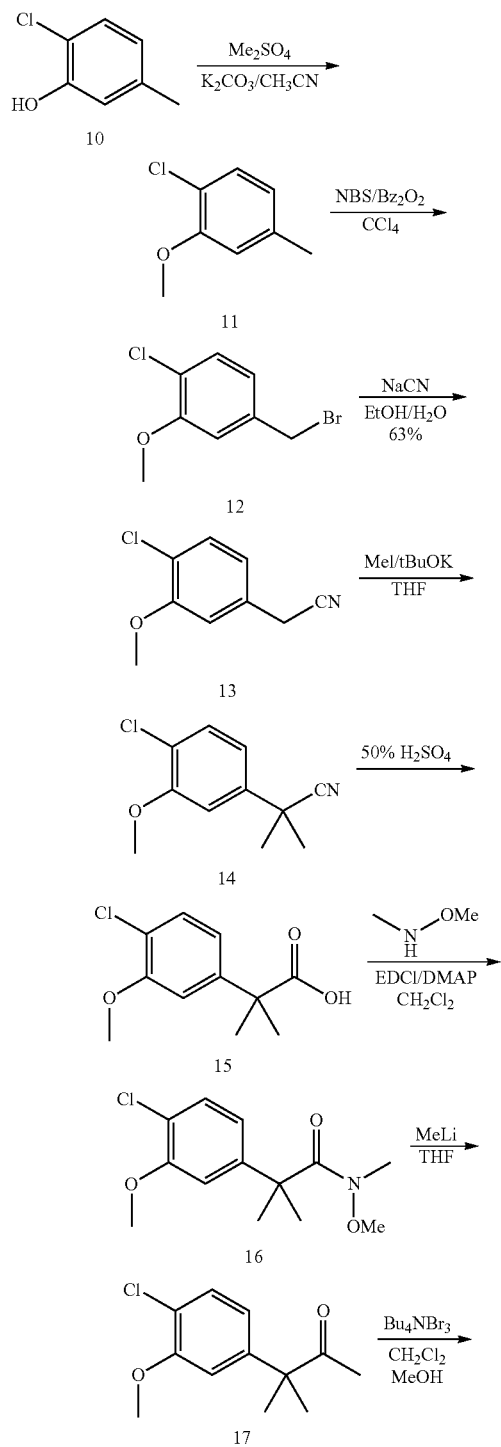

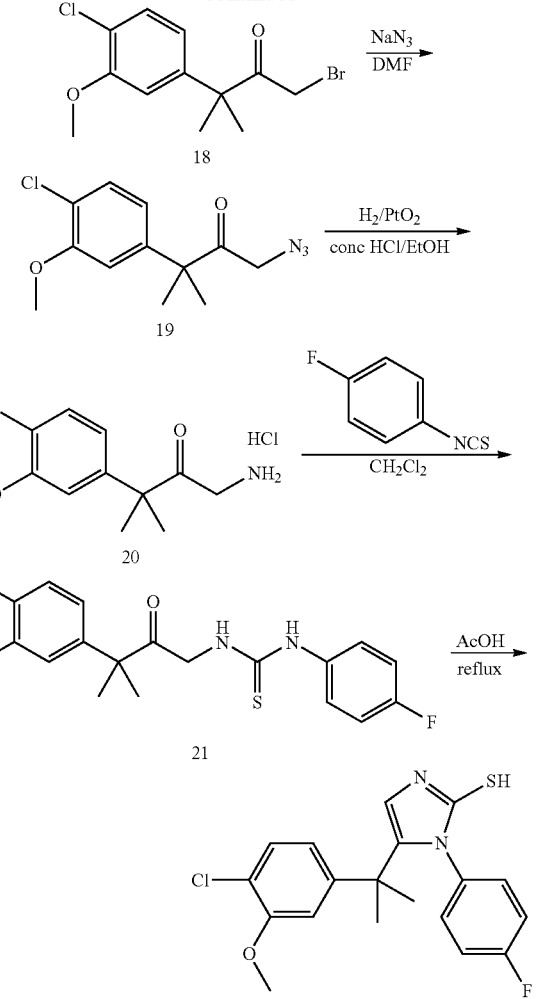

To a solution of 2-chloro-5-methylphenol (10) (250 g, 1.75 mol) in CH$_3$N (2.5 L) was added Me$_2$SO$_4$ (184 mL, 1.93 mol) and K$_2$CO$_3$ (314 g, 2.28 mol). The reaction mixture was heated to reflux for 6 h with mechanical stirring. The reaction mixture was cooled to ambient temperature and filtered through Celite. The filtrate was evaporated. The residue was diluted with EtOAc (1.5 L), washed with water (1.5 L*2) and brine (1.5 L) successively, dried over MgSO$_4$, filtered and concentrated under reduced pressure to give 2-chloro-5-methylanisole (11) as a light yellow oil (274 g, quantitative). $^1$H NMR (400 MHz, CDCl$_3$): δ 7.20-7.25 (d, 1H), 6.73 (s, 1H), 6.68-6.71 (d, 1H), 3.86 (s, 3H), 2.31 (s, 3H).

To a solution of 2-chloro-5-methylanisole (11) (274 g, 1.75 mol) in CCl$_4$ (2.5 L) was added benzoyl peroxide (4.23 g, 0.02 mol) and NBS (321 g, 1.80 mol). The reaction mixture was heated to reflux for 1 h with mechanical stirring. The reaction mixture was cooled, washed with 1N HCl (2 L), satd NaHCO$_3$ (2 L) and brine (2 L), dried over MgSO$_4$, filtered and concentrated under reduced pressure to give the 5-(bromomethyl)-3-chloroanisole (12) as a light yellow solid (412 g, quantitative). $^1$H NMR (400 MHz, CDCl$_3$): δ 7.30-7.34 (d, 1H), 6.95 (s, 1H), 6.91-6.93 (d, 1H), 4.45 (s, 2H), 3.92 (s, 3H).

To a solution of 5-(bromomethyl)-3-chloroanisole (12) (412 g, 1.75 mol) in EtOH (2 L) and H$_2$O (0.5 L) was added NaCN (129 g, 2.63 mol) and the reaction mixture was heated to reflux for 2 h with mechanical stirring. The reaction mixture was cooled and diluted with water (3.5 L). The mixture was extracted with diethyl ether (2 L×2) and the combined organic layers were washed with aq. 5% HCl (2.5 L), satd NaHCO$_3$ (2.5 L) and brine (2.5 L), dried over anhydrous MgSO$_4$, filtered and concentrated under reduced pressure. The resulting residue was purified by column chromatography (Hex/EtOAc=5:1) to afford 2-(4-chloro-3-methoxyphenyl)acetonitrile (13) (240 g, 75%) as yellow solid. $^1$H NMR (400 MHz, CDCl$_3$): δ 7.35-7.36 (d, 1H), 6.86 (s, 1H), 6.84-6.86 (d, 1H), 3.92 (s, 3H), 3.74 (s, 2H).

KOtBu (370 g, 3.3 mol) was dissolved in THF (1.7 L) and stirred at −20° C. After 30 min, to the reaction mixture was added 2-(4-chloro-3-methoxyphenyl)acetonitrile (13) (240 g, 1.32 mol) in THF (0.5 L) and then the resulting mixture was stirred for additional 30 min at the same temperature. CH$_3$I (563 g, 3.96 mol) was added and the mixture was slowly warm to room temperature over 2 h with mechanical stirring. The reaction mixture was quenched with water in ice-bath and extracted with EtOAc (1.5 L×2). The combined organic layers were washed with brine (3 L), dried over anhydrous MgSO$_4$, filtered and concentrated under reduced pressure to give 2-(4-chloro-3-methoxyphenyl)-2-methylpropanenitrile (14) as a amber liquid (269 g, 97%). $^1$H NMR (400 MHz, CDCl$_3$): δ 7.35-7.37 (d, 1H), 7.05 (s, 1H), 6.95-6.97 (d, 1H), 3.94 (s, 3H), 1.72 (s, 6H).

2-(4-Chloro-3-methoxyphenyl)-2-methylpropanenitrile (14) (269 g, 1.28 mol) was dissolved in 50% H$_2$SO$_4$ (2.7 L) and heated to reflux for 20 h with mechanical stirring. The reaction mixture was cooled to room temperature, diluted with water (5 L), and extracted with CH$_2$Cl$_2$ (1.5 L×3). The combined organic layers were washed with brine (5 L), dried over anhydrous MgSO$_4$, filtered and concentrated under reduced pressure to give 2-(4-chloro-3-methoxyphenyl)-2-methylpropanoic acid (15) as a brown solid (268 g, 92%). $^1$H NMR (400 MHz, CDCl$_3$): δ 7.30-7.32 (d, 1H), 6.92-6.96 (m, 3H), 3.89 (s, 3H), 1.59 (s, 6H).

To a solution of 2-(4-chloro-3-methoxyphenyl)-2-methylpropanoic acid (15) (268 g, 1.17 mol) in CH$_2$Cl$_2$ (1.7 L) was added N,O-dimethylhydroxylamine hydrochloride (137 g, 1.4 mol), EDCI (270 g, 1.4 mol), and DMAP (172 g, 1.4 mol). The resulting mixture was stirred for 3 h and washed with 10% citric acid solution (1.5 L), satd NaHCO$_3$ (1.5 L), and brine (1.5 L) successfully. The organic phase was dried over MgSO$_4$, filtered, and concentrated at reduced pressure to afford 2-(4-chloro-3-methoxyphenyl)-N-methoxy-N,2-dimethylpropanamide (16) as a brown solid (276 g, 96%). $^1$H NMR (400 MHz, CDCl$_3$): δ 7.30-7.32 (d, 1H), 6.81-6.84 (m, 3H), 3.89 (s, 3H), 3.12 (s, 3H), 2.78 (s, 3H), 1.53 (s, 6H).

To a solution of 2-(4-chloro-3-methoxyphenyl)-N-methoxy-N,2-dimethylpropanamide (16) (290 g, 1.06 mmol) in THF (1.5 L) was added MeLi (3M in THF, 462 mL, 1.38 mol) at −78° C. and the reaction mixture was warm to room temperature over 2 h. The reaction mixture was quenched with 2N HCl (1 L) in ice-bath, extracted with EtOAc (2 L). The separated organic layer was washed with brine (2 L), dried over anhydrous MgSO$_4$, filtered and concentrated under reduced pressure to give 3-(4-chloro-3-methoxyphenyl)-3-methyl-2-methylbutan-2-one (17) as a brown solid (241 g, quantitative). $^1$H NMR (400 MHz, CDCl$_3$): δ 7.32-7.34 (d, 1H), 6.82-6.84 (d, 1H), 6.75 (s, 1H), 3.88 (s, 3H), 1.94 (s, 3H), 1.47 (s, 6H).

To a solution of 3-(4-chloro-3-methoxyphenyl)-3-methyl-2-methylbutan-2-one (17) (241 g, 1.06 mmol) in CH$_2$Cl$_2$ (2.2 L) and MeOH (1.1 L) was added Bu$_4$NBr$_3$ (514 g, 1.06 mol) at 0° C. and the reaction mixture was warm to room temperature over 3 h. The reaction mixture was quenched with 1N HCl (1 L) and evaporated. The residual diluted with EA (1.5 L) and EtOAc layer was washed with water (1.5 L), 1N HCl (1.5 L) and brine (1.5 L) successively. The organic layer was dried over MgSO$_4$, filtered and concentrated under reduced pressure to give 1-bromo-3-(4-chloro-3-methoxyphenyl)-3-methyl-2-methylbutan-2-one (18) as a brown solid (326 g, quantitative). $^1$H NMR (400 MHz, CDCl$_3$): δ 7.35-7.37 (d, 1H), 6.81-6.84 (d, 1H), 6.72 (s, 1H), 3.89 (s, 3H), 3.86 (s, 2H), 1.53 (s, 6H).

To a solution of 1-bromo-3-(4-chloro-3-methoxyphenyl)-3-methyl-2-methylbutan-2-one (18) (326 g, 1.06 mmol) in DMF (1 L) was added NaN$_3$ (90 g, 1.39 mol, 1.3 eq.) at 0° C. and the reaction mixture was warm to room temperature and stirred for 2 h. The reaction mixture was diluted with water (4 L) and extracted with diethyl ether (2 L×2). The combined organic layers were washed with brine (4 L×3), dried over anhydrous MgSO$_4$, filtered and concentrated under reduced pressure. Recrystallization of the residue from ethanol gave 1-azido-3-(4-Chloro-3-methoxyphenyl)-3-methyl-2-methylbutan-2-one (19) (146 g, 0.54 mol, 51%, white solid) along with impure product (120 g). $^1$H NMR (400 MHz, CD$_3$OD): δ 7.35-7.36 (d, 1H), 6.90 (s, 1H), 6.86-6.88 (d, 1H), 3.92 (s, 2H), 3.88 (s, 3H), 1.52 (s, 6H).

A pressure bottle was charged with a solution of 1-azido-3-(4-Chloro-3-methoxyphenyl)-3-methyl-2-methylbutan-2-one (19) (146 g, 0.54 mol) in MeOH (1.4 L), PtO$_2$ (2.5 g, 0.01 mol.) and conc HCl (10 mL, 1.1 mol). The bottle was purged with hydrogen gas (40 psi×2), pressurized with hydrogen (65 psi) and agitated for 5 h. The reaction mixture was filtered through Celite™ and the filtrate was evaporated to give a residue which was triturated with Et$_2$O to give 1-amido-3-(4-chloro-3-methoxyphenyl)-3-methyl-2-methylbutan-2-one hydrochloride (20) (131 g, 0.47 mol) as a white solid. $^1$H NMR (400 MHz, CD$_3$OD): δ 7.37-7.39 (d, 1H), 6.96 (s, 1H), 6.91-6.93 (d, 1H), 3.91 (s, 3H), 3.84 (s, 2H), 1.59 (s, 6H).

To a solution of 1-amido-3-(4-chloro-3-methoxyphenyl)-3-methyl-2-methylbutan-2-one HCl (20) (179 g, 0.643 mmol) and 4-fluorophenylisothiocyanate (93.6 g, 0.61 mol) in CH$_2$Cl$_2$ (1.5 L) were added TEA (179 mL, 1.29 mol) at 0° C. and the mixture was warm to room temperature and stirred for 1 h. The reaction mixture was washed with 10% citric acid (1.5 L), sat'd NaHCO$_3$ (1.5 L) and brine (1.5 L) successively, dried over MgSO$_4$, filtered and concentrated under reduced pressure to give a residue which was treated with Et$_2$O/Hex to afford 1-(3-(4-chloro-3-methoxyphenyl)-3-methyl-2-oxobutyl)-3-(4-fluorophenyl)thiourea (21) (230 g, 90%, white solid). $^1$H NMR (400 MHz, CDCl$_3$): δ 7.98 (s, 1H), 7.30-7.32 (d, 1H), 7.21-7.25 (m, 3H), 7.11-7.15 (t, 2H), 6.78-6.80 (d, 1H), 6.76 (s, 1H), 6.64 (s, 1H), 3.38 (d, 2H), 3.86 (s, 3H), 1.53 (s, 6H).

A solution of 1-(3-(4-chloro-3-methoxyphenyl)-3-methyl-2-oxobutyl)-3-(4-fluorophenyl)-thiourea (21) (230 g, 0.58 mmol) in HOAc (1 L) was heated to reflux for 4 h with mechanical stirring. The reaction mixture was cooled and evaporated to give a residue which was treated with diethyl ether to give 5-(2-(4-chloro-3-methoxyphenyl)propan-2-yl)-1-(4-fluorophenyl)-1H-imidazole-2-thiol (22) (207 g, 95%) as a white solid. $^1$H NMR (400 MHz, CDCl$_3$) δ 6.91-7.19 (d, 1H), 6.86-6.88 (t, 2H), 6.81 (s, 1H), 6.86-6.91 (t, 2H), 6.81 (s, 1H), 6.59-6.63 (m, 2H), 6.50-6.53 (d, 2H), 6.45 (s, 1H), 3.74 (s, 3H), 1.46 (s, 6H).

Under similar conditions the following intermediates were prepared from appropriate starting materials:

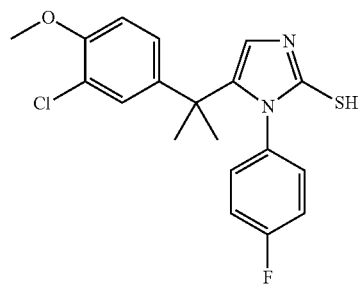 [SMILES: COc1ccc(C(C)(C)c2cnc(S)n2-c2ccc(F)cc2)cc1Cl]
5-(2-(3-chloro-4-methoxyphenyl)propan-2-yl)-1-(4-fluorophenyl)-1H-imidazole-2-thiol
$^1$H NMR (400 MHz, CDCl$_3$) δ 11.71 (s, 1H), 6.93 (t, J=3.10 Hz, 1H), 6.92-6.86 (m, 3H), 6.82-6.77 (m, 3H), 6.76-6.71 (m, 1H), 6.61 (ddd, J=6.83, 5.15, 2.70 Hz, 2H), 3.89 (s, 4H), 1.43 (s, 8H).
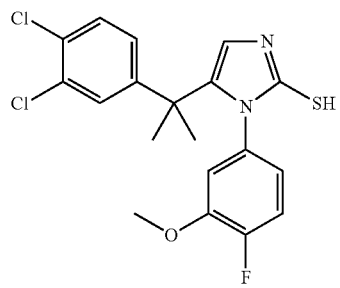 [SMILES: COc1cc(-n2c(C(C)(C)c3ccc(Cl)c(Cl)c3)cnc2S)ccc1F]
5-(2-(3,4-dichlorophenyl)propan-2-yl)-1-(4-fluoro-3-methoxyphenyl)-1H-imidazole-2-thiol
$^1$H NMR (400 MHz, CDCl$_3$) δ 11.80 (dd, 1H), 7.31-7.24 (m, 2H), 7.07 (d, 1H), 7.00 (dd, 1H), 6.83 (s, 1H), 6.83-6.76 (m, 1H), 6.46 (ddd, 1H), 6.03 (dd, 1H), 3.55 (s, 3H), 2.11 (s, 1H), 1.48 (d, 7H).
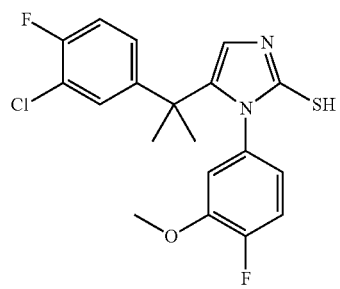 [SMILES: COc1cc(-n2c(C(C)(C)c3ccc(F)c(Cl)c3)cnc2S)ccc1F]
5-(2-(3-chloro-4-fluorophenyl)propan-2-yl)-1-(4-fluoro-3-methoxyphenyl)-1H-imidazole-2-thiol
$^1$H NMR (400 MHz, CDCl$_3$) δ 10.99 (br s, 1H), 7.03-6.96 (m, 3H), 6.86-6.82 (m, 2H), 6.41-6.37 (m, 1H), 6.10 (d, 1H), 3.58 (s, 3H), 1.48 (d, 6H).
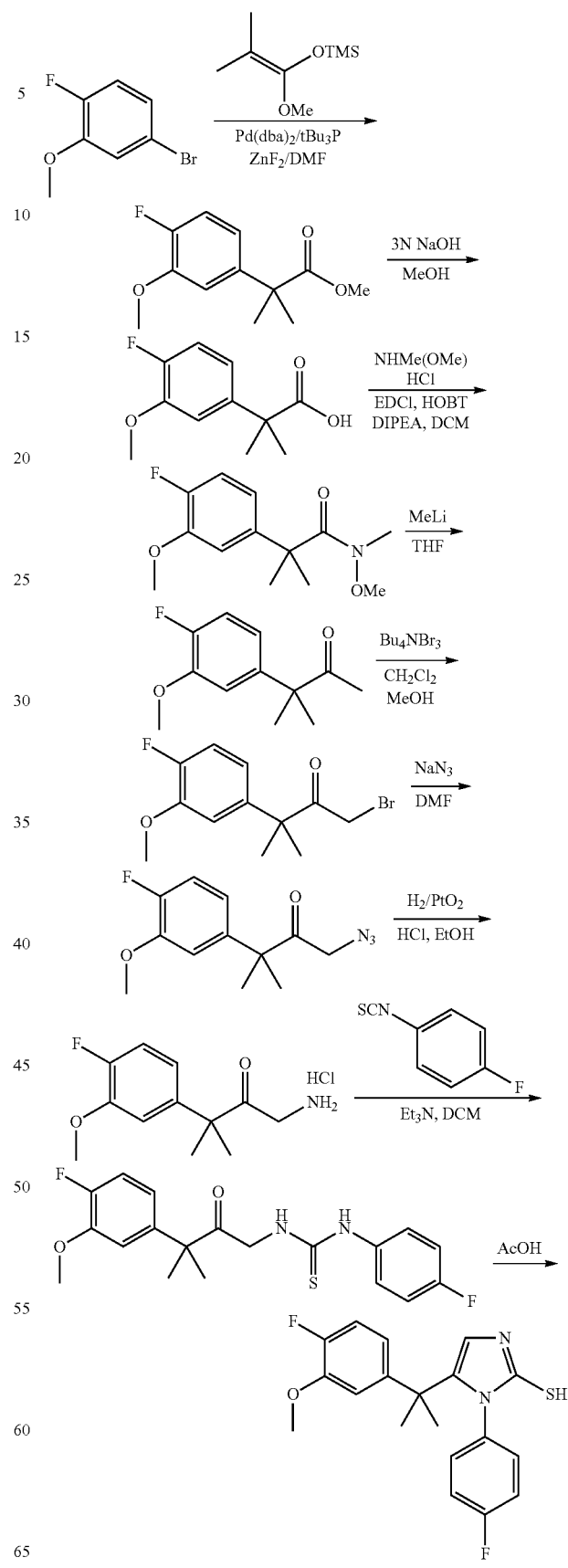

To a solution 5-bromo-2-fluoroanisole (109 g, 0.54 mol), ZnF$_2$ (2.52 g, 24.39 mmol), Pd(dba)$_2$ (3.08 g, 5.35 mmol), and P$^t$Bu$_3$ (5.2 mL of a 50% solution in toluene, 11 mmol) in DMF (1 L) was added trimethylsilyl methyl ketene acetal (121 g, 0.7 mol). The reaction mixture was stirred at 80-90° C. for 5 h under nitrogen atmosphere and then was allowed to cool to room temperature and diluted with EtOAc. The reaction mixture was filtered through Celite™. The filtrate was washed with H$_2$O (2 L) and the aqueous layer was extracted with EtOAc (2.5 L). The combined extracts were washed with brine (2 L×2), dried over MgSO$_4$, and concentrated at reduced pressure to give methyl 2-(4-fluoro-3-methoxyphenyl)-2-methylpropanoate (151 g), which was used for the next step without further purification. $^1$H NMR (400 MHz, CDCl$_3$): δ 7.04-6.98 (m, 1H), 6.95-6.92 (dd, 1H), 6.88-6.85 (m, 1H), 3.89 (s, 3H), 3.67 (s, 3H), 1.57 (s, 6H).

A solution of methyl 2-(4-fluoro-3-methoxyphenyl)-2-methylpropanoate (146 g) in MeOH (2 L) and 25% NaOH in H$_2$O (590 mL) was heated at reflux for 5 h. The reaction mixture was then allowed to cool to room temperature and concentrated at reduced pressure. The residue was dissolved in H$_2$O (2 L) and washed with ether (500 mL). The aqueous layer was acidified cautiously with conc HCl to pH 2. The resulting mixture was extracted with DCM (3 L), and combined extracts were dried over MgSO$_4$, and concentrated at reduced pressure to give 2-(4-fluoro-3-methoxyphenyl)-2-methylpropanoic acid (95 g, 84% over 2 steps). $^1$H NMR (400 MHz, CDCl$_3$): δ 7.06-7.00 (m, 2H), 6.93 (m, 1H), 3.90 (s, 3H), 3.86 (s, 2H), 1.60 (s, 6H).

To a solution of 2-(4-fluoro-3-methoxyphenyl)-2-methyl-propanoic acid (114.75 g, 4.71 mmol) in DCM (2 L) was added N,O-dimethylhydroxylamine hydrochloride (79 g, 0.81 mol), EDCI (145 g, 0.72 mol), DMAP (33 g, 0.27 mol), and DIPEA (471 mL, 2.7 mol). The resulting mixture was stirred 5 h and quenched with H$_2$O (1 L). The organic layer was washed with 1N HCl (1 L×2), satd NaHCO$_3$ (1 L), and brine (1 L) successfully. The organic phase was dried over MgSO$_4$ and concentrated at reduced pressure to afford 2-(4-fluoro-3-methoxyphenyl)-N-methoxy-N,2-dimethylpropanamide as yellow color oil (123 g, 89%). $^1$H NMR (400 MHz, CDCl$_3$): δ 7.03 (t, 1H), 6.83 (d, 1H), 6.80 (m, 1H), 3.89 (s, 3H), 3.12 (s, 3H), 2.77 (s, 3H), 1.53 (s, 6H).

To a solution of 2-(4-fluoro-3-methoxyphenyl)-N-methoxy-N,2-dimethylpropanamide (123 g, 0.48 mol) in THF (1 L)-78° C. was added 3M ethereal solution of MeLi (210 mL, 0.627 mol). The resulting solution was warmed to ambient temperature and stirred 16 h. The reaction mixture was quenched with 3N HCl (400 mL) and extracted with EtOAc (600 mL×2). The combined extracts were washed with satd NaHCO$_3$ (1.0 L) and brine (1.0 L), then dried over MgSO$_4$ and concentrated at reduced pressure to give 3-(4-fluoro-3-methoxyphenyl)-3-methylbutan-2-one as yellow color oil (92.5 g, 91%). $^1$H NMR (400 MHz, CDCl$_3$): δ 7.05 (m, 1H), 6.83-6.78 (m, 2H), 3.88 (s, 3H), 1.95 (s, 3H), 1.47 (s, 6H).

To a solution of 3-(4-fluoro-3-methoxyphenyl)-3-methylbutan-2-one (92.52 g, 0.44 mmol) in DCM-MeOH (2:1, 1.2 L) was added Bu$_4$NBr$_3$ (222.8 g, 0.462 mol) at 0° C. The mixture was slowly warmed to room temperature and stirred 16 h. The reaction mixture was quenched with 0.5N Na$_2$S$_2$O$_3$5H$_2$O solution (2 L) and extracted with EtOAc (3 L). Combined extracts were washed with 1N HCl (2 L), satd NaHCO$_3$ (1.0 L), and brine (1.0 L) successively, then dried over MgSO$_4$, filtered and concentrated under reduced pressure to give 1-bromo-3-(4-fluoro-3-methoxyphenyl)-3-methylbutan-2-one as a brown solid (125.4 g, 98%). $^1$H NMR (400 MHz, CDCl$_3$): δ 7.10 (m, 1H), 6.82 (m, 1H), 6.76 (dd, 1H), 3.88 (s, 3H), 3.86 (s, 2H), 1.53 (s, 6H).

To a solution of 1-bromo-3-(4-fluoro-3-methoxyphenyl)-3-methylbutan-2-one (125.4 g, 0.44 mol) in DMF (500 mL) was added NaN$_3$ (37.2 g, 0.572 mol) at 0° C., and the mixture was warmed to room temperature over 3 h with stirring. The reaction mixture was diluted with water (2 L) and extracted with EtOAc (1 L×2). Combined extracts were washed with brine, dried over MgSO$_4$, and concentrated to give 1-azido-3-(4-fluoro-3-methoxyphenyl)-3-methylbutan-2-one (99.5 g), which was used in the next step without further purification. $^1$H NMR (400 MHz, CDCl$_3$): δ 7.07 (m, 1H), 6.79 (m, 2H), 3.92 (s, 3H), 3.78 (s, 2H), 1.53 (s, 6H).

A pressure bottle was charged with a solution of 1-azido-3-(4-fluoro-3-methoxyphenyl)-3-methylbutan-2-one (99.5 g, 0.396 mol) in MeOH (1.0 L), 50% wet 10% Pd/C (25 g, 25% w/w.) and conc HCl (105 mL, 1.19 mol). The bottle was purged with hydrogen gas (40 psi×2), pressurized with hydrogen (45 psi) and agitated overnight. The reaction mixture was filtered through a Celite™ pad. The filtrate was evaporated to give a residue, which was triturated with Et$_2$O to give 1-amino-3-(4-fluoro-3-methoxyphenyl)-3-methylbutan-2-one hydrochloride (57.4 g, 55%) as a white solid. $^1$H NMR (400 MHz, DMSO-d$_6$): δ 8.26 (b, 2H), 7.22 (m, 1H), 6.99 (dd, 1H), 6.89 (m, 1H), 3.87 (s, 3H), 3.81 (s, 2H), 1.50 (s, 6H).

To a mixture of 1-amino-3-(4-fluoro-3-methoxyphenyl)-3-methylbutan-2-one hydrochloride (35.4 g, 0.135 mol) and 4-fluorophenyl isothiocyanate (21.75 g, 0.142 mol) in DCM (500 mL) was added Et$_3$N (37.6 ml, 0.27 mol) at 0° C., and the reaction mixture was warm to room temperature over 1 h. The reaction mixture was washed with 1N HCl (500 mL), satd NaHCO$_3$ (500 mL) and brine (500 mL) successively, dried over MgSO$_4$, filtered and concentrated under reduced pressure give a residue, which was triturated with Hex-EtOAc to afford 1-(3-(4-fluoro-3-methoxyphenyl)-3-methyl-2-oxobutyl)-3-(4-fluorophenyl)thiourea (45 g, 88%) as a white solid. $^1$H NMR (400 MHz, CDCl$_3$) δ 7.85 (b, 1H), 7.25 (m, 2H), 7.15 (m, 2H), 7.05 (m, 1H), 6.79 (m, 2H), 6.67 (b, 1H), 3.88 (s, 3H), 1.54 (s, 6H).

A solution of 1-(3-(4-fluoro-3-methoxyphenyl)-3-methyl-2-oxobutyl)-3-(4-fluorophenyl)-thiourea (45 g, 0.119 mol) in AcOH (500 mL) was heated at reflux overnight. The cooled reaction mixture was concentrated and triturated with Et$_2$O to give 5-(2-(4-fluoro-3-methoxyphenyl)propan-2-yl)-1-(4-fluorophenyl)-1H-imidazole-2(3H)-thione (40.5 g, 94%) as a white solid. $^1$H NMR (400 MHz, CDCl$_3$) δ 6.90 (t, 3H), 6.81 (s, 1H), 6.61 (m, 2H), 6.50 (m, 2H), 3.76 (s, 3H), 1.46 (s, 6H); MS (ESI) m/z 361 (MH$^+$).

Preparation of 2-chloro-4-(2-(1-(4-fluoro-3-methoxyphenyl)-2-mercapto-1H-imidazol-5-yl)propan-2-yl)benzenesulfonamide

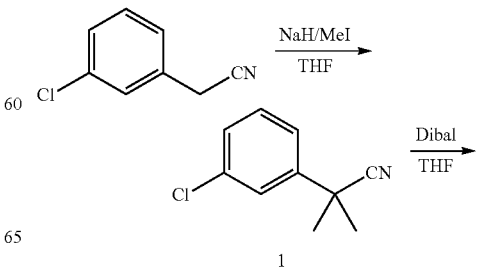

1

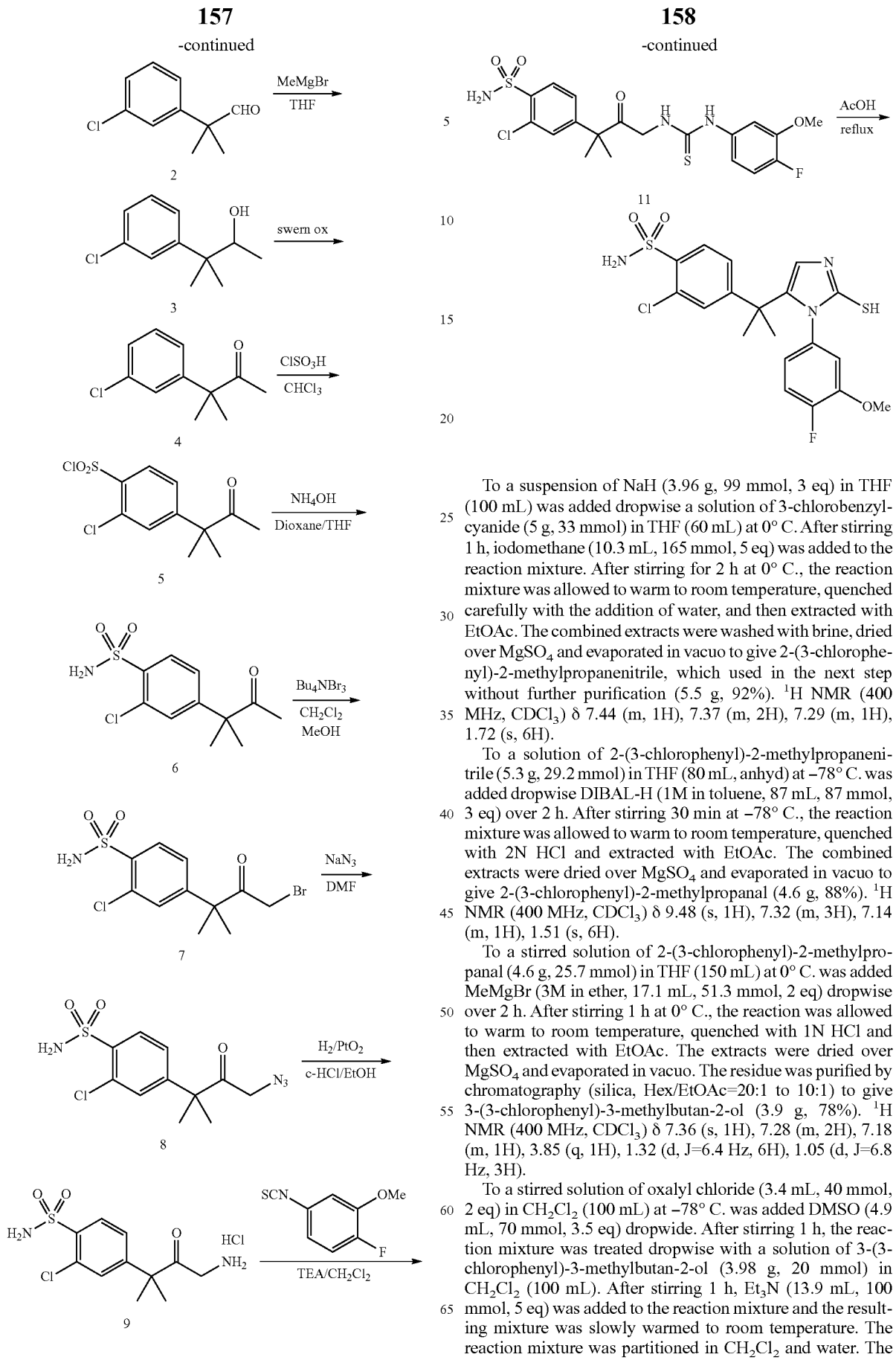

To a suspension of NaH (3.96 g, 99 mmol, 3 eq) in THF (100 mL) was added dropwise a solution of 3-chlorobenzyl-cyanide (5 g, 33 mmol) in THF (60 mL) at 0° C. After stirring 1 h, iodomethane (10.3 mL, 165 mmol, 5 eq) was added to the reaction mixture. After stirring for 2 h at 0° C., the reaction mixture was allowed to warm to room temperature, quenched carefully with the addition of water, and then extracted with EtOAc. The combined extracts were washed with brine, dried over MgSO$_4$ and evaporated in vacuo to give 2-(3-chlorophenyl)-2-methylpropanenitrile, which used in the next step without further purification (5.5 g, 92%). $^1$H NMR (400 MHz, CDCl$_3$) δ 7.44 (m, 1H), 7.37 (m, 2H), 7.29 (m, 1H), 1.72 (s, 6H).

To a solution of 2-(3-chlorophenyl)-2-methylpropanenitrile (5.3 g, 29.2 mmol) in THF (80 mL, anhyd) at −78° C. was added dropwise DIBAL-H (1M in toluene, 87 mL, 87 mmol, 3 eq) over 2 h. After stirring 30 min at −78° C., the reaction mixture was allowed to warm to room temperature, quenched with 2N HCl and extracted with EtOAc. The combined extracts were dried over MgSO$_4$ and evaporated in vacuo to give 2-(3-chlorophenyl)-2-methylpropanal (4.6 g, 88%). $^1$H NMR (400 MHz, CDCl$_3$) δ 9.48 (s, 1H), 7.32 (m, 3H), 7.14 (m, 1H), 1.51 (s, 6H).

To a stirred solution of 2-(3-chlorophenyl)-2-methylpropanal (4.6 g, 25.7 mmol) in THF (150 mL) at 0° C. was added MeMgBr (3M in ether, 17.1 mL, 51.3 mmol, 2 eq) dropwise over 2 h. After stirring 1 h at 0° C., the reaction was allowed to warm to room temperature, quenched with 1N HCl and then extracted with EtOAc. The extracts were dried over MgSO$_4$ and evaporated in vacuo. The residue was purified by chromatography (silica, Hex/EtOAc=20:1 to 10:1) to give 3-(3-chlorophenyl)-3-methylbutan-2-ol (3.9 g, 78%). $^1$H NMR (400 MHz, CDCl$_3$) δ 7.36 (s, 1H), 7.28 (m, 2H), 7.18 (m, 1H), 3.85 (q, 1H), 1.32 (d, J=6.4 Hz, 6H), 1.05 (d, J=6.8 Hz, 3H).

To a stirred solution of oxalyl chloride (3.4 mL, 40 mmol, 2 eq) in CH$_2$Cl$_2$ (100 mL) at −78° C. was added DMSO (4.9 mL, 70 mmol, 3.5 eq) dropwide. After stirring 1 h, the reaction mixture was treated dropwise with a solution of 3-(3-chlorophenyl)-3-methylbutan-2-ol (3.98 g, 20 mmol) in CH$_2$Cl$_2$ (100 mL). After stirring 1 h, Et$_3$N (13.9 mL, 100 mmol, 5 eq) was added to the reaction mixture and the resulting mixture was slowly warmed to room temperature. The reaction mixture was partitioned in CH$_2$Cl$_2$ and water. The organic layer was separated, washed with 1N HCl and water, dried over MgSO₄ and evaporated in vacuo to give 3-(3-chlorophenyl)-3-methylbutan-2-one (3.9 g, 99%). ¹H NMR (400 MHz, CDCl₃) δ 7.29 (m, 3H), 7.13 (m, 1H), 1.97 (s, 3H), 1.47 (s, 6H).

To a solution of 3-(3-chlorophenyl)-3-methylbutan-2-one (15 g, 76 mmol) in CHCl₃ (100 mL) was added chlorosulfuric acid (101 mL, 20 eq) at 0° C. over 2 h. Next SOCl₂ (20 mL) was added dropwise to the reaction mixture over 30 min under nitrogen. The reaction mixture was slowly warmed to room temperature and stirred overnight. The mixture was slowly added to ice-water and then extracted with EtOAc. The combined extracts were washed with brine, dried over MgSO₄ and evaporated. The residue was purified by chromatography (silica, Hex/EtOAc=9:1 to 4:1) to give 2-chloro-4-(2-methyl-3-oxobutan-2-yl)benzene-1-sulfonyl chloride as a yellow solid (9.8 g, 43%). ¹H NMR (400 MHz, CDCl₃) δ 8.12 (d, J=8.4 Hz, 1H), 7.54 (s, 1H), 7.37 (d, J=2.2 Hz, 1H), 2.03 (s, 3H), 1.56 (s, 6H).

To a stirred solution of NH₄OH (30 mL) was added a solution of 2-chloro-4-(2-methyl-3-oxobutan-2-yl)benzene-1-sulfonyl chloride (9.8 g, 33.2 mmol) in THF (150 mL) at 0° C. After stirring 2 h, volatiles were removed under reduced pressure. The residue was diluted with water and extracted with EtOAc (100 mL×2). The combined extracts were dried over MgSO₄, concentrated and purified by column chromatography (Hex/EtOAc=4:1 to 2:1) to give 2-chloro-4-(2-methyl-3-oxobutan-2-yl)benzenesulfonamide (8.9 g, 96% yield) as yellow oil. ¹H NMR (400 MHz, CDCl₃) δ 8.09 (d, J=8.4 Hz, 1H), 7.43 (s, 1H), 7.27 (d, J=2.2 Hz, 1H), 5.09 (s, 2H), 2.04 (s, 3H), 1.52 (s, 6H).

To a solution of 2-chloro-4-(2-methyl-3-oxobutan-2-yl)benzenesulfonamide (8.9 g, 32.1 mmol) in CH₂Cl₂/MeOH (150 mL, 2:1, v/v) was added Bu₄NBr₃ (16.3 g, 33.7 mmol, 1.05 eq) in one portion. After 20 h, volatiles were removed and then the residue was partitioned in EtOAc and water. The organic layer was washed with 1M HCl solution and water sequentially, dried over MgSO4, filtered and evaporated to give 4-(4-bromo-2-methyl-3-oxobutan-2-yl)-2-chlorobenzenesulfonamide (11.4 g, quant) as yellow oil, which was used for the next reaction without further purification. ¹H NMR (400 MHz, CDCl₃) δ 8.11 (d, J=8.4 Hz, 1H), 7.44 (s, 1H), 7.30 (d, J=2.2 Hz, 1H), 5.16 (s, 2H), 3.88 (s, 2H), 1.61 (s, 6H).

To a solution of 4-(4-bromo-2-methyl-3-oxobutan-2-yl)-2-chlorobenzenesulfonamide (11.3 g, 31.8 mmol) in DMF (50 mL) was added NaN₃ (3.1 g, 47.8 mmol, 1.5 eq) at 0° C. After stirring 2 h, the residue was diluted with water and extracted with EtOAc. The combined extracts were washed with 1M HCl and water successively, dried over MgSO₄, filtered and evaporated. The residue was purified by chromatography (Hex/EtOAc=4:1 to 2:1) to give 4-(4-azido-2-methyl-3-oxobutan-2-yl)-2-chlorobenzenesulfonamide (8.0 g, 79% yield) as yellow sticky oil. ¹H NMR (400 MHz, CDCl₃) δ 8.11 (d, J=8.4 Hz, 1H), 7.43 (s, 1H), 7.29 (d, J=2.2 Hz, 1H), 5.12 (s, 2H), 4.11 (s, 2H), 1.58 (s, 6H).

A pressure bottle was charged with a solution of 4-(4-azido-2-methyl-3-oxobutan-2-yl)-2-chlorobenzenesulfonamide (8 g, 25.2 mmol) in EtOH (100 mL), conc HCl (20 mL) and PtO₂ (114 mg, 0.5 mmol, 0.02 eq) and then was purged with hydrogen (2×45 psi). The bottle was pressurized with hydrogen (45 psi) and agitated 2 h. The reaction mixture was filtered through Celite™ and the filtrate was evaporated. The residue was triturated with Et₂O, filtered and dried to afford 4-(4-amino-2-methyl-3-oxobutan-2-yl)-2-chlorobenzenesulfonamide hydrochloride (7.8 g, 94% yield) as yellow solid. ¹H NMR (400 MHz, DMSO) δ 8.22 (br s, 3H), 7.91 (d, J=8.4 Hz, 1H), 7.60 (s, 2H), 7.50 (s, 1H), 7.43 (d, J=8.4 Hz, 1H), 3.92 (m, 2H), 1.49 (s, 6H).

To a stirred mixture of 4-(4-amino-2-methyl-3-oxobutan-2-yl)-2-chlorobenzenesulfonamide hydrochloride (7.8 g, 23.7 mmol) in DCM (150 mL) was added Et₃N (9.9 mL, 71.1 mmol, 3 eq) and 1-fluoro-4-isothiocyanato-2-methoxybenzene (4.35 g, 23.7 mmol). After stirring 2 h, DCM and water were added to the reaction mixture. The organic layer was separated, dried over MgSO₄ and evaporated in vacuo. The residue was purified by flash column chromatography (Hex/EtOAc=1:1 to EtOAc/DCM=1:1) to give 2-chloro-4-(4-(3-(4-fluoro-3-methoxyphenyl)thioureido)-2-methyl-3-oxobutan-2-yl)benzenesulfonamide (8.6 g, 76%). ¹H NMR (400 MHz, CDCl₃) δ 8.08 (d, J=8.4 Hz, 1H), 7.80 (s, 1H), 7.43 (d, J=2.0 Hz, 1H), 7.30 (d, J=8.8 Hz, 1H), 7.15 (m, 1H), 6.89 (d, J=7.6 Hz, 1H), 6.77 (m, 2H), 5.30 (s, 2H), 4.43 (d, J=4.4 Hz, 2H), 3.91 (s, 3H), 1.59 (s, 6H).

A solution of 2-chloro-4-(4-(3-(4-fluoro-3-methoxyphenyl)thioureido)-2-methyl-3-oxobutan-2-yl)benzenesulfonamide (8.6 g, 18.1 mmol) in AcOH (100 mL) was refluxed 3 h. After the reaction was complete, the solution was cooled to room temperature and azeotroped with toluene. The residue was triturated with Et₂O, filtered and dried to provide the title compound (6.8 g, 82% yield) as a light yellow solid. ¹H NMR (400 MHz, CDCl₃+MeOD) δ 7.92 (d, J=8.4 Hz, 1H), 7.09 (s, 1H), 7.06 (d, J=8.4 Hz, 1H), 6.97 (t, J=8.4 Hz, 1H), 6.89 (s, 1H), 6.38 (m, 1H), 6.13 (d, J=7.2 Hz, 1H), 3.58 (s, 3H), 1.54 (s, 6H); MS (EI) m/z 456 (MH⁺).

Preparation of 2-fluoro-5-(2-(1-(4-fluoro-3-methoxyphenyl)-2-mercapto-1H-imidazol-5-yl)propan-2-yl)benzonitrile

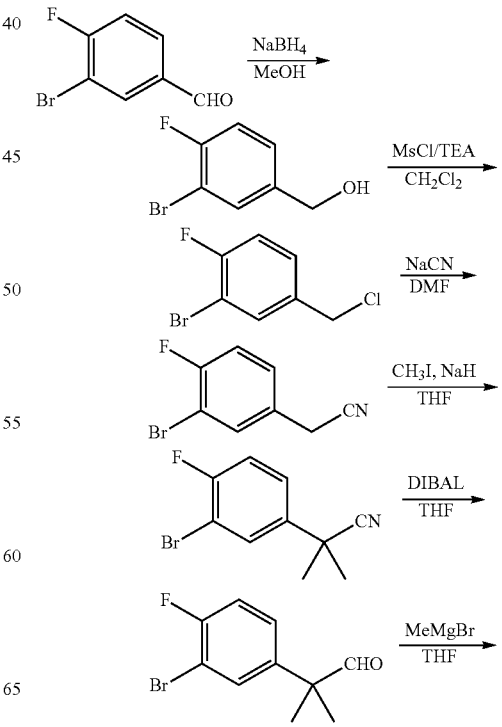

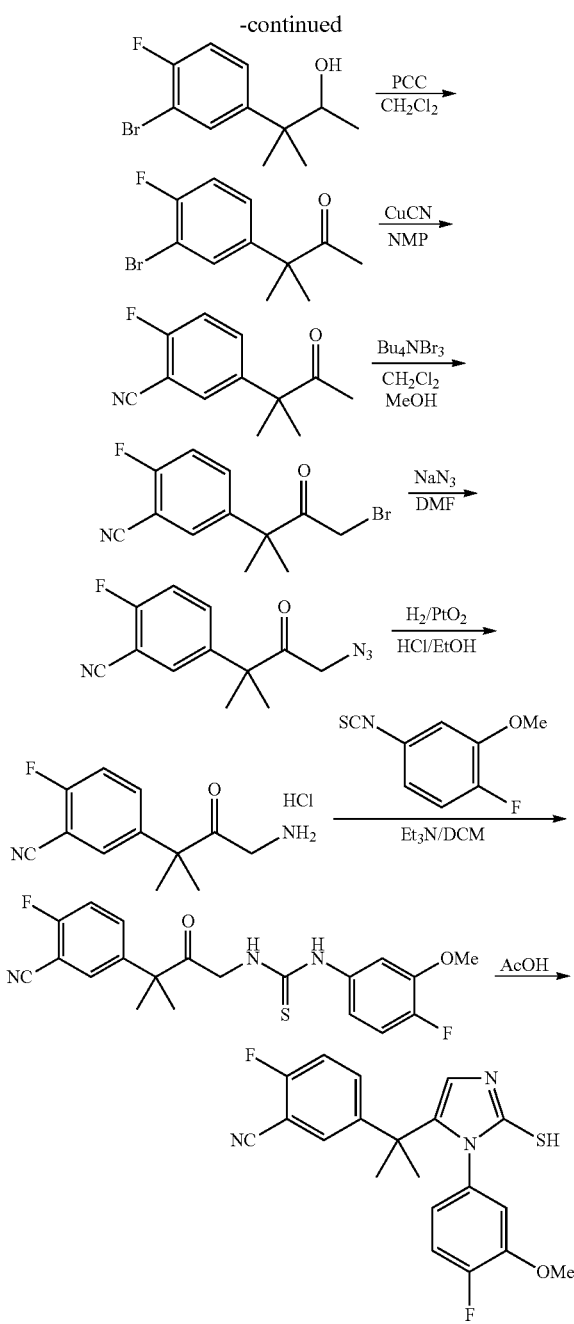

To a solution of 3-bromo-4-fluorobenzaldehyde (50 g, 0.246 mol) in MeOH (500 mL) at 0° C. was added NaBH₄ (9.3 g, 0.246 mol) portionwise. After 1 h, the reaction was concentrated in vacuo, diluted with water and extracted with DCM. The combined extracts were dried over MgSO₄ and concentrated in vacuo to give (3-bromo-4-fluorophenyl)methanol (53 g). ¹H NMR (400 MHz, CDCl₃) δ 7.58-7.56 (m, 1H), 7.28-7.25 (m, 1H), 7.09 (t, J=4.4 Hz, 1H), 4.65 (d, J=5.2 Hz, 2H), 1.82 (t, J=5.6 Hz, 1H).

To a solution of (3-bromo-4-fluorophenyl)methanol (53 g, 0.258 mol) in DCM (500 mL) at 0° C. was added Et₃N (108 mL, 775 mmol, 3 eq) and methanesulfonyl chloride (24 mL, 310 mmol, 1.2 eq) successively. After stirring 30 min, the reaction mixture was partitioned in DCM and water. The organic layer was dried over MgSO₄ and evaporated in vacuo to give 3-bromo-4-fluorobenzyl methanesulfonate (60 g), which used to the next step without further purification. ¹H NMR (400 MHz, CDCl₃) δ 7.65-7.62 (m, 1H), 7.37-7.33 (m, 1H), 7.16 (t, J=4.4 Hz, 1H), 5.17 (s, 2H), 2.99 (s, 3H).

To a stirred solution of 3-bromo-4-fluorobenzyl methanesulfonate (60 g, 0.212 mol) in DMF (300 mL) at 0° C. was added NaCN (31.1 g, 0.635 mol, 3 eq) portionwise. After stirring at room temperature 4 h, the reaction mixture was partitioned in EtOAc and water. The organic layer was dried over MgSO₄ and evaporated in vacuo. The residue was purified by column chromatography (Hex/EtOAc=4:1) to give 2-(3-bromo-4-fluorophenyl)acetonitrile (30 g, 3 step overall yield: 55%). ¹H NMR (400 MHz, CDCl₃) δ 7.56-7.54 (m, 1H), 7.28-7.24 (m, 1H), 7.14 (t, J=4.4 Hz, 1H), 3.73 (s, 2H).

To a stirred suspension of NaH (16.3 g, 406 mmol, 3 eq) in anhyd THF (100 mL) at 0° C. was added dropwise a solution of 2-(3-bromo-4-fluorophenyl)acetonitrile (29 g, 135 mmol) in anhyd THF (200 mL). After stirring 1 h, MeI (42.1 mL, 675 mmol, 5 eq) was added to the reaction mixture. After stirring 2 h at 0° C., the reaction was allowed to warm to room temperature, quenched carefully with H₂O and extracted with EtOAc. The combined extracts were washed with brine, dried over MgSO₄ and evaporated in vacuo to give 2-(3-bromo-4-fluorophenyl)-2-methylpropanenitrile (29 g, 88%). ¹H NMR (400 MHz, CDCl₃) δ 7.66-7.64 (m, 1H), 7.44-7.40 (m, 1H), 7.15 (t, J=8.4 Hz, 1H), 1.72 (s, 6H).

To a stirred solution of 2-(3-bromo-4-fluorophenyl)-2-methylpropanenitrile (29 g, 120 mmol) in THF (500 mL) at −78° C. was dropwise added DIBALH (1M in toluene, 360 mL, 3 eq) over 2 h. After the reaction mixture was stirred at same temperature for 30 minutes, it was allowed to warm to room temperature. After the reaction was complete, the mixture was quenched by 1N HCl and extracted with EA. The separated organic layer was dried over MgSO₄ and evaporated in vacuo to give 2-(3-bromo-4-fluorophenyl)-2-methylpropanal (27 g, 92%). ¹H NMR (400 MHz, CDCl₃) δ 9.46 (s, 1H), 7.47-7.44 (m, 1H), 7.19-7.15 (m, 1H), 7.12 (t, J=8.4 Hz, 1H), 1.45 (s, 6H).

To a stirred solution of 2-(3-bromo-4-fluorophenyl)-2-methylpropanal (27 g, 110 mmol) in anhyd THF (300 mL) at 0° C. was added MeMgBr (3M in ether, 73 mL, 220 mmol, 2 eq) dropwise over 2 h. After stirring 1 h, the reaction was allowed to warm to room temperature, quenched carefully with 1N HCl and extracted with EtOAc. The combined extracts were washed with brine, dried over MgSO₄ and evaporated in vacuo. The residue was purified by column chromatography (Hex/EA=10:1) to give 3-(3-bromo-4-fluorophenyl)-3-methylbutan-2-ol (19 g, 66%). ¹H NMR (400 MHz, CDCl₃) δ 7.56-7.54 (m, 1H), 7.32-7.28 (m, 1H), 7.07 (t, J=8.4 Hz, 1H), 3.84-3.79 (m, 1H), 1.31 (d, J=6.4 Hz, 6H), 1.04 (d, J=6.4 Hz, 3H).

To a stirred solution of 3-(3-bromo-4-fluorophenyl)-3-methylbutan-2-ol (18 g, 69 mmol) in DCM (300 mL) at 0° C. was added PCC (29.7 g, 2 eq) portionwise. After stirring 24 h at room temperature, the reaction mixture was combined with water and extracted with DCM. The combined extracts were dried over MgSO₄ and evaporated in vacuo. The residue was purified by flash column chromatography (Hex/EtOAc=10:1) to give 3-(3-bromo-4-fluorophenyl)-3-methylbutan-2-one (13 g, 73%). ¹H NMR (400 MHz, CDCl₃) δ 7.47-7.45 (m, 1H), 7.17-7.14 (m, 1H), 7.09 (t, J=8.8 Hz, 1H), 1.98 (s, 3H), 1.45 (s, 6H).

To a solution of 3-(3-bromo-4-fluorophenyl)-3-methylbutan-2-one (13 g, 50 mmol) in NMP (100 mL) was added CuCN (17.9 g, 200 mmol, 4 eq). The mixture was heated 24 h at 160° C. After cooling, the reaction was diluted with EtOAc, washed with 2N HCl (200 mL), satd NaHCO₃ (200 mL) and brine (200 mL) successively, dried over MgSO₄ and evaporated in vacuo. The residue was purified by column chromatography (Hex/EtOAc=4:1) to give 2-fluoro-5-(2-methyl-3-oxobutan-2-yl)benzonitrile (7.1 g, 69%). $^1$H NMR (400 MHz, CDCl$_3$) δ 7.56-7.54 (m, 1H), 7.49-7.45 (m, 1H), 7.20 (t, J=8.4 Hz, 1H), 1.96 (s, 3H), 1.50 (s, 6H).

To a stirred solution of 2-fluoro-5-(2-methyl-3-oxobutan-2-yl)benzonitrile (7.1 g, 34.5 mmol) in CH$_2$Cl$_2$ and MeOH (2:1, 100 mL) was added Bu$_4$NBr$_3$ (17.5 g, 36.5 mmol, 1.05 eq) portionwise. The reaction mixture was stirred 48 h and evaporated in vacuo. The residue was diluted with 1N HCl (300 mL) and extracted with EtOAc (150 mL). The combined extracts were washed with satd NaHCO$_3$ solution (200 mL), dried over MgSO$_4$ and evaporated in vacuo to give 5-(4-bromo-2-methyl-3-oxobutan-2-yl)-2-fluorobenzonitrile (10 g), which used to the next step without further purification.

To a stirred solution of 5-(4-bromo-2-methyl-3-oxobutan-2-yl)-2-fluorobenzonitrile (10 g, 35.2 mmol) in DMF (100 mL) at 0° C. was added NaN$_3$ (2.52 g, 38.7 mmol, 1.1 eq) portionwise. After stirring 2 h, the residue was diluted with water and extracted with EtOAc. The combined extracts were washed with brine (100 mL), dried over MgSO$_4$ and evaporated in vacuo. The residue was purified by flash column chromatography (silica, Hex/EtOAc=4:1) to give 5-(4-azido-2-methyl-3-oxobutan-2-yl)-2-fluorobenzonitrile (6.6 g, 2 step overall yield 78%). $^1$H NMR (400 MHz, CDCl$_3$) δ 7.57-7.55 (m, 1H), 7.50-7.46 (m, 1H), 7.25 (t, J=7.2 Hz, 1H), 3.8 (s, 2H), 1.55 (s, 6H).

To a stirred solution of 5-(4-azido-2-methyl-3-oxobutan-2-yl)-2-fluorobenzonitrile (6.1 g, 24.7 mmol) in EtOH (100 mL) was added conc HCl (20 mL) and PtO$_2$ (112 mg, 0.49 mmol, 0.02 eq). The mixture was stirred at 1 atm of H$_2$ gas for 12 h, filtered through Celite™ and evaporated in vacuo. The residue was partitioned in DCM and water, and the aqueous layer was evaporated in vacuo. The resulting residue was triturated with Et$_2$O-Hex to give 5-(4-amino-2-methyl-3-oxobutan-2-yl)-2-fluorobenzonitrile hydrochloride as a yellow solid (6 g, 65%). $^1$H NMR (400 MHz, CD$_3$OD) δ 7.74-7.68 (m, 2H), 7.37 (t, J=8.8 Hz, 1H), 3.89 (s, 2H), 1.58 (s, 6H).

To a suspension of 5-(4-amino-2-methyl-3-oxobutan-2-yl)-2-fluorobenzonitrile hydrochloride (2.8 g, 10.9 mmol) in DCM (50 mL) were added Et$_3$N (4.6 mL, 32.7 mmol, 3 eq) and 1-fluoro-4-isothiocyanato-2-methoxybenzene (2.2 g, 12 mmol, 1.1 eq). After stirring 2 h, the reaction mixture was partitioned in DCM and water. The organic layer was separated, dried over MgSO$_4$ and evaporated in vacuo. The residue was purified by flash column chromatography (silica, Hex:EA=1:1) to give 1-(3-(3-cyano-4-fluorophenyl)-3-methyl-2-oxobutyl)-3-(4-fluoro-3-methoxyphenyl)thiourea (3.7 g, 84%). $^1$H NMR (400 MHz, CDCl$_3$) δ 7.59 (bs, 1H), 7.53-7.49 (m, 2H), 7.26-7.18 (m, 2H), 6.89-6.79 (m, 2H), 6.70 (bs, 1H), 4.44 (d, J=4.4 Hz, 2H), 3.90 (s, 3H), 1.58 (s, 6H).

A solution of 1-(3-(3-cyano-4-fluorophenyl)-3-methyl-2-oxobutyl)-3-(4-fluoro-3-methoxyphenyl)thiourea (3.7 g, 9.17 mmol) in AcOH (50 mL) was refluxed 2 h at 110° C. After the reaction was complete, it was cooled to room temperature and co-evaporated with toluene in vacuo. The residue was purified by flash column chromatography (Hex: EA=1:3) to give 2-fluoro-5-(2-(1-(4-fluoro-3-methoxyphenyl)-2-mercapto-1H-imidazol-5-yl)propan-2-yl)benzonitrile (2.3 g, 65%) as a yellow solid. $^1$H NMR (400 MHz, CDCl$_3$) δ 10.6 (bs, 1H), 7.26-7.23 (m, 1H), 7.08 (t, J=9.2 Hz, 1H), 6.96 (t, J=8.8 Hz, 1H), 6.84 (d, J=2.0 Hz, 1H), 6.25-6.25 (m, 1H), 6.17-6.15 (m, 1H), 3.59 (s, 3H), 1.51 (s, 6H).

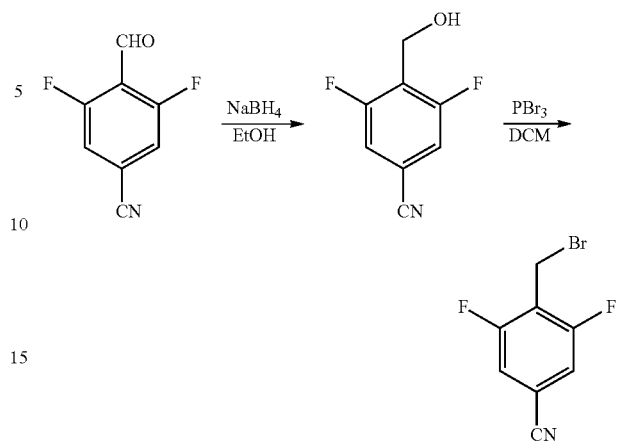

To a solution of 3,5-difluoro-4-formylbenzonitrile (1.0 g, 6.0 mmol) in EtOH (15 mL) at 0° C. was added NaBH$_4$ (113 mg, 0.5 equiv). After stirring 2 h at 0° C., the reaction mixture was quenched with water and concentrated under reduced pressure. The crude residue was dissolved in DCM, washed with brine, dried over Na$_2$SO$_4$ and concentrated to give 3,5-difluoro-4-(hydroxymethyl)benzonitrile as a solid. All material was used in the next step. $^1$H NMR (400 MHz, CDCl$_3$) δ 7.29-7.15 (m, 2H), 4.82 (d, J=6.2, 2H), 2.02 (dd, J=12.0, 5.6, 1H); GC-MS (ES) m/z 169 (M).

To a solution of 3,5-difluoro-4-(hydroxymethyl)benzonitrile (all material from above reaction) in DCM at 0° C. was added PBr$_3$ (283 µL, 3 mmol). After stirring 1 h at 0° C., the reaction mixture was quenched with water and then extracted with DCM. The combined extracts were washed with satd NaHCO$_3$, dried over Na$_2$SO$_4$ and concentrated to yield 4-(bromomethyl)-3,5-difluorobenzonitrile (0.88 g, 63%, combined yield) as a white solid. $^1$H NMR (400 MHz, CDCl$_3$) δ 7.31-7.18 (m, 1H), 4.51 (d, J=10.1, 1H); GC-MS (ES) m/z 231 (M).

Preparation of tert-butyl 3,5-difluoro-4-((methylsulfonyloxy)methyl)benzoate

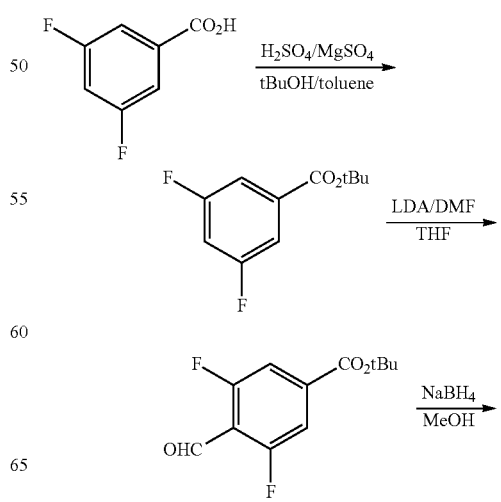

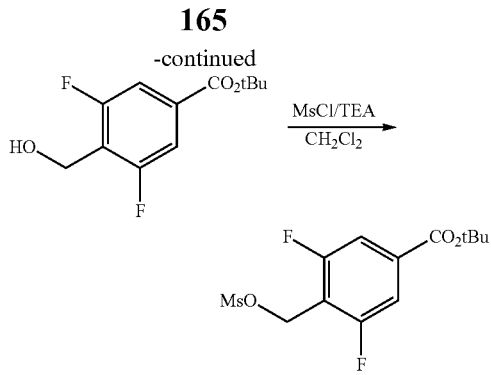

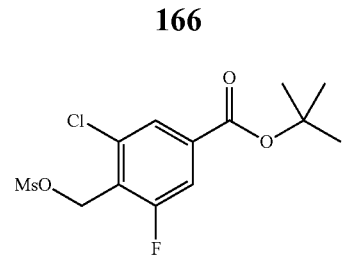

Concentrated H$_2$SO$_4$ (1.74 mL, 31.6 mmol) was added to a vigorously stirred suspension of MgSO$_4$ (15.2 g, 126.4 mmol, 4 eq) in toluene (100 mL). The mixture was stirred for 15 minutes, after which 3,5-difluorobenzoic acid (5 g, 31.6 mmol) and t-BuOH (14.9 mL, 158 mmol, 5 eq) were added successively. The mixture was stoppered tightly and stirred at room temperature until the reaction was complete by TLC analysis. The reaction mixture was then quenched with saturated NaHCO$_3$ solution and stirred until all MgSO$_4$ had dissolved. The organic layer was washed with brine, dried over MgSO$_4$ and concentrated to afford the crude product. The residue was purified by chromatography (silica, Hex) to give tert-butyl 3,5-difluorobenzoate (5.3 g, 78%) as a colorless oil.

To a stirred solution of diisopropylamine (5 mL, 35.5 mmol, 1.2 eq) in THF (100 mL, anhyd) was slowly added BuLi (1.6M in hexanes, 20 mL, 32.3 mmol, 1.1 eq) at below 0° C. After addition was completed, the solution was cooled to −78° C. and then charged dropwise with a solution of tert-butyl 3,5-difluorobenzoate (6.3 g, 29 mmol) in THF (50 mL, anhyd) over 1 h. The resulting solution was stirred for another 2 h at −78° C. Next anhyd DMF (2.5 mL, 32.3 mmol, 1.1 eq) was added dropwise and, after 30 min, AcOH (4 mL) and water were added successively to quench the reaction. The reaction mixture was warmed to room temperature and diluted with EtOAc (100 mL). The organic layer was washed with brine, dried over MgSO$_4$ and concentrated in vacuo. The residue was purified by flash column chromatography (Hex/EtOAc=4:1) to give tert-butyl 3,5-difluoro-4-formylbenzoate (5.8 g, 83%) as a white solid.

To a stirred solution of tert-butyl 3,5-difluoro-4-formylbenzoate (21 g, 86.7 mmol) in MeOH was portionwise added NaBH$_4$ (3.28 g, 86.7 mmol) at 0° C. After 20 min, the reaction mixture was evaporated in vacuo and the product was extracted with ethyl acetate. The organic layer was washed with brine, dried over MgSO$_4$ and evaporated in vacuo. The residue was purified by flash column chromatography (Hex/EtOAc=4:1) to give tert-butyl 3,5-difluoro-4-(hydroxymethyl)benzoate (20.7 g, 97%) as a white solid.

To a stirred solution of tert-butyl 3,5-difluoro-4-(hydroxymethyl)benzoate (1.9 g, 7.78 mmol) in DCM was added Et$_3$N (3.27 mL, 23.4 mmol, 3 eq) and methanesulfonylchloride (0.72 mL, 9.3 mmol, 1.2 eq) successively at 0° C. After the reaction was stirred for 30 min, it was extracted with CH2Cl2C and water. Organic layer was dried over MgSO$_4$ and evaporated in vacuo. The residue was purified by column chromatography (Hex/EtOAc=4:1) to give tert-butyl 3,5-difluoro-4-((methylsulfonyloxy)methyl)benzoate (2.25 g, 89% yield) as a ivory solid.

Under similar conditions, tert-butyl 3-chloro-5-fluoro-4-((methylsulfonyloxy)methyl)benzoate was prepared from 3-chloro-5-fluorobenzoic acid. $^1$H NMR (400 MHz, CDCl$_3$) δ 7.87-7.85 (m, 1H), 7.67-7.62 (m, 1H), 5.42 (d, 2H), 3.07 (s, 3H), 1.60 (s, 9H).

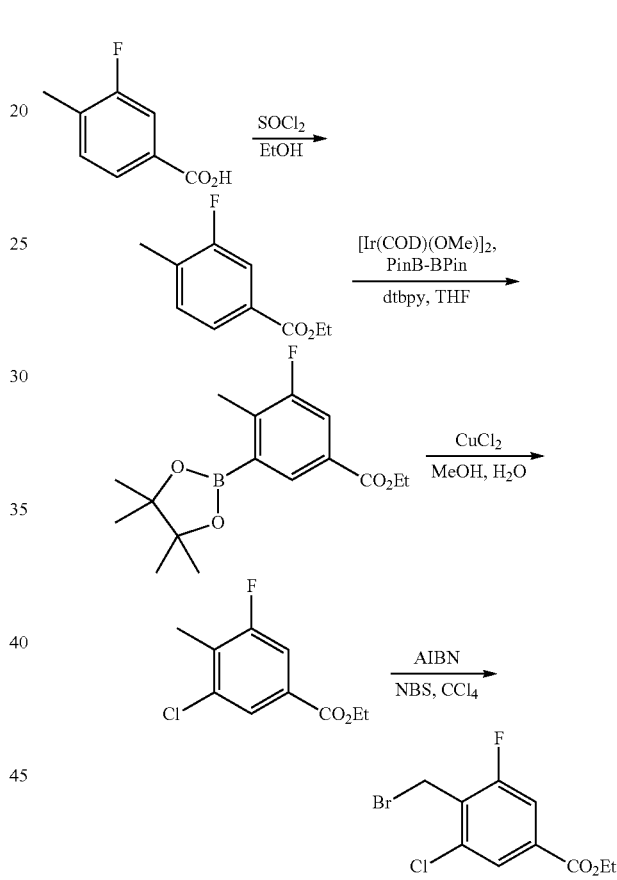

To a solution of 3-fluoro-4-methylbenzoic acid (13.23 g, 85.85 mmol) in EtOH (200 mL) at 0° C. was added SOCl$_2$ (3 mL) dropwise. The reaction mixture was heated at 60° C. overnight, then cooled to room temperature, concentrated under reduced pressure and diluted with DCM. The organic layer was washed with 1N NaOH (100 mL×2), dried (MgSO$_4$) and concentrated to give ethyl 3-fluoro-4-methylbenzoate (15.02 g, 96%).

To a solution of ethyl 3-fluoro-4-methylbenzoate (15.02 g, 82.42 mmol) and bispinacolotodiboron (20.93 g, 82.42 mmol) in THF (200 mL, anhyd) was added 4,4'-di-t-butylbipyridine (930 mg, 3.46 mmol) followed by 1-5-cyclooctadiene(methoxy)iridium (I) dimer (710 mg, 1.07 mmol) under nitrogen atmosphere. The reaction mixture was heated at 80° C. overnight. GC-MS showed conversion (>74%) of starting material to a mixture of two isomers (55:45). Ice was added slowly to the reaction mixture, which then was concentrated under reduced pressure, diluted with DCM and washed with H₂O (150 mL×2). The organic layer was dried (Na₂SO₄), concentrated and purified by flash chromatography (20-80% EtOAc/hexanes) to furnish ethyl 3-fluoro-4-methyl-5-(4,4,5,5-tetramethyl-1,3,2-dioxaborolan-2-yl)benzoate (8.664 g, 34%) as a white solid. ¹H NMR (400 MHz, DMSO-d₆) δ 8.05 (d, J=1.7 Hz, 1H), 7.71 (dt, J=14.2, 7.1 Hz, 1H), 4.33 (q, J=7.1 Hz, 2H), 2.47 (d, J=2.5 Hz, 3H), 1.37-1.29 (m, 15H).

To a solution of ethyl 3-fluoro-4-methyl-5-(4,4,5,5-tetramethyl-1,3,2-dioxaborolan-2-yl)benzoate (8.664 g, 28.12 mmol) in MeOH (50 mL) was added CuCl₂ (11.34 g, 84.35 mmol) in H₂O (10 mL). The reaction mixture was heated at 90° C. overnight. GC-MS confirmed complete conversion to product. The volatiles were removed in vacuo. The resulting material was diluted with an additional 10 mL of H₂O, and extracted with DCM (50 mL×2). The combined extracts were dried (Na₂SO₄), concentrated and purified by flash chromatography to yield ethyl 3-chloro-5-fluoro-4-methylbenzoate (5.3 g, 87%) as a clear and colorless oil. ¹H NMR (400 MHz, DMSO-d₆) δ 7.74 (s, 1H), 7.61 (dd, J=9.5, 1.5 Hz, 1H), 4.37-4.24 (m, 2H), 2.29 (t, J=7.2 Hz, 3H), 1.37-1.25 (m, 3H).

To a solution of ethyl 3-chloro-5-fluoro-4-methylbenzoate (5.3 g, 24.46 mmol) in CCl₄ (100 mL) was added NBS (4.79 g, 26.91 mmol) followed by AIBN (0.4 g, 2.45 mmol). The reaction mixture was heated at 80° C. overnight. After cooling, the reaction mixture was diluted with H₂O and washed with DCM (2×). The combined extracts were dried (Na₂SO₄), concentrated and purified by flash chromatography (12% EtOAc/Hex) to yield ethyl 4-(bromomethyl)-3-chloro-5-fluorobenzoate (3.53 g, 49%) as a light yellow solid. ¹H NMR (400 MHz, DMSO-d₆) δ 7.96-7.85 (m, 1H), 7.83 (dd, J=9.6, 1.5 Hz, 1H), 4.80 (t, J=5.7 Hz, 2H), 4.41 (q, J=7.1 Hz, 2H), 3.47 (s, 1H), 1.47-1.30 (m, 3H).

Preparation of 4-(bromomethyl)-3,5-difluorobenzenesulfonamide

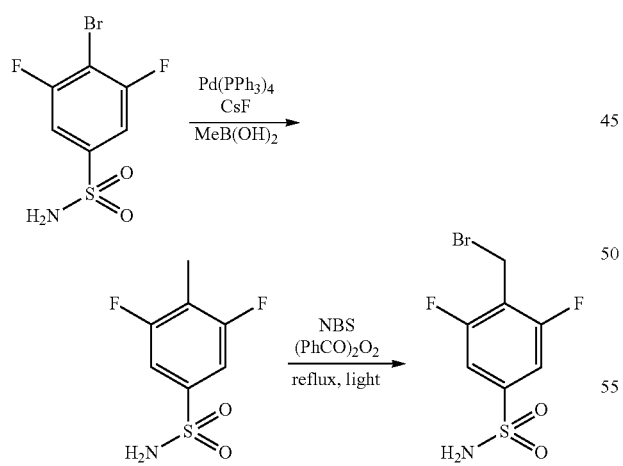

A mixture of 4-bromo-3,5-difluorobenzenesulfonamide (1.09 g, 4 mmol), CsF (1.34 g, 3 eq), methylboronic acid (494 mg, 2 equiv) and Pd(PPh₃)₄ (140 mg, 0.3 eq) in 1,2-dimethoxyethane (16 mL) was heated to 120° C. under microwave irradiation for 4 h. After cooling, solids were removed by filtration and washed with EtOAc. The filtrate was concentrated and then purified by column chromatography (silica, EtOAc-Hex, 1:4 to 4:1) to give 3,5-difluoro-4-methylbenzenesulfonamide (776 mg). ¹H NMR (400 MHz, CD₃OD) δ 7.65 (d, 2H), 2.46 (s, 3H); GC-MS (ES) m/z 207 (M).

A mixture of 3,5-difluoro-4-methylbenzenesulfonamide (1.237 g, 6 mmol), N-bromosuccinimide (1.4 g, 1.3 eq) and benzoyl peroxide (87 mg, 0.1 eq) in carbon tetrachloride (24 mL) was heated to reflux for 6 h under a halogen light. After the reaction was determined to be complete by GC-MS, the mixture was concentrated and purified by column chromatography (silica, EtOAc-hexane, 1:4 to 4:1) to give the title compound (524 mg). ¹H NMR (400 MHz, CD₃OD) δ 7.75 (d, 2H), 4.83 (s, 3H); GC-MS (ES) m/z 285 (M), 287 (M+2).

Preparation of 4-(N-((dimethylamino)methylene)sulfamoyl)-2,6-difluorobenzyl methanesulfonate

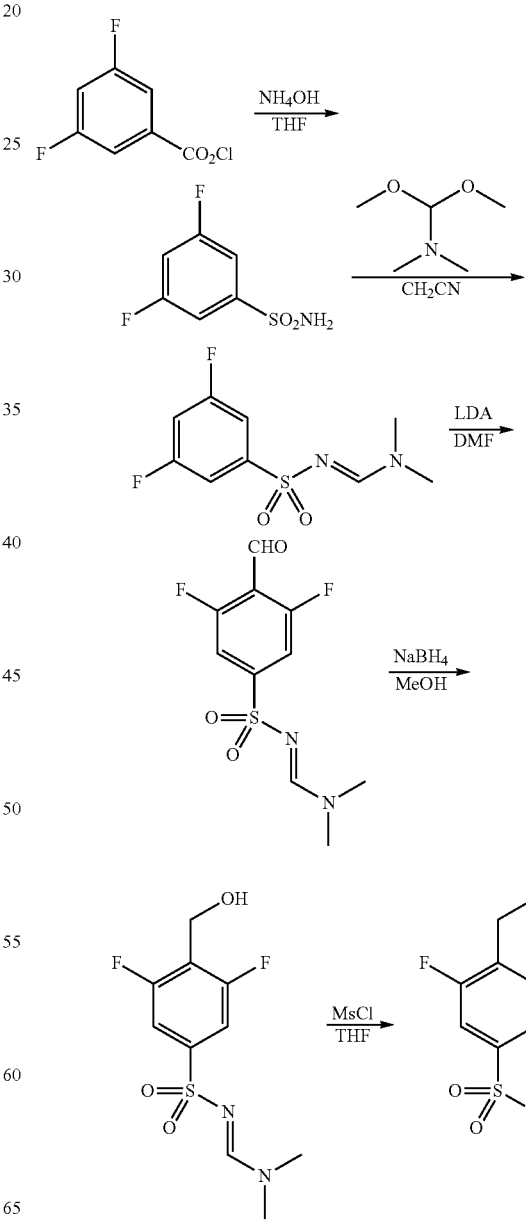

To a solution of 3,5-difluorobenzenesulfonyl chloride (25 g, 0.117 mol) in THF (150 mL) was added 35% aq. NH₄OH (120 mL) over 1 h in an ice-bath. After the reaction was complete, it was evaporated in vacuo. To a solution of this residue in water (150 mL) was added 2N HCl (1 mL). After stirring 1 h, the reaction mixture was filtered and dried under high vacuum to give 3,5-difluorobenzenesulfonamide as a light brown solid (19.9 g, 88%). $^1$H NMR (400 MHz, CDCl₃) δ 7.49-7.44 (m, 2H), 7.04-6.99 (m, 2H).

To a solution of 3,5-difluorobenzenesulfonamide (154 g, 0.797 mol) in CH₃CN (1 L) was added N,N-dimethylformamide dimethylacetal (224 mL, 1.67 mmol, 2.1 eq). After stirring 1 h, the reaction mixture was concentrated under reduced pressure. This material was triturated with Et₂O and dried in vacuo to give N'-(3,5-difluorophenylsulfonyl)-N,N-dimethylformimidamide (190 g, 96%) as a light brown solid. $^1$H NMR (400 MHz, CDCl₃) δ 8.12 (s, 1H), 7.44-7.38 (m, 2H), 6.98-6.91 (m, 1H), 3.17 (s, 3H), 3.05 (s, 3H).

To a solution of diisopropylamine (231 mL, 1.63 mmol, 2.1 eq) in THF (1 L) was slowly added BuLi (2.5M in Hex, 653 mL, 1.63 mmol, 2.1 eq) at 0° C. The solution was cooled to −78° C., and then a solution of N'-(3,5-difluorophenylsulfonyl)-N,N-dimethylformimidamide (193 g, 777 mmol) in THF (1 L) was added dropwise to the stirred LDA solution over 1 h at −78° C. and allowed to stir another 2 h at same temperature. To the reaction mixture was added anhyd DMF (72 mL, 932 mmol, 1.2 eq) and, 30 minutes later, was added AcOH (50 mL) and water. The reaction mixture was extracted with EtOAc (500 mL×3). The combined extracts were washed with brine (1 L), dried over MgSO₄ and concentrated in vacuo to give N'-(3,5-difluoro-4-formylphenylsulfonyl)-N,N-dimethylformimidamide (171 g), which was used in the next step without further purification.

To a solution of N'-(3,5-difluoro-4-formylphenylsulfonyl)-N,N-dimethylformimidamide (171 g, 619 mmol) in MeOH (1 L) was added NaBH₄ (23.4 g, 619 mmol) at 0° C. After 1 h, the reaction mixture was concentrated, neutralized to pH 6 with 1N HCl, and extracted with EtOAc. The combined extracts were washed with water and brine, dried over MgSO₄ and evaporated in vacuo. To a solution of this residue in CH₃CN (1 L) was added N,N-dimethylformamide dimethylacetal (166 mL, 1.24 mmol, 2 eq). The solution was evaporated in vacuo and then purified by chromatography (silica, DCM/EtOAc, 1:1) to give N'-(3,5-difluoro-4-(hydroxymethyl)phenylsulfonyl)-N,N-dimethylformimidamide (80 g). $^1$H NMR (400 MHz, CDCl₃) δ 8.10 (s, 1H), 7.45-7.40 (m, 2H), 4.8 (d, J=3.6 Hz), 3.17 (s, 3H), 3.05 (s, 3H).

To a solution of N'-(3,5-difluoro-4-(hydroxymethyl)phenylsulfonyl)-N,N-dimethyl-formimidamide (80 g, 287 mmol) in DCM (500 mL) was added Et₃N (121 mL, 862 mmol, 3 eq) and methanesulfonylchloride (27 mL, 245 mmol, 1.2 eq) successively at 0° C. After 30 min, the reaction mixture was extracted with DCM (300 mL×3). The combined extracts were washed with water (1 L), dried over MgSO₄, concentrated and then purified by chromatography (silica, DCM/EtOAc, 1:1) to give 4-(N-((dimethylamino)methylene)sulfamoyl)-2,6-difluorobenzyl methanesulfonate (77.5 g, 28% over 4 steps) as a ivory solid. $^1$H NMR (400 MHz, CDCl₃) δ 8.11 (s, 1H), 7.59-7.39 (m, 2H), 5.32 (s, 2H), 3.18 (s, 3H), 3.09 (s, 3H), 3.08 (s, 3H).

Preparation of N'-(4-(bromomethyl)-3-chloro-5-fluorophenylsulfonyl)-N,N-dimethylformimidamide

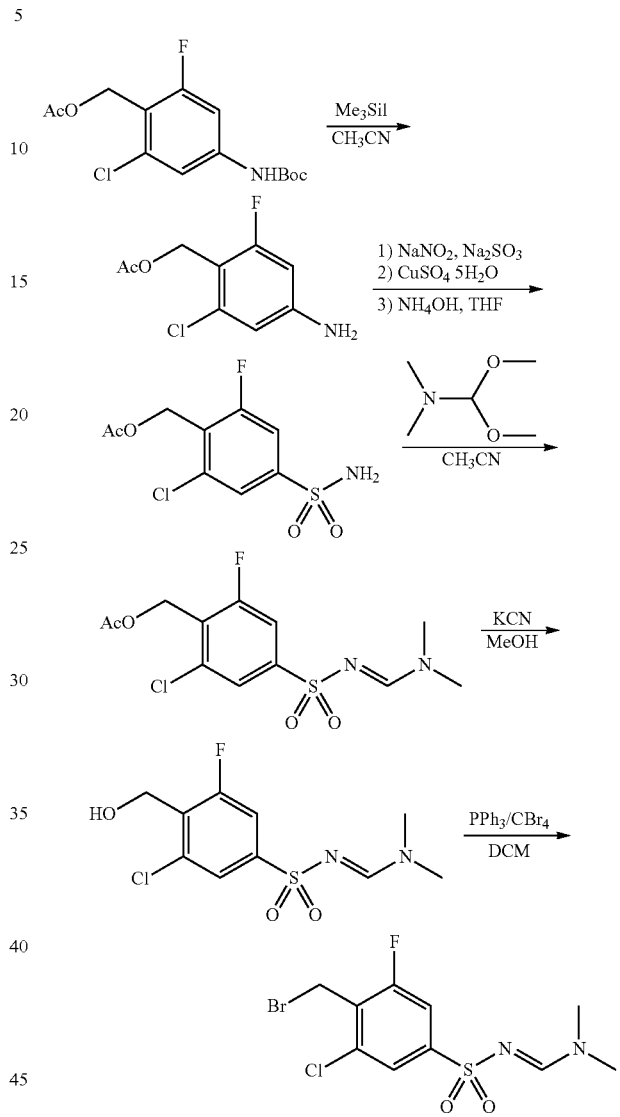

To a solution of 4-(tert-butoxycarbonylamino)-2-chloro-6-fluorobenzyl acetate (8.5 g, 24 mmol) in CH₃CN (300 mL) was added trimethylsilyl iodide (4.12 mL, 28 mmol) at 0° C. under N₂. After stirring 15 min, the reaction mixture was quenched with 5% Na₂S₂O₃ (10 mL) in ice-bath, concentrated in vacuo, and extracted with EtOAc. The combined extracts were washed with H₂O and brine successively, dried over anhyd MgSO₄, concentrated and purified by column chromatography (Hex/DCM=1:1) to afford 4-amino-2-chloro-6-fluorobenzyl acetate as yellow solid. $^1$H NMR (400 MHz, CDCl₃) δ 6.55-6.49 (m, 1H), 6.33-6.27 (m, 1H), 5.15 (d, 2H), 3.97 (d, 2H), 2.07 (s, 3H).

To a solution of 4-amino-2-chloro-6-fluorobenzyl acetate (5.2 g, 0.024 mol) in DMF (10 mL) at 0° C. was added slowly 3M HCl (100 mL) followed by NaNO₂ (2 g, 0.029 mol). After stirring at the same temperature for 20 min, the mixture was added dropwise to a solution of Na₂SO₃ (12 g, 0.096 mol) and CuSO₄·5H₂O in 3N HCl (100 mL). After stirring for 30 min, the reaction mixture was then poured into ice-water and extracted with EtOAc. The combined extracts were concentrated, dried over anhydrous MgSO₄, filtered and concentrated in vacuo. The material was dissolved in THF and added dropwise to a stirred solution of NH₄OH (17 mL) in THF (17 mL) at 5° C. After stirring 30 min, the mixture was concentrated under reduced pressure and extracted with EtOAc. The combined extracts were washed with H₂O, dried over anhyd MgSO₄, concentrated and purified by column chromatography (Hex/EtOAc=5:1) to afford 2-chloro-6-fluoro-4-sulfamoylbenzyl acetate (1.02 g, 15%, 3 steps) as an orange solid. ¹H NMR (400 MHz, CDCl₃) δ 7.80 (t, 1H), 7.59 (dd, 1H), 5.28 (d, 2H), 5.16 (s, 2H), 2.10 (d, 3H); MS (EI) m/z 303 (M+Na⁺).

To a solution of 2-chloro-6-fluoro-4-sulfamoylbenzyl acetate (1 g, 3.6 mmol) in CH₃CN (20 mL) at 0° C. under N₂ was added 1,1-dimethoxy-N,N-dimethylmethanamine (0.7 ml, 5.4 mmol). The resulting solution was stirred at room temperature 1 h, concentrated under reduced pressure, and purified by column chromatography (DCM/EtOAc=9:1) to afford 2-chloro-4-(N-((dimethylamino)methylene)sulfamoyl)-6-fluorobenzyl acetate (850 mg, 76%) as ivory solid. ¹H NMR (400 MHz, CDCl₃) δ 8.12 (s, 1H), 7.76 (s, 1H), 7.55 (d, 1H), 5.26 (s, 2H), 3.18 (s, 3H), 3.05 (s, 3H), 2.08 (s, 3H).

To a solution of KCN (82 mg, 1.26 mmol) in MeOH (80 mL) was added 2-chloro-4-(N-((dimethylamino)methylene)sulfamoyl)-6-fluorobenzyl acetate (850 mg, 2.52 mmol) at 0° C. The mixture was allowed to attain room temperature and then refluxed 1 h. After cooling, the reaction mixture was quenched with H₂O, concentrated, and extracted with EtOAc. The combined extracts were washed with brine, dried over anhyd MgSO₄, filtered and concentrated under reduced pressure to give N'-(3-chloro-5-fluoro-4-(hydroxymethyl)phenylsulfonyl)-N,N-dimethylformimidamide (600 mg, 80%) as ivory solid. ¹H NMR (400 MHz, CDCl₃) δ 8.10 (s, 1H), 7.74 (s, 1H), 7.55 (d, 1H), 4.86 (d, 2H), 3.17 (s, 3H), 3.05 (s, 3H), 2.07 (s, 1H).

To a solution of N'-(3-chloro-5-fluoro-4-(hydroxymethyl)phenylsulfonyl)-N,N-dimethylformimidamide (600 mg, 2 mmol) in DCM (10 mL) at 0° C. were added PPh₃ (1.06 g, 4.06 mmol) and CBr₄ (1.3 g, 4.06 mmol). The resulting solution was stirred at room temperature for 30 min, concentrated, and purified by column chromatography (silica, DCM/EtOAc=20:1) to afford N'-(4-(bromomethyl)-3-chloro-5-fluorophenylsulfonyl)-N,N-dimethylformimidamide (673 mg, 92%) as ivory solid. ¹H NMR (400 MHz, CDCl₃) δ 8.18-8.11 (m, 1H), 7.78 (d, 1H), 7.57 (dd, 1H), 4.64 (d, 2H), 3.22 (d, 3H), 3.10 (t, 3H); MS (EI) m/z 379 (M+Na⁺).

Preparation of (4-(2-(tert-butyldimethylsilyloxy)ethoxy)-2,6-difluoro)benzylalcohol

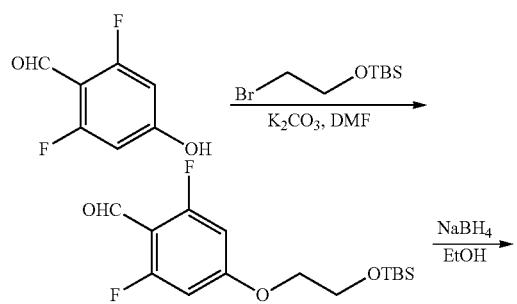

To a solution of 2,6-difluoro-4-hydroxybenzaldehyde (5.00 g, 31.60 mmol) in DMF (80 mL) were added K₂CO₃ (6.50 g, 47.40 mmol) and (2-bromoethoxy)-tert-butyldimethylsilane (8.90 mL, 41.10 mmol). The reaction mixture was heated to 85° C. for 3 h and was complete by LCMS analysis. The cooled mixture was combined with water and extracted with EtOAc (3×100 mL). The combined extracts were washed with brine, dried over anhyd Na₂SO₄, concentrated and purified by flash chromatography (20% EtOAc/Hex) to achieve 4-(2-(tert-butyldimethylsilyloxy)ethoxy)-2,6-difluorobenzaldehyde as a while solid (10.00 g, 100%). MS (EI) m/z 317.3 (MH⁺).

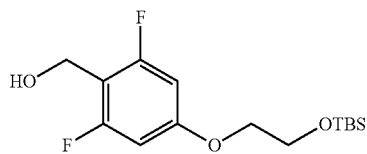

To a solution 4-(2-(tert-butyldimethylsilyloxy)ethoxy)-2,6-difluorobenzaldehyde (10.00 g, 31.60 mmol) in EtOH (100 mL) was added NaBH₄ (1.45 g, 37.90 mmol) in one portion. After stirring for 1 h, the reaction was complete by LCMS analysis and was quenched with H₂O. The crude mixture was extracted with EtOAc (3×150 mL), washed with H₂O and brine, and purified by flash chromatography to yield the title compound (9.15 g, 90%). ¹HNMR (400 MHz, CDCl₃) δ6.48 (m, 2H), 4.71 (s, 2H), 4.04-3.98 (m, 4H), 0.9 (s, 9H), 0.1 (s, 6H).

(4-(3-(tert-butyldimethylsilyloxy)propoxy)-2,6-difluoro)benzylalcohol

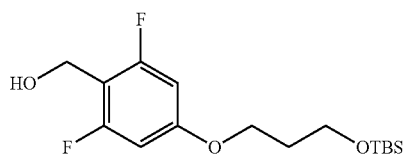 [SMILES: CC(C)(C)[Si](C)(C)OCCCOc1cc(F)c(CO)c(F)c1]

As described in the previous experiment, a mixture of 2,6-difluoro-4-hydroxybenzaldehyde (515 mg, 3.25 mmol), K₂CO₃ (675 mg, 4.88 mmol) and (3-bromopropoxy)-tert-butyldimethylsilane (1.00 mL, 4.23 mmol) in DMF (8 mL) were reacted, processed and purified by flash chromatography (15% EtOAc/Hex) to afford 4-(3-(tert-butyldimethylsilyloxy)propoxy)-2,6-difluorobenzaldehyde as a white solid (1.03 g, 96%). MS (EI) m/z 331.3 (MH⁺).

A mixture of 4-(3-(tert-butyldimethylsilyloxy)propoxy)-2,6-difluorobenzaldehyde (1.02 g, 3.10 mmol), NaBH₄ (140 mg, 3.70 mmol) and EtOH (10 mL) was stirred 1 h, processed as described previously and purified by flash chromatography (15% EtOAc/Hex) to yield the title compound (933 mg, 90%). ¹HNMR (400 MHz, CDCl₃) δ6.46 (m, 2H), 4.71 (s, 2H), 4.04 (t, J=6.0 Hz, 2H), 3.78 (t, J=5.9 Hz, 2H), 1.97 (m, 2H), 0.89 (s, 9H), 0.05 (s, 6H).

Preparation of 2-(3,5-difluoro-4-(hydroxymethyl)phenoxy)acetonitrile

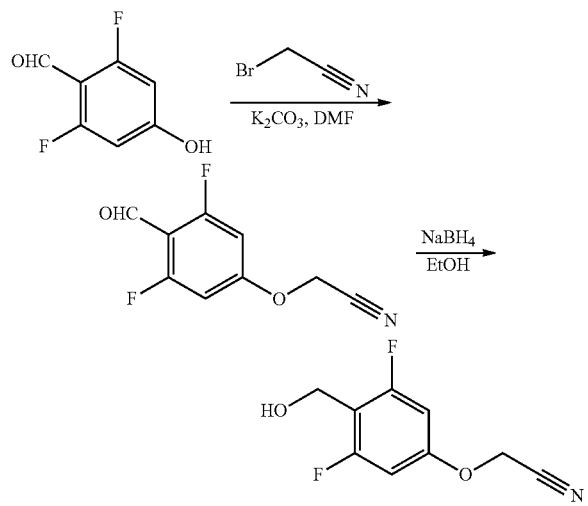

In a manner described previously, a mixture of 2,6-difluoro-4-hydroxybenzaldehyde (538 mg, 3.40 mmol), K₂CO₃ (705 mg, 5.10 mmol) and bromoacetonitrile (303 µL, 4.40 mmol) in DMF (9 mL) was reacted, processed and purified by flash chromatography (0 to 100% EtOAc/Hex) to provide 2-(3,5-difluoro-4-formylphenoxy)acetonitrile (553 mg, 83%). $^1$HNMR (400 MHz, CDCl$_3$) δ10.24 (s, 1H), 6.75-6.52 (m, 2H), 4.85 (s, 2H).

A mixture of 2-(3,5-difluoro-4-formylphenoxy)acetonitrile (531 mg, 2.69 mmol) and NaBH$_4$ (123 mg, 3.20 mmol) in EtOH (7 mL) was stirred 1 h, processed as described previously, and purified by flash chromatography (80% EtOAc/Hex) to afford the title compound (264 mg, 49%). GCMS (EI) m/z 199.0 (M$^+$).

Preparation of 5-(3,4-dimethoxybenzyl)-4-(4-fluorophenyl)-4H-1,2,4-triazole-3-thiol

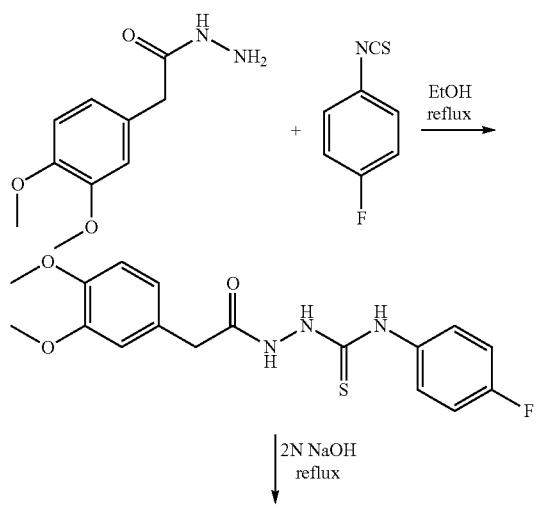

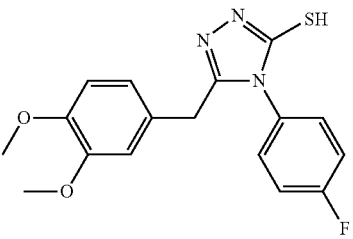

A solution of 4-fluoroisothiocyanate (2.0 g, 13 mmol) in EtOH (15 mL, anhyd) was added dropwise to a solution of 3,4-dimethoxyphenylacetic acid hydrazide (1.4 g, 6.5 mmol) in EtOH (80 mL, anhyd). The reaction mixture was refluxed gently for 1.5 h. After cooling to room temperature, the reaction mixture was concentrated under reduced pressure and diluted with CH$_2$Cl$_2$. White solids precipitated and were filtered and dried under vacuum to yield 2-(2-(3,4-dimethoxyphenyl)acetyl)-N-(4-fluorophenyl)hydrazine-carbothioamide (2.03 g, 86%), which was used without further purification.

A solution of 2-(2-(3,4-dimethoxyphenyl)acetyl)-N-(4-fluorophenyl)hydrazine-carbothioamide (2.03 g) in 2N NaOH (200 mL) was heated at reflux 3 h. The reaction was cooled and acidified to pH 5 with 2N HCl. White solids precipitated, were collected by filtration and washed with water. The solids were dried under vacuum to yield the title compound (1.56 g, 81%).

3-(2-(3,4-dimethoxyphenyl)propan-2-yl)-4-(4-fluorophenyl)-1H-1,2,4-triazole-5(4H)-thione

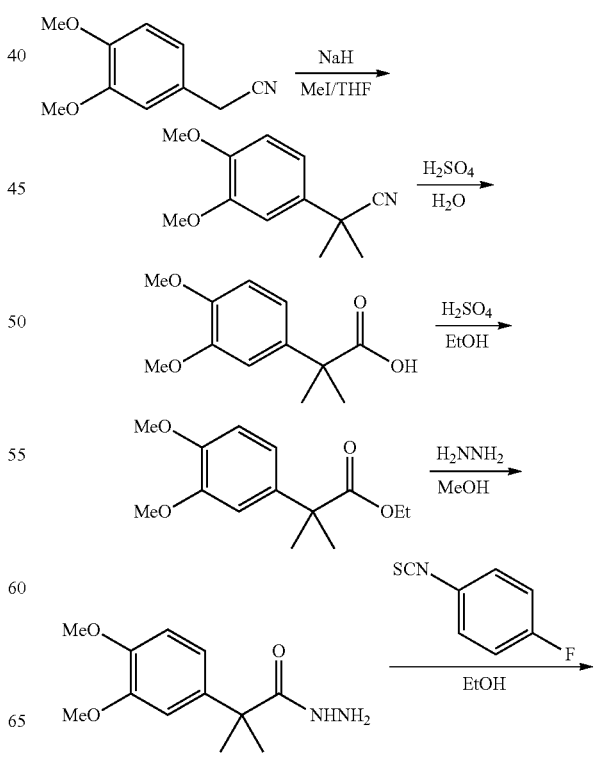

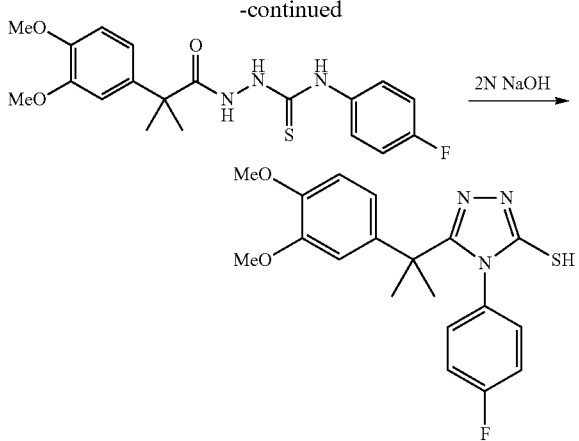

To a dispersion of NaH (60% in mineral oil, 3.60 g, 90 mmol) in THF (50 mL) was added 3,4-dimethoxybenzyl cyanide (5.316 g, 30 mmol) at 0° C. under nitrogen. The mixture was stirred for 30 min, and iodomethane (9.4 mL, 150 mmol) was added. The resulting mixture was stirred for 12 h, carefully quenched with satd $NH_4Cl$, and extracted with EtOAc. The combined extracts were washed with brine, dried over $MgSO_4$, filtered, concentrated to give the crude producenyl)-2-methylpropanenitrile (5.77 g, 94%) as white solid. $^1H$ NMR (400 MHz, $CDCl_3$) δ 7.01-6.97 (m, 2H), 6.86 (d, 1H), 3.92 (s, 3H), 3.89 (s, 3H), 1.72 (s, 6H).

A solution of 2-(3,4-dimethoxyphenyl)-2-methylpropanenitrile (4.59 g, 22.36 mmol) in $H_2O/H_2SO_4$ (60 mL, 8:7, v/v) was heated at reflux 7 h. The reaction mixture was cooled to room temperature, poured into ice-water and then extracted with DCM (50 mL×2). The combined extracts were dried over $MgSO_4$, filtered, and concentrated to give 2-(3,4-dimethoxyphenyl)-2-methylpropanoic acid (5.01 g, 99%), which was used without further purification. $^1H$ NMR (400 MHz, $CDCl_3$) δ 7.00-6.91 (m, 2H), 6.82 (d, 1H), 3.87 (s, 3H), 3.86 (s, 3H), 1.58 (s, 6H).

A solution of 2-(3,4-dimethoxyphenyl)-2-methylpropanoic acid (2.5 g, 11.15 mmol) in EtOH (50 mL) with $H_2SO_4$ (cat.) was heated at reflux 12 h. The mixture was cooled to room temperature and the solvent was evaporated under reduced pressure. The residue was dissolved in EtOAc and washed with satd $NaHCO_3$ and brine. The organic layer was dried over $MgSO_4$, filtered and concentrated to give ethyl 2-(3,4-dimethoxyphenyl)-2-methylpropanoate (2.81 g, quant), which was used without further purification. $^1H$ NMR (400 MHz, $CDCl_3$) δ 6.95-6.78 (m, 3H), 4.14 (q, 2H), 3.88 (s, 3H), 3.87 (s, 3H), 1.56 (s, 6H), 1.19 (t. 3H).

A solution of ethyl 2-(3,4-dimethoxyphenyl)-2-methylpropanoate (2.84 g, 11.26 mmol) and hydrazine hydrate (7.00 mL, 112.56 mmol) in MeOH (15 mL) was heated at 110° C. in a sealed tube. After 12 h, additional hydrazine hydrate (10 mL) was added to the reaction mixture, which then was heated for additional 6 h. The cooled mixture was concentrated to afford 2-(3,4-dimethoxyphenyl)-2-methylpropanehydrazide (2.75 g, quant) as a liquid. $^1H$ NMR (400 MHz, $CDCl_3$) δ 6.94-6.91 (m, 1H), 6.87-6.81 (m, 2H), 3.88 (s, 3H), 3.87 (s, 3H), 3.69 (br s, 3H), 1.56 (s, 6H).

A mixture of 2-(3,4-dimethoxyphenyl)-2-methylpropanehydrazide (1.04 g, 4.37 mmol) and 4-fluorophenyl isothiocyanate (1.34 g, 8.73 mmol) in EtOH (30 mL) was heated at reflux 2 h. The reaction mixture was cooled and filtered. The filtrate was concentrated in vacuo and the residue was triturated with $Et_2O$. The solids were collected by filtration and dried in vacuo to give 2-(2-(3,4-dimethoxyphenyl)-2-methylpropanoyl)-N-(4-fluorophenyl)hydrazinecarbothioamide (1.23 g, 72%). $^1H$ NMR (400 MHz, DMSO-$d_6$) δ 9.70 (br s, 1H), 9.65 (br s, 1H), 7.38 (b, 1H), 7.17 (t, 3H), 6.94-6.82 (m, 4H), 3.73 (s, 3H), 3.71 (s, 3H), 1.52 (s, 6H).

A mixture of 2-(2-(3,4-dimethoxyphenyl)-2-methylpropanoyl)-N-(4-fluorophenyl)-hydrazinecarbothioamide (1.23 g, 3.14 mmol) and 2N NaOH (25 mL) was refluxed overnight. The reaction mixture was cooled to room temperature and acidified with 3N HCl to pH 5. The aqueous solution was extracted with DCM (30 mL×2). The combined organic layers were dried over $MgSO_4$, filtered, and evaporated. The residue was purified by flash chromatography to give the title compound (760 mg, 65%) as a white solid. $^1H$ NMR (400 MHz, $CDCl_3$) δ 12.52 (s, 1H), 6.94-6.90 (m, 2H), 6.70 (d, 1H), 6.60-6.57 (m, 2H), 6.50-6.46 (m, 2H), 3.89 (s, 3H), 3.77 (s, 3H), 1.57 (s, 6H).

5-(2-(4-chloro-3-methoxyphenyl)propan-2-yl)-4-(4-fluorophenyl)-4H-1,2,4-triazole-3-thiol

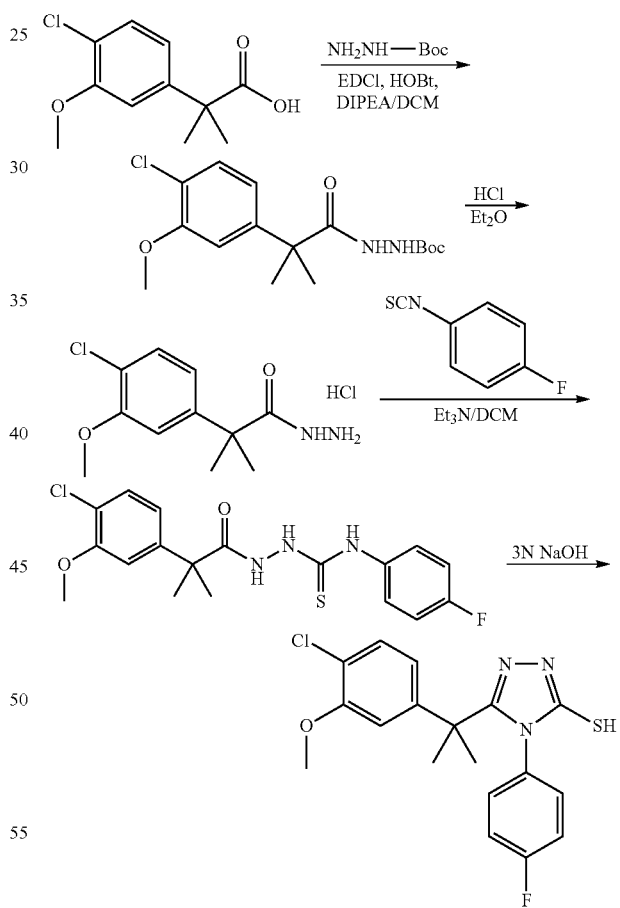

To a solution of carboxylic acid 1 (10 g, 0.04 mol) in $CH_2Cl_2$ (100 mL) was added DIPEA (38 mL, 0.22 mol, 5.0 eq.), tert-butyl carbazate (6.94 g, 0.05 mol, 1.2 eq.), HOBt (0.3 g, 0.002 mol, 0.05 eq.) and EDCI (25.15 g, 0.13 mol, 3.0 eq.). The reaction mixture was stirred for 15 h and mixture was washed with 10% citric acid, said $NaHCO_3$ and brine successively, dried over $MgSO_4$, filtered and concentrated under reduced pressure to give tert-butyl 2-(2-(4-chloro-3- methoxyphenyl)-2-methylpropanoyl)hydrazine carboxylate as a brown solid (12.63 g, 84%). $^1$H NMR (400 MHz, CDCl$_3$) δ 7.35-7.34 (d, 1H), 6.99 (s, 1H), 6.96-6.93 (dd, 1H), 6.86 (s, 1H), 6.28 (s, 1H), 3.94 (s, 3H), 1.60 (s, 6H), 1.45 (s, 9H).

To a solution of tert-butyl 2-(2-(4-chloro-3-methoxyphenyl)-2-methylpropanoyl)hydrazine carboxylate (12.63 g, 0.04 mol) in EtOAc (100 mL) at 0° C. was added 2M HCl in Et$_2$O (92 mL). The resulting solution was stirred at room temperature 18 h and concentrated in vacuo. The residue was triturated with Et$_2$O, collected by filtration and dried to give 2-(4-chloro-3-methoxyphenyl)-2-methylpropanehydrazide hydrochloride (6.88 g, 67%) as a white solid. $^1$H NMR (400 MHz, DMSO) δ 11.64 (s, 1H), 7.41-7.39 (d, 1H), 7.01 (s, 1H), 6.92-6.89 (d, 1H), 3.91 (s, 3H), 1.53 (s, 6H).

To a solution of 2-(4-chloro-3-methoxyphenyl)-2-methylpropanehydrazide hydrochloride (6.88 g, 0.02 mol) and 4-fluorophenylisothiocyanate (3.96 g, 0.03 mol, 1.05 eq.) in DCM (500 mL) at 0° C. was added Et$_3$N (7 mL, 1.29 mol, 2.0 eq.) and the resulting solution was stirred for 1.5 h at room temperature. The reaction mixture was washed with 1M HCl, satd NaHCO$_3$ and brine, dried over MgSO$_4$, filtered and concentrated in vacuo. The residue was triturated with DCM/Et$_2$O, collected by filtration and dried to give 2-(2-(4-Chloro-3-methoxyphenyl)-2-methylpropanoyl)-N-(4-fluorophenyl)hydrazine carbothioamide (8.13 g, 83% as a white solid. $^1$H NMR (400 MHz, CDCl$_3$) δ 7.32-7.30 (d, 1H), 7.25-7.22 (m, 2H), 7.01-7.05 (t, 2H), 6.95-6.94 (d, 1H), 6.93-6.90 (dd, 1H), 3.88 (s, 3H), 1.64 (s, 6H).

A solution of 2-(2-(4-chloro-3-methoxyphenyl)-2-methylpropanoyl)-N-(4-fluorophenyl)-hydrazine carbothioamide (8.13 g, 0.02 mol) in 3N NaOH (270 mL) was heated at reflux 4 h with mechanical stirring. The reaction mixture was cooled to 5° C. and acidified with 5N HCl to pH=4. The resulting whited solids were collected by filtration, washed with Et$_2$O and dried to give the title compound (7.5 g, 96%). $^1$H NMR (400 MHz, DMSO-d$_6$) δ 7.23-7.21 (d, 1H), 6.95-6.91 (t, 2H), 6.54 (d, 1H), 6.52-6.49 (dd, 1H), 6.45-6.41 (m, 2H), 3.67 (s, 3H), 1.45 (s, 6H).

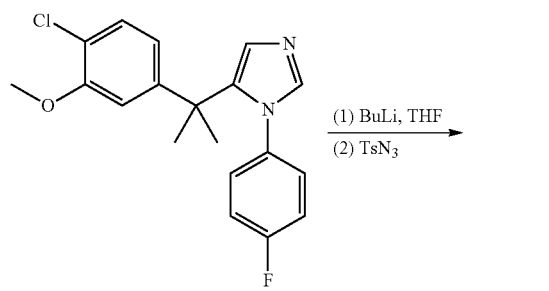

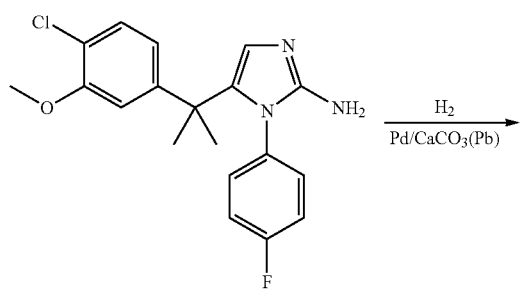

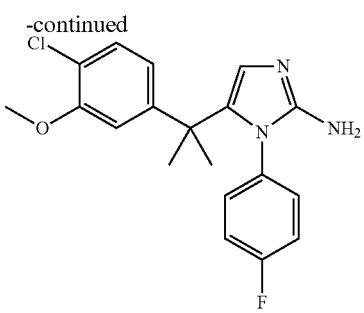

To a −78° C. solution of 5-(2-(4-chloro-3-methoxyphenyl)propan-2-yl)-1-(4-fluorophenyl)-1H-imidazole (0.215 g, 0.62 mmol) in 3 mL of THF (3 mL) was added 1.67 M BuLi (0.45 mL, 0.75 mmol). The reaction was stirred at −78° C. for 30 min and then tosyl azide (0.160 g, 0.81 mmol) in THF (0.5 mL) was added dropwise. The reaction was stirred at −78° C. for 1 h when it was determined to be complete by LCMS. The reaction was quenched at −78° C. with pH 7 buffer and allowed to warm to room temperature. The mixture was extracted with DCM (3×10 mL) and dried with MgSO$_4$. The residue was purified by column chromatography using Hex:EtOAc as eluents to afford 2-azido-5-(2-(4-chloro-3-methoxyphenyl)propan-2-yl)-1-(4-fluorophenyl)-1H-imidazole (131 mg) as a yellow oil. MS (EI) m/z 386 [M+H]$^+$.

A solution of 2-azido-5-(2-(4-chloro-3-methoxyphenyl)propan-2-yl)-1-(4-fluorophenyl)-1H-imidazole (0.126 g, 0.33 mmol) was added MeOH-THF (3 mL, 1:1, v/v) was sparged with argon briefly. Next 5% Pd on CaCO$_3$ poisoned with lead was added to the flask, which then was purged with hydrogen and stirred under 1 atm hydrogen. After 3 h, when the reaction was shown to be complete by LCMS, the mixture was filtered through Celite™ and concentrated in vacuo to afford 5-(2-(4-chloro-3-methoxyphenyl)propan-2-yl)-1-(4-fluorophenyl)-1H-imidazol-2-amine (93 mg) as a beige solid. MS (EI) m/z 360 [M+H]$^+$.

Effect of Compounds on Oral Glucose Tolerance in Fasted and Chow Fed Normal C57BL6 Mice After an overnight fast, 64 male C57BL6 mice are given an oral glucose bolus (3 g/kg) followed by blood sampling via tail vein for glucose measurement by glucometer. Animal weights are collected the day before the study for calculation of glucose dose volume.

Compounds or vehicle are administered 15 minutes before glucose administration. Glucose (45%) purchased from SIGMA (St. Louis, Mo.) is used. Vehicle is 80% PEG 400, 20% Tween™ 80 for groups 1-4 and CMC for groups 5-8. Animals are dosed at 3 g/kg once PO via a 5 cc syringe with a feeding needle (0.1 mL/mouse).

Blood glucose levels are measured from the tail vein using a glucometer at 0, 15, 30, 60 and 120 minutes following oral glucose administration (3 g/kg).

Groups:

| Group # | Animals | Treatment |
|---|---|---|
| 1 | 1-8 | Vehicle-PEG |
| 2 | 9-16 | Compound 11-30 mg/kg-PEG |
| 3 | 17-24 | Compound 259-30 mg/kg-PEG |
| 4 | 25-32 | Vehicle-CMC |

-continued

| Group # | Animals | Treatment |
| --- | --- | --- |
| 5 | 33-40 | Compound 11-30 mg/kg-CMC |
| 6 | 41-48 | Compound 259-30 mg/kg-CMC |

Figure 3:
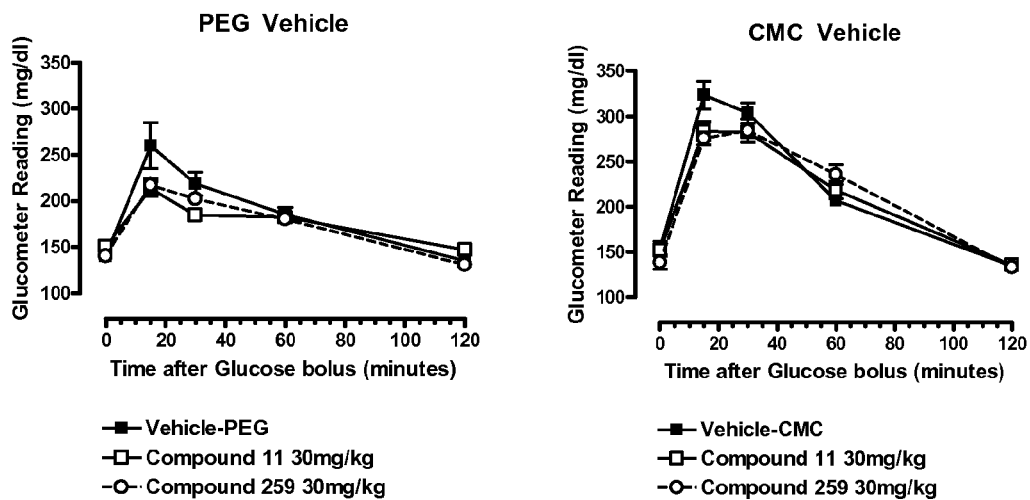
FIG. 3 is a graph illustrating the effect of compounds on oral glucose tolerance in fasted and chow-fed normal C57BL6 mice.

The results for the effect on blood glucose for each of the preceding groups are shown in FIG. 3.

Example 1

Effect of Compounds 11 and 259 on Plasma Total GLP-1 Secretion in C57BL6 Mice

Twenty-four male C57BL6 mice fasted overnight are treated with compounds followed by blood sampling (250 μL, 15 minutes post-dose) via orbital sinus for GLP-1 (total) measurement. Compounds or vehicle are administered 15 minutes before T0 bleed. The blood is collected from the (Isoflurane anesthetized) orbital sinus in EDTA coated tubes containing 500 KIU aprotinin/mL of blood (MP Biomedicals, #190779) and 10 μL DPP-IV inhibitor/ml of blood (Linco, # DPPIV-010).

Plasma is analyzed for total GLP-1 by MSD.
Groups:

| Group # | Animals | Treatment |
| --- | --- | --- |
| 1 | 1-8 | Vehicle |
| 2 | 9-16 | Compound 11-30 mg/kg |
| 3 | 17-24 | Compound 259-30 mg/kg |

Figure 4:
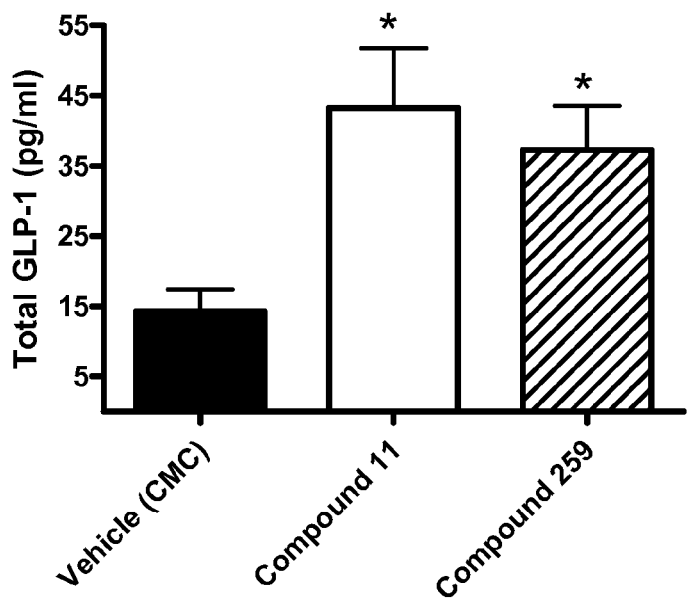
FIG. 4 is a graph illustrating the effect of compounds 11 and 259 on plasma total GLP-1 secretion in C57BL6 mice.

The results for the effect on GLP-1 secretion for each of the preceding groups are shown in FIG. 4.

TGR5 cAMP Assay Using Cisbio™ cAMP Dynamic2 htrf Assay Kit

Compounds were diluted in DPBS with 5% DMSO (8-point serial dilution by half logs) in a 96-well plate and 1 μL was transferred to a 384-well assay plate in quadruplicate. The d2-cAMP and anti-cAMP Ab-cryptate stock solution were prepared as per the instructions in the Cisbio™ (Bedford, Mass.) kit. Cells (hTGR5CRE-luc HEK 293 and mTGR5CRE-luc HEK 293) were harvested using cell dissociation buffer and resuspended in DPBS. Cells were adjusted to $0.44 \times 10^6$ cells/ml followed by addition of IBMX to a final concentration of 0.5 mM. The cells were then mixed with d2-cAMP solution (7.1 mL cells+100 ul d2-cAMP) and 4000 cells (9 μL) were transferred to each well of the 384-well assay plate. Cells without d2-cAMP were added to eight wells as a negative control. The plate was covered and incubated at room temp for 30 min. Then 10 μL of Ab-cryptate solution was added to each well of the assay plate and incubated for 1 hr. The plate was read on an EnVision™ plate reader (Perkin-Elmer, Waltham, Mass.) and the DeltaF value was calculated as per the instructions in the Cisbio™ kit.

Glucagon-like Peptide-1 (GLP-1) Secretion Assays

Mouse enteroendocrine STC-1 cells were cultured and maintained in high glucose DMEM (31053-036; Invitrogen, Carlsbad, Calif.) supplemented with 2 mM L-GlutaMAX-I (35050-079; Invitrogen), 15% horse serum, 5% fetal bovine serum (FBS), and 1% penicillin/streptomycin. Two days prior to analysis of GLP-1 secretion, $2 \times 10^5$ cells were seeded in 24-well culture plates in 500 μL of high glucose DMEM media containing 2 mM GlutaMAX-I, 10% charcoal-dextran stripped fetal bovine serum (CD-FBS) (100-119; GEMINI, West Sacramento, Calif.), and 50 μg/mL Gentamicin. On the day of the experiment, cells were washed twice with Hanks' Balanced Salt solution (HBSS) (H8264; Sigma, St. Louis, Mo.) and pre-incubated for 1 hour in 500 μL HBSS. After removal of the HBSS, cells were treated with test compounds in HBSS containing protease inhibitor cocktail (11836153001; Roche, Indianapolis, Ind.), DPP-IV inhibitor (DPP4-010; St. Charles, Mo.), aprotinin, and 0.1% fatty acid free bovine serum albumin (FAF-BSA) (A-0281, Sigma). Supernatants were then collected and 25 μL were used to measure GLP-1 using the Mouse/Rat Total Active GLP-1 MSD Assay Kit (K150HZC; Meso Scale Discovery, Gaithersburg, Md.). The data are presented in FIG. 1.

Figure 2:
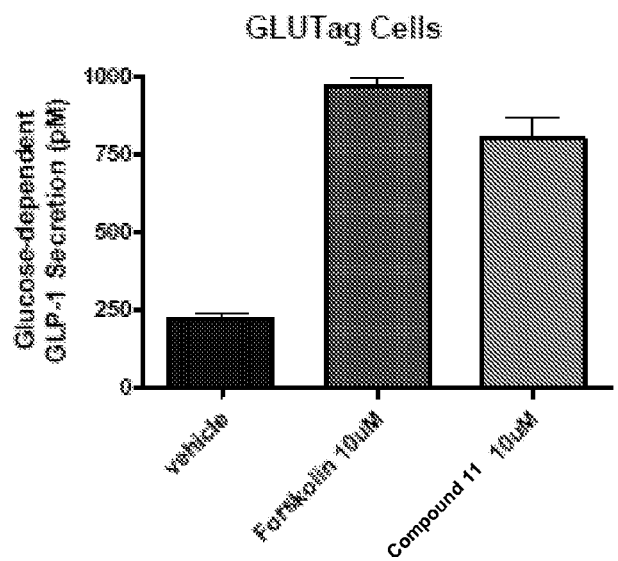
FIG. 2 is a graph illustrating GLP-1 levels in treated murine enteroendocrine GLUTag cells.

Murine enteroendocrine GLUTag cells were cultured and maintained in low glucose DMEM (10567-014; Invitrogen) supplemented with 2 mM L-GlutaMAX-I, 10% FBS, and 1% penicillin/streptomycin. The day before analysis of GLP-1 secretion, $2.5 \times 10^5$ cells were seeded in 24-well Matrigel-coated plates in 500 μL of DMEM containing 3 mM glucose, 10% CD-FBS, and 50 μg/mL Gentamicin. On the day of the experiment, cells were washed with PBS and treated with test compounds for 1 hour in 200 μL DMEM containing 15 mM glucose, protease inhibitor cocktail, DPP-IV inhibitor, aprotinin, and 0.1% FAF-BSA. Supernatants were then collected and 25 μL were used to measure GLP-1 using the Mouse/Rat Total Active GLP-1 MSD Assay Kit. The data are presented in FIG. 2.

TGR5/CRE-Luciferiase Assay

HEK 293 cells stably expressing human TGR5 (h-TGR5) or mouse TGR5 (m-TGR5) were generated from HEK 293 CRE-Luciferase cells. The day before the assay, HEK 293 hTGR5/CRE-Luc cells were plated in DMEM in a 384 well assay plate at a density of 25 k cells/45 μL per well and grown for 18-20 hours. Compounds were serially diluted in DMEM containing 5% DMSO and 5 μL of compound or media alone was transferred to each well and plates were incubated for 6 hours. Following incubation, 30 μL of lysis/luciferase buffer was added to each well. The luciferase activity was then measured on the EnVision™ plate reader and the dose response data was analyzed using ActivityBase.

TGR5 Assay Results

In the following tables, $EC_{50}$ values determined according to the TGR5 cAMP Assay described herein (cAMP); $EC_{50}$ values determined according to the TGR5/CRE-Luciferiase Assay described herein (CRE-Luc). Tables 1 and 2 display h-TGR5CRE-Luc $EC_{50}$ (nM) and h-TGR5 cAMP $EC_{50}$ (nM) data, coded as follows: A<100 nM; C=100-1000 nM; D>1000 nM and less than 10,000 nM. The following compounds in Tables 1 and 2 were made by using procedures described in the above Schemes and Examples, and, where applicable, by making any necessary substitutions of known materials that one skilled in the art would ordinarily understand how to do.

TABLE 1

| Structure | NAME | cAMP (EC$_{50}$) (nM) | CRE-Luc (EC$_{50}$) (nM) |
|---|---|---|---|
| 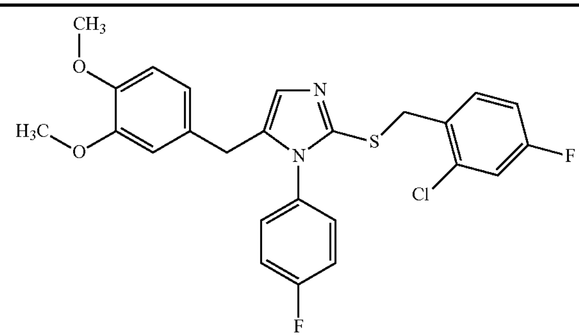 | 5-{[3,4-bis(methyloxy)phenyl]methyl}-2-{[(2-chloro-4-fluorophenyl)methyl]thio}-1-(4-fluorophenyl)-1H-imidazole | A | A |
| 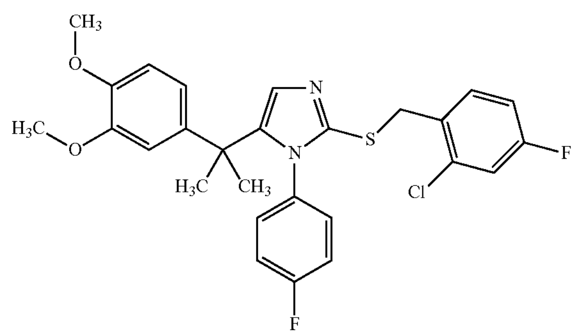 [SMILES: COc1ccc(C(C)(C)c2cnc(SCc3ccc(F)cc3Cl)n2-c2ccc(F)cc2)cc1OC] | 5-{1-[3,4-bis(methyloxy)phenyl]-1-methylethyl}-2-{[(2-chloro-4-fluorophenyl)methyl]thio}-1-(4-fluorophenyl)-1H-imidazole | C | A |
| 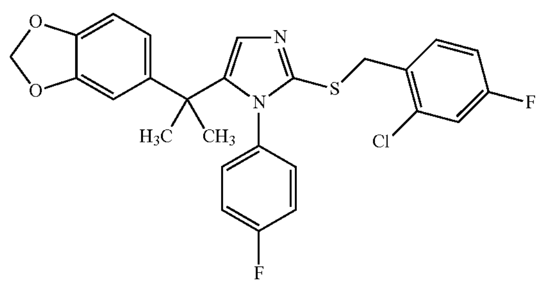 [SMILES: CC(C)(c1ccc2c(c1)OCO2)c1cnc(SCc2ccc(F)cc2Cl)n1-c1ccc(F)cc1] | 5-[1-(1,3-benzodioxol-5-yl)-1-methylethyl]-2-{[(2-chloro-4-fluorophenyl)methyl]thio}-1-(4-fluorophenyl)-1H-imidazole | | C |

TABLE 1-continued

| Structure | NAME | cAMP (EC$_{50}$) (nM) | CRE-Luc (EC$_{50}$) (nM) |
|---|---|---|---|
| 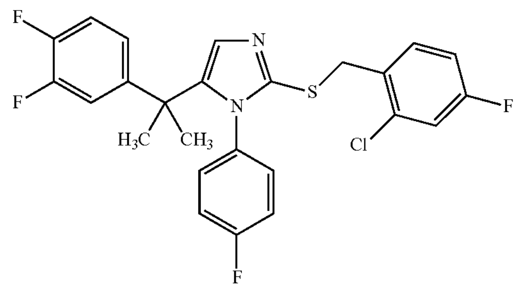 [SMILES: CC(C)(c1ccc(F)c(F)c1)c1cnc(SCc2ccc(F)cc2Cl)n1-c1ccc(F)cc1] | 2-{[(2-chloro-4-fluorophenyl)methyl]thio}-5-[1-(3,4-difluorophenyl)-1-methylethyl]-1-(4-fluorophenyl)-1H-imidazole | | C |
| 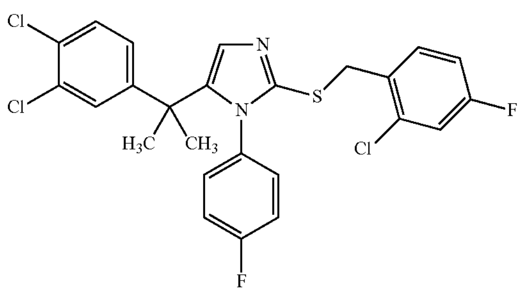 [SMILES: CC(C)(c1ccc(Cl)c(Cl)c1)c1cnc(SCc2ccc(F)cc2Cl)n1-c1ccc(F)cc1] | 2-{[(2-chloro-4-fluorophenyl)methyl]thio}-5-[1-(3,4-dichlorophenyl)-1-methylethyl]-1-(4-fluorophenyl)-1H-imidazole | | C |
| 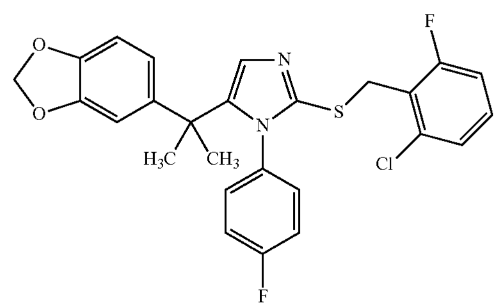 [SMILES: CC(C)(c1ccc2c(c1)OCO2)c1cnc(SCc2c(F)cccc2Cl)n1-c1ccc(F)cc1] | 5-[1-(1,3-benzodioxol-5-yl)-1-methylethyl]-2-{[(2-chloro-6-fluorophenyl)methyl]thio}-1-(4-fluorophenyl)-1H-imidazole | | A |

TABLE 1-continued

| Structure | NAME | cAMP (EC$_{50}$) (nM) | CRE-Luc (EC$_{50}$) (nM) |
|---|---|---|---|
| 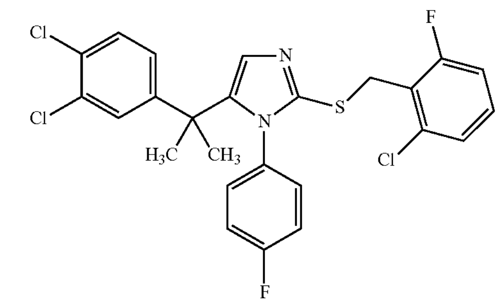 | 2-{[(2-chloro-6-fluorophenyl)methyl]thio}-5-[1-(3,4-dichlorophenyl)-1-methylethyl]-1-(4-fluorophenyl)-1H-imidazole | C | A |
| 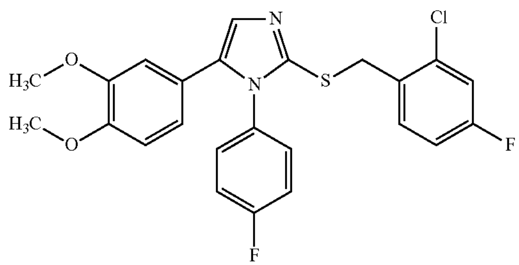 [SMILES: COc1ccc(-c2cnc(SCc3ccc(F)cc3Cl)n2-c2ccc(F)cc2)cc1OC] | 5-[3,4-bis(methyloxy)phenyl]-2-{[(2-chloro-4-fluorophenyl)methyl]thio}-1-(4-fluorophenyl)-1H-imidazole | | D |
| 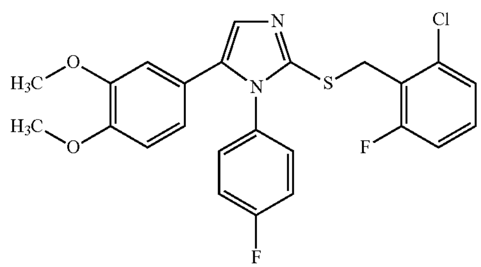 [SMILES: COc1ccc(-c2cnc(SCc3c(F)cccc3Cl)n2-c2ccc(F)cc2)cc1OC] | 5-[3,4-bis(methyloxy)phenyl]-2-{[(2-chloro-6-fluorophenyl)methyl]thio}-1-(4-fluorophenyl)-1H-imidazole | | D |

TABLE 1-continued

| Structure | NAME | cAMP (EC$_{50}$) (nM) | CRE-Luc (EC$_{50}$) (nM) |
|---|---|---|---|
| 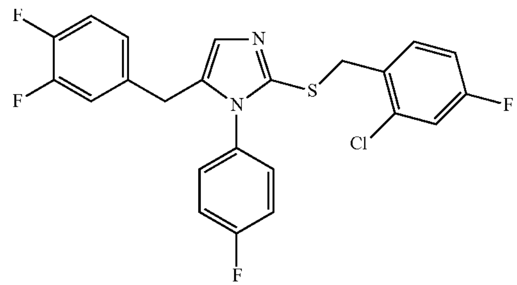 [SMILES: Fc1ccc(-n2c(Cc3ccc(F)c(F)c3)cnc2SCc2ccc(F)cc2Cl)cc1] | 2-{[(2-chloro-4-fluorophenyl)methyl]thio}-5-[(3,4-difluorophenyl)methyl]-1-(4-fluorophenyl)-1H-imidazole | | C |
| 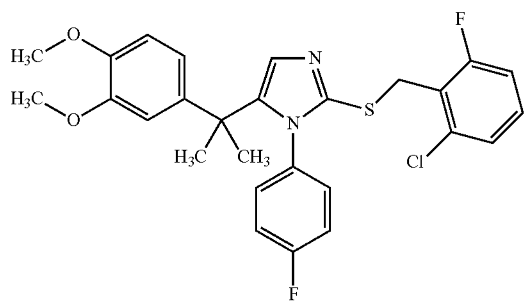 | 5-{1-[3,4-bis(methyloxy)phenyl]-1-methylethyl}-2-{[(2-chloro-6-fluorophenyl)methyl]thio}-1-(4-fluorophenyl)-1H-imidazole | A | A |
| 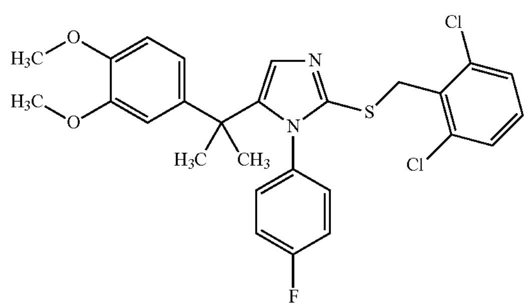 [SMILES: COc1ccc(C(C)(C)c2cnc(SCc3c(Cl)cccc3Cl)n2-c2ccc(F)cc2)cc1OC] | 5-{1-[3,4-bis(methyloxy)phenyl]-1-methylethyl}-2-{[(2,6-dichlorophenyl)methyl]thio}-1-(4-fluorophenyl)-1H-imidazole | A | A |

TABLE 1-continued

| Structure | NAME | cAMP (EC$_{50}$) (nM) | CRE-Luc (EC$_{50}$) (nM) |
|---|---|---|---|
| 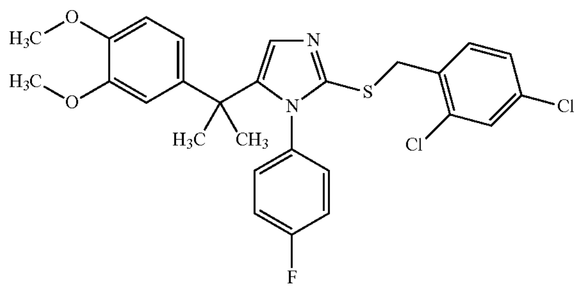 [SMILES: COc1ccc(C(C)(C)c2cnc(SCc3ccc(Cl)cc3Cl)n2-c2ccc(F)cc2)cc1OC] | 5-{1-[3,4-bis(methyloxy)phenyl]-1-methylethyl}-2-{[(2,4-dichlorophenyl)methyl]thio}-1-(4-fluorophenyl)-1H-imidazole | | A |
| 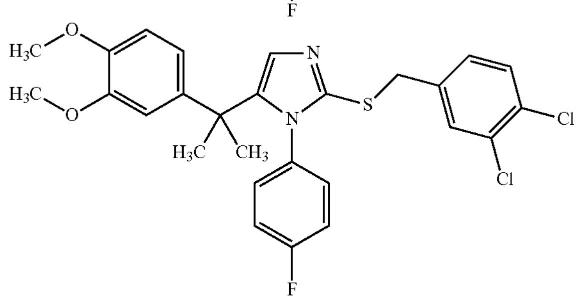 | 5-{1-[3,4-bis(methyloxy)phenyl]-1-methylethyl}-2-{[(3,4-dichlorophenyl)methyl]thio}-1-(4-fluorophenyl)-1H-imidazole | | A |
| | 5-{1-[3,4-bis(methyloxy)phenyl]-1-methylethyl}-1-(4-fluorophenyl)-2-{[[2-fluoro-6-(trifluoromethyl)phenyl]methyl]thio}-1H-imidazole | A | A |

TABLE 1-continued

| Structure | NAME | cAMP (EC$_{50}$) (nM) | CRE-Luc (EC$_{50}$) (nM) |
|---|---|---|---|
| 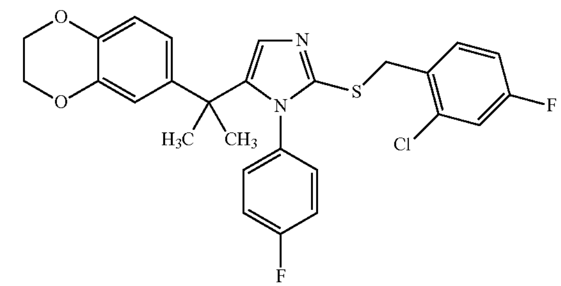 [SMILES: CC(C)(c1ccc2c(c1)OCCO2)c1cnc(SCc2ccc(F)cc2Cl)n1-c1ccc(F)cc1] | 2-{[(2-chloro-4-fluorophenyl)methyl]thio}-5-[1-(2,3-dihydro-1,4-benzodioxin-6-yl)-1-methylethyl]-1-(4-fluorophenyl)-1H-imidazole | | A |
| 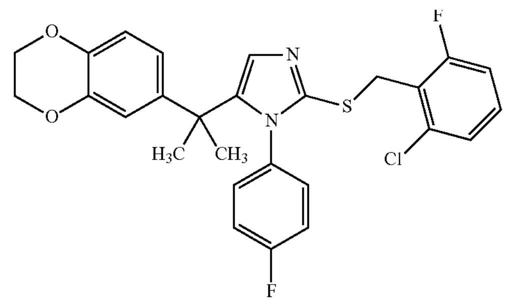 [SMILES: CC(C)(c1ccc2c(c1)OCCO2)c1cnc(SCc2c(F)cccc2Cl)n1-c1ccc(F)cc1] | 2-{[(2-chloro-6-fluorophenyl)methyl]thio}-5-[1-(2,3-dihydro-1,4-benzodioxin-6-yl)-1-methylethyl]-1-(4-fluorophenyl)-1H-imidazole | | A |
| 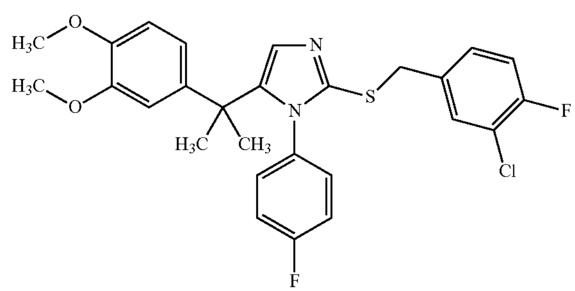 [SMILES: COc1ccc(C(C)(C)c2cnc(SCc3ccc(F)c(Cl)c3)n2-c2ccc(F)cc2)cc1OC] | 5-{1-[3,4-bis(methyloxy)phenyl]-1-methylethyl}-2-{[(3-chloro-4-fluorophenyl)methyl]thio}-1-(4-fluorophenyl)-1H-imidazole | | A |

TABLE 1-continued

| Structure | NAME | cAMP (EC$_{50}$) (nM) | CRE-Luc (EC$_{50}$) (nM) |
|---|---|---|---|
| | 5-{1-[3,4-bis(methyloxy)phenyl]-1-methylethyl}-2-{[(2-chloro-6-fluorophenyl)methyl]sulfonyl]}-1-(4-fluorophenyl)-1H-imidazole | | A |
| | 5-{1-[3,4-bis(methyloxy)phenyl]-1-methylethyl}-2-{[(2-chloro-5-fluorophenyl)methyl]thio]}-1-(4-fluorophenyl)-1H-imidazole | A | A |
| | 5-{1-[3,4-bis(methyloxy)phenyl]-1-methylethyl}-2-{[(3-chloro-5-fluorophenyl)methyl]thio]}-1-(4-fluorophenyl)-1H-imidazole | A | A |

TABLE 1-continued

| Structure | NAME | cAMP (EC$_{50}$) (nM) | CRE-Luc (EC$_{50}$) (nM) |
|---|---|---|---|
| 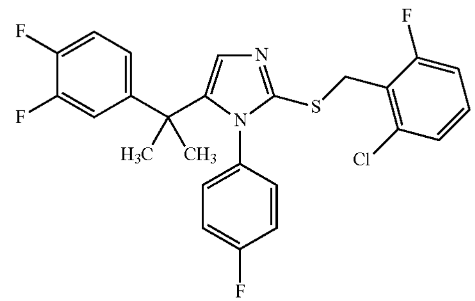 [SMILES: CC(C)(c1ccc(F)c(F)c1)c1cnc(SCc2c(F)cccc2Cl)n1-c1ccc(F)cc1] | 2-{[(2-chloro-6-fluorophenyl)methyl]thio}-5-[1-(3,4-difluorophenyl)-1-methylethyl]-1-(4-fluorophenyl)-1H-imidazole | | A |
| 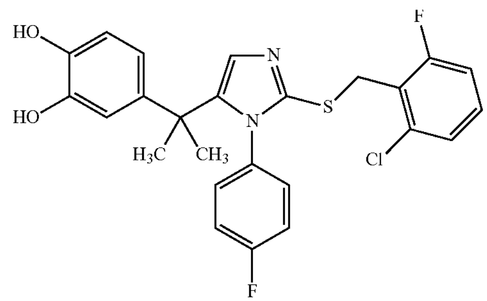 [SMILES: CC(C)(c1ccc(O)c(O)c1)c1cnc(SCc2c(F)cccc2Cl)n1-c1ccc(F)cc1] | 4-{1-[2-{[(2-chloro-6-fluorophenyl)methyl]thio}-1-(4-fluorophenyl)-1H-imidazol-5-yl]-1-methylethyl}benzene-1,2-diol | C | A |
| 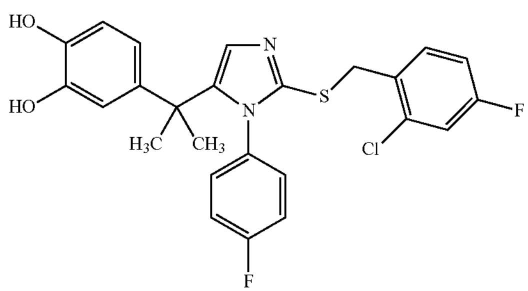 [SMILES: CC(C)(c1ccc(O)c(O)c1)c1cnc(SCc2ccc(F)cc2Cl)n1-c1ccc(F)cc1] | 4-{1-[2-{[(2-chloro-4-fluorophenyl)methyl]thio}-1-(4-fluorophenyl)-1H-imidazol-5-yl]-1-methylethyl}benzene-1,2-diol | | A |

TABLE 1-continued

| Structure | NAME | cAMP (EC$_{50}$) (nM) | CRE-Luc (EC$_{50}$) (nM) |
|---|---|---|---|
| 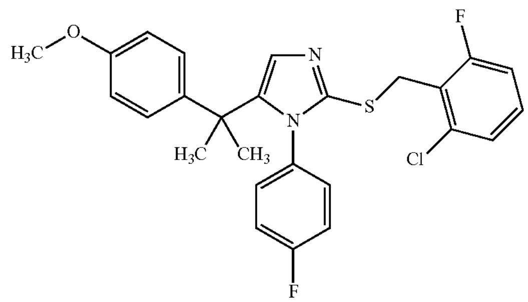 [SMILES: COc1ccc(C(C)(C)c2cnc(SCc3c(F)cccc3Cl)n2-c2ccc(F)cc2)cc1] | 2-{[(2-chloro-6-fluorophenyl)methyl]thio}-1-(4-fluorophenyl)-5-{1-methyl-1-[4-(methyloxy)phenyl]ethyl}-1H-imidazole | C | A |
| 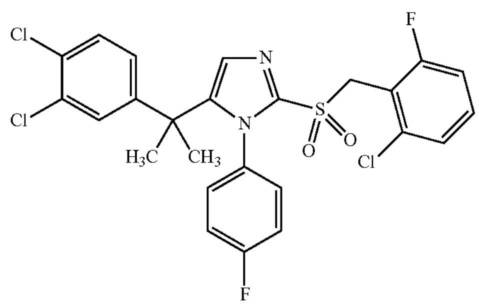 [SMILES: CC(C)(c1ccc(Cl)c(Cl)c1)c1cnc(S(=O)(=O)Cc2c(F)cccc2Cl)n1-c1ccc(F)cc1] | 2-{[(2-chloro-6-fluorophenyl)methyl]sulfonyl}-5-[1-(3,4-dichlorophenyl)-1-methylethyl]-1-(4-fluorophenyl)-1H-imidazole | | C |
| 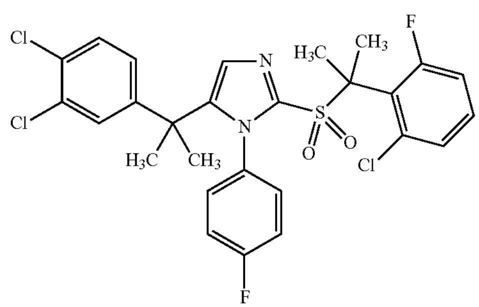 [SMILES: CC(C)(c1ccc(Cl)c(Cl)c1)c1cnc(S(=O)(=O)C(C)(C)c2c(F)cccc2Cl)n1-c1ccc(F)cc1] | 2-{[1-(2-chloro-6-fluorophenyl)-1-methylethyl]sulfonyl}-5-[1-(3,4-dichlorophenyl)-1-methylethyl]-1-(4-fluorophenyl)-1H-imidazole | | C |

TABLE 1-continued

| Structure | NAME | cAMP (EC$_{50}$) (nM) | CRE-Luc (EC$_{50}$) (nM) |
|---|---|---|---|
| 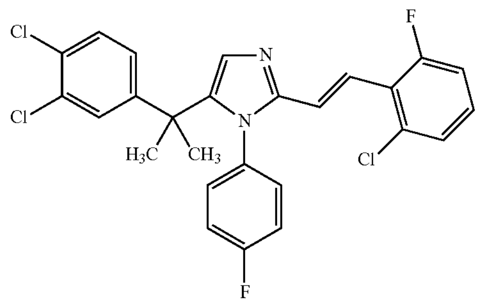 [SMILES: CC(C)(c1ccc(Cl)c(Cl)c1)c1cnc(/C=C/c2c(F)cccc2Cl)n1-c1ccc(F)cc1] | 2-[(E)-2-(2-chloro-6-fluorophenyl)ethenyl]-5-[1-(3,4-dichlorophenyl)-1-methylethyl]-1-(4-fluorophenyl)-1H-imidazole | | D |
| 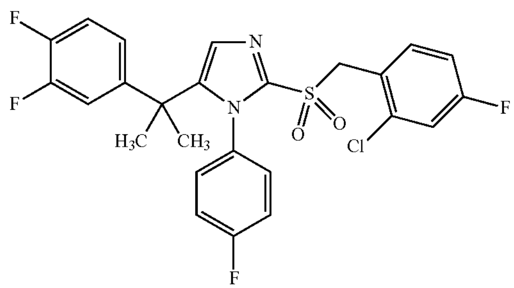 [SMILES: CC(C)(c1ccc(F)c(F)c1)c1cnc(S(=O)(=O)Cc2ccc(F)cc2Cl)n1-c1ccc(F)cc1] | 2-{[(2-chloro-4-fluorophenyl)methyl]sulfonyl}-5-[1-(3,4-difluorophenyl)-1-methylethyl]-1-(4-fluorophenyl)-1H-imidazole | | D |
| 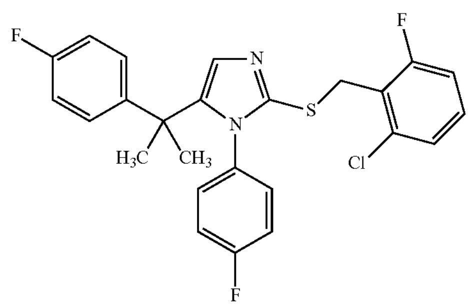 [SMILES: CC(C)(c1ccc(F)cc1)c1cnc(SCc2c(F)cccc2Cl)n1-c1ccc(F)cc1] | 2-{[(2-chloro-6-fluorophenyl)methyl]thio}-1-(4-fluorophenyl)-5-[1-(4-fluorophenyl)-1-methylethyl]-1H-imidazole | | C |

TABLE 1-continued
| Structure | NAME | cAMP (EC$_{50}$) (nM) | CRE-Luc (EC$_{50}$) (nM) |
|---|---|---|---|
| 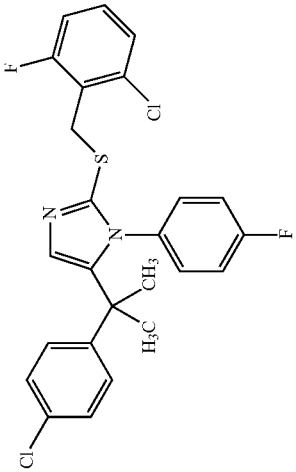 | 2-{[(2-chloro-6-fluorophenyl)methyl]thio}-5-[1-(4-chlorophenyl)-1-methylethyl]-1-(4-fluorophenyl)-1H-imidazole | | C |
| 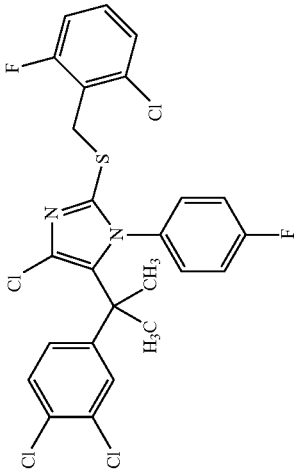 | 4-chloro-2-{[(2-chloro-6-fluorophenyl)methyl]thio}-5-[1-(3,4-dichlorophenyl)-1-methylethyl]-1-(4-fluorophenyl)-1H-imidazole | | C |
| 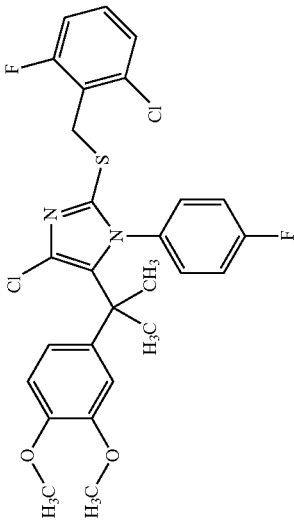 | 5-{1-[3,4-bis(methyloxy)phenyl]-1-methylethyl}-4-chloro-2-{[(2-chloro-6-fluorophenyl)methyl]thio}-1-(4-fluorophenyl)-1H-imidazole | A | A |

TABLE 1-continued

| Structure | NAME | cAMP (EC$_{50}$) (nM) | CRE-Luc (EC$_{50}$) (nM) |
|---|---|---|---|
| 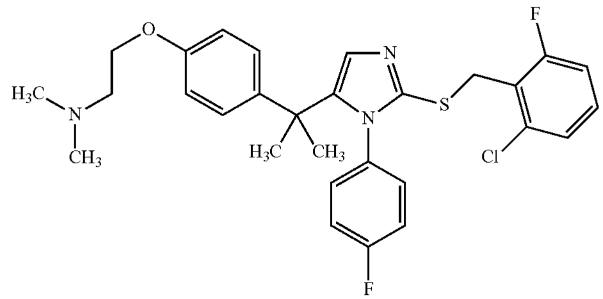 [SMILES: CN(C)CCOc1ccc(C(C)(C)c2cnc(SCc3c(F)cccc3Cl)n2-c2ccc(F)cc2)cc1] | 2-[(4-{1-[2-{[(2-chloro-6-fluorophenyl)methyl]thio}-1-(4-fluorophenyl)-1H-imidazol-5-yl]-1-methylethyl}phenyl)oxy]-N,N-dimethylethanamine | | D |
| 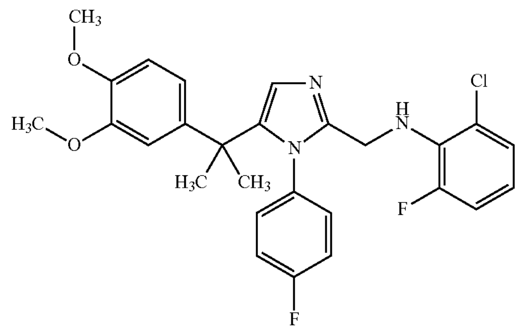 [SMILES: COc1ccc(C(C)(C)c2cnc(CNc3c(F)cccc3Cl)n2-c2ccc(F)cc2)cc1OC] | N-{[5-{1-[3,4-bis(methyloxy)phenyl]-1-methylethyl}-1-(4-fluorophenyl)-1H-imidazol-2-yl]methyl}-2-chloro-6-fluoroaniline | C | A |
| 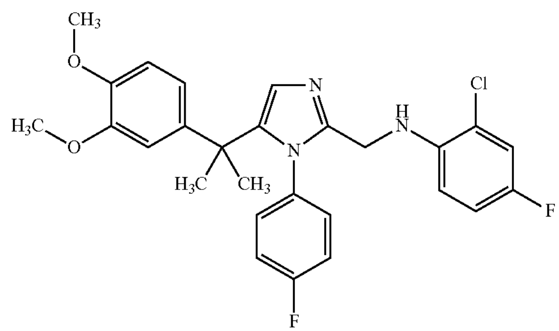 [SMILES: COc1ccc(C(C)(C)c2cnc(CNc3ccc(F)cc3Cl)n2-c2ccc(F)cc2)cc1OC] | N-{[5-{1-[3,4-bis(methyloxy)phenyl]-1-methylethyl}-1-(4-fluorophenyl)-1H-imidazol-2-yl]methyl}-2-chloro-4-fluoroaniline | | A |

TABLE 1-continued

| Structure | NAME | cAMP (EC$_{50}$) (nM) | CRE-Luc (EC$_{50}$) (nM) |
|---|---|---|---|
| 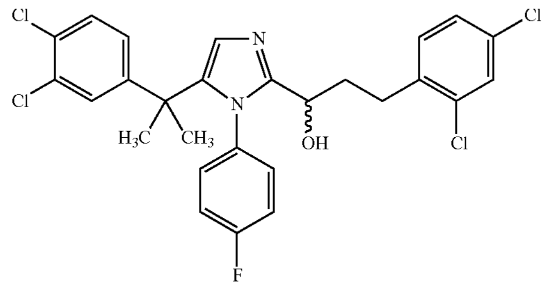 [SMILES: CC(C)(c1ccc(Cl)c(Cl)c1)c1cnc(C(O)CCc2ccc(Cl)cc2Cl)n1-c1ccc(F)cc1] | 3-(2,4-dichlorophenyl)-1-{5-[1-(3,4-dichlorophenyl)-1-methylethyl]-1-(4-fluorophenyl)-1H-imidazol-2-yl}propan-1-ol |  | D |
| 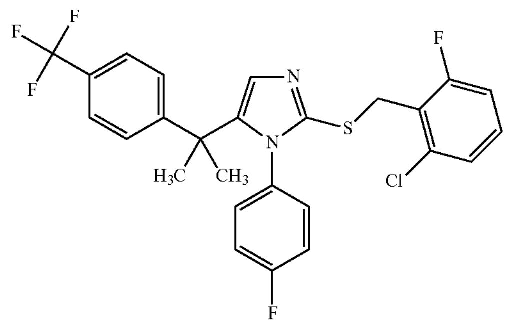 [SMILES: CC(C)(c1ccc(C(F)(F)F)cc1)c1cnc(SCc2c(F)cccc2Cl)n1-c1ccc(F)cc1] | 2-{[(2-chloro-6-fluorophenyl)methyl]thio}-1-(4-fluorophenyl)-5-{1-methyl-1-[4-(trifluoromethyl)phenyl]ethyl}-1H-imidazole |  | C |
| 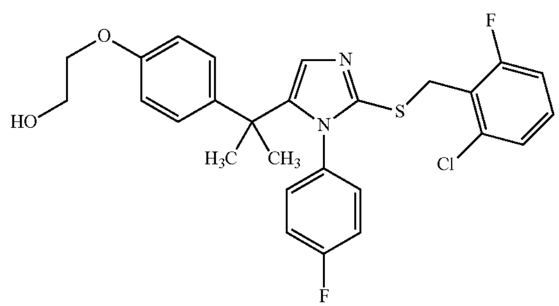 [SMILES: CC(C)(c1ccc(OCCO)cc1)c1cnc(SCc2c(F)cccc2Cl)n1-c1ccc(F)cc1] | 2-[(4-{1-[2-{[(2-chloro-6-fluorophenyl)methyl]thio}-1-(4-fluorophenyl)-1H-imidazol-5-yl]-1-methylethyl}phenyl)oxy]ethanol |  | C |

TABLE 1-continued

| Structure | NAME | cAMP (EC$_{50}$) (nM) | CRE-Luc (EC$_{50}$) (nM) |
|---|---|---|---|
| 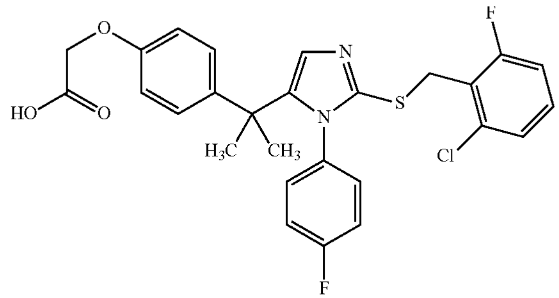 [SMILES: CC(C)(c1ccc(OCC(=O)O)cc1)c1cnc(SCc2c(F)cccc2Cl)n1-c1ccc(F)cc1] | [(4-{1-[2-{[(2-chloro-6-fluorophenyl)methyl]thio}-1-(4-fluorophenyl)-1H-imidazol-5-yl]-1-methylethyl}phenyl)oxy]acetic acid |  | D |
| 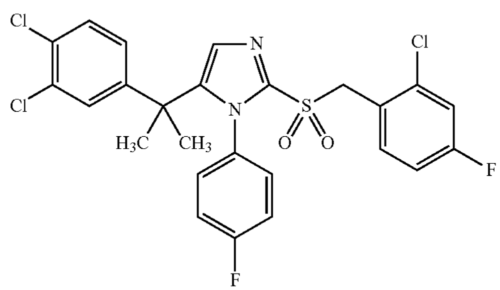 [SMILES: CC(C)(c1ccc(Cl)c(Cl)c1)c1cnc(S(=O)(=O)Cc2ccc(F)cc2Cl)n1-c1ccc(F)cc1] | 2-{[(2-chloro-4-fluorophenyl)methyl]sulfonyl}-5-[1-(3,4-dichlorophenyl)-1-methylethyl]-1-(4-fluorophenyl)-1H-imidazole |  | D |
| 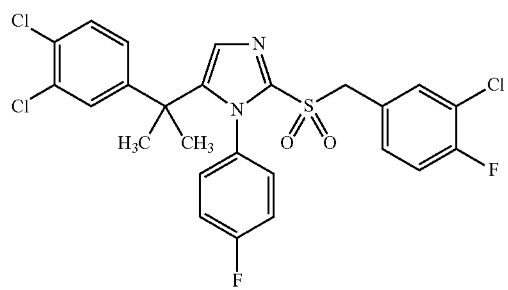 [SMILES: CC(C)(c1ccc(Cl)c(Cl)c1)c1cnc(S(=O)(=O)Cc2ccc(F)c(Cl)c2)n1-c1ccc(F)cc1] | 2-{[(3-chloro-4-fluorophenyl)methyl]sulfonyl}-5-[1-(3,4-dichlorophenyl)-1-methylethyl]-1-(4-fluorophenyl)-1H-imidazole |  | C |

TABLE 1-continued

| Structure | NAME | cAMP (EC$_{50}$) (nM) | CRE-Luc (EC$_{50}$) (nM) |
|---|---|---|---|
| 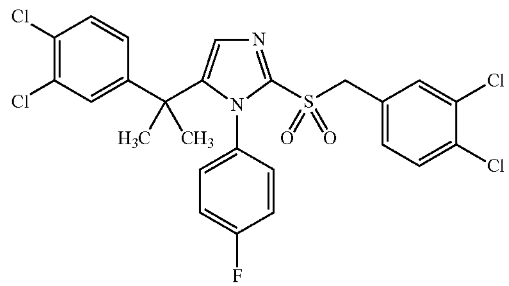 | 5-[1-(3,4-dichlorophenyl)-1-methylethyl]-2-{[(3,4-dichlorophenyl)methyl]sulfonyl}-1-(4-fluorophenyl)-1H-imidazole | | D |
| 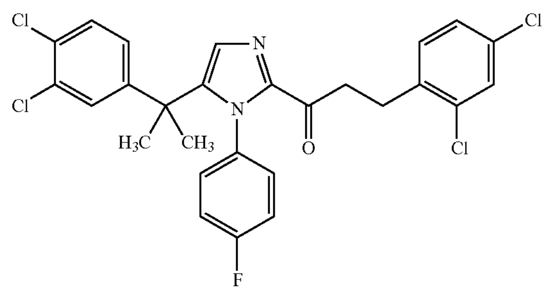 [SMILES: CC(C)(c1ccc(Cl)c(Cl)c1)c1cnc(C(=O)CCc2ccc(Cl)cc2Cl)n1-c1ccc(F)cc1] | 3-(2,4-dichlorophenyl)-1-{5-[1-(3,4-dichlorophenyl)-1-methylethyl]-1-(4-fluorophenyl)-1H-imidazol-2-yl}propan-1-one | | D |
| 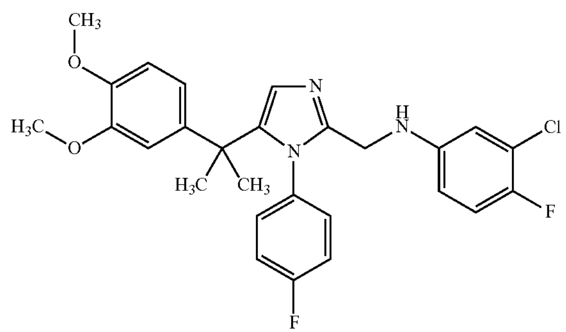 [SMILES: COc1ccc(C(C)(C)c2cnc(CNc3ccc(Cl)c(Cl)c3)n2-c2ccc(F)cc2)cc1OC] | N-{[5-{1-[3,4-bis(methyloxy)phenyl]-1-methylethyl}-1-(4-fluorophenyl)-1H-imidazol-2-yl]methyl}-3-chloro-4-fluoroaniline | | C |

TABLE 1-continued

| Structure | NAME | cAMP (EC$_{50}$) (nM) | CRE-Luc (EC$_{50}$) (nM) |
|---|---|---|---|
| 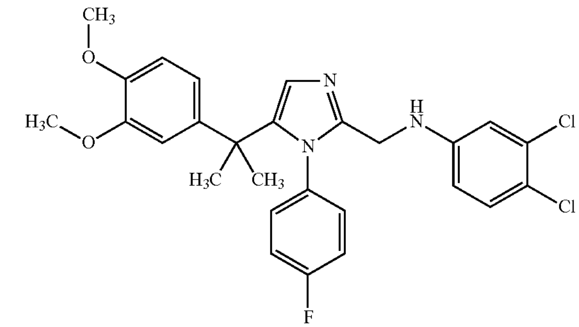 | N-{[5-{1-[3,4-bis(methyloxy)phenyl]-1-methylethyl}-1-(4-fluorophenyl)-1H-imidazol-2-yl]methyl}-3,4-dichloroaniline |  | A |
| 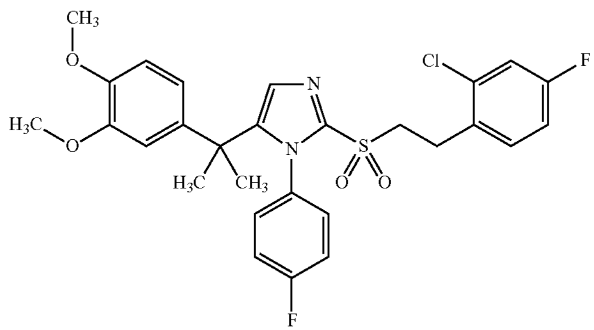 [SMILES: COc1ccc(C(C)(C)c2cnc(S(=O)(=O)CCc3ccc(F)cc3Cl)n2-c2ccc(F)cc2)cc1OC] | 5-{1-[3,4-bis(methyloxy)phenyl]-1-methylethyl}-2-{[2-(2-chloro-4-fluorophenyl)ethyl]sulfonyl}-1-(4-fluorophenyl)-1H-imidazole |  | A |
| 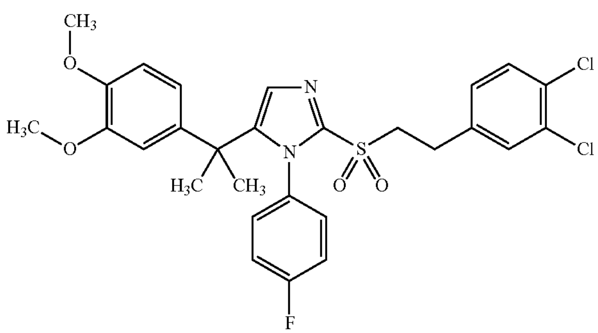 | 5-{1-[3,4-bis(methyloxy)phenyl]-1-methylethyl}-2-{[2-(3,4-dichlorophenyl)ethyl]sulfonyl}-1-(4-fluorophenyl)-1H-imidazole |  | A |

TABLE 1-continued

| Structure | NAME | cAMP (EC$_{50}$) (nM) | CRE-Luc (EC$_{50}$) (nM) |
|---|---|---|---|
| 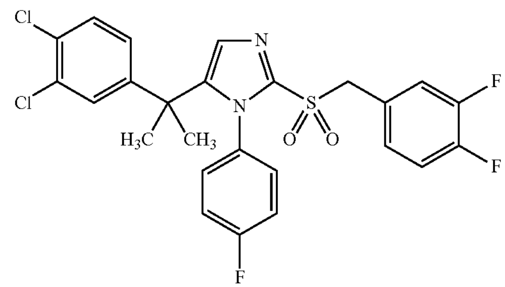 [SMILES: CC(C)(c1ccc(Cl)c(Cl)c1)c1cnc(S(=O)(=O)Cc2ccc(F)c(F)c2)n1-c1ccc(F)cc1] | 5-[1-(3,4-dichlorophenyl)-1-methylethyl]-2-{[(3,4-difluorophenyl)methyl]sulfonyl}-1-(4-fluorophenyl)-1H-imidazole | | C |
| 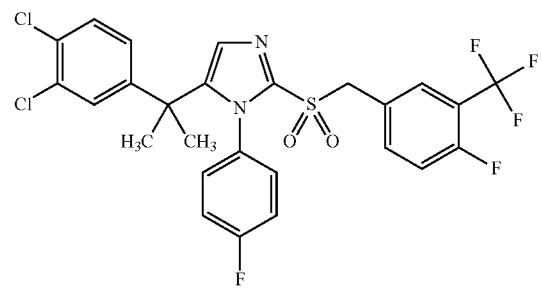 [SMILES: CC(C)(c1ccc(Cl)c(Cl)c1)c1cnc(S(=O)(=O)Cc2ccc(F)c(C(F)(F)F)c2)n1-c1ccc(F)cc1] | 5-[1-(3,4-dichlorophenyl)-1-methylethyl]-1-(4-fluorophenyl)-2-({[4-fluoro-3-(trifluoromethyl)phenyl]methyl}sulfonyl)-1H-imidazole | | C |
| 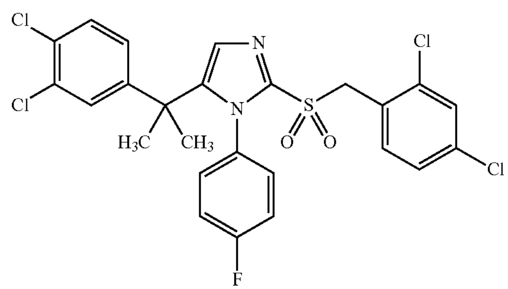 [SMILES: CC(C)(c1ccc(Cl)c(Cl)c1)c1cnc(S(=O)(=O)Cc2ccc(Cl)cc2Cl)n1-c1ccc(F)cc1] | 5-[1-(3,4-dichlorophenyl)-1-methylethyl]-2-{[(2,4-dichlorophenyl)methyl]sulfonyl}-1-(4-fluorophenyl)-1H-imidazole | | D |

TABLE 1-continued

| Structure | NAME | cAMP (EC$_{50}$) (nM) | CRE-Luc (EC$_{50}$) (nM) |
|---|---|---|---|
| 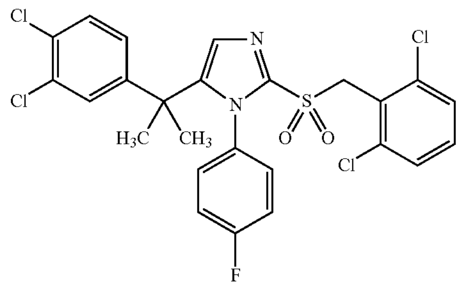 [SMILES: CC(C)(c1ccc(Cl)c(Cl)c1)c1cnc(S(=O)(=O)Cc2c(Cl)cccc2Cl)n1-c1ccc(F)cc1] | 5-[1-(3,4-dichlorophenyl)-1-methylethyl]-2-{[(2,6-dichlorophenyl)methyl]sulfonyl}-1-(4-fluorophenyl)-1H-imidazole |  | C |
| 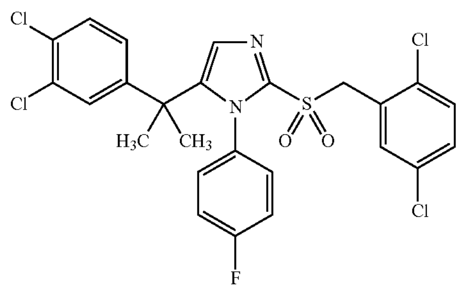 [SMILES: CC(C)(c1ccc(Cl)c(Cl)c1)c1cnc(S(=O)(=O)Cc2cc(Cl)ccc2Cl)n1-c1ccc(F)cc1] | 5-[1-(3,4-dichlorophenyl)-1-methylethyl]-2-{[(2,5-dichlorophenyl)methyl]sulfonyl}-1-(4-fluorophenyl)-1H-imidazole |  | C |
| 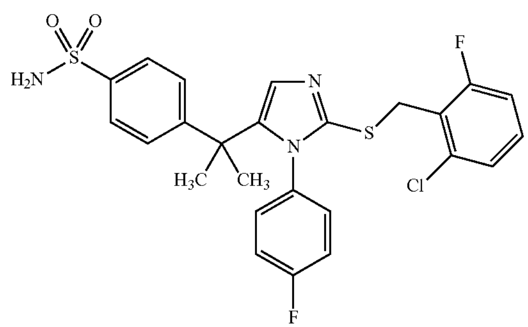 [SMILES: CC(C)(c1ccc(S(N)(=O)=O)cc1)c1cnc(SCc2c(F)cccc2Cl)n1-c1ccc(F)cc1] | 4-{1-[2-{[(2-chloro-6-fluorophenyl)methyl]thio}-1-(4-fluorophenyl)-1H-imidazol-5-yl]-1-methylethyl}benzenesulfonamide | C | C |

TABLE 1-continued

| Structure | NAME | cAMP (EC$_{50}$) (nM) | CRE-Luc (EC$_{50}$) (nM) |
|---|---|---|---|
| | 5-[1-[3,4-bis(methyloxy)phenyl]-1-methylethyl]-2-{[2-(3-chloro-4-fluorophenyl)ethyl]sulfonyl}-1-(4-fluorophenyl)-1H-imidazole | | A |
| 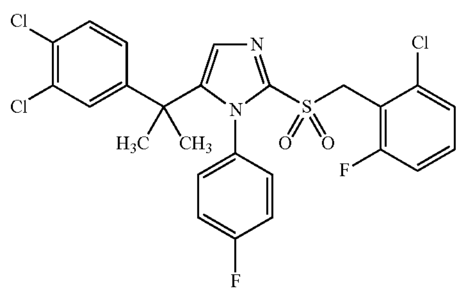 | 2-{[(2-chloro-6-fluorophenyl)methyl]sulfonyl}-1-(4-chlorophenyl)-5-[1-(3,4-dichlorophenyl)-1-methylethyl]-1H-imidazole | | C |
| 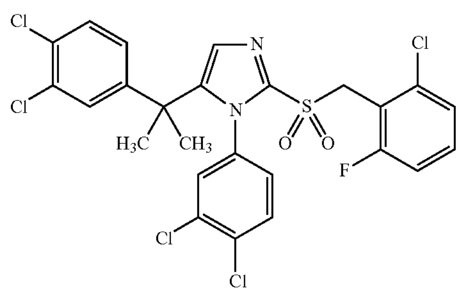 [SMILES: CC(C)(c1ccc(Cl)c(Cl)c1)c1cnc(S(=O)(=O)Cc2c(F)cccc2Cl)n1-c1ccc(Cl)c(Cl)c1] | 2-{[(2-chloro-6-fluorophenyl)methyl]sulfonyl}-1-(3,4-dichlorophenyl)-5-[1-(3,4-dichlorophenyl)-1-methylethyl]-1H-imidazole | | D |

TABLE 1-continued

| Structure | NAME | cAMP (EC$_{50}$) (nM) | CRE-Luc (EC$_{50}$) (nM) |
|---|---|---|---|
| | 2-{[(2-chloro-4-fluorophenyl)thio]methyl}-5-[1-(3,4-dichlorophenyl)-1-methylethyl]-1-(4-fluorophenyl)-1H-imidazole | | C |
| | 5-[1-(3,4-dichlorophenyl)thio]methyl]-2-{[(3,4-dichlorophenyl)thio]methyl}-1-(4-fluorophenyl)-1H-imidazole | | C |
| | 2-{[(2-chloro-6-fluorophenyl)methyl]thio)-1-(4-fluorophenyl)-5-{1-methyl-1-[4-(methylsulfonyl)phenyl]ethyl}-1H-imidazole | | C |

TABLE 1-continued

| Structure | NAME | cAMP (EC$_{50}$) (nM) | CRE-Luc (EC$_{50}$) (nM) |
|---|---|---|---|
| 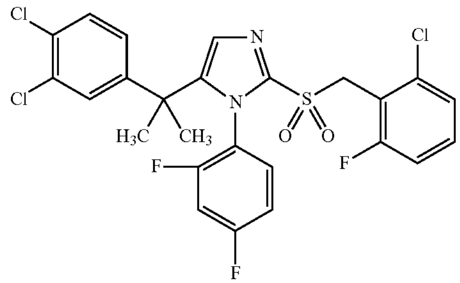 | 2-{[(2-chloro-6-fluorophenyl)methyl]sulfonyl}-5-[1-(3,4-dichlorophenyl)-1-methylethyl]-1-(2,4-difluorophenyl)-1H-imidazole | | C |
| 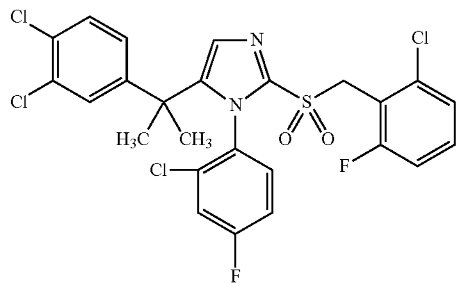 [SMILES: CC(C)(c1ccc(Cl)c(Cl)c1)c1cnc(S(=O)(=O)Cc2c(F)cccc2Cl)n1-c1ccc(F)cc1Cl] | 1-(2-chloro-4-fluorophenyl)-2-{[(2-chloro-6-fluorophenyl)methyl]sulfonyl}-5-[1-(3,4-dichlorophenyl)-1-methylethyl]-1H-imidazole | | D |
| | 2-{[(2-chloro-6-fluorophenyl)methyl]thio}-1-(3,4-dichlorophenyl)-5-[1-(3,4-dichlorophenyl)-1-methylethyl]-1H-imidazole | | C |

TABLE 1-continued

| Structure | NAME | cAMP (EC$_{50}$) (nM) | CRE-Luc (EC$_{50}$) (nM) |
|---|---|---|---|
| 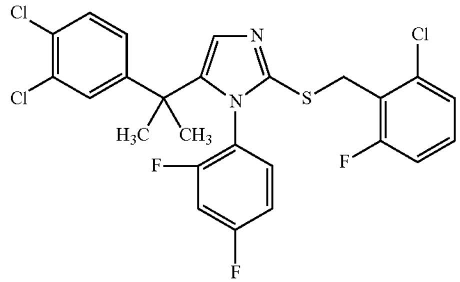 [SMILES: CC(C)(c1ccc(Cl)c(Cl)c1)c1cnc(SCc2c(F)cccc2Cl)n1-c1ccc(F)cc1F] | 2-{[(2-chloro-6-fluorophenyl)methyl]thio}-5-[1-(3,4-dichlorophenyl)-1-methylethyl]-1-(2,4-difluorophenyl)-1H-imidazole | C | C |
| 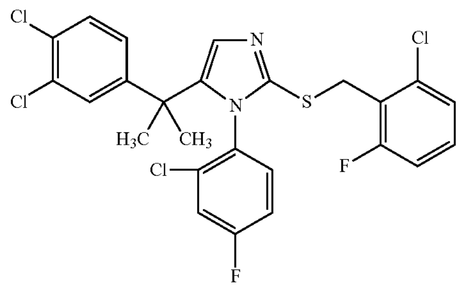 | 1-(2-chloro-4-fluorophenyl)-2-{[(2-chloro-6-fluorophenyl)methyl]thio}-5-[1-(3,4-dichlorophenyl)-1-methylethyl]-1H-imidazole | | C |
| 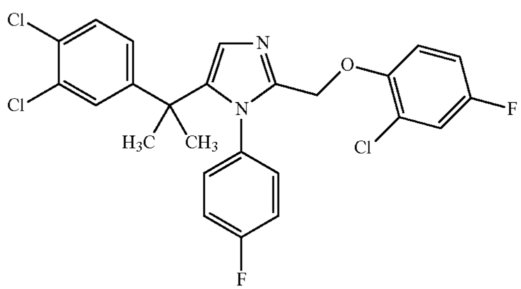 [SMILES: CC(C)(c1ccc(Cl)c(Cl)c1)c1cnc(COc2ccc(F)cc2Cl)n1-c1ccc(F)cc1] | 2-{[(2-chloro-4-fluorophenyl)oxy]methyl}-5-[1-(3,4-dichlorophenyl)-1-methylethyl]-1-(4-fluorophenyl)-1H-imidazole | | D |

TABLE 1-continued

| Structure | NAME | cAMP (EC$_{50}$) (nM) | CRE-Luc (EC$_{50}$) (nM) |
|---|---|---|---|
|  | 2-{[(2-chloro-4-fluorophenyl)methyl]oxy}methyl)-5-[1-(3,4-dichlorophenyl)-1-methylethyl]-1-(4-fluorophenyl)-1H-imidazole |  | D |
| 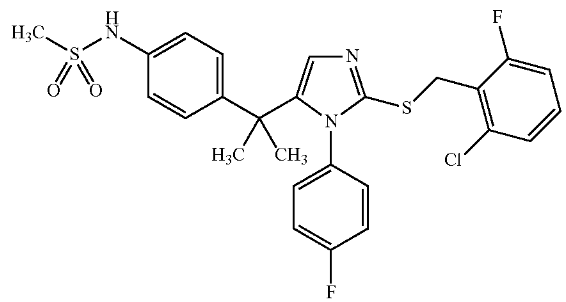 [SMILES: CC(C)(c1ccc(NS(C)(=O)=O)cc1)c1cnc(SCc2c(F)cccc2Cl)n1-c1ccc(F)cc1] | N-(4-{1-[2-{[(2-chloro-6-fluorophenyl)methyl]thio}-1-(4-fluorophenyl)-1H-imidazol-5-yl]-1-methylethyl}phenyl)methanesulfonamide |  | C |
| 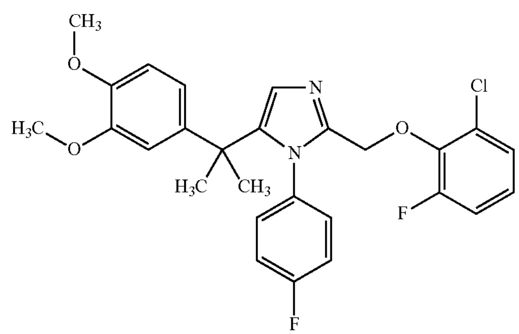 [SMILES: COc1ccc(C(C)(C)c2cnc(COc3c(F)cccc3Cl)n2-c2ccc(F)cc2)cc1OC] | 5-{1-[3,4-bis(methyloxy)phenyl]-1-methylethyl}-2-{[(2-chloro-6-fluorophenyl)oxy]methyl}-1-(4-fluorophenyl)-1H-imidazole | A | A |

TABLE 1-continued

| Structure | NAME | cAMP (EC$_{50}$) (nM) | CRE-Luc (EC$_{50}$) (nM) |
|---|---|---|---|
| 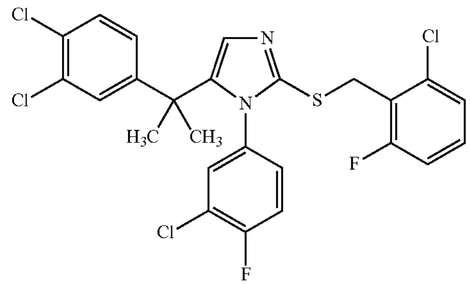 [SMILES: CC(C)(c1ccc(Cl)c(Cl)c1)c1cnc(SCc2c(F)cccc2Cl)n1-c1ccc(F)c(Cl)c1] | 1-(3-chloro-4-fluorophenyl)-2-{[(2-chloro-6-fluorophenyl)methyl]thio}-5-[1-(3,4-dichlorophenyl)-1-methylethyl]-1H-imidazole |  | A |
| 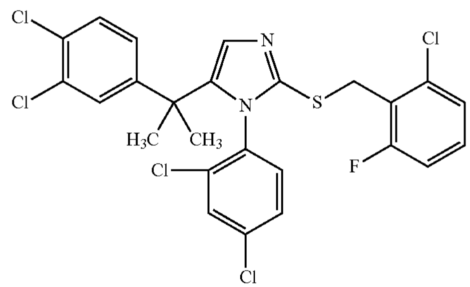 [SMILES: CC(C)(c1ccc(Cl)c(Cl)c1)c1cnc(SCc2c(F)cccc2Cl)n1-c1ccc(Cl)cc1Cl] | 2-{[(2-chloro-6-fluorophenyl)methyl]thio}-1-(2,4-dichlorophenyl)-5-[1-(3,4-dichlorophenyl)-1-methylethyl]-1H-imidazole |  | D |
| 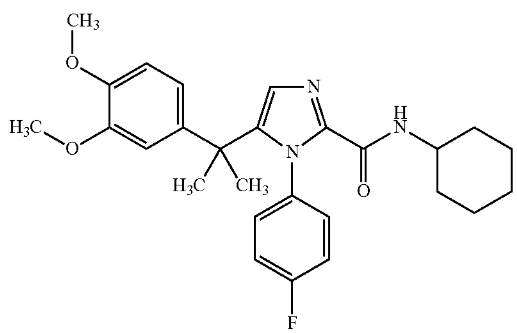 [SMILES: COc1ccc(C(C)(C)c2cnc(C(=O)NC3CCCCC3)n2-c2ccc(F)cc2)cc1OC] | 5-{1-[3,4-bis(methyloxy)phenyl]-1-methylethyl}-N-cyclohexyl-1-(4-fluorophenyl)-1H-imidazole-2-carboxamide |  | D |

TABLE 1-continued

| Structure | NAME | cAMP (EC$_{50}$) (nM) | CRE-Luc (EC$_{50}$) (nM) |
|---|---|---|---|
| 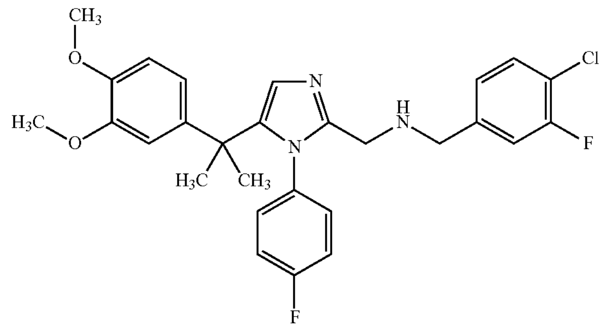 [SMILES: COc1ccc(C(C)(C)c2cnc(CNCc3ccc(Cl)c(F)c3)n2-c2ccc(F)cc2)cc1OC] | 1-[5-{1-[3,4-bis(methyloxy)phenyl]-1-methylethyl}-1-(4-fluorophenyl)-1H-imidazol-2-yl]-N-[(4-chloro-3-fluorophenyl)methyl]methanamine | | A |
| 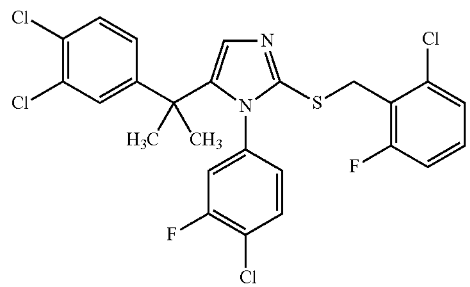 [SMILES: CC(C)(c1ccc(Cl)c(Cl)c1)c1cnc(SCc2c(F)cccc2Cl)n1-c1ccc(Cl)c(F)c1] | 1-(4-chloro-3-fluorophenyl)-2-{[(2-chloro-6-fluorophenyl)methyl]thio}-5-[1-(3,4-dichlorophenyl)-1-methylethyl]-1H-imidazole | | C |
| 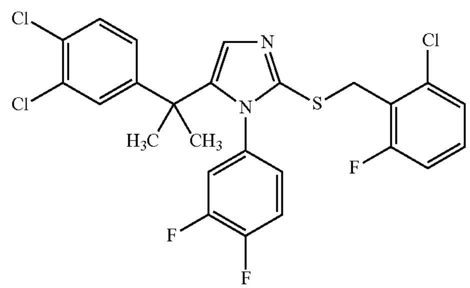 | 2-{[(2-chloro-6-fluorophenyl)methyl]thio}-5-[1-(3,4-dichlorophenyl)-1-methylethyl]-1-(3,4-difluorophenyl)-1H-imidazole | C | A |

TABLE 1-continued

| Structure | NAME | cAMP (EC$_{50}$) (nM) | CRE-Luc (EC$_{50}$) (nM) |
|---|---|---|---|
| 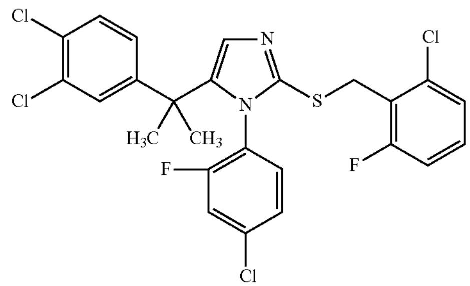 | 1-(4-chloro-2-fluorophenyl)-2-{[(2-chloro-6-fluorophenyl)methyl]thio}-5-[1-(3,4-dichlorophenyl)-1-methylethyl]-1H-imidazole | | C |
| 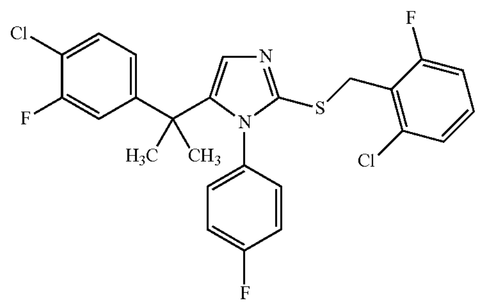 [SMILES: CC(C)(c1ccc(Cl)c(F)c1)c1cnc(SCc2c(F)cccc2Cl)n1-c1ccc(F)cc1] | 5-[1-(4-chloro-3-fluorophenyl)-1-methylethyl]-2-{[(2-chloro-6-fluorophenyl)methyl]thio}-1-(4-fluorophenyl)-1H-imidazole | | A |
| 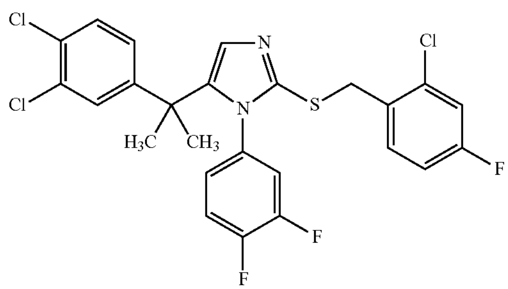 [SMILES: CC(C)(c1ccc(Cl)c(Cl)c1)c1cnc(SCc2ccc(F)cc2Cl)n1-c1ccc(F)c(F)c1] | 2-{[(2-chloro-4-fluorophenyl)methyl]thio}-5-[1-(3,4-dichlorophenyl)-1-methylethyl]-1-(3,4-difluorophenyl)-1H-imidazole | | C |

TABLE 1-continued

| Structure | NAME | cAMP (EC$_{50}$) (nM) | CRE-Luc (EC$_{50}$) (nM) |
|---|---|---|---|
| 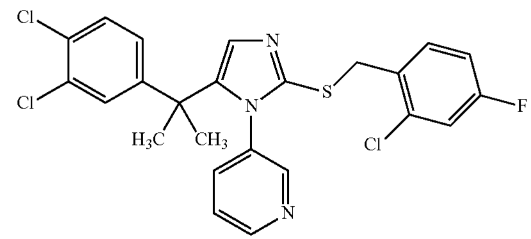 [SMILES: CC(C)(c1ccc(Cl)c(Cl)c1)c1cnc(SCc2ccc(F)cc2Cl)n1-c1cccnc1] | 3-(2-{[(2-chloro-4-fluorophenyl)methyl]thio}-5-[1-(3,4-dichlorophenyl)-1-methylethyl]-1H-imidazol-1-yl)pyridine | D | C |
| 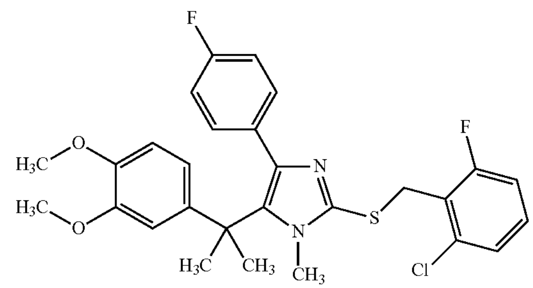 [SMILES: COc1ccc(C(C)(C)c2c(-c3ccc(F)cc3)nc(SCc3c(F)cccc3Cl)n2C)cc1OC] | 5-{1-[3,4-bis(methyloxy)phenyl]-1-methylethyl}-2-{[(2-chloro-6-fluorophenyl)methyl]thio}-4-(4-fluorophenyl)-1-methyl-1H-imidazole | | D |
| 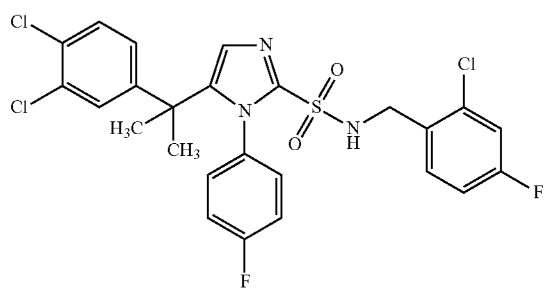 [SMILES: CC(C)(c1ccc(Cl)c(Cl)c1)c1cnc(S(=O)(=O)NCc2ccc(F)cc2Cl)n1-c1ccc(F)cc1] | N-[(2-chloro-4-fluorophenyl)methyl]-5-[1-(3,4-dichlorophenyl)-1-methylethyl]-1-(4-fluorophenyl)-1H-imidazole-2-sulfonamide | C | A |

TABLE 1-continued
| Structure | NAME | cAMP (EC$_{50}$) (nM) | CRE-Luc (EC$_{50}$) (nM) |
|---|---|---|---|
| 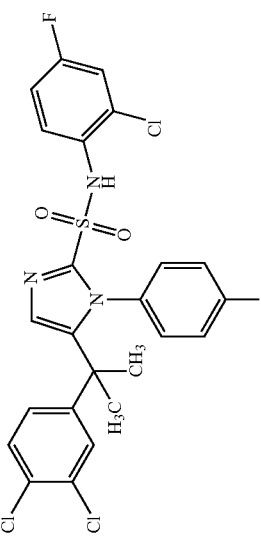 | N-(2-chloro-4-fluorophenyl)-5-[1-(3,4-dichlorophenyl)-1-methylethyl]-1-(4-fluorophenyl)-1H-imidazole-2-sulfonamide | | D |
| 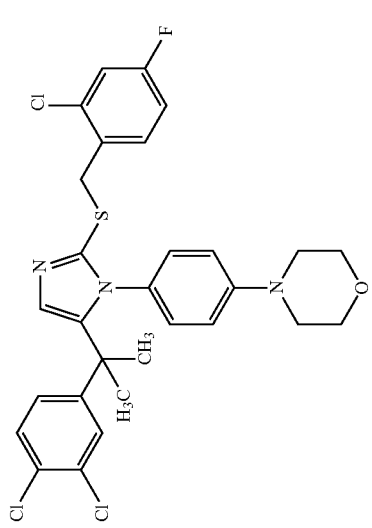 | 4-[4-(2-{[(2-chloro-4-fluorophenyl)methyl]thio}-5-[1-(3,4-dichlorophenyl)-1-methylethyl]-1H-imidazol-1-yl)phenyl]morpholine | | D |
| 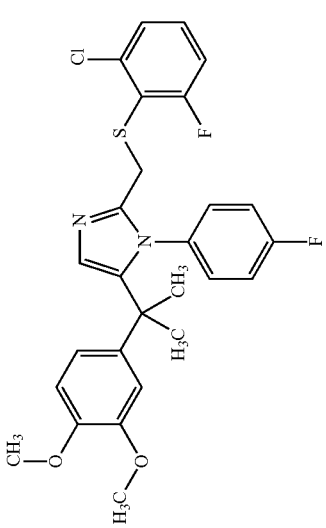 | 5-{1-[3,4-bis(methyloxy)phenyl]-1-methylethyl}-2-{[(2-chloro-6-fluorophenyl)thio]methyl}-1-(4-fluorophenyl)-1H-imidazole | A | A |

TABLE 1-continued

| Structure | NAME | cAMP (EC$_{50}$) (nM) | CRE-Luc (EC$_{50}$) (nM) |
|---|---|---|---|
|  | 2-[[(2-chloro-6-fluorophenyl)methyl]thio]-1-(4-fluorophenyl)-5-{1-methyl-1-[3-(methylsulfonyl)phenyl]ethyl}-1H-imidazole | A | C |
| 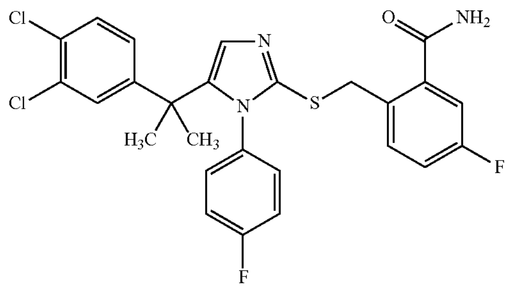 [SMILES: CC(C)(c1ccc(Cl)c(Cl)c1)c1cnc(SCc2ccc(F)cc2C(N)=O)n1-c1ccc(F)cc1] | 2-[({5-[1-(3,4-dichlorophenyl)-1-methylethyl]-1-(4-fluorophenyl)-1H-imidazol-2-yl}thio)methyl]-5-fluorobenzamide |  | C |
| 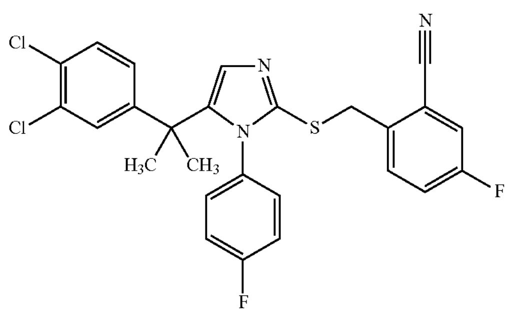 [SMILES: CC(C)(c1ccc(Cl)c(Cl)c1)c1cnc(SCc2ccc(F)cc2C#N)n1-c1ccc(F)cc1] | 2-[({5-[1-(3,4-dichlorophenyl)-1-methylethyl]-1-(4-fluorophenyl)-1H-imidazol-2-yl}thio)methyl]-5-fluorobenzonitrile |  | C |

TABLE 1-continued

| Structure | NAME | cAMP (EC$_{50}$) (nM) | CRE-Luc (EC$_{50}$) (nM) |
|---|---|---|---|
| 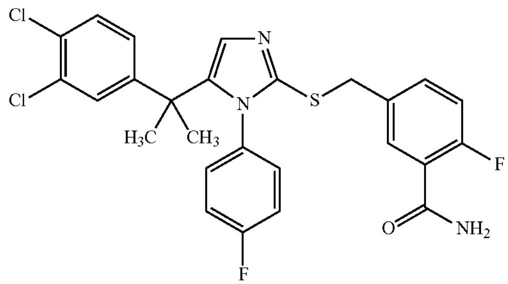 [SMILES: CC(C)(c1ccc(Cl)c(Cl)c1)c1cnc(SCc2ccc(F)c(C(N)=O)c2)n1-c1ccc(F)cc1] | 5-[({5-[1-(3,4-dichlorophenyl)-1-methylethyl]-1-(4-fluorophenyl)-1H-imidazol-2-yl}thio)methyl]-2-fluorobenzamide | C | C |
| 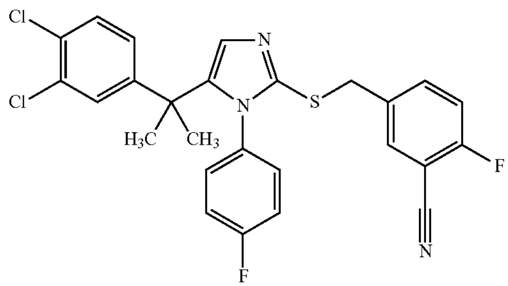 [SMILES: CC(C)(c1ccc(Cl)c(Cl)c1)c1cnc(SCc2ccc(F)c(C#N)c2)n1-c1ccc(F)cc1] | 5-[({5-[1-(3,4-dichlorophenyl)-1-methylethyl]-1-(4-fluorophenyl)-1H-imidazol-2-yl}thio)methyl]-2-fluorobenzonitrile | | C |
| 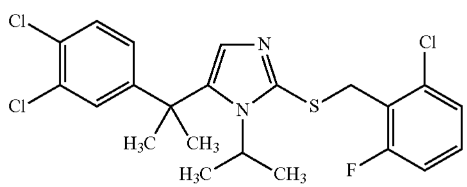 [SMILES: CC(C)n1c(C(C)(C)c2ccc(Cl)c(Cl)c2)cnc1SCc1c(F)cccc1Cl] | 2-{[(2-chloro-6-fluorophenyl)methyl]thio}-5-[1-(3,4-dichlorophenyl)-1-methylethyl]-1-(1-methylethyl)-1H-imidazole | | D |
| 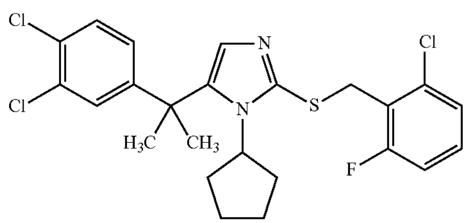 [SMILES: CC(C)(c1ccc(Cl)c(Cl)c1)c1cnc(SCc2c(F)cccc2Cl)n1C1CCCC1] | 2-{[(2-chloro-6-fluorophenyl)methyl]thio}-1-cyclopentyl-5-[1-(3,4-dichlorophenyl)-1-methylethyl]-1H-imidazole | | D |

TABLE 1-continued

| Structure | NAME | cAMP (EC$_{50}$) (nM) | CRE-Luc (EC$_{50}$) (nM) |
|---|---|---|---|
| 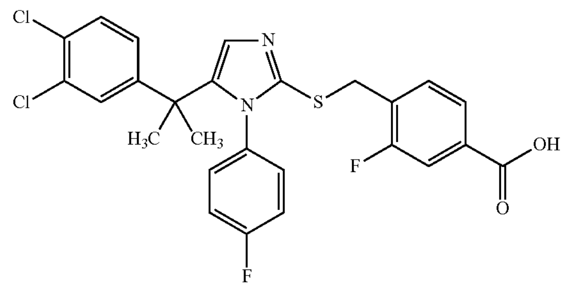 [SMILES: CC(C)(c1ccc(Cl)c(Cl)c1)c1cnc(SCc2ccc(C(=O)O)cc2F)n1-c1ccc(F)cc1] | 4-[({5-[1-(3,4-dichlorophenyl)-1-methylethyl]-1-(4-fluorophenyl)-1H-imidazol-2-yl}thio)methyl]-3-fluorobenzoic acid | C | C |
| 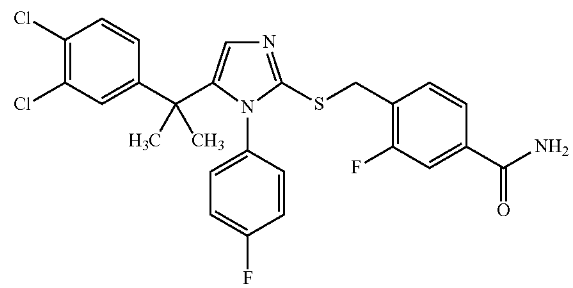 [SMILES: CC(C)(c1ccc(Cl)c(Cl)c1)c1cnc(SCc2ccc(C(N)=O)cc2F)n1-c1ccc(F)cc1] | 4-[({5-[1-(3,4-dichlorophenyl)-1-methylethyl]-1-(4-fluorophenyl)-1H-imidazol-2-yl}thio)methyl]-3-fluorobenzamide | | C |
| 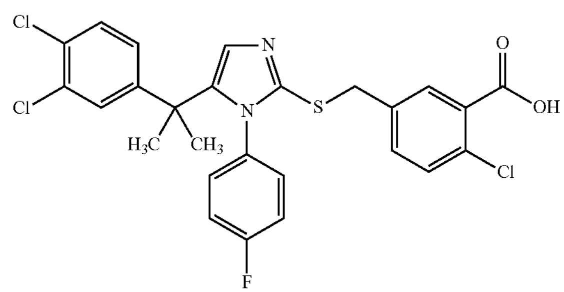 [SMILES: CC(C)(c1ccc(Cl)c(Cl)c1)c1cnc(SCc2ccc(Cl)c(C(=O)O)c2)n1-c1ccc(F)cc1] | 2-chloro-5-[({5-[1-(3,4-dichlorophenyl)-1-methylethyl]-1-(4-fluorophenyl)-1H-imidazol-2-yl}thio)methyl]benzoic acid | | C |

TABLE 1-continued

| Structure | NAME | cAMP (EC$_{50}$) (nM) | CRE-Luc (EC$_{50}$) (nM) |
|---|---|---|---|
| 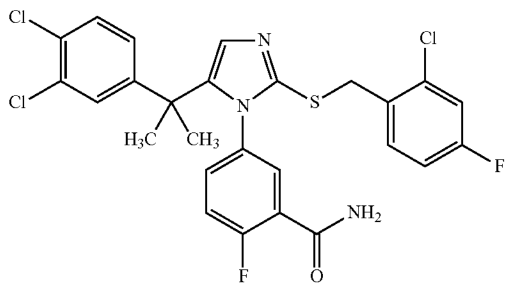 [SMILES: CC(C)(c1ccc(Cl)c(Cl)c1)c1cnc(SCc2ccc(F)cc2Cl)n1-c1ccc(F)c(C(N)=O)c1] | 5-(2-{[(2-chloro-4-fluorophenyl)methyl]thio}-5-[1-(3,4-dichlorophenyl)-1-methylethyl]-1H-imidazol-1-yl)-2-fluorobenzamide | | C |
| 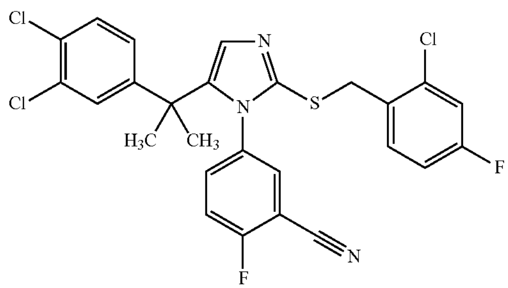 [SMILES: CC(C)(c1ccc(Cl)c(Cl)c1)c1cnc(SCc2ccc(F)cc2Cl)n1-c1ccc(F)c(C#N)c1] | 5-(2-{[(2-chloro-4-fluorophenyl)methyl]thio}-5-[1-(3,4-dichlorophenyl)-1-methylethyl]-1H-imidazol-1-yl)-2-fluorobenzonitrile | | C |
| 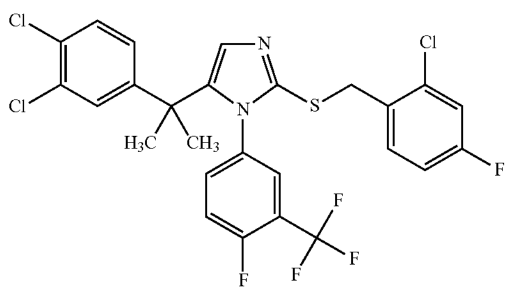 [SMILES: CC(C)(c1ccc(Cl)c(Cl)c1)c1cnc(SCc2ccc(F)cc2Cl)n1-c1ccc(F)c(C(F)(F)F)c1] | 2-{[(2-chloro-4-fluorophenyl)methyl]thio}-5-[1-(3,4-dichlorophenyl)-1-methylethyl]-1-[4-fluoro-3-(trifluoromethyl)phenyl]-1H-imidazole | | D |

TABLE 1-continued

| Structure | NAME | cAMP (EC$_{50}$) (nM) | CRE-Luc (EC$_{50}$) (nM) |
|---|---|---|---|
| 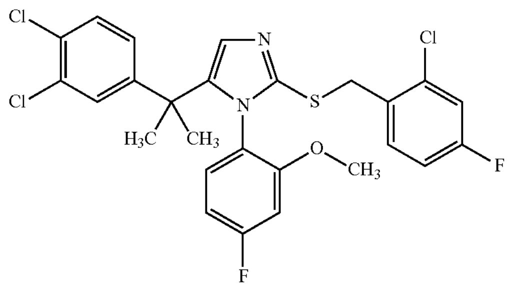 [SMILES: COc1cc(F)ccc1-n1c(C(C)(C)c2ccc(Cl)c(Cl)c2)cnc1SCc1ccc(F)cc1Cl] | 2-{[(2-chloro-4-fluorophenyl)methyl]thio}-5-[1-(3,4-dichlorophenyl)-1-methylethyl]-1-[4-fluoro-2-(methyloxy)phenyl]-1H-imidazole | | C |
| 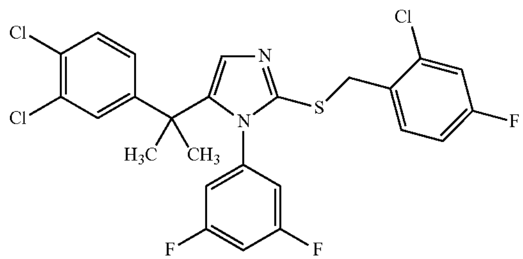 [SMILES: CC(C)(c1ccc(Cl)c(Cl)c1)c1cnc(SCc2ccc(F)cc2Cl)n1-c1cc(F)cc(F)c1] | 2-{[(2-chloro-4-fluorophenyl)methyl]thio}-5-[1-(3,4-dichlorophenyl)-1-methylethyl]-1-(3,5-difluorophenyl)-1H-imidazole | | C |
| 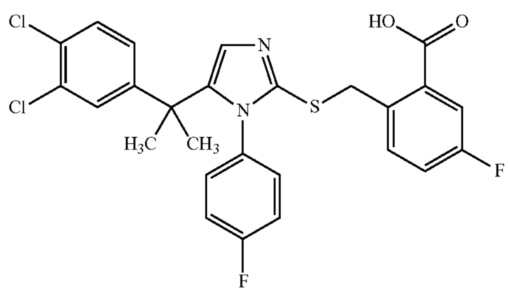 [SMILES: CC(C)(c1ccc(Cl)c(Cl)c1)c1cnc(SCc2ccc(F)cc2C(=O)O)n1-c1ccc(F)cc1] | 2-[({5-[1-(3,4-dichlorophenyl)-1-methylethyl]-1-(4-fluorophenyl)-1H-imidazol-2-yl}thio)methyl]-5-fluorobenzoic acid | | C |

TABLE 1-continued

| Structure | NAME | cAMP (EC$_{50}$) (nM) | CRE-Luc (EC$_{50}$) (nM) |
|---|---|---|---|
| 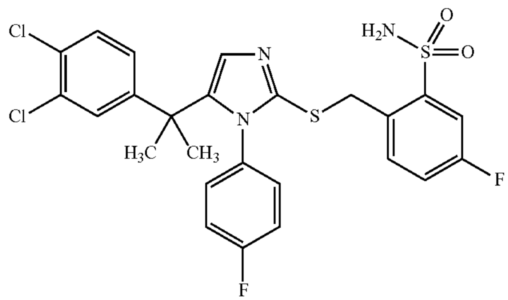 [SMILES: CC(C)(c1ccc(Cl)c(Cl)c1)c1cnc(SCc2ccc(F)cc2S(N)(=O)=O)n1-c1ccc(F)cc1] | 2-[({5-[1-(3,4-dichlorophenyl)-1-methylethyl]-1-(4-fluorophenyl)-1H-imidazol-2-yl}thio)methyl]-5-fluorobenzenesulfonamide | | C |
| 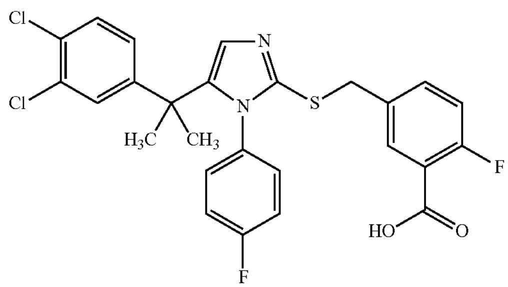 [SMILES: CC(C)(c1ccc(Cl)c(Cl)c1)c1cnc(SCc2ccc(F)c(C(=O)O)c2)n1-c1ccc(F)cc1] | 5-[({5-[1-(3,4-dichlorophenyl)-1-methylethyl]-1-(4-fluorophenyl)-1H-imidazol-2-yl}thio)methyl]-2-fluorobenzoic acid | C | C |
| 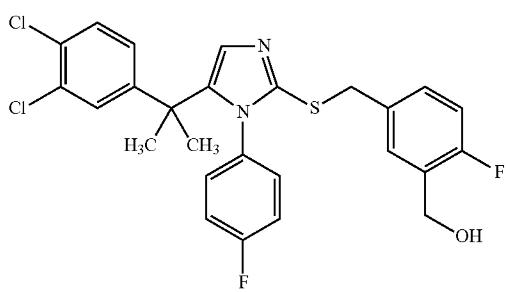 [SMILES: CC(C)(c1ccc(Cl)c(Cl)c1)c1cnc(SCc2ccc(F)c(CO)c2)n1-c1ccc(F)cc1] | {5-[({5-[1-(3,4-dichlorophenyl)-1-methylethyl]-1-(4-fluorophenyl)-1H-imidazol-2-yl}thio)methyl]-2-fluorophenyl}methanol | | C |

TABLE 1-continued

| Structure | NAME | cAMP (EC$_{50}$) (nM) | CRE-Luc (EC$_{50}$) (nM) |
|---|---|---|---|
| 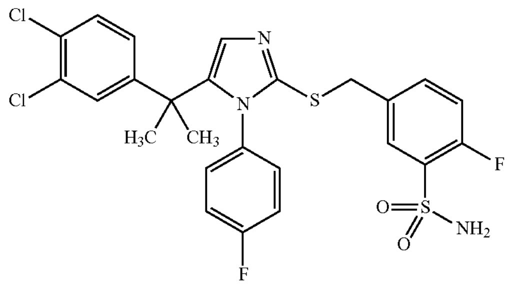 [SMILES: CC(C)(c1ccc(Cl)c(Cl)c1)c1cnc(SCc2ccc(F)c(S(N)(=O)=O)c2)n1-c1ccc(F)cc1] | 5-[({5-[1-(3,4-dichlorophenyl)-1-methylethyl]-1-(4-fluorophenyl)-1H-imidazol-2-yl}thio)methyl]-2-fluorobenzenesulfonamide | C | A |
| 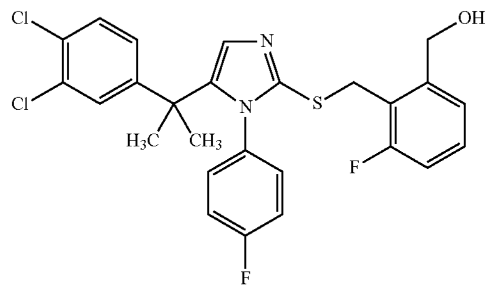 [SMILES: CC(C)(c1ccc(Cl)c(Cl)c1)c1cnc(SCc2c(F)cccc2CO)n1-c1ccc(F)cc1] | {2-[({5-[1-(3,4-dichlorophenyl)-1-methylethyl]-1-(4-fluorophenyl)-1H-imidazol-2-yl}thio)methyl]-3-fluorophenyl}methanol | | C |
| 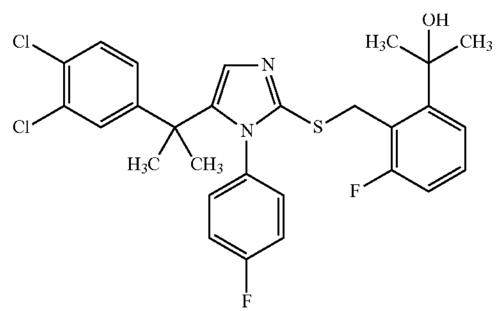 [SMILES: CC(C)(O)c1cccc(F)c1CSc1ncc(C(C)(C)c2ccc(Cl)c(Cl)c2)n1-c1ccc(F)cc1] | 2-{2-[({5-[1-(3,4-dichlorophenyl)-1-methylethyl]-1-(4-fluorophenyl)-1H-imidazol-2-yl}thio)methyl]-3-fluorophenyl}propan-2-ol | | C |

TABLE 1-continued

| Structure | NAME | cAMP (EC$_{50}$) (nM) | CRE-Luc (EC$_{50}$) (nM) |
|---|---|---|---|
| | 2-[[(2-chloro-4-fluorophenyl)sulfonyl]methyl]-5-[1-(3,4-dichlorophenyl)-1-methylethyl]-1-(4-fluorophenyl)-1H-imidazole | | D |
| | 4-[1-[2-{[(2-chloro-4-fluorophenyl)methyl]thio}-1-(4-fluorophenyl)-1H-imidazol-5-yl]-1-methylethyl]-N-methylbenzenesulfonamide | | C |
| | 4-{5-{1-[3,4-bis(methyloxy)phenyl]-1-methylethyl}-1-(4-fluorophenyl)-1H-imidazol-2-yl]carbonyl}morpholine | | D |

TABLE 1-continued

| Structure | NAME | cAMP (EC$_{50}$) (nM) | CRE-Luc (EC$_{50}$) (nM) |
|---|---|---|---|
| 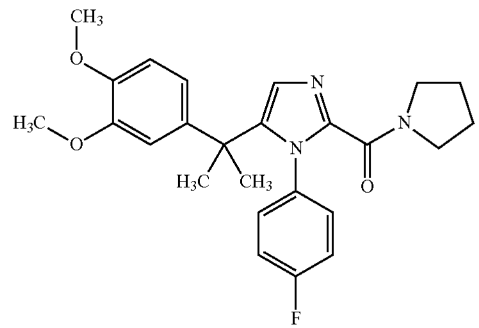 [SMILES: COc1ccc(C(C)(C)c2cnc(C(=O)N3CCCC3)n2-c2ccc(F)cc2)cc1OC] | 5-{1-[3,4-bis(methyloxy)phenyl]-1-methylethyl}-1-(4-fluorophenyl)-2-(pyrrolidin-1-ylcarbonyl)-1H-imidazole | | D |
| 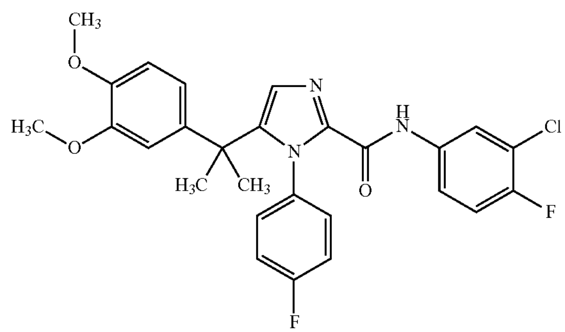 [SMILES: COc1ccc(C(C)(C)c2cnc(C(=O)Nc3ccc(F)c(Cl)c3)n2-c2ccc(F)cc2)cc1OC] | 5-{1-[3,4-bis(methyloxy)phenyl]-1-methylethyl}-N-(3-chloro-4-fluorophenyl)-1-(4-fluorophenyl)-1H-imidazole-2-carboxamide | | D |
| 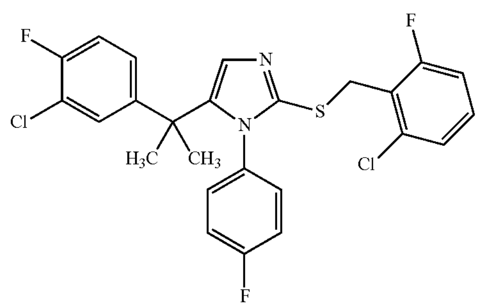 [SMILES: CC(C)(c1ccc(F)c(Cl)c1)c1cnc(SCc2c(F)cccc2Cl)n1-c1ccc(F)cc1] | 5-[1-(3-chloro-4-fluorophenyl)-1-methylethyl]-2-{[(2-chloro-6-fluorophenyl)methyl]thio}-1-(4-fluorophenyl)-1H-imidazole | C | A |

TABLE 1-continued

| Structure | NAME | cAMP (EC$_{50}$) (nM) | CRE-Luc (EC$_{50}$) (nM) |
|---|---|---|---|
| 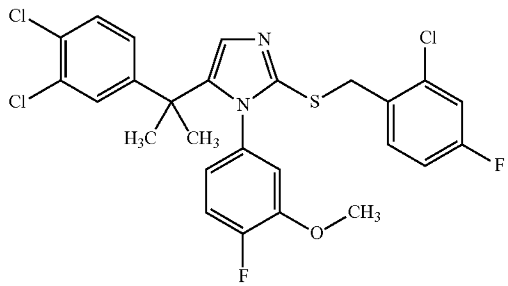 [SMILES: COc1cc(-n2c(C(C)(C)c3ccc(Cl)c(Cl)c3)cnc2SCc2ccc(F)cc2Cl)ccc1F] | 2-{[(2-chloro-4-fluorophenyl)methyl]thio}-5-[1-(3,4-dichlorophenyl)-1-methylethyl]-1-[4-fluoro-3-(methyloxy)phenyl]-1H-imidazole | C | C |
| 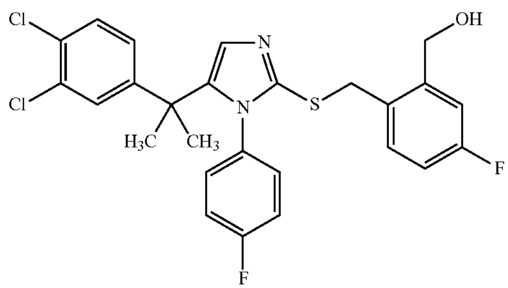 [SMILES: CC(C)(c1ccc(Cl)c(Cl)c1)c1cnc(SCc2ccc(F)cc2CO)n1-c1ccc(F)cc1] | {2-[({5-[1-(3,4-dichlorophenyl)-1-methylethyl]-1-(4-fluorophenyl)-1H-imidazol-2-yl}thio)methyl]-5-fluorophenyl}methanol | | D |
| | 5-[1-(3,4-dichlorophenyl)-1-methylethyl]-2-({[4-fluoro-2-(methylsulfonyl)phenyl]methyl]thio})-1-(4-fluorophenyl)-1H-imidazole | | C |

TABLE 1-continued

| Structure | NAME | cAMP (EC$_{50}$) (nM) | CRE-Luc (EC$_{50}$) (nM) |
|---|---|---|---|
| 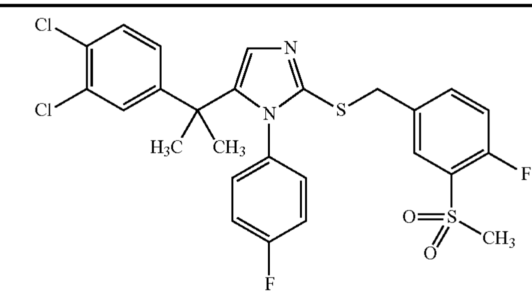 | 5-[1-(3,4-dichlorophenyl)-1-methylethyl]-2-({[4-fluoro-3-(methylsulfonyl)phenyl]methyl}thio)-1-(4-fluorophenyl)-1H-imidazole | C | A |
| 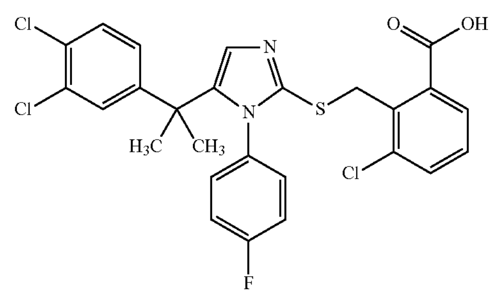 [SMILES: CC(C)(c1ccc(Cl)c(Cl)c1)c1cnc(SCc2c(Cl)cccc2C(=O)O)n1-c1ccc(F)cc1] | 3-chloro-2-[({5-[1-(3,4-dichlorophenyl)-1-methylethyl]-1-(4-fluorophenyl)-1H-imidazol-2-yl}thio)methyl]benzoic acid |  | C |
| 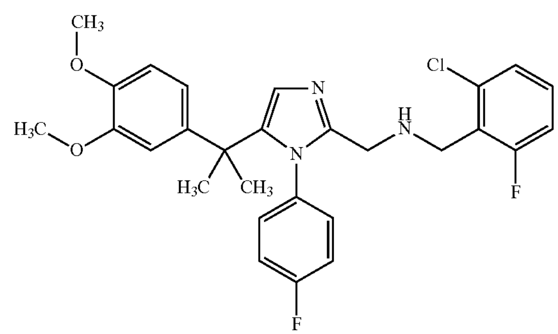 [SMILES: COc1ccc(C(C)(C)c2cnc(CNCc3c(F)cccc3Cl)n2-c2ccc(F)cc2)cc1OC] | 1-[5-{1-[3,4-bis(methyloxy)phenyl]-1-methylethyl}-1-(4-fluorophenyl)-1H-imidazol-2-yl]-N-[(2-chloro-6-fluorophenyl)methyl]methanamine |  | A |

TABLE 1-continued
| Structure | NAME | cAMP (EC$_{50}$) (nM) | CRE-Luc (EC$_{50}$) (nM) |
|---|---|---|---|
| 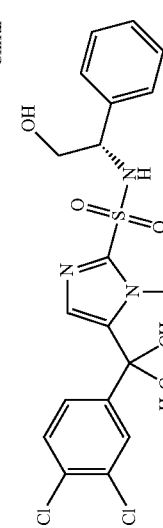 | 5-[1-(3,4-dichlorophenyl)-1-methylethyl]-1-(4-fluorophenyl)-N-[(1S)-2-hydroxy-1-phenylethyl]-1H-imidazole-2-sulfonamide | | D |
| 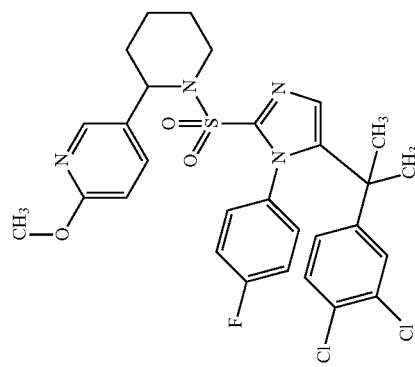 | 5-[1-({5-[1-(3,4-dichlorophenyl)-1-methylethyl]-1-(4-fluorophenyl)-1H-imidazol-2-yl}sulfonyl)piperidin-2-yl]-2-(methyloxy)pyridine | C | C |

TABLE 1-continued

| Structure | NAME | cAMP (EC$_{50}$) (nM) | CRE-Luc (EC$_{50}$) (nM) |
|---|---|---|---|
| 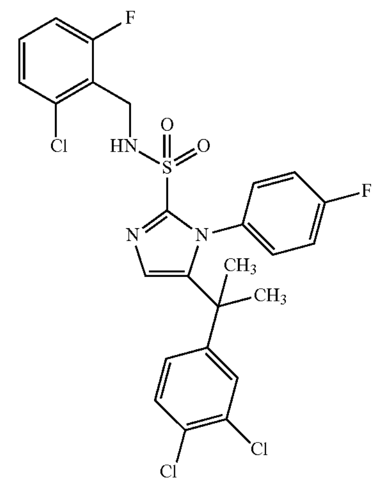 [SMILES: CC(C)(c1ccc(Cl)c(Cl)c1)c1cnc(S(=O)(=O)NCc2c(F)cccc2Cl)n1-c1ccc(F)cc1] | N-[(2-chloro-6-fluorophenyl)methyl]-5-[1-(3,4-dichlorophenyl)-1-methylethyl]-1-(4-fluorophenyl)-1H-imidazole-2-sulfonamide | C | C |
| 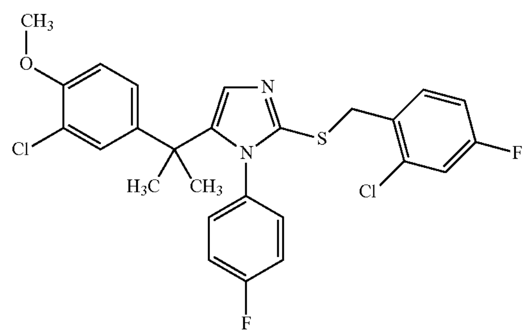 [SMILES: COc1ccc(C(C)(C)c2cnc(SCc3ccc(F)cc3Cl)n2-c2ccc(F)cc2)cc1Cl] | 2-{[(2-chloro-4-fluorophenyl)methyl]thio}-5-{1-[3-chloro-4-(methyloxy)phenyl]-1-methylethyl}-1-(4-fluorophenyl)-1H-imidazole | | A |

TABLE 1-continued

| Structure | NAME | cAMP (EC$_{50}$) (nM) | CRE-Luc (EC$_{50}$) (nM) |
|---|---|---|---|
| 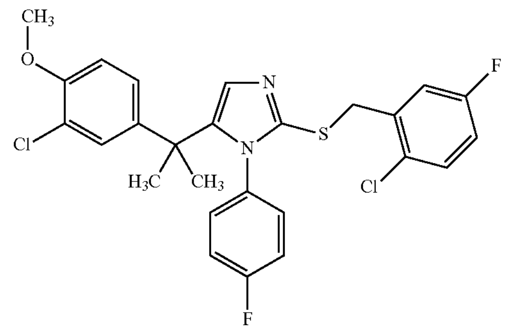 [SMILES: COc1ccc(C(C)(C)c2cnc(SCc3cc(F)ccc3Cl)n2-c2ccc(F)cc2)cc1Cl] | 2-{[(2-chloro-5-fluorophenyl)methyl]thio}-5-{1-[3-chloro-4-(methyloxy)phenyl]-1-methylethyl}-1-(4-fluorophenyl)-1H-imidazole | C | A |
| 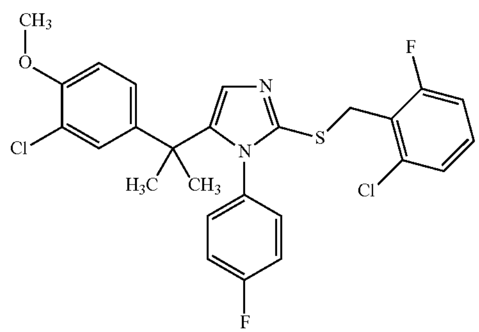 [SMILES: COc1ccc(C(C)(C)c2cnc(SCc3c(F)cccc3Cl)n2-c2ccc(F)cc2)cc1Cl] | 2-{[(2-chloro-6-fluorophenyl)methyl]thio}-5-{1-[3-chloro-4-(methyloxy)phenyl]-1-methylethyl}-1-(4-fluorophenyl)-1H-imidazole | A | A |
| 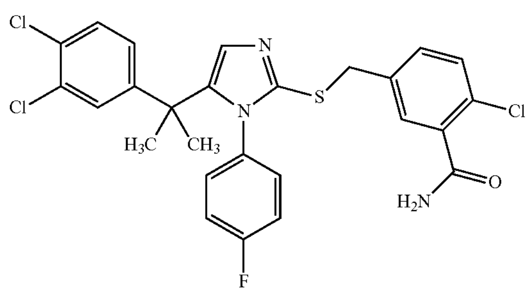 [SMILES: CC(C)(c1ccc(Cl)c(Cl)c1)c1cnc(SCc2ccc(Cl)c(C(N)=O)c2)n1-c1ccc(F)cc1] | 2-chloro-5-[({5-[1-(3,4-dichlorophenyl)-1-methylethyl]-1-(4-fluorophenyl)-1H-imidazol-2-yl}thio)methyl]benzamide | | A |

TABLE 1-continued

| Structure | NAME | cAMP (EC$_{50}$) (nM) | CRE-Luc (EC$_{50}$) (nM) |
|---|---|---|---|
| 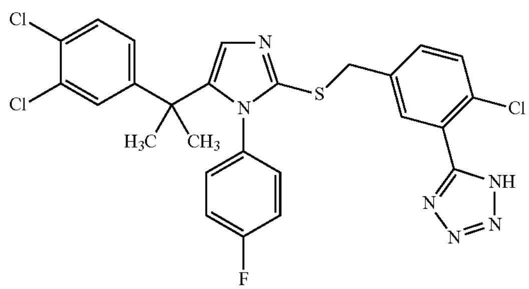 [SMILES: CC(C)(c1ccc(Cl)c(Cl)c1)c1cnc(SCc2ccc(Cl)c(-c3nnn[nH]3)c2)n1-c1ccc(F)cc1] | 5-{2-chloro-5-[({5-[1-(3,4-dichlorophenyl)-1-methylethyl]-1-(4-fluorophenyl)-1H-imidazol-2-yl}thio)methyl]phenyl}-1H-tetrazole | C | C |
| 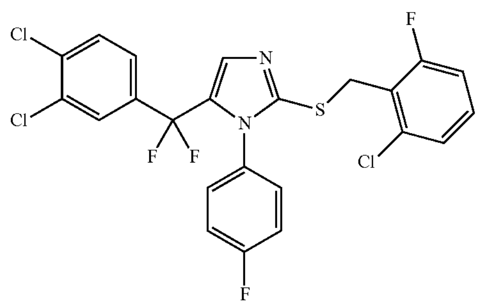 [SMILES: Fc1ccc(-n2c(C(F)(F)c3ccc(Cl)c(Cl)c3)cnc2SCc2c(F)cccc2Cl)cc1] | 2-{[(2-chloro-6-fluorophenyl)methyl]thio}-5-[(3,4-dichlorophenyl)(difluoro)methyl]-1-(4-fluorophenyl)-1H-imidazole |  | D |
| 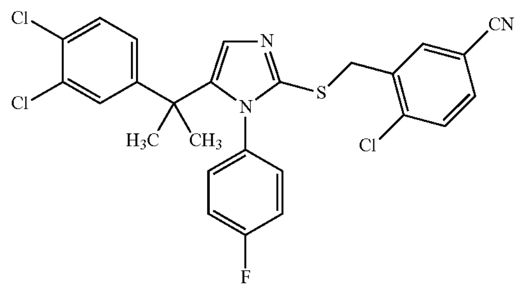 [SMILES: CC(C)(c1ccc(Cl)c(Cl)c1)c1cnc(SCc2cc(C#N)ccc2Cl)n1-c1ccc(F)cc1] | 4-chloro-3-[({5-[1-(3,4-dichlorophenyl)-1-methylethyl]-1-(4-fluorophenyl)-1H-imidazol-2-yl}thio)methyl]benzonitrile |  | A |

TABLE 1-continued

| Structure | NAME | cAMP (EC$_{50}$) (nM) | CRE-Luc (EC$_{50}$) (nM) |
|---|---|---|---|
| 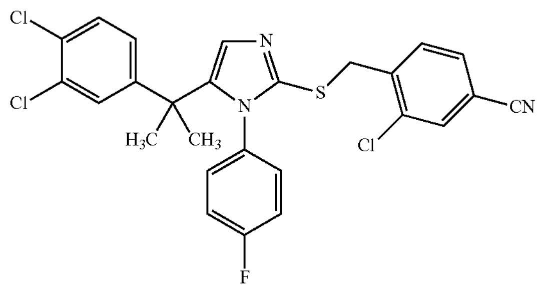 [SMILES: CC(C)(c1ccc(Cl)c(Cl)c1)c1cnc(SCc2ccc(C#N)cc2Cl)n1-c1ccc(F)cc1] | 3-chloro-4-[({5-[1-(3,4-dichlorophenyl)-1-methylethyl]-1-(4-fluorophenyl)-1H-imidazol-2-yl}thio)methyl]benzonitrile | | C |
| 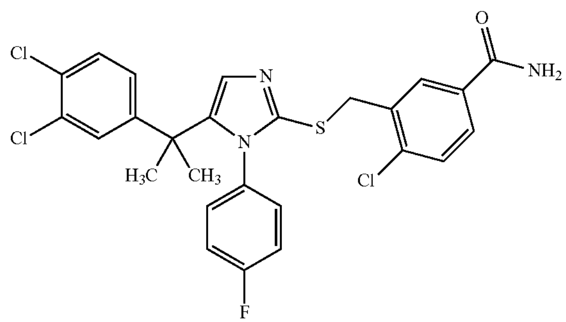 [SMILES: CC(C)(c1ccc(Cl)c(Cl)c1)c1cnc(SCc2cc(C(N)=O)ccc2Cl)n1-c1ccc(F)cc1] | 4-chloro-3-[({5-[1-(3,4-dichlorophenyl)-1-methylethyl]-1-(4-fluorophenyl)-1H-imidazol-2-yl}thio)methyl]benzamide | | C |
| 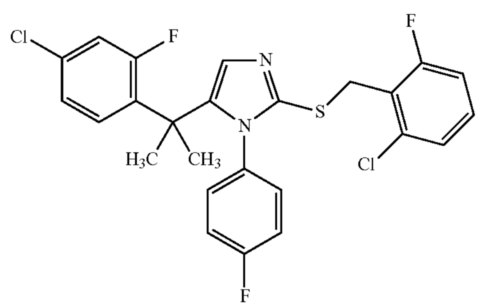 | 5-[1-(4-chloro-2-fluorophenyl)-1-methylethyl]-2-{[(2-chloro-6-fluorophenyl)methyl]thio}-1-(4-fluorophenyl)-1H-imidazole | C | C |

TABLE 1-continued

| Structure | NAME | cAMP (EC$_{50}$) (nM) | CRE-Luc (EC$_{50}$) (nM) |
|---|---|---|---|
| 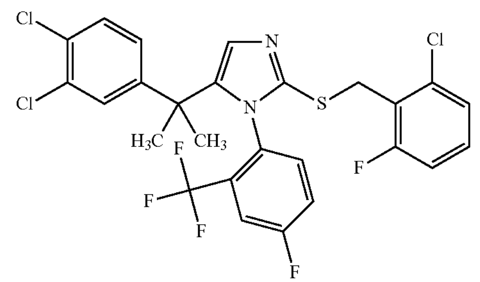 [SMILES: CC(C)(c1ccc(Cl)c(Cl)c1)c1cnc(SCc2c(F)cccc2Cl)n1-c1ccc(F)cc1C(F)(F)F] | 2-{[(2-chloro-6-fluorophenyl)methyl]thio}-5-[1-(3,4-dichlorophenyl)-1-methylethyl]-1-[4-fluoro-2-(trifluoromethyl)phenyl]-1H-imidazole |  | D |
| 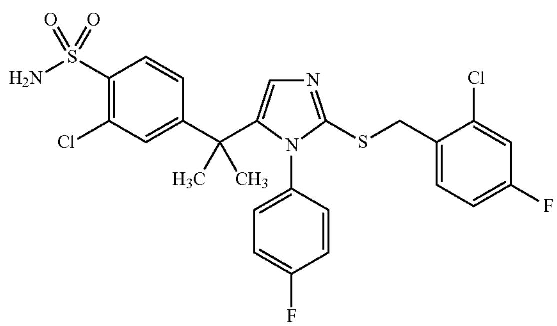 [SMILES: CC(C)(c1ccc(S(N)(=O)=O)c(Cl)c1)c1cnc(SCc2ccc(F)cc2Cl)n1-c1ccc(F)cc1] | 2-chloro-4-{1-[2-{[(2-chloro-4-fluorophenyl)methyl]thio}-1-(4-fluorophenyl)-1H-imidazol-5-yl]-1-methylethyl}benzenesulfonamide | C | A |
| 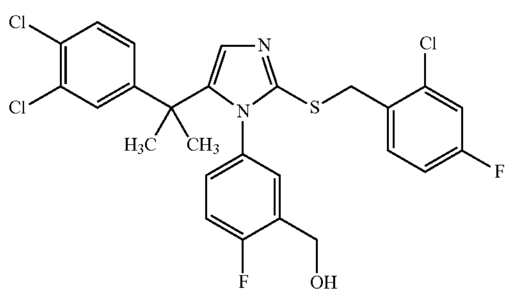 [SMILES: CC(C)(c1ccc(Cl)c(Cl)c1)c1cnc(SCc2ccc(F)cc2Cl)n1-c1ccc(F)c(CO)c1] | [5-(2-{[(2-chloro-4-fluorophenyl)methyl]thio}-5-[1-(3,4-dichlorophenyl)-1-methylethyl]-1H-imidazol-1-yl)-2-fluorophenyl]methanol | C | C |

TABLE 1-continued

| Structure | NAME | cAMP (EC$_{50}$) (nM) | CRE-Luc (EC$_{50}$) (nM) |
|---|---|---|---|
| 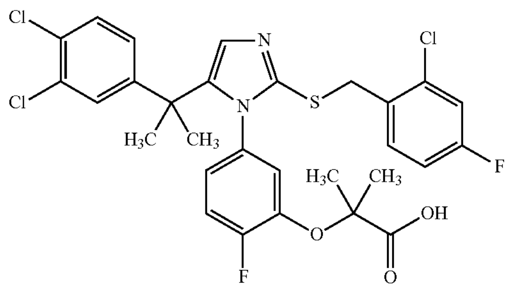 [SMILES: CC(C)(Oc1cc(-n2c(C(C)(C)c3ccc(Cl)c(Cl)c3)cnc2SCc2ccc(F)cc2Cl)ccc1F)C(=O)O] | 2-{[5-(2-{[(2-chloro-4-fluorophenyl)methyl]thio}-5-[1-(3,4-dichlorophenyl)-1-methylethyl]-1H-imidazol-1-yl)-2-fluorophenyl]oxy}-2-methylpropanoic acid | | D |
| 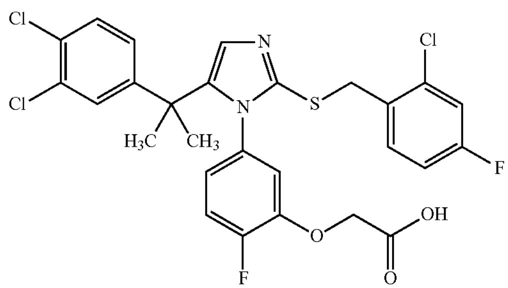 [SMILES: CC(C)(c1ccc(Cl)c(Cl)c1)c1cnc(SCc2ccc(F)cc2Cl)n1-c1ccc(F)c(OCC(=O)O)c1] | {[5-(2-{[(2-chloro-4-fluorophenyl)methyl]thio}-5-[1-(3,4-dichlorophenyl)-1-methylethyl]-1H-imidazol-1-yl)-2-fluorophenyl]oxy}acetic acid | | D |
| 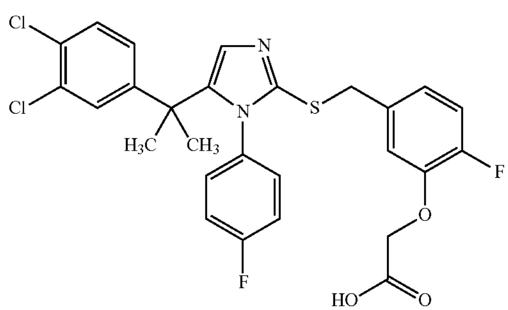 [SMILES: CC(C)(c1ccc(Cl)c(Cl)c1)c1cnc(SCc2ccc(F)c(OCC(=O)O)c2)n1-c1ccc(F)cc1] | ({5-[({5-[1-(3,4-dichlorophenyl)-1-methylethyl]-1-(4-fluorophenyl)-1H-imidazol-2-yl}thio)methyl]-2-fluorophenyl}oxy)acetic acid | C | C |

TABLE 1-continued

| Structure | NAME | cAMP (EC$_{50}$) (nM) | CRE-Luc (EC$_{50}$) (nM) |
|---|---|---|---|
| 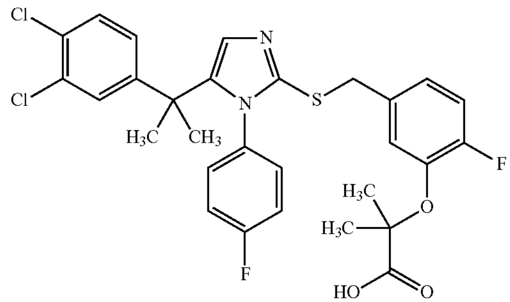 [SMILES: CC(C)(Oc1cc(CSc2ncc(C(C)(C)c3ccc(Cl)c(Cl)c3)n2-c2ccc(F)cc2)ccc1F)C(=O)O] | 2-({5-[({5-[1-(3,4-dichlorophenyl)-1-methylethyl]-1-(4-fluorophenyl)-1H-imidazol-2-yl}thio)methyl]-2-fluorophenyl}oxy)-2-methylpropanoic acid | | C |
| 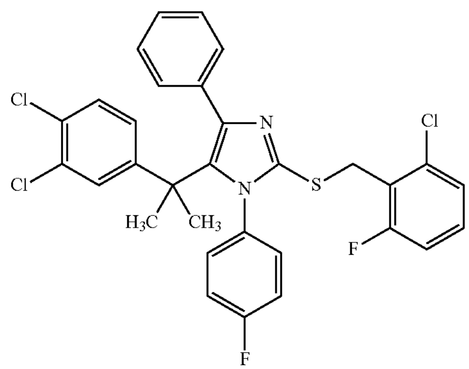 [SMILES: CC(C)(c1ccc(Cl)c(Cl)c1)c1c(-c2ccccc2)nc(SCc2c(F)cccc2Cl)n1-c1ccc(F)cc1] | 2-{[(2-chloro-6-fluorophenyl)methyl]thio}-5-[1-(3,4-dichlorophenyl)-1-methylethyl]-1-(4-fluorophenyl)-4-phenyl-1H-imidazole | | D |
| 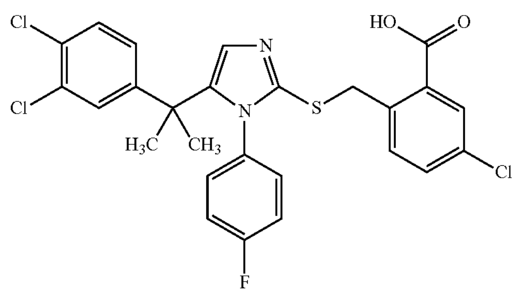 [SMILES: CC(C)(c1ccc(Cl)c(Cl)c1)c1cnc(SCc2ccc(Cl)cc2C(=O)O)n1-c1ccc(F)cc1] | 5-chloro-2-[({5-[1-(3,4-dichlorophenyl)-1-methylethyl]-1-(4-fluorophenyl)-1H-imidazol-2-yl}thio)methyl]benzoic acid | | C |

TABLE 1-continued

| Structure | NAME | cAMP (EC$_{50}$) (nM) | CRE-Luc (EC$_{50}$) (nM) |
|---|---|---|---|
| 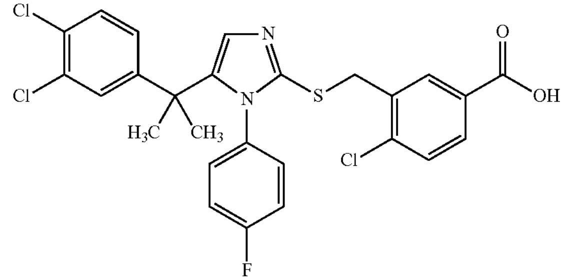 [SMILES: CC(C)(c1ccc(Cl)c(Cl)c1)c1cnc(SCc2cc(C(=O)O)ccc2Cl)n1-c1ccc(F)cc1] | 4-chloro-3-[({5-[1-(3,4-dichlorophenyl)-1-methylethyl]-1-(4-fluorophenyl)-1H-imidazol-2-yl}thio)methyl]benzoic acid | C | C |
| 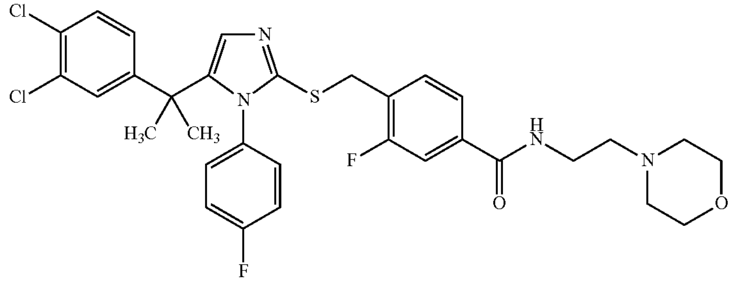 [SMILES: CC(C)(c1ccc(Cl)c(Cl)c1)c1cnc(SCc2ccc(C(=O)NCCN3CCOCC3)cc2F)n1-c1ccc(F)cc1] | 4-[({5-[1-(3,4-dichlorophenyl)-1-methylethyl]-1-(4-fluorophenyl)-1H-imidazol-2-yl}thio)methyl]-3-fluoro-N-(2-morpholin-4-ylethyl)benzamide |  | C |
| 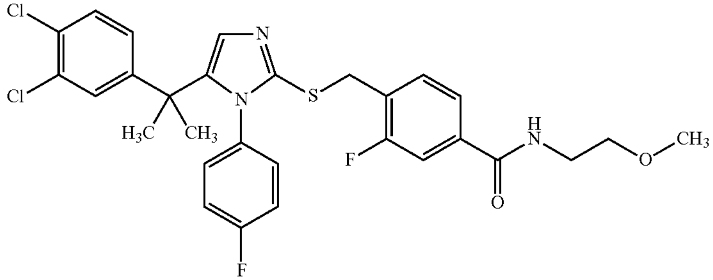 [SMILES: COCCNC(=O)c1ccc(CSc2ncc(C(C)(C)c3ccc(Cl)c(Cl)c3)n2-c2ccc(F)cc2)c(F)c1] | 4-[({5-[1-(3,4-dichlorophenyl)-1-methylethyl]-1-(4-fluorophenyl)-1H-imidazol-2-yl}thio)methyl]-3-fluoro-N-[2-(methyloxy)ethyl]benzamide |  | C |

TABLE 1-continued

| Structure | NAME | cAMP (EC$_{50}$) (nM) | CRE-Luc (EC$_{50}$) (nM) |
|---|---|---|---|
| 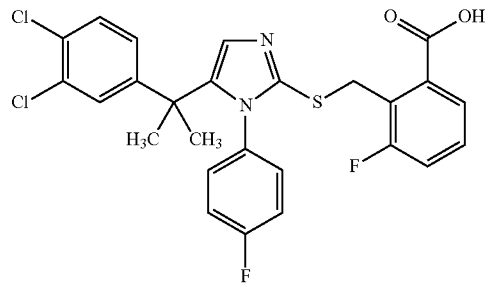 [SMILES: CC(C)(c1ccc(Cl)c(Cl)c1)c1cnc(SCc2c(F)cccc2C(=O)O)n1-c1ccc(F)cc1] | 2-[({5-[1-(3,4-dichlorophenyl)-1-methylethyl]-1-(4-fluorophenyl)-1H-imidazol-2-yl}thio)methyl]-3-fluorobenzoic acid | | C |
| 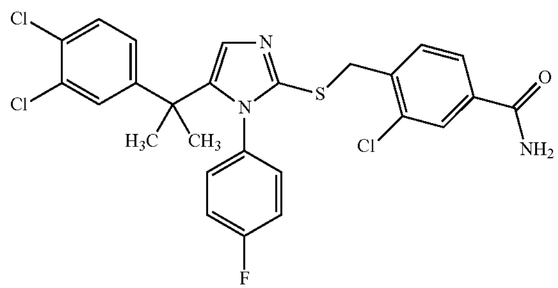 [SMILES: CC(C)(c1ccc(Cl)c(Cl)c1)c1cnc(SCc2ccc(C(N)=O)cc2Cl)n1-c1ccc(F)cc1] | 3-chloro-4-[({5-[1-(3,4-dichlorophenyl)-1-methylethyl]-1-(4-fluorophenyl)-1H-imidazol-2-yl}thio)methyl]benzamide | C | C |
| 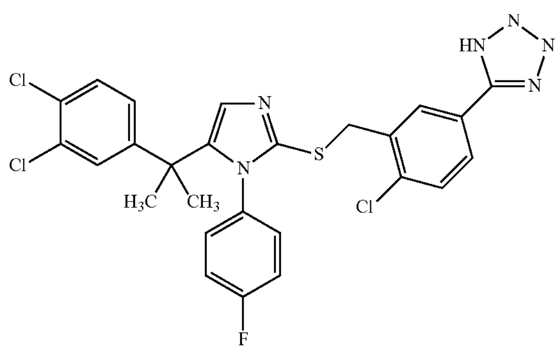 [SMILES: CC(C)(c1ccc(Cl)c(Cl)c1)c1cnc(SCc2cc(C3=NNNN3)ccc2Cl)n1-c1ccc(F)cc1] | 5-{4-chloro-3-[({5-[1-(3,4-dichlorophenyl)-1-methylethyl]-1-(4-fluorophenyl)-1H-imidazol-2-yl}thio)methyl]phenyl}-1H-tetrazole | | C |

TABLE 1-continued
| Structure | NAME | cAMP (EC$_{50}$) (nM) | CRE-Luc (EC$_{50}$) (nM) |
|---|---|---|---|
| 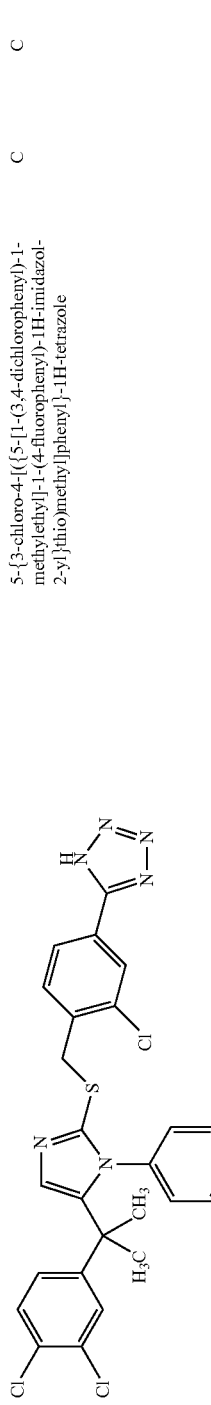 | 5-{3-chloro-4-[({5-[1-(3,4-dichlorophenyl)-1-methylethyl]-1-(4-fluorophenyl)-1H-imidazol-2-yl}thio)methyl]phenyl}-1H-tetrazole | C | C |
| 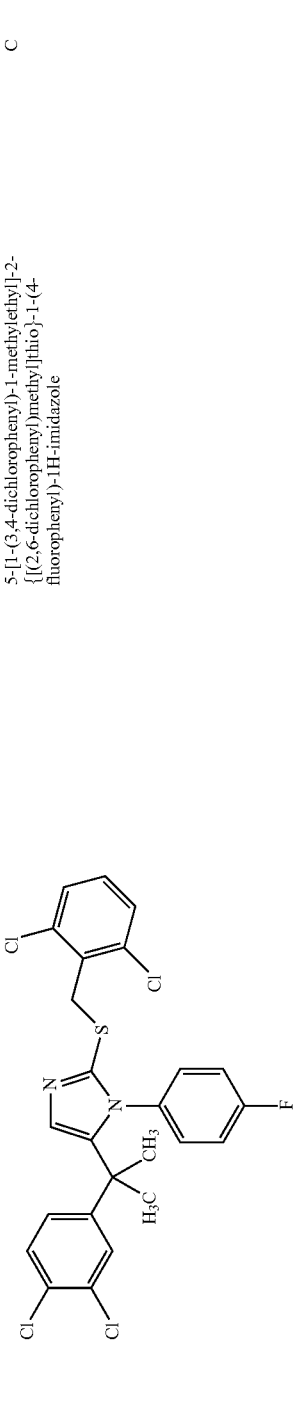 | 5-[1-(3,4-dichlorophenyl)-1-methylethyl]-2-{[(2,6-dichlorophenyl)methyl]thio}-1-(4-fluorophenyl)-1H-imidazole | | C |
| 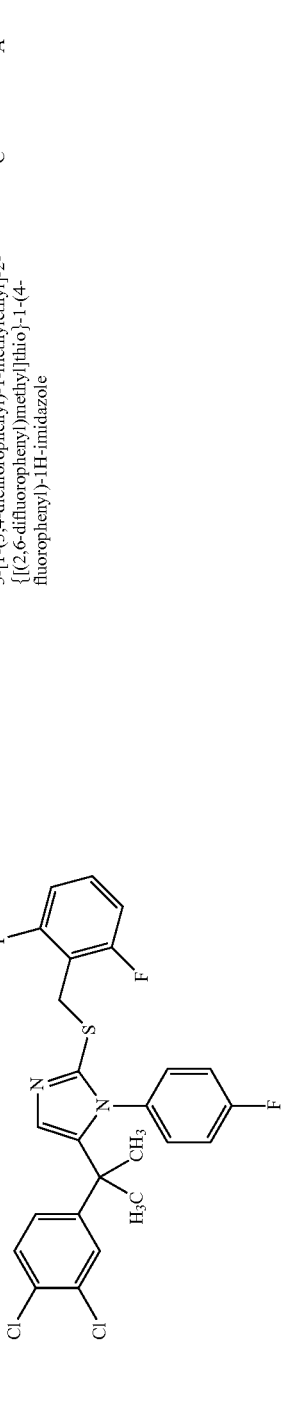 | 5-[1-(3,4-dichlorophenyl)-1-methylethyl]-2-{[(2,6-difluorophenyl)methyl]thio}-1-(4-fluorophenyl)-1H-imidazole | C | A |

TABLE 1-continued

| Structure | NAME | cAMP (EC$_{50}$) (nM) | CRE-Luc (EC$_{50}$) (nM) |
|---|---|---|---|
| 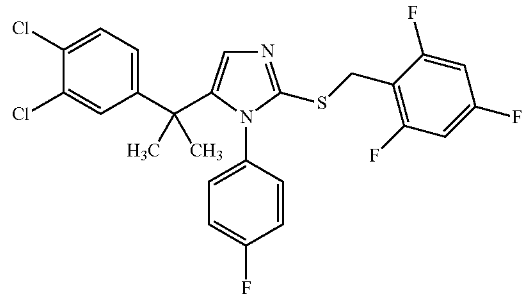 [SMILES: CC(C)(c1ccc(Cl)c(Cl)c1)c1cnc(SCc2c(F)cc(F)cc2F)n1-c1ccc(F)cc1] | 5-[1-(3,4-dichlorophenyl)-1-methylethyl]-1-(4-fluorophenyl)-2-{[(2,4,6-trifluorophenyl)methyl]thio}-1H-imidazole | | A |
| 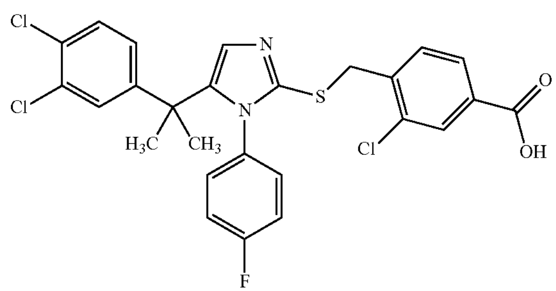 [SMILES: CC(C)(c1ccc(Cl)c(Cl)c1)c1cnc(SCc2ccc(C(=O)O)cc2Cl)n1-c1ccc(F)cc1] | 3-chloro-4-[({5-[1-(3,4-dichlorophenyl)-1-methylethyl]-1-(4-fluorophenyl)-1H-imidazol-2-yl}thio)methyl]benzoic acid | C | C |
| | 4-({[5-{1-[3-chloro-4-(methyloxyphenyl)-1-methylethyl]-1-(4-fluorophenyl)-1H-imidazol-2-yl]thio}methyl)-3-fluorobenzoic acid | | C |

TABLE 1-continued

| Structure | NAME | cAMP (EC$_{50}$) (nM) | CRE-Luc (EC$_{50}$) (nM) |
|---|---|---|---|
| | 5-({[5-[1-[3-chloro-4-(methyloxy)phenyl]-1-methylethyl]-1-(4-fluorophenyl)-1H-imidazol-2-yl]thio}methyl)-2-fluorobenzoic acid | | C |
| 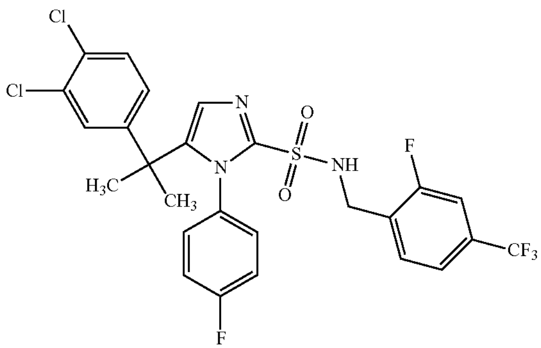 [SMILES: CC(C)(c1ccc(Cl)c(Cl)c1)c1cnc(S(=O)(=O)NCc2ccc(C(F)(F)F)cc2F)n1-c1ccc(F)cc1] | 5-[1-(3,4-dichlorophenyl)-1-methylethyl]-1-(4-fluorophenyl)-N-{[2-fluoro-4-(trifluoromethyl)phenyl]methyl}-1H-imidazole-2-sulfonamide | | C |
| 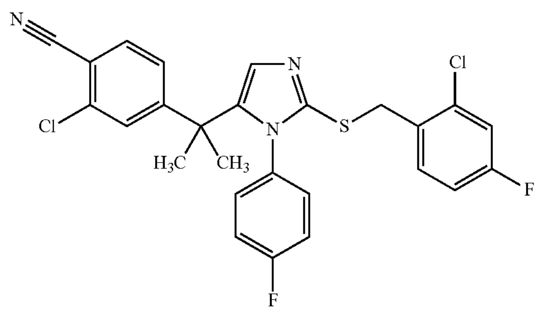 [SMILES: CC(C)(c1ccc(C#N)c(Cl)c1)c1cnc(SCc2ccc(F)cc2Cl)n1-c1ccc(F)cc1] | 2-chloro-4-{1-[2-{[(2-chloro-4-fluorophenyl)methyl]thio}-1-(4-fluorophenyl)-1H-imidazol-5-yl]-1-methylethyl}benzonitrile | C | C |

TABLE 1-continued

| Structure | NAME | cAMP (EC$_{50}$) (nM) | CRE-Luc (EC$_{50}$) (nM) |
|---|---|---|---|
| 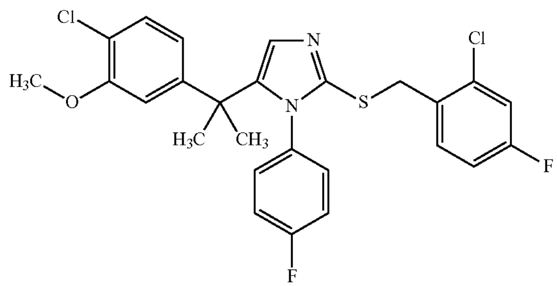 [SMILES: COc1cc(C(C)(C)c2cnc(SCc3ccc(F)cc3Cl)n2-c2ccc(F)cc2)ccc1Cl] | 2-{[(2-chloro-4-fluorophenyl)methyl]thio}-5-{1-[4-chloro-3-(methyloxy)phenyl]-1-methylethyl}-1-(4-fluorophenyl)-1H-imidazole | C | A |
| 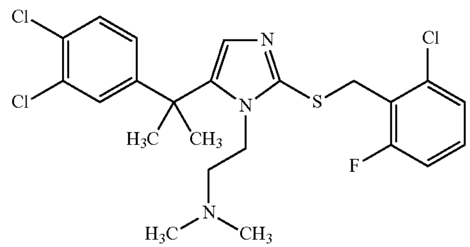 [SMILES: CN(C)CCn1c(C(C)(C)c2ccc(Cl)c(Cl)c2)cnc1SCc1c(F)cccc1Cl] | 2-(2-{[(2-chloro-6-fluorophenyl)methyl]thio}-5-[1-(3,4-dichlorophenyl)-1-methylethyl]-1H-imidazol-1-yl)-N,N-dimethylethanamine | | D |
| 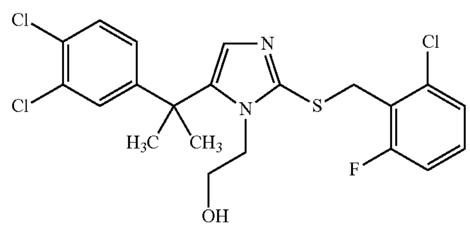 [SMILES: CC(C)(c1ccc(Cl)c(Cl)c1)c1cnc(SCc2c(F)cccc2Cl)n1CCO] | 2-(2-{[(2-chloro-6-fluorophenyl)methyl]thio}-5-[1-(3,4-dichlorophenyl)-1-methylethyl]-1H-imidazol-1-yl)ethanol | | C |

TABLE 1-continued

| Structure | NAME | cAMP (EC$_{50}$) (nM) | CRE-Luc (EC$_{50}$) (nM) |
|---|---|---|---|
| | N-({4-[({5-[1-(3,4-dichlorophenyl)-1-methylethyl]-1-(4-fluorophenyl)-1H-imidazol-2-yl]thio}methyl]-3-fluorophenyl}carbonyl)glycine | C | C |
| 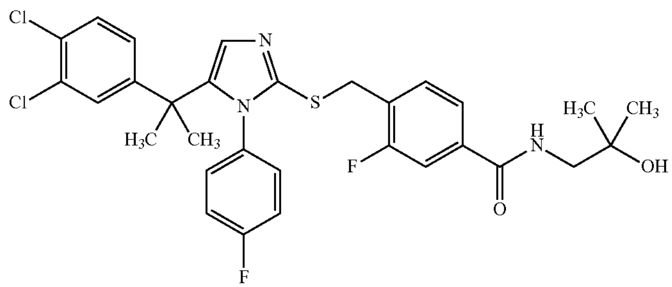 [SMILES: CC(C)(O)CNC(=O)c1ccc(CSc2ncc(C(C)(C)c3ccc(Cl)c(Cl)c3)n2-c2ccc(F)cc2)c(F)c1] | 4-[({5-[1-(3,4-dichlorophenyl)-1-methylethyl]-1-(4-fluorophenyl)-1H-imidazol-2-yl}thio)methyl]-3-fluoro-N-(2-hydroxy-2-methylpropyl)benzamide | C | |
| 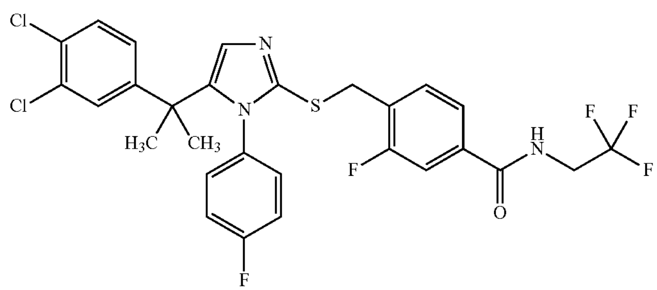 [SMILES: CC(C)(c1ccc(Cl)c(Cl)c1)c1cnc(SCc2ccc(C(=O)NCC(F)(F)F)cc2F)n1-c1ccc(F)cc1] | 4-[({5-[1-(3,4-dichlorophenyl)-1-methylethyl]-1-(4-fluorophenyl)-1H-imidazol-2-yl}thio)methyl]-3-fluoro-N-(2,2,2-trifluoroethyl)benzamide | | C |

TABLE 1-continued

| Structure | NAME | cAMP (EC$_{50}$) (nM) | CRE-Luc (EC$_{50}$) (nM) |
|---|---|---|---|
| 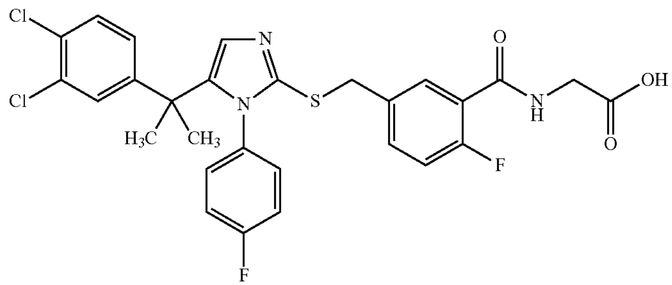 [SMILES: CC(C)(c1ccc(Cl)c(Cl)c1)c1cnc(SCc2ccc(F)c(C(=O)NCC(=O)O)c2)n1-c1ccc(F)cc1] | N-({5-[({5-[1-(3,4-dichlorophenyl)-1-methylethyl]-1-(4-fluorophenyl)-1H-imidazol-2-yl}thio)methyl]-2-fluorophenyl}carbonyl)glycine | C | C |
| 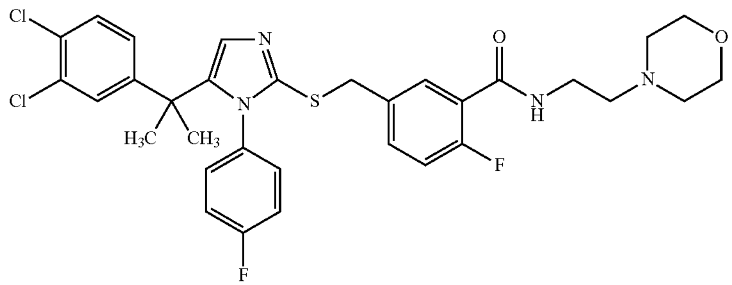 [SMILES: CC(C)(c1ccc(Cl)c(Cl)c1)c1cnc(SCc2ccc(F)c(C(=O)NCCN3CCOCC3)c2)n1-c1ccc(F)cc1] | 5-[({5-[1-(3,4-dichlorophenyl)-1-methylethyl]-1-(4-fluorophenyl)-1H-imidazol-2-yl}thio)methyl]-2-fluoro-N-(2-morpholin-4-ylethyl)benzamide | | C |
| 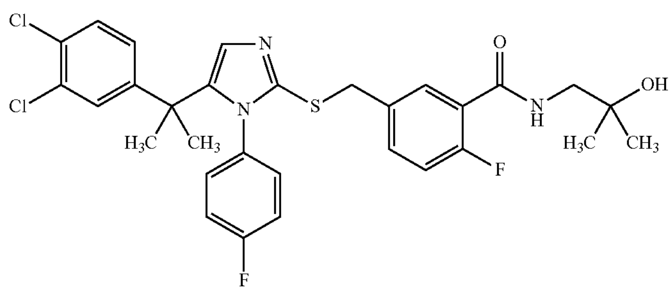 [SMILES: CC(C)(O)CNC(=O)c1cc(CSc2ncc(C(C)(C)c3ccc(Cl)c(Cl)c3)n2-c2ccc(F)cc2)ccc1F] | 5-[({5-[1-(3,4-dichlorophenyl)-1-methylethyl]-1-(4-fluorophenyl)-1H-imidazol-2-yl}thio)methyl]-2-fluoro-N-(2-hydroxy-2-methylpropyl)benzamide | | C |

TABLE 1-continued

| Structure | NAME | cAMP (EC$_{50}$) (nM) | CRE-Luc (EC$_{50}$) (nM) |
|---|---|---|---|
| 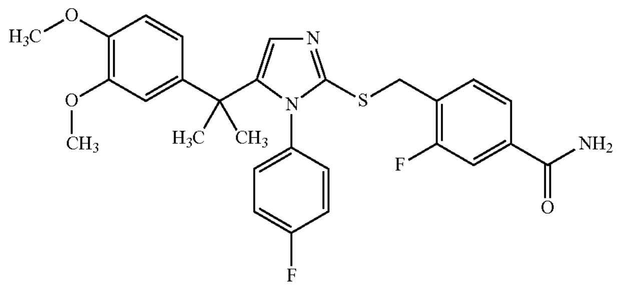 [SMILES: COc1ccc(C(C)(C)c2cnc(SCc3ccc(C(N)=O)cc3F)n2-c2ccc(F)cc2)cc1OC] | 4-({[5-{1-[3,4-bis(methyloxy)phenyl]-1-methylethyl}-1-(4-fluorophenyl)-1H-imidazol-2-yl]thio}methyl)-3-fluorobenzamide | A | C |
| 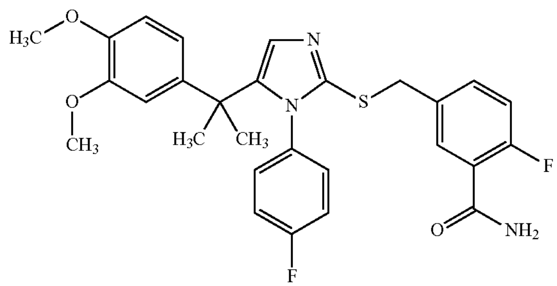 [SMILES: COc1ccc(C(C)(C)c2cnc(SCc3ccc(F)c(C(N)=O)c3)n2-c2ccc(F)cc2)cc1OC] | 5-({[5-{1-[3,4-bis(methyloxy)phenyl]-1-methylethyl}-1-(4-fluorophenyl)-1H-imidazol-2-yl]thio}methyl)-2-fluorobenzamide | A | A |
| 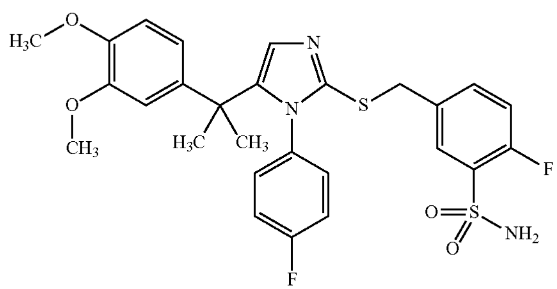 [SMILES: COc1ccc(C(C)(C)c2cnc(SCc3ccc(F)c(S(N)(=O)=O)c3)n2-c2ccc(F)cc2)cc1OC] | 5-({[5-{1-[3,4-bis(methyloxy)phenyl]-1-methylethyl}-1-(4-fluorophenyl)-1H-imidazol-2-yl]thio}methyl)-2-fluorobenzenesulfonamide | A | A |

TABLE 1-continued

| Structure | NAME | cAMP (EC$_{50}$) (nM) | CRE-Luc (EC$_{50}$) (nM) |
|---|---|---|---|
| 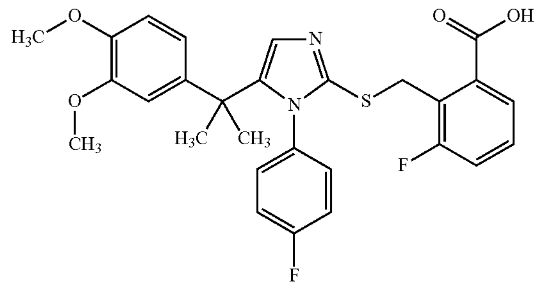 [SMILES: COc1ccc(C(C)(C)c2cnc(SCc3c(F)cccc3C(=O)O)n2-c2ccc(F)cc2)cc1OC] | 2-({[5-{1-[3,4-bis(methyloxy)phenyl]-1-methylethyl}-1-(4-fluorophenyl)-1H-imidazol-2-yl]thio}methyl)-3-fluorobenzoic acid | | C |
| 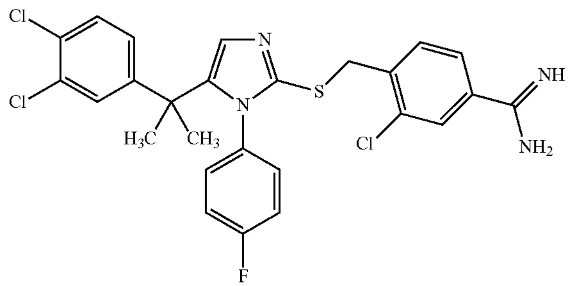 [SMILES: CC(C)(c1ccc(Cl)c(Cl)c1)c1cnc(SCc2ccc(C(=N)N)cc2Cl)n1-c1ccc(F)cc1] | 3-chloro-4-[({5-[1-(3,4-dichlorophenyl)-1-methylethyl]-1-(4-fluorophenyl)-1H-imidazol-2-yl}thio)methyl]benzenecarboximidamide | | C |
| 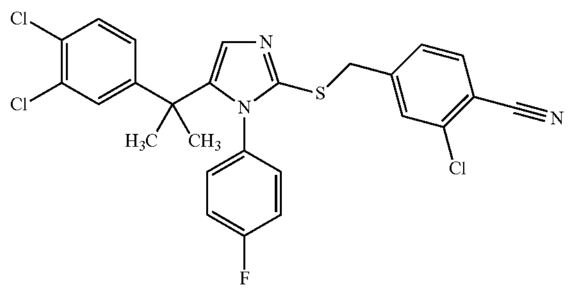 [SMILES: CC(C)(c1ccc(Cl)c(Cl)c1)c1cnc(SCc2ccc(C#N)c(Cl)c2)n1-c1ccc(F)cc1] | 2-chloro-4-[({5-[1-(3,4-dichlorophenyl)-1-methylethyl]-1-(4-fluorophenyl)-1H-imidazol-2-yl}thio)methyl]benzonitrile | | C |

TABLE 1-continued

| Structure | NAME | cAMP (EC$_{50}$) (nM) | CRE-Luc (EC$_{50}$) (nM) |
|---|---|---|---|
| 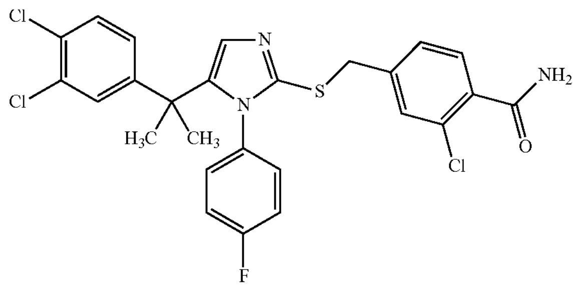 [SMILES: CC(C)(c1ccc(Cl)c(Cl)c1)c1cnc(SCc2ccc(C(N)=O)c(Cl)c2)n1-c1ccc(F)cc1] | 2-chloro-4-[({5-[1-(3,4-dichlorophenyl)-1-methylethyl]-1-(4-fluorophenyl)-1H-imidazol-2-yl}thio)methyl]benzamide |  | C |
| 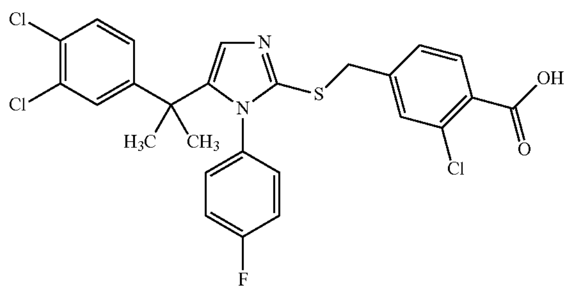 [SMILES: CC(C)(c1ccc(Cl)c(Cl)c1)c1cnc(SCc2ccc(C(=O)O)c(Cl)c2)n1-c1ccc(F)cc1] | 2-chloro-4-[({5-[1-(3,4-dichlorophenyl)-1-methylethyl]-1-(4-fluorophenyl)-1H-imidazol-2-yl}thio)methyl]benzoic acid | C | C |
| 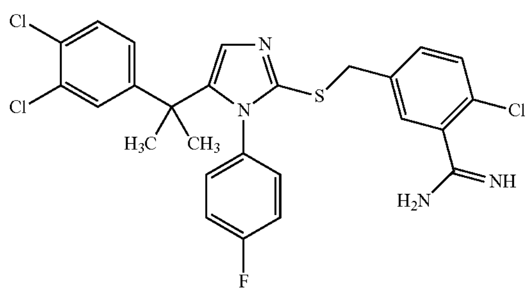 [SMILES: CC(C)(c1ccc(Cl)c(Cl)c1)c1cnc(SCc2ccc(Cl)c(C(=N)N)c2)n1-c1ccc(F)cc1] | 2-chloro-5-[({5-[1-(3,4-dichlorophenyl)-1-methylethyl]-1-(4-fluorophenyl)-1H-imidazol-2-yl}thio)methyl]benzenecarboximidamide |  | D |

TABLE 1-continued
| Structure | NAME | cAMP (EC$_{50}$) (nM) | CRE-Luc (EC$_{50}$) (nM) |
|---|---|---|---|
| 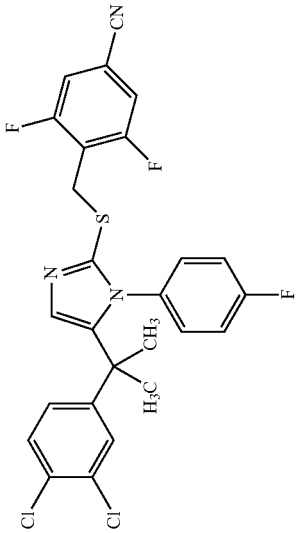 | 4-[({5-[1-(3,4-dichlorophenyl)-1-methylethyl]-1-(4-fluorophenyl)-1H-imidazol-2-yl}thio)methyl]-3,5-difluorobenzonitrile | | A |
| 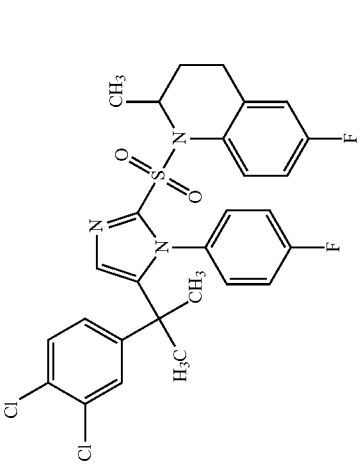 | 1-({5-[1-(3,4-dichlorophenyl)-1-methylethyl]-1-(4-fluorophenyl)-1H-imidazol-2-yl}sulfonyl)-6-fluoro-2-methyl-1,2,3,4-tetrahydroquinoline | | D |
| 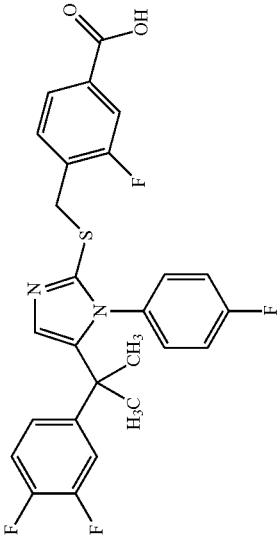 | 4-[({5-[1-(3,4-difluorophenyl)-1-methylethyl]-1-(4-fluorophenyl)-1H-imidazol-2-yl}thio)methyl]-3-fluorobenzoic acid | | C |

TABLE 1-continued

| Structure | NAME | cAMP (EC$_{50}$) (nM) | CRE-Luc (EC$_{50}$) (nM) |
|---|---|---|---|
| 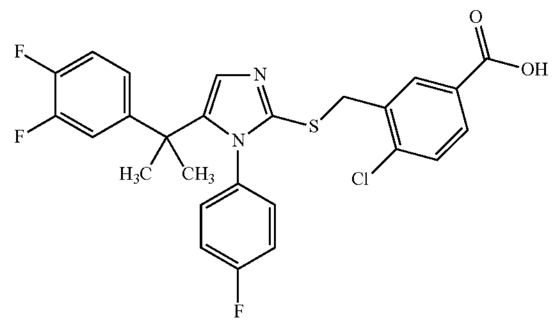 [SMILES: CC(C)(c1ccc(F)c(F)c1)c1cnc(SCc2cc(C(=O)O)ccc2Cl)n1-c1ccc(F)cc1] | 4-chloro-3-[({5-[1-(3,4-difluorophenyl)-1-methylethyl]-1-(4-fluorophenyl)-1H-imidazol-2-yl}thio)methyl]benzoic acid | C | C |
| 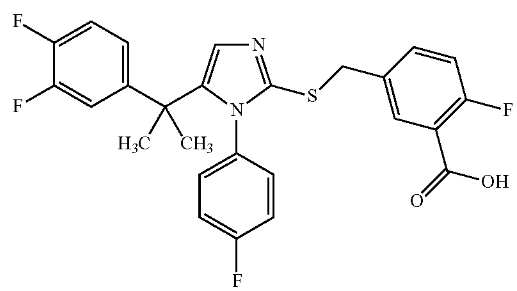 [SMILES: CC(C)(c1ccc(F)c(F)c1)c1cnc(SCc2ccc(F)c(C(=O)O)c2)n1-c1ccc(F)cc1] | 5-[({5-[1-(3,4-difluorophenyl)-1-methylethyl]-1-(4-fluorophenyl)-1H-imidazol-2-yl}thio)methyl]-2-fluorobenzoic acid | | C |
| 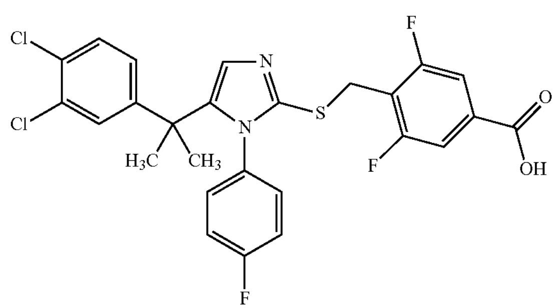 [SMILES: CC(C)(c1ccc(Cl)c(Cl)c1)c1cnc(SCc2c(F)cc(C(=O)O)cc2F)n1-c1ccc(F)cc1] | 4-[({5-[1-(3,4-dichlorophenyl)-1-methylethyl]-1-(4-fluorophenyl)-1H-imidazol-2-yl}thio)methyl]-3,5-difluorobenzoic acid | C | A |

TABLE 1-continued

| Structure | NAME | cAMP (EC$_{50}$) (nM) | CRE-Luc (EC$_{50}$) (nM) |
|---|---|---|---|
| 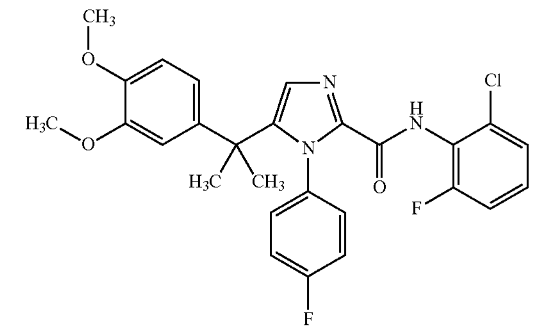 [SMILES: COc1ccc(C(C)(C)c2cnc(C(=O)Nc3c(F)cccc3Cl)n2-c2ccc(F)cc2)cc1OC] | 5-{1-[3,4-bis(methyloxy)phenyl]-1-methylethyl}-N-(2-chloro-6-fluorophenyl)-1-(4-fluorophenyl)-1H-imidazole-2-carboxamide | | D |
| 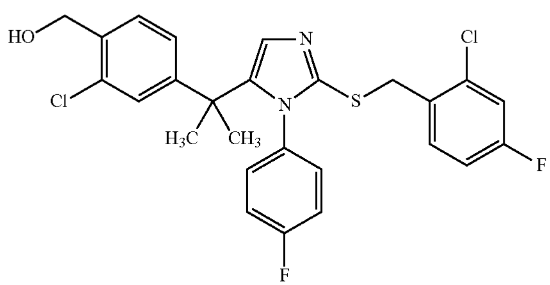 [SMILES: CC(C)(c1ccc(CO)c(Cl)c1)c1cnc(SCc2ccc(F)cc2Cl)n1-c1ccc(F)cc1] | (2-chloro-4-{1-[2-{[(2-chloro-4-fluorophenyl)methyl]thio}-1-(4-fluorophenyl)-1H-imidazol-5-yl]-1-methylethyl}phenyl)methanol | C | C |
| 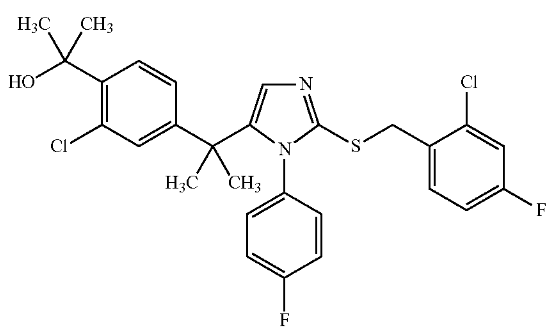 [SMILES: CC(C)(O)c1ccc(C(C)(C)c2cnc(SCc3ccc(F)cc3Cl)n2-c2ccc(F)cc2)cc1Cl] | 2-(2-chloro-4-{1-[2-{[(2-chloro-4-fluorophenyl)methyl]thio}-1-(4-fluorophenyl)-1H-imidazol-5-yl]-1-methylethyl}phenyl)propan-2-ol | | C |

TABLE 1-continued

| Structure | NAME | cAMP (EC$_{50}$) (nM) | CRE-Luc (EC$_{50}$) (nM) |
|---|---|---|---|
| 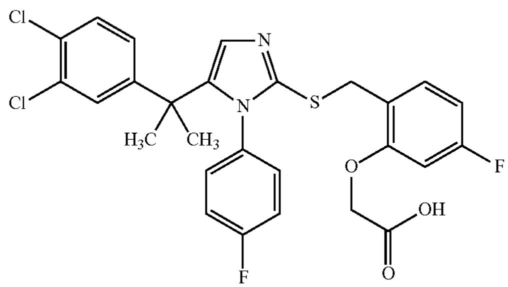 [SMILES: CC(C)(c1ccc(Cl)c(Cl)c1)c1cnc(SCc2ccc(F)cc2OCC(=O)O)n1-c1ccc(F)cc1] | ({2-[({5-[1-(3,4-dichlorophenyl)-1-methylethyl]-1-(4-fluorophenyl)-1H-imidazol-2-yl}thio)methyl]-5-fluorophenyl}oxy)acetic acid |  | C |
| 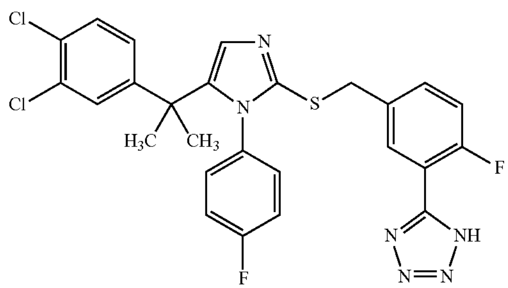 [SMILES: CC(C)(c1ccc(Cl)c(Cl)c1)c1cnc(SCc2ccc(F)c(-c3nnn[nH]3)c2)n1-c1ccc(F)cc1] | 5-{5-[({5-[1-(3,4-dichlorophenyl)-1-methylethyl]-1-(4-fluorophenyl)-1H-imidazol-2-yl}thio)methyl]-2-fluorophenyl}-1H-tetrazole |  | C |
| 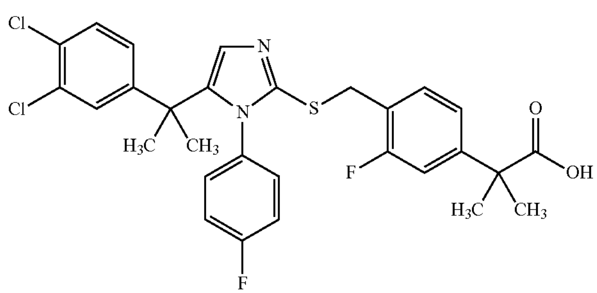 [SMILES: CC(C)(C(=O)O)c1ccc(CSc2ncc(C(C)(C)c3ccc(Cl)c(Cl)c3)n2-c2ccc(F)cc2)c(F)c1] | 2-{4-[({5-[1-(3,4-dichlorophenyl)-1-methylethyl]-1-(4-fluorophenyl)-1H-imidazol-2-yl}thio)methyl]-3-fluorophenyl}-2-methylpropanoic acid |  | C |

TABLE 1-continued

| Structure | NAME | cAMP (EC$_{50}$) (nM) | CRE-Luc (EC$_{50}$) (nM) |
|---|---|---|---|
| 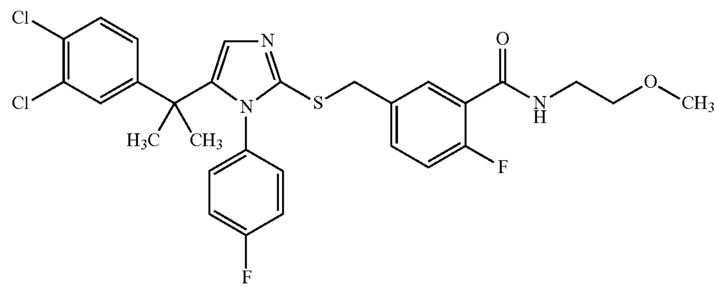 [SMILES: COCCNC(=O)c1cc(CSc2ncc(C(C)(C)c3ccc(Cl)c(Cl)c3)n2-c2ccc(F)cc2)ccc1F] | 5-[({5-[1-(3,4-dichlorophenyl)-1-methylethyl]-1-(4-fluorophenyl)-1H-imidazol-2-yl}thio)methyl]-2-fluoro-N-[2-(methyloxy)ethyl]benzamide | | C |
| 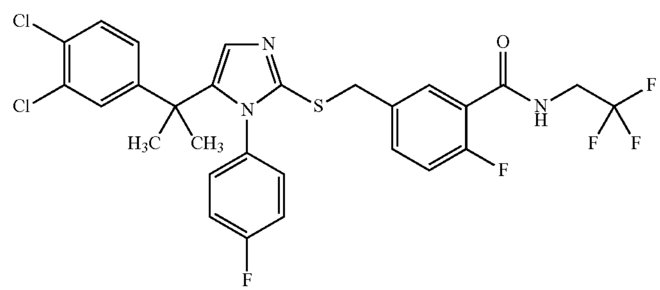 [SMILES: CC(C)(c1ccc(Cl)c(Cl)c1)c1cnc(SCc2ccc(F)c(C(=O)NCC(F)(F)F)c2)n1-c1ccc(F)cc1] | 5-[({5-[1-(3,4-dichlorophenyl)-1-methylethyl]-1-(4-fluorophenyl)-1H-imidazol-2-yl}thio)methyl]-2-fluoro-N-(2,2,2-trifluoroethyl)benzamide | | C |
| | 2-[[(2-chloro-6-fluorophenyl)methyl]thio]-5-{1-[4-chloro-3-(methyloxy)phenyl]-1-methylethyl}-1-(4-fluorophenyl)-1H-imidazole | A | A |

TABLE 1-continued

| Structure | NAME | cAMP (EC$_{50}$) (nM) | CRE-Luc (EC$_{50}$) (nM) |
|---|---|---|---|
| 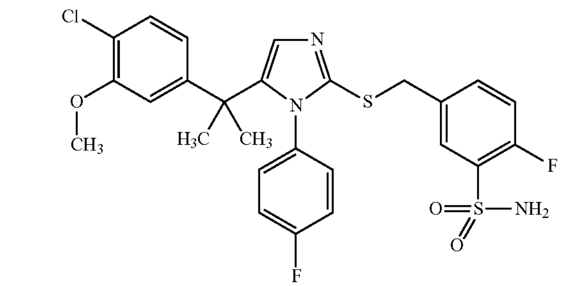 [SMILES: COc1cc(C(C)(C)c2cnc(SCc3ccc(F)c(S(N)(=O)=O)c3)n2-c2ccc(F)cc2)ccc1Cl] | 5-({[5-{1-[4-chloro-3-(methyloxy)phenyl]-1-methylethyl}-1-(4-fluorophenyl)-1H-imidazol-2-yl]thio}methyl)-2-fluorobenzenesulfonamide | A | A |
| 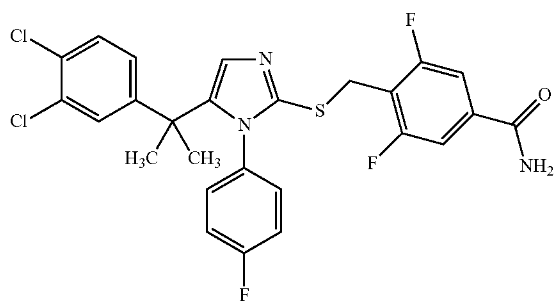 | 4-[({5-[1-(3,4-dichlorophenyl)-1-methylethyl]-1-(4-fluorophenyl)-1H-imidazol-2-yl}thio)methyl]-3,5-difluorobenzamide | C | C |
| 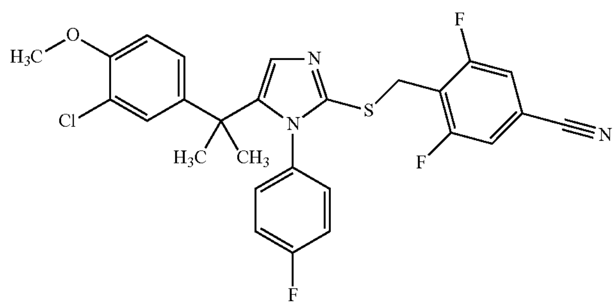 [SMILES: COc1ccc(C(C)(C)c2cnc(SCc3c(F)cc(C#N)cc3F)n2-c2ccc(F)cc2)cc1Cl] | 4-({[5-{1-[3-chloro-4-(methyloxy)phenyl]-1-methylethyl}-1-(4-fluorophenyl)-1H-imidazol-2-yl]thio}methyl)-3,5-difluorobenzonitrile | A | A |

TABLE 1-continued

| Structure | NAME | cAMP (EC$_{50}$) (nM) | CRE-Luc (EC$_{50}$) (nM) |
|---|---|---|---|
| 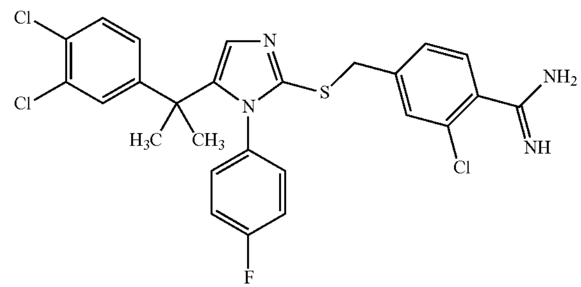 | 2-chloro-4-[({5-[1-(3,4-dichlorophenyl)-1-methylethyl]-1-(4-fluorophenyl)-1H-imidazol-2-yl}thio)methyl]benzenecarboximidamide | | D |
| 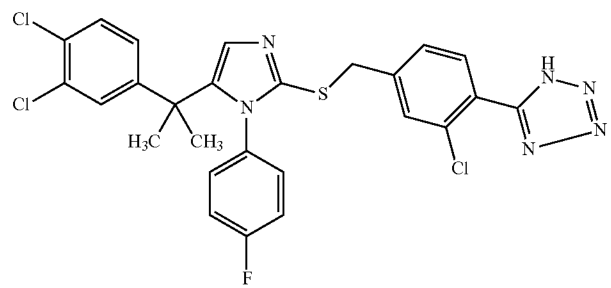 [SMILES: CC(C)(c1ccc(Cl)c(Cl)c1)c1cnc(SCc2ccc(-c3nnn[nH]3)c(Cl)c2)n1-c1ccc(F)cc1] | 5-{2-chloro-4-[({5-[1-(3,4-dichlorophenyl)-1-methylethyl]-1-(4-fluorophenyl)-1H-imidazol-2-yl}thio)methyl]phenyl}-1H-tetrazole | | C |
| | 2-[[(2-chloro-6-fluorophenyl)methyl]thio]-5-{1-[3,5-dichloro-4-(methyloxy)phenyl]-1-methylethyl}-1-(4-fluorophenyl)-1H-imidazole | A | A |

TABLE 1-continued

| Structure | NAME | cAMP (EC$_{50}$) (nM) | CRE-Luc (EC$_{50}$) (nM) |
|---|---|---|---|
| 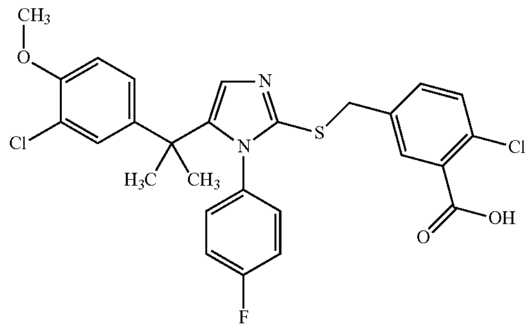 [SMILES: COc1ccc(C(C)(C)c2cnc(SCc3ccc(Cl)c(C(=O)O)c3)n2-c2ccc(F)cc2)cc1Cl] | 2-chloro-5-({[5-{1-[3-chloro-4-(methyloxy)phenyl]-1-methylethyl}-1-(4-fluorophenyl)-1H-imidazol-2-yl]thio}methyl)benzoic acid | C | C |
| 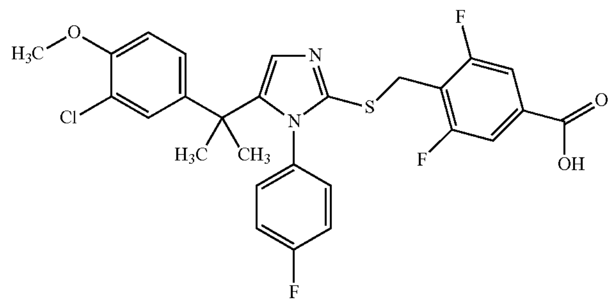 | 4-({[5-{1-[3-chloro-4-(methyloxy)phenyl]-1-methylethyl}-1-(4-fluorophenyl)-1H-imidazol-2-yl]thio}methyl)-3,5-difluorobenzoic acid | A | A |
| 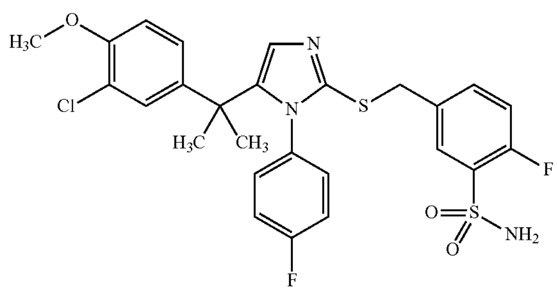 [SMILES: COc1ccc(C(C)(C)c2cnc(SCc3ccc(F)c(S(N)(=O)=O)c3)n2-c2ccc(F)cc2)cc1Cl] | 5-({[5-{1-[3-chloro-4-(methyloxy)phenyl]-1-methylethyl}-1-(4-fluorophenyl)-1H-imidazol-2-yl]thio}methyl)-2-fluorobenzenesulfonamide | A | A |

TABLE 1-continued

| Structure | NAME | cAMP (EC$_{50}$) (nM) | CRE-Luc (EC$_{50}$) (nM) |
|---|---|---|---|
| 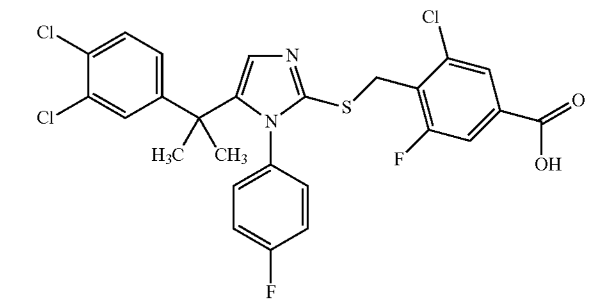 [SMILES: CC(C)(c1ccc(Cl)c(Cl)c1)c1cnc(SCc2c(F)cc(C(=O)O)cc2Cl)n1-c1ccc(F)cc1] | 3-chloro-4-[({5-[1-(3,4-dichlorophenyl)-1-methylethyl]-1-(4-fluorophenyl)-1H-imidazol-2-yl}thio)methyl]-5-fluorobenzoic acid | C | A |
| 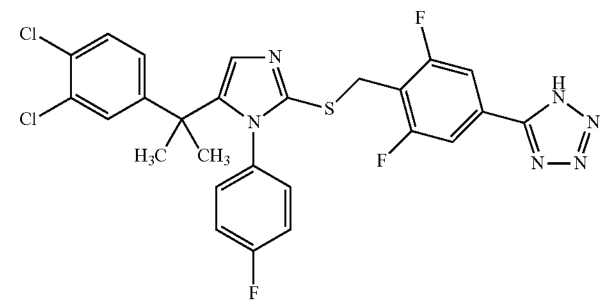 [SMILES: CC(C)(c1ccc(Cl)c(Cl)c1)c1cnc(SCc2c(F)cc(-c3nnn[nH]3)cc2F)n1-c1ccc(F)cc1] | 5-{4-[({5-[1-(3,4-dichlorophenyl)-1-methylethyl]-1-(4-fluorophenyl)-1H-imidazol-2-yl}thio)methyl]-3,5-difluorophenyl}-1H-tetrazole | C | C |
| | 3-chloro-4-{[(5-[1-[3-chloro-4-(methyloxy)phenyl]-1-methylethyl}-1-(4-fluorophenyl)-1H-imidazol-2-yl]thio)methyl)-5-fluorobenzoic acid | A | A |

TABLE 1-continued

| Structure | NAME | cAMP (EC$_{50}$) (nM) | CRE-Luc (EC$_{50}$) (nM) |
|---|---|---|---|
| | 2-{[(2-chloro-4-fluorophenyl)methylthio]}-5-{1-[3,5-dichloro-4-(methyloxy)phenyl]-1-methylethyl}-1-(4-fluorophenyl)-1H-imidazole | | A |
| | 3-chloro-4-({[5-{1-[3,5-dichloro-4-(methyloxy)phenyl]-1-methylethyl}-1-(4-fluorophenyl)-1H-imidazol-2-yl]thio}methyl)benzenesulfonamide | | A |
| | 3-chloro-4-[({5-[1-(3,4-dichlorophenyl)-1-methylethyl]-1-(4-fluorophenyl)-1H-imidazol-2-yl]thio}methyl)]benzenesulfonamide | C | C |

TABLE 1-continued

| Structure | NAME | cAMP (EC$_{50}$) (nM) | CRE-Luc (EC$_{50}$) (nM) |
|---|---|---|---|
| 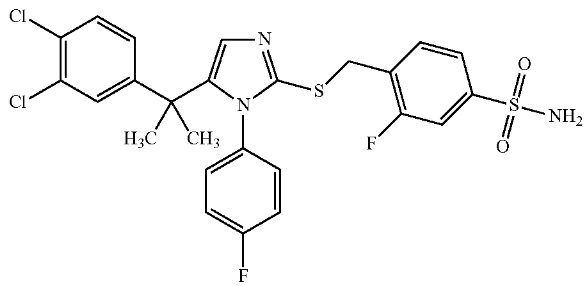 [SMILES: CC(C)(c1ccc(Cl)c(Cl)c1)c1cnc(SCc2ccc(S(N)(=O)=O)cc2F)n1-c1ccc(F)cc1] | 4-[({5-[1-(3,4-dichlorophenyl)-1-methylethyl]-1-(4-fluorophenyl)-1H-imidazol-2-yl}thio)methyl]-3-fluorobenzenesulfonamide | C | C |
| 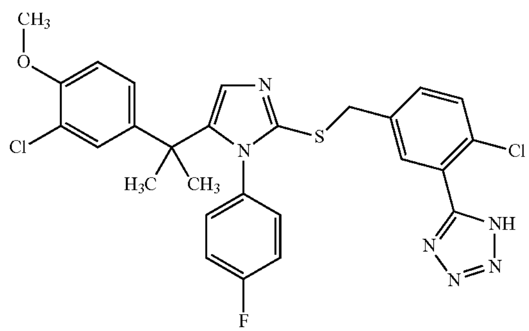 [SMILES: COc1ccc(C(C)(C)c2cnc(SCc3ccc(Cl)c(-c4nnn[nH]4)c3)n2-c2ccc(F)cc2)cc1Cl] | 5-[2-chloro-5-({[5-{1-[3-chloro-4-(methyloxy)phenyl]-1-methylethyl}-1-(4-fluorophenyl)-1H-imidazol-2-yl]thio}methyl)phenyl]-1H-tetrazole | C | A |
| 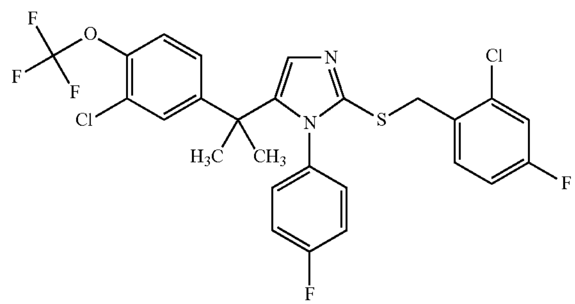 [SMILES: CC(C)(c1ccc(OC(F)(F)F)c(Cl)c1)c1cnc(SCc2ccc(F)cc2Cl)n1-c1ccc(F)cc1] | 2-{[(2-chloro-4-fluorophenyl)methyl]thio}-5-(1-{3-chloro-4-[(trifluoromethyl)oxy]phenyl}-1-methylethyl)-1-(4-fluorophenyl)-1H-imidazole | | D |

TABLE 1-continued

| Structure | NAME | cAMP (EC$_{50}$) (nM) | CRE-Luc (EC$_{50}$) (nM) |
|---|---|---|---|
| 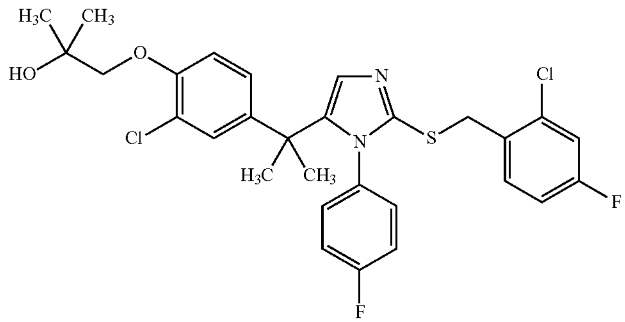 [SMILES: CC(C)(O)COc1ccc(C(C)(C)c2cnc(SCc3ccc(F)cc3Cl)n2-c2ccc(F)cc2)cc1Cl] | 1-[(2-chloro-4-{1-[2-{[(2-chloro-4-fluorophenyl)methyl]thio}-1-(4-fluorophenyl)-1H-imidazol-5-yl]-1-methylethyl}phenyl)oxy]-2-methylpropan-2-ol | | C |
| 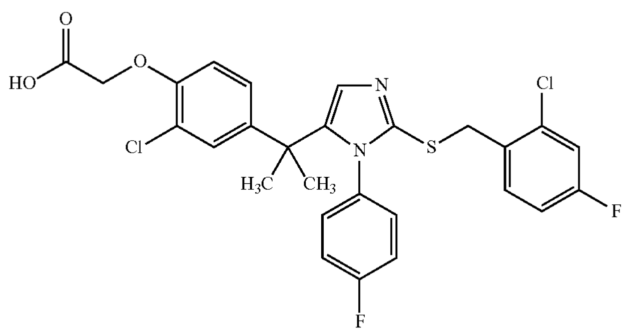 [SMILES: CC(C)(c1ccc(OCC(=O)O)c(Cl)c1)c1cnc(SCc2ccc(F)cc2Cl)n1-c1ccc(F)cc1] | [(2-chloro-4-{1-[2-{[(2-chloro-4-fluorophenyl)methyl]thio}-1-(4-fluorophenyl)-1H-imidazol-5-yl]-1-methylethyl}phenyl)oxy]acetic acid | | D |
| 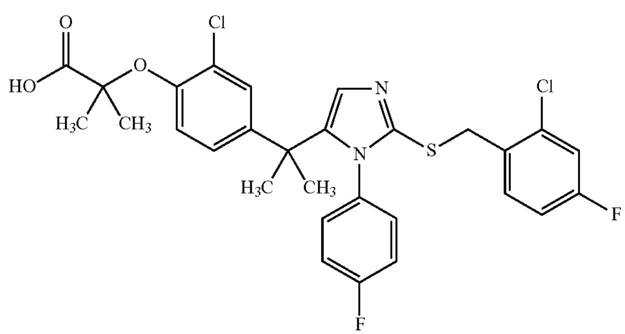 [SMILES: CC(C)(Oc1ccc(C(C)(C)c2cnc(SCc3ccc(F)cc3Cl)n2-c2ccc(F)cc2)cc1Cl)C(=O)O] | 2-[(2-chloro-4-{1-[2-{[(2-chloro-4-fluorophenyl)methyl]thio}-1-(4-fluorophenyl)-1H-imidazol-5-yl]-1-methylethyl}phenyl)oxy]-2-methylpropanoic acid | | C |

TABLE 1-continued

| Structure | NAME | cAMP (EC$_{50}$) (nM) | CRE-Luc (EC$_{50}$) (nM) |
|---|---|---|---|
| 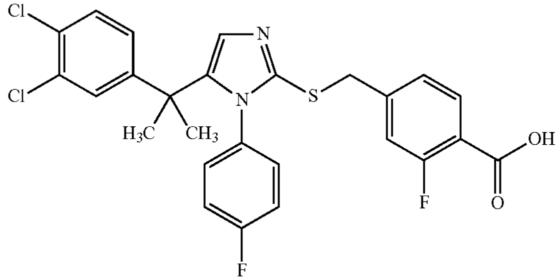 [SMILES: CC(C)(c1ccc(Cl)c(Cl)c1)c1cnc(SCc2ccc(C(=O)O)c(F)c2)n1-c1ccc(F)cc1] | 4-[({5-[1-(3,4-dichlorophenyl)-1-methylethyl]-1-(4-fluorophenyl)-1H-imidazol-2-yl}thio)methyl]-2-fluorobenzoic acid | | C |
| 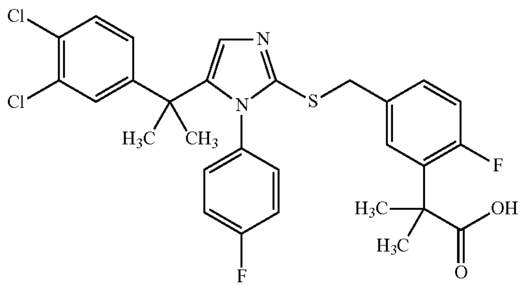 [SMILES: CC(C)(C(=O)O)c1cc(CSc2ncc(C(C)(C)c3ccc(Cl)c(Cl)c3)n2-c2ccc(F)cc2)ccc1F] | 2-{5-[({5-[1-(3,4-dichlorophenyl)-1-methylethyl]-1-(4-fluorophenyl)-1H-imidazol-2-yl}thio)methyl]-2-fluorophenyl}-2-methylpropanoic acid | | D |
| 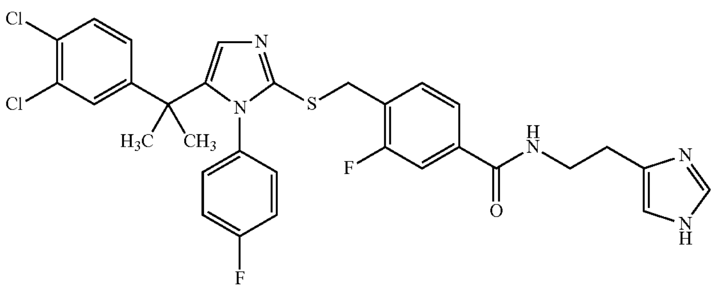 [SMILES: CC(C)(c1ccc(Cl)c(Cl)c1)c1cnc(SCc2ccc(C(=O)NCCc3c[nH]cn3)cc2F)n1-c1ccc(F)cc1] | 4-[({5-[1-(3,4-dichlorophenyl)-1-methylethyl]-1-(4-fluorophenyl)-1H-imidazol-2-yl}thio)methyl]-3-fluoro-N-[2-(1H-imidazol-4-yl)ethyl]benzamide | C | C |

TABLE 1-continued

| Structure | NAME | cAMP (EC$_{50}$) (nM) | CRE-Luc (EC$_{50}$) (nM) |
|---|---|---|---|
| 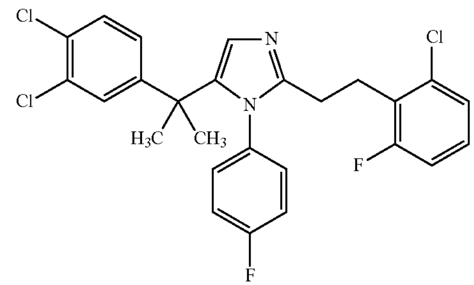 [SMILES: CC(C)(c1ccc(Cl)c(Cl)c1)c1cnc(CCc2c(F)cccc2Cl)n1-c1ccc(F)cc1] | 2-[2-(2-chloro-6-fluorophenyl)ethyl]-5-[1-(3,4-dichlorophenyl)-1-methylethyl]-1-(4-fluorophenyl)-1H-imidazole | C | C |
| 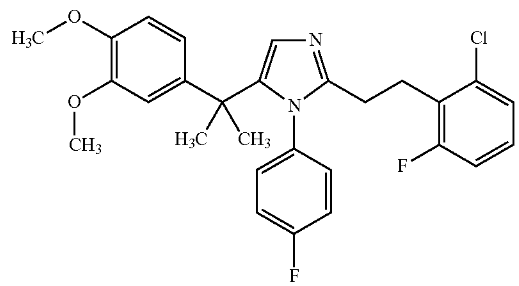 [SMILES: COc1ccc(C(C)(C)c2cnc(CCc3c(F)cccc3Cl)n2-c2ccc(F)cc2)cc1OC] | 5-{1-[3,4-bis(methyloxy)phenyl]-1-methylethyl}-2-[2-(2-chloro-6-fluorophenyl)ethyl]-1-(4-fluorophenyl)-1H-imidazole | A | A |
| | 4-chloro-3-({[5-[1-[4-chloro-3-(methyloxy)phenyl]-1-methylethyl]-1-(4-fluorophenyl)-1H-imidazol-2-yl]thio}methyl)benzoic acid | A | A |

TABLE 1-continued

| Structure | NAME | cAMP (EC$_{50}$) (nM) | CRE-Luc (EC$_{50}$) (nM) |
|---|---|---|---|
| | 4-({[5-[1-[4-chloro-3-(methyloxy)phenyl]-1-methylethyl]-1-(4-fluorophenyl)-1H-imidazol-2-yl]thio}methyl)-3-fluorobenzoic acid | A | A |
| 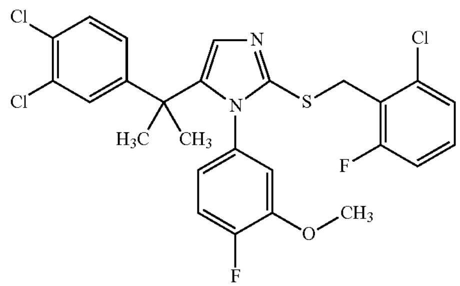 [SMILES: COc1cc(-n2c(C(C)(C)c3ccc(Cl)c(Cl)c3)cnc2SCc2c(F)cccc2Cl)ccc1F] | 2-{[(2-chloro-6-fluorophenyl)methyl]thio}-5-[1-(3,4-dichlorophenyl)-1-methylethyl]-1-[4-fluoro-3-(methyloxy)phenyl]-1H-imidazole | A | A |
| 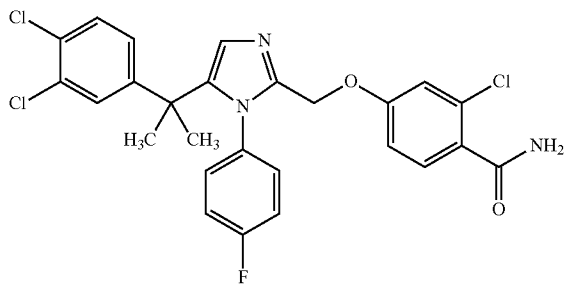 [SMILES: CC(C)(c1ccc(Cl)c(Cl)c1)c1cnc(COc2ccc(C(N)=O)c(Cl)c2)n1-c1ccc(F)cc1] | 2-chloro-4-[({5-[1-(3,4-dichlorophenyl)-1-methylethyl]-1-(4-fluorophenyl)-1H-imidazol-2-yl}methyl)oxy]benzamide | | D |

TABLE 1-continued

| Structure | NAME | cAMP (EC$_{50}$) (nM) | CRE-Luc (EC$_{50}$) (nM) |
|---|---|---|---|
| 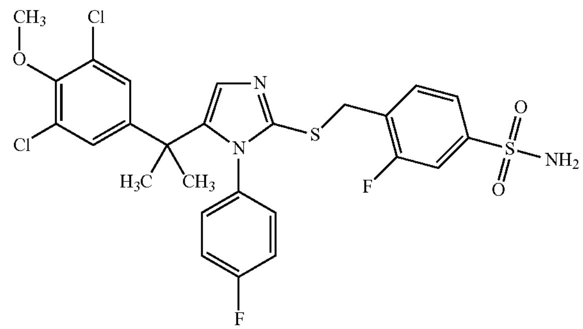 [SMILES: COc1c(Cl)cc(C(C)(C)c2cnc(SCc3ccc(S(N)(=O)=O)cc3F)n2-c2ccc(F)cc2)cc1Cl] | 4-({[5-{1-[3,5-dichloro-4-(methyloxy)phenyl]-1-methylethyl}-1-(4-fluorophenyl)-1H-imidazol-2-yl]thio}methyl)-3-fluorobenzenesulfonamide | | A |
| 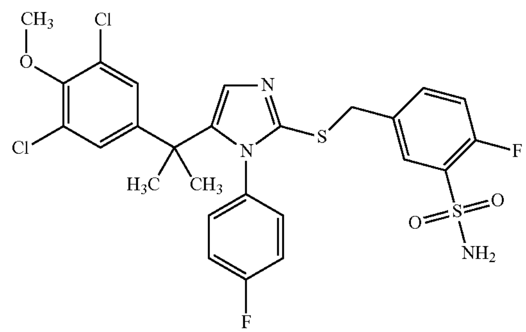 [SMILES: COc1c(Cl)cc(C(C)(C)c2cnc(SCc3ccc(F)c(S(N)(=O)=O)c3)n2-c2ccc(F)cc2)cc1Cl] | 5-({[5-{1-[3,5-dichloro-4-(methyloxy)phenyl]-1-methylethyl}-1-(4-fluorophenyl)-1H-imidazol-2-yl]thio}methyl)-2-fluorobenzenesulfonamide | | A |
| 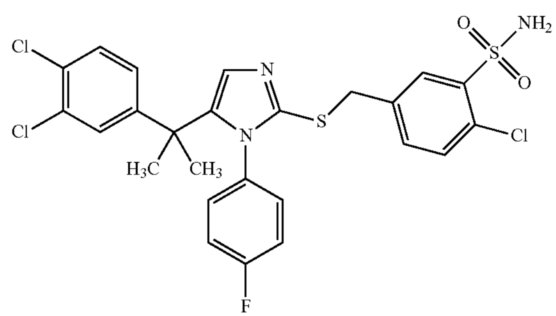 [SMILES: CC(C)(c1ccc(Cl)c(Cl)c1)c1cnc(SCc2ccc(Cl)c(S(N)(=O)=O)c2)n1-c1ccc(F)cc1] | 2-chloro-5-[({5-[1-(3,4-dichlorophenyl)-1-methylethyl]-1-(4-fluorophenyl)-1H-imidazol-2-yl}thio)methyl]benzenesulfonamide | A | A |

TABLE 1-continued

| Structure | NAME | cAMP (EC$_{50}$) (nM) | CRE-Luc (EC$_{50}$) (nM) |
|---|---|---|---|
|  | 4-[({5-[1-(3,4-dichlorophenyl)-1-methylethyl]-1-(4-fluorophenyl)-1H-imidazol-2-yl}thio)methyl]-2-fluorobenzenesulfonamide |  | C |
| 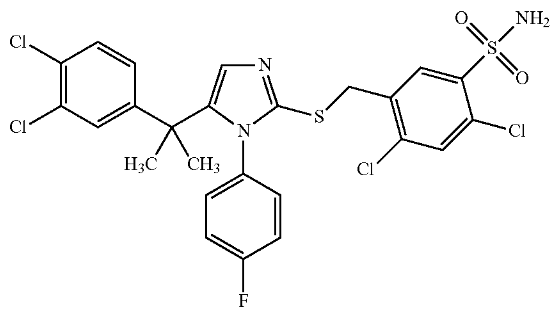 [SMILES: CC(C)(c1ccc(Cl)c(Cl)c1)c1cnc(SCc2cc(S(N)(=O)=O)c(Cl)cc2Cl)n1-c1ccc(F)cc1] | 2,4-dichloro-5-[({5-[1-(3,4-dichlorophenyl)-1-methylethyl]-1-(4-fluorophenyl)-1H-imidazol-2-yl}thio)methyl]benzenesulfonamide | C | A |
| 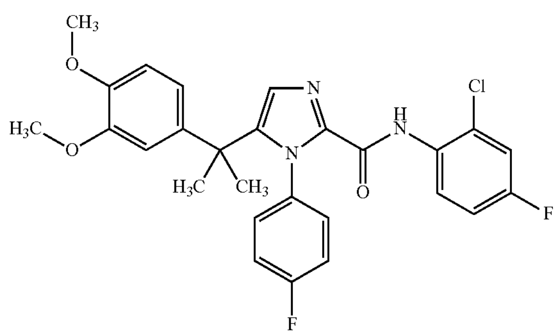 [SMILES: COc1ccc(C(C)(C)c2cnc(C(=O)Nc3ccc(F)cc3Cl)n2-c2ccc(F)cc2)cc1OC] | 5-{1-[3,4-bis(methyloxy)phenyl]-1-methylethyl}-N-(2-chloro-4-fluorophenyl)-1-(4-fluorophenyl)-1H-imidazole-2-carboxamide |  | D |

TABLE 1-continued

| Structure | NAME | cAMP (EC$_{50}$) (nM) | CRE-Luc (EC$_{50}$) (nM) |
|---|---|---|---|
| 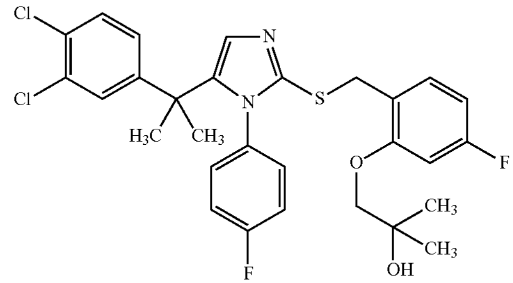 [SMILES: CC(C)(O)COc1cc(F)ccc1CSc1ncc(C(C)(C)c2ccc(Cl)c(Cl)c2)n1-c1ccc(F)cc1] | 1-({2-[({5-[1-(3,4-dichlorophenyl)-1-methylethyl]-1-(4-fluorophenyl)-1H-imidazol-2-yl}thio)methyl]-5-fluorophenyl}oxy)-2-methylpropan-2-ol | | C |
| 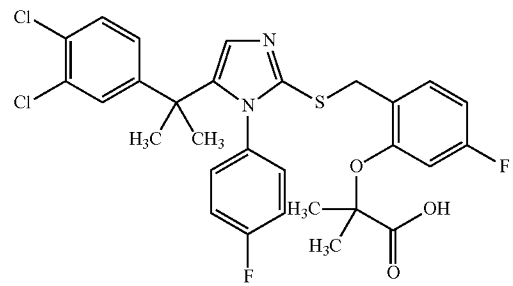 [SMILES: CC(C)(Oc1cc(F)ccc1CSc1ncc(C(C)(C)c2ccc(Cl)c(Cl)c2)n1-c1ccc(F)cc1)C(=O)O] | 2-({2-[({5-[1-(3,4-dichlorophenyl)-1-methylethyl]-1-(4-fluorophenyl)-1H-imidazol-2-yl}thio)methyl]-5-fluorophenyl}oxy)-2-methylpropanoic acid | | D |
| 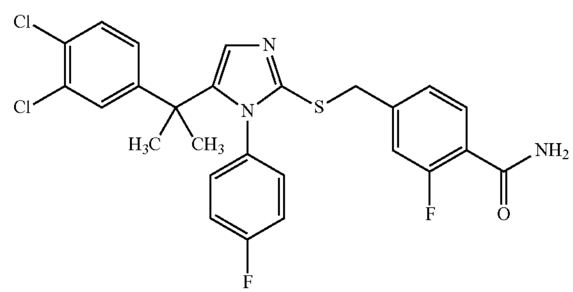 [SMILES: CC(C)(c1ccc(Cl)c(Cl)c1)c1cnc(SCc2ccc(C(N)=O)c(F)c2)n1-c1ccc(F)cc1] | 4-[({5-[1-(3,4-dichlorophenyl)-1-methylethyl]-1-(4-fluorophenyl)-1H-imidazol-2-yl}thio)methyl]-2-fluorobenzamide | | C |

TABLE 1-continued

| Structure | NAME | cAMP (EC$_{50}$) (nM) | CRE-Luc (EC$_{50}$) (nM) |
|---|---|---|---|
| 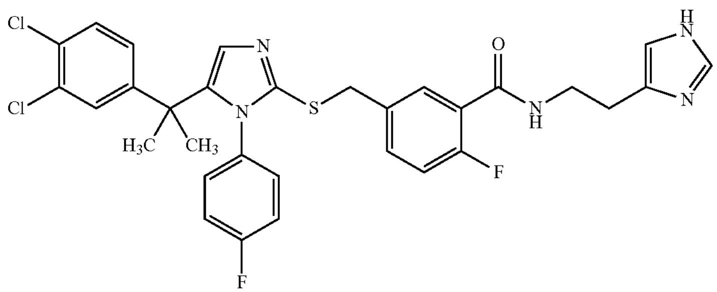 [SMILES: CC(C)(c1ccc(Cl)c(Cl)c1)c1cnc(SCc2ccc(F)c(C(=O)NCCc3c[nH]cn3)c2)n1-c1ccc(F)cc1] | 5-[({5-[1-(3,4-dichlorophenyl)-1-methylethyl]-1-(4-fluorophenyl)-1H-imidazol-2-yl}thio)methyl]-2-fluoro-N-[2-(1H-imidazol-4-yl)ethyl]benzamide | | C |
| 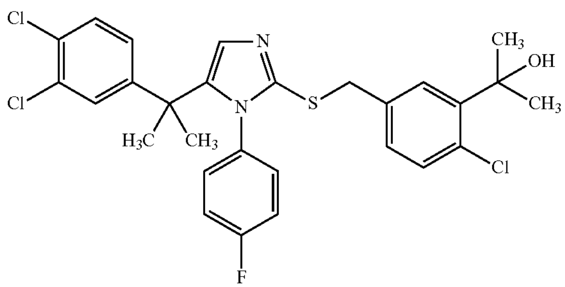 [SMILES: CC(C)(O)c1cc(CSc2ncc(C(C)(C)c3ccc(Cl)c(Cl)c3)n2-c2ccc(F)cc2)ccc1Cl] | 2-{2-chloro-5-[({5-[1-(3,4-dichlorophenyl)-1-methylethyl]-1-(4-fluorophenyl)-1H-imidazol-2-yl}thio)methyl]phenyl}propan-2-ol | | C |
| 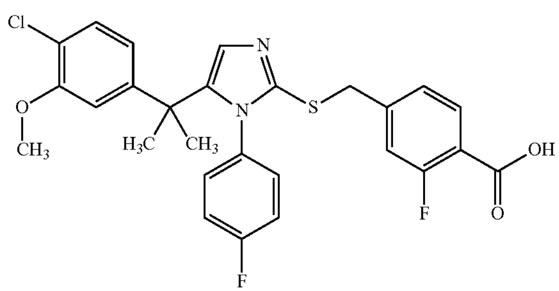 [SMILES: COc1cc(C(C)(C)c2cnc(SCc3ccc(C(=O)O)c(F)c3)n2-c2ccc(F)cc2)ccc1Cl] | 4-({[5-{1-[4-chloro-3-(methyloxy)phenyl]-1-methylethyl}-1-(4-fluorophenyl)-1H-imidazol-2-yl]thio}methyl)-2-fluorobenzoic acid | A | C |

TABLE 1-continued

| Structure | NAME | cAMP (EC$_{50}$) (nM) | CRE-Luc (EC$_{50}$) (nM) |
|---|---|---|---|
| 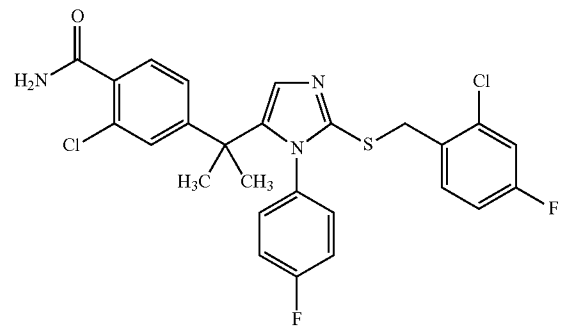 [SMILES: CC(C)(c1ccc(C(N)=O)c(Cl)c1)c1cnc(SCc2ccc(F)cc2Cl)n1-c1ccc(F)cc1] | 2-chloro-4-{1-[2-{[(2-chloro-4-fluorophenyl)methyl]thio}-1-(4-fluorophenyl)-1H-imidazol-5-yl]-1-methylethyl}benzamide | A | C |
| 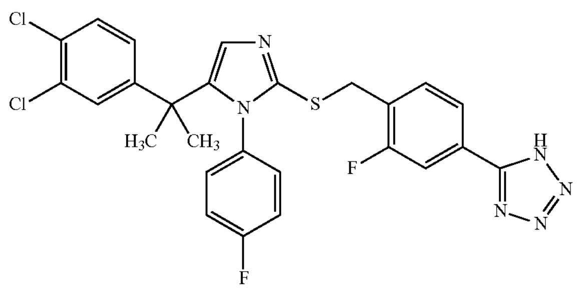 [SMILES: CC(C)(c1ccc(Cl)c(Cl)c1)c1cnc(SCc2ccc(-c3nnn[nH]3)cc2F)n1-c1ccc(F)cc1] | 5-{4-[({5-[1-(3,4-dichlorophenyl)-1-methylethyl]-1-(4-fluorophenyl)-1H-imidazol-2-yl}thio)methyl]-3-fluorophenyl}-1H-tetrazole | C | C |
| 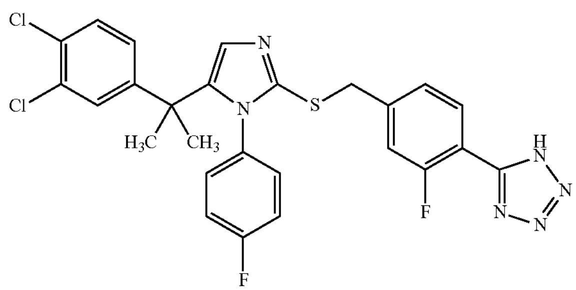 [SMILES: CC(C)(c1ccc(Cl)c(Cl)c1)c1cnc(SCc2ccc(-c3nnn[nH]3)c(F)c2)n1-c1ccc(F)cc1] | 5-{4-[({5-[1-(3,4-dichlorophenyl)-1-methylethyl]-1-(4-fluorophenyl)-1H-imidazol-2-yl}thio)methyl]-2-fluorophenyl}-1H-tetrazole | | C |

TABLE 1-continued
| Structure | NAME | cAMP (EC$_{50}$) (nM) | CRE-Luc (EC$_{50}$) (nM) |
|---|---|---|---|
| 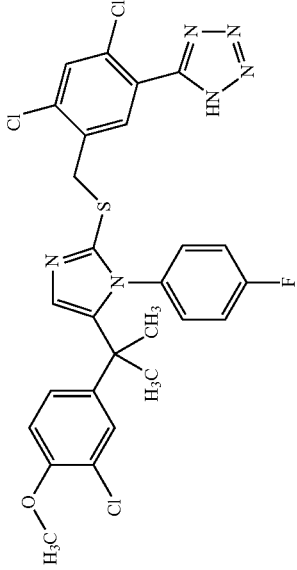 | 5-[2,4-dichloro-5-({[5-{1-[3-chloro-4-(methyloxy)phenyl]-1-methylethyl}-1-(4-fluorophenyl)-1H-imidazol-2-yl]thio}methyl)phenyl]-1H-tetrazole | C | A |
| 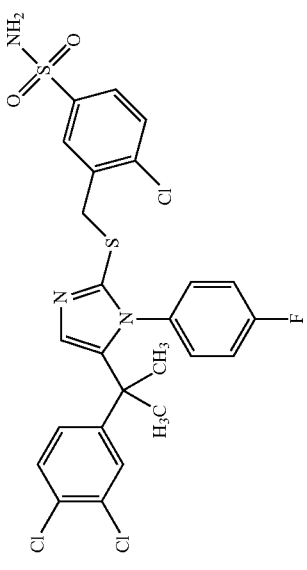 | 4-chloro-3-[({5-[1-(3,4-dichlorophenyl)-1-methylethyl]-1-(4-fluorophenyl)-1H-imidazol-2-yl}thio)methyl]benzenesulfonamide | | C |
| 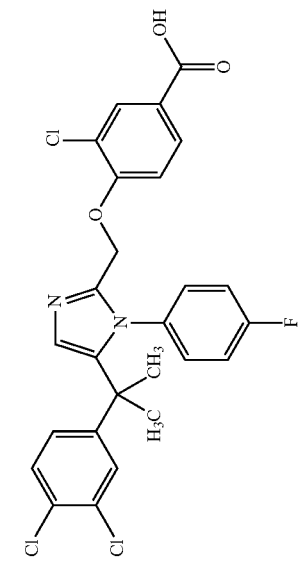 | 3-chloro-4-[({5-[1-(3,4-dichlorophenyl)-1-methylethyl]-1-(4-fluorophenyl)-1H-imidazol-2-yl}methyl)oxy]benzoic acid | | D |

TABLE 1-continued

| Structure | NAME | cAMP (EC$_{50}$) (nM) | CRE-Luc (EC$_{50}$) (nM) |
|---|---|---|---|
| 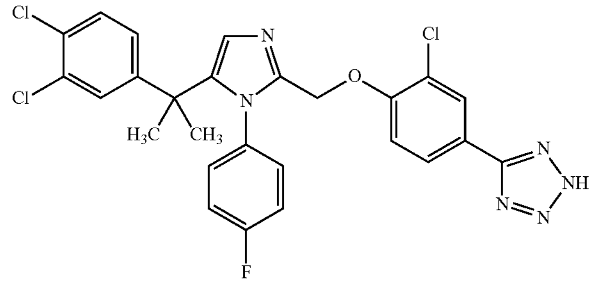 [SMILES: CC(C)(c1ccc(Cl)c(Cl)c1)c1cnc(COc2ccc(-c3nn[nH]n3)cc2Cl)n1-c1ccc(F)cc1] | 5-{3-chloro-4-[({5-[1-(3,4-dichlorophenyl)-1-methylethyl]-1-(4-fluorophenyl)-1H-imidazol-2-yl}methyl)oxy]phenyl}-2H-tetrazole | | D |
| 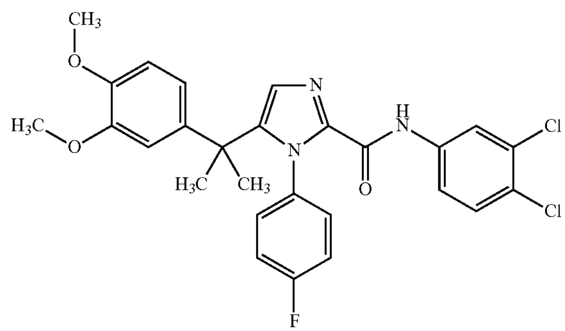 [SMILES: COc1ccc(C(C)(C)c2cnc(C(=O)Nc3ccc(Cl)c(Cl)c3)n2-c2ccc(F)cc2)cc1OC] | 5-{1-[3,4-bis(methyloxy)phenyl]-1-methylethyl}-N-(3,4-dichlorophenyl)-1-(4-fluorophenyl)-1H-imidazole-2-carboxamide | | D |
| 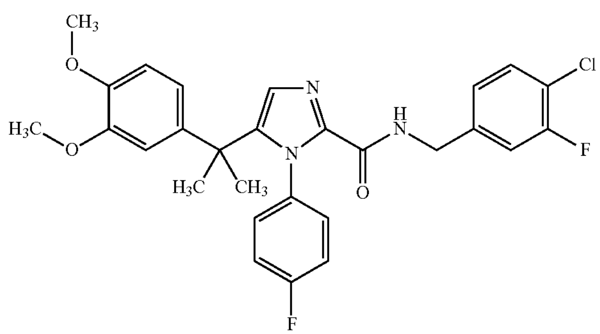 [SMILES: COc1ccc(C(C)(C)c2cnc(C(=O)NCc3ccc(Cl)c(F)c3)n2-c2ccc(F)cc2)cc1OC] | 5-{1-[3,4-bis(methyloxy)phenyl]-1-methylethyl}-N-[(4-chloro-3-fluorophenyl)methyl]-1-(4-fluorophenyl)-1H-imidazole-2-carboxamide | | C |

TABLE 1-continued

| Structure | NAME | cAMP (EC$_{50}$) (nM) | CRE-Luc (EC$_{50}$) (nM) |
|---|---|---|---|
| 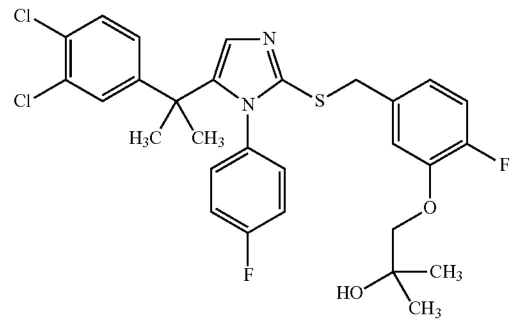 [SMILES: CC(C)(O)COc1cc(CSc2ncc(C(C)(C)c3ccc(Cl)c(Cl)c3)n2-c2ccc(F)cc2)ccc1F] | 1-({5-[({5-[1-(3,4-dichlorophenyl)-1-methylethyl]-1-(4-fluorophenyl)-1H-imidazol-2-yl}thio)methyl]-2-fluorophenyl}oxy)-2-methylpropan-2-ol |  | C |
| 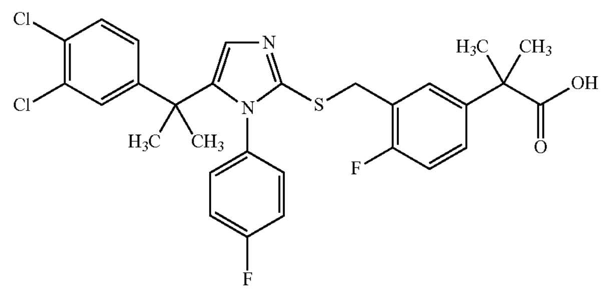 [SMILES: CC(C)(C(=O)O)c1ccc(F)c(CSc2ncc(C(C)(C)c3ccc(Cl)c(Cl)c3)n2-c2ccc(F)cc2)c1] | 2-{3-[({5-[1-(3,4-dichlorophenyl)-1-methylethyl]-1-(4-fluorophenyl)-1H-imidazol-2-yl}thio)methyl]-4-fluorophenyl}-2-methylpropanoic acid |  | D |
| 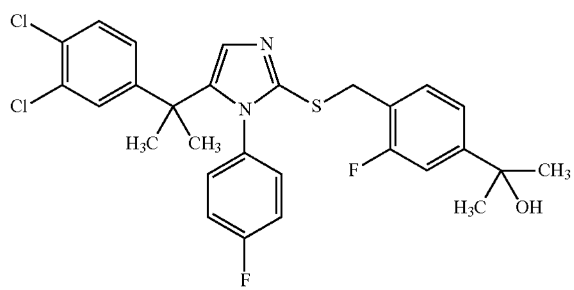 [SMILES: CC(C)(O)c1ccc(CSc2ncc(C(C)(C)c3ccc(Cl)c(Cl)c3)n2-c2ccc(F)cc2)c(F)c1] | 2-{4-[({5-[1-(3,4-dichlorophenyl)-1-methylethyl]-1-(4-fluorophenyl)-1H-imidazol-2-yl}thio)methyl]-3-fluorophenyl}propan-2-ol |  | C |

TABLE 1-continued
| Structure | NAME | cAMP (EC$_{50}$) (nM) | CRE-Luc (EC$_{50}$) (nM) |
|---|---|---|---|
| 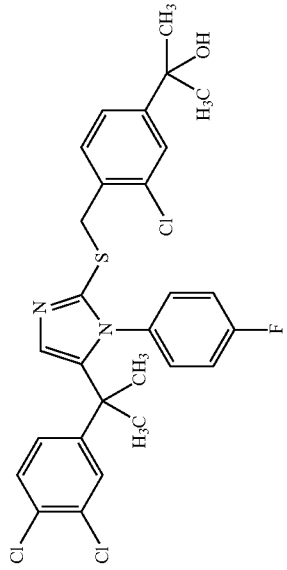 | 2-{3-chloro-4-[({5-[1-(3,4-dichlorophenyl)-1-methylethyl]-1-(4-fluorophenyl)-1H-imidazol-2-yl}thio)methyl]phenyl}propan-2-ol | | C |
| 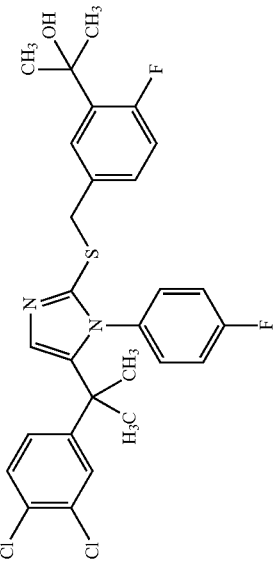 | 2-{5-[({5-[1-(3,4-dichlorophenyl)-1-methylethyl]-1-(4-fluorophenyl)-1H-imidazol-2-yl}thio)methyl]-2-fluorophenyl}propan-2-ol | | C |
| 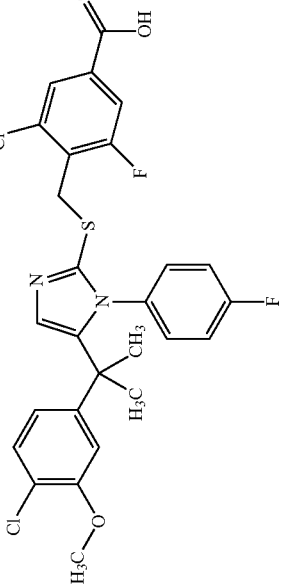 | 3-chloro-4-{[(5-{1-[4-chloro-3-(methyloxy)phenyl]-1-methylethyl}-1-(4-fluorophenyl)-1H-imidazol-2-yl]thio}methyl)-5-fluorobenzoic acid | A | A |

TABLE 1-continued

| Structure | NAME | cAMP (EC$_{50}$) (nM) | CRE-Luc (EC$_{50}$) (nM) |
|---|---|---|---|
| 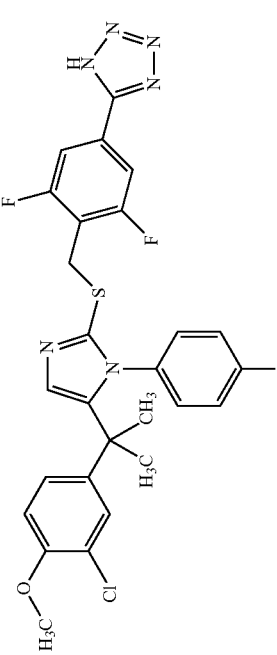 | 5-[4-({[5-{1-[3-chloro-4-(methyloxy)phenyl]-1-methylethyl}-1-(4-fluorophenyl)-1H-imidazol-2-yl]thio}methyl)-3,5-difluorophenyl]-1H-tetrazole | | A |
| 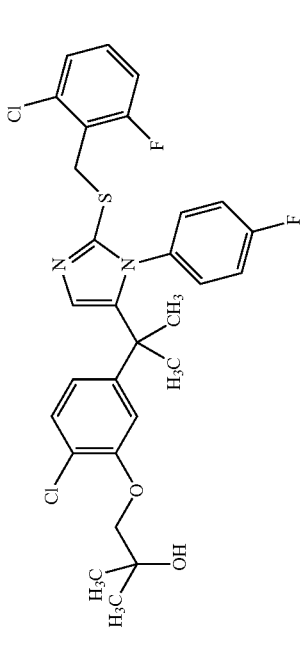 | 1-[(2-chloro-5-{1-[2-{[(2-chloro-6-fluorophenyl)methyl]thio}-1-(4-fluorophenyl)-1H-imidazol-5-yl]-1-methylethyl}phenyl)oxy]-2-methylpropan-2-ol | C | C |
| 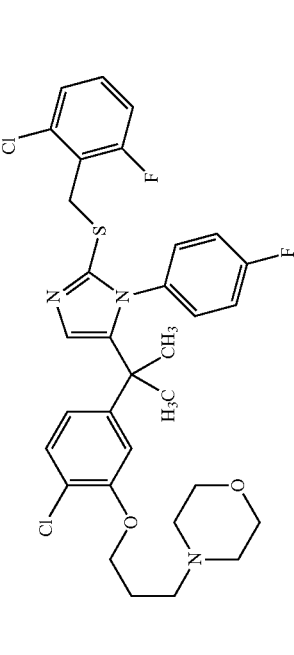 | 4-{3-[(2-chloro-5-{1-[2-{[(2-chloro-6-fluorophenyl)methyl]thio}-1-(4-fluorophenyl)-1H-imidazol-5-yl]-1-methylethyl}phenyl)oxy]propyl}morpholine | | C |

TABLE 1-continued
| Structure | NAME | cAMP (EC$_{50}$) (nM) | CRE-Luc (EC$_{50}$) (nM) |
|---|---|---|---|
| 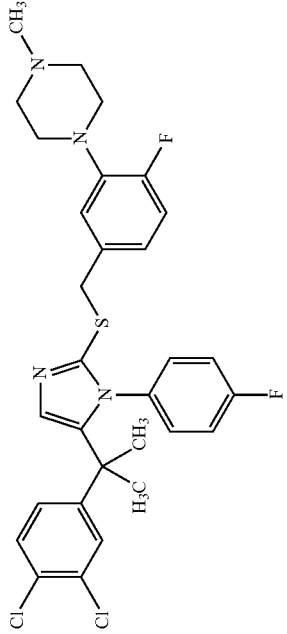 | 1-{5-[({5-[1-(3,4-dichlorophenyl)-1-methylethyl]-1-(4-fluorophenyl)-1H-imidazol-2-yl}thio)methyl]-2-fluorophenyl}-4-methylpiperazine | | D |
| 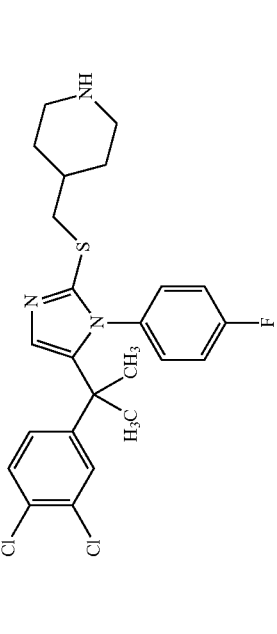 | 4-[({5-[1-(3,4-dichlorophenyl)-1-methylethyl]-1-(4-fluorophenyl)-1H-imidazol-2-yl}thio)methyl]piperidine | | D |
| 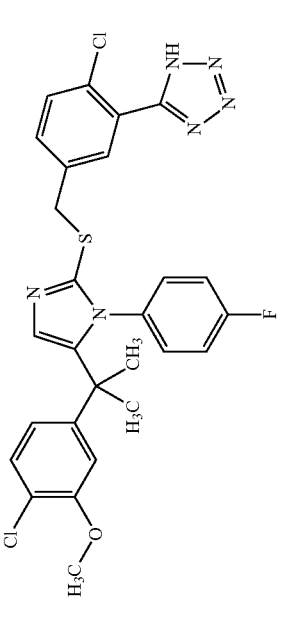 | 5-[2-chloro-5-({[5-{1-[4-chloro-3-(methyloxy)phenyl]-1-methylethyl}-1-(4-fluorophenyl)-1H-imidazol-2-yl]thio}methyl)phenyl]-1H-tetrazole | C | A |

TABLE 1-continued

| Structure | NAME | cAMP (EC$_{50}$) (nM) | CRE-Luc (EC$_{50}$) (nM) |
|---|---|---|---|
| 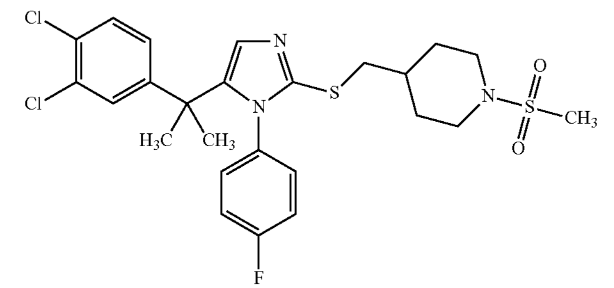 [SMILES: CC(C)(c1ccc(Cl)c(Cl)c1)c1cnc(SCC2CCN(S(C)(=O)=O)CC2)n1-c1ccc(F)cc1] | 4-[({5-[1-(3,4-dichlorophenyl)-1-methylethyl]-1-(4-fluorophenyl)-1H-imidazol-2-yl}thio)methyl]-1-(methylsulfonyl)piperidine | C | A |
| 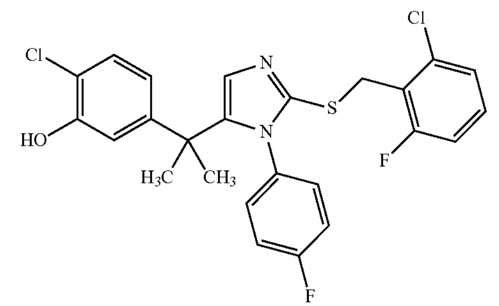 [SMILES: CC(C)(c1ccc(Cl)c(O)c1)c1cnc(SCc2c(F)cccc2Cl)n1-c1ccc(F)cc1] | 2-chloro-5-{1-[2-{[(2-chloro-6-fluorophenyl)methyl]thio}-1-(4-fluorophenyl)-1H-imidazol-5-yl]-1-methylethyl}phenol | | A |
| 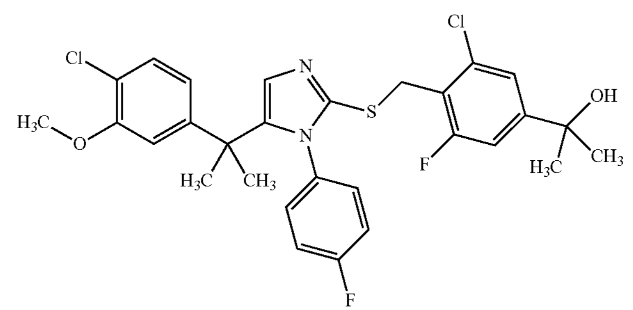 [SMILES: COc1cc(C(C)(C)c2cnc(SCc3c(F)cc(C(C)(C)O)cc3Cl)n2-c2ccc(F)cc2)ccc1Cl] | 2-[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]propan-2-ol | A | A |

TABLE 1-continued

| Structure | NAME | cAMP (EC$_{50}$) (nM) | CRE-Luc (EC$_{50}$) (nM) |
|---|---|---|---|
| | 4-({[5-{1-[4-chloro-3-(methyloxy)phenyl]-1-methylethyl}-1-(4-fluorophenyl)-1H-imidazol-2-yl]thio}methyl)-3,5-difluorobenzoic acid | A | A |
| 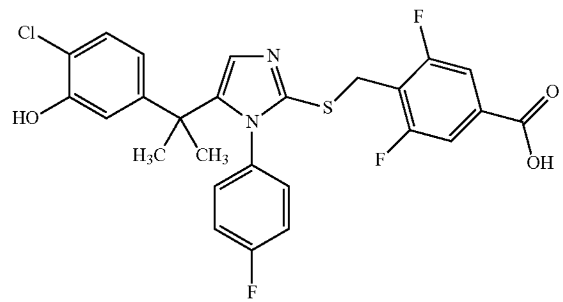 [SMILES: CC(C)(c1ccc(Cl)c(O)c1)c1cnc(SCc2c(F)cc(C(=O)O)cc2F)n1-c1ccc(F)cc1] | 4-[({5-[1-(4-chloro-3-hydroxyphenyl)-1-methylethyl]-1-(4-fluorophenyl)-1H-imidazol-2-yl}thio)methyl]-3,5-difluorobenzoic acid | | C |
| 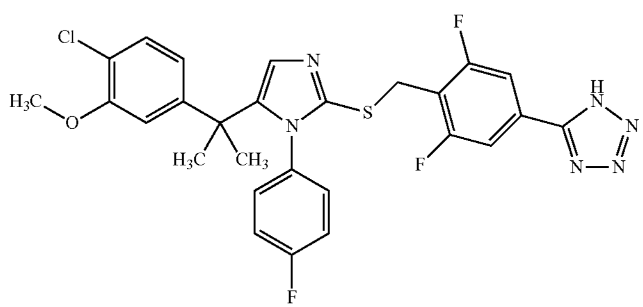 [SMILES: COc1cc(C(C)(C)c2cnc(SCc3c(F)cc(-c4nnn[nH]4)cc3F)n2-c2ccc(F)cc2)ccc1Cl] | 5-[4-({[5-{1-[4-chloro-3-(methyloxy)phenyl]-1-methylethyl}-1-(4-fluorophenyl)-1H-imidazol-2-yl]thio}methyl)-3,5-difluorophenyl]-1H-tetrazole | A | A |

TABLE 1-continued

| Structure | NAME | cAMP (EC$_{50}$) (nM) | CRE-Luc (EC$_{50}$) (nM) |
|---|---|---|---|
| 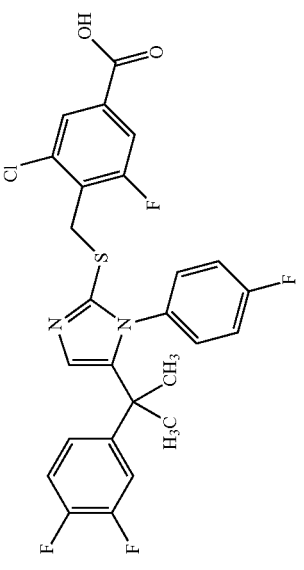 | 3-chloro-4-[({5-[1-(3,4-difluorophenyl)-1-methylethyl]-1-(4-fluorophenyl)-1H-imidazol-2-yl}thio)methyl]-5-fluorobenzoic acid | | C |
| 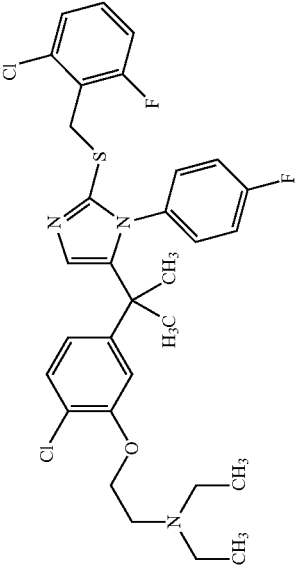 | 2-[(2-chloro-5-{1-[2-{[(2-chloro-6-fluorophenyl)methyl]thio}-1-(4-fluorophenyl)-1H-imidazol-5-yl]-1-methylethyl}phenyl)oxy]-N,N-diethylethanamine | | C |
| 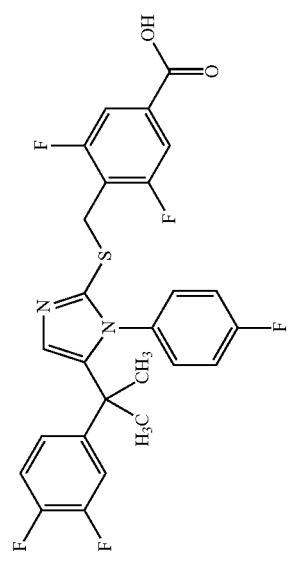 | 4-[(5-[1-(3,4-difluorophenyl)-1-methylethyl]-1-(4-fluorophenyl)-1H-imidazol-2-yl]thio)methyl]-3,5-difluorobenzoic acid | A | C |

TABLE 1-continued

| Structure | NAME | cAMP (EC$_{50}$) (nM) | CRE-Luc (EC$_{50}$) (nM) |
|---|---|---|---|
| | 4-[{(2-chloro-4-fluorophenyl)thio}methyl]-2-[1-(3,4-dichlorophenyl)-1-methylethyl]-1-(4-fluorophenyl)-1H-imidazole | | D |
| 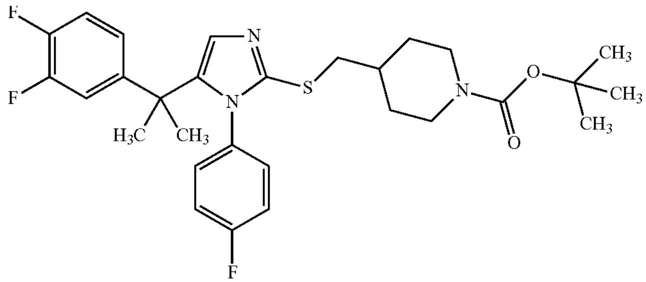 [SMILES: CC(C)(C)OC(=O)N1CCC(CSc2ncc(C(C)(C)c3ccc(F)c(F)c3)n2-c2ccc(F)cc2)CC1] | 1,1-dimethylethyl 4-[({5-[1-(3,4-difluorophenyl)-1-methylethyl]-1-(4-fluorophenyl)-1H-imidazol-2-yl}thio)methyl]piperidine-1-carboxylate | | C |
| 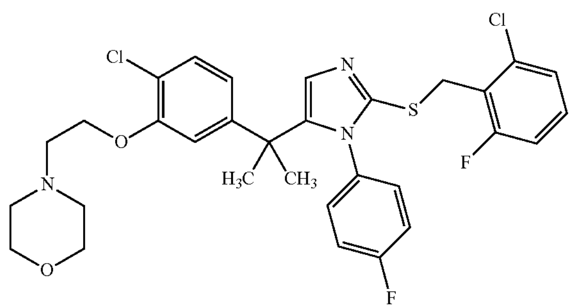 [SMILES: CC(C)(c1ccc(Cl)c(OCCN2CCOCC2)c1)c1cnc(SCc2c(F)cccc2Cl)n1-c1ccc(F)cc1] | 4-{2-[(2-chloro-5-{1-[2-{[(2-chloro-6-fluorophenyl)methyl]thio}-1-(4-fluorophenyl)-1H-imidazol-5-yl]-1-methylethyl}phenyl)oxy]ethyl}morpholine | | C |

TABLE 1-continued

| Structure | NAME | cAMP (EC$_{50}$) (nM) | CRE-Luc (EC$_{50}$) (nM) |
|---|---|---|---|
| 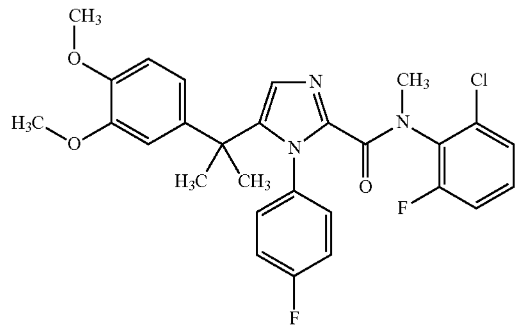 [SMILES: COc1ccc(C(C)(C)c2cnc(C(=O)N(C)c3c(F)cccc3Cl)n2-c2ccc(F)cc2)cc1OC] | 5-{1-[3,4-bis(methyloxy)phenyl]-1-methylethyl}-N-(2-chloro-6-fluorophenyl)-1-(4-fluorophenyl)-N-methyl-1H-imidazole-2-carboxamide | | D |
| 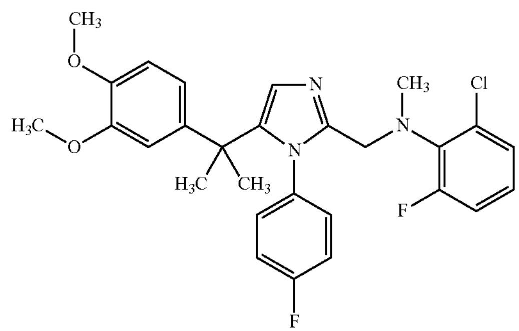 [SMILES: COc1ccc(C(C)(C)c2cnc(CN(C)c3c(F)cccc3Cl)n2-c2ccc(F)cc2)cc1OC] | N-{[5-{1-[3,4-bis(methyloxy)phenyl]-1-methylethyl}-1-(4-fluorophenyl)-1H-imidazol-2-yl]methyl}-2-chloro-6-fluoro-N-methylaniline | A | A |
| | 5-(2-chloro-5-{[(5-{1-[4-chloro-3-(methyloxy)phenyl]-1-methylethyl}-1-[4-fluoro-3-(methyloxy)phenyl]-1H-imidazol-2-yl}thio]methyl}phenyl)-1H-tetrazole | A | A |

TABLE 1-continued

| Structure | NAME | cAMP (EC$_{50}$) (nM) | CRE-Luc (EC$_{50}$) (nM) |
|---|---|---|---|
| 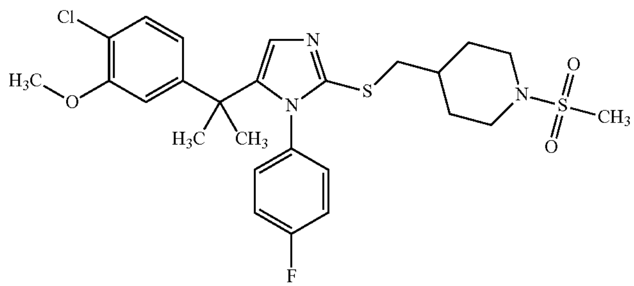 | 4-({[5-{1-[4-chloro-3-(methyloxy)phenyl]-1-methylethyl}-1-(4-fluorophenyl)-1H-imidazol-2-yl]thio}methyl)-1-(methylsulfonyl)piperidine | A | A |
| 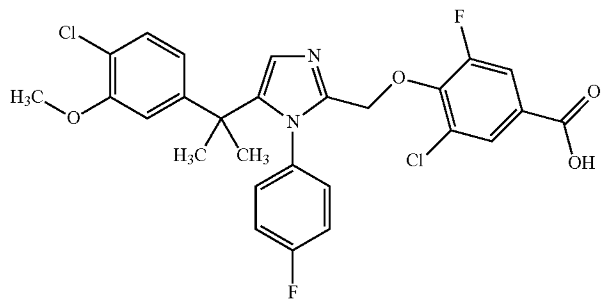 [SMILES: COc1cc(C(C)(C)c2cnc(COc3c(F)cc(C(=O)O)cc3Cl)n2-c2ccc(F)cc2)ccc1Cl] | 3-chloro-4-({[5-{1-[4-chloro-3-(methyloxy)phenyl]-1-methylethyl}-1-(4-fluorophenyl)-1H-imidazol-2-yl]methyl}oxy)-5-fluorobenzoic acid | C | C |
| 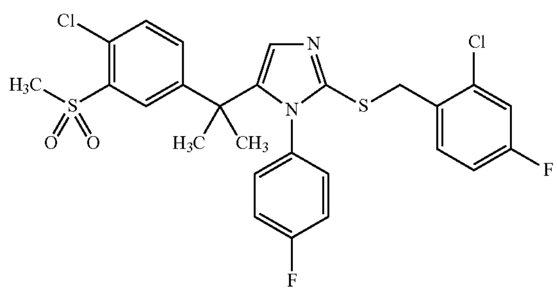 [SMILES: CC(C)(c1ccc(Cl)c(S(C)(=O)=O)c1)c1cnc(SCc2ccc(F)cc2Cl)n1-c1ccc(F)cc1] | 2-chloro-5-{1-[2-{(2-chloro-4-fluorophenyl)methyl]thio}-1-(4-fluorophenyl)-1H-imidazol-5-yl]-1-methylethyl}benzenesulfonamide | | C |

TABLE 1-continued

| Structure | NAME | cAMP (EC$_{50}$) (nM) | CRE-Luc (EC$_{50}$) (nM) |
|---|---|---|---|
| 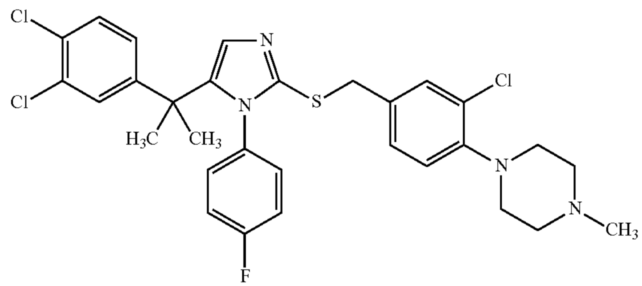 [SMILES: CN1CCN(c2ccc(CSc3ncc(C(C)(C)c4ccc(Cl)c(Cl)c4)n3-c3ccc(F)cc3)cc2Cl)CC1] | 1-{2-chloro-4-[({5-[1-(3,4-dichlorophenyl)-1-methylethyl]-1-(4-fluorophenyl)-1H-imidazol-2-yl}thio)methyl]phenyl}-4-methylpiperazine | | D |
| 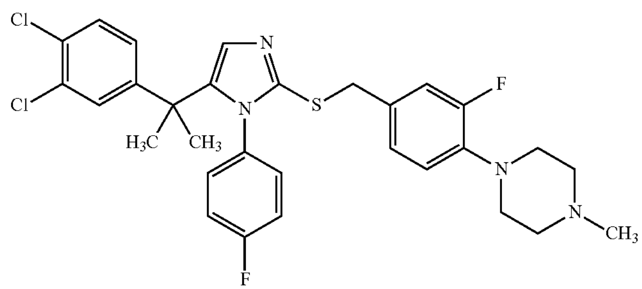 [SMILES: CN1CCN(c2ccc(CSc3ncc(C(C)(C)c4ccc(Cl)c(Cl)c4)n3-c3ccc(F)cc3)cc2F)CC1] | 1-{4-[({5-[1-(3,4-dichlorophenyl)-1-methylethyl]-1-(4-fluorophenyl)-1H-imidazol-2-yl}thio)methyl]-2-fluorophenyl}-4-methylpiperazine | | C |
| 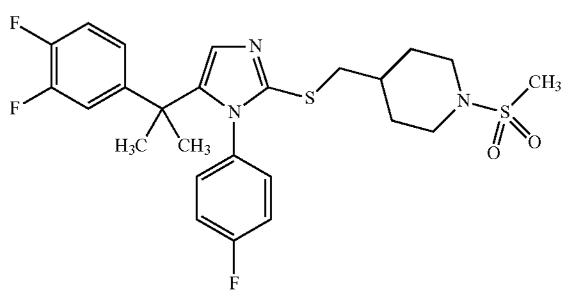 [SMILES: CC(C)(c1ccc(F)c(F)c1)c1cnc(SCC2CCN(S(C)(=O)=O)CC2)n1-c1ccc(F)cc1] | 4-[({5-[1-(3,4-difluorophenyl)-1-methylethyl]-1-(4-fluorophenyl)-1H-imidazol-2-yl}thio)methyl]-1-(methylsulfonyl)piperidine | C | A |

TABLE 1-continued

| Structure | NAME | cAMP (EC$_{50}$) (nM) | CRE-Luc (EC$_{50}$) (nM) |
|---|---|---|---|
| 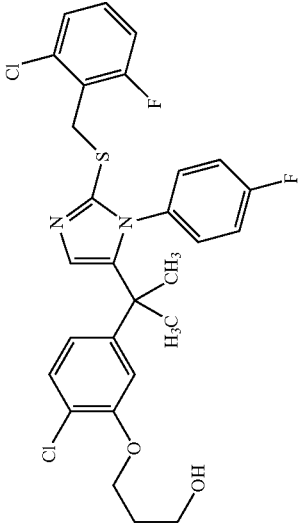 | 3-[(2-chloro-5-{1-[2-{[(2-chloro-6-fluorophenyl)methyl]thio}-1-(4-fluorophenyl)-1H-imidazol-5-yl]-1-methylethyl}phenyl)oxy]propan-1-ol | | C |
| 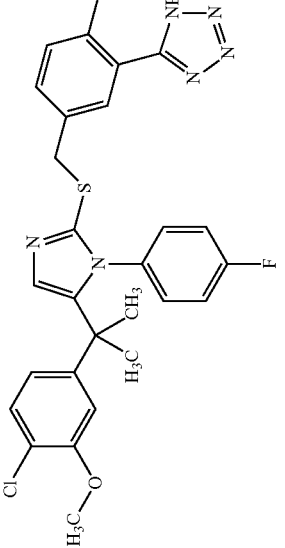 | 5-{5-({[5-{1-[4-chloro-3-(methyloxy)phenyl]-1-methylethyl}-1-(4-fluorophenyl)-1H-imidazol-2-yl]thio}methyl)-2-fluorophenyl]-1H-tetrazole | A | A |
| 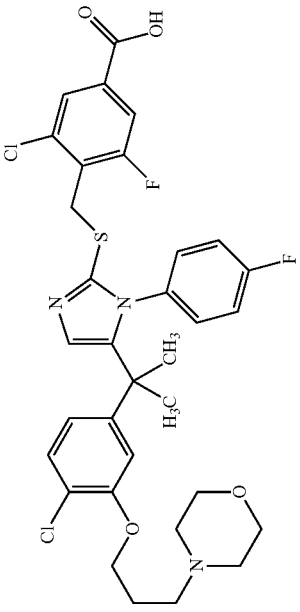 | 3-chloro-4-{[[5-(1-{4-chloro-3-[(3-morpholin-4-ylpropyl)oxy]phenyl}-1-methylethyl)-1-(4-fluorophenyl)-1H-imidazol-2-yl]thio}methyl)-5-fluorobenzoic acid | C | C |

TABLE 1-continued

| Structure | NAME | cAMP (EC$_{50}$) (nM) | CRE-Luc (EC$_{50}$) (nM) |
|---|---|---|---|
| 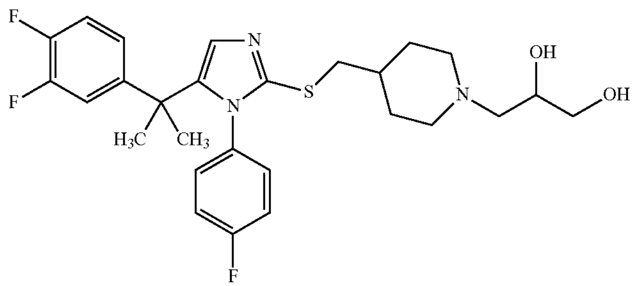 [SMILES: CC(C)(c1ccc(F)c(F)c1)c1cnc(SCC2CCN(CC(O)CO)CC2)n1-c1ccc(F)cc1] | 3-{4-[({5-[1-(3,4-difluorophenyl)-1-methylethyl]-1-(4-fluorophenyl)-1H-imidazol-2-yl}thio)methyl]piperidin-1-yl}propane-1,2-diol | | D |
| 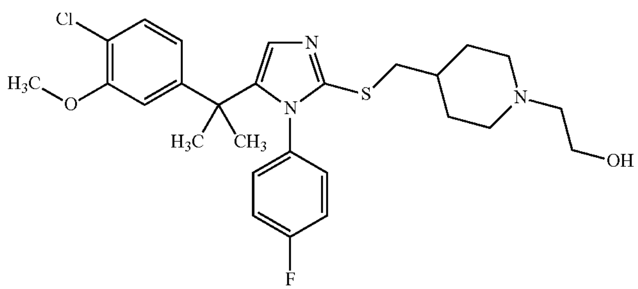 [SMILES: COc1cc(C(C)(C)c2cnc(SCC3CCN(CCO)CC3)n2-c2ccc(F)cc2)ccc1Cl] | 2-[4-({[5-{1-[4-chloro-3-(methyloxy)phenyl]-1-methylethyl}-1-(4-fluorophenyl)-1H-imidazol-2-yl]thio}methyl)piperidin-1-yl]ethanol | | D |
| 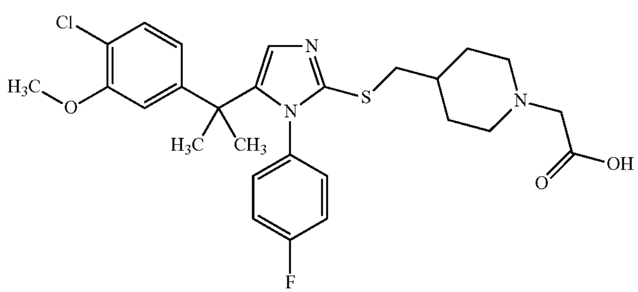 [SMILES: COc1cc(C(C)(C)c2cnc(SCC3CCN(CC(=O)O)CC3)n2-c2ccc(F)cc2)ccc1Cl] | [4-({[5-{1-[4-chloro-3-(methyloxy)phenyl]-1-methylethyl}-1-(4-fluorophenyl)-1H-imidazol-2-yl]thio}methyl)piperidin-1-yl]acetic acid | | D |

TABLE 1-continued

| Structure | NAME | cAMP (EC$_{50}$) (nM) | CRE-Luc (EC$_{50}$) (nM) |
|---|---|---|---|
| | | | D |
| 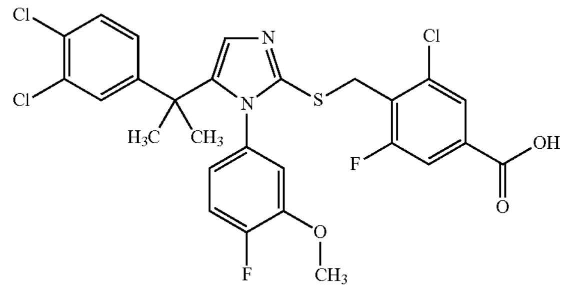 [SMILES: COc1cc(-n2c(C(C)(C)c3ccc(Cl)c(Cl)c3)cnc2SCc2c(F)cc(C(=O)O)cc2Cl)ccc1F] | 3-chloro-4-[({5-[1-(3,4-dichlorophenyl)-1-methylethyl]-1-[4-fluoro-3-(methyloxy)phenyl]-1H-imidazol-2-yl}thio)methyl]-5-fluorobenzoic acid | A | A |
| 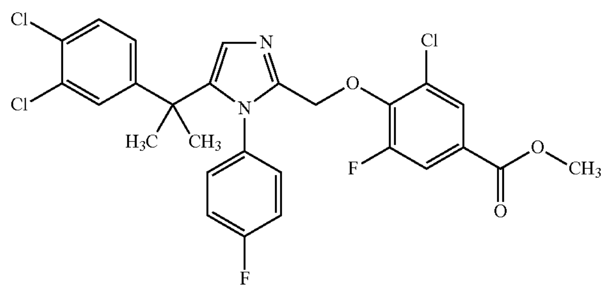 [SMILES: COC(=O)c1cc(F)c(OCc2ncc(C(C)(C)c3ccc(Cl)c(Cl)c3)n2-c2ccc(F)cc2)c(Cl)c1] | methyl 3-chloro-4-[({5-[1-(3,4-dichlorophenyl)-1-methylethyl]-1-(4-fluorophenyl)-1H-imidazol-2-yl}methyl)oxy]-5-fluorobenzoate | | C |

TABLE 1-continued

| Structure | NAME | cAMP (EC$_{50}$) (nM) | CRE-Luc (EC$_{50}$) (nM) |
|---|---|---|---|
| 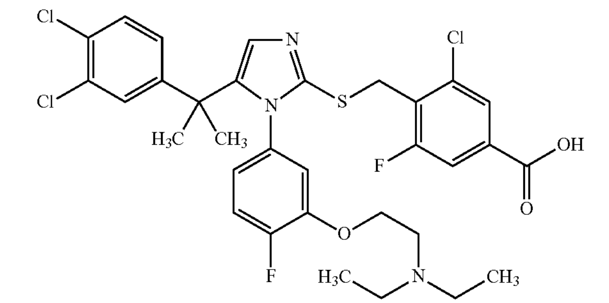 [SMILES: CCN(CC)CCOc1cc(-n2c(C(C)(C)c3ccc(Cl)c(Cl)c3)cnc2SCc2c(F)cc(C(=O)O)cc2Cl)ccc1F] | 3-chloro-4-[({5-[1-(3,4-dichlorophenyl)-1-methylethyl]-1-(3-{[2-(diethylamino)ethyl]oxy}-4-fluorophenyl)-1H-imidazol-2-yl}thio)methyl]-5-fluorobenzoic acid | | C |
| 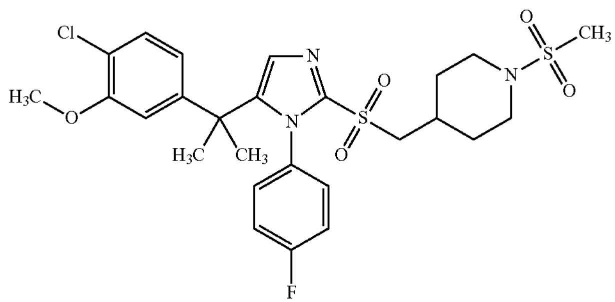 | 4-({[5-{1-[4-chloro-3-(methyloxy)phenyl]-1-methylethyl}-1-(4-fluorophenyl)-1H-imidazol-2-yl]sulfonyl}methyl)-1-(methylsulfonyl)piperidine | C | C |
| 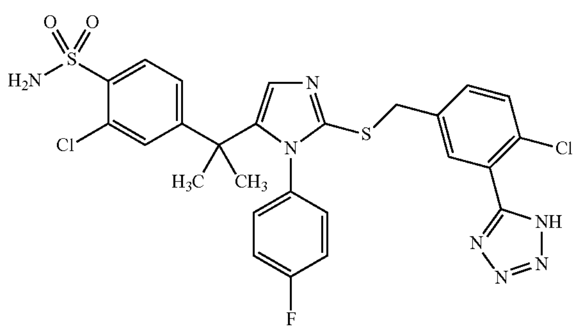 [SMILES: CC(C)(c1ccc(S(N)(=O)=O)c(Cl)c1)c1cnc(SCc2ccc(Cl)c(-c3nnn[nH]3)c2)n1-c1ccc(F)cc1] | 2-chloro-4-{1-[2-({[4-chloro-3-(1H-tetrazol-5-yl)phenyl]methyl}thio)-1-(4-fluorophenyl)-1H-imidazol-5-yl]-1-methylethyl}benzenesulfonamide | C | C |

TABLE 1-continued

| Structure | NAME | cAMP (EC$_{50}$) (nM) | CRE-Luc (EC$_{50}$) (nM) |
|---|---|---|---|
| 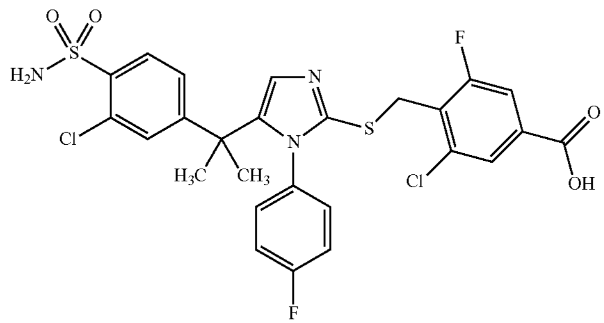 | 4-({[5-{1-[4-(aminosulfonyl)-3-chlorophenyl]-1-methylethyl}-1-(4-fluorophenyl)-1H-imidazol-2-yl]thio}methyl)-3-chloro-5-fluorobenzoic acid | A | A |
| 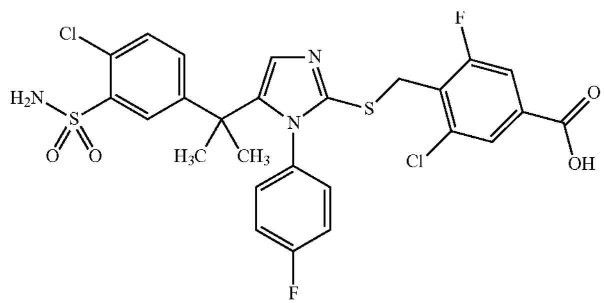 | 4-({[5-{1-[3-(aminosulfonyl)-4-chlorophenyl]-1-methylethyl}-1-(4-fluorophenyl)-1H-imidazol-2-yl]thio}methyl)-3-chloro-5-fluorobenzoic acid | C | C |
| 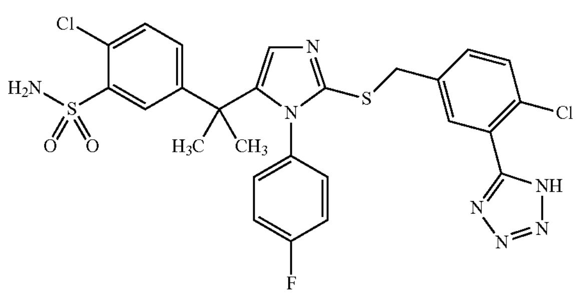 [SMILES: CC(C)(c1ccc(Cl)c(S(N)(=O)=O)c1)c1cnc(SCc2ccc(Cl)c(-c3nnn[nH]3)c2)n1-c1ccc(F)cc1] | 2-chloro-5-{1-[2-({[4-chloro-3-(1H-tetrazol-5-yl)phenyl]methyl}thio)-1-(4-fluorophenyl)-1H-imidazol-5-yl]-1-methylethyl}benzenesulfonamide | | C |

TABLE 1-continued

| Structure | NAME | cAMP (EC$_{50}$) (nM) | CRE-Luc (EC$_{50}$) (nM) |
|---|---|---|---|
| 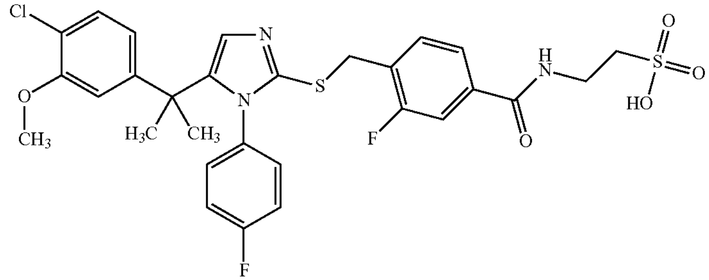 [SMILES: COc1cc(C(C)(C)c2cnc(SCc3ccc(C(=O)NCCS(=O)(=O)O)cc3F)n2-c2ccc(F)cc2)ccc1Cl] | 2-({[4-({[5-{1-[4-chloro-3-(methyloxy)phenyl]-1-methylethyl}-1-(4-fluorophenyl)-1H-imidazol-2-yl]thio}methyl)-3-fluorophenyl]carbonyl}amino)ethanesulfonic acid | A | A |
| 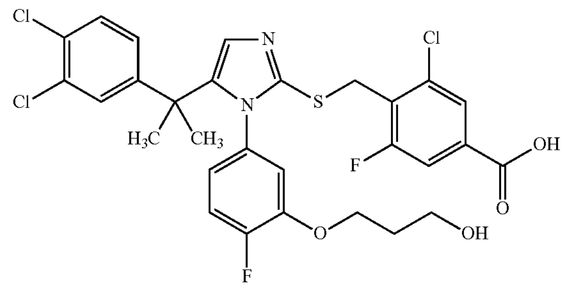 [SMILES: CC(C)(c1ccc(Cl)c(Cl)c1)c1cnc(SCc2c(F)cc(C(=O)O)cc2Cl)n1-c1ccc(F)c(OCCCO)c1] | 3-chloro-4-{[(5-[1-(3,4-dichlorophenyl)-1-methylethyl]-1-{4-fluoro-3-[(3-hydroxypropyl)oxy]phenyl}-1H-imidazol-2-yl)thio]methyl}-5-fluorobenzoic acid | C | C |
| 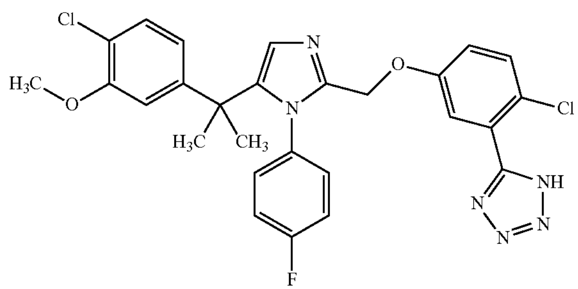 [SMILES: COc1cc(C(C)(C)c2cnc(COc3ccc(Cl)c(-c4nnn[nH]4)c3)n2-c2ccc(F)cc2)ccc1Cl] | 5-[2-chloro-5-({[5-{1-[4-chloro-3-(methyloxy)phenyl]-1-methylethyl}-1-(4-fluorophenyl)-1H-imidazol-2-yl]methyl}oxy)phenyl]-1H-tetrazole | C | A |

TABLE 1-continued

| Structure | NAME | cAMP (EC$_{50}$) (nM) | CRE-Luc (EC$_{50}$) (nM) |
|---|---|---|---|
| | 3-chloro-4-[({5-[1-(3,4-dichlorophenyl)-1-methylethyl]-1-(4-fluorophenyl)-1H-imidazol-2-yl}methyl)oxy]-5-fluorobenzoic acid | C | C |
| 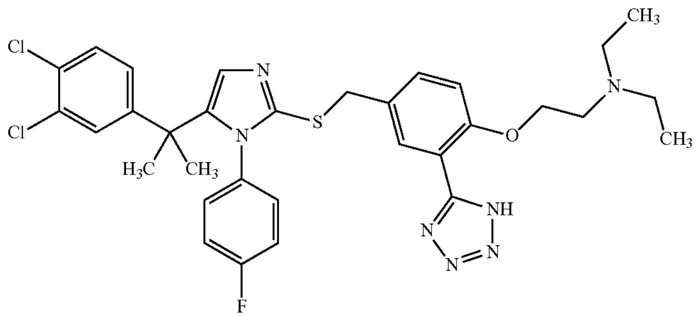 [SMILES: CCN(CC)CCOc1ccc(CSc2ncc(C(C)(C)c3ccc(Cl)c(Cl)c3)n2-c2ccc(F)cc2)cc1-c1nnn[nH]1] | 2-({4-[({5-[1-(3,4-dichlorophenyl)-1-methylethyl]-1-(4-fluorophenyl)-1H-imidazol-2-yl}thio)methyl]-2-(1H-tetrazol-5-yl)phenyl}oxy)-N,N-diethylethanamine | | C |
| 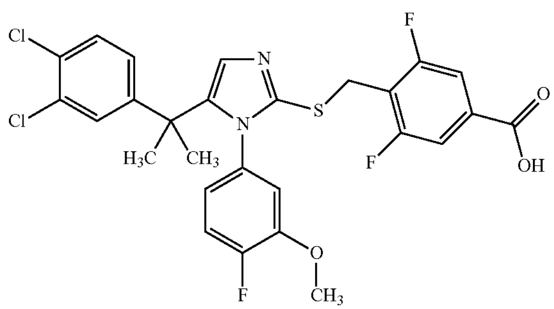 [SMILES: COc1cc(-n2c(C(C)(C)c3ccc(Cl)c(Cl)c3)cnc2SCc2c(F)cc(C(=O)O)cc2F)ccc1F] | 4-[({5-[1-(3,4-dichlorophenyl)-1-methylethyl]-1-[4-fluoro-3-(methyloxy)phenyl]-1H-imidazol-2-yl}thio)methyl]-3,5-difluorobenzoic acid | A | A |

TABLE 1-continued

| Structure | NAME | cAMP (EC$_{50}$) (nM) | CRE-Luc (EC$_{50}$) (nM) |
|---|---|---|---|
| 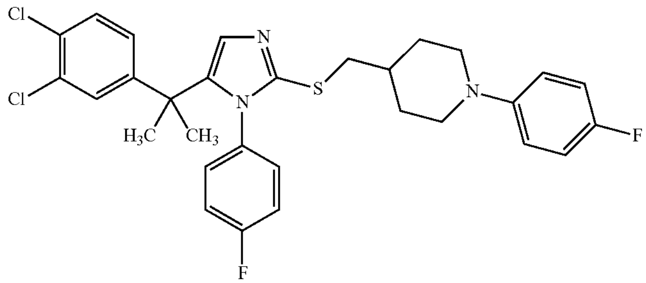 [SMILES: CC(C)(c1ccc(Cl)c(Cl)c1)c1cnc(SCC2CCN(c3ccc(F)cc3)CC2)n1-c1ccc(F)cc1] | 4-[({5-[1-(3,4-dichlorophenyl)-1-methylethyl]-1-(4-fluorophenyl)-1H-imidazol-2-yl}thio)methyl]-1-(4-fluorophenyl)piperidine | | D |
| 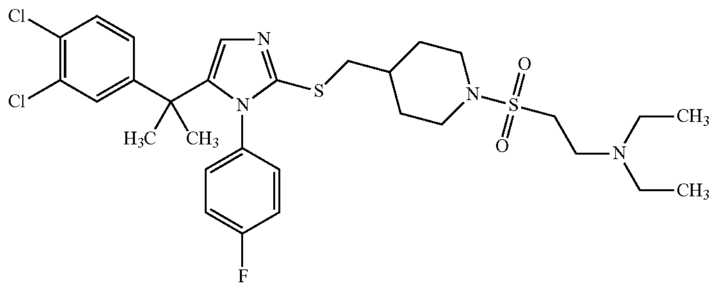 [SMILES: CCN(CC)CCS(=O)(=O)N1CCC(CSc2ncc(C(C)(C)c3ccc(Cl)c(Cl)c3)n2-c2ccc(F)cc2)CC1] | 2-({4-[({5-[1-(3,4-dichlorophenyl)-1-methylethyl]-1-(4-fluorophenyl)-1H-imidazol-2-yl}thio)methyl]piperidin-1-yl}sulfonyl)-N,N-diethylethanamine | C | C |
| 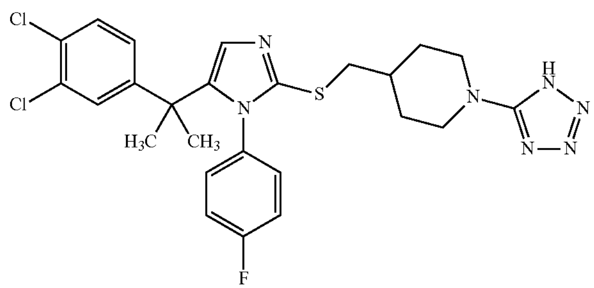 [SMILES: CC(C)(c1ccc(Cl)c(Cl)c1)c1cnc(SCC2CCN(c3nnn[nH]3)CC2)n1-c1ccc(F)cc1] | 4-[({5-[1-(3,4-dichlorophenyl)-1-methylethyl]-1-(4-fluorophenyl)-1H-imidazol-2-yl}thio)methyl]-1-(1H-tetrazol-5-yl)piperidine | C | A |

TABLE 1-continued

| Structure | NAME | cAMP (EC$_{50}$) (nM) | CRE-Luc (EC$_{50}$) (nM) |
|---|---|---|---|
| 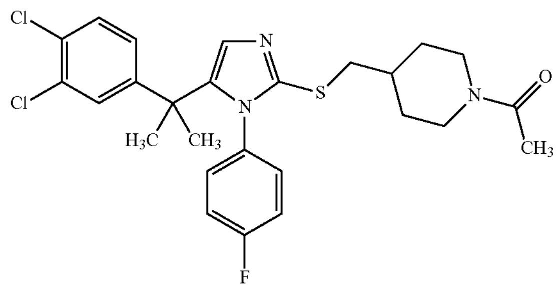 [SMILES: CC(=O)N1CCC(CSc2ncc(C(C)(C)c3ccc(Cl)c(Cl)c3)n2-c2ccc(F)cc2)CC1] | 1-acetyl-4-[({5-[1-(3,4-dichlorophenyl)-1-methylethyl]-1-(4-fluorophenyl)-1H-imidazol-2-yl}thio)methyl]piperidine | C | A |
| 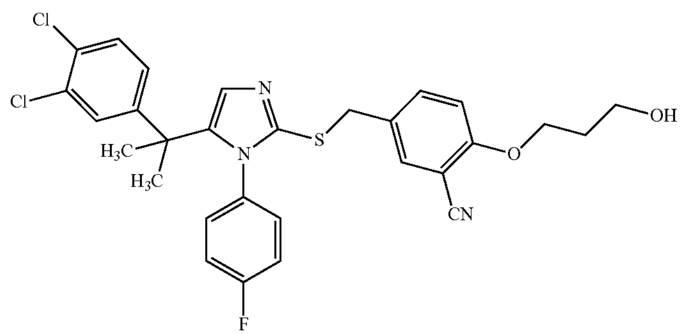 [SMILES: CC(C)(c1ccc(Cl)c(Cl)c1)c1cnc(SCc2ccc(OCCCO)c(C#N)c2)n1-c1ccc(F)cc1] | 5-[({5-[1-(3,4-dichlorophenyl)-1-methylethyl]-1-(4-fluorophenyl)-1H-imidazol-2-yl}thio)methyl]-2-[(3-hydroxypropyl)oxy]benzonitrile |  | C |
| 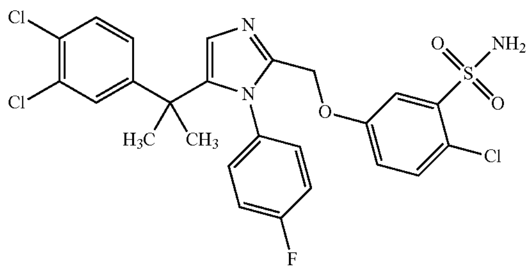 [SMILES: CC(C)(c1ccc(Cl)c(Cl)c1)c1cnc(COc2ccc(Cl)c(S(N)(=O)=O)c2)n1-c1ccc(F)cc1] | 2-chloro-5-[({5-[1-(3,4-dichlorophenyl)-1-methylethyl]-1-(4-fluorophenyl)-1H-imidazol-2-yl}methyl)oxy]benzenesulfonamide |  | C |

TABLE 1-continued

| Structure | NAME | cAMP (EC$_{50}$) (nM) | CRE-Luc (EC$_{50}$) (nM) |
|---|---|---|---|
| 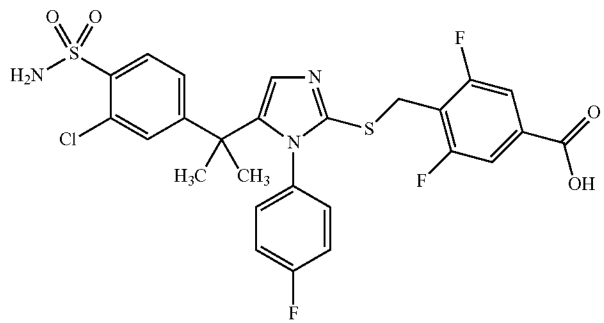 [SMILES: CC(C)(c1ccc(S(N)(=O)=O)c(Cl)c1)c1cnc(SCc2c(F)cc(C(=O)O)cc2F)n1-c1ccc(F)cc1] | 4-({[5-{1-[4-(aminosulfonyl)-3-chlorophenyl]-1-methylethyl}-1-(4-fluorophenyl)-1H-imidazol-2-yl]thio}methyl)-3,5-difluorobenzoic acid | A | A |
| 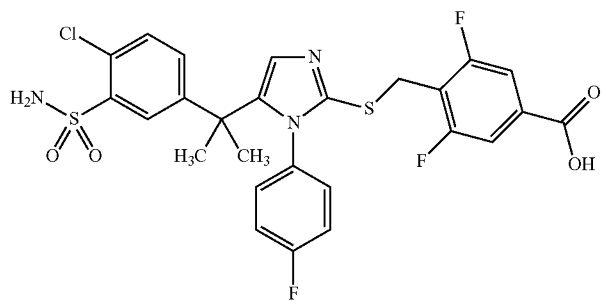 [SMILES: CC(C)(c1ccc(Cl)c(S(N)(=O)=O)c1)c1cnc(SCc2c(F)cc(C(=O)O)cc2F)n1-c1ccc(F)cc1] | 4-({[5-{1-[3-(aminosulfonyl)-4-chlorophenyl]-1-methylethyl}-1-(4-fluorophenyl)-1H-imidazol-2-yl]thio}methyl)-3,5-difluorobenzoic acid | | D |
| 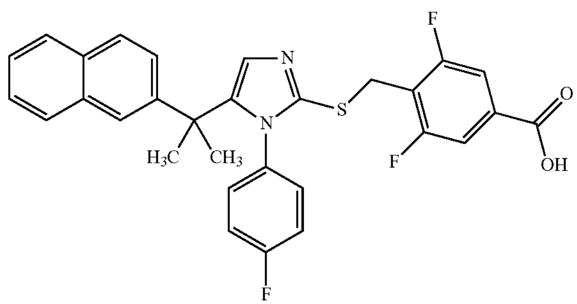 [SMILES: CC(C)(c1ccc2ccccc2c1)c1cnc(SCc2c(F)cc(C(=O)O)cc2F)n1-c1ccc(F)cc1] | 3,5-difluoro-4-({[1-(4-fluorophenyl)-5-(1-methyl-1-naphthalen-2-ylethyl)-1H-imidazol-2-yl]thio}methyl)benzoic acid | C | C |

TABLE 1-continued
| Structure | NAME | cAMP (EC$_{50}$) (nM) | CRE-Luc (EC$_{50}$) (nM) |
|---|---|---|---|
| 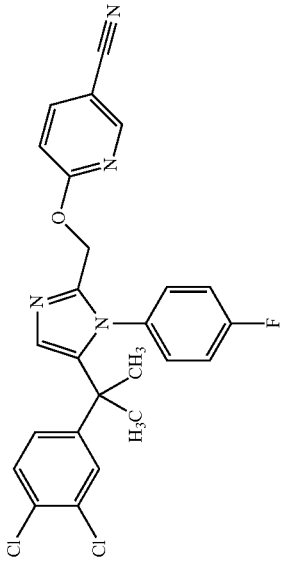 | 6-[({5-[1-(3,4-dichlorophenyl)-1-methylethyl]-1-(4-fluorophenyl)-1H-imidazol-2-yl}methyl)oxy]pyridine-3-carbonitrile | | C |
| 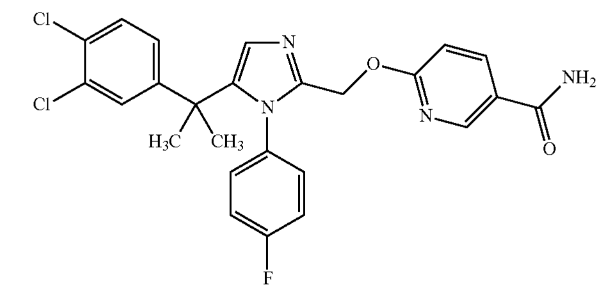 [SMILES: CC(C)(c1ccc(Cl)c(Cl)c1)c1cnc(COc2ccc(C(N)=O)cn2)n1-c1ccc(F)cc1] | 6-[({5-[1-(3,4-dichlorophenyl)-1-methylethyl]-1-(4-fluorophenyl)-1H-imidazol-2-yl}methyl)oxy]pyridine-3-carboxamide | | C |
| 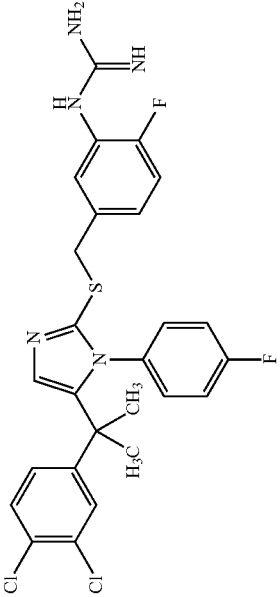 | 1-{5-[({5-[1-(3,4-dichlorophenyl)-1-methylethyl]-1-(4-fluorophenyl)-1H-imidazol-2-yl}thio)methyl]-2-fluorophenyl}guanidine | | C |

TABLE 1-continued
| Structure | NAME | cAMP (EC$_{50}$) (nM) | CRE-Luc (EC$_{50}$) (nM) |
|---|---|---|---|
| 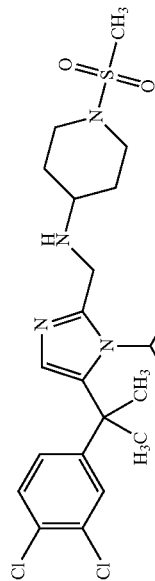 | N-({5-[1-(3,4-dichlorophenyl)-1-methylethyl]-1-(4-fluorophenyl)-1H-imidazol-2-yl}methyl)-1-(methylsulfonyl)piperidin-4-amine | D | D |
| 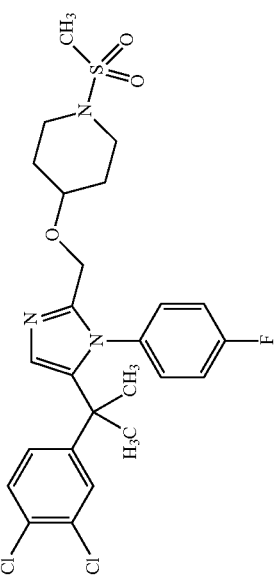 | 4-[({5-[1-(3,4-dichlorophenyl)-1-methylethyl]-1-(4-fluorophenyl)-1H-imidazol-2-yl}methyl)oxy]-1-(methylsulfonyl)piperidine | C | D |
| 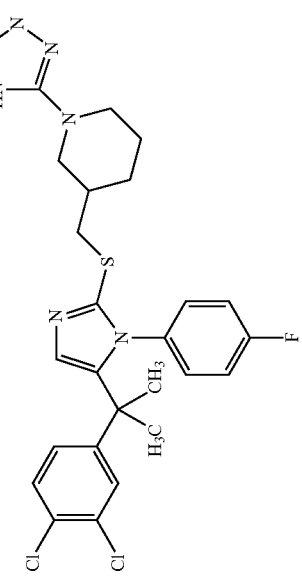 | 3-[({5-[1-(3,4-dichlorophenyl)-1-methylethyl]-1-(4-fluorophenyl)-1H-imidazol-2-yl}thio)methyl]-1-(1H-tetrazol-5-yl)piperidine | D | D |

TABLE 1-continued

| Structure | NAME | cAMP (EC$_{50}$) (nM) | CRE-Luc (EC$_{50}$) (nM) |
|---|---|---|---|
| 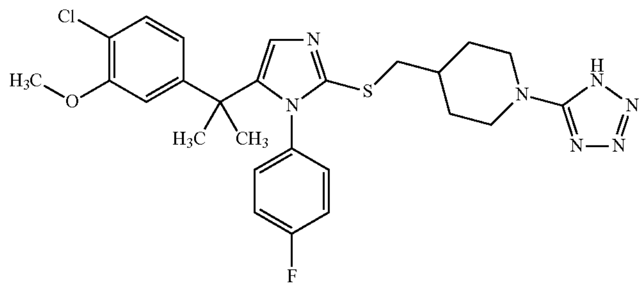 [SMILES: COc1cc(C(C)(C)c2cnc(SCC3CCN(c4nnn[nH]4)CC3)n2-c2ccc(F)cc2)ccc1Cl] | 4-({[5-{1-[4-chloro-3-(methyloxy)phenyl]-1-methylethyl}-1-(4-fluorophenyl)-1H-imidazol-2-yl]thio}methyl)-1-(1H-tetrazol-5-yl)piperidine | C | A |
| 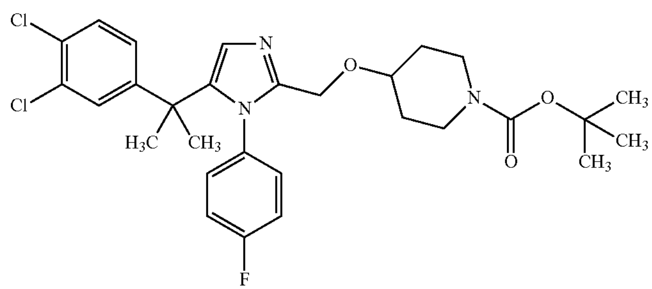 [SMILES: CC(C)(C)OC(=O)N1CCC(OCc2ncc(C(C)(C)c3ccc(Cl)c(Cl)c3)n2-c2ccc(F)cc2)CC1] | 1,1-dimethylethyl 4-[({5-[1-(3,4-dichlorophenyl)-1-methylethyl]-1-(4-fluorophenyl)-1H-imidazol-2-yl}methyl)oxy]piperidine-1-carboxylate | | D |
| 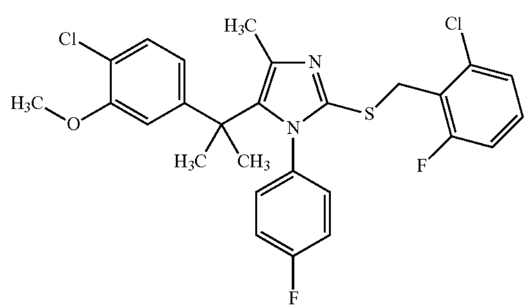 [SMILES: COc1cc(C(C)(C)c2c(C)nc(SCc3c(F)cccc3Cl)n2-c2ccc(F)cc2)ccc1Cl] | 2-{[(2-chloro-6-fluorophenyl)methyl]thio}-5-{1-[4-chloro-3-(methyloxy)phenyl]-1-methylethyl}-1-(4-fluorophenyl)-4-methyl-1H-imidazole | C | C |

TABLE 1-continued

| Structure | NAME | cAMP (EC$_{50}$) (nM) | CRE-Luc (EC$_{50}$) (nM) |
|---|---|---|---|
| | ethyl 3-chloro-4-{[5-{1-[4-chloro-3-(methyloxy)phenyl]-1-methylethyl}-1-(4-fluorophenyl)-4-methyl-1H-imidazol-2-yl]thio}methyl)-5-fluorobenzoate | | C |
| | 3-chloro-4-{[5-{1-[4-chloro-3-(methyloxy)phenyl]-1-methylethyl}-1-(4-fluorophenyl)-4-methyl-1H-imidazol-2-yl]thio}methyl)-5-fluorobenzoic acid | A | C |
| | 3-chloro-4-{[(5-{1-[4-chloro-3-(methyloxy)phenyl]-1-methylethyl}-1-pyridin-3-yl-1H-imidazol-2-yl}thio]methyl}-5-fluorobenzoic acid | D | D |

TABLE 1-continued

| Structure | NAME | cAMP (EC$_{50}$) (nM) | CRE-Luc (EC$_{50}$) (nM) |
|---|---|---|---|
| 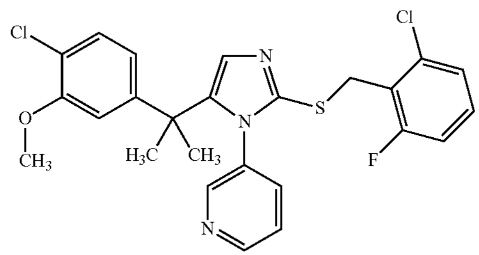 [SMILES: COc1cc(C(C)(C)c2cnc(SCc3c(F)cccc3Cl)n2-c2cccnc2)ccc1Cl] | 3-(2-{[(2-chloro-6-fluorophenyl)methyl]thio}-5-{1-[4-chloro-3-(methyloxy)phenyl]-1-methylethyl}-1H-imidazol-1-yl)pyridine | C | C |
| | 3-chloro-4-{[5-{1-[4-chloro-3-(methyloxy)phenyl]-1-methylethyl}-1-(5-fluoropyridin-2-yl)-1H-imidazol-2-yl]thio}methyl)-5-fluorobenzoic acid | A | A |
| 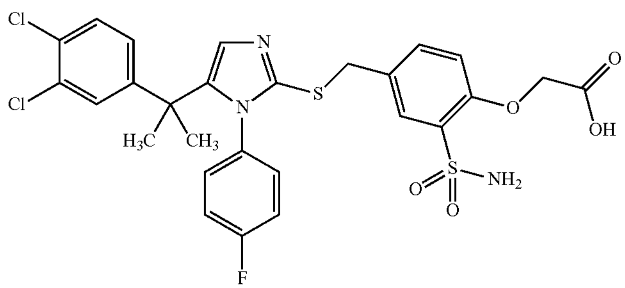 [SMILES: CC(C)(c1ccc(Cl)c(Cl)c1)c1cnc(SCc2ccc(OCC(=O)O)c(S(N)(=O)=O)c2)n1-c1ccc(F)cc1] | ({2-(aminosulfonyl)-4-[({5-[1-(3,4-dichlorophenyl)-1-methylethyl]-1-(4-fluorophenyl)-1H-imidazol-2-yl}thio)methyl]phenyl}oxy)acetic acid | C | C |

TABLE 1-continued
| Structure | NAME | cAMP (EC$_{50}$) (nM) | CRE-Luc (EC$_{50}$) (nM) |
|---|---|---|---|
| 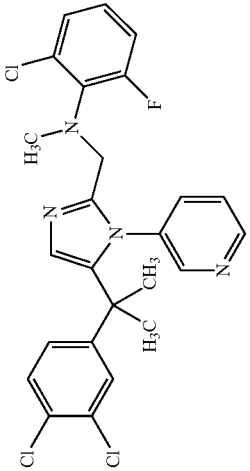 | 2-chloro-N-({5-[1-(3,4-dichlorophenyl)-1-methylethyl]-1-(4-fluorophenyl)-1H-imidazol-2-yl}methyl)-6-fluoro-N-methylaniline | | C |
| 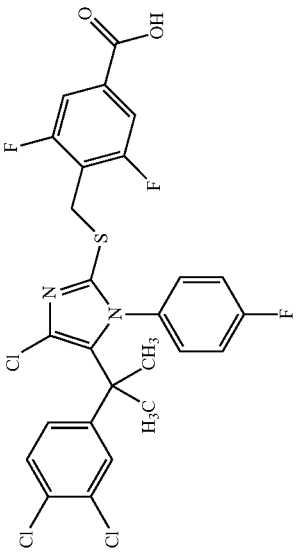 | 4-[({4-chloro-5-[1-(3,4-dichlorophenyl)-1-methylethyl]-1-(4-fluorophenyl)-1H-imidazol-2-yl}thio)methyl]-3,5-difluorobenzoic acid | C | C |
| 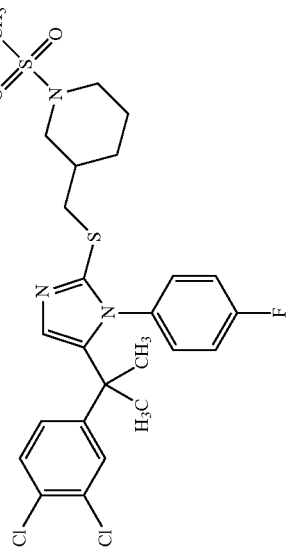 | 3-[({5-[1-(3,4-dichlorophenyl)-1-methylethyl]-1-(4-fluorophenyl)-1H-imidazol-2-yl}thio)methyl]-1-(methylsulfonyl)piperidine | | C |

TABLE 1-continued

| Structure | NAME | cAMP (EC$_{50}$) (nM) | CRE-Luc (EC$_{50}$) (nM) |
|---|---|---|---|
| 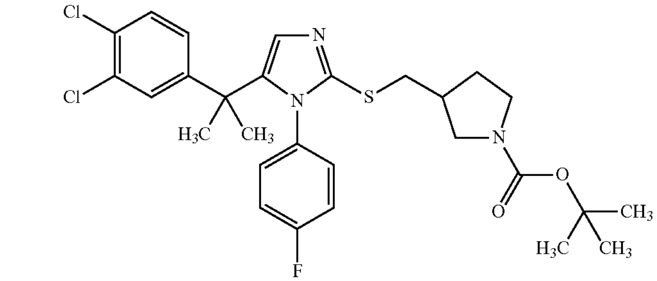 [SMILES: CC(C)(C)OC(=O)N1CCC(CSc2ncc(C(C)(C)c3ccc(Cl)c(Cl)c3)n2-c2ccc(F)cc2)C1] | 1,1-dimethylethyl 3-[({5-[1-(3,4-dichlorophenyl)-1-methylethyl]-1-(4-fluorophenyl)-1H-imidazol-2-yl}thio)methyl]pyrrolidine-1-carboxylate | | C |
| 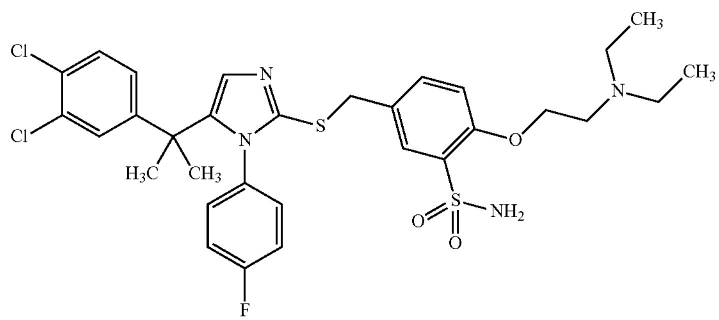 [SMILES: CCN(CC)CCOc1ccc(CSc2ncc(C(C)(C)c3ccc(Cl)c(Cl)c3)n2-c2ccc(F)cc2)cc1S(N)(=O)=O] | 5-[({5-[1-(3,4-dichlorophenyl)-1-methylethyl]-1-(4-fluorophenyl)-1H-imidazol-2-yl}thio)methyl]-2-[2-(diethylamino)ethyl]oxy}benzenesulfonamide | | C |
| 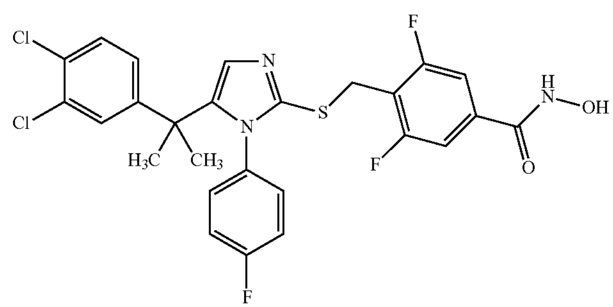 [SMILES: CC(C)(c1ccc(Cl)c(Cl)c1)c1cnc(SCc2c(F)cc(C(=O)NO)cc2F)n1-c1ccc(F)cc1] | 4-[({5-[1-(3,4-dichlorophenyl)-1-methylethyl]-1-(4-fluorophenyl)-1H-imidazol-2-yl}thio)methyl]-3,5-difluoro-N-hydroxybenzamide | A | A |

TABLE 1-continued
| Structure | NAME | cAMP (EC$_{50}$) (nM) | CRE-Luc (EC$_{50}$) (nM) |
|---|---|---|---|
| 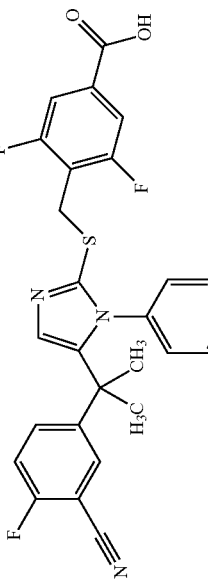 | 4-[({5-[1-(3-cyano-4-fluorophenyl)-1-methylethyl]-1-(4-fluorophenyl)-1H-imidazol-2-yl}thio)methyl]-3,5-difluorobenzoic acid | A | A |
| 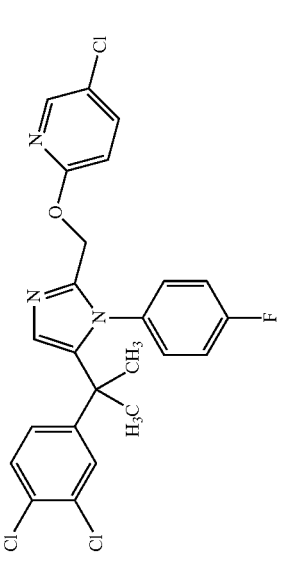 | 5-chloro-2-[({5-[1-(3,4-dichlorophenyl)-1-methylethyl]-1-(4-fluorophenyl)-1H-imidazol-2-yl}methyl)oxy]pyridine | | C |
| 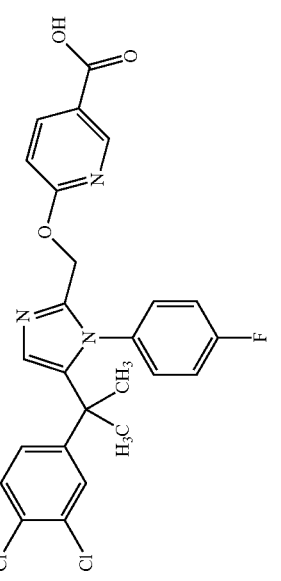 | 6-[({5-[1-(3,4-dichlorophenyl)-1-methylethyl]-1-(4-fluorophenyl)-1H-imidazol-2-yl}methyl)oxy]pyridine-3-carboxylic acid | | C |

TABLE 1-continued

| Structure | NAME | cAMP (EC$_{50}$) (nM) | CRE-Luc (EC$_{50}$) (nM) |
|---|---|---|---|
| 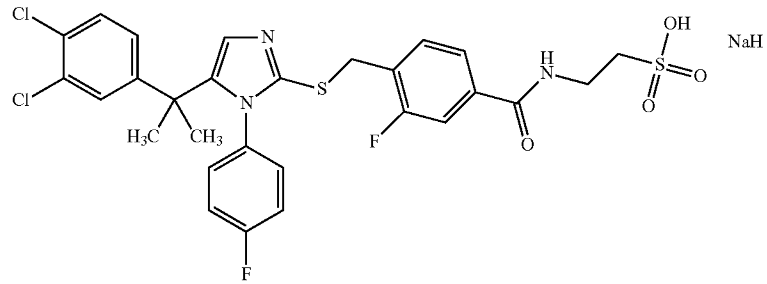 | 2-[({4-[({5-[1-(3,4-dichlorophenyl)-1-methylethyl]-1-(4-fluorophenyl)-1H-imidazol-2-yl}thio)methyl]-3-fluorophenyl}carbonyl)amino]ethanesulfonic acid-sodium (1:1) | A | C |
| 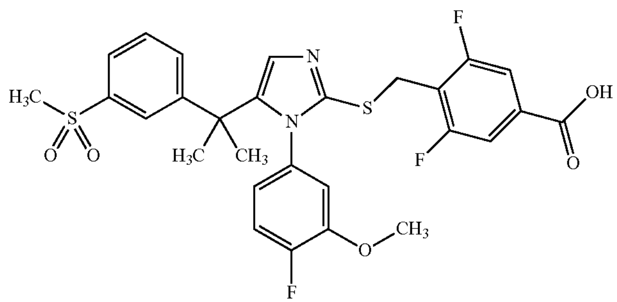 [SMILES: COc1cc(-n2c(C(C)(C)c3cccc(S(C)(=O)=O)c3)cnc2SCc2c(F)cc(C(=O)O)cc2F)ccc1F] | 3,5-difluoro-4-{[(1-[4-fluoro-3-(methyloxy)phenyl]-5-{1-methyl-1-[3-(methylsulfonyl)phenyl]ethyl}-1H-imidazol-2-yl)thio]methyl}benzoic acid | C | C |
| 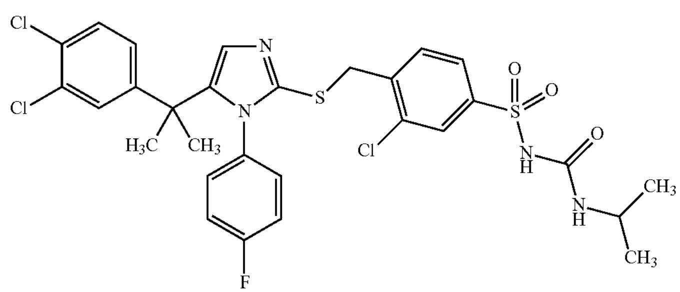 [SMILES: CC(C)NC(=O)NS(=O)(=O)c1ccc(CSc2ncc(C(C)(C)c3ccc(Cl)c(Cl)c3)n2-c2ccc(F)cc2)c(Cl)c1] | 3-chloro-4-[({5-[1-(3,4-dichlorophenyl)-1-methylethyl]-1-(4-fluorophenyl)-1H-imidazol-2-yl}thio)methyl]-N-{[(1-methylethyl)amino]carbonyl}benzenesulfonamide | C | C |

TABLE 1-continued

| Structure | NAME | cAMP (EC$_{50}$) (nM) | CRE-Luc (EC$_{50}$) (nM) |
|---|---|---|---|
|  | 5-[({5-[1-(3,4-dichlorophenyl)-1-methylethyl]-1-(4-fluorophenyl)-1H-imidazol-2-yl}thio)methyl]-2-fluoro-N-{[(1-methylethyl)amino carbonyl}benzenesulfonamide | C | C |
| 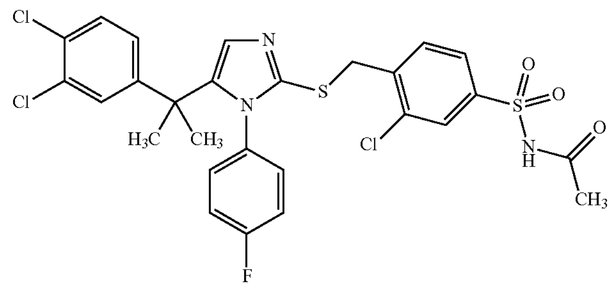 [SMILES: CC(=O)NS(=O)(=O)c1ccc(CSc2ncc(C(C)(C)c3ccc(Cl)c(Cl)c3)n2-c2ccc(F)cc2)c(Cl)c1] | N-({3-chloro-4-[({5-[1-(3,4-dichlorophenyl)-1-methylethyl]-1-(4-fluorophenyl)-1H-imidazol-2-yl}thio)methyl]phenyl}sulfonyl)acetamide | C |  |
| 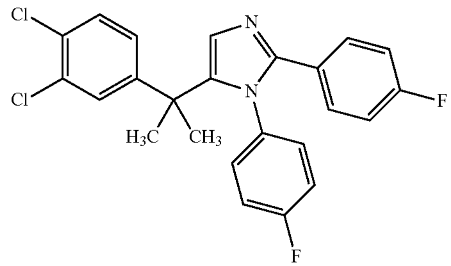 [SMILES: CC(C)(c1ccc(Cl)c(Cl)c1)c1cnc(-c2ccc(F)cc2)n1-c1ccc(F)cc1] | 5-[1-(3,4-dichlorophenyl)-1-methylethyl]-1,2-bis(4-fluorophenyl)-1H-imidazole |  | C |

TABLE 1-continued

| Structure | NAME | cAMP (EC$_{50}$) (nM) | CRE-Luc (EC$_{50}$) (nM) |
|---|---|---|---|
| 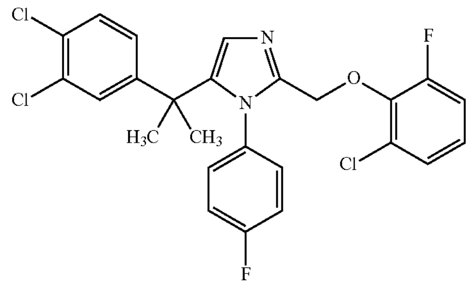 [SMILES: CC(C)(c1ccc(Cl)c(Cl)c1)c1cnc(COc2c(F)cccc2Cl)n1-c1ccc(F)cc1] | 2-{[(2-chloro-6-fluorophenyl)oxy]methyl}-5-[1-(3,4-dichlorophenyl)-1-methylethyl]-1-(4-fluorophenyl)-1H-imidazole | | C |
| 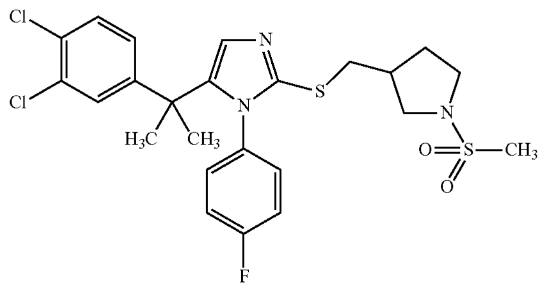 [SMILES: CC(C)(c1ccc(Cl)c(Cl)c1)c1cnc(SCC2CCN(S(C)(=O)=O)C2)n1-c1ccc(F)cc1] | 5-[1-(3,4-dichlorophenyl)-1-methylethyl]-1-(4-fluorophenyl)-2-({[1-(methylsulfonyl)pyrrolidin-3-yl]methyl}thio)-1H-imidazole | C | C |
| 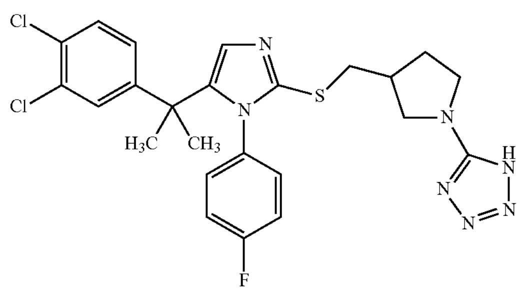 [SMILES: CC(C)(c1ccc(Cl)c(Cl)c1)c1cnc(SCC2CCN(c3nnn[nH]3)C2)n1-c1ccc(F)cc1] | 5-{3-[({5-[1-(3,4-dichlorophenyl)-1-methylethyl]-1-(4-fluorophenyl)-1H-imidazol-2-yl}thio)methyl]pyrrolidin-1-yl}-1H-tetrazole | D | C |

TABLE 1-continued

| Structure | NAME | cAMP (EC$_{50}$) (nM) | CRE-Luc (EC$_{50}$) (nM) |
|---|---|---|---|
| 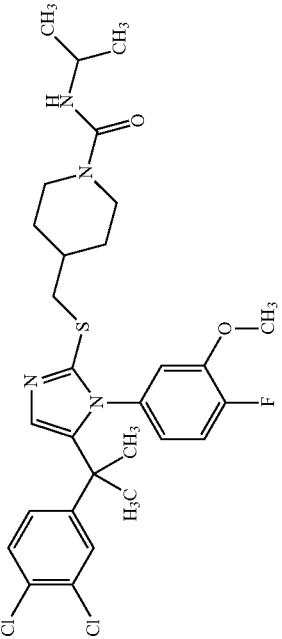 | 4-[({5-[1-(3,4-dichlorophenyl)-1-methylethyl]-1-[4-fluoro-3-(methyloxy)phenyl]-1H-imidazol-2-yl}thio)methyl]-N-(1-methylethyl)piperidine-1-carboxamide | C | A |
| 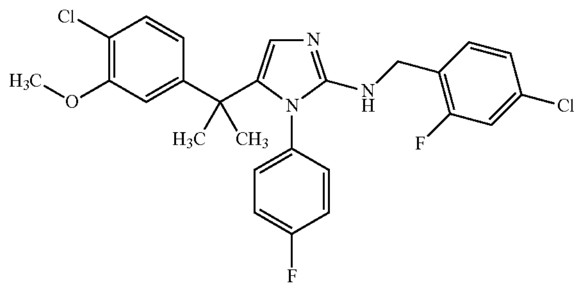 [SMILES: COc1cc(C(C)(C)c2cnc(NCc3ccc(Cl)cc3F)n2-c2ccc(F)cc2)ccc1Cl] | N-[(4-chloro-2-fluorophenyl)methyl]-5-{1-[4-chloro-3-(methyloxy)phenyl]-1-methylethyl}-1-(4-fluorophenyl)-1H-imidazol-2-amine | D | D |
| 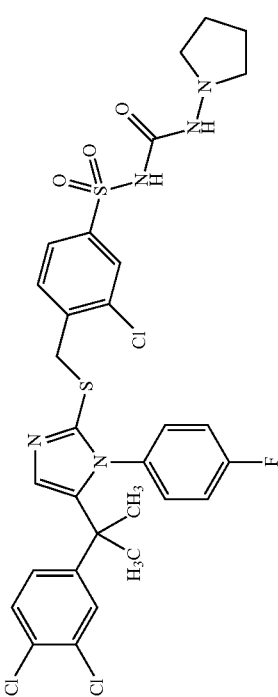 | 3-chloro-4-[({5-[1-(3,4-dichlorophenyl)-1-methylethyl]-1-(4-fluorophenyl)-1H-imidazol-2-yl}thio)methyl]-N-[(pyrrolidin-1-ylamino)carbonyl]benzenesulfonamide | D | C |

TABLE 1-continued

| Structure | NAME | cAMP (EC$_{50}$) (nM) | CRE-Luc (EC$_{50}$) (nM) |
|---|---|---|---|
| 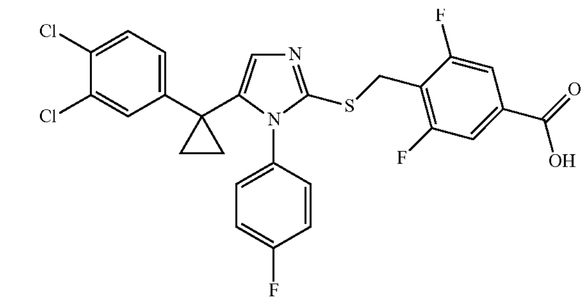 [SMILES: O=C(O)c1cc(F)c(CSc2ncc(C3(c4ccc(Cl)c(Cl)c4)CC3)n2-c2ccc(F)cc2)c(F)c1] | 4-[({5-[1-(3,4-dichlorophenyl)cyclopropyl]-1-(4-fluorophenyl)-1H-imidazol-2-yl}thio)methyl]-3,5-difluorobenzoic acid | C | C |
| 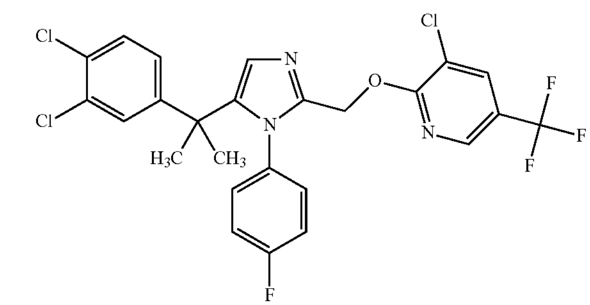 [SMILES: CC(C)(c1ccc(Cl)c(Cl)c1)c1cnc(COc2ncc(C(F)(F)F)cc2Cl)n1-c1ccc(F)cc1] | 3-chloro-2-[({5-[1-(3,4-dichlorophenyl)-1-methylethyl]-1-(4-fluorophenyl)-1H-imidazol-2-yl}methyl)oxy]-5-(trifluoromethyl)pyridine | | D |
| | 3,5-difluoro-4-[[(1-[4-fluoro-3-(methyloxy)phenyl]-5-{1-methyl-1-[4-(methylsulfonyl)phenyl]ethyl}-1H-imidazol-2-yl]thio]methyl]benzoic acid | A | C |

TABLE 1-continued

| Structure | NAME | cAMP (EC$_{50}$) (nM) | CRE-Luc (EC$_{50}$) (nM) |
|---|---|---|---|
| | 4-[[(5-{1-[4-(aminosulfonyl)phenyl]-1-methylethyl}-1-[4-fluoro-3-(methyloxy)phenyl]-1H-imidazol-2-yl)thio]methyl]-3,5-difluorobenzoic acid | C | C |
| 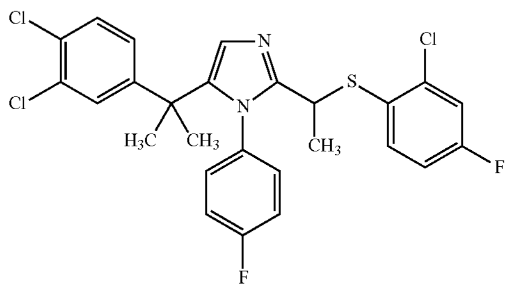 [SMILES: CC(Sc1ccc(F)cc1Cl)c1ncc(C(C)(C)c2ccc(Cl)c(Cl)c2)n1-c1ccc(F)cc1] | 2-{1-[(2-chloro-4-fluorophenyl)thio]ethyl}-5-[1-(3,4-dichlorophenyl)-1-methylethyl]-1-(4-fluorophenyl)-1H-imidazole | | D |
| 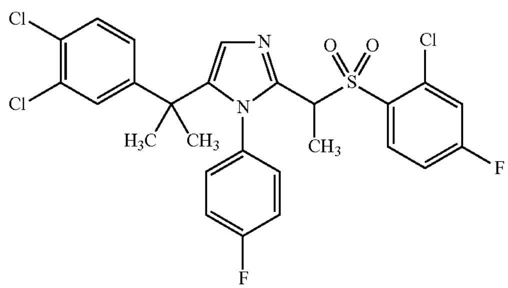 [SMILES: CC(c1ncc(C(C)(C)c2ccc(Cl)c(Cl)c2)n1-c1ccc(F)cc1)S(=O)(=O)c1ccc(F)cc1Cl] | 2-{1-[(2-chloro-4-fluorophenyl)sulfonyl]ethyl}-5-[1-(3,4-dichlorophenyl)-1-methylethyl]-1-(4-fluorophenyl)-1H-imidazole | | D |

TABLE 1-continued

| Structure | NAME | cAMP (EC$_{50}$) (nM) | CRE-Luc (EC$_{50}$) (nM) |
|---|---|---|---|
| 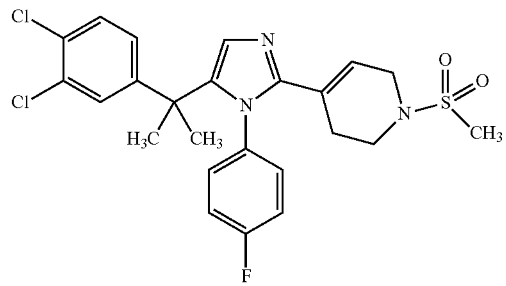 [SMILES: CC(C)(c1ccc(Cl)c(Cl)c1)c1cnc(C2=CCN(S(C)(=O)=O)CC2)n1-c1ccc(F)cc1] | 4-{5-[1-(3,4-dichlorophenyl)-1-methylethyl]-1-(4-fluorophenyl)-1H-imidazol-2-yl}-1-(methylsulfonyl)-1,2,3,6-tetrahydropyridine | | D |
| 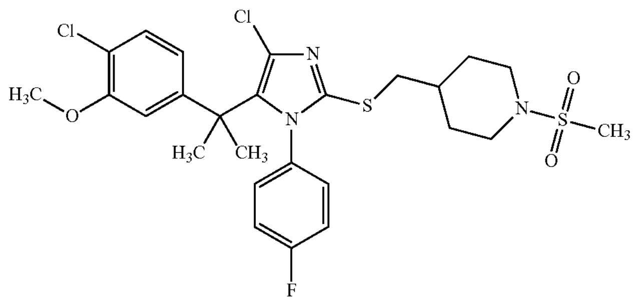 | 4-({[4-chloro-5-{1-[4-chloro-3-(methyloxy)phenyl]-1-methylethyl}-1-(4-fluorophenyl)-1H-imidazol-2-yl]thio}methyl)-1-(methylsulfonyl)piperidine | C | C |
| 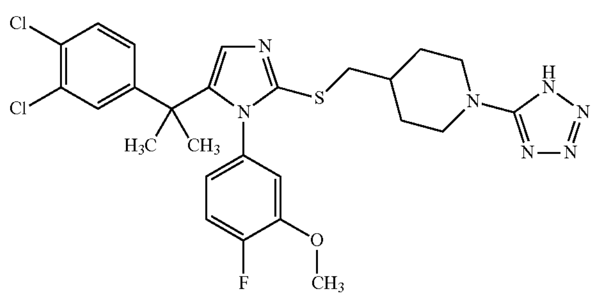 [SMILES: COc1cc(-n2c(C(C)(C)c3ccc(Cl)c(Cl)c3)cnc2SCC2CCN(c3nnn[nH]3)CC2)ccc1F] | 4-[({5-[1-(3,4-dichlorophenyl)-1-methylethyl]-1-[4-fluoro-3-(methyloxy)phenyl]-1H-imidazol-2-yl}thio)methyl]-1-(1H-tetrazol-5-yl)piperidine | A | A |

TABLE 1-continued

| Structure | NAME | cAMP (EC$_{50}$) (nM) | CRE-Luc (EC$_{50}$) (nM) |
|---|---|---|---|
| | 3-chloro-4-{[5-{1-[4-chloro-3-(methyloxy)phenyl]-1-methylethyl}-1-(4-fluorophenyl)-1H-imidazol-2-yl]thio}methyl)-N-{[(1-methylethyl)amino]carbonyl}benzenesulfonamide | A | C |
| 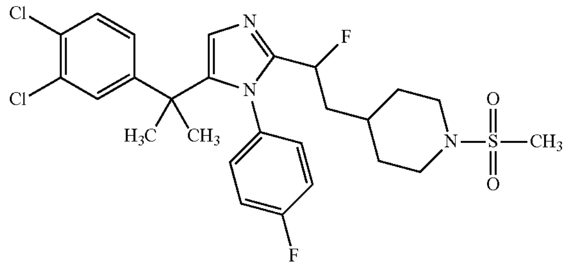 [SMILES: CC(C)(c1ccc(Cl)c(Cl)c1)c1cnc(C(F)CC2CCN(S(C)(=O)=O)CC2)n1-c1ccc(F)cc1] | 4-(2-{5-[1-(3,4-dichlorophenyl)-1-methylethyl]-1-(4-fluorophenyl)-1H-imidazol-2-yl}-2-fluoroethyl)-1-(methylsulfonyl)piperidine | | D |
| 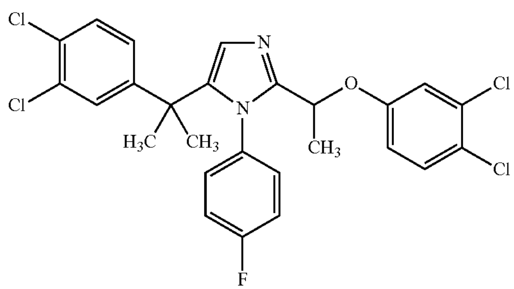 [SMILES: CC(Oc1ccc(Cl)c(Cl)c1)c1ncc(C(C)(C)c2ccc(Cl)c(Cl)c2)n1-c1ccc(F)cc1] | 5-[1-(3,4-dichlorophenyl)-1-methylethyl]-2-{1-[(3,4-dichlorophenyl)oxy]ethyl}-1-(4-fluorophenyl)-1H-imidazole | | D |

TABLE 1-continued

| Structure | NAME | cAMP (EC$_{50}$) (nM) | CRE-Luc (EC$_{50}$) (nM) |
|---|---|---|---|
| 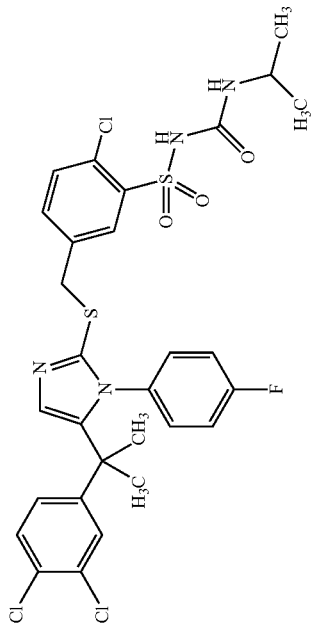 | 2-chloro-5-[({5-[1-(3,4-dichlorophenyl)-1-methylethyl]-1-(4-fluorophenyl)-1H-imidazol-2-yl]thio}methyl)-N-{[(1-methylethyl)amino]carbonyl}benzenesulfonamide | C | C |
| 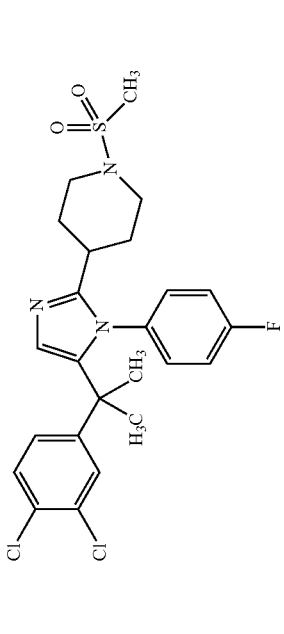 | 4-{5-[1-(3,4-dichlorophenyl)-1-methylethyl]-1-(4-fluorophenyl)-1H-imidazol-2-yl}-1-(methylsulfonyl)piperidine | | D |
| 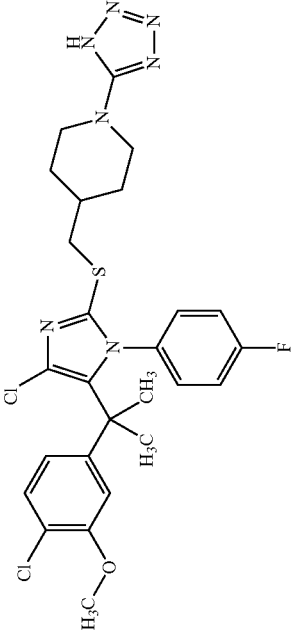 | 4-{[(4-chloro-5-{1-[4-chloro-3-(methyloxy)phenyl]-1-methylethyl}-1-(4-fluorophenyl)-1H-imidazol-2-yl]thio}methyl)-1-(1H-tetrazol-5-yl)piperidine | D | A |

TABLE 1-continued

| Structure | NAME | cAMP (EC$_{50}$) (nM) | CRE-Luc (EC$_{50}$) (nM) |
|---|---|---|---|
| 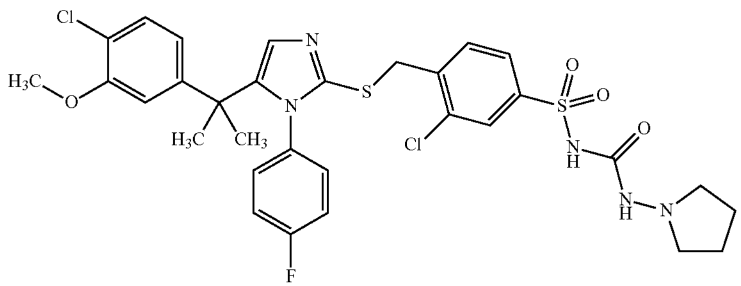 [SMILES: COc1cc(C(C)(C)c2cnc(SCc3ccc(S(=O)(=O)NC(=O)NN4CCCC4)cc3Cl)n2-c2ccc(F)cc2)ccc1Cl] | 3-chloro-4-({[5-{1-[4-chloro-3-(methyloxy)phenyl]-1-methylethyl}-1-(4-fluorophenyl)-1H-imidazol-2-yl]thio}methyl)-N-[(pyrrolidin-1-ylamino)carbonyl]benzenesulfonamide | C | C |
| 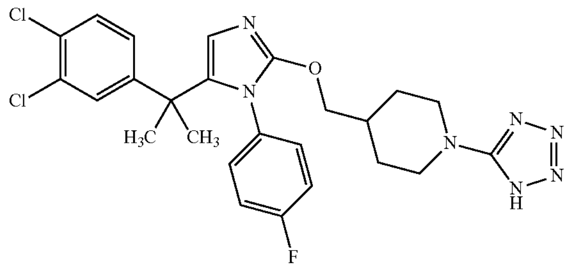 [SMILES: CC(C)(c1ccc(Cl)c(Cl)c1)c1cnc(OCC2CCN(c3nnn[nH]3)CC2)n1-c1ccc(F)cc1] | 4-[({5-[1-(3,4-dichlorophenyl)-1-methylethyl]-1-(4-fluorophenyl)-1H-imidazol-2-yl}oxy)methyl]-1-(1H-tetrazol-5-yl)piperidine | | D |
| 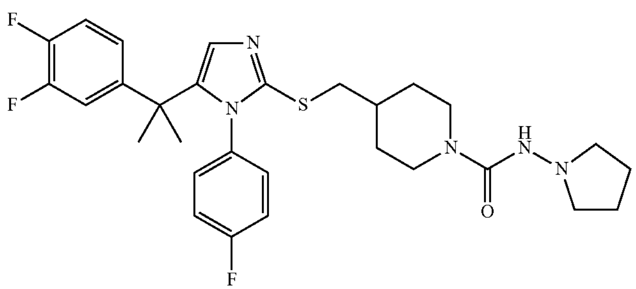 [SMILES: CC(C)(c1ccc(F)c(F)c1)c1cnc(SCC2CCN(C(=O)NN3CCCC3)CC2)n1-c1ccc(F)cc1] | 4-[({5-[1-(3,4-difluorophenyl)-1-methylethyl]-1-(4-fluorophenyl)-1H-imidazol-2-yl}thio)methyl]-N-pyrrolidin-1-ylpiperidine-1-carboxamide | C | C |

TABLE 1-continued

| Structure | NAME | cAMP (EC$_{50}$) (nM) | CRE-Luc (EC$_{50}$) (nM) |
|---|---|---|---|
| 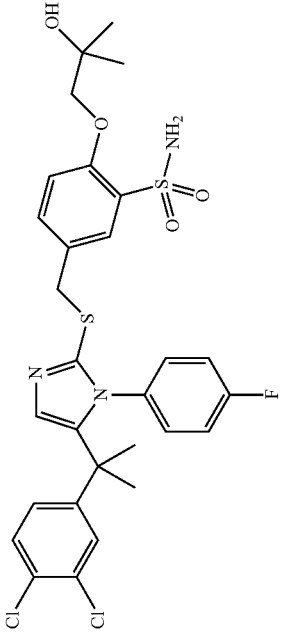 | 5-[({5-[1-(3,4-dichlorophenyl)-1-methylethyl]-1-(4-fluorophenyl)-1H-imidazol-2-yl}thio)methyl]-2-[(2-hydroxy-2-methylpropyl)oxy]benzenesulfonamide | C | A |
| 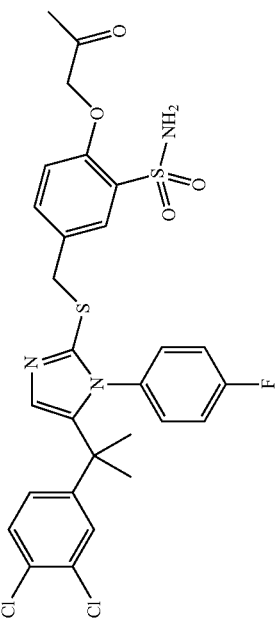 | 5-[({5-[1-(3,4-dichlorophenyl)-1-methylethyl]-1-(4-fluorophenyl)-1H-imidazol-2-yl}thio)methyl]-2-[(2-oxopropyl)oxy]benzenesulfonamide | C | A |
| 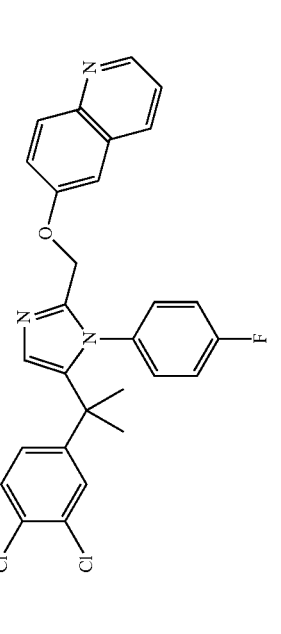 | 6-[({5-[1-(3,4-dichlorophenyl)-1-methylethyl]-1-(4-fluorophenyl)-1H-imidazol-2-yl}methyl)oxy]quinoline | | C |

TABLE 1-continued

| Structure | NAME | cAMP (EC$_{50}$) (nM) | CRE-Luc (EC$_{50}$) (nM) |
|---|---|---|---|
| 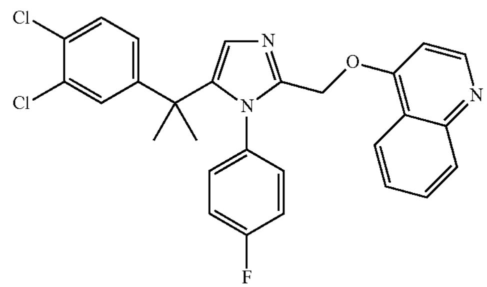 [SMILES: CC(C)(c1ccc(Cl)c(Cl)c1)c1cnc(COc2ccnc3ccccc23)n1-c1ccc(F)cc1] | 4-[({5-[1-(3,4-dichlorophenyl)-1-methylethyl]-1-(4-fluorophenyl)-1H-imidazol-2-yl}methyl)oxy]quinoline | | D |
| 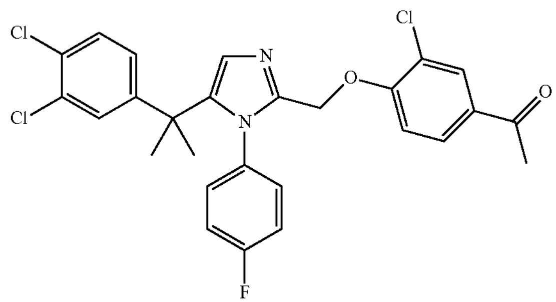 [SMILES: CC(=O)c1ccc(OCc2ncc(C(C)(C)c3ccc(Cl)c(Cl)c3)n2-c2ccc(F)cc2)c(Cl)c1] | 1-{3-chloro-4-[({5-[1-(3,4-dichlorophenyl)-1-methylethyl]-1-(4-fluorophenyl)-1H-imidazol-2-yl}methyl)oxy]phenyl}ethanone | | D |
| 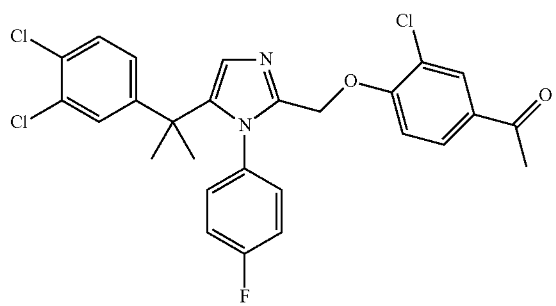 [SMILES: CC(=O)c1ccc(OCc2ncc(C(C)(C)c3ccc(Cl)c(Cl)c3)n2-c2ccc(F)cc2)c(Cl)c1] | 4-[({5-[1-(3,4-dichlorophenyl)-1-methylethyl]-4-[4-fluoro-3-(methyloxy)phenyl]-4H-1,2,4-triazol-3-yl}thio)methyl]-3,5-difluorobenzoic acid | C | C |

TABLE 1-continued

| Structure | NAME | cAMP (EC$_{50}$) (nM) | CRE-Luc (EC$_{50}$) (nM) |
|---|---|---|---|
| 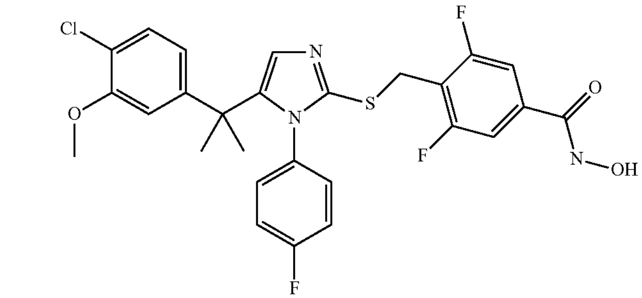 [SMILES: COc1cc(C(C)(C)c2cnc(SCc3c(F)cc(C(=O)NO)cc3F)n2-c2ccc(F)cc2)ccc1Cl] | 4-({[5-{1-[4-chloro-3-(methyloxy)phenyl]-1-methylethyl}-1-(4-fluorophenyl)-1H-imidazol-2-yl]thio}methyl)-3,5-difluoro-N-hydroxybenzamide | A | A |
| 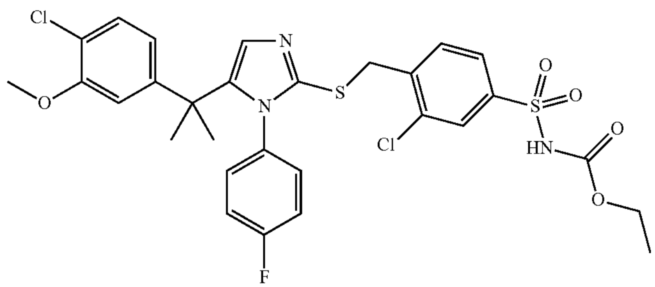 [SMILES: CCOC(=O)NS(=O)(=O)c1ccc(CSc2ncc(C(C)(C)c3ccc(Cl)c(OC)c3)n2-c2ccc(F)cc2)c(Cl)c1] | ethyl {[3-chloro-4-({[5-{1-[4-chloro-3-(methyloxy)phenyl]-1-methylethyl}-1-(4-fluorophenyl)-1H-imidazol-2-yl]thio}methyl)phenyl]sulfonyl}carbamate | A | A |
| 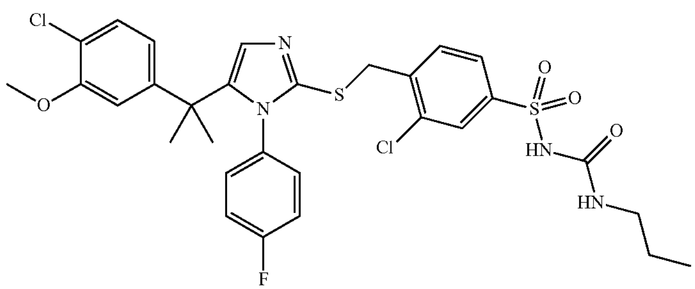 [SMILES: CCCNC(=O)NS(=O)(=O)c1ccc(CSc2ncc(C(C)(C)c3ccc(Cl)c(OC)c3)n2-c2ccc(F)cc2)c(Cl)c1] | 3-chloro-4-({[5-{1-[4-chloro-3-(methyloxy)phenyl]-1-methylethyl}-1-(4-fluorophenyl)-1H-imidazol-2-yl]thio}methyl)-N-[(propylamino)carbonyl]benzenesulfonamide | A | A |

TABLE 1-continued

| Structure | NAME | cAMP (EC$_{50}$) (nM) | CRE-Luc (EC$_{50}$) (nM) |
|---|---|---|---|
|  | 4-[({5-[1-(3,4-difluorophenyl)-1-methylethyl]-1-(4-fluorophenyl)]-1H-imidazol-2-yl}thio)methyl]-N-(1-methylethyl)piperidine-1-carboxamide |  | C |
|  | 3-chloro-4-({[5-{1-[4-chloro-3-(methyloxy)phenyl]-1-methylethyl}-1-(4-fluorophenyl)-1H-imidazol-2-yl]thio}methyl)-N-[(morpholin-4-ylamino)carbonyl]benzenesulfonamide | A | C |
|  | 3-chloro-4-[({5-[1-(3,4-difluorophenyl)-1-methylethyl]-1-(4-fluorophenyl)-1H-imidazol-2-yl]thio)methyl]benzenesulfonamide | C | C |

TABLE 1-continued

| Structure | NAME | cAMP (EC$_{50}$) (nM) | CRE-Luc (EC$_{50}$) (nM) |
|---|---|---|---|
| 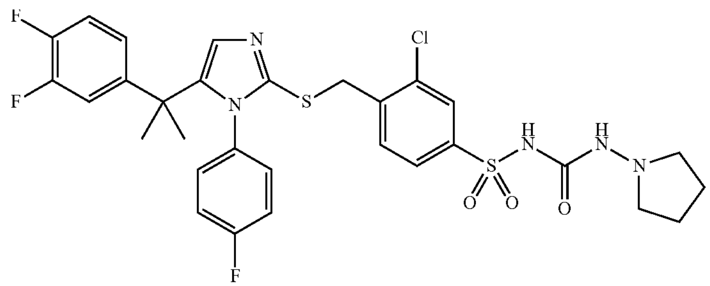 [SMILES: CC(C)(c1ccc(F)c(F)c1)c1cnc(SCc2ccc(S(=O)(=O)NC(=O)NN3CCCC3)cc2Cl)n1-c1ccc(F)cc1] | 3-chloro-4-[({5-[1-(3,4-difluorophenyl)-1-methylethyl]-1-(4-fluorophenyl)-1H-imidazol-2-yl}thio)methyl]-N-[(pyrrolidin-1-ylamino)carbonyl]benzenesulfonamide | D | C |
| 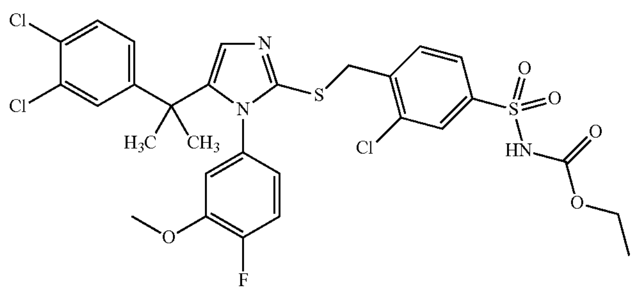 [SMILES: CCOC(=O)NS(=O)(=O)c1ccc(CSc2ncc(C(C)(C)c3ccc(Cl)c(Cl)c3)n2-c2ccc(F)c(OC)c2)c(Cl)c1] | ethyl ({3-chloro-4-[({5-[1-(3,4-dichlorophenyl)-1-methylethyl]-1-[4-fluoro-3-(methyloxy)phenyl]-1H-imidazol-2-yl}thio)methyl]phenyl}sulfonyl)carbamate | C | C |
| 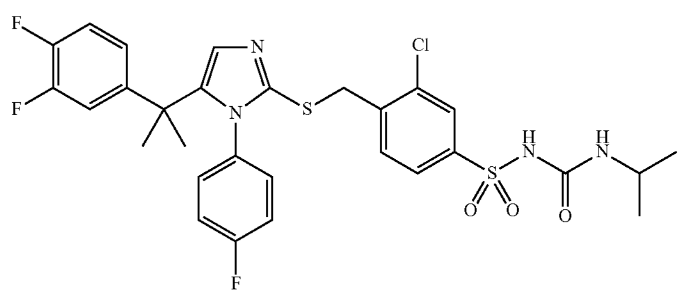 [SMILES: CC(C)NC(=O)NS(=O)(=O)c1ccc(CSc2ncc(C(C)(C)c3ccc(F)c(F)c3)n2-c2ccc(F)cc2)c(Cl)c1] | 3-chloro-4-[({5-[1-(3,4-difluorophenyl)-1-methylethyl]-1-(4-fluorophenyl)-1H-imidazol-2-yl}thio)methyl]-N-{[(1-methylethyl)amino]carbonyl}benzenesulfonamide | C | C |

TABLE 1-continued

| Structure | NAME | cAMP (EC$_{50}$) (nM) | CRE-Luc (EC$_{50}$) (nM) |
|---|---|---|---|
| 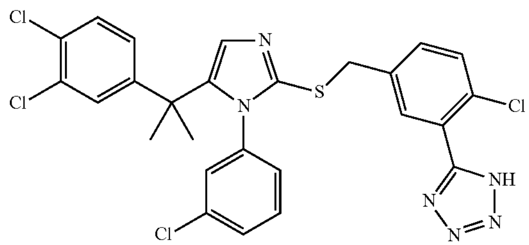 [SMILES: CC(C)(c1ccc(Cl)c(Cl)c1)c1cnc(SCc2ccc(Cl)c(-c3nnn[nH]3)c2)n1-c1cccc(Cl)c1] | 5-{2-chloro-5-[({1-(3-chlorophenyl)-5-[1-(3,4-dichlorophenyl)-1-methylethyl]-1H-imidazol-2-yl}thio)methyl]phenyl}-1H-tetrazole | C | C |
| 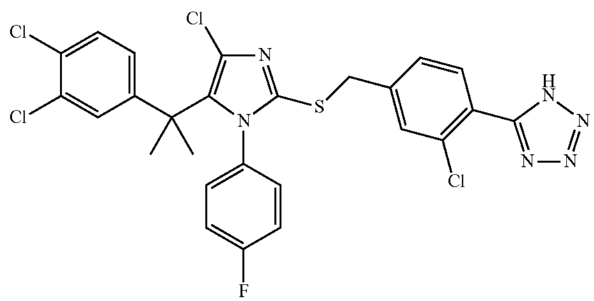 [SMILES: CC(C)(c1ccc(Cl)c(Cl)c1)c1c(Cl)nc(SCc2ccc(-c3nnn[nH]3)c(Cl)c2)n1-c1ccc(F)cc1] | 5-{2-chloro-4-[({4-chloro-5-[1-(3,4-dichlorophenyl)-1-methylethyl]-1-(4-fluorophenyl)-1H-imidazol-2-yl}thio)methyl]phenyl}-1H-tetrazole | D | C |
| 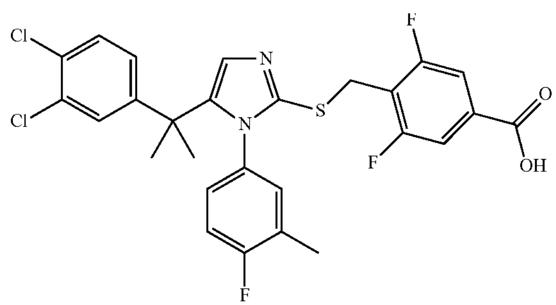 | 4-[({5-[1-(3,4-dichlorophenyl)-1-methylethyl]-1-(4-fluoro-3-methylphenyl)-1H-imidazol-2-yl}thio)methyl]-3,5-difluorobenzoic acid | A | A |

TABLE 1-continued

| Structure | NAME | cAMP (EC$_{50}$) (nM) | CRE-Luc (EC$_{50}$) (nM) |
|---|---|---|---|
| 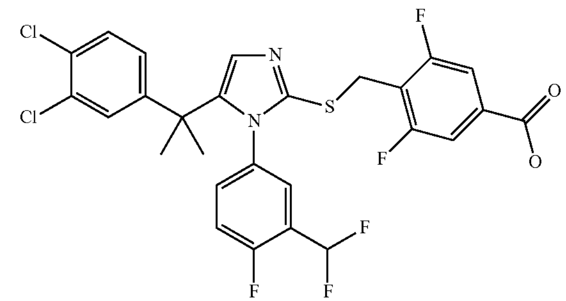 [SMILES: CC(C)(c1ccc(Cl)c(Cl)c1)c1cnc(SCc2c(F)cc(C(=O)O)cc2F)n1-c1ccc(F)c(C(F)F)c1] | 4-[({5-[1-(3,4-dichlorophenyl)-1-methylethyl]-1-[3-(difluoromethyl)-4-fluorophenyl]-1H-imidazol-2-yl}thio)methyl]-3,5-difluorobenzoic acid | C | A |
| 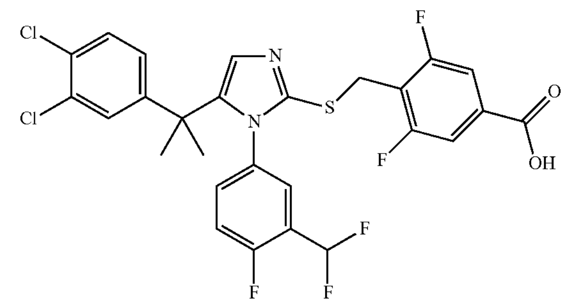 [SMILES: CC(C)(c1ccc(Cl)c(Cl)c1)c1cnc(SCc2c(F)cc(C(=O)O)cc2F)n1-c1ccc(F)c(C(F)F)c1] | 4-[({5-[1-(3,4-dichlorophenyl)-1-methylethyl]-1-[4-fluoro-3-(methyloxy)phenyl]-1H-imidazol-2-yl}thio)methyl]-3,5-difluoro-N-hydroxybenzamide | A | A |
| 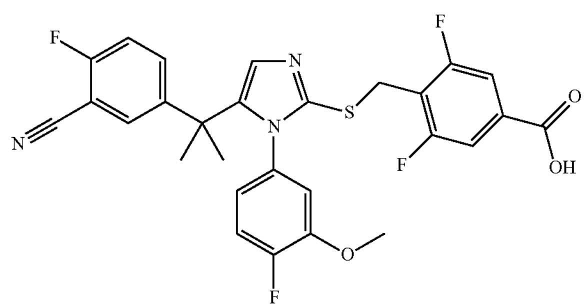 [SMILES: COc1cc(-n2c(C(C)(C)c3ccc(F)c(C#N)c3)cnc2SCc2c(F)cc(C(=O)O)cc2F)ccc1F] | 4-[({5-[1-(3-cyano-4-fluorophenyl)-1-methylethyl]-1-[4-fluoro-3-(methyloxy)phenyl]-1H-imidazol-2-yl}thio)methyl]-3,5-difluorobenzoic acid | A | A |

TABLE 1-continued

| Structure | NAME | cAMP (EC$_{50}$) (nM) | CRE-Luc (EC$_{50}$) (nM) |
|---|---|---|---|
| 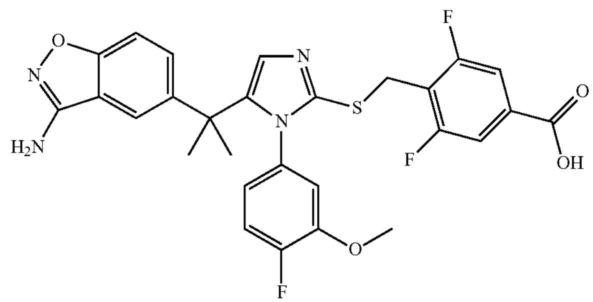 [SMILES: COc1cc(-n2c(C(C)(C)c3ccc4onc(N)c4c3)cnc2SCc2c(F)cc(C(=O)O)cc2F)ccc1F] | 4-[({5-[1-(3-amino-1,2-benzisoxazol-5-yl)-1-methylethyl]-1-[4-fluoro-3-(methyloxy)phenyl]-1H-imidazol-2-yl}thio)methyl]-3,5-difluorobenzoic acid | A | A |
| 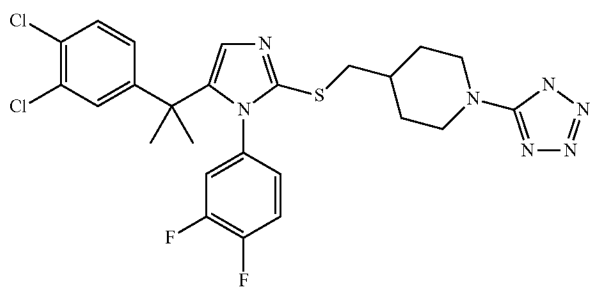 [SMILES: CC(C)(c1ccc(Cl)c(Cl)c1)c1cnc(SCC2CCN(c3nnn[nH]3)CC2)n1-c1ccc(F)c(F)c1] | 4-[({5-[1-(3,4-dichlorophenyl)-1-methylethyl]-1-(3,4-difluorophenyl)-1H-imidazol-2-yl}thio)methyl]-1-(1H-tetrazol-5-yl)piperidine | | A |
| 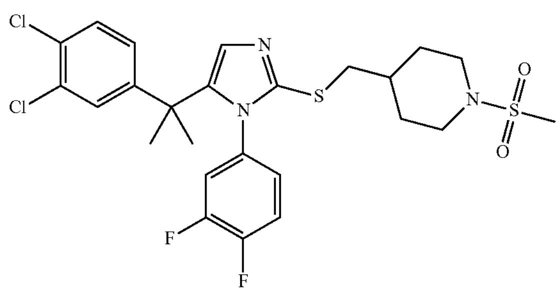 [SMILES: CC(C)(c1ccc(Cl)c(Cl)c1)c1cnc(SCC2CCN(S(C)(=O)=O)CC2)n1-c1ccc(F)c(F)c1] | 4-[({5-[1-(3,4-dichlorophenyl)-1-methylethyl]-1-(3,4-difluorophenyl)-1H-imidazol-2-yl}thio)methyl]-1-(methylsulfonyl)piperidine | | A |

TABLE 1-continued

| Structure | NAME | cAMP (EC$_{50}$) (nM) | CRE-Luc (EC$_{50}$) (nM) |
|---|---|---|---|
| 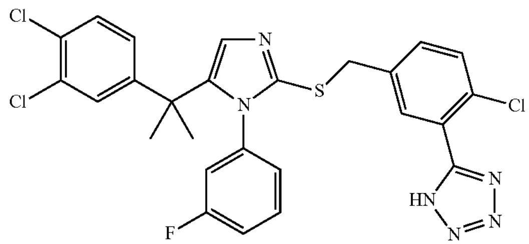 [SMILES: CC(C)(c1ccc(Cl)c(Cl)c1)c1cnc(SCc2ccc(Cl)c(-c3nnn[nH]3)c2)n1-c1cccc(F)c1] | 5-{2-chloro-5-[({5-[1-(3,4-dichlorophenyl)-1-methylethyl]-1-(3-fluorophenyl)-1H-imidazol-2-yl}thio)methyl]phenyl}-1H-tetrazole | | C |
| 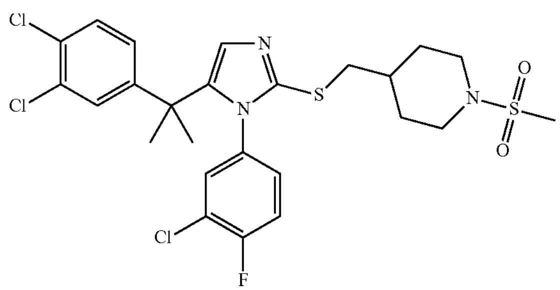 [SMILES: CC(C)(c1ccc(Cl)c(Cl)c1)c1cnc(SCC2CCN(S(C)(=O)=O)CC2)n1-c1ccc(F)c(Cl)c1] | 4-[({1-(3-chloro-4-fluorophenyl)-5-[1-(3,4-dichlorophenyl)-1-methylethyl]-1H-imidazol-2-yl}thio)methyl]-1-(methylsulfonyl)piperidine | C | A |
| | ethyl [(4-({[5-[1-[4-chloro-3-(methyloxy)phenyl]-1-methylethyl]-1-(4-fluorophenyl)-1H-imidazol-2-yl]thio}methyl)-3-fluorophenyl]sulfonyl]carbamate | A | A |

TABLE 1-continued

| Structure | NAME | cAMP (EC$_{50}$) (nM) | CRE-Luc (EC$_{50}$) (nM) |
|---|---|---|---|
| 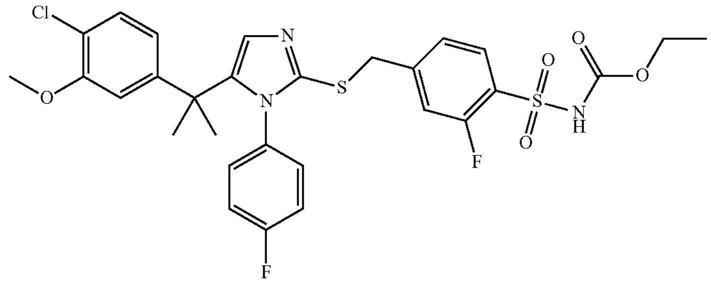 [SMILES: CCOC(=O)NS(=O)(=O)c1ccc(CSc2ncc(C(C)(C)c3ccc(Cl)c(OC)c3)n2-c2ccc(F)cc2)cc1F] | ethyl {[4-({[5-{1-[4-chloro-3-(methyloxy)phenyl]-1-methylethyl}-1-(4-fluorophenyl)-1H-imidazol-2-yl]thio}methyl)-2-fluorophenyl]sulfonyl}carbamate | A | A |
| 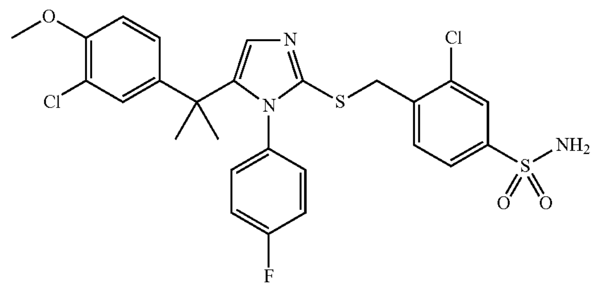 [SMILES: COc1ccc(C(C)(C)c2cnc(SCc3ccc(S(N)(=O)=O)cc3Cl)n2-c2ccc(F)cc2)cc1Cl] | 3-chloro-4-({[5-{1-[3-chloro-4-(methyloxy)phenyl]-1-methylethyl}-1-(4-fluorophenyl)-1H-imidazol-2-yl]thio}methyl)benzenesulfonamide | A | A |
| 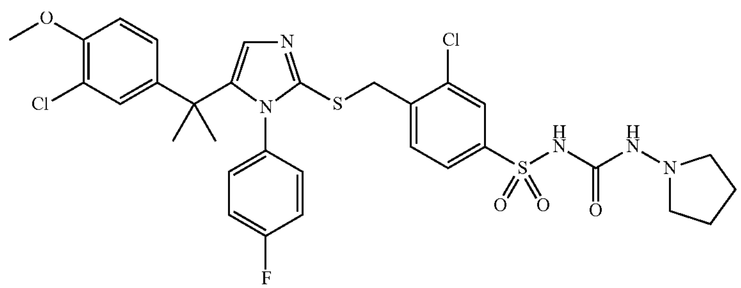 [SMILES: COc1ccc(C(C)(C)c2cnc(SCc3ccc(S(=O)(=O)NC(=O)NN4CCCC4)cc3Cl)n2-c2ccc(F)cc2)cc1Cl] | 3-chloro-4-({[5-{1-[3-chloro-4-(methyloxy)phenyl]-1-methylethyl}-1-(4-fluorophenyl)-1H-imidazol-2-yl]thio}methyl)-N-[(pyrrolidin-1-ylamino)carbonyl]benzenesulfonamide | C | C |

TABLE 1-continued

| Structure | NAME | cAMP (EC$_{50}$) (nM) | CRE-Luc (EC$_{50}$) (nM) |
|---|---|---|---|
| | ethyl {[3-chloro-4-({[5-[1-[3-chloro-4-(methyloxy)phenyl]-1-methylethyl]-1-(4-fluorophenyl)-1H-imidazol-2-yl]thio}methyl)phenyl]sulfonyl}carbamate | A | A |
| | 3-chloro-4-(2-{5-[1-(3,4-dichlorophenyl)-1-methylethyl]-1-(4-fluorophenyl)-1H-imidazol-2-yl}ethyl)benzenesulfonamide | D | C |
| | 4-[({1-[1-(3-chloro-4-fluorophenyl)-5-[1-(3,4-dichlorophenyl)-1-methylethyl]-1H-imidazol-2-yl]thio}methyl]-1-(1H-tetrazol-5-yl)piperidine | C | A |

TABLE 1-continued

| Structure | NAME | cAMP (EC$_{50}$) (nM) | CRE-Luc (EC$_{50}$) (nM) |
|---|---|---|---|
|  | 3-chloro-4-{[(5-[1-(3,4-dichlorophenyl)-1-methylethyl]-1-[4-fluoro-3-(methyloxy)phenyl]-1H-imidazol-2-yl]thio)methyl]-N-[(pyrrolidin-1-ylamino)carbonyl]benzenesulfonamide | D | C |
|  | 4-{[5-{1-[4-(aminosulfonyl)-3-chlorophenyl]-1-methylethyl}-1-(4-fluorophenyl)-1H-imidazol-2-yl]thio}methyl)-3-chloro-N-[(pyrrolidin-1-ylamino)carbonyl]benzenesulfonamide | C | C |
|  | 3-chloro-4-{[5-{1-[3-chloro-4-(methyloxy)phenyl]-1-methylethyl}-1-(4-fluorophenyl)-1H-imidazol-2-yl]thio}methyl)-N-{[(1-methylethyl)amino]carbonyl}benzenesulfonamide | C | C |

TABLE 1-continued

| Structure | NAME | cAMP (EC$_{50}$) (nM) | CRE-Luc (EC$_{50}$) (nM) |
|---|---|---|---|
| 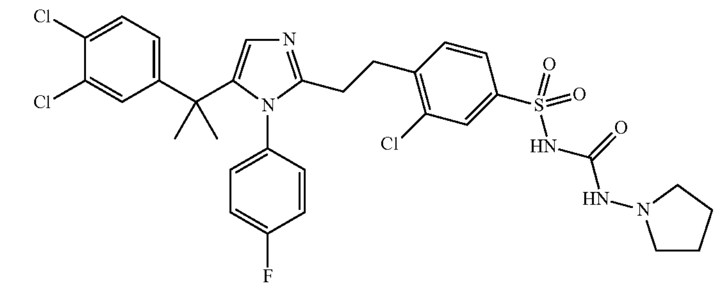 [SMILES: CC(C)(c1ccc(Cl)c(Cl)c1)c1cnc(CCc2ccc(S(=O)(=O)NC(=O)NN3CCCC3)cc2Cl)n1-c1ccc(F)cc1] | 3-chloro-4-(2-{5-[1-(3,4-dichlorophenyl)-1-methylethyl]-1-(4-fluorophenyl)-1H-imidazol-2-yl}ethyl)-N-[(pyrrolidin-1-ylamino)carbonyl]benzenesulfonamide | | D |
| 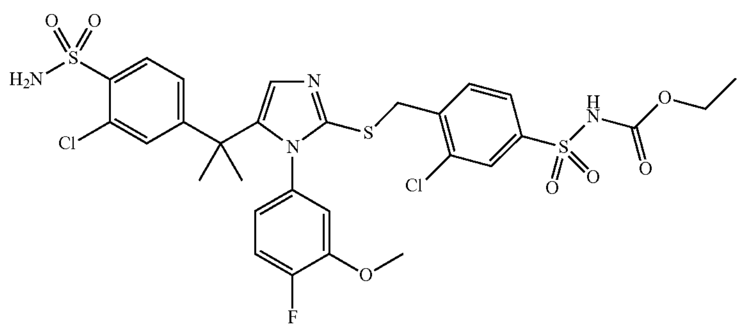 [SMILES: CCOC(=O)NS(=O)(=O)c1ccc(CSc2ncc(C(C)(C)c3ccc(S(N)(=O)=O)c(Cl)c3)n2-c2ccc(F)c(OC)c2)c(Cl)c1] | ethyl [(4-{[(5-{1-[4-(aminosulfonyl)-3-chlorophenyl]-1-methylethyl}-1-[4-fluoro-3-(methyloxy)phenyl]-1H-imidazol-2-yl)thio]methyl}-3-chlorophenyl)sulfonyl]carbamate | A | A |
| 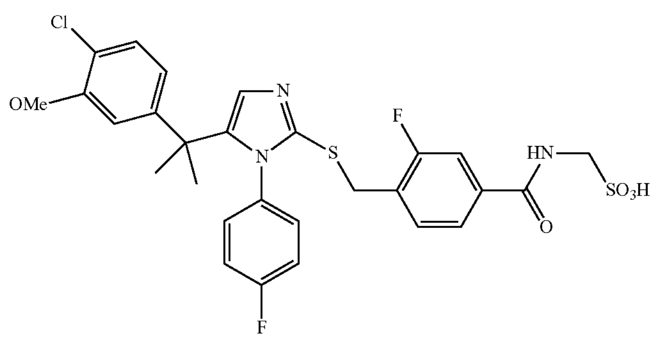 [SMILES: COc1cc(C(C)(C)c2cnc(SCc3ccc(C(=O)NCS(=O)(=O)O)cc3F)n2-c2ccc(F)cc2)ccc1Cl] | ({[4-({[5-{1-[4-chloro-3-(methyloxy)phenyl]-1-methylethyl}-1-(4-fluorophenyl)-1H-imidazol-2-yl]thio}methyl)-3-fluorophenyl]carbonyl}amino)methanesulfonic acid | A | A |

TABLE 1-continued

| Structure | NAME | cAMP (EC$_{50}$) (nM) | CRE-Luc (EC$_{50}$) (nM) |
|---|---|---|---|
| 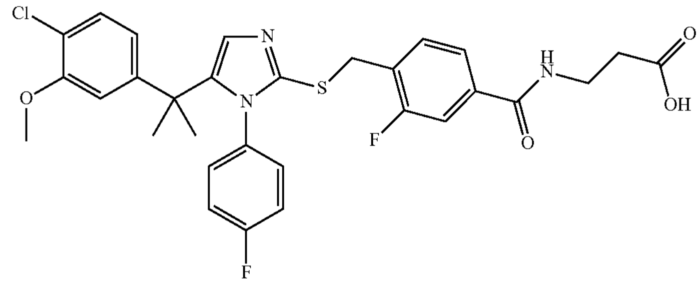 [SMILES: COc1cc(C(C)(C)c2cnc(SCc3ccc(C(=O)NCCC(=O)O)cc3F)n2-c2ccc(F)cc2)ccc1Cl] | N-{[4-({[5-{1-[4-chloro-3-(methyloxy)phenyl]-1-methylethyl}-1-(4-fluorophenyl)-1H-imidazol-2-yl]thio}methyl)-3-fluorophenyl]carbonyl}-beta-alanine | A | A |
| 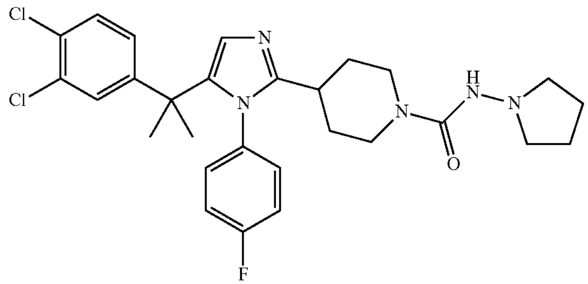 [SMILES: CC(C)(c1ccc(Cl)c(Cl)c1)c1cnc(C2CCN(C(=O)NN3CCCC3)CC2)n1-c1ccc(F)cc1] | 4-{5-[1-(3,4-dichlorophenyl)-1-methylethyl]-1-(4-fluorophenyl)-1H-imidazol-2-yl}-N-pyrrolidin-1-ylpiperidine-1-carboxamide | | D |
| 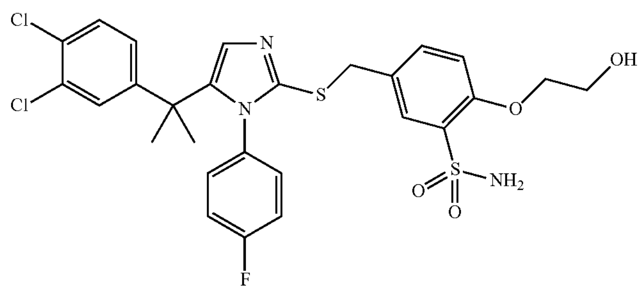 [SMILES: CC(C)(c1ccc(Cl)c(Cl)c1)c1cnc(SCc2ccc(OCCO)c(S(N)(=O)=O)c2)n1-c1ccc(F)cc1] | 5-[({5-[1-(3,4-dichlorophenyl)-1-methylethyl]-1-(4-fluorophenyl)-1H-imidazol-2-yl}thio)methyl]-2-[(2-hydroxyethyl)oxy]benzenesulfonamide | C | A |

TABLE 1-continued

| Structure | NAME | cAMP (EC$_{50}$) (nM) | CRE-Luc (EC$_{50}$) (nM) |
|---|---|---|---|
| 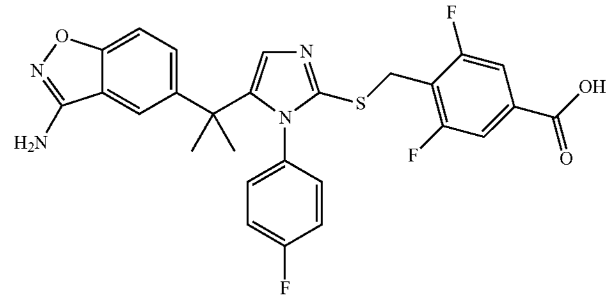 [SMILES: CC(C)(c1ccc2onc(N)c2c1)c1cnc(SCc2c(F)cc(C(=O)O)cc2F)n1-c1ccc(F)cc1] | 4-[({5-[1-(3-amino-1,2-benzisoxazol-5-yl)-1-methylethyl]-1-(4-fluorophenyl)-1H-imidazol-2-yl}thio)methyl]-3,5-difluorobenzoic acid | A | A |
| | 4-[[(5-{1-[4-(aminosulfonyl)-3-chlorophenyl]-1-methylethyl}-1-[4-fluoro-3-(methyloxy)phenyl]-1H-imidazol-2-yl)thio]methyl]-3,5-difluorobenzoic acid | A | A |
| 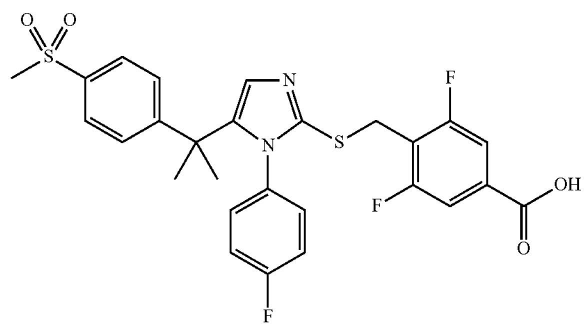 [SMILES: CC(C)(c1ccc(S(C)(=O)=O)cc1)c1cnc(SCc2c(F)cc(C(=O)O)cc2F)n1-c1ccc(F)cc1] | 3,5-difluoro-4-({[1-(4-fluorophenyl)-5-{1-methyl-1-[4-(methylsulfonyl)phenyl]ethyl}-1H-imidazol-2-yl]thio}methyl)benzoic acid | A | A |

TABLE 1-continued

| Structure | NAME | cAMP (EC$_{50}$) (nM) | CRE-Luc (EC$_{50}$) (nM) |
|---|---|---|---|
| 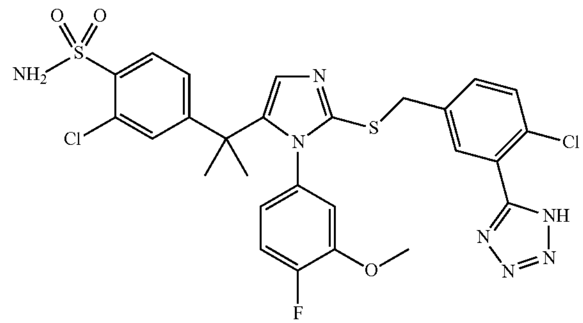 [SMILES: COc1cc(-n2c(C(C)(C)c3ccc(S(N)(=O)=O)c(Cl)c3)cnc2SCc2ccc(Cl)c(-c3nnn[nH]3)c2)ccc1F] | 2-chloro-4-(1-{2-({[4-chloro-3-(1H-tetrazol-5-yl)phenyl]methyl}thio)-1-[4-fluoro-3-(methyloxy)phenyl]-1H-imidazol-5-yl}-1-methylethyl)benzenesulfonamide | C | C |
| 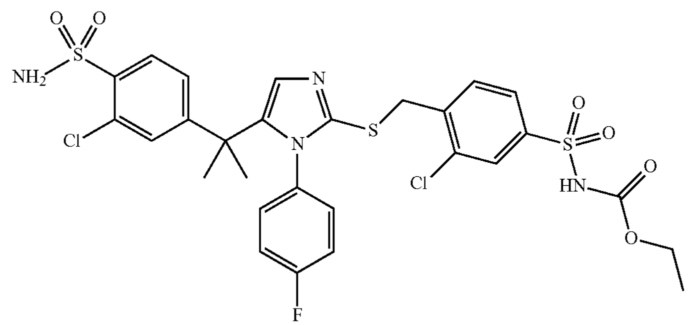 [SMILES: CCOC(=O)NS(=O)(=O)c1ccc(CSc2ncc(C(C)(C)c3ccc(S(N)(=O)=O)c(Cl)c3)n2-c2ccc(F)cc2)c(Cl)c1] | ethyl {[4-({[5-{1-[4-(aminosulfonyl)-3-chlorophenyl]-1-methylethyl}-1-(4-fluorophenyl)-1H-imidazol-2-yl]thio}methyl)-3-chlorophenyl]sulfonyl}carbamate | A | C |
| 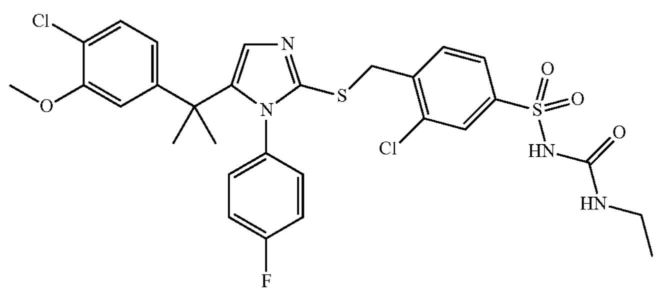 [SMILES: CCNC(=O)NS(=O)(=O)c1ccc(CSc2ncc(C(C)(C)c3ccc(Cl)c(OC)c3)n2-c2ccc(F)cc2)c(Cl)c1] | 3-chloro-4-({[5-{1-[4-chloro-3-(methyloxy)phenyl]-1-methylethyl}-1-(4-fluorophenyl)-1H-imidazol-2-yl]thio}methyl)-N-[(ethylamino)carbonyl]benzenesulfonamide | A | C |

TABLE 1-continued

| Structure | NAME | cAMP (EC$_{50}$) (nM) | CRE-Luc (EC$_{50}$) (nM) |
|---|---|---|---|
| 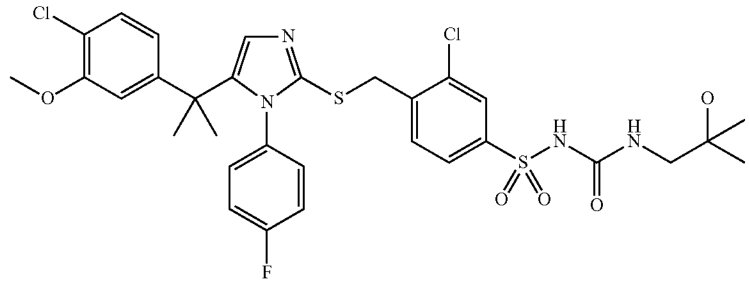 [SMILES: COc1cc(C(C)(C)c2cnc(SCc3ccc(S(=O)(=O)NC(=O)NCC(C)(C)O)cc3Cl)n2-c2ccc(F)cc2)ccc1Cl] | 3-chloro-4-({[5-{1-[4-chloro-3-(methyloxy)phenyl]-1-methylethyl}-1-(4-fluorophenyl)-1H-imidazol-2-yl]thio}methyl)-N-{[(2-hydroxy-2-methylpropyl)amino]carbonyl}benzenesulfonamide | C | C |
| 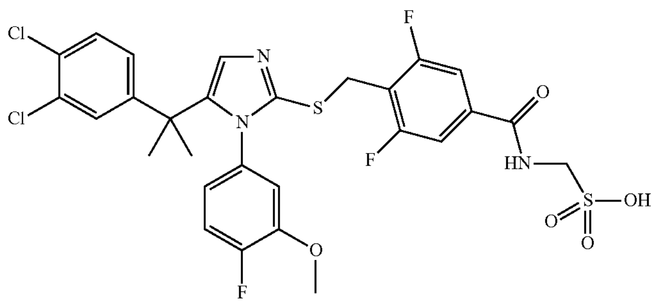 [SMILES: COc1cc(-n2c(C(C)(C)c3ccc(Cl)c(Cl)c3)cnc2SCc2c(F)cc(C(=O)NCS(=O)(=O)O)cc2F)ccc1F] | [({4-[({5-[1-(3,4-dichlorophenyl)-1-methylethyl]-1-[4-fluoro-3-(methyloxy)phenyl]-1H-imidazol-2-yl}thio)methyl]-3,5-difluorophenyl}carbonyl)amino]methanesulfonic acid | A | A |
| | 4-({[5-{1-[4-chloro-3-(methyloxy)phenyl]-1-methylethyl}-1-(4-fluorophenyl)-1H-imidazol-2-yl]thio}methyl)-3-fluoro-N-{(pyrrolidin-1-ylamino)carbonyl]benzenesulfonamide | C | A |

TABLE 1-continued

| Structure | NAME | cAMP (EC$_{50}$) (nM) | CRE-Luc (EC$_{50}$) (nM) |
|---|---|---|---|
| 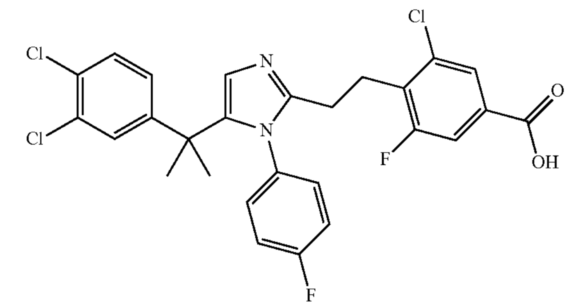 [SMILES: CC(C)(c1ccc(Cl)c(Cl)c1)c1cnc(CCc2c(F)cc(C(=O)O)cc2Cl)n1-c1ccc(F)cc1] | 3-chloro-4-(2-{5-[1-(3,4-dichlorophenyl)-1-methylethyl]-1-(4-fluorophenyl)-1H-imidazol-2-yl}ethyl)-5-fluorobenzoic acid | | C |
| 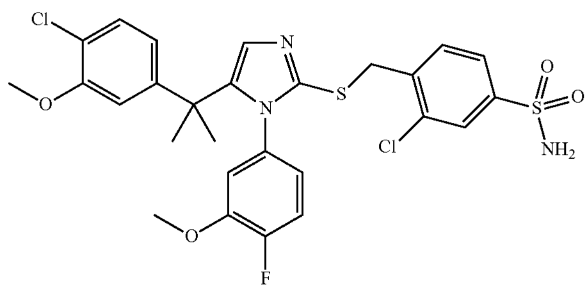 [SMILES: COc1cc(-n2c(C(C)(C)c3ccc(Cl)c(OC)c3)cnc2SCc2ccc(S(N)(=O)=O)cc2Cl)ccc1F] | 3-chloro-4-{[(5-{1-[4-chloro-3-(methyloxy)phenyl]-1-methylethyl}-1-[4-fluoro-3-(methyloxy)phenyl]-1H-imidazol-2-yl)thio]methyl}benzenesulfonamide | A | A |
| | N-{[3-chloro-4-({[5-{1-[4-chloro-3-(methyloxy)phenyl]-1-methylethyl}-1-(4-fluorophenyl)-1H-imidazol-2-yl][thio]methyl)phenyl]sulfonyl}pyrrolidine-1-carboxamide | | C |

TABLE 1-continued

| Structure | NAME | cAMP (EC$_{50}$) (nM) | CRE-Luc (EC$_{50}$) (nM) |
|---|---|---|---|
| 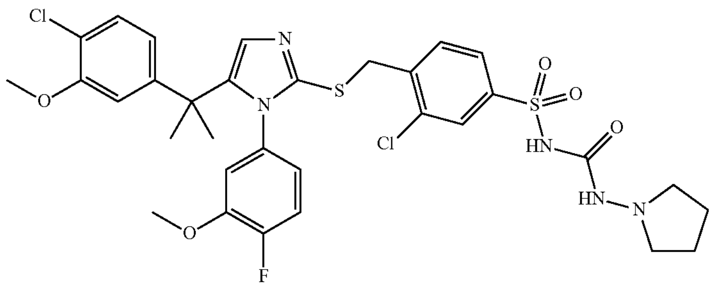 [SMILES: COc1cc(-n2c(C(C)(C)c3ccc(Cl)c(OC)c3)cnc2SCc2ccc(S(=O)(=O)NC(=O)NN3CCCC3)cc2Cl)ccc1F] | 3-chloro-4-{[(5-{1-[4-chloro-3-(methyloxy)phenyl]-1-methylethyl}-1-[4-fluoro-3-(methyloxy)phenyl]-1H-imidazol-2-yl)thio]methyl}-N-[(pyrrolidin-1-ylamino)carbonyl]benzenesulfonamide | A | A |
| 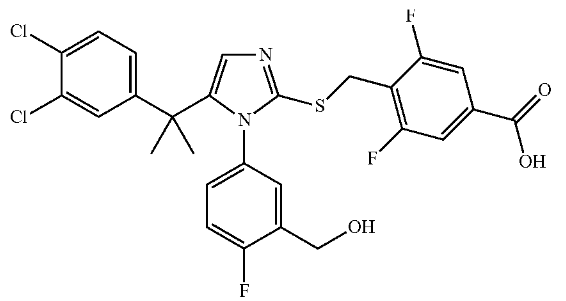 [SMILES: CC(C)(c1ccc(Cl)c(Cl)c1)c1cnc(SCc2c(F)cc(C(=O)O)cc2F)n1-c1ccc(F)c(CO)c1] | 4-[({5-[1-(3,4-dichlorophenyl)-1-methylethyl]-1-[4-fluoro-3-(hydroxymethyl)phenyl]-1H-imidazol-2-yl}thio)methyl]-3,5-difluorobenzoic acid |  | C |
| 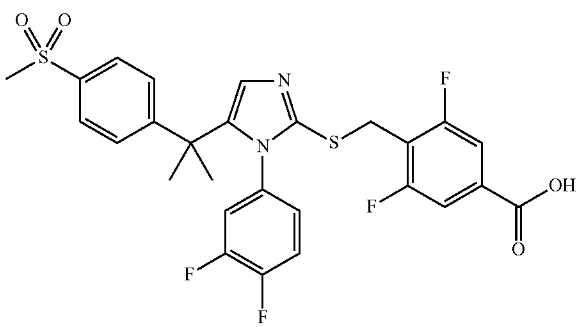 [SMILES: CC(C)(c1ccc(S(C)(=O)=O)cc1)c1cnc(SCc2c(F)cc(C(=O)O)cc2F)n1-c1ccc(F)c(F)c1] | 4-({[1-(3,4-difluorophenyl)-5-{1-methyl-1-[4-(methylsulfonyl)phenyl]ethyl}-1H-imidazol-2-yl]thio}methyl)-3,5-difluorobenzoic acid |  | D |

TABLE 1-continued

| Structure | NAME | cAMP (EC$_{50}$) (nM) | CRE-Luc (EC$_{50}$) (nM) |
|---|---|---|---|
| 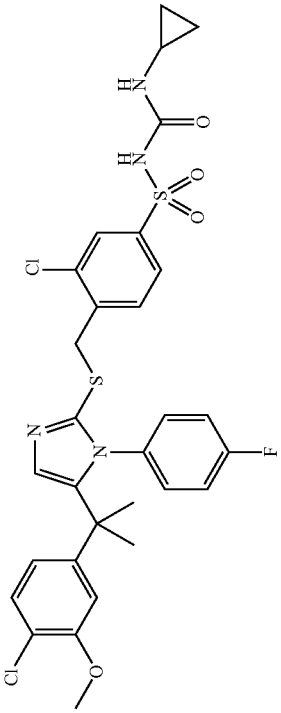 | 3-chloro-4-({[5-{1-[4-chloro-3-(methyloxy)phenyl]-1-methylethyl}-1-(4-fluorophenyl)-1H-imidazol-2-yl]thio}methyl)-N-[(cyclopropylamino)carbonyl]benzenesulfonamide | A | A |
| 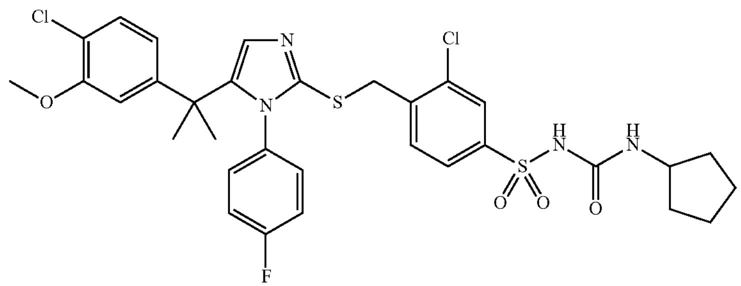 [SMILES: COc1cc(C(C)(C)c2cnc(SCc3ccc(S(=O)(=O)NC(=O)NC4CCCC4)cc3Cl)n2-c2ccc(F)cc2)ccc1Cl] | 3-chloro-4-({[5-{1-[4-chloro-3-(methyloxy)phenyl]-1-methylethyl}-1-(4-fluorophenyl)-1H-imidazol-2-yl]thio}methyl)-N-[(cyclopentylamino)carbonyl]benzenesulfonamide | A | A |
| 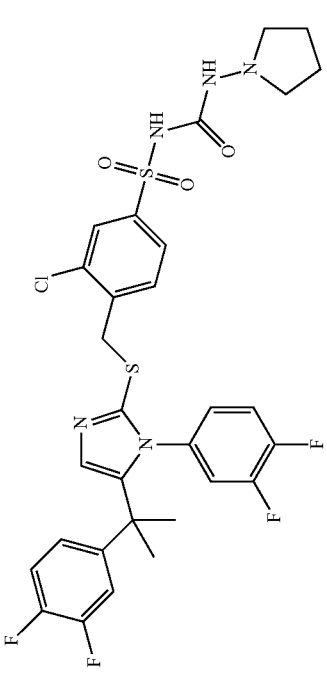 | 3-chloro-4-[({1-[1-(3,4-difluorophenyl)-1-methylethyl]-1H-imidazol-2-yl}thio)methyl]-N-[(pyrrolidin-1-ylamino)carbonyl]benzenesulfonamide | D | C |

TABLE 1-continued

| Structure | NAME | cAMP (EC$_{50}$) (nM) | CRE-Luc (EC$_{50}$) (nM) |
|---|---|---|---|
| 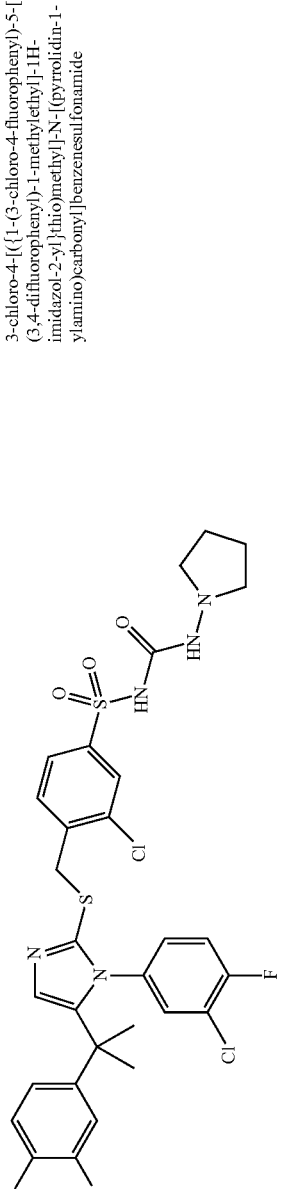 | 3-chloro-4-[({1-[(3-chloro-4-fluorophenyl)-5-[1-(3,4-difluorophenyl)-1-methylethyl]-1H-imidazol-2-yl}thio)methyl]-N-[(pyrrolidin-1-ylamino)carbonyl]benzenesulfonamide | D | C |
| 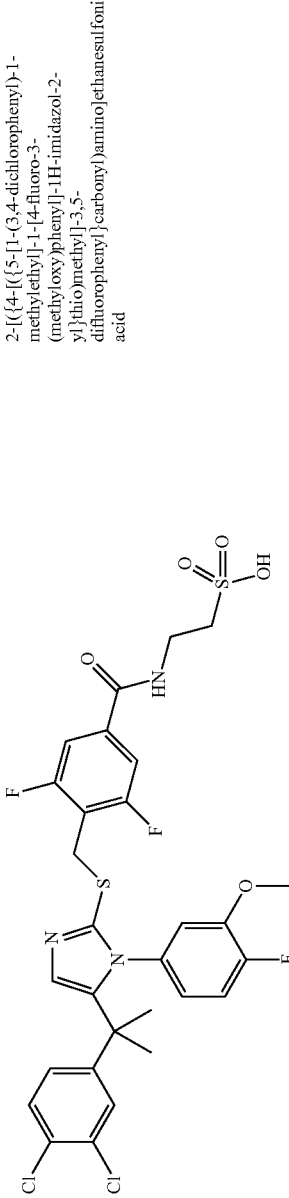 | 3-chloro-4-[({5-[1-(3,4-dichlorophenyl)-1-methylethyl]-1-[4-fluoro-3-(methyloxy)phenyl]-1H-imidazol-2-yl}thio)methyl]-N-[(morpholin-4-ylamino)carbonyl]benzenesulfonamide | C | C |
| 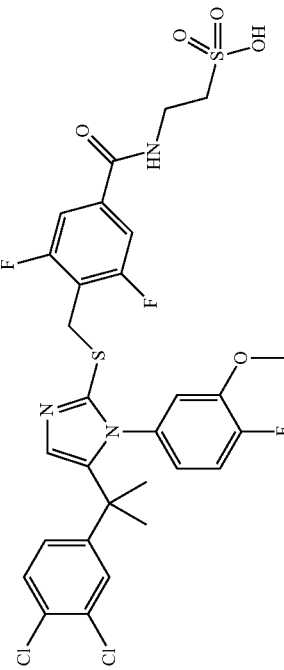 | 2-[({4-[({5-[1-(3,4-dichlorophenyl)-1-methylethyl]-1-[4-fluoro-3-(methyloxy)phenyl]-1H-imidazol-2-yl}thio)methyl]-3,5-difluorophenyl}carbonyl)amino]ethanesulfonic acid | A | A |

TABLE 1-continued

| Structure | NAME | cAMP (EC$_{50}$) (nM) | CRE-Luc (EC$_{50}$) (nM) |
|---|---|---|---|
| 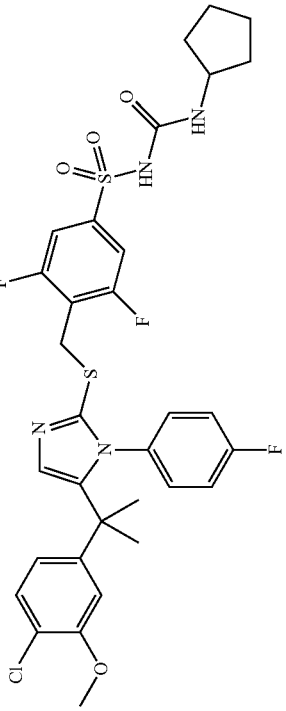 | 4-{[5-{1-[4-chloro-3-(methyloxy)phenyl]-1-methylethyl}-1-(4-fluorophenyl)-1H-imidazol-2-yl]thio}methyl)-3,5-difluoro-N-[(pyrrolidin-1-ylamino)carbonyl]benzenesulfonamide | A | A |
| 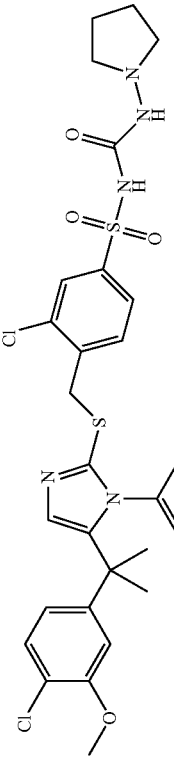 | 3-chloro-4-({[1-(3-chloro-4-fluorophenyl)-5-{1-[4-chloro-3-(methyloxy)phenyl]-1-methylethyl}-1H-imidazol-2-yl]thio}methyl)-N-[(pyrrolidine-1-ylamino)carbonyl]benzenesulfonamide | C | A |
| 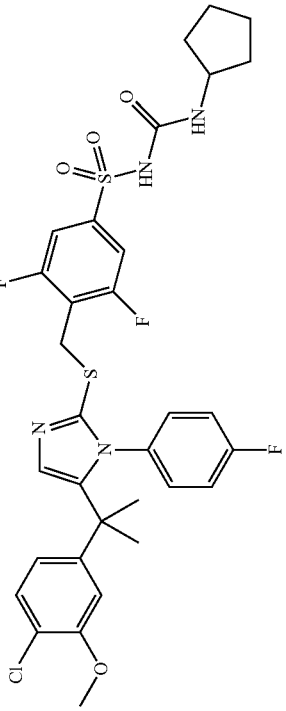 | 3-chloro-4-({[5-{1-[4-chloro-3-(methyloxy)phenyl]-1-methylethyl}-1-(3,4-difluorophenyl)-1H-imidazol-2-yl]thio}methyl)-N-[(pyrrolidin-1-ylamino)carbonyl]benzenesulfonamide | C | C |

TABLE 1-continued

| Structure | NAME | cAMP (EC$_{50}$) (nM) | CRE-Luc (EC$_{50}$) (nM) |
|---|---|---|---|
| 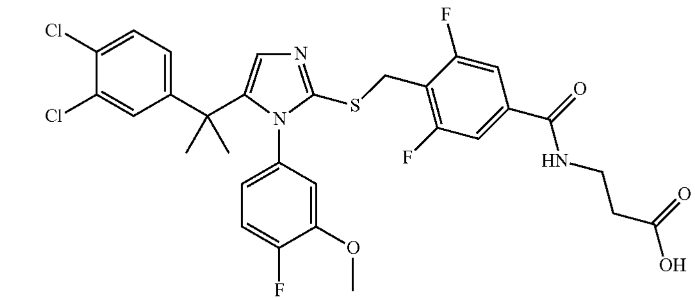 [SMILES: COc1cc(-n2c(C(C)(C)c3ccc(Cl)c(Cl)c3)cnc2SCc2c(F)cc(C(=O)NCCC(=O)O)cc2F)ccc1F] | N-({4-[({5-[1-(3,4-dichlorophenyl)-1-methylethyl]-1-[4-fluoro-3-(methyloxy)phenyl]-1H-imidazol-2-yl}thio)methyl]-3,5-difluorophenyl}carbonyl)-beta-alanine | A | A |
| | N-[({3-chloro-4-({[5-{1-[4-chloro-3-(methyloxy)phenyl]-1-methylethyl}-1-(4-fluorophenyl)-1H-imidazol-2-yl]thio}methyl)phenyl]sulfonyl}amino)carbonyl]-beta-alanine | | C |
| 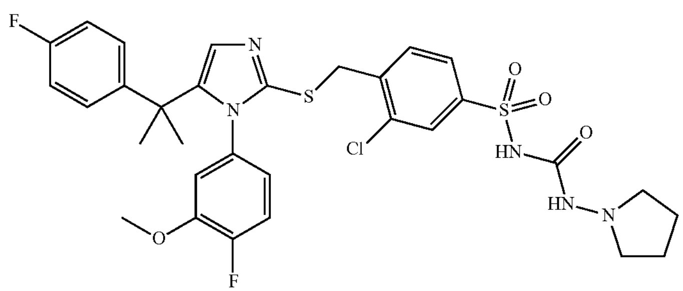 [SMILES: COc1cc(-n2c(C(C)(C)c3ccc(F)cc3)cnc2SCc2ccc(S(=O)(=O)NC(=O)NN3CCCC3)cc2Cl)ccc1F] | 3-chloro-4-[({1-[4-fluoro-3-(methyloxy)phenyl]-5-[1-(4-fluorophenyl)-1-methylethyl]-1H-imidazol-2-yl}thio)methyl]-N-[(pyrrolidin-1-ylamino)carbonyl]benzenesulfonamide | C | |

TABLE 1-continued

| Structure | NAME | cAMP (EC$_{50}$) (nM) | CRE-Luc (EC$_{50}$) (nM) |
|---|---|---|---|
| | 4-(1-{2-({[4-(aminosulfonyl)-2-chlorophenyl]methyl}thio)-1-[4-fluoro-3-(methyloxy)phenyl]-1H-imidazol-5-yl}-1-methylethyl)-2-chlorobenzenesulfonamide | A | A |
| | 4-{[(5-{1-[4-(aminosulfonyl)-3-chlorophenyl]-1-methylethyl}-1-[4-fluoro-3-(methyloxy)phenyl]-1H-imidazol-2-yl]thio]methyl}-3-chloro-N-[(morpholin-4-ylamino)carbonyl]benzenesulfonamide | A | C |
| | 4-{[5-{1-[4-(aminosulfonyl)-3-chlorophenyl]-1-methylethyl}-1-(3,4-difluorophenyl)-1H-imidazol-2-yl]thio]methyl}-3-chloro-N-[(morpholin-4-ylamino)carbonyl]benzenesulfonamide | C | C |

TABLE 1-continued

| Structure | NAME | cAMP (EC$_{50}$) (nM) | CRE-Luc (EC$_{50}$) (nM) |
|---|---|---|---|
| 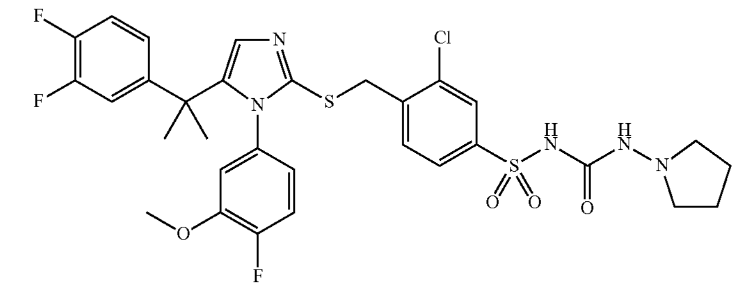 [SMILES: COc1cc(-n2c(C(C)(C)c3ccc(F)c(F)c3)cnc2SCc2ccc(S(=O)(=O)NC(=O)NN3CCCC3)cc2Cl)ccc1F] | 3-chloro-4-[({5-[1-(3,4-difluorophenyl)-1-methylethyl]-1-[4-fluoro-3-(methyloxy)phenyl]-1H-imidazol-2-yl}thio)methyl]-N-[(pyrrolidin-1-ylamino)carbonyl]benzenesulfonamide | C | C |
| 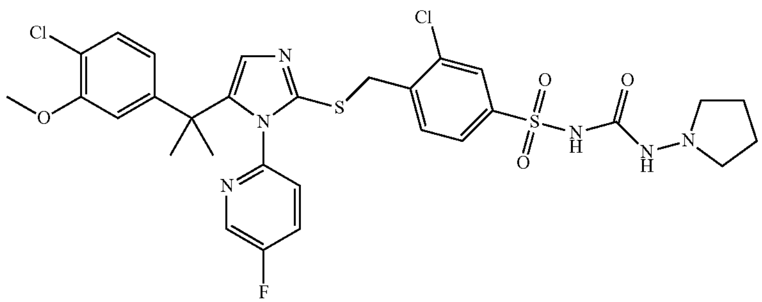 [SMILES: COc1cc(C(C)(C)c2cnc(SCc3ccc(S(=O)(=O)NC(=O)NN4CCCC4)cc3Cl)n2-c2ccc(F)cn2)ccc1Cl] | 3-chloro-4-({[5-{1-[4-chloro-3-(methyloxy)phenyl]-1-methylethyl}-1-(5-fluoropyridin-2-yl)-1H-imidazol-2-yl]thio}methyl)-N-[(pyrrolidin-1-ylamino)carbonyl]benzenesulfonamide | C | C |
| 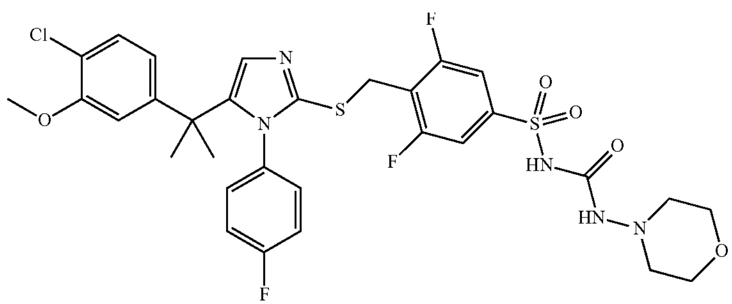 [SMILES: COc1cc(C(C)(C)c2cnc(SCc3c(F)cc(S(=O)(=O)NC(=O)NN4CCOCC4)cc3F)n2-c2ccc(F)cc2)ccc1Cl] | 4-({[5-{1-[4-chloro-3-(methyloxy)phenyl]-1-methylethyl}-1-(4-fluorophenyl)-1H-imidazol-2-yl]thio}methyl)-3,5-difluoro-N-[(morpholin-4-ylamino)carbonyl]benzenesulfonamide | A | A |

TABLE 1-continued

| Structure | NAME | cAMP (EC$_{50}$) (nM) | CRE-Luc (EC$_{50}$) (nM) |
|---|---|---|---|
| | 3-chloro-4-[({5-[1-(3,4-dichlorophenyl)-1-methylethyl]-1-(5-fluoropyridin-2-yl)-1H-imidazol-2-yl]thio}methyl)-N-[(pyrrolidin-1-ylamino)carbonyl]benzenesulfonamide | C | C |
| 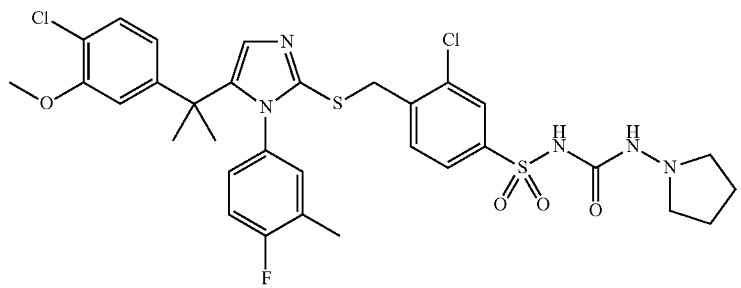 [SMILES: COc1cc(C(C)(C)c2cnc(SCc3ccc(S(=O)(=O)NC(=O)NN4CCCC4)cc3Cl)n2-c2ccc(F)c(C)c2)ccc1Cl] | 3-chloro-4-({[5-{1-[4-chloro-3-(methyloxy)phenyl]-1-methylethyl}-1-(4-fluoro-3-methylphenyl)-1H-imidazol-2-yl]thio}methyl)-N-[(pyrrolidin-1-ylamino)carbonyl]benzenesulfonamide | C | A |
| 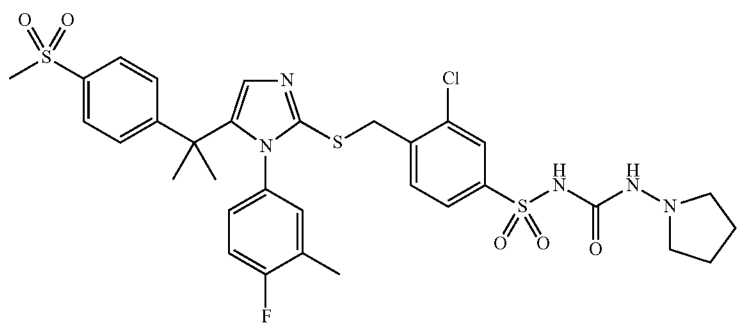 [SMILES: Cc1cc(-n2c(C(C)(C)c3ccc(S(C)(=O)=O)cc3)cnc2SCc2ccc(S(=O)(=O)NC(=O)NN3CCCC3)cc2Cl)ccc1F] | 3-chloro-4-({[1-(4-fluoro-3-methylphenyl)-5-{1-methyl-1-[4-(methylsulfonyl)phenyl]ethyl}-1H-imidazol-2-yl]thio}methyl)-N-[(pyrrolidin-1-ylamino)carbonyl]benzenesulfonamide | D | |

TABLE 1-continued

| Structure | NAME | cAMP (EC$_{50}$) (nM) | CRE-Luc (EC$_{50}$) (nM) |
|---|---|---|---|
| | 3-chloro-4-{[(1-[4-fluoro-3-(methyloxy)phenyl]-5-{1-methyl-1-[4-(methylsulfonyl)phenyl]ethyl]-1H-imidazol-2-yl}thio]methyl}-N-[(pyrrolidin-1-ylamino)carbonyl]benzenesulfonamide | D | C |
| | 3-chloro-4-{[1-(5-fluoropyridin-2-yl)-5-{1-methyl-1-[4-(methylsulfonyl)phenyl]ethyl}-1H-imidazol-2-yl]thio}methyl)-N-[(pyrrolidin-1-ylamino)carbonyl]benzenesulfonamide | | D |
| | 3-chloro-4-{[5-{1-[4-chloro-3-(methyloxy)phenyl]-1-methylethyl}-1H-imidazol-2-yl]thio]methyl)-N-[(pyrrolidin-1-ylamino)carbonyl]benzenesulfonamide | C | C |

TABLE 1-continued

| Structure | NAME | cAMP (EC$_{50}$) (nM) | CRE-Luc (EC$_{50}$) (nM) |
|---|---|---|---|
| 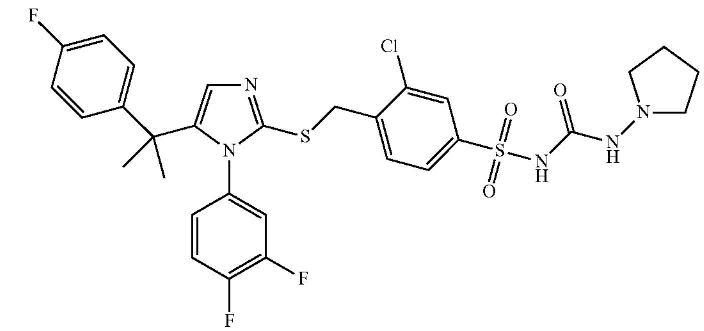 | 3-chloro-4-[({1-(3,4-difluorophenyl)-5-[1-(4-fluorophenyl)-1-methylethyl]-1H-imidazol-2-yl}thio)methyl]-N-[(pyrrolidin-1-ylamino)carbonyl]benzenesulfonamide | | D |
| 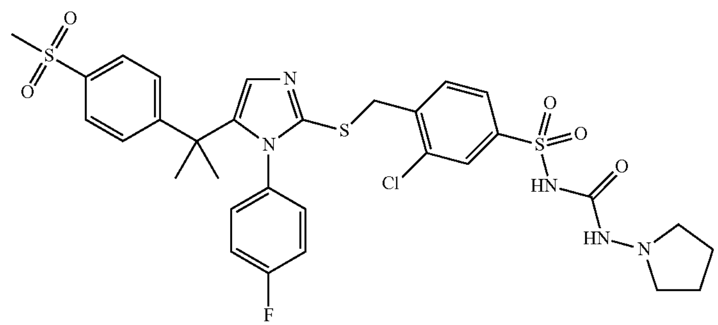 [SMILES: CC(C)(c1ccc(S(C)(=O)=O)cc1)c1cnc(SCc2ccc(S(=O)(=O)NC(=O)NN3CCCC3)cc2Cl)n1-c1ccc(F)cc1] | 3-chloro-4-({[1-(4-fluorophenyl)-5-{1-methyl-1-[4-(methylsulfonyl)phenyl]ethyl}-1H-imidazol-2-yl]thio}methyl)-N-[(pyrrolidin-1-ylamino)carbonyl]benzenesulfonamide | | D |
| 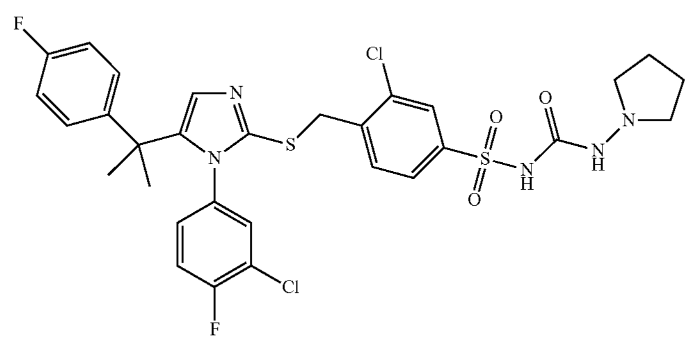 [SMILES: CC(C)(c1ccc(F)cc1)c1cnc(SCc2ccc(S(=O)(=O)NC(=O)NN3CCCC3)cc2Cl)n1-c1ccc(F)c(Cl)c1] | 3-chloro-4-[({1-(3-chloro-4-fluorophenyl)-5-[1-(4-fluorophenyl)-1-methylethyl]-1H-imidazol-2-yl}thio)methyl]-N-[(pyrrolidin-1-ylamino)carbonyl]benzenesulfonamide | D | C |

TABLE 1-continued

| Structure | Name | cAMP (EC$_{50}$) (nM) | CRE-Luc (EC$_{50}$) (nM) |
|---|---|---|---|
| 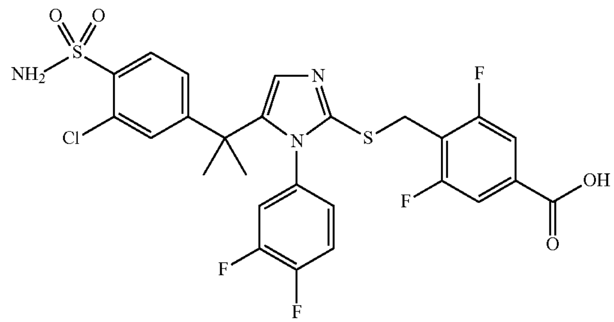 [SMILES: CC(C)(c1ccc(S(N)(=O)=O)c(Cl)c1)c1cnc(SCc2c(F)cc(C(=O)O)cc2F)n1-c1ccc(F)c(F)c1] | 4-({[5-{1-[4-(aminosulfonyl)-3-chlorophenyl]-1-methylethyl}-1-(3,4-difluorophenyl)-1H-imidazol-2-yl]thio}methyl)-3,5-difluorobenzoic acid | A | A |
| 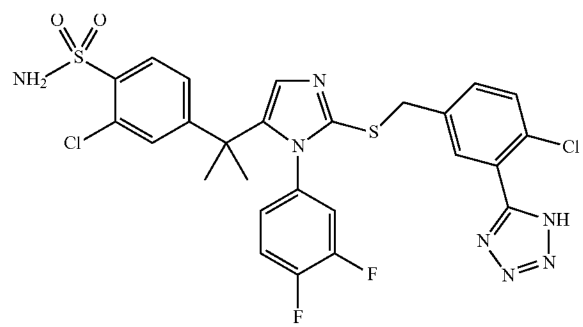 [SMILES: CC(C)(c1ccc(S(N)(=O)=O)c(Cl)c1)c1cnc(SCc2ccc(Cl)c(-c3nnn[nH]3)c2)n1-c1ccc(F)c(F)c1] | 2-chloro-4-{1-[2-({[4-chloro-3-(1H-tetrazol-5-yl)phenyl]methyl}thio)-1-(3,4-difluorophenyl)-1H-imidazol-5-yl]-1-methylethyl}benzenesulfonamide | C | C |
| 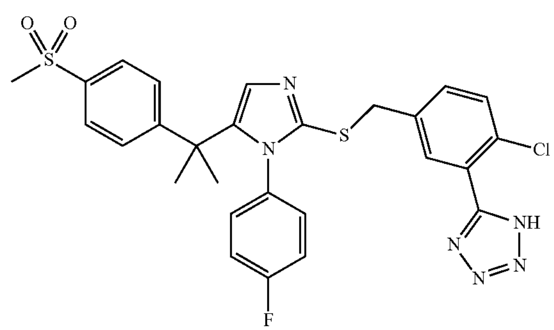 [SMILES: CC(C)(c1ccc(S(C)(=O)=O)cc1)c1cnc(SCc2ccc(Cl)c(-c3nnn[nH]3)c2)n1-c1ccc(F)cc1] | 5-[2-chloro-5-({[1-(4-fluorophenyl)-5-{1-methyl-1-[4-(methylsulfonyl)phenyl]ethyl}-1H-imidazol-2-yl]thio}methyl)phenyl]-1H-tetrazole | D | |

TABLE 1-continued

| Structure | NAME | cAMP (EC$_{50}$) (nM) | CRE-Luc (EC$_{50}$) (nM) |
|---|---|---|---|
| 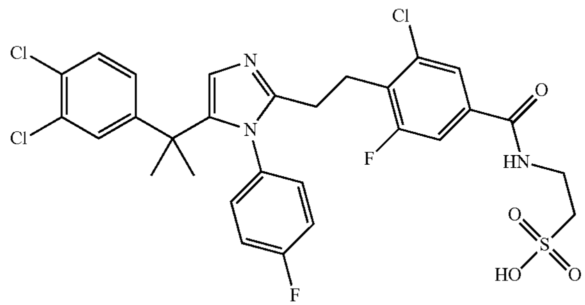 [SMILES: CC(C)(c1ccc(Cl)c(Cl)c1)c1cnc(CCc2c(F)cc(C(=O)NCCS(=O)(=O)O)cc2Cl)n1-c1ccc(F)cc1] | 2-({[3-chloro-4-(2-{5-[1-(3,4-dichlorophenyl)-1-methylethyl]-1-(4-fluorophenyl)-1H-imidazol-2-yl}ethyl)-5-fluorophenyl]carbonyl}amino)ethanesulfonic acid | A | A |
| 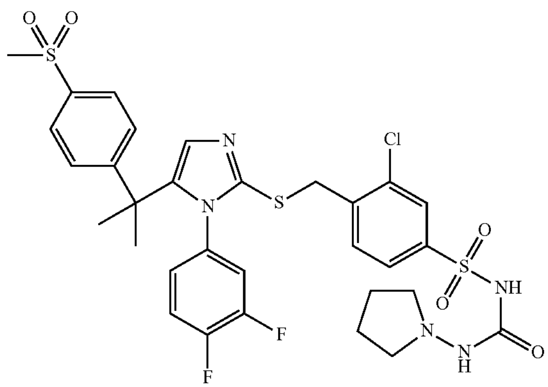 [SMILES: CC(C)(c1ccc(S(C)(=O)=O)cc1)c1cnc(SCc2ccc(S(=O)(=O)NC(=O)NN3CCCC3)cc2Cl)n1-c1ccc(F)c(F)c1] | 3-chloro-4-({[1-(3,4-difluorophenyl)-5-{1-methyl-1-[4-(methylsulfonyl)phenyl]ethyl}-1H-imidazol-2-yl]thio}methyl)-N-[(pyrrolidin-1-ylamino)carbonyl]benzenesulfonamide | D | |
| 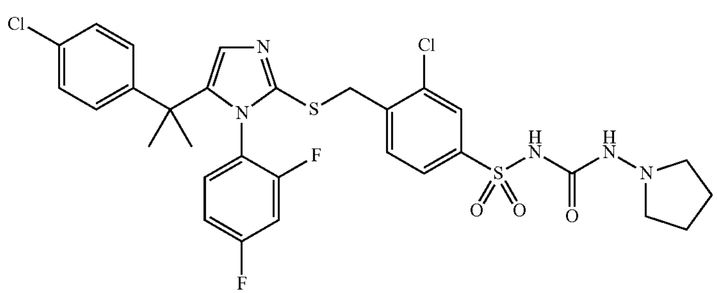 [SMILES: CC(C)(c1ccc(Cl)cc1)c1cnc(SCc2ccc(S(=O)(=O)NC(=O)NN3CCCC3)cc2Cl)n1-c1ccc(F)cc1F] | 3-chloro-4-[({5-[1-(4-chlorophenyl)-1-methylethyl]-1-(2,4-difluorophenyl)-1H-imidazol-2-yl}thio)methyl]-N-[(pyrrolidin-1-ylamino)carbonyl]benzenesulfonamide | D | |

TABLE 1-continued

| Structure | NAME | cAMP (EC$_{50}$) (nM) | CRE-Luc (EC$_{50}$) (nM) |
|---|---|---|---|
| 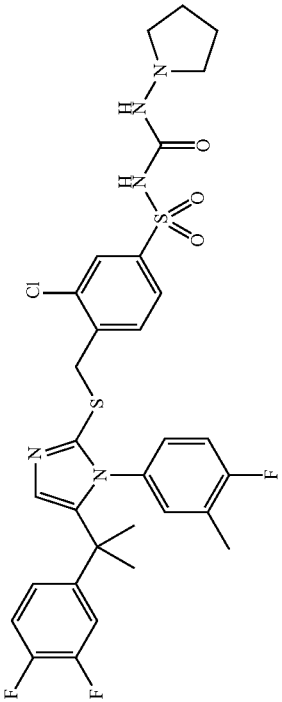 | 3-chloro-4-{[(5-[1-(3,4-difluorophenyl)-1-methylethyl]-1-(4-fluoro-3-methylphenyl)-1H-imidazol-2-yl]thio)methyl]-N-[(pyrrolidin-1-ylamino)carbonyl]benzenesulfonamide | D | C |
| 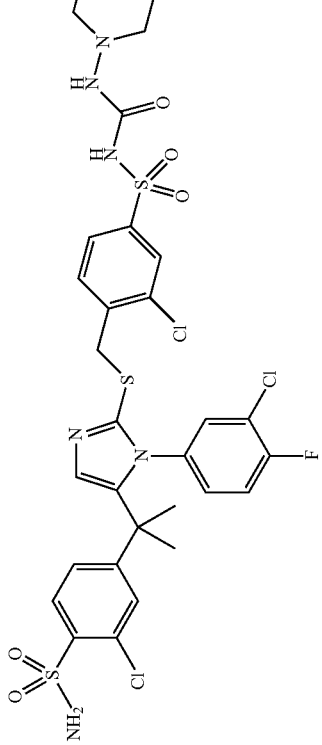 | 4-{[[5-{1-[4-(aminosulfonyl)-3-chlorophenyl]-1-methylethyl}-1-(3-chloro-4-fluorophenyl)-1H-imidazol-2-yl]thio}methyl)-3-chloro-N-[(morpholin-4-ylamino)carbonyl]benzenesulfonamide | C | C |
| 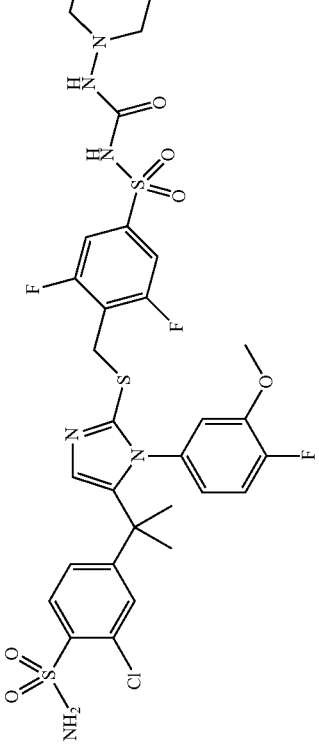 | 4-{[(5-{1-[4-(aminosulfonyl)-3-chlorophenyl]-1-methylethyl}-1-[4-fluoro-3-(methyloxy)phenyl]-1H-imidazol-2-yl]thio)methyl]-3,5-difluoro-N-[(morpholin-4-ylamino)carbonyl]benzenesulfonamide | A | A |

TABLE 1-continued

| Structure | NAME | cAMP (EC$_{50}$) (nM) | CRE-Luc (EC$_{50}$) (nM) |
|---|---|---|---|
| 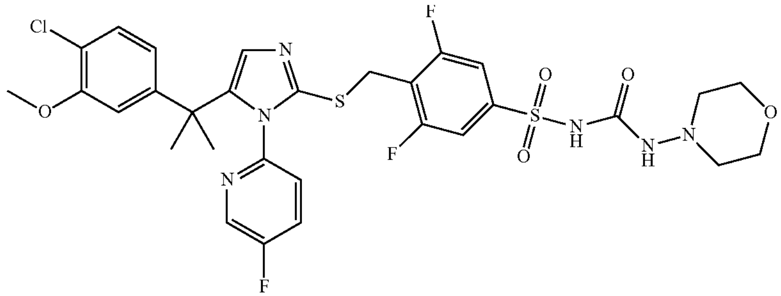 [SMILES: COc1cc(C(C)(C)c2cnc(SCc3c(F)cc(S(=O)(=O)NC(=O)NN4CCOCC4)cc3F)n2-c2ccc(F)cn2)ccc1Cl] | 4-({[5-{1-[4-chloro-3-(methyloxy)phenyl]-1-methylethyl}-1-(5-fluoropyridin-2-yl)-1H-imidazol-2-yl]thio}methyl)-3,5-difluoro-N-[(morpholin-4-ylamino)carbonyl]benzenesulfonamide | C | C |
| 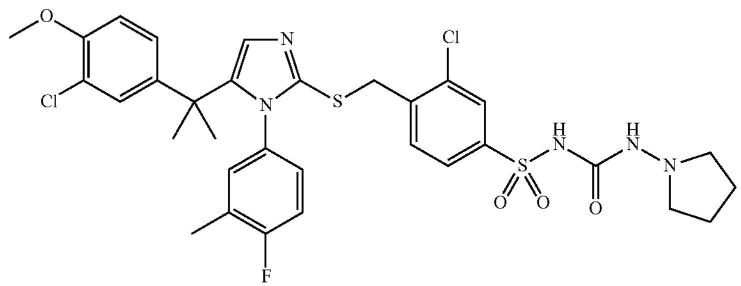 [SMILES: COc1ccc(C(C)(C)c2cnc(SCc3ccc(S(=O)(=O)NC(=O)NN4CCCC4)cc3Cl)n2-c2ccc(F)c(C)c2)cc1Cl] | 3-chloro-4-({[5-{1-[3-chloro-4-(methyloxy)phenyl]-1-methylethyl}-1-(4-fluoro-3-methylphenyl)-1H-imidazol-2-yl]thio}methyl)-N-[(pyrrolidin-1-ylamino)carbonyl]benzenesulfonamide | C | C |
| 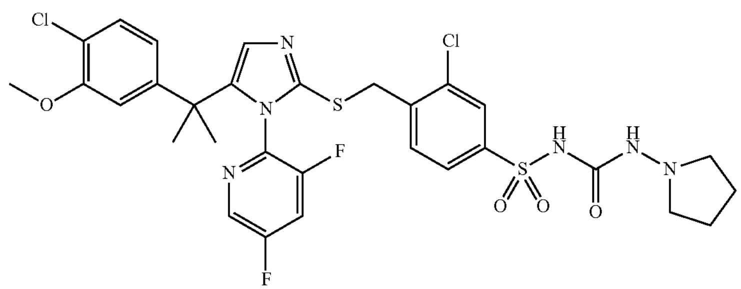 [SMILES: COc1cc(C(C)(C)c2cnc(SCc3ccc(S(=O)(=O)NC(=O)NN4CCCC4)cc3Cl)n2-c2ncc(F)cc2F)ccc1Cl] | 3-chloro-4-({[5-{1-[4-chloro-3-(methyloxy)phenyl]-1-methylethyl}-1-(3,5-difluoropyridin-2-yl)-1H-imidazol-2-yl]thio}methyl)-N-[(pyrrolidin-1-ylamino)carbonyl]benzenesulfonamide | D | |

TABLE 1-continued

| Structure | NAME | cAMP (EC$_{50}$) (nM) | CRE-Luc (EC$_{50}$) (nM) |
|---|---|---|---|
| 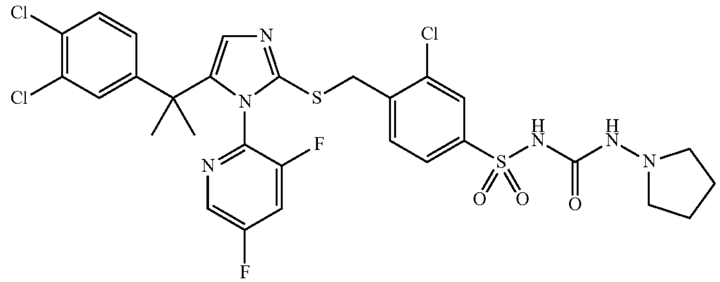 [SMILES: CC(C)(c1ccc(Cl)c(Cl)c1)c1cnc(SCc2ccc(S(=O)(=O)NC(=O)NN3CCCC3)cc2Cl)n1-c1ncc(F)cc1F] | 3-chloro-4-[({5-[1-(3,4-dichlorophenyl)-1-methylethyl]-1-(3,5-difluoropyridin-2-yl)-1H-imidazol-2-yl}thio)methyl]-N-[(pyrrolidin-1-ylamino)carbonyl]benzenesulfonamide | D | C |
| 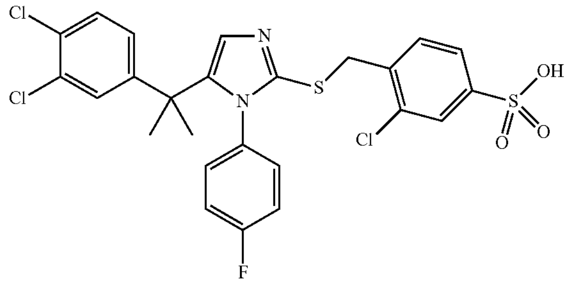 [SMILES: CC(C)(c1ccc(Cl)c(Cl)c1)c1cnc(SCc2ccc(S(=O)(=O)O)cc2Cl)n1-c1ccc(F)cc1] | 3-chloro-4-[({5-[1-(3,4-dichlorophenyl)-1-methylethyl]-1-(4-fluorophenyl)-1H-imidazol-2-yl}thio)methyl]benzenesulfonic acid | C | C |
| 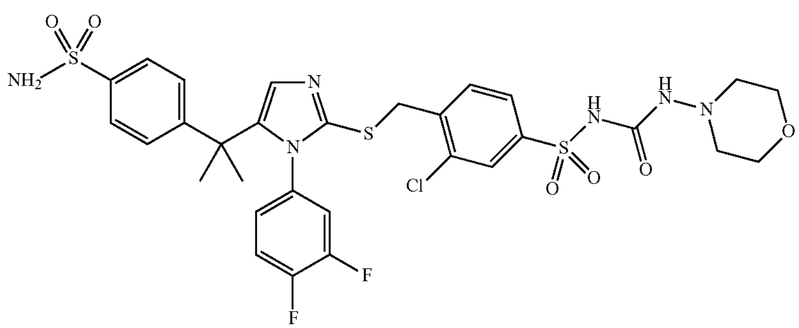 [SMILES: CC(C)(c1ccc(S(N)(=O)=O)cc1)c1cnc(SCc2ccc(S(=O)(=O)NC(=O)NN3CCOCC3)cc2Cl)n1-c1ccc(F)c(F)c1] | 4-({[5-{1-[4-(aminosulfonyl)phenyl]-1-methylethyl}-1-(3,4-difluorophenyl)-1H-imidazol-2-yl]thio}methyl)-3-chloro-N-[(morpholin-4-ylamino)carbonyl]benzenesulfonamide | D | |

TABLE 1-continued

| Structure | NAME | cAMP (EC$_{50}$) (nM) | CRE-Luc (EC$_{50}$) (nM) |
|---|---|---|---|
| 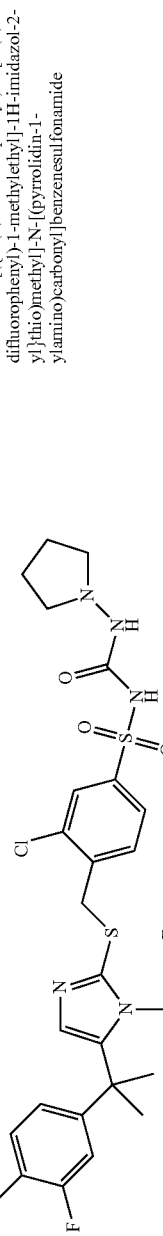 | 3-chloro-4-[({1-[2,4-difluorophenyl)-5-[1-(3,4-difluorophenyl)-1-methylethyl]-1H-imidazol-2-yl}thio)methyl]-N-[(pyrrolidin-1-ylamino)carbonyl]benzenesulfonamide | D | C |
| 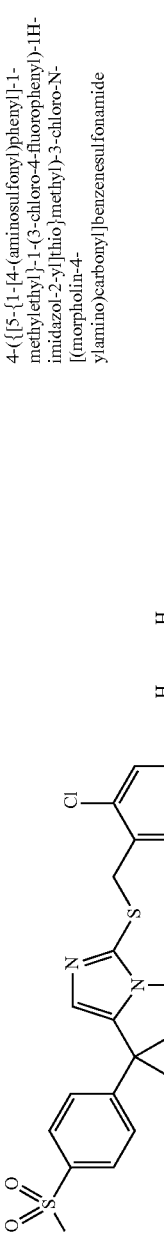 | 4-({[5-{1-[4-(aminosulfonyl)phenyl]-1-methylethyl}-1-(3-chloro-4-fluorophenyl)-1H-imidazol-2-yl]thio}methyl)-3-chloro-N-[(morpholin-4-ylamino)carbonyl]benzenesulfonamide | D | |
| 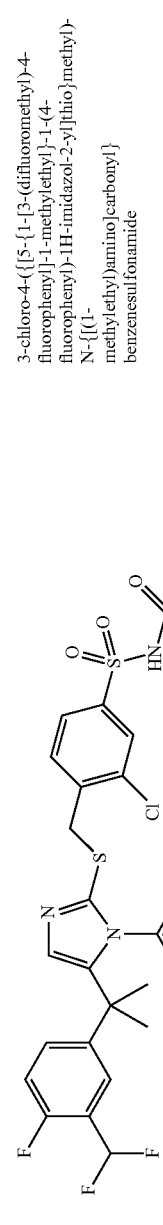 | 3-chloro-4-({[5-{1-[3-(difluoromethyl)-4-fluorophenyl]-1-methylethyl}-1-(4-fluorophenyl)-1H-imidazol-2-yl]thio}methyl)-N-{[(1-methylethyl)amino]carbonyl}benzenesulfonamide | C | C |

TABLE 1-continued

| Structure | NAME | cAMP (EC$_{50}$) (nM) | CRE-Luc (EC$_{50}$) (nM) |
|---|---|---|---|
| 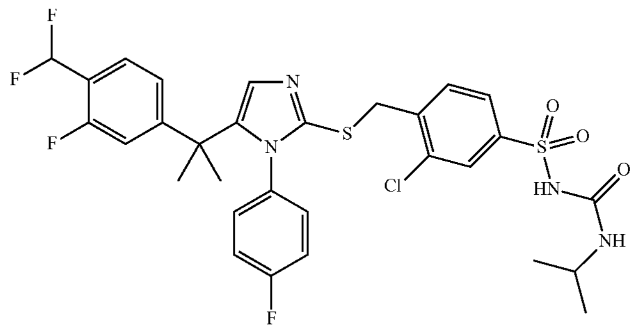 [SMILES: CC(C)NC(=O)NS(=O)(=O)c1ccc(CSc2ncc(C(C)(C)c3ccc(C(F)F)c(F)c3)n2-c2ccc(F)cc2)c(Cl)c1] | 3-chloro-4-({[5-{1-[4-(difluoromethyl)-3-fluorophenyl]-1-methylethyl}-1-(4-fluorophenyl)-1H-imidazol-2-yl]thio}methyl)-N-{[(1-methylethyl)amino]carbonyl}benzenesulfonamide | C | C |
| 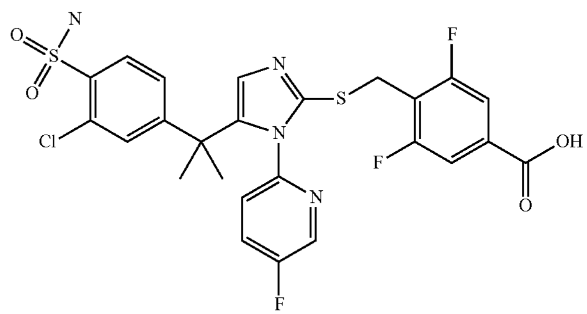 [SMILES: CC(C)(c1ccc(S(N)(=O)=O)c(Cl)c1)c1cnc(SCc2c(F)cc(C(=O)O)cc2F)n1-c1ccc(F)cn1] | 4-({[5-{1-[4-(aminosulfonyl)-3-chlorophenyl]-1-methylethyl}-1-(5-fluoropyridin-2-yl)-1H-imidazol-2-yl]thio}methyl)-3,5-difluorobenzoic acid | C | C |
| 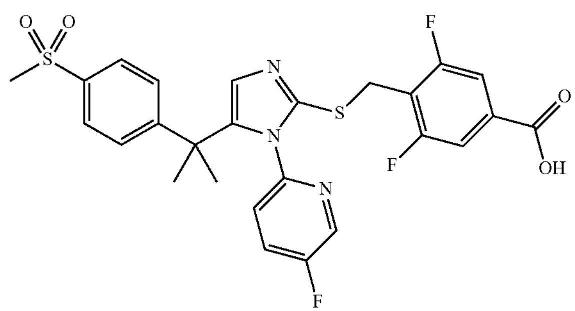 [SMILES: CC(C)(c1ccc(S(C)(=O)=O)cc1)c1cnc(SCc2c(F)cc(C(=O)O)cc2F)n1-c1ccc(F)cn1] | 3,5-difluoro-4-({[1-(5-fluoropyridin-2-yl)-5-{1-methyl-1-[4-(methylsulfonyl)phenyl]ethyl}-1H-imidazol-2-yl]thio}methyl)benzoic acid | D | |

TABLE 1-continued

| Structure | NAME | cAMP (EC$_{50}$) (nM) | CRE-Luc (EC$_{50}$) (nM) |
|---|---|---|---|
| | 5-(2-chloro-5-{[(1-[4-fluoro-3-(methyloxy)phenyl]-5-{1-methyl-1-[4-(methylsulfonyl)phenyl]ethyl]-1H-imidazol-2-yl)thio]methyl}phenyl)-1H-tetrazole | C | C |
| | 5-[2-chloro-5-({[1-(3,4-difluorophenyl)-5-{1-methyl-1-[4-(methylsulfonyl)phenyl]ethyl}-1H-imidazol-2-yl]thio}methyl)phenyl]-1H-tetrazole | D | |
| | 3-chloro-4-[({5-[1-(3,4-dichlorophenyl)-1-methylethyl]-1-(4-fluoro-3-methylphenyl)-1H-imidazol-2-yl]thio}methyl)-N-[(pyrrolidin-1-ylamino)carbonyl]benzenesulfonamide | C | C |

TABLE 1-continued

| Structure | NAME | cAMP (EC$_{50}$) (nM) | CRE-Luc (EC$_{50}$) (nM) |
|---|---|---|---|
| 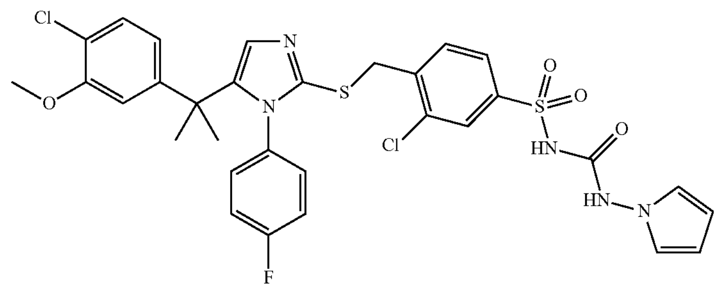 [SMILES: COc1cc(C(C)(C)c2cnc(SCc3ccc(S(=O)(=O)NC(=O)Nn4cccc4)cc3Cl)n2-c2ccc(F)cc2)ccc1Cl] | 3-chloro-4-({[5-{1-[4-chloro-3-(methyloxy)phenyl]-1-methylethyl}-1-(4-fluorophenyl)-1H-imidazol-2-yl]thio}methyl)-N-[(1H-pyrrol-1-ylamino)carbonyl]benzenesulfonamide | C | C |
| 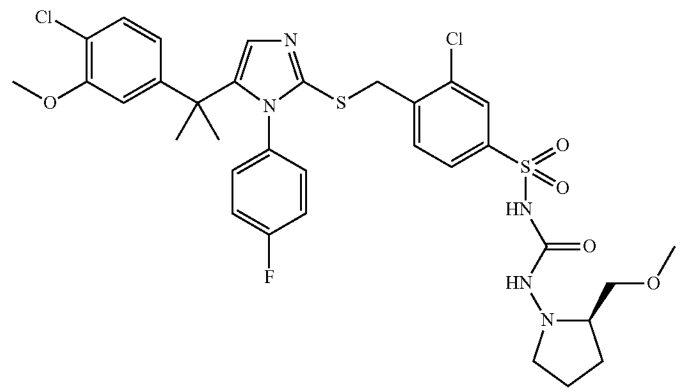 | 3-chloro-4-({[5-{1-[4-chloro-3-(methyloxy)phenyl]-1-methylethyl}-1-(4-fluorophenyl)-1H-imidazol-2-yl]thio}methyl)-N-[({(2R)-2-[(methyloxy)methyl]pyrrolidin-1-yl}amino)carbonyl]benzenesulfonamide | C | C |
| 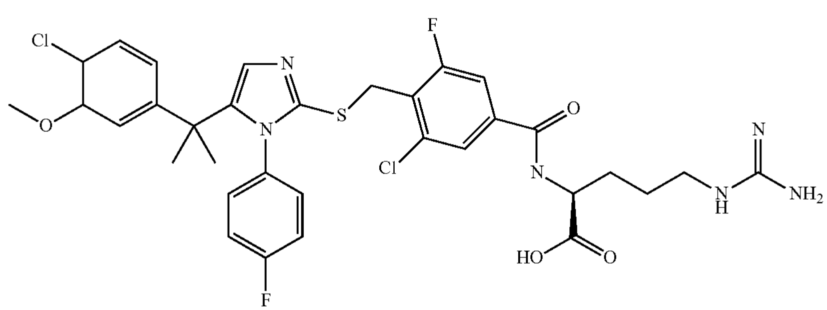 [SMILES: COC1C=C(C(C)(C)c2cnc(SCc3c(F)cc(C(=O)N[C@@H](CCCNC(=N)N)C(=O)O)cc3Cl)n2-c2ccc(F)cc2)C=CC1Cl] | N-2-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}-L-arginine | A | A |

TABLE 1-continued

| Structure | NAME | cAMP (EC$_{50}$) (nM) | CRE-Luc (EC$_{50}$) (nM) |
|---|---|---|---|
| | 3-chloro-4-({[5-{1-[4-chloro-3-(methyloxy)phenyl]-1-methylethyl}-1-(5-chloro-4-methylpyridin-2-yl)-1H-imidazol-2-yl]thio}methyl)-N-(pyrrolidin-1-ylamino)carbonyl]benzenesulfonamide | D | |
| | 3-chloro-4-{[(5-{1-[4-chloro-3-(methyloxy)phenyl]-1-methylethyl}-1-[4-fluoro-3-(hydroxymethyl)phenyl]-1H-imidazol-2-yl]thio}methyl]-N-[(pyrrolidin-1-ylamino)carbonyl]benzenesulfonamide | C | C |
| | ({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}amino)methanesulfonic acid | A | A |

TABLE 1-continued

| Structure | NAME | cAMP (EC$_{50}$) (nM) | CRE-Luc (EC$_{50}$) (nM) |
|---|---|---|---|
| 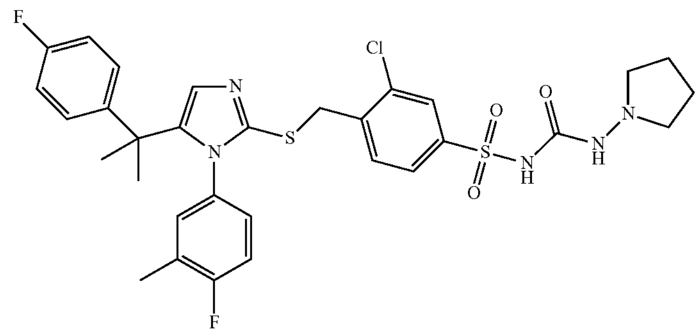 [SMILES: Cc1cc(-n2c(C(C)(C)c3ccc(F)cc3)cnc2SCc2ccc(S(=O)(=O)NC(=O)NN3CCCC3)cc2Cl)ccc1F] | 3-chloro-4-[({1-(4-fluoro-3-methylphenyl)-5-[1-(4-fluorophenyl)-1-methylethyl]-1H-imidazol-2-yl}thio)methyl]-N-[(pyrrolidin-1-ylamino)carbonyl]benzenesulfonamide | C |  |
| 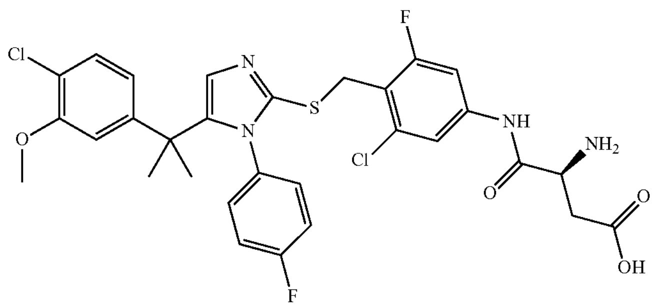 [SMILES: COc1cc(C(C)(C)c2cnc(SCc3c(F)cc(NC(=O)[C@@H](N)CC(=O)O)cc3Cl)n2-c2ccc(F)cc2)ccc1Cl] | N-[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]-L-alpha-asparagine | A | A |
| 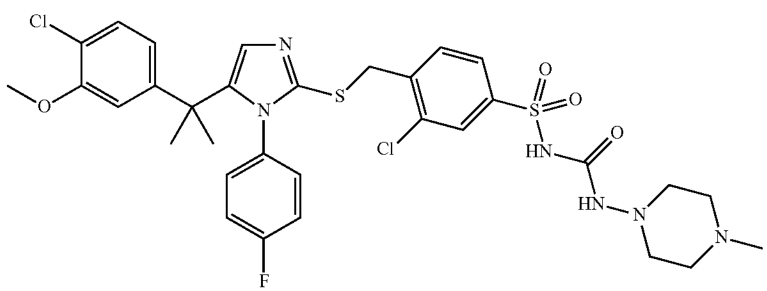 | 3-chloro-4-({[5-{1-[4-chloro-3-(methyloxy)phenyl]-1-methylethyl}-1-(4-fluorophenyl)-1H-imidazol-2-yl]thio}methyl)-N-{[(4-methylpiperazin-1-yl)amino]carbonyl}benzenesulfonamide | C | C |

TABLE 1-continued

| Structure | NAME | cAMP (EC$_{50}$) (nM) | CRE-Luc (EC$_{50}$) (nM) |
|---|---|---|---|
| 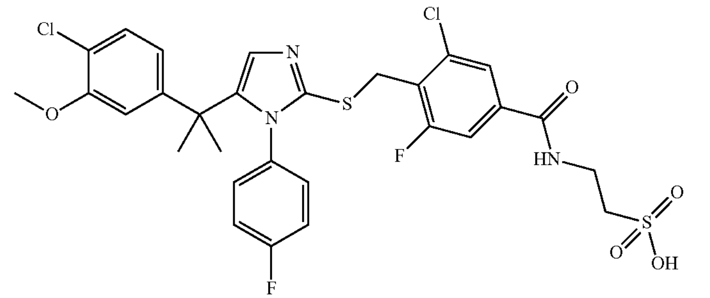 [SMILES: COc1cc(C(C)(C)c2cnc(SCc3c(F)cc(C(=O)NCCS(=O)(=O)O)cc3Cl)n2-c2ccc(F)cc2)ccc1Cl] | 2-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}amino)ethanesulfonic acid | A | A |
| | 4-[(5-{1-[4-(aminosulfonyl)-3-chlorophenyl]-1-methylethyl}-1-[4-fluoro-3-(methyloxy)phenyl]-1H-imidazol-2-yl]thio)methyl]-3-chloro-N-[(piperidin-1-yl)amino)carbonyl]benzenesulfonamide | C | C |
| 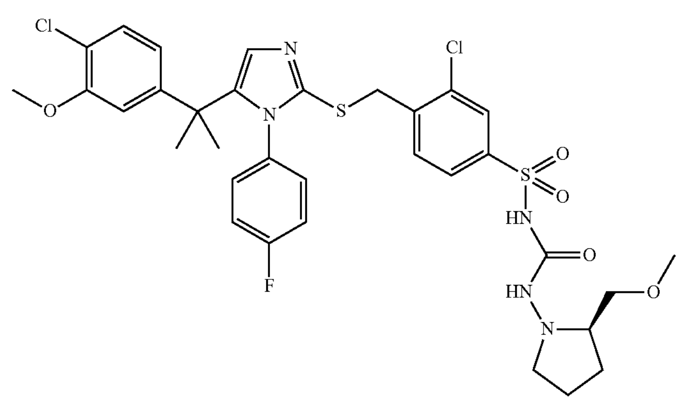 | 3-chloro-4-({[5-{1-[4-chloro-3-(methyloxy)phenyl]-1-methylethyl}-1-(4-fluorophenyl)-1H-imidazol-2-yl]thio}methyl)-N-[({(2S)-2-[(methyloxy)methyl]pyrrolidin-1-yl}amino)carbonyl]benzenesulfonamide | C | C |

TABLE 1-continued

| Structure | NAME | cAMP (EC$_{50}$) (nM) | CRE-Luc (EC$_{50}$) (nM) |
|---|---|---|---|
| 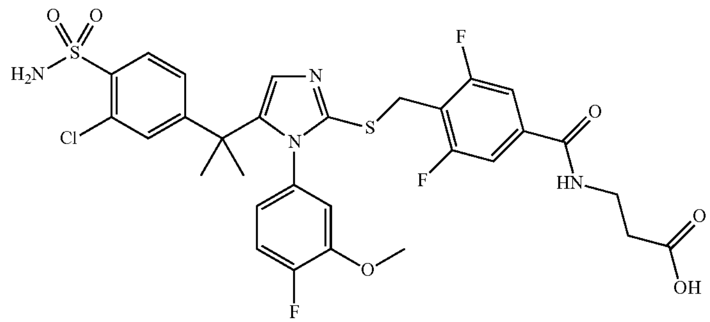 [SMILES: COc1cc(-n2c(C(C)(C)c3ccc(S(N)(=O)=O)c(Cl)c3)cnc2SCc2c(F)cc(C(=O)NCCC(=O)O)cc2F)ccc1F] | N-[(4-{[(5-{1-[4-(aminosulfonyl)-3-chlorophenyl]-1-methylethyl}-1-[4-fluoro-3-(methyloxy)phenyl]-1H-imidazol-2-yl)thio]methyl}-3,5-difluorophenyl)carbonyl]-beta-alanine | A | A |
| 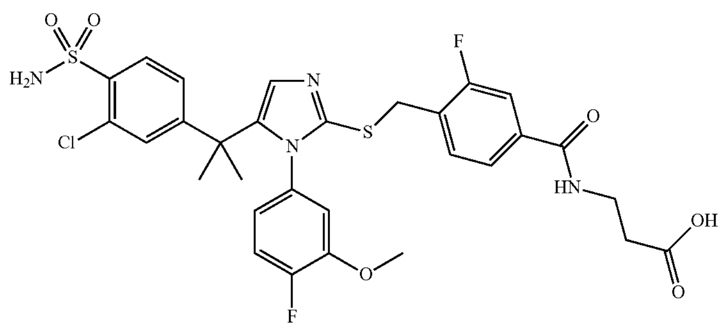 [SMILES: COc1cc(-n2c(C(C)(C)c3ccc(S(N)(=O)=O)c(Cl)c3)cnc2SCc2ccc(C(=O)NCCC(=O)O)cc2F)ccc1F] | N-[(4-{[(5-{1-[4-(aminosulfonyl)-3-chlorophenyl]-1-methylethyl}-1-[4-fluoro-3-(methyloxy)phenyl]-1H-imidazol-2-yl)thio]methyl}-3-fluorophenyl)carbonyl]-beta-alanine | A | A |
| | 2-{[(4-{[(5-{1-[4-chloro-3-(methyloxy)phenyl]-1-methylethyl}-1-(4-fluorophenyl)-1H-imidazol-2-yl]thio}methyl)-3,5-difluorophenyl]carbonyl}amino)ethanesulfonic acid | A | A |

TABLE 1-continued

| Structure | NAME | cAMP (EC$_{50}$) (nM) | CRE-Luc (EC$_{50}$) (nM) |
|---|---|---|---|
| 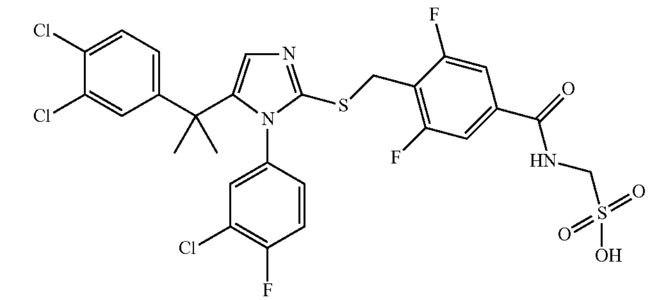 [SMILES: CC(C)(c1ccc(Cl)c(Cl)c1)c1cnc(SCc2c(F)cc(C(=O)NCS(=O)(=O)O)cc2F)n1-c1ccc(F)c(Cl)c1] | [({4-[({1-(3-chloro-4-fluorophenyl)-5-[1-(3,4-dichlorophenyl)-1-methylethyl]-1H-imidazol-2-yl}thio)methyl]-3,5-difluorophenyl}carbonyl)amino]methanesulfonic acid | A | A |
| 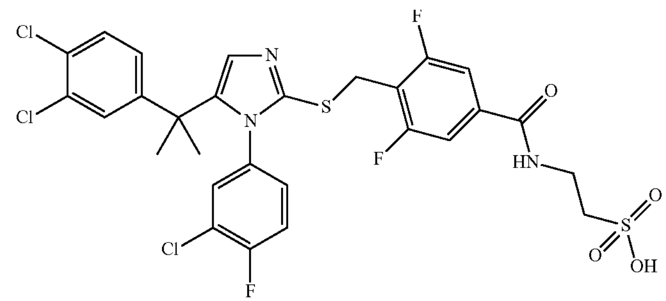 [SMILES: CC(C)(c1ccc(Cl)c(Cl)c1)c1cnc(SCc2c(F)cc(C(=O)NCCS(=O)(=O)O)cc2F)n1-c1ccc(F)c(Cl)c1] | 2-[({4-[({1-(3-chloro-4-fluorophenyl)-5-[1-(3,4-dichlorophenyl)-1-methylethyl]-1H-imidazol-2-yl}thio)methyl]-3,5-difluorophenyl}carbonyl)amino]ethanesulfonic acid | A | A |
| 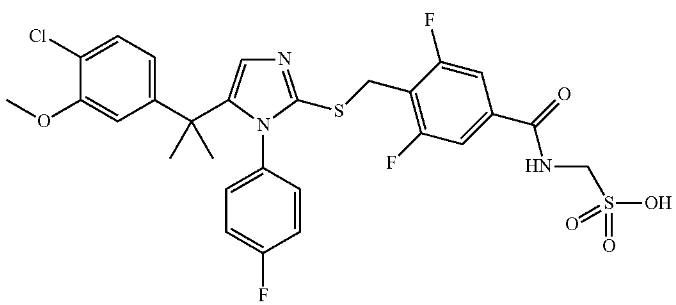 [SMILES: COc1cc(C(C)(C)c2cnc(SCc3c(F)cc(C(=O)NCS(=O)(=O)O)cc3F)n2-c2ccc(F)cc2)ccc1Cl] | ({[4-({[5-{1-[4-chloro-3-(methyloxy)phenyl]-1-methylethyl}-1-(4-fluorophenyl)-1H-imidazol-2-yl]thio}methyl)-3,5-difluorophenyl]carbonyl}amino)methanesulfonic acid | A | A |

TABLE 1-continued

| Structure | NAME | cAMP (EC$_{50}$) (nM) | CRE-Luc (EC$_{50}$) (nM) |
|---|---|---|---|
| | N-5-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}-L-ornithine | A | A |
| | 2-[[(4-{[(5-{1-[4-(aminosulfonyl)-3-chlorophenyl]-1-methylethyl}-1-[4-fluoro-3-(methyloxy)phenyl]-1H-imidazol-2-yl]thio}methyl)-3,5-difluorophenyl]carbonyl]amino]ethanesulfonic acid | A | A |
| | 2-{[(4-{[(5-{1-[4-(aminosulfonyl)-3-chlorophenyl]-1-methylethyl}-1-[4-fluoro-3-(methyloxy)phenyl]-1H-imidazol-2-yl]thio]methyl}-3-fluorophenyl)carbonyl]amino}ethanesulfonic acid | A | A |

TABLE 1-continued

| Structure | NAME | cAMP (EC$_{50}$) (nM) | CRE-Luc (EC$_{50}$) (nM) |
|---|---|---|---|
| 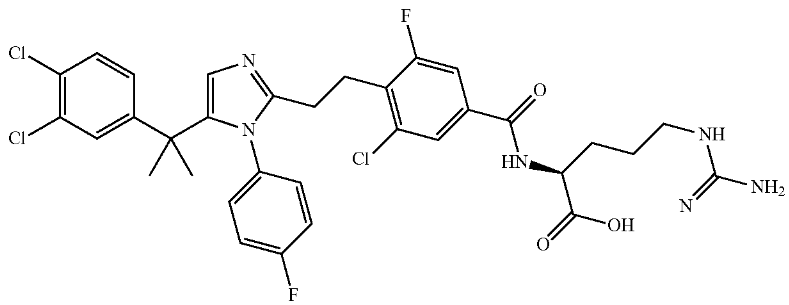 [SMILES: CC(C)(c1ccc(Cl)c(Cl)c1)c1cnc(CCc2c(F)cc(C(=O)N[C@@H](CCCNC(=N)N)C(=O)O)cc2Cl)n1-c1ccc(F)cc1] | N-2-{[3-chloro-4-(2-{5-[1-(3,4-dichlorophenyl)-1-methylethyl]-1-(4-fluorophenyl)-1H-imidazol-2-yl}ethyl)-5-fluorophenyl]carbonyl}-L-arginine | C | C |
| 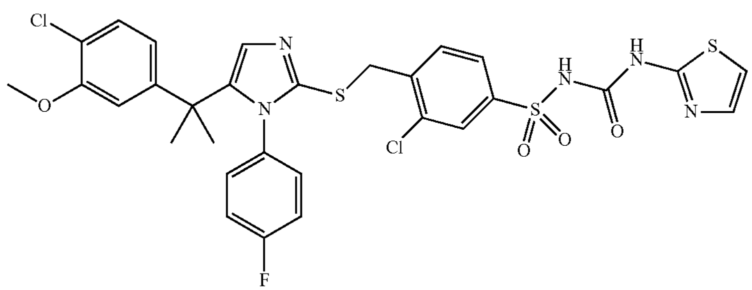 [SMILES: COc1cc(C(C)(C)c2cnc(SCc3ccc(S(=O)(=O)NC(=O)Nc4nccs4)cc3Cl)n2-c2ccc(F)cc2)ccc1Cl] | 3-chloro-4-({[5-{1-[4-chloro-3-(methyloxy)phenyl]-1-methylethyl}-1-(4-fluorophenyl)-1H-imidazol-2-yl]thio}methyl)-N-[(1,3-thiazol-2-ylamino)carbonyl]benzenesulfonamide | C | C |
| 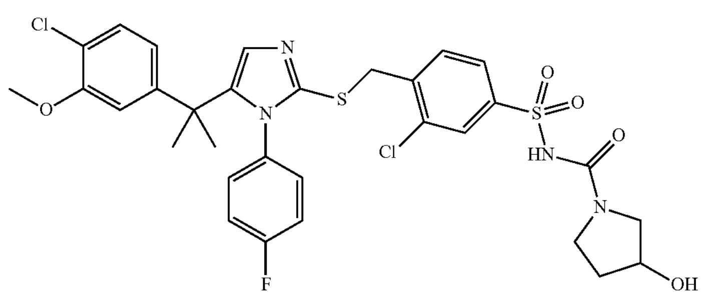 [SMILES: COc1cc(C(C)(C)c2cnc(SCc3ccc(S(=O)(=O)NC(=O)N4CCC(O)C4)cc3Cl)n2-c2ccc(F)cc2)ccc1Cl] | N-{[3-chloro-4-({[5-{1-[4-chloro-3-(methyloxy)phenyl]-1-methylethyl}-1-(4-fluorophenyl)-1H-imidazol-2-yl]thio}methyl)phenyl]sulfonyl}-3-hydroxypyrrolidine-1-carboxamide | A | D |

TABLE 1-continued

| Structure | NAME | cAMP (EC$_{50}$) (nM) | CRE-Luc (EC$_{50}$) (nM) |
|---|---|---|---|
| 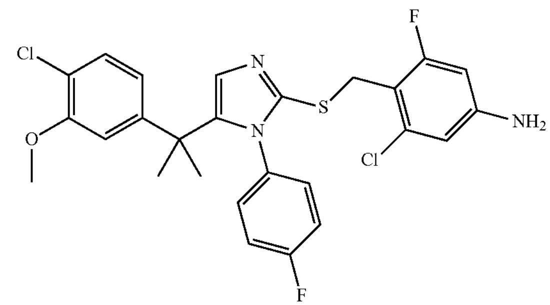 [SMILES: COc1cc(C(C)(C)c2cnc(SCc3c(F)cc(N)cc3Cl)n2-c2ccc(F)cc2)ccc1Cl] | 3-chloro-4-({[5-{1-[4-chloro-3-(methyloxy)phenyl]-1-methylethyl}-1-(4-fluorophenyl)-1H-imidazol-2-yl]thio}methyl)-5-fluoroaniline | A | A |
| | N-[({3-chloro-4-({[5-{1-[4-chloro-3-(methyloxy)phenyl]-1-methylethyl}-1-(4-fluorophenyl)-1H-imidazol-2-yl]thio}methyl)phenyl]sulfonyl}amino)carbonyl]glycine | C | |
| 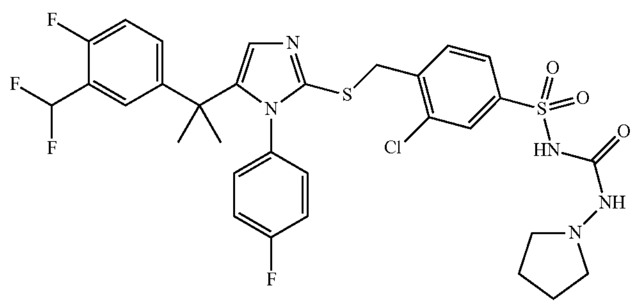 [SMILES: CC(C)(c1ccc(F)c(C(F)F)c1)c1cnc(SCc2ccc(S(=O)(=O)NC(=O)NN3CCCC3)cc2Cl)n1-c1ccc(F)cc1] | 3-chloro-4-({[5-{1-[3-(difluoromethyl)-4-fluorophenyl]-1-methylethyl}-1-(4-fluorophenyl)-1H-imidazol-2-yl]thio}methyl)-N-[(pyrrolidin-1-ylamino)carbonyl]benzenesulfonamide | D | |

TABLE 1-continued

| Structure | NAME | cAMP (EC$_{50}$) (nM) | CRE-Luc (EC$_{50}$) (nM) |
|---|---|---|---|
| 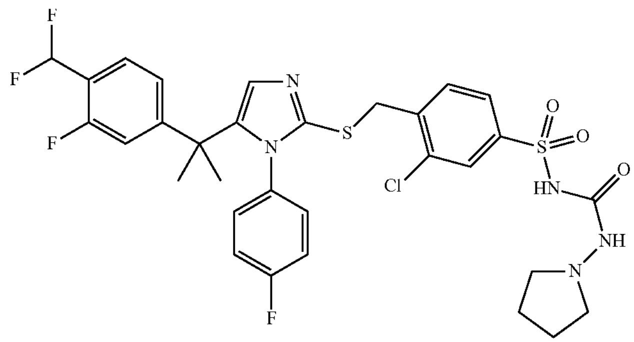 [SMILES: CC(C)(c1ccc(C(F)F)c(F)c1)c1cnc(SCc2ccc(S(=O)(=O)NC(=O)NN3CCCC3)cc2Cl)n1-c1ccc(F)cc1] | 3-chloro-4-({[5-{1-[4-(difluoromethyl)-3-fluorophenyl]-1-methylethyl}-1-(4-fluorophenyl)-1H-imidazol-2-yl]thio}methyl)-N-[(pyrrolidin-1-ylamino)carbonyl]benzenesulfonamide | C | C |
| 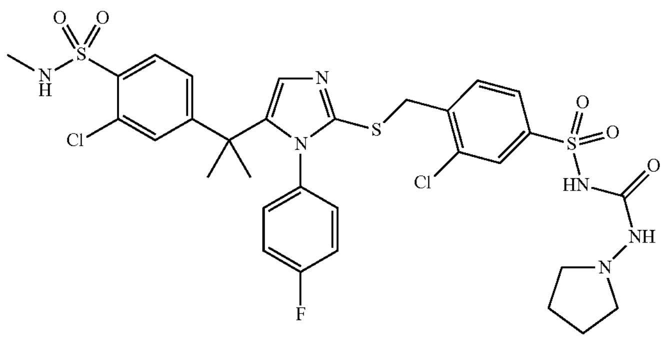 [SMILES: CNS(=O)(=O)c1ccc(C(C)(C)c2cnc(SCc3ccc(S(=O)(=O)NC(=O)NN4CCCC4)cc3Cl)n2-c2ccc(F)cc2)cc1Cl] | 2-chloro-4-{1-[2-({[2-chloro-4-({[(pyrrolidin-1-ylamino)carbonyl]amino}sulfonyl)phenyl]methyl}thio)-1-(4-fluorophenyl)-1H-imidazol-5-yl]-1-methylethyl}-N-methylbenzenesulfonamide | D |  |
| 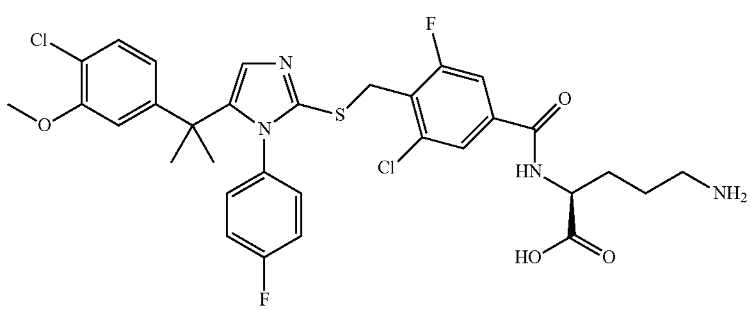 [SMILES: COc1cc(C(C)(C)c2cnc(SCc3c(F)cc(C(=O)N[C@@H](CCCN)C(=O)O)cc3Cl)n2-c2ccc(F)cc2)ccc1Cl] | N-2-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}-L-ornithine | A | A |

TABLE 1-continued

| Structure | NAME | cAMP (EC$_{50}$) (nM) | CRE-Luc (EC$_{50}$) (nM) |
|---|---|---|---|
| 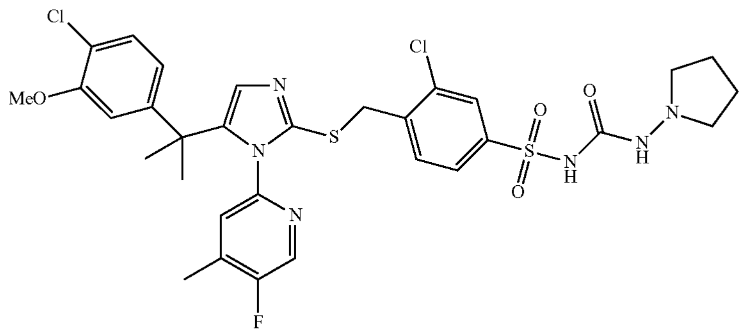 [SMILES: COc1cc(C(C)(C)c2cnc(SCc3ccc(S(=O)(=O)NC(=O)NN4CCCC4)cc3Cl)n2-c2cc(C)c(F)cn2)ccc1Cl] | 3-chloro-4-({[5-{1-[4-chloro-3-(methyloxy)phenyl]-1-methylethyl}-1-(5-fluoro-4-methylpyridin-2-yl)-1H-imidazol-2-yl]thio}methyl)-N-[(pyrrolidin-1-ylamino)carbonyl]benzenesulfonamide | D | C |
| 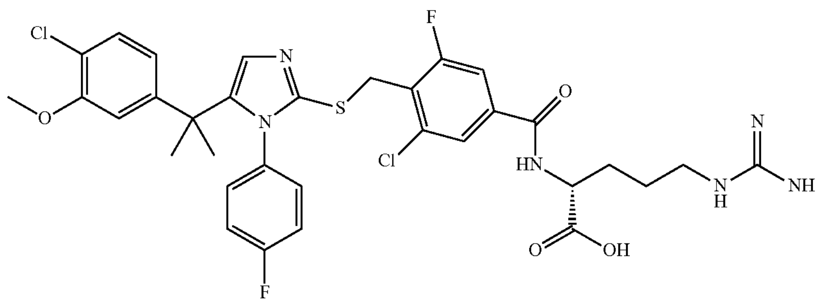 [SMILES: COc1cc(C(C)(C)c2cnc(SCc3c(F)cc(C(=O)N[C@H](CCCNC(=N)N)C(=O)O)cc3Cl)n2-c2ccc(F)cc2)ccc1Cl] | N-2-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}-D-arginine | A | A |
| 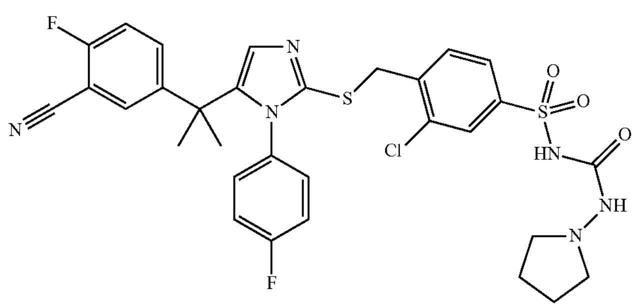 [SMILES: CC(C)(c1ccc(F)c(C#N)c1)c1cnc(SCc2ccc(S(=O)(=O)NC(=O)NN3CCCC3)cc2Cl)n1-c1ccc(F)cc1] | 3-chloro-4-[({5-[1-(3-cyano-4-fluorophenyl)-1-methylethyl]-1-(4-fluorophenyl)-1H-imidazol-2-yl}thio)methyl]-N-[(pyrrolidin-1-ylamino)carbonyl]benzenesulfonamide | C | C |

TABLE 1-continued

| Structure | NAME | cAMP (EC$_{50}$) (nM) | CRE-Luc (EC$_{50}$) (nM) |
|---|---|---|---|
| 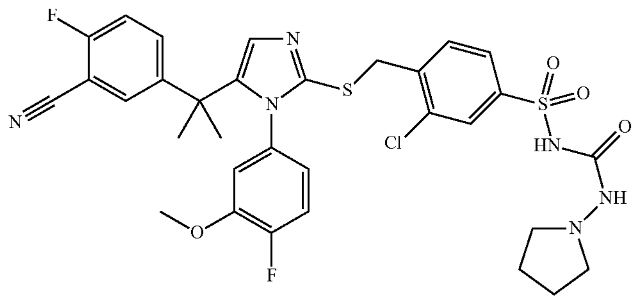 [SMILES: COc1cc(-n2c(C(C)(C)c3ccc(F)c(C#N)c3)cnc2SCc2ccc(S(=O)(=O)NC(=O)NN3CCCC3)cc2Cl)ccc1F] | 3-chloro-4-[({5-[1-(3-cyano-4-fluorophenyl)-1-methylethyl]-1-[4-fluoro-3-(methyloxy)phenyl]-1H-imidazol-2-yl}thio)methyl]-N-[(pyrrolidin-1-ylamino)carbonyl]benzenesulfonamide | C | C |
| 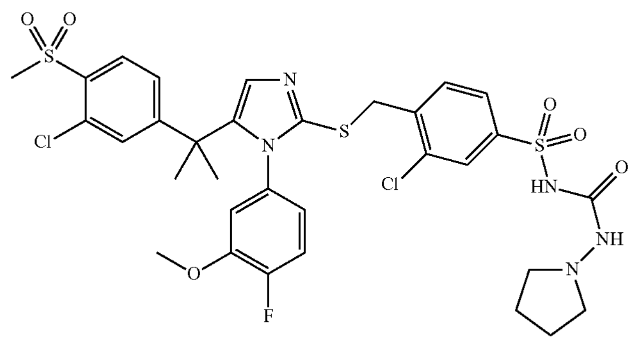 [SMILES: COc1cc(-n2c(C(C)(C)c3ccc(S(C)(=O)=O)c(Cl)c3)cnc2SCc2ccc(S(=O)(=O)NC(=O)NN3CCCC3)cc2Cl)ccc1F] | 3-chloro-4-{[(5-{1-[3-chloro-4-(methylsulfonyl)phenyl]-1-methylethyl}-1-[4-fluoro-3-(methyloxy)phenyl]-1H-imidazol-2-yl)thio]methyl}-N-[(pyrrolidin-1-ylamino)carbonyl]benzenesulfonamide | C | C |
| 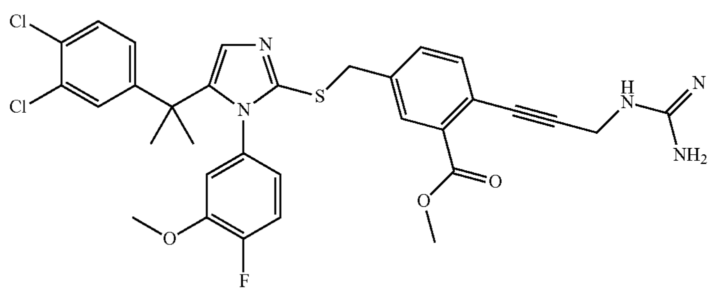 [SMILES: COC(=O)c1cc(CSc2ncc(C(C)(C)c3ccc(Cl)c(Cl)c3)n2-c2ccc(F)c(OC)c2)ccc1C#CCNC(=N)N] | methyl 2-(3-{[amino(imino)methyl]amino}prop-1-yn-1-yl)-5-[({5-[1-(3,4-dichlorophenyl)-1-methylethyl]-1-[4-fluoro-3-(methyloxy)phenyl]-1H-imidazol-2-yl}thio)methyl]benzoate | C | C |

TABLE 1-continued

| Structure | NAME | cAMP (EC$_{50}$) (nM) | CRE-Luc (EC$_{50}$) (nM) |
|---|---|---|---|
| 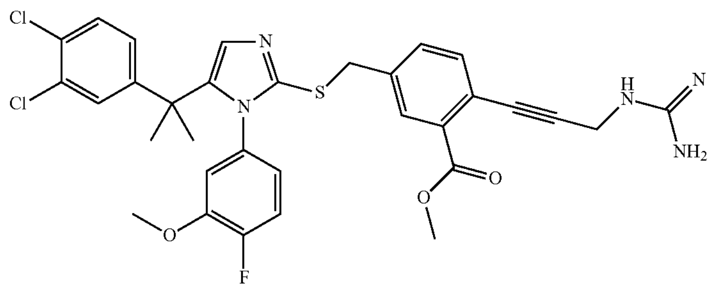 [SMILES: COC(=O)c1cc(CSc2ncc(C(C)(C)c3ccc(Cl)c(Cl)c3)n2-c2ccc(F)c(OC)c2)ccc1C#CCNC(=N)N] | N-2-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]amino}carbonyl)-L-arginine | A | A |
| 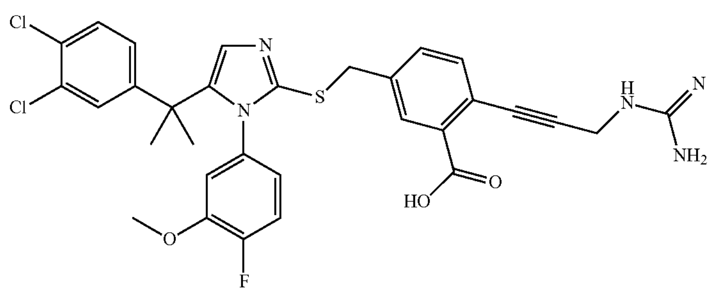 [SMILES: COc1cc(-n2c(C(C)(C)c3ccc(Cl)c(Cl)c3)cnc2SCc2ccc(C#CCNC(=N)N)c(C(=O)O)c2)ccc1F] | 2-(3-{[amino(imino)methyl]amino}prop-1-yn-1-yl)-5-[({5-[1-(3,4-dichlorophenyl)-1-methylethyl]-1-[4-fluoro-3-(methyloxy)phenyl]-1H-imidazol-2-yl}thio)methyl]benzoic acid | C | C |
| 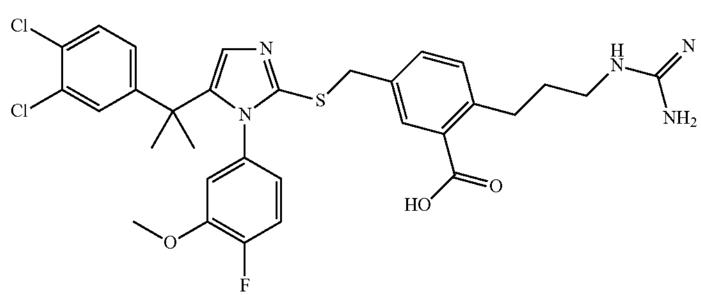 [SMILES: COc1cc(-n2c(C(C)(C)c3ccc(Cl)c(Cl)c3)cnc2SCc2ccc(CCCNC(=N)N)c(C(=O)O)c2)ccc1F] | 2-(3-{[amino(imino)methyl]amino}propyl)-5-[({5-[1-(3,4-dichlorophenyl)-1-methylethyl]-1-[4-fluoro-3-(methyloxy)phenyl]-1H-imidazol-2-yl}thio)methyl]benzoic acid | C | C |

TABLE 1-continued

| Structure | NAME | cAMP (EC$_{50}$) (nM) | CRE-Luc (EC$_{50}$) (nM) |
|---|---|---|---|
|  | N-6-[amino(imino)methyl]-N-2-{[3-chloro-4-({[5-[1-[4-chloro-3-(methyloxy)phenyl]-1-methylethyl}-1-(4-fluorophenyl)-1H-imidazol-2-yl]thio}methyl)-5-fluorophenyl]carbonyl}-L-lysine | A | A |
| 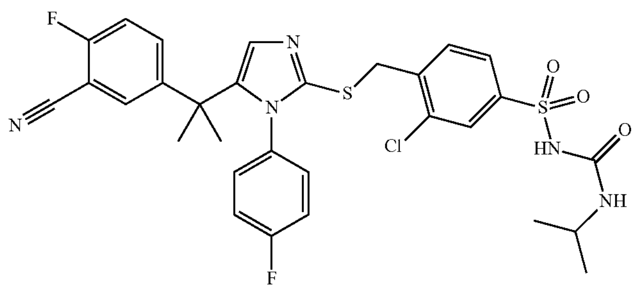 [SMILES: CC(C)NC(=O)NS(=O)(=O)c1ccc(CSc2ncc(C(C)(C)c3ccc(F)c(C#N)c3)n2-c2ccc(F)cc2)c(Cl)c1] | 3-chloro-4-[({5-[1-(3-cyano-4-fluorophenyl)-1-methylethyl]-1-(4-fluorophenyl)-1H-imidazol-2-yl}thio)methyl]-N-{[(1-methylethyl)amino]carbonyl}benzenesulfonamide | C | C |
| 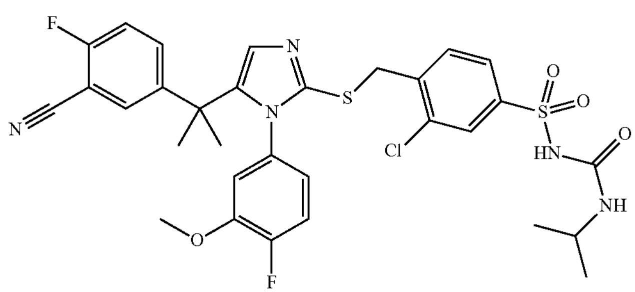 [SMILES: COc1cc(-n2c(C(C)(C)c3ccc(F)c(C#N)c3)cnc2SCc2ccc(S(=O)(=O)NC(=O)NC(C)C)cc2Cl)ccc1F] | 3-chloro-4-[({5-[1-(3-cyano-4-fluorophenyl)-1-methylethyl]-1-[4-fluoro-3-(methyloxy)phenyl]-1H-imidazol-2-yl}thio)methyl]-N-{[(1-methylethyl)amino]carbonyl}benzenesulfonamide | A | A |

TABLE 1-continued

| Structure | NAME | cAMP (EC$_{50}$) (nM) | CRE-Luc (EC$_{50}$) (nM) |
|---|---|---|---|
| | 3-chloro-4-[({5-[1-(3-chloro-4-fluorophenyl)-1-methylethyl]-1-(4-fluorophenyl)-1H-imidazol-2-yl]thio}methyl)-N-[(pyrrolidin-1-ylamino)carbonyl]benzenesulfonamide | C | C |
| 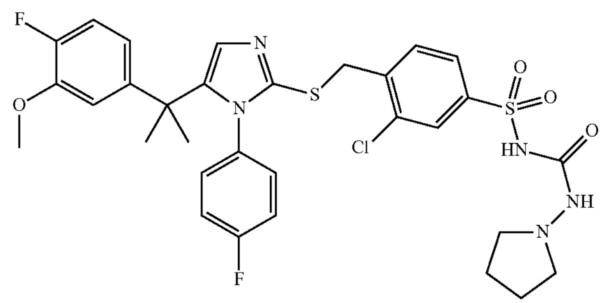 [SMILES: COc1cc(C(C)(C)c2cnc(SCc3ccc(S(=O)(=O)NC(=O)NN4CCCC4)cc3Cl)n2-c2ccc(F)cc2)ccc1F] | 3-chloro-4-({[5-{1-[4-fluoro-3-(methyloxy)phenyl]-1-methylethyl}-1-(4-fluorophenyl)-1H-imidazol-2-yl]thio}methyl)-N-[(pyrrolidin-1-ylamino)carbonyl]benzenesulfonamide | C | C |
| 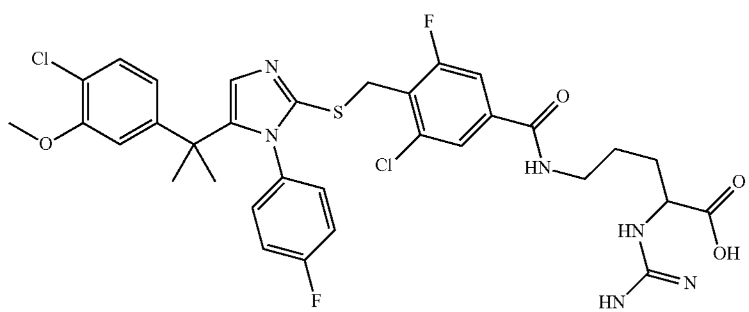 [SMILES: COc1cc(C(C)(C)c2cnc(SCc3c(F)cc(C(=O)NCCCC(NC(=N)N)C(=O)O)cc3Cl)n2-c2ccc(F)cc2)ccc1Cl] | N-2-[amino(imino)methyl]-N-5-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}-L-ornithine | A | A |

TABLE 1-continued

| Structure | NAME | cAMP (EC$_{50}$) (nM) | CRE-Luc (EC$_{50}$) (nM) |
|---|---|---|---|
| 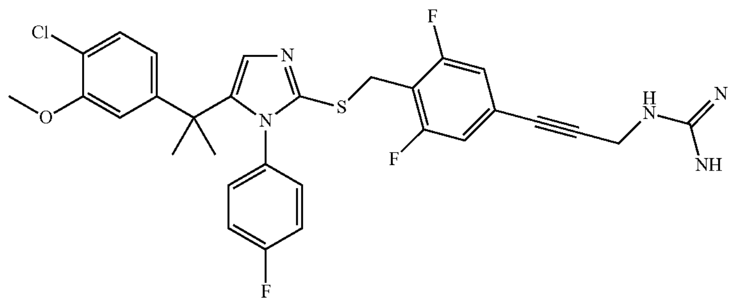 [SMILES: COc1cc(C(C)(C)c2cnc(SCc3c(F)cc(C#CCNC(=N)N)cc3F)n2-c2ccc(F)cc2)ccc1Cl] | 1-{3-[4-({[5-{1-[4-chloro-3-(methyloxy)phenyl]-1-methylethyl}-1-(4-fluorophenyl)-1H-imidazol-2-yl]thio}methyl)-3,5-difluorophenyl]prop-2-yn-1-yl}guanidine | A | A |
| | 2-(3-{[amino(imino)methyl][amino]propyl)-5-({[5-{1-[4-chloro-3-(methyloxy)phenyl]-1-methylethyl}-1-(4-fluorophenyl)-1H-imidazol-2-yl]thio}methyl)benzoic acid | C | A |
| 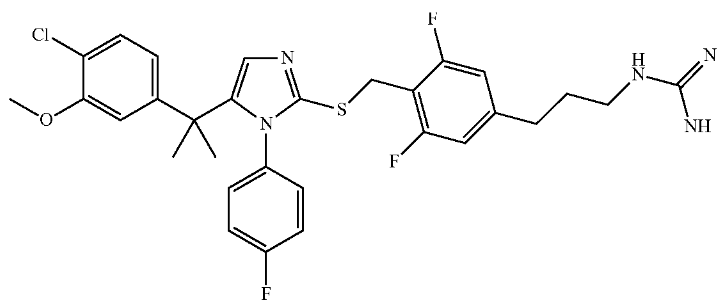 | 1-{3-[4-({[5-{1-[4-chloro-3-(methyloxy)phenyl]-1-methylethyl}-1-(4-fluorophenyl)-1H-imidazol-2-yl]thio}methyl)-3,5-difluorophenyl]propyl}guanidine | A | A |

TABLE 1-continued

| Structure | NAME | cAMP (EC$_{50}$) (nM) | CRE-Luc (EC$_{50}$) (nM) |
|---|---|---|---|
| | 2-(3-{[amino(imino)methyl]amino}prop-1-yn-1-yl)-5-{[5-{1-[4-chloro-3-(methyloxy)phenyl]-1-methylethyl}-1-(4-fluorophenyl)-1H-imidazol-2-yl]thio}methyl)benzoic acid | A | A |
| 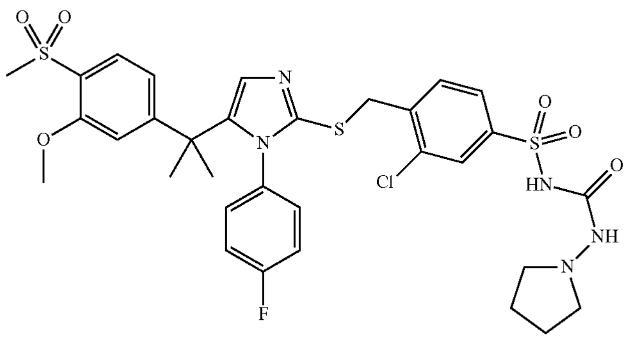 [SMILES: COc1cc(C(C)(C)c2cnc(SCc3ccc(S(=O)(=O)NC(=O)NN4CCCC4)cc3Cl)n2-c2ccc(F)cc2)ccc1S(C)(=O)=O] | 3-chloro-4-({[1-(4-fluorophenyl)-5-{1-methyl-1-[3-(methyloxy)-4-(methylsulfonyl)phenyl]ethyl}-1H-imidazol-2-yl]thio}methyl)-N-[(pyrrolidin-1-ylamino)carbonyl]benzenesulfonamide | C | C |
| 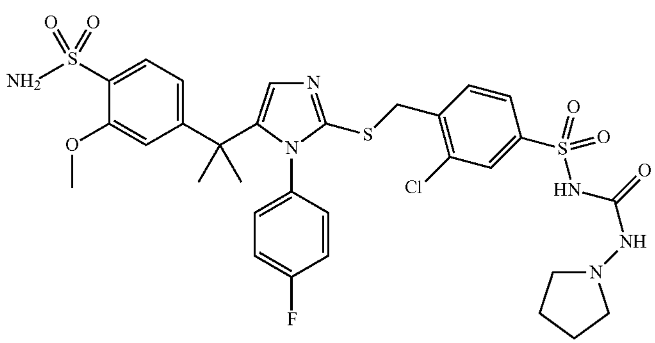 [SMILES: COc1cc(C(C)(C)c2cnc(SCc3ccc(S(=O)(=O)NC(=O)NN4CCCC4)cc3Cl)n2-c2ccc(F)cc2)ccc1S(N)(=O)=O] | 4-({[5-{1-[4-(aminosulfonyl)-3-(methyloxy)phenyl]-1-methylethyl}-1-(4-fluorophenyl)-1H-imidazol-2-yl]thio}methyl)-3-chloro-N-[(pyrrolidine-1-ylamino)carbonyl]benzenesulfonamide | C | C |

TABLE 1-continued

| Structure | NAME | cAMP (EC$_{50}$) (nM) | CRE-Luc (EC$_{50}$) (nM) |
|---|---|---|---|
| | 4-{1-[2-chloro-4-({[(pyrrolidin-1-ylamino)carbonyl]amino}sulfonyl)phenyl]methyl]thio)-1-(4-fluorophenyl)-1H-imidazol-5-yl]-1-methylethyl}-N-methyl-2-(methyloxy)benzenesulfonamide | C | |
| | 1-{4-[4-({[5-{1-[4-chloro-3-(methyloxy)phenyl]-1-methylethyl}-1-(4-fluorophenyl)-1H-imidazol-2-yl]thio}methyl)-3,5-difluorophenyl]butyl}guanidine | A | A |
| | 1-{5-[4-({[5-{1-[4-chloro-3-(methyloxy)phenyl]-1-methylethyl}-1-(4-fluorophenyl)-1H-imidazol-2-yl]thio}methyl)-3,5-difluorophenyl]pentyl}guanidine | A | A |

TABLE 1-continued

| Structure | NAME | cAMP (EC$_{50}$) (nM) | CRE-Luc (EC$_{50}$) (nM) |
|---|---|---|---|
| 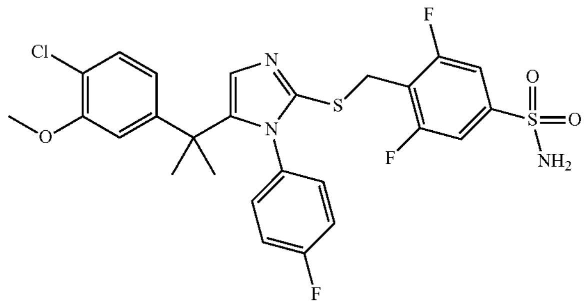 [SMILES: COc1cc(C(C)(C)c2cnc(SCc3c(F)cc(S(N)(=O)=O)cc3F)n2-c2ccc(F)cc2)ccc1Cl] | 4-({[5-{1-[4-chloro-3-(methyloxy)phenyl]-1-methylethyl}-1-(4-fluorophenyl)-1H-imidazol-2-yl]thio}methyl)-3,5-difluorobenzenesulfonamide | A | A |
| 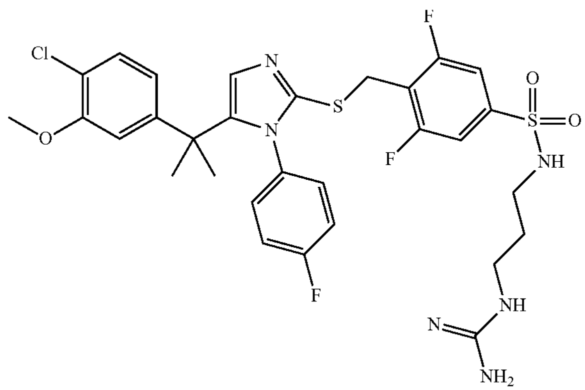 [SMILES: COc1cc(C(C)(C)c2cnc(SCc3c(F)cc(S(=O)(=O)NCCCNC(=N)N)cc3F)n2-c2ccc(F)cc2)ccc1Cl] | N-(3-{[amino(imino)methyl]amino}propyl)-4-({[5-{1-[4-chloro-3-(methyloxy)phenyl]-1-methylethyl}-1-(4-fluorophenyl)-1H-imidazol-2-yl]thio}methyl)-3,5-difluorobenzenesulfonamide | A | A |
| 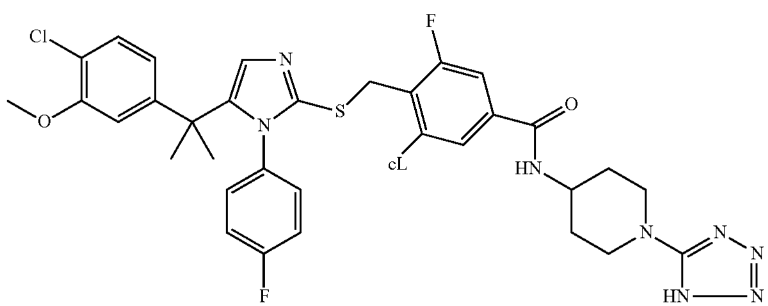 | 3-chloro-4-({[5-{1-[4-chloro-3-(methyloxy)phenyl]-1-methylethyl}-1-(4-fluorophenyl)-1H-imidazol-2-yl]thio}methyl)-5-fluoro-N-[1-(1H-tetrazol-5-yl)piperidin-4-yl]benzamide | A | A |

TABLE 1-continued

| Structure | NAME | cAMP (EC$_{50}$) (nM) | CRE-Luc (EC$_{50}$) (nM) |
|---|---|---|---|
| 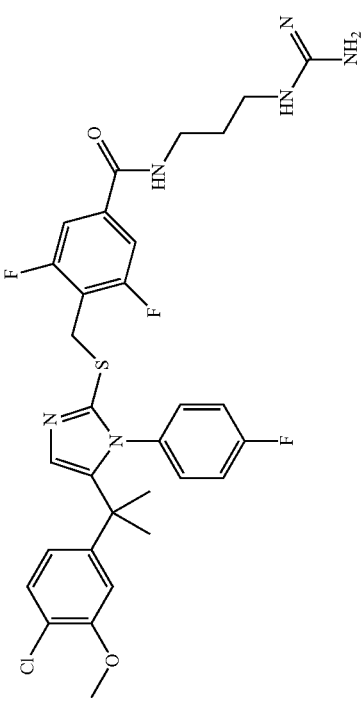 | N-(3-{[amino(imino)methyl]amino}propyl)-3-chloro-4-({[5-{1-[4-chloro-3-(methyloxy)phenyl]-1-methylethyl}-1-(4-fluorophenyl)-1H-imidazol-2-yl]thio}methyl)-5-fluorobenzamide | A | A |
| 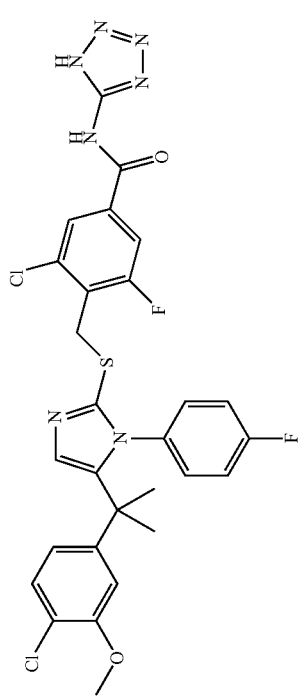 | 3-chloro-4-({[5-{1-[4-chloro-3-(methyloxy)phenyl]-1-methylethyl}-1-(4-fluorophenyl)-1H-imidazol-2-yl]thio}methyl)-5-fluoro-N-1H-tetrazol-5-ylbenzamide | A | A |
| 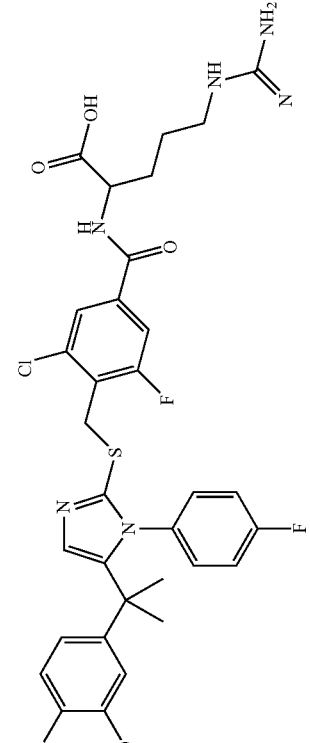 | N-2-{[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]carbonyl}-D-arginine | A | A |

TABLE 1-continued

| Structure | NAME | cAMP (EC$_{50}$) (nM) | CRE-Luc (EC$_{50}$) (nM) |
|---|---|---|---|
| 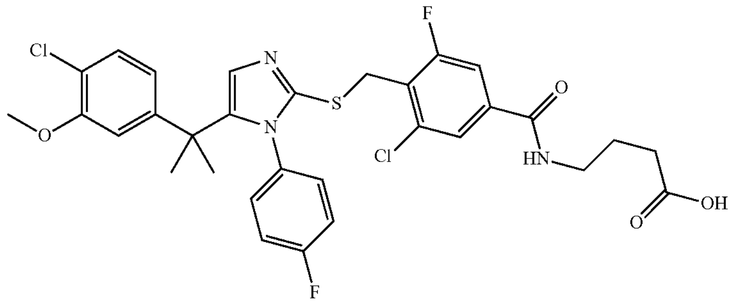 [SMILES: COc1cc(C(C)(C)c2cnc(SCc3c(F)cc(C(=O)NCCCC(=O)O)cc3Cl)n2-c2ccc(F)cc2)ccc1Cl] | 4-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}amino)butanoic acid | A | A |
| 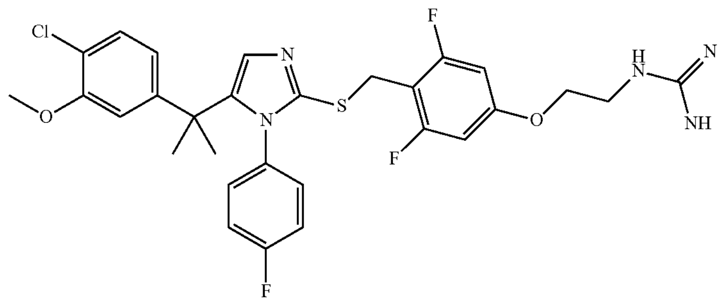 | 3-chloro-4-({[5-{1-[4-chloro-3-(methyloxy)phenyl]-1-methylethyl}-1-(4-fluorophenyl)-1H-imidazol-2-yl]thio}methyl)-N-[(1H-tetrazol-5-ylamino)carbonyl]benzenesulfonamide | C | C |
| 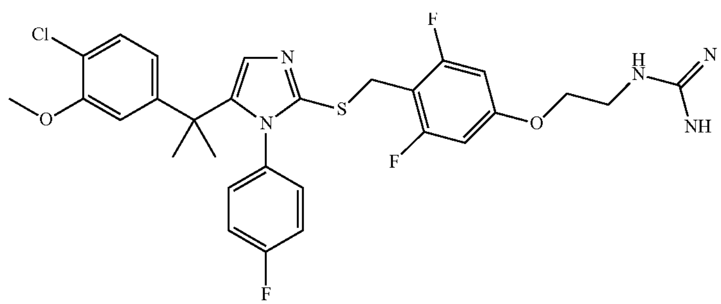 [SMILES: COc1cc(C(C)(C)c2cnc(SCc3c(F)cc(OCCNC(=N)N)cc3F)n2-c2ccc(F)cc2)ccc1Cl] | 1-(2-{[4-({[5-{1-[4-chloro-3-(methyloxy)phenyl]-1-methylethyl}-1-(4-fluorophenyl)-1H-imidazol-2-yl]thio}methyl)-3,5-difluorophenyl]oxy}ethyl)guanidine | A | A |

TABLE 1-continued

| Structure | NAME | cAMP (EC$_{50}$) (nM) | CRE-Luc (EC$_{50}$) (nM) |
|---|---|---|---|
| | 4-({[5-[1-[4-chloro-3-(methyloxy)phenyl]-1-methylethyl]-1-(4-fluorophenyl)-1H-imidazol-2-yl]thio}methyl)pyridin-2-amine | C | C |
| 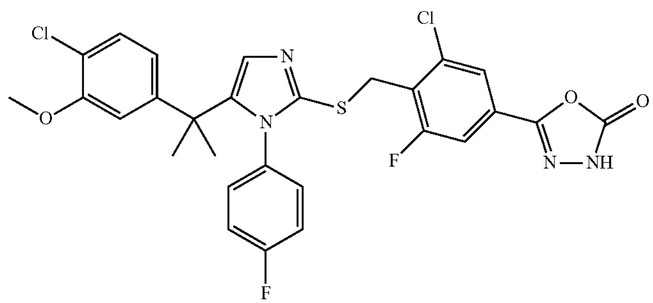 [SMILES: COc1cc(C(C)(C)c2cnc(SCc3c(F)cc(-c4n[nH]c(=O)o4)cc3Cl)n2-c2ccc(F)cc2)ccc1Cl] | 5-[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]-1,3,4-oxadiazol-2(3H)-one | A | A |
| 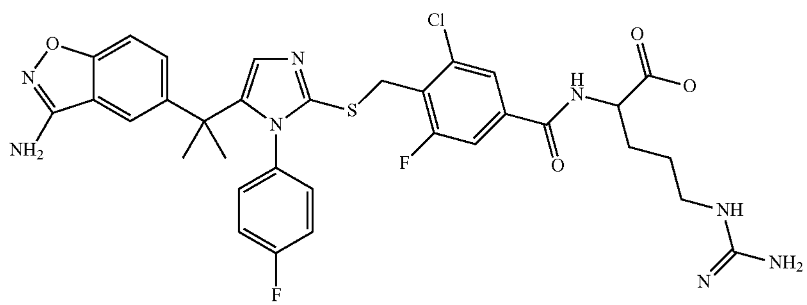 [SMILES: CC(C)(c1ccc2onc(N)c2c1)c1cnc(SCc2c(F)cc(C(=O)NC(CCCNC(=N)N)C(=O)O)cc2Cl)n1-c1ccc(F)cc1] | N-2-({4-[({5-[1-(3-amino-1,2-benzisoxazol-5-yl)-1-methylethyl]-1-(4-fluorophenyl)-1H-imidazol-2-yl}thio)methyl]-3-chloro-5-fluorophenyl}carbonyl)-D-arginine | A | A |

TABLE 1-continued

| Structure | NAME | cAMP (EC$_{50}$) (nM) | CRE-Luc (EC$_{50}$) (nM) |
|---|---|---|---|
| 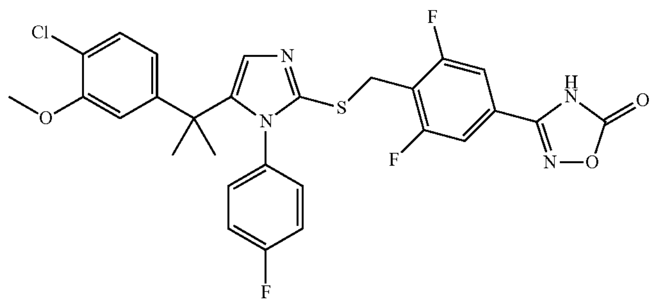 [SMILES: COc1cc(C(C)(C)c2cnc(SCc3c(F)cc(-c4noc(=O)[nH]4)cc3F)n2-c2ccc(F)cc2)ccc1Cl] | 3-[4-({[5-{1-[4-chloro-3-(methyloxy)phenyl]-1-methylethyl}-1-(4-fluorophenyl)-1H-imidazol-2-yl]thio}methyl)-3,5-difluorophenyl]-1,2,4-oxadiazol-5(4H)-one | A | A |
| 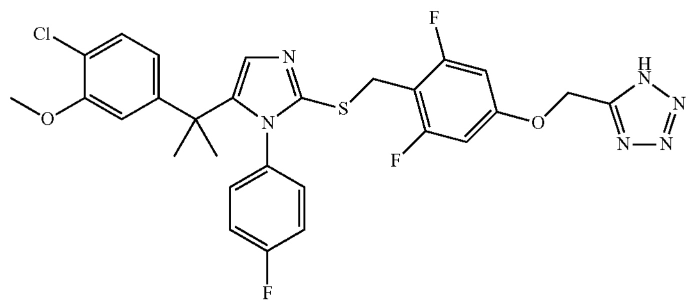 [SMILES: COc1cc(C(C)(C)c2cnc(SCc3c(F)cc(OCc4nnn[nH]4)cc3F)n2-c2ccc(F)cc2)ccc1Cl] | 5-({[4-({[5-{1-[4-chloro-3-(methyloxy)phenyl]-1-methylethyl}-1-(4-fluorophenyl)-1H-imidazol-2-yl]thio}methyl)-3,5-difluorophenyl]oxy}methyl)-1H-tetrazole | A | A |
| | N-2-[(4-{[(5-{1-[4-(aminosulfonyl)-3-chlorophenyl]-1-methylethyl}-1-[4-fluoro-3-(methyloxy)phenyl]-1H-imidazol-2-yl]thio]methyl}-3-chloro-5-fluorophenyl)carbonyl]-D-arginine | A | A |

TABLE 1-continued

| Structure | NAME | cAMP (EC$_{50}$) (nM) | CRE-Luc (EC$_{50}$) (nM) |
|---|---|---|---|
| | N-2-({4-[({5-[1-(3-amino-1,2-benzisoxazol-5-yl)-1-methylethyl]-1-[4-fluoro-3-(methyloxy)phenyl]-1H-imidazol-2-yl}thio)methyl]-3-chloro-5-fluorophenyl}carbonyl)-D-arginine | A | A |
| | 3-chloro-4-({[5-[1-[4-chloro-3-(methyloxy)phenyl]-1-methylethyl]-1-(4-fluorophenyl)-1H-imidazol-2-yl]thio}methyl)-5-fluorobenzenesulfonic acid | A | A |
| | 3-{4-[({5-[1-(3-chloro-4-fluorophenyl)-1-methylethyl]-1-[4-fluoro-3-(methyloxy)phenyl]-1H-imidazol-2-yl]thio)methyl]-3,5-difluorophenyl}-N,N-dimethylpropan-1-amine | A | A |

TABLE 1-continued

| Structure | NAME | cAMP (EC$_{50}$) (nM) | CRE-Luc (EC$_{50}$) (nM) |
|---|---|---|---|
| 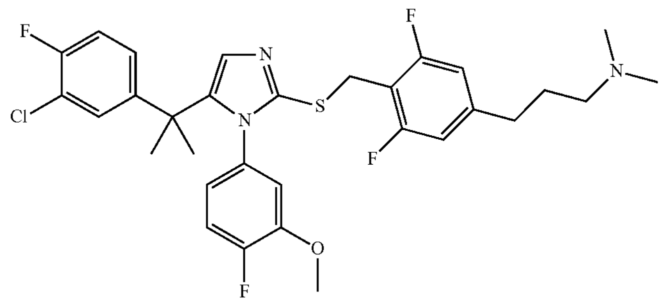 [SMILES: COc1cc(-n2c(C(C)(C)c3ccc(F)c(Cl)c3)cnc2SCc2c(F)cc(CCCN(C)C)cc2F)ccc1F] | 2-chloro-5-({[5-{1-[4-chloro-3-(methyloxy)phenyl]-1-methylethyl}-1-(4-fluorophenyl)-1H-imidazol-2-yl]thio}methyl)benzenesulfonamide | A | A |
| 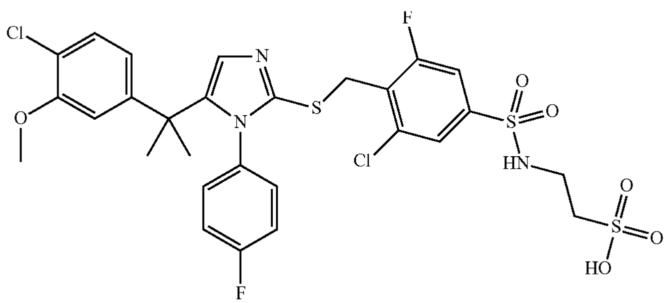 | 2-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}amino)ethanesulfonic acid | A | A |
| 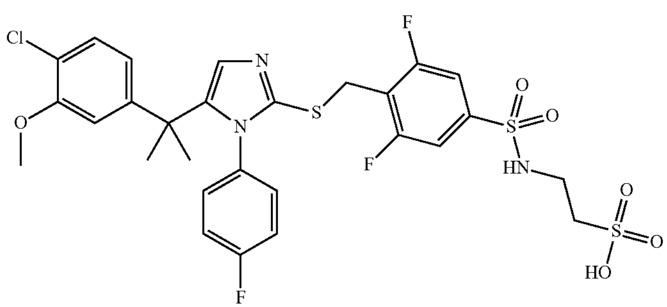 [SMILES: COc1cc(C(C)(C)c2cnc(SCc3c(F)cc(S(=O)(=O)NCCS(=O)(=O)O)cc3F)n2-c2ccc(F)cc2)ccc1Cl] | 2-({[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino)ethanesulfonic acid | A | A |

TABLE 1-continued

| Structure | NAME | cAMP (EC$_{50}$) (nM) | CRE-Luc (EC$_{50}$) (nM) |
|---|---|---|---|
| 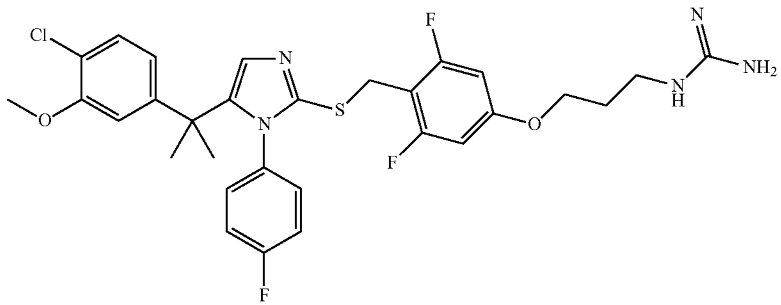 | 1-(3-{[4-({[5-{1-[4-chloro-3-(methyloxy)phenyl]-1-methylethyl}-1-(4-fluorophenyl)-1H-imidazol-2-yl]thio}methyl)-3,5-difluorophenyl]oxy}propyl)guanidine | A | A |
| 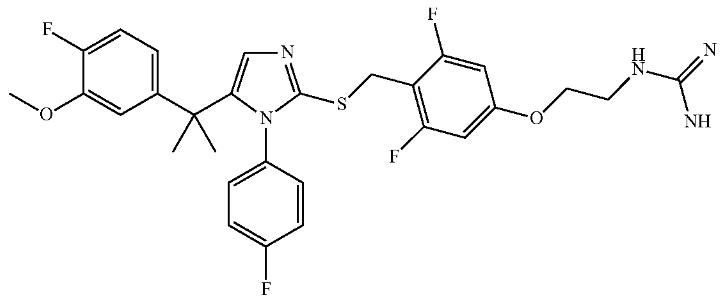 [SMILES: COc1cc(C(C)(C)c2cnc(SCc3c(F)cc(OCCNC(=N)N)cc3F)n2-c2ccc(F)cc2)ccc1F] | 1-(2-{[3,5-difluoro-4-({[5-{1-[4-fluoro-3-(methyloxy)phenyl]-1-methylethyl}-1-(4-fluorophenyl)-1H-imidazol-2-yl]thio}methyl)phenyl]oxy}ethyl)guanidine | A | A |
| 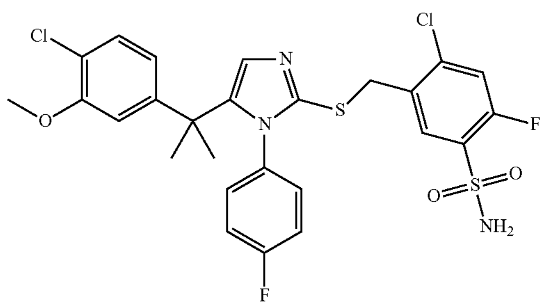 [SMILES: COc1cc(C(C)(C)c2cnc(SCc3cc(S(N)(=O)=O)c(F)cc3Cl)n2-c2ccc(F)cc2)ccc1Cl] | 4-chloro-5-({[5-{1-[4-chloro-3-(methyloxy)phenyl]-1-methylethyl}-1-(4-fluorophenyl)-1H-imidazol-2-yl]thio}methyl)-2-fluorobenzenesulfonamide | A | A |

TABLE 1-continued

| Structure | NAME | cAMP (EC$_{50}$) (nM) | CRE-Luc (EC$_{50}$) (nM) |
|---|---|---|---|
| 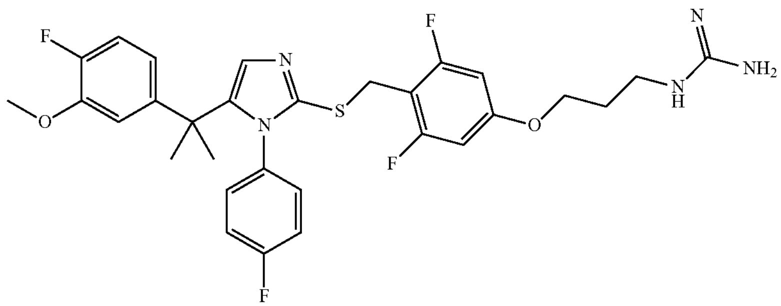 [SMILES: COc1cc(C(C)(C)c2cnc(SCc3c(F)cc(OCCCNC(=N)N)cc3F)n2-c2ccc(F)cc2)ccc1F] | 1-(3-{[3,5-difluoro-4-({[5-{1-[4-fluoro-3-(methyloxy)phenyl]-1-methylethyl}-1-(4-fluorophenyl)-1H-imidazol-2-yl]thio}methyl)phenyl]oxy}propyl)guanidine | A | A |
| 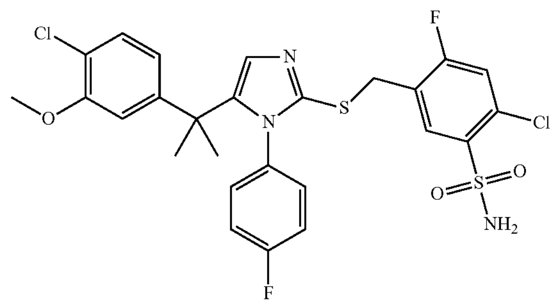 [SMILES: COc1cc(C(C)(C)c2cnc(SCc3cc(S(N)(=O)=O)c(Cl)cc3F)n2-c2ccc(F)cc2)ccc1Cl] | 2-chloro-5-({[5-{1-[4-chloro-3-(methyloxy)phenyl]-1-methylethyl}-1-(4-fluorophenyl)-1H-imidazol-2-yl]thio}methyl)-4-fluorobenzenesulfonamide | A | A |
| 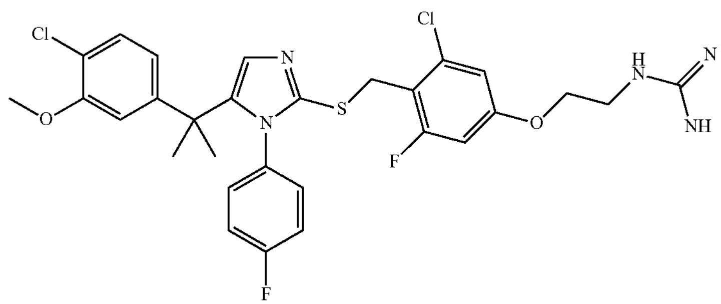 | 1-(2-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]oxy}ethyl)guanidine | A | A |

TABLE 1-continued

| Structure | NAME | cAMP (EC$_{50}$) (nM) | CRE-Luc (EC$_{50}$) (nM) |
|---|---|---|---|
| 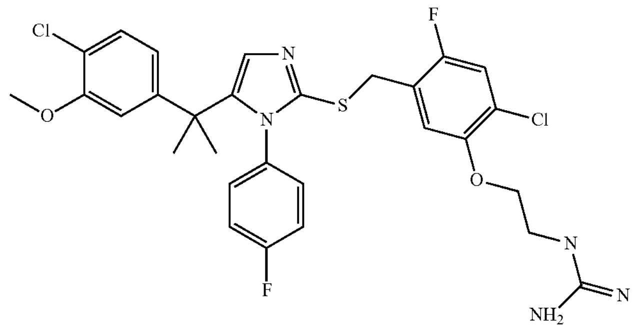 [SMILES: COc1cc(C(C)(C)c2cnc(SCc3cc(OCCNC(=N)N)c(Cl)cc3F)n2-c2ccc(F)cc2)ccc1Cl] | 1-(2-{[2-chloro-5-({[5-{1-[4-chloro-3-(methyloxy)phenyl]-1-methylethyl}-1-(4-fluorophenyl)-1H-imidazol-2-yl]thio}methyl)-4-fluorophenyl]oxy}ethyl)guanidine | A | C |
| 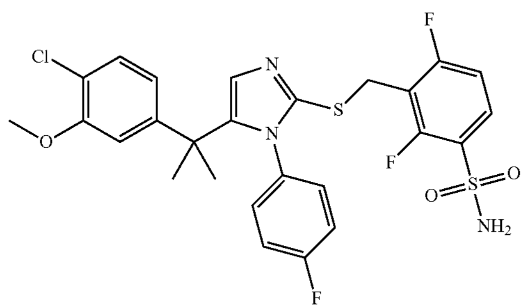 [SMILES: COc1cc(C(C)(C)c2cnc(SCc3c(F)ccc(S(N)(=O)=O)c3F)n2-c2ccc(F)cc2)ccc1Cl] | 3-({[5-{1-[4-chloro-3-(methyloxy)phenyl]-1-methylethyl}-1-(4-fluorophenyl)-1H-imidazol-2-yl]thio}methyl)-2,4-difluorobenzenesulfonamide | A | A |
| 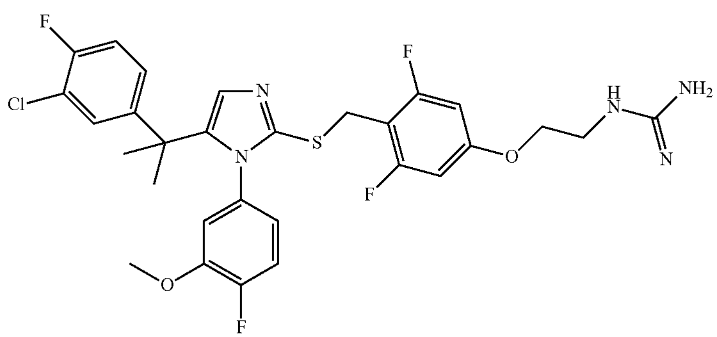 [SMILES: COc1cc(-n2c(C(C)(C)c3ccc(F)c(Cl)c3)cnc2SCc2c(F)cc(OCCNC(=N)N)cc2F)ccc1F] | 1-[2-({4-[({5-[1-(3-chloro-4-fluorophenyl)-1-methylethyl]-1-[4-fluoro-3-(methyloxy)phenyl]-1H-imidazol-2-yl}thio)methyl]-3,5-difluorophenyl}oxy)ethyl]guanidine | A | A |

TABLE 1-continued

| Structure | NAME | cAMP (EC$_{50}$) (nM) | CRE-Luc (EC$_{50}$) (nM) |
|---|---|---|---|
| 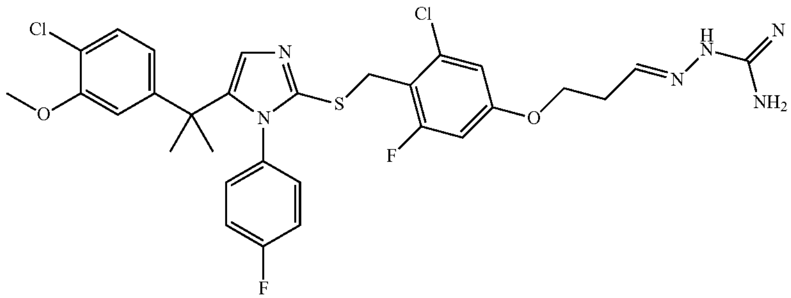 [SMILES: COc1cc(C(C)(C)c2cnc(SCc3c(F)cc(OCC/C=N/NC(=N)N)cc3Cl)n2-c2ccc(F)cc2)ccc1Cl] | (2E)-2-(3-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]oxy}propylidene)hydrazinecarboximidamide | A | A |
| 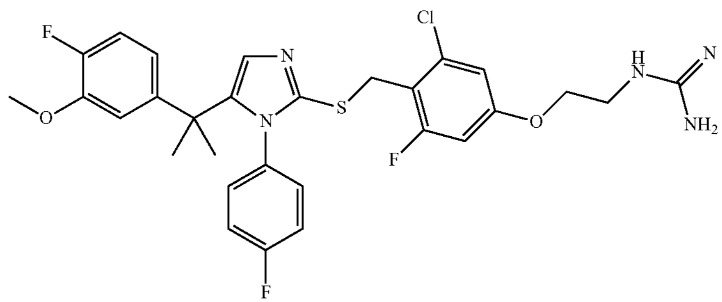 [SMILES: COc1cc(C(C)(C)c2cnc(SCc3c(F)cc(OCCNC(=N)N)cc3Cl)n2-c2ccc(F)cc2)ccc1F] | 1-(2-{[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]oxy}ethyl)guanidine | A | A |
| 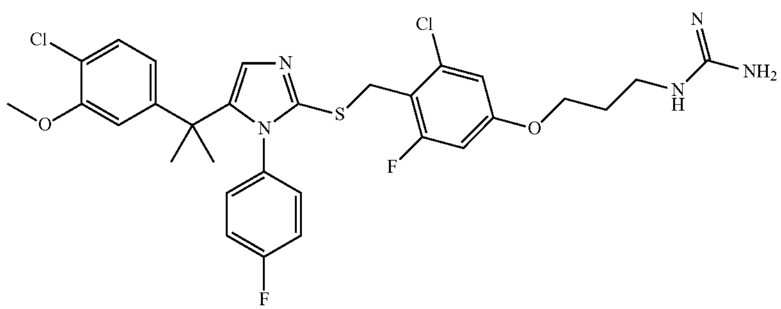 [SMILES: COc1cc(C(C)(C)c2cnc(SCc3c(F)cc(OCCCNC(=N)N)cc3Cl)n2-c2ccc(F)cc2)ccc1Cl] | 1-(3-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]oxy}propyl)guanidine | A | A |

TABLE 1-continued

| Structure | NAME | cAMP (EC$_{50}$) (nM) | CRE-Luc (EC$_{50}$) (nM) |
|---|---|---|---|
| 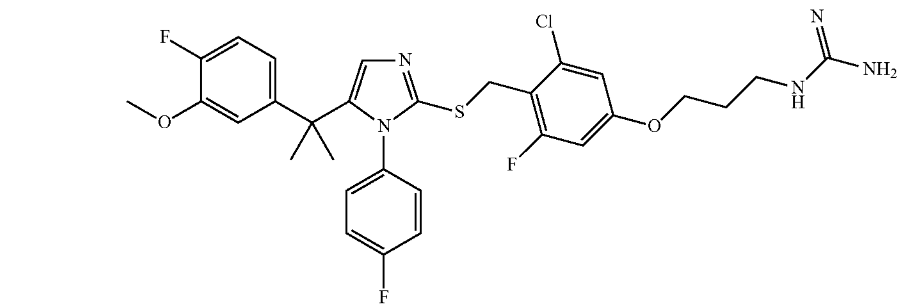 | 1-(3-{[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]oxy}propyl)guanidine | A | A |
| 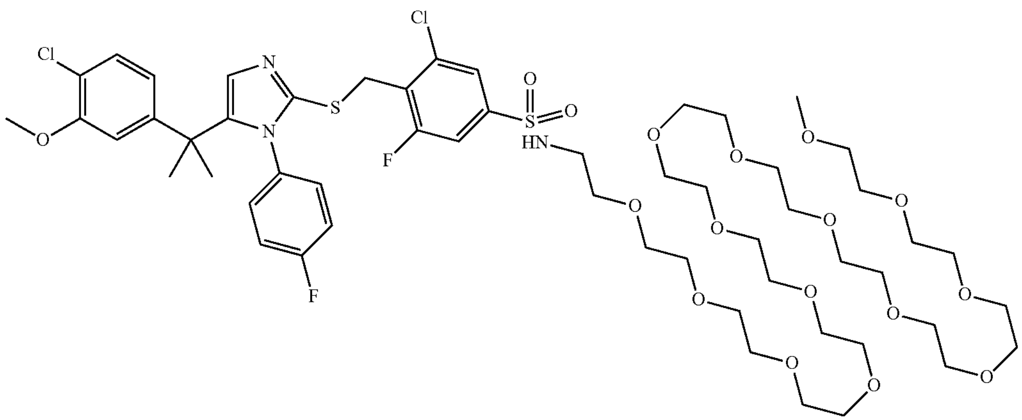 | 3-chloro-4-({[5-{1-[4-chloro-3-(methyloxy)phenyl]-1-methylethyl}-1-(4-fluorophenyl)-1H-imidazol-2-yl]thio}methyl)-5-fluoro-N-3,6,9,12,15,18,21,24,27,30,33,36,39,42-tetradecaoxatritetracont-1-ylbenzenesulfonamide | A | A |

TABLE 1-continued
| Structure | NAME | cAMP (EC$_{50}$) (nM) | CRE-Luc (EC$_{50}$) (nM) |
|---|---|---|---|
| 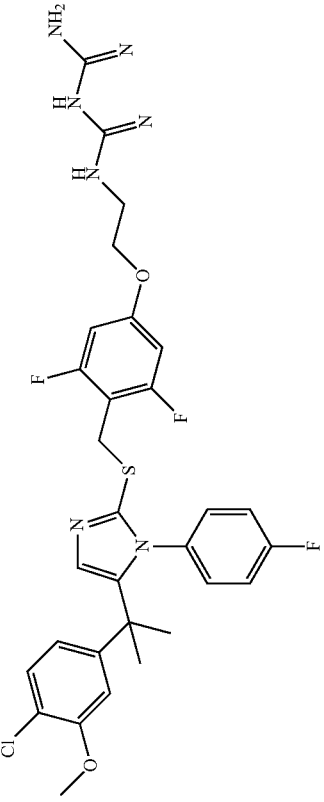 | N-(2-{[4-({[5-{1-[4-chloro-3-(methyloxy)phenyl]-1-methylethyl}-1-(4-fluorophenyl)-1H-imidazol-2-yl]thio}methyl)-3,5-difluorophenyl]oxy}ethyl)imido dicarbonimidic diamide | A | A |
| 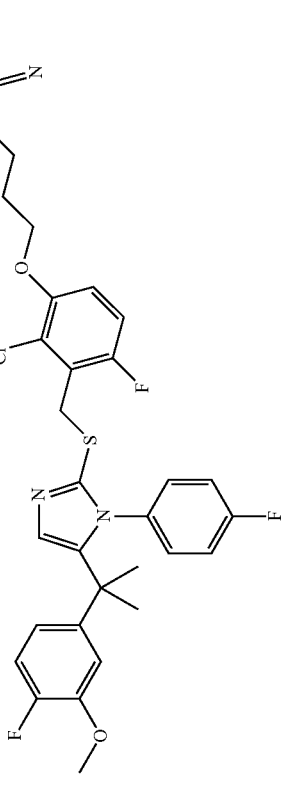 | 1-(3-{[2-chloro-4-fluoro-3-({[5-{1-[4-fluoro-3-(methyloxy)phenyl]-1-methylethyl}-1-(4-fluorophenyl)-1H-imidazol-2-yl]thio}methyl)phenyl]oxy}propyl)guanidine | A | A |

TABLE 2

| # | Structure | CRE-Luc | cAMP |
|---|-----------|---------|------|
| 1 | 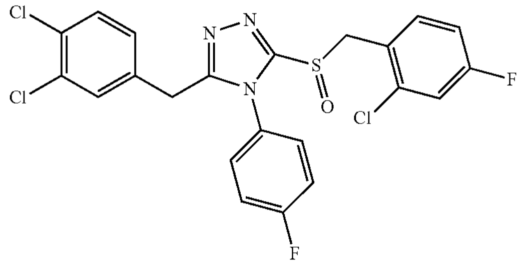 [SMILES: O=S(Cc1ccc(F)cc1Cl)c1nnc(Cc2ccc(Cl)c(Cl)c2)n1-c1ccc(F)cc1] | D | |
| 2 | 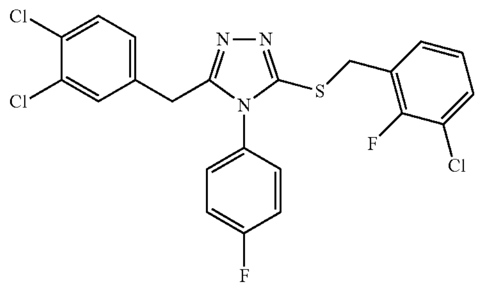 [SMILES: Fc1ccc(-n2c(Cc3ccc(Cl)c(Cl)c3)nnc2SCc2cccc(Cl)c2F)cc1] | D | |
| 3 | 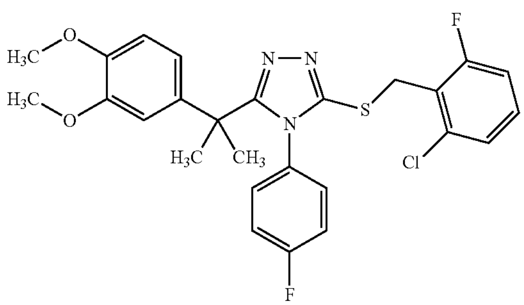 [SMILES: COc1ccc(C(C)(C)c2nnc(SCc3c(F)cccc3Cl)n2-c2ccc(F)cc2)cc1OC] | A | |
| 4 | 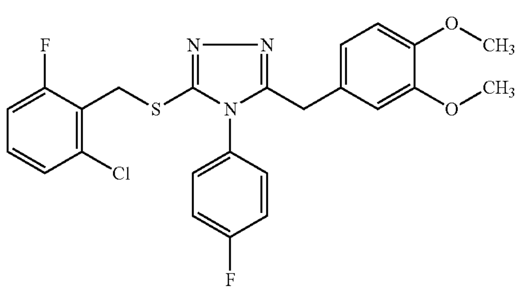 [SMILES: COc1ccc(Cc2nnc(SCc3c(F)cccc3Cl)n2-c2ccc(F)cc2)cc1OC] | A | |
| 5 | 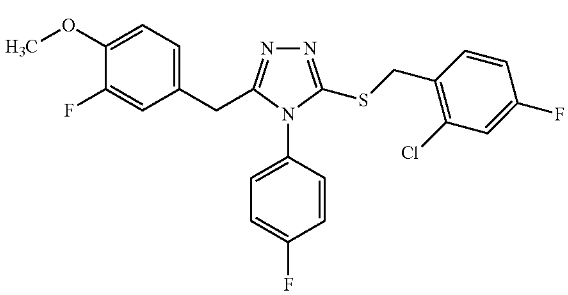 [SMILES: COc1ccc(Cc2nnc(SCc3ccc(F)cc3Cl)n2-c2ccc(F)cc2)cc1F] | D | |

TABLE 2-continued

| # | Structure | CRE-Luc | cAMP |
|---|-----------|---------|------|
| 6 | 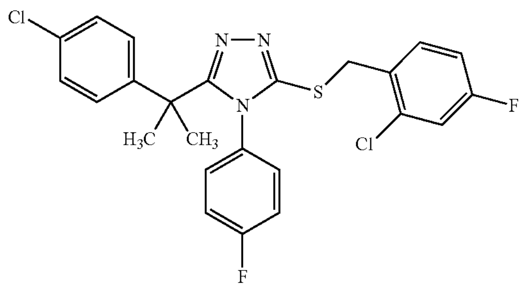 [SMILES: CC(C)(c1ccc(Cl)cc1)c1nnc(SCc2ccc(F)cc2Cl)n1-c1ccc(F)cc1] | D | |
| 7 | 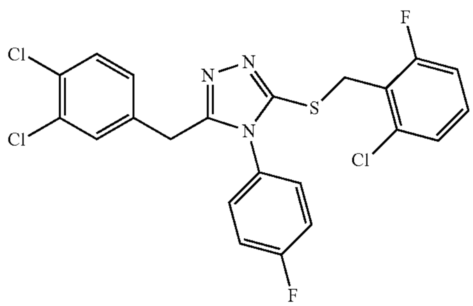 [SMILES: Fc1ccc(-n2c(Cc3ccc(Cl)c(Cl)c3)nnc2SCc2c(F)cccc2Cl)cc1] | C | |
| 8 | 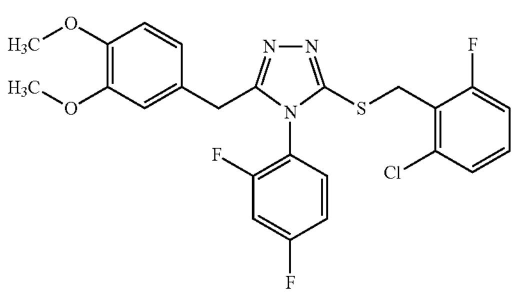 [SMILES: COc1ccc(Cc2nnc(SCc3c(F)cccc3Cl)n2-c2ccc(F)cc2F)cc1OC] | A | |
| 9 | 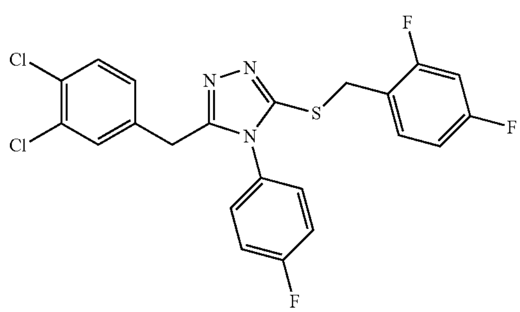 [SMILES: Fc1ccc(-n2c(Cc3ccc(Cl)c(Cl)c3)nnc2SCc2ccc(F)cc2F)cc1] | D | |
| 10 | 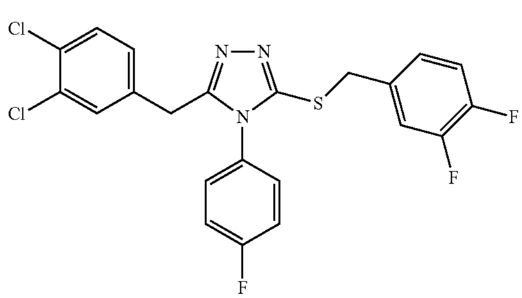 | D | |

TABLE 2-continued

| # | Structure | CRE-Luc | cAMP |
|---|---|---|---|
| 11 | 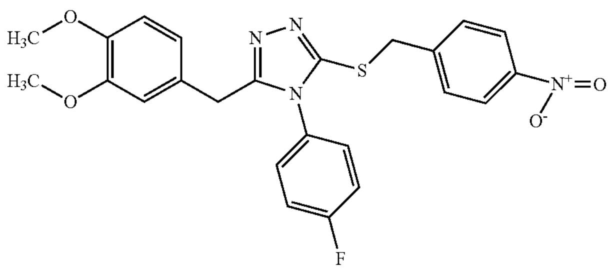 [SMILES: COc1ccc(Cc2nnc(SCc3ccc([N+](=O)[O-])cc3)n2-c2ccc(F)cc2)cc1OC] | C | |
| 12 | 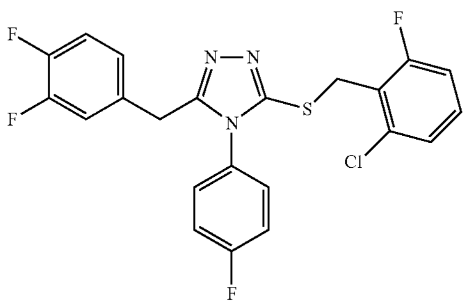 [SMILES: Fc1ccc(-n2c(Cc3ccc(F)c(F)c3)nnc2SCc2c(F)cccc2Cl)cc1] | D | |
| 13 | 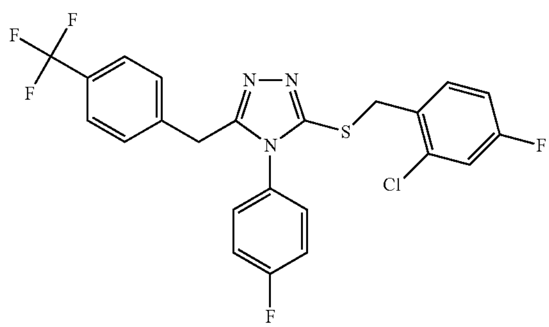 [SMILES: Fc1ccc(-n2c(Cc3ccc(C(F)(F)F)cc3)nnc2SCc2ccc(F)cc2Cl)cc1] | D | |
| 14 | 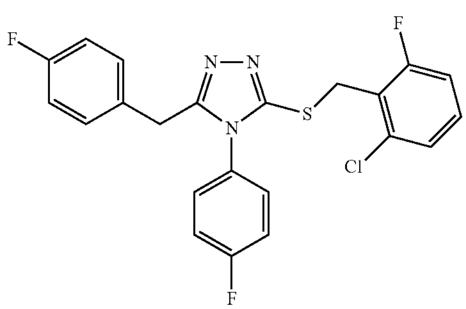 [SMILES: Fc1ccc(Cc2nnc(SCc3c(F)cccc3Cl)n2-c2ccc(F)cc2)cc1] | D | |
| 15 | 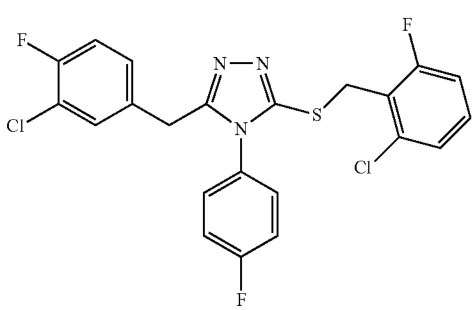 [SMILES: Fc1ccc(-n2c(Cc3ccc(F)c(Cl)c3)nnc2SCc2c(F)cccc2Cl)cc1] | D | |

TABLE 2-continued

| # | Structure | CRE-Luc | cAMP |
|---|---|---|---|
| 16 | 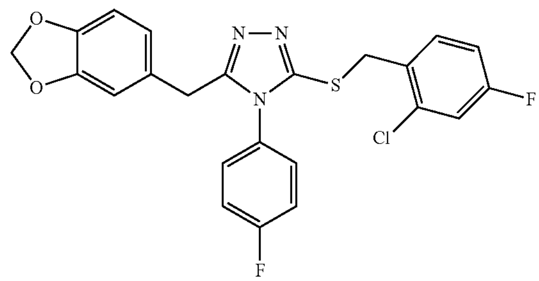 [SMILES: Fc1ccc(-n2c(Cc3ccc4c(c3)OCO4)nnc2SCc2ccc(F)cc2Cl)cc1] | | C |
| 17 | 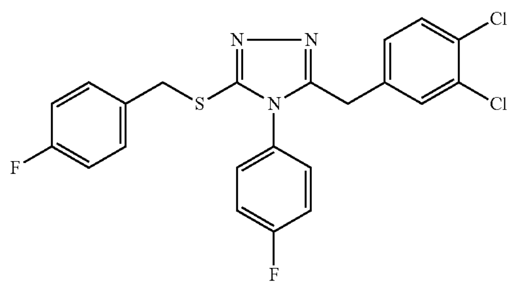 [SMILES: Fc1ccc(CSc2nnc(Cc3ccc(Cl)c(Cl)c3)n2-c2ccc(F)cc2)cc1] | | D |
| 18 | 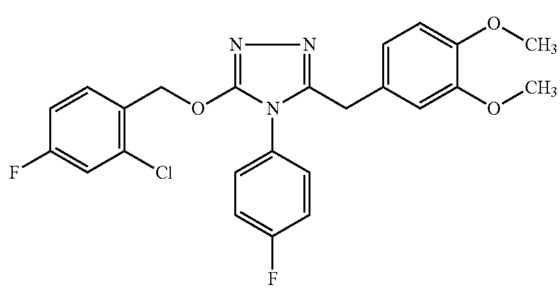 [SMILES: COc1ccc(Cc2nnc(OCc3ccc(F)cc3Cl)n2-c2ccc(F)cc2)cc1OC] | | D |
| 19 | 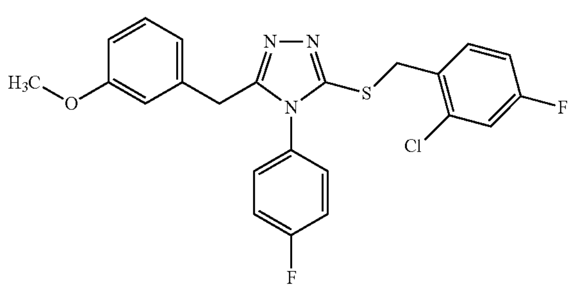 [SMILES: COc1cccc(Cc2nnc(SCc3ccc(F)cc3Cl)n2-c2ccc(F)cc2)c1] | | C |
| 20 | 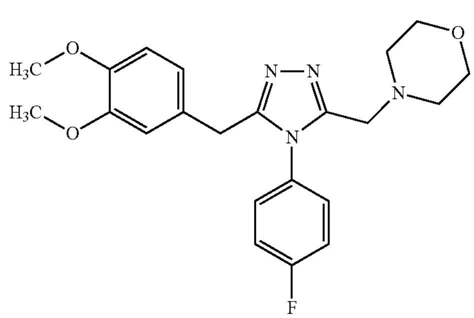 [SMILES: COc1ccc(Cc2nnc(CN3CCOCC3)n2-c2ccc(F)cc2)cc1OC] | | D |

TABLE 2-continued

| # | Structure | CRE-Luc | cAMP |
|---|-----------|---------|------|
| 21 | 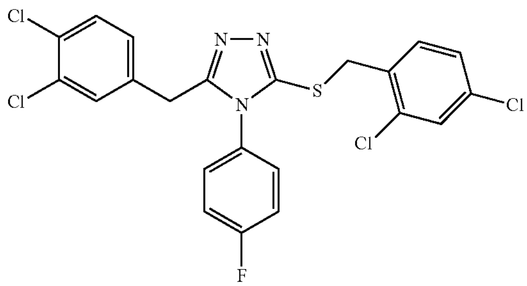 [SMILES: Fc1ccc(-n2c(Cc3ccc(Cl)c(Cl)c3)nnc2SCc2ccc(Cl)cc2Cl)cc1] | D | |
| 22 | 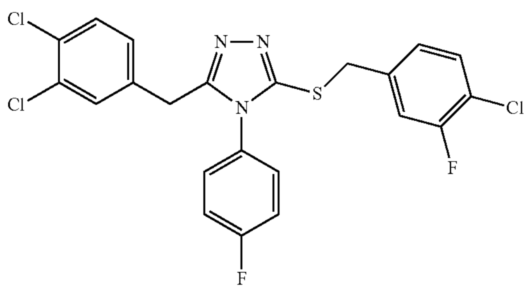 [SMILES: Fc1ccc(-n2c(Cc3ccc(Cl)c(Cl)c3)nnc2SCc2ccc(Cl)c(F)c2)cc1] | D | |
| 23 | 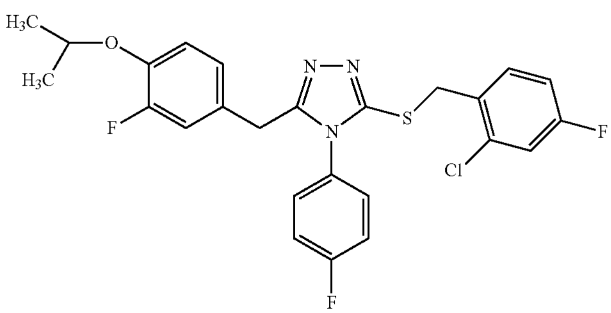 [SMILES: CC(C)Oc1ccc(Cc2nnc(SCc3ccc(F)cc3Cl)n2-c2ccc(F)cc2)cc1F] | D | |
| 24 | 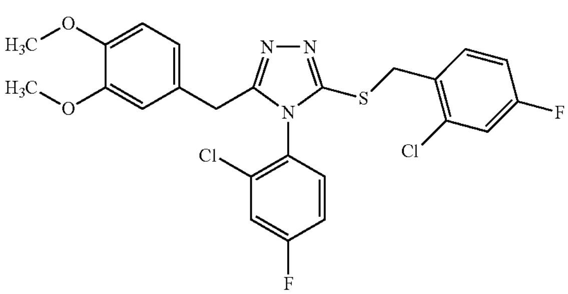 [SMILES: COc1ccc(Cc2nnc(SCc3ccc(F)cc3Cl)n2-c2ccc(F)cc2Cl)cc1OC] | A | |
| 25 | 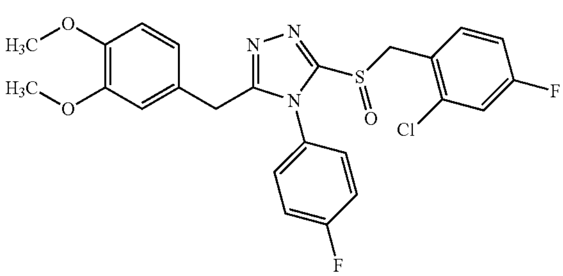 [SMILES: COc1ccc(Cc2nnc(S(=O)Cc3ccc(F)cc3Cl)n2-c2ccc(F)cc2)cc1OC] | C | |

TABLE 2-continued

| # | Structure | CRE-Luc | cAMP |
|---|---|---|---|
| 26 | 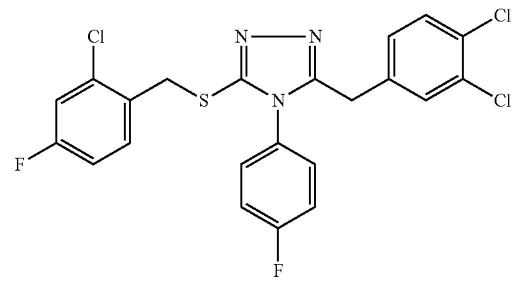 [SMILES: Fc1ccc(-n2c(Cc3ccc(Cl)c(Cl)c3)nnc2SCc2ccc(F)cc2Cl)cc1] | C | |
| 27 | 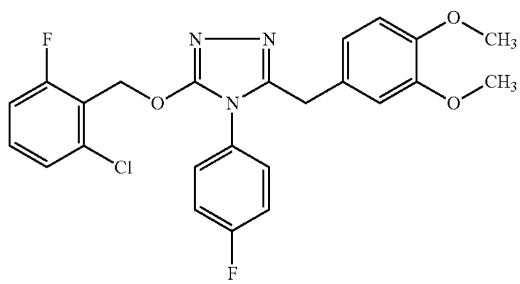 [SMILES: COc1ccc(Cc2nnc(OCc3c(F)cccc3Cl)n2-c2ccc(F)cc2)cc1OC] | D | |
| 28 | 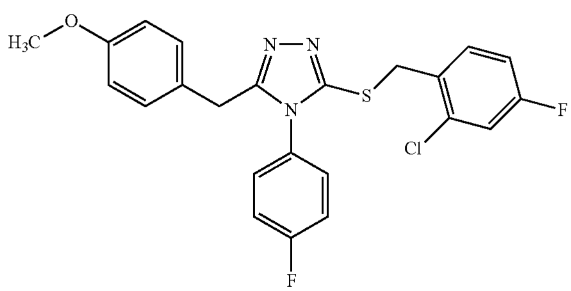 [SMILES: COc1ccc(Cc2nnc(SCc3ccc(F)cc3Cl)n2-c2ccc(F)cc2)cc1] | D | |
| 29 | 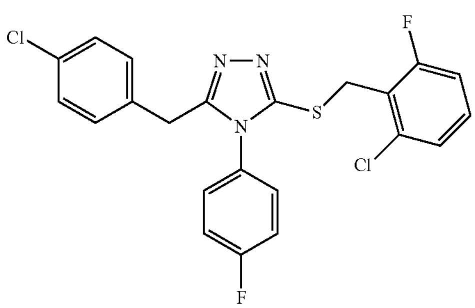 [SMILES: Fc1ccc(-n2c(Cc3ccc(Cl)cc3)nnc2SCc2c(F)cccc2Cl)cc1] | C | |
| 30 | 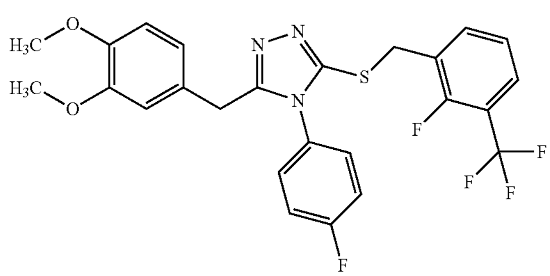 [SMILES: COc1ccc(Cc2nnc(SCc3cccc(C(F)(F)F)c3F)n2-c2ccc(F)cc2)cc1OC] | A | |

TABLE 2-continued

| # | Structure | CRE-Luc | cAMP |
|---|-----------|---------|------|
| 31 | 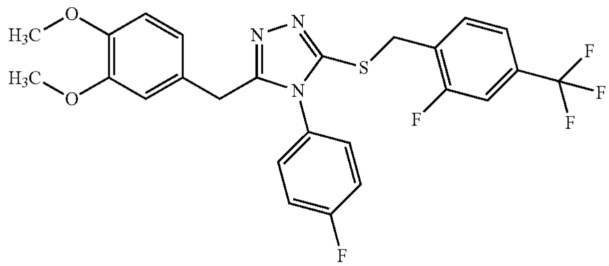 [SMILES: COc1ccc(Cc2nnc(SCc3ccc(C(F)(F)F)cc3F)n2-c2ccc(F)cc2)cc1OC] | C | |
| 32 | 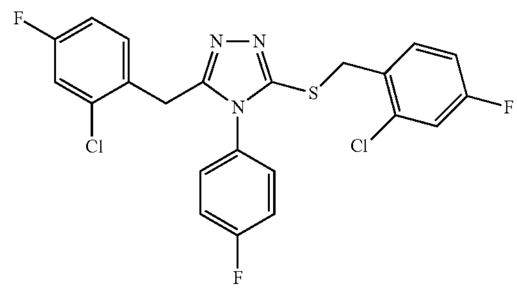 [SMILES: Fc1ccc(-n2c(Cc3ccc(F)cc3Cl)nnc2SCc2ccc(F)cc2Cl)cc1] | D | |
| 33 | 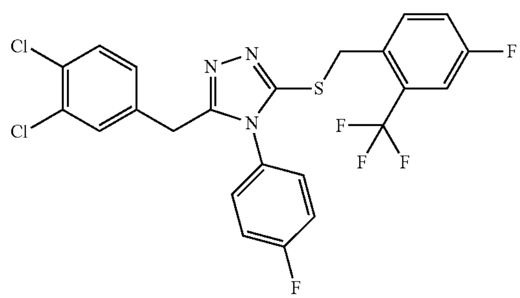 [SMILES: Fc1ccc(-n2c(Cc3ccc(Cl)c(Cl)c3)nnc2SCc2ccc(F)cc2C(F)(F)F)cc1] | D | |
| 34 | 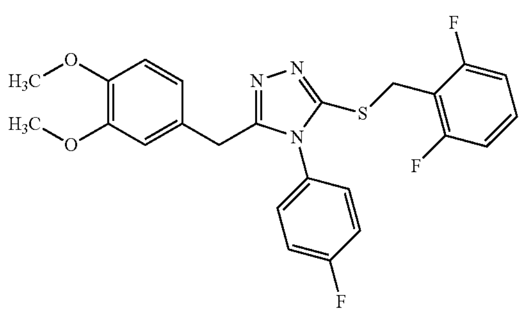 [SMILES: COc1ccc(Cc2nnc(SCc3c(F)cccc3F)n2-c2ccc(F)cc2)cc1OC] | A | |
| 35 | 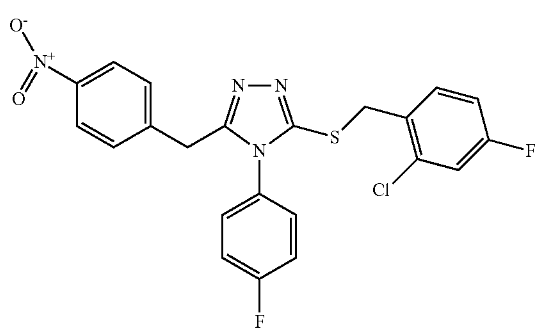 [SMILES: O=[N+]([O-])c1ccc(Cc2nnc(SCc3ccc(F)cc3Cl)n2-c2ccc(F)cc2)cc1] | D | |

TABLE 2-continued

| # | Structure | CRE-Luc | cAMP |
|---|---|---|---|
| 36 | 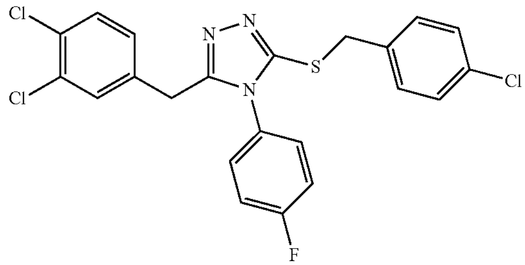 [SMILES: Fc1ccc(-n2c(Cc3ccc(Cl)c(Cl)c3)nnc2SCc2ccc(Cl)cc2)cc1] | D | |
| 37 | 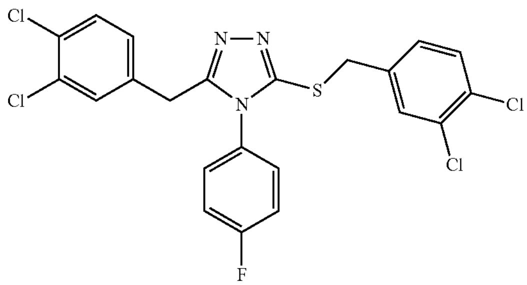 [SMILES: Fc1ccc(-n2c(Cc3ccc(Cl)c(Cl)c3)nnc2SCc2ccc(Cl)c(Cl)c2)cc1] | D | |
| 38 | 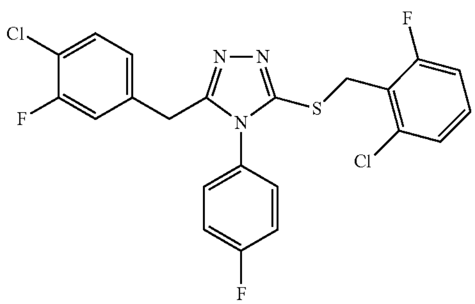 [SMILES: Fc1ccc(-n2c(Cc3ccc(Cl)c(F)c3)nnc2SCc2c(F)cccc2Cl)cc1] | C | |
| 39 | 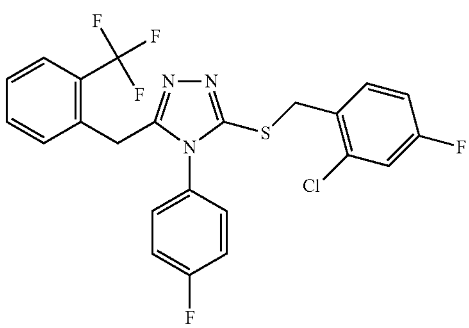 [SMILES: Fc1ccc(-n2c(Cc3ccccc3C(F)(F)F)nnc2SCc2ccc(F)cc2Cl)cc1] | D | |
| 40 | 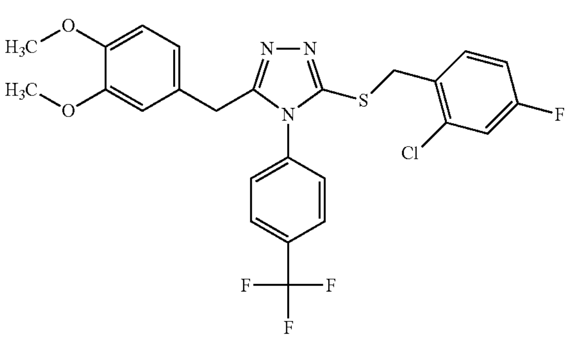 [SMILES: COc1ccc(Cc2nnc(SCc3ccc(F)cc3Cl)n2-c2ccc(C(F)(F)F)cc2)cc1OC] | D | |

TABLE 2-continued

| # | Structure | CRE-Luc | cAMP |
|---|-----------|---------|------|
| 41 | 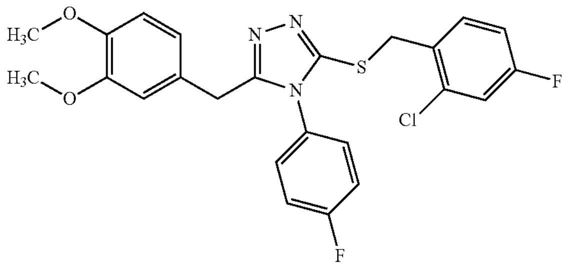 [SMILES: COc1ccc(Cc2nnc(SCc3ccc(F)cc3Cl)n2-c2ccc(F)cc2)cc1OC] | A | |
| 42 | 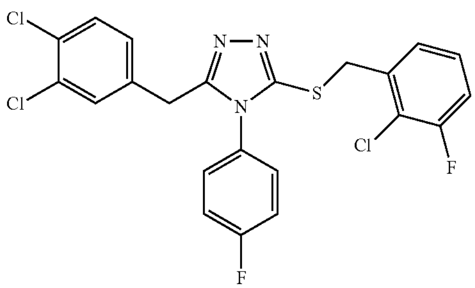 [SMILES: Fc1ccc(-n2c(Cc3ccc(Cl)c(Cl)c3)nnc2SCc2cccc(F)c2Cl)cc1] | C | |
| 43 | 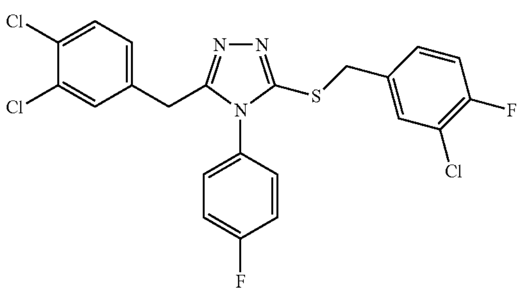 [SMILES: Fc1ccc(-n2c(Cc3ccc(Cl)c(Cl)c3)nnc2SCc2ccc(F)c(Cl)c2)cc1] | D | |
| 44 | 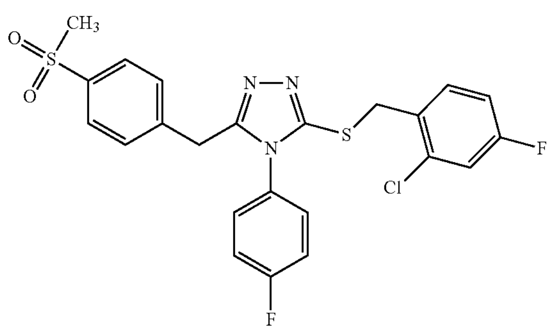 [SMILES: CS(=O)(=O)c1ccc(Cc2nnc(SCc3ccc(F)cc3Cl)n2-c2ccc(F)cc2)cc1] | D | |
| 45 | 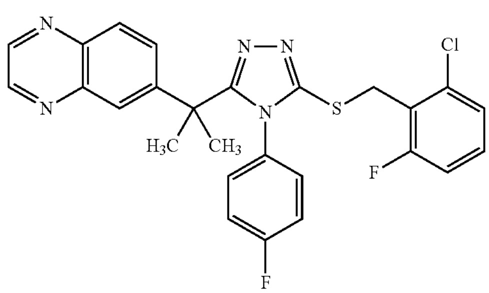 [SMILES: CC(C)(c1ccc2nccnc2c1)c1nnc(SCc2c(F)cccc2Cl)n1-c1ccc(F)cc1] | A | A |

TABLE 2-continued
| # | Structure | CRE-Luc | cAMP |
|---|---|---|---|
| 46 | 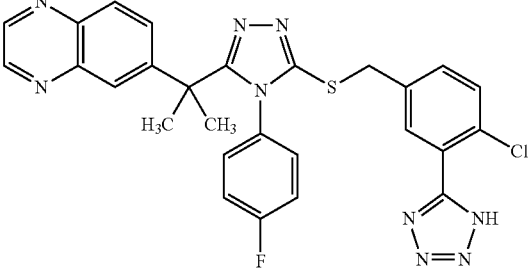 | D | |
| 47 | 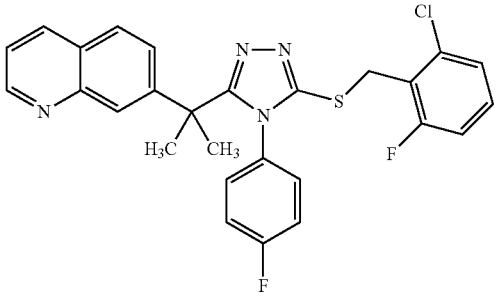 [SMILES: CC(C)(c1ccc2cccnc2c1)c1nnc(SCc2c(F)cccc2Cl)n1-c1ccc(F)cc1] | A | A |
| 48 | 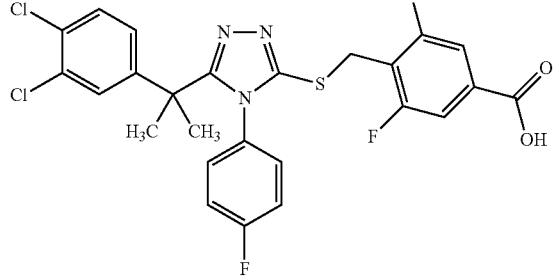 | C | C |
| 49 | 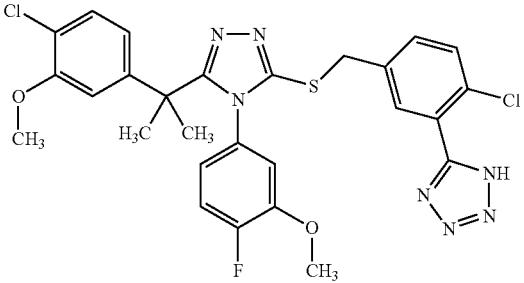 [SMILES: COc1cc(-n2c(SCc3ccc(Cl)c(-c4nnn[nH]4)c3)nnc2C(C)(C)c2ccc(Cl)c(OC)c2)ccc1F] | A | C |
| 50 | 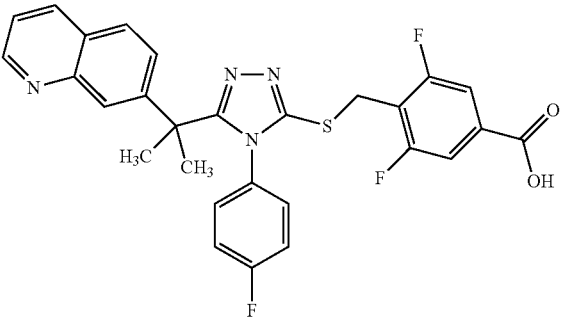 [SMILES: CC(C)(c1ccc2cccnc2c1)c1nnc(SCc2c(F)cc(C(=O)O)cc2F)n1-c1ccc(F)cc1] | D | |

We claim:
1. A compound of Formula VIII:

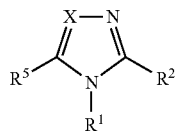

or pharmaceutically acceptable salt thereof, wherein:
X is =C($R^4$)—;
$R^1$ is $R^C$;
or X can be =C($R^C$)— only when $R^1$ is phenyl optionally substituted with one, two, or three $R^{C10}$ groups;
$R^C$ is selected from phenyl, —($C_5$-$C_6$)-cycloalkyl, —$CH_2$-phenyl, heteroaryl, optionally substituted with —$OR^{C13}$, —N($R^{C13}$)$_2$ or —S($R^{C13}$), wherein the cyclic group of $R^C$ can be optionally substituted with 1, 2, 3, 4 or 5 $R^{C10}$ groups, wherein the 1, 2, 3, 4, or 5 $R^{C10}$ groups are independently selected from $R^{C10A}$ and $R^{C10B}$, provided that $R^C$ cannot be substituted with more than 2 $R^{C10B}$ groups, and provided that substitution of $R^C$ with $R^{C10}$ can only occur by replacing a hydrogen that is covalently bound to either a carbon or a nitrogen of $R^C$, wherein
each $R^{C10A}$ is independently selected from halo, cyano and —($C_1$-$C_4$)alkyl optionally substituted with 1-3 groups selected from —OH and halo;
each $R^{C10B}$ is independently selected from —C(O)$NH_2$, (5-6 membered)heterocycloalkyl, —O—($C_1$-$C_4$)alkyl-$R^{C11}$, —C(O)$OR^{C12}$, —OC(O)$OR^{C12}$ and —O—($C_1$-$C_4$)alkyl optionally substituted with —OH or —C(O)OH;
$R^{C11}$ is cyano, nitro, —N($R^{C12}$)$_2$, —$OR^{C12}$, —$SR^{C12}$, —C(O)$R^{C12}$, —C(O)$OR^{C12}$, —C(O)N($R^{C12}$)$_2$, —S(O)N($R^{C12}$)$_2$, —S(O)$_2$N($R^{C12}$)$_2$, —S(O)$_2R^{C12}$, —OC(O)$R^{C12}$, —OC(O)$OR^{C12}$, —OC(O)N($R^{C12}$)$_2$, —N($R^{C12}$)C(O)$R^{C12}$, —N($R^{C12}$)C(O)$OR^{C12}$, —N($R^{C12}$)C(O)N($R^{C12}$)$_2$, or —N($R^{C12}$)C(=N$R^{C12}$)N($R^{C12}$)$_2$;
each $R^{C12}$ is independently selected from hydrogen, —($C_1$-$C_4$)alkyl, and —($C_1$-$C_4$)haloalkyl;
each $R^{C13}$ is independently selected from hydrogen, —($C_1$-$C_4$)alkyl, and —($C_1$-$C_4$)haloalkyl;
$R^2$ is -$L^D$-$R^{D1}$;
$L^D$ is —[C(R)$_2$]$_p$—Y—[C(R)$_2$]$_q$—;
p is 0 or 1;
q is 0 or 1;
each R is independently selected from H, —($C_1$-$C_3$)alkyl, halo, —OH, and —$CH_2$OH;
Y is a bond, —S—, —S(O)$_2$—, —CH(OH)—, —O—, —C(H)=C(H)—, —C(O)—($C_1$-$C_4$)alkyl-, —($C_1$-$C_4$)alkyl-S—($C_1$-$C_4$)alkyl-, —($C_1$-$C_4$)alkyl-N($R^Y$)—($C_1$-$C_4$)alkyl-, —C(H)(halo)-, —($C_1$-$C_4$)alkyl-S(O)$_2$—, —S(O)$_2$—N($R^Y$)—, —($C_1$-$C_4$)alkyl-O—, or —C(O)—N($R^Y$)—, wherein $R^Y$ is H, —($C_1$-$C_4$)alkyl, hydroxyl ($C_1$-$C_4$)alkyl or —C≡C—($C_1$-$C_3$)alkyl-;
$R^{D1}$ is selected from —($C_6$-$C_{10}$)aryl, —N(H)-phenyl, cycloalkyl, heterocycloalkyl, and heteroaryl, wherein $R^{D1}$ can be optionally substituted with 1, 2, 3, 4 or 5 $R^{D10}$, provided that substitution of $R^{D1}$ with $R^{D10}$ can only occur by replacing a hydrogen that is covalently bound to either a carbon or a nitrogen of $R^{D1}$, wherein the 1-5 $R^{D10}$ groups are independently selected from A groups and B groups, provided that $R^{D1}$ cannot be substituted with more than 2 B groups;
each A group, when they occur, is independently selected from halo, —$CF_3$, —CN, —$NO_2$, —OH, —$NH_2$, —O—($C_1$-$C_4$)alkyl optionally substituted at the alkyl group with 1-3 substituents independently selected from —OH and halo, and —($C_1$-$C_4$)alkyl optionally substituted with 1-3 substituents independently selected from —OH and halo;
each B group, when they occur, is independently selected from —($C_1$-$C_4$)alkylN($R^{D11}$)$_2$, —C(O)—$NH_2$, —C(O)—N(H)—OH, —C(O)—N(H)—$R^{D11C}$, —C(O)—($C_1$-$C_4$)alkyl optionally substituted with $R^{D11B}$, —C(O)OH, —S(O)$_2$—($C_1$-$C_4$)alkyl-N($R^{D11}$)$_2$, —S(O)$_2$—N($R^{D11}$)$R^{D11C}$, —S(O)$_2$—N(H)C(O)—N($R^{D11}$)$R^{D11B}$, —C(=NH)—$NH_2$, —C(O)O—($C_1$-$C_4$)alkyl optionally substituted with $R^{D11B}$, —O—($C_1$-$C_4$)alkyl optionally substituted at the alkyl group with 1 or 2 $R^{D11B}$, —C(O)-heterocycloalkyl, wherein the —C(O)-heterocycloalkyl can be optionally substituted with $R^{D11B}$, provided that substitution of —C(O)-heterocycloalkyl with $R^{D11B}$ can only occur by replacing a hydrogen that is covalently bound to either a carbon or a nitrogen of —C(O)-heterocycloalkyl, —C(O)—N(H)—($C_1$-$C_6$)alkyl optionally substituted at the alkyl group with 1 or 2 $R^{D11B}$, heterocycloalkyl optionally substituted with oxo or $R^{D11}$, provided that substitution of the heterocycloalkyl with $R^{D11}$ can only occur by replacing a hydrogen that is covalently bound to either a carbon or a nitrogen of the heterocycloalkyl, heterocycloalkenyl optionally substituted with oxo or $R^{D11}$, provided that substitution of the heterocycloalkenyl with $R^{D11}$ can only occur by replacing a hydrogen that is covalently bound to either a carbon or a nitrogen of the heterocycloalkenyl, heteroaryl optionally substituted with $R^{D11}$, provided that substitution of the heteroaryl with $R^{D11}$ can only occur by replacing a hydrogen that is covalently bound to either a carbon or a nitrogen of the heteroaryl, —S(O)$_2$-(4-6 membered)heterocycloalkyl optionally substituted with $R^{D11C}$ provided that substitution of the —S(O)$_2$-(4-6 membered)heterocycloalkyl with $R^{D11C}$ can only occur by replacing a hydrogen that is covalently bound to either a carbon or a nitrogen of the —S(O)$_2$-(4-6 membered)heterocycloalkyl, —S(O)$_2$—N(H)C(O)—($C_1$-$C_4$)alkyl optionally substituted with $R^{D11B}$, —S(O)$_2$—N(H)C(O)O—($C_1$-$C_4$)alkyl optionally substituted with $R^{D11B}$, —S(O)$_2$—($C_1$-$C_4$)alkyl optionally substituted with $R^{D11B}$, —N(H)—C(O)—($C_1$-$C_4$)alkyl optionally substituted at the alkyl group with 1 or 2 $R^{D11B}$, —N(H)—C(O)—N(H)—($C_1$-$C_3$)alkyl optionally substituted at the alkyl group with $R^{D11B}$, —($C_1$-$C_6$)alkyl optionally substituted with 1 or 2 $R^{D11B}$, and —C≡C—($C_1$-$C_3$)alkyl optionally substituted with $R^{D11B}$;
each $R^{D11}$ is independently selected from H, —($C_3$-$C_6$)cycloalkyl, —OH, —($C_1$-$C_4$)haloalkyl, —($C_1$-$C_4$)alkyl optionally substituted with halo, —OH, —C(O)OH, —S(O)$_2$OH, C(O)OH, —$NH_2$, or —N(H)C(=NH)$NH_2$, and —($C_1$-$C_3$)alkyl-phenyl optionally substituted at the phenyl group with 1-3 substituents selected from methoxy, hydroxyl and halo;

$R^{D11B}$ is selected from H, —OH, —CF$_3$, a PEG polymer, —N(R$^{D11}$)$_2$, —C(O)OH, —O—(C$_1$-C$_4$)alkyl, —S(O)$_2$OH, —C(=NH)—NH$_2$, —N(H)C(=NH)NH$_2$, —C(H)=NC(=NH)NH$_2$, —C(H)=NN(H)C(=NH)NH$_2$, —N(H)C(=NH)—N(H)C(=NH)NH$_2$, —C(O)—(C$_1$-C$_3$)alkyl, —O—(C$_1$-C$_4$)alkyl-C(O)OH, (5-6 membered)heteroaryl, —(C$_1$-C$_4$)alkyl optionally substituted with 1-3 groups independently selected from halo, —OH, —S(O)$_2$OH, C(O)OH, —NH$_2$, and —N(H)C(=NH)NH$_2$, —(C$_0$-C$_3$)alkyl-(5-8 membered)heterocycloalkyl, optionally substituted with 1, 2 or 3 R$^{D11}$, provided that substitution of —(C$_0$-C$_3$)alkyl-(5-8 membered)heterocycloalkyl with R$^{D11}$ can only occur by replacing a hydrogen that is covalently bound to either a carbon or a nitrogen of —(C$_0$-C$_3$)alkyl-(5-8 membered) heterocycloalkyl, —(C$_0$-C$_3$)alkyl-(C$_3$-C$_6$)cycloalkyl optionally substituted with R$^{D11}$, and aryl optionally substituted with 1-5 halo;

or R$^{D11}$ and R$^{D11B}$, when they both exist and are each attached to nitrogen, can join together with the nitrogen to which they are attached to form a (5-6 membered) heterocycloalkyl optionally substituted with a group selected from —(C$_3$-C$_6$)cycloalkyl, —(C$_1$-C$_4$)haloalkyl, —OH, —S(O)$_2$OH, C(O)OH, —NH$_2$, —N(H)C(=NH)NH$_2$, —(C$_1$-C$_4$)alkyl optionally substituted with halo, —OH or —C(O)OH, and —(C$_1$-C$_3$)alkyl-phenyl optionally substituted at the phenyl group with 1-3 substituents selected from methoxy, hydroxyl and halo, provided that substitution of the (5-6 membered) heterocycloalkyl can only occur by replacing a hydrogen that is covalently bound to either a carbon or a nitrogen of the (5-6 membered) heterocycloalkyl;

$R^{D11C}$ is selected from H, —OH, —CF$_3$, —O—(C$_1$-C$_4$)alkyl, —(C$_1$-C$_4$)alkyl-N(H)C(=NH)—NH$_2$, —(C$_0$-C$_3$)alkyl-(5-6 membered)heteroaryl, —(C$_1$-C$_4$)alkyl optionally substituted with 1-3 groups independently selected from halo, —OH, —S(O)$_2$OH, C(O)OH, —NH$_2$, and —N(H)C(=NH)NH$_2$, —(C$_0$-C$_3$)alkyl-(5-6 membered)heterocycloalkyl optionally substituted with one (5-6 membered)heteroaryl, provided that substitution of the —(C$_0$-C$_3$)alkyl-(5-6 membered)heterocycloalkyl with (5-6 membered)heteroaryl can only occur by replacing a hydrogen that is covalently bound to either a carbon or a nitrogen of the —(C$_0$-C$_3$)alkyl-(5-6 membered)heterocycloalkyl, —(C$_0$-C$_3$)alkyl-(5-6 membered)heterocycloalkyl substituted with 1, 2 or 3 groups selected from —OH and —(C$_1$-C$_3$)alkyl, provided that substitution of the —(C$_0$-C$_3$)alkyl-(5-6 membered)heterocycloalkyl can only occur by replacing a hydrogen that is covalently bound to either a carbon or a nitrogen of the —(C$_0$-C$_3$)alkyl-(5-6 membered)heterocycloalkyl, and —(C$_0$-C$_3$)alkyl-aryl optionally substituted at the aryl group with 1-3 halo;

$R^4$ is H, —(C$_1$-C$_3$)alkyl or halo;

$R^5$ is —[C(R$^8$)$_2$]-phenyl, —[C(R$^8$)$_2$]-naphthalenyl, or —[C(R$^8$)$_2$]-(5-10 membered) heteroaryl, wherein the heteroaryl is selected from (benzo[d][1,3]dioxolyl, benzo[d]isoxazole, quinoxalinyl, quinolinyl and 2,3,4a,8a-tetrahydrobenzo[b][1,4]dioxinyl, wherein the cyclic group of R$^5$ is optionally substituted with 1, 2, 3, 4 or 5 R$^{410}$, provided that substitution of R$^5$ with R$^{410}$ can only occur by replacing a hydrogen that is covalently bound to either a carbon or a nitrogen of R$^5$, wherein the 1-5 R$^{410}$ groups are independently selected from R$^{410A}$ groups and R$^{410B}$ groups, provided that R$^5$ cannot be substituted with more than 2 R$^{410B}$ groups;

each R$^{410A}$, when they occur, is independently selected from halo, alkoxyl, hydroxyl, —CN, —OCF$_3$, —(C$_1$-C$_4$)alkyl and —NH$_2$, each R$^{410B}$, when they occur, is selected from —O—(C$_1$-C$_4$)alkyl-R$^{411}$, —S(O)$_2$—NH$_2$, —S(O)$_2$CH$_3$, —N(H)—S(O)$_2$CH$_3$, —S(O)$_2$N(H)—CH$_3$, —C(O)OH, —(C$_1$-C$_4$)alkyl-OH, —C(O)NH$_2$, and —(C$_1$-C$_4$)alkyl substituted with 1-3 groups selected from —OH and halo;

$R^{411}$ is selected from —C(O)OH, (5-6 membered)heterocycloalkyl, halogen, cyano, nitro, —(C$_1$-C$_4$)alkyl, —N(R$^{412}$)$_2$, —OR$^{412}$, —SR$^{412}$, —N(OR$^{412}$)R$^{412}$, —C(O)R$^{412}$, —C(O)OR$^{412}$, —C(O)N(R$^{412}$)$_2$, —N(R$^{412}$)S(O)R$^{412}$, —N(R$^{412}$)S(O)$_2$R$^{412}$, —S(O)N(R$^{412}$)$_2$, —S(O)$_2$N(R$^{412}$)$_2$, —S(O)$_2$R$^{412}$, —OC(O)R$^{412}$, —OC(O)OR$^{412}$, —OC(O)N(R$^{412}$)$_2$, —N(R$^{412}$)C(O)R$^{412}$, —N(R$^{412}$)S(O)$_2$R$^{412}$, —N(R$^{412}$)C(O)OR$^{412}$, —N(R$^{412}$)C(O)N(R$^{412}$)$_2$, —N(R$^{412}$)C(=NR$^{412}$)N(R$^{412}$)$_2$, and heteroaryl, wherein each R$^{412}$ is independently hydrogen, —(C$_1$-C$_4$)alkyl, or —(C$_1$-C$_4$)haloalkyl; and each R$^8$ is independently hydrogen, halogen, or methyl, or both R$^8$ taken together with the carbon to which they are both attached form either a (C$_3$-C$_6$)cycloalkyl or a (3-6 membered)heterocycloalkyl.

2. The compound according to claim 1 having structural formulae (VI):

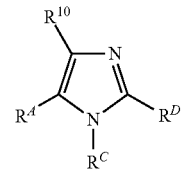

(VI)

or pharmaceutically acceptable salt thereof, wherein:

$R^A$ is —[C(CH$_3$)$_2$]-phenyl, —[C(CH$_3$)$_2$]-naphthalenyl, or —[C(CH$_3$)$_2$]-(5-10 membered)heteroaryl, wherein the heteroaryl is selected from (benzo[d][1,3]dioxolyl, benzo[d]isoxazole, quinoxalinyl, quinolinyl and 2,3,4a, 8a-tetrahydrobenzo[b][1,4]dioxinyl, wherein the cyclic group of R$^A$ is optionally substituted with 1, 2 or 3 R$^{410}$, provided that substitution of the cyclic group of R$^A$ with R$^{410}$ can only occur by replacing a hydrogen that is covalently bound to either a carbon or a nitrogen of the cyclic group of R$^A$;

each R$^{410}$ is independently selected from halo, alkoxyl, hydroxyl, —(C$_1$-C$_4$)alkyl optionally substituted with 1-3 groups selected from —OH and halo, —NH$_2$, —S(O)$_2$—NH$_2$, —S(O)$_2$CH$_3$, —N(H)—S(O)$_2$CH$_3$, —SO$_2$N(H)—CH$_3$, —CN, —C(O)OH, —(C$_1$-C$_4$)alkyl—OH, —OCF$_3$, and —C(O)NH$_2$;

$R^C$ is phenyl, —CH$_2$-phenyl, —(C$_5$-C$_6$)-cycloalkyl, or pyridinyl, wherein the cyclic group of R$^C$ can be optionally substituted with 1, 2 or 3 R$^{C10}$, provided that substitution of the cyclic group of R$^C$ with R$^{C10}$ can only occur by replacing a hydrogen that is covalently bound to either a carbon or a nitrogen of the cyclic group of R$^C$, and wherein the 1, 2, or 3 R$^{C10}$ groups are independently selected from RC$^{10A}$ and RC$^{10B}$, provided that R$^C$ cannot be substituted with more than 1 R$^{C10B}$ group;

each R$^{C10A}$ is independently selected from halo, and —(C$_1$-C$_3$)alkyl optionally substituted with 1-3 groups selected from —OH, methoxy, —CF$_3$ and halo;

$R^{C10B}$ is selected from —C(O)NH$_2$, (5-6 membered)heterocycloalkyl, —O—(C$_1$-C$_4$)alkyl optionally substituted with —OH, —C(O)OH, or —N[—(C$_1$-C$_4$)alkyl]$_2$, and —(C$_1$-C$_4$)alkyl substituted with —N[—(C$_1$-C$_4$)alkyl]$_2$;

$R^D$ is -L$^D$-R$^{D1}$;

L$^D$ is —Y—[C(R)$_2$]$_q$—;

q is 0 or 1;

each R is independently selected from H, —(C$_1$-C$_3$)alkyl, halo, —OH, and —CH$_2$OH;

Y is a bond, —S—, —S(O)$_2$—, —O—, —C(H)=C(H)—, —C(O)—(C$_1$-C$_4$)alkyl-, —(C$_1$-C$_4$)alkyl-S—(C$_1$-C$_4$)alkyl-, —(C$_1$-C$_4$)alkyl-N(R$^Y$)—(C$_1$-C$_4$)alkyl-, —C(H)(halo)-, —(C$_1$-C$_4$)alkyl-S(O)$_2$—, —S(O)$_2$—N(R$^Y$)—, —(C$_1$-C$_4$)alkyl-O—, —C(H)(OH)—, or —C(O)—N(R$^Y$)—, wherein R$^Y$ is H, —(C$_1$-C$_4$)alkyl, hydroxyl(C$_1$-C$_4$)alkyl or —C≡C—(C$_1$-C$_3$)alkyl-; or $R^D$ is -L$^D$-R$^{D1}$;

L$^D$ is —[C(R)$_2$]$_p$—Y—[C(R)$_2$]$_q$—;

p is 0 or 1;

q is 0 or 1;

each R is independently selected from H, —(C$_1$-C$_3$)alkyl, halo, —OH, and —CH$_2$OH;

Y is a bond, —S—, —S(O)$_2$—, —CH(OH)—, —O—, —C(H)=C(H)—, —C(O)—(C$_1$-C$_4$)alkyl-, —(C$_1$-C$_4$)alkyl-S—(C$_1$-C$_4$)alkyl-, —(C$_1$-C$_4$)alkyl-N(R$^Y$)—(C$_1$-C$_4$)alkyl-, —C(H)(halo)-, —(C$_1$-C$_4$)alkyl-S(O)$_2$—, —S(O)$_2$—N(R$^Y$)—, —(C$_1$-C$_4$)alkyl-O—, or —C(O)—N(R$^Y$)—, wherein R$^Y$ is H, —(C$_1$-C$_4$)alkyl, hydroxyl (C$_1$-C$_4$)alkyl or —C≡C—(C$_1$-C$_3$)alkyl-;

$R^{D1}$ is selected from —(C$_6$-C$_{10}$)aryl, —N(H)-phenyl, cycloalkyl, heterocycloalkyl, and heteroaryl, wherein $R^{D1}$ can be optionally substituted with 1, 2, 3, or 4 $R^{D10}$, provided that substitution of $R^{D1}$ with $R^{D10}$ can only occur by replacing a hydrogen that is covalently bound to either a carbon or a nitrogen of $R^{D1}$, wherein the 1-4 $R^{D10}$ groups are independently selected from A groups and B groups, provided that $R^{D1}$ cannot be substituted with more than 2 B groups;

each A group, when they occur, is independently selected from halo, —CF$_3$, —CN, —NO$_2$, —OH, —NH$_2$, —O—(C$_1$-C$_4$)alkyl optionally substituted at the alkyl group with 1-3 substituents independently selected from —OH and halo, and —(C$_1$-C$_4$)alkyl optionally substituted with 1-3 substituents independently selected from —OH and halo;

each B group, when they occur, is independently selected from —(C$_1$-C$_4$)alkylN(R$^{D11}$)$_2$, —C(O)—NH$_2$, —C(O)—N(H)—OH, —C(O)—N(H)—R$^{D11C}$, —C(O)—(C$_1$-C$_4$)alkyl, —C(O)OH, —C(O)O—(C$_1$-C$_4$)alkyl, —S(O)$_2$—(C$_1$-C$_4$)alkyl-N(R$^{D11}$)$_2$, —S(O)$_2$—N(R$^{D11}$)R$^{D11C}$, —S(O)$_2$—N(H)C(O)—(C$_1$-C$_4$)alkyl, —S(O)$_2$—N(H)C(O)O—(C$_1$-C$_4$)alkyl, —S(O)$_2$—N(H)C(O)—N(R$^{D11}$)R$^{D11B}$, —S(O)$_2$—(C$_1$-C$_4$)alkyl, —C(O)-heterocycloalkyl optionally substituted with R$^{D11B}$, provided that substitution of the —C(O)-heterocycloalkyl with R$^{D11B}$ can only occur by replacing a hydrogen that is covalently bound to either a carbon or a nitrogen of —C(O)-heterocycloalkyl, —C(O)—N(H)—(C$_1$-C$_6$)alkyl optionally substituted at the alkyl group with 1 or 2 R$^{D11B}$, heterocycloalkyl optionally substituted with oxo or R$^{D11}$, provided that substitution of the heterocycloalkyl with R$^{D11}$ can only occur by replacing a hydrogen that is covalently bound to either a carbon or a nitrogen of the heterocycloalkyl, heterocycloalkenyl optionally substituted with oxo or R$^{D11}$, provided that substitution of the heterocycloalkenyl with R$^{D11}$ can only occur by replacing a hydrogen that is covalently bound to either a carbon or a nitrogen of the heterocycloalkenyl, heteroaryl optionally substituted with R$^{D11}$, provided that substitution of the heteroaryl with R$^{D11}$ can only occur by replacing a hydrogen that is covalently bound to either a carbon or a nitrogen of the heteroaryl, —O—(C$_1$-C$_4$)alkyl optionally substituted at the alkyl group with 1 or 2 R$^{D11B}$, —S(O)$_2$-(4-6 membered)heterocycloalkyl optionally substituted with R$^{D11C}$, provided that substitution of the —S(O)$_2$-(4-6 membered)heterocycloalkyl with R$^{D11C}$ can only occur by replacing a hydrogen that is covalently bound to either a carbon or a nitrogen of the —S(O)$_2$-(4-6 membered)heterocycloalkyl, —N(H)—C(O)—(C$_1$-C$_4$)alkyl optionally substituted at the alkyl group with 1 or 2 R$^{D11B}$, —N(H)—C(O)—N(H)—(C$_1$-C$_3$)alkyl optionally substituted at the alkyl group with R$^{D11B}$, —(C$_1$-C$_6$)alkyl optionally substituted with 1 or 2 R$^{D11B}$, —C(=NH)—NH$_2$, and —C≡C—(C$_1$-C$_3$)alkyl optionally substituted with R$^{D11B}$;

each R$^{D11}$ is independently selected from H, —(C$_1$-C$_4$)haloalkyl, —(C$_3$-C$_6$)cycloalkyl, —OH, —(C$_1$-C$_3$)alkyl-phenyl optionally substituted at the phenyl group with 1-3 substituents selected from methoxy, hydroxyl and halo, and —(C$_1$-C$_4$)alkyl optionally substituted with halo, —C(O)OH, —OH, —S(O)$_2$OH, C(O)OH, —NH$_2$, or —N(H)C(=NH)NH$_2$;

R$^{D11B}$ is selected from H, —OH, —CF$_3$, —NH$_2$, —C(O)OH, —(CH$_2$)$_{1-4}$—C(O)OH, —O—(C$_1$-C$_4$)alkyl, —S(O)$_2$OH, —C(=NH)—NH$_2$, —N(H)C(=NH)NH$_2$, —C(H)=NN(H)C(=NH)NH$_2$, —N(H)C(=NH)—N(H)C(=NH)NH$_2$, —C(O)—(C$_1$-C$_3$)alkyl, —O—(C$_1$-C$_4$)alkyl-C(O)OH, —(C$_3$-C$_6$)cycloalkyl, (5-6 membered)heteroaryl, —(C$_1$-C$_4$)alkyl optionally substituted with 1-3 groups independently selected from halo, —OH, —S(O)$_2$OH, C(O)OH, —NH$_2$, and —N(H)C(=NH)NH$_2$, -(5-6 membered)heterocycloalkyl optionally substituted with 1, 2 or 3 R$^{D11}$, provided that substitution of the -(5-6 membered)heterocycloalkyl with R$^{D11}$ can only occur by replacing a hydrogen that is covalently bound to either a carbon or a nitrogen of the -(5-6 membered)heterocycloalkyl, and aryl optionally substituted with 1-3 halo;

or R$^{D11}$ and R$^{D11B}$, when they both exist and are each attached to nitrogen, can join together with the nitrogen to which they are attached to form a (5-6 membered) heterocycloalkyl optionally substituted with a group selected from —(C$_3$-C$_6$)cycloalkyl, —(C$_1$-C$_4$)haloalkyl, —OH, —S(O)$_2$OH, C(O)OH, —NH$_2$, —N(H)C(=NH)NH$_2$, —(C$_1$-C$_4$)alkyl optionally substituted with halo, —OH or —C(O)OH, and —(C$_1$-C$_3$)alkyl-phenyl optionally substituted at the phenyl group with 1-3 substituents selected from methoxy, hydroxyl and halo, provided that substitution of the (5-6 membered) heterocycloalkyl can only occur by replacing a hydrogen that is covalently bound to either a carbon or a nitrogen of the (5-6 membered) heterocycloalkyl; and R$^{D11C}$ is selected from H, —OH, —CF$_3$, —O—(C$_1$-C$_4$)alkyl, —(C$_1$-C$_4$)alkyl-N(H)C(=NH)—NH$_2$, —(C$_0$-C$_3$)alkyl-(5-6 membered)heteroaryl, —(C$_1$-C$_4$)alkyl optionally substituted with 1-3 groups independently selected from halo, —OH, —S(O)$_2$OH, C(O)OH, —NH$_2$, and —N(H)C(=NH)NH$_2$, —(C$_0$-C$_3$)alkyl-(5-6 membered)heterocycloalkyl optionally substituted with a -(5-6 membered)heteroaryl, provided that substitution of the —(C$_0$-C$_3$)alkyl-(5-6 membered)heterocycloalkyl can only occur by replacing a hydrogen that is covalently bound to either a carbon or a nitrogen of the —(C$_0$-C$_3$)alkyl-(5-6 membered)heterocycloalkyl, —(C$_0$-C$_3$)alkyl-(5-6 membered)heterocycloalkyl substituted 1, 2 or 3 groups selected from selected from —OH and —(C$_1$-C$_3$)alkyl, provided that substitution of the —(C$_0$-C$_3$)alkyl-(5-6 membered)heterocycloalkyl can only occur by replacing a hydrogen that is covalently bound to either a carbon or a nitrogen of the —(C$_0$-C$_3$)alkyl-(5-6 membered)heterocycloalkyl, and —C$_0$-C$_3$) alkyl-aryl optionally substituted at the aryl group with 1-3 halo.

3. The compound according to claim 1, or a pharmaceutically acceptable salt thereof, wherein:

L$^D$ is selected from —(C$_1$-C$_3$)alkyl-O—, —(C$_0$-C$_3$)alkyl-NR$^Y$—(C$_0$-C$_3$)alkyl-, —(C$_0$-C$_3$)alkyl-S—(C$_0$-C$_3$)alkyl-, —(C$_0$-C$_3$)alkyl-S(O)$_2$—(C$_0$-C$_3$)alkyl-; —C(O)N(R$^Y$)—(C$_0$-C$_3$)alkyl-, —S(O)$_2$—N(R$^Y$)—(C$_0$-C$_3$)alkyl-, —C(O)—(C$_0$-C$_3$)alkyl-, —(C$_1$-C$_4$)alkyl- optionally substituted with halo or —OH, —C≡C—(C$_0$-C$_3$)alkyl-and —(C$_0$-C$_3$)alkyl-.

4. The compound according to claim 1, or a pharmaceutically acceptable salt thereof, wherein the B group of R$^{D1}$ is selected from:

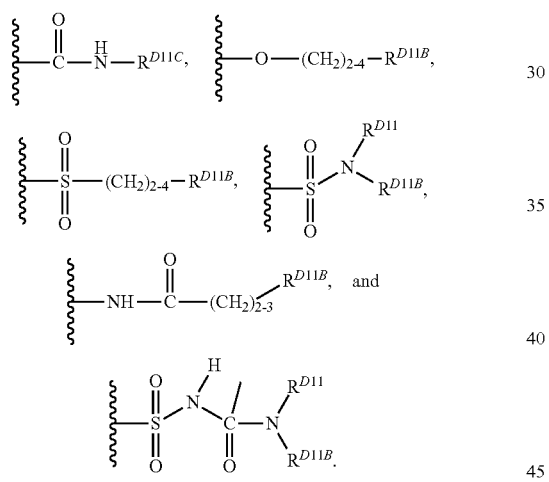

5. The compound according to claim 1, or a pharmaceutically acceptable salt thereof, wherein R$^C$ is phenyl, —CH$_2$-phenyl, —(C$_5$-C$_6$)-cycloalkyl, or pyridinyl, wherein R$^C$ can be optionally substituted with 1, 2 or 3 R$^{C10}$, provided that substitution of R$^C$ can only occur by replacing a hydrogen that is covalently bound to either a carbon or a nitrogen of the R$^C$, and wherein the 1, 2 or 3 R$^{C10}$ groups are independently selected from R$^{C10A}$ and R$^{C10B}$, provided that R$^C$ cannot be substituted with more than 1 R$^{C10B}$ group;

each R$^{C10A}$, when they occur, is independently selected from —(C$_1$-C$_3$)alkyl optionally substituted with 1-3 groups selected from halo and —OH, methoxy, —CF$_3$ and halo; and R$^{C10B}$ is selected from —C(O)NH$_2$, (5-6 membered)heterocycloalkyl, —O—(C$_1$-C$_4$)alkyl optionally substituted with —OH, —C(O)OH, or —N[—(C$_1$-C$_4$)alkyl]$_2$, and —(C$_1$-C$_4$)alkyl substituted with —N[—(C$_1$-C$_4$)alkyl]$_2$.

6. The compound according to claim 1, or a pharmaceutically acceptable salt thereof, having formula IX, X, XI, XII, XIII, XIV or XV:

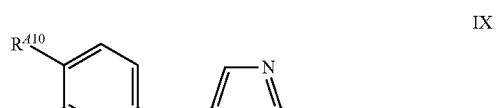

IX

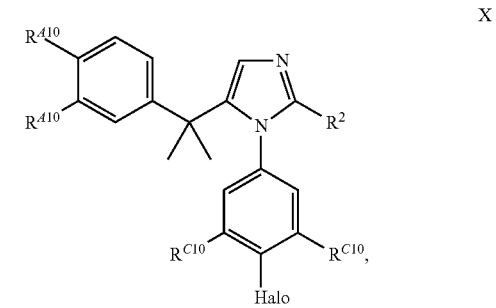

X

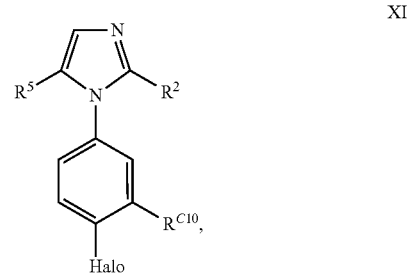

XI

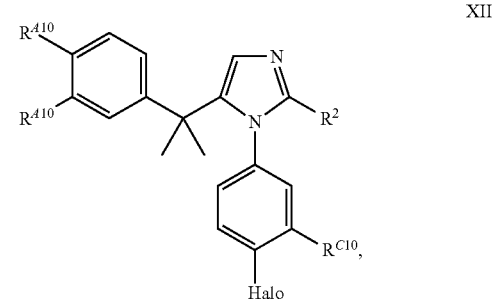

XII

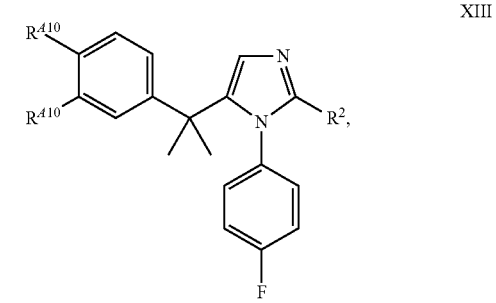

XIII

-continued

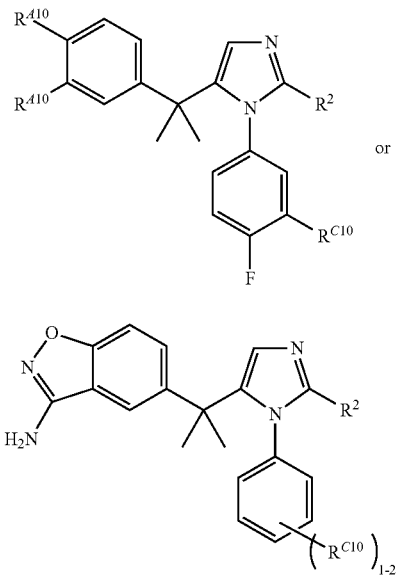

7. The compound according to claim 6, or a pharmaceutically acceptable salt thereof, wherein each $R^{A10}$ is selected from fluoro, chloro and methoxy;

each $R^{C10}$ is selected from fluoro, chloro and methoxy;

$R^2$ is -$L^D$-$R^{D1}$, wherein:

$L^D$ is selected from —(CH$_2$)—O—, —(CH$_2$)—NH—, —(CH$_2$)—S—, —S—(CH$_2$)—, —S(O)$_2$—, —S(O)$_2$—(CH$_2$)—, —C(O)N(H)—(CH$_2$)$_{1-3}$—, —S(O)$_2$—N(H)—(CH$_2$)$_{1-3}$—, —C(O)—(CH$_2$)$_{1-2}$—, —(C$_1$-C$_3$)alkyl-optionally substituted with halo or —OH, and —C≡C—(C$_2$-C$_3$)alkyl; and $R^{D1}$ is one of:

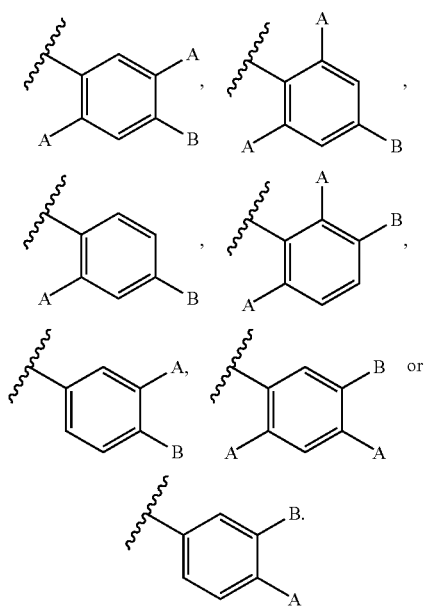

wherein each A is chloro or fluoro, and B is selected from:

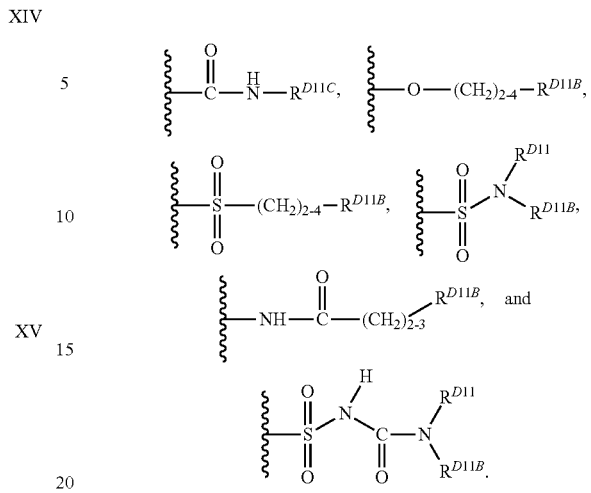

8. The compound according to claim 1, or a pharmaceutically acceptable salt thereof, wherein $R^5$ is —[C(CH$_3$)$_2$]-phenyl, —[C(CH$_3$)$_2$]-naphthalenyl, or —[C(CH$_3$)$_2$]-(5-10 membered) heteroaryl, wherein the heteroaryl is selected from (benzo[d][1,3]dioxolyl, benzo[d]isoxazole, quinoxalinyl, quinolinyl and 2,3,4a,8a-tetrahydrobenzo[b][1,4]dioxinyl, wherein the cyclic group of $R^5$ is optionally substituted with one, two, or three $R^{A10}$ groups, wherein the one, two, or three $R^{A10}$ groups are independently selected from $R^{A10A}$ and $R^{A10B}$, provided that $R^5$ cannot be substituted with more than 1 $R^{A10B}$ group; and each $R^{A10A}$, when they occur, is independently selected from halo, —(C$_1$-C$_3$)alkoxyl and hydroxyl;

$R^{A10B}$ is —(C$_1$-C$_4$)alkyl optionally substituted with 1-3 groups selected from —OH and halo, —O—(C$_1$-C$_4$)alkyl-C(O)OH, O—(C$_1$-C$_4$)alkyl-N[(C$_1$-C$_3$)alkyl]$_2$, —NH$_2$, —S(O)$_2$—NH$_2$, —SO$_2$CH$_3$, —N(H)—SO$_2$CH$_3$, —SO$_2$N(H)—CH$_3$, —CN, —C(O)OH, —(C$_1$-C$_4$)alkyl-OH, —OCF$_3$, or —C(O)NH$_2$.

9. The compound according to claim 1, or a pharmaceutically acceptable salt thereof, wherein $R^5$ is:

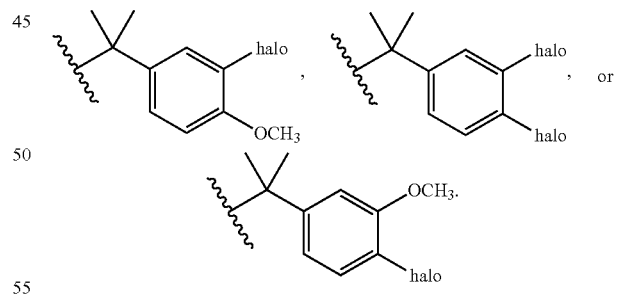

10. The compound according to claim 1 selected from one of the following compounds:

5-{[3,4-bis(methyloxy)phenyl]methyl}-2-{[(2-chloro-4-fluorophenyl)methyl]thio}-1-(4-fluorophenyl)-1H-imidazole;

5-{1-[3,4-bis(methyloxy)phenyl]-1-methylethyl}-2-{[(2-chloro-4-fluorophenyl)methyl]thio}-1-(4-fluorophenyl)-1H-imidazole;

5-[1-(1,3-benzodioxol-5-yl)-1-methylethyl]-2-{[(2-chloro-4-fluorophenyl)methyl]thio}-1-(4-fluorophenyl)-1H-imidazole;

2-{[(2-chloro-4-fluorophenyl)methyl]thio}-5-[1-(3,4-difluorophenyl)-1-methylethyl]-1-(4-fluorophenyl)-1H-imidazole;

2-{[(2-chloro-4-fluorophenyl)methyl]thio}-5-[1-(3,4-dichlorophenyl)-1-methylethyl]-1-(4-fluorophenyl)-1H-imidazole;

5-[1-(1,3-benzodioxol-5-yl)-1-methylethyl]-2-{[(2-chloro-6-fluorophenyl)methyl]thio}-1-(4-fluorophenyl)-1H-imidazole;

2-{[(2-chloro-6-fluorophenyl)methyl]thio}-5-[1-(3,4-dichlorophenyl)-1-methylethyl]-1-(4-fluorophenyl)-1H-imidazole;

2-{[(2-chloro-4-fluorophenyl)methyl]thio}-5-[(3,4-difluorophenyl)methyl]-1-(4-fluorophenyl)-1H-imidazole;

5-{1-[3,4-bis(methyloxy)phenyl]-1-methylethyl}-2-{[(2-chloro-6-fluorophenyl)methyl]thio}-1-(4-fluorophenyl)-1H-imidazole;

5-{1-[3,4-bis(methyloxy)phenyl]-1-methylethyl}-2-{[(2,6-dichlorophenyl)methyl]thio}-1-(4-fluorophenyl)-1H-imidazole;

5-{1-[3,4-bis(methyloxy)phenyl]-1-methylethyl}-2-{[(2,4-dichlorophenyl)methyl]thio}-1-(4-fluorophenyl)-1H-imidazole;

5-{1-[3,4-bis(methyloxy)phenyl]-1-methylethyl}-2-{[(3,4-dichlorophenyl)methyl]thio}-1-(4-fluorophenyl)-1H-imidazole;

5-{1-[3,4-bis(methyloxy)phenyl]-1-methylethyl}-1-(4-fluorophenyl)-2-({[2-fluoro-6-(trifluoromethyl)phenyl]methyl}thio)-1H-imidazole;

2-{[(2-chloro-4-fluorophenyl)methyl]thio}-5-[1-(2,3-dihydro-1,4-benzodioxin-6-yl)-1-methylethyl]-1-(4-fluorophenyl)-1H-imidazole;

2-{[(2-chloro-6-fluorophenyl)methyl]thio}-5-[1-(2,3-dihydro-1,4-benzodioxin-6-yl)-1-methylethyl]-1-(4-fluorophenyl)-1H-imidazole;

5-{1-[3,4-bis(methyloxy)phenyl]-1-methylethyl}-2-{[(3-chloro-4-fluorophenyl)methyl]thio}-1-(4-fluorophenyl)-1H-imidazole;

5-{1-[3,4-bis(methyloxy)phenyl]-1-methylethyl}-2-{[(2-chloro-6-fluorophenyl)methyl]sulfonyl}-1-(4-fluorophenyl)-1H-imidazole;

5-{1-[3,4-bis(methyloxy)phenyl]-1-methylethyl}-2-{[(2-chloro-5-fluorophenyl)methyl]thio}-1-(4-fluorophenyl)-1H-imidazole;

5-{1-[3,4-bis(methyloxy)phenyl]-1-methylethyl}-2-{[(3-chloro-5-fluorophenyl)methyl]thio}-1-(4-fluorophenyl)-1H-imidazole;

2-{[(2-chloro-6-fluorophenyl)methyl]thio}-5-[1-(3,4-difluorophenyl)-1-methylethyl]-1-(4-fluorophenyl)-1H-imidazole;

4-{1-[2-{[(2-chloro-6-fluorophenyl)methyl]thio}-1-(4-fluorophenyl)-1H-imidazol-5-yl]-1-methylethyl}benzene-1,2-diol;

4-{1-[2-{[(2-chloro-4-fluorophenyl)methyl]thio}-1-(4-fluorophenyl)-1H-imidazol-5-yl]-1-methylethyl}benzene-1,2-diol;

2-{[(2-chloro-6-fluorophenyl)methyl]thio}-1-(4-fluorophenyl)-5-{1-methyl-1-[4-(methyloxy)phenyl]ethyl}-1H-imidazole;

2-{[(2-chloro-6-fluorophenyl)methyl]sulfonyl}-5-[1-(3,4-dichlorophenyl)-1-methylethyl]-1-(4-fluorophenyl)-1H-imidazole;

2-{[1-(2-chloro-6-fluorophenyl)-1-methylethyl]sulfonyl}-5-[1-(3,4-dichlorophenyl)-1-methylethyl]-1-(4-fluorophenyl)-1H-imidazole;

2-[(E)-2-(2-chloro-6-fluorophenyl)ethenyl]-5-[1-(3,4-dichlorophenyl)-1-methylethyl]-1-(4-fluorophenyl)-1H-imidazole;

2-{[(2-chloro-4-fluorophenyl)methyl]sulfonyl}-5-[1-(3,4-difluorophenyl)-1-methylethyl]-1-(4-fluorophenyl)-1H-imidazole;

2-{[(2-chloro-6-fluorophenyl)methyl]thio}-1-(4-fluorophenyl)-5-[1-(4-fluorophenyl)-1-methylethyl]-1H-imidazole;

2-{[(2-chloro-6-fluorophenyl)methyl]thio}-5-[1-(4-chlorophenyl)-1-methylethyl]-1-(4-fluorophenyl)-1H-imidazole;

4-chloro-2-{[(2-chloro-6-fluorophenyl)methyl]thio}-5-[1-(3,4-dichlorophenyl)-1-methylethyl]-1-(4-fluorophenyl)-1H-imidazole;

5-{1- [3,4-bis(methyloxy)phenyl]-1-methylethyl}-4-chloro-2-{[(2-chloro-6-fluorophenyl)methyl]thio}-1-(4-fluorophenyl)-1H-imidazole;

2-[(4-{1-[2-{[(2-chloro-6-fluorophenyl)methyl]thio}-1-(4-fluorophenyl)-1H-imidazol-5-yl]-1-methylethyl}phenyl)oxy]-N,N-dimethylethanamine;

N-{[5-{1- [3,4-bis(methyloxy)phenyl]-1-methylethyl}-1-(4-fluorophenyl)-1H-imidazol-2-yl]methyl}-2-chloro-6-fluoroaniline;

N-{[5-{1-[3,4-bis(methyloxy)phenyl]-1-methylethyl}-1-(4-fluorophenyl)-1H-imidazol-2-yl]methyl}-2-chloro-4-fluoroaniline;

3-(2,4-dichlorophenyl)-1-{5-[1-(3,4-dichlorophenyl)-1-methylethyl]-1-(4-fluorophenyl)-1H-imidazol-2-yl}propan-1-ol;

2-{[(2-chloro-6-fluorophenyl)methyl]thio}-1-(4-fluorophenyl)-5-{1-methyl-1-[4-(trifluoromethyl)phenyl]ethyl}-1H-imidazole;

2-[(4-{1-[2-{[(2-chloro-6-fluorophenyl)methyl]thio}-1-(4-fluorophenyl)-1H-imidazol-5-yl]-1-methylethyl}phenyl)oxy]ethanol;

[(4-{1-[2-{[(2-chloro-6-fluorophenyl)methyl]thio}-1-(4-fluorophenyl)-1H-imidazol-5-yl]-1-methylethyl}phenyl)oxy]acetic acid;

2-{[(2-chloro-4-fluorophenyl)methyl]sulfonyl}-5-[1-(3,4-dichlorophenyl)-1-methylethyl]-1-(4-fluorophenyl)-1H-imidazole;

2-{[(3-chloro-4-fluorophenyl)methyl]sulfonyl}-5-[1-(3,4-dichlorophenyl)-1-methylethyl]-1-(4-fluorophenyl)-1H-imidazole;

5-[1-(3,4-dichlorophenyl)-1-methylethyl]-2-{[(3,4-dichlorophenyl)methyl]sulfonyl}-1-(4-fluorophenyl)-1H-imidazole;

3-(2,4-dichlorophenyl)-1-{5-[1-(3,4-dichlorophenyl)-1-methylethyl]-1-(4-fluorophenyl)-1H-imidazol-2-yl}propan-1-one;

N-{[5-{1[3,4-bis(methyloxy)phenyl]-1-methylethyl}-1-(4-fluorophenyl)-1H-imidazol-2-yl]methyl}-3-chloro-4-fluoroaniline;

N-{[5-{1-[3,4-bis(methyloxy)phenyl]-1-methylethyl}-1-(4-fluorophenyl)-1H-imidazol-2-yl]methyl}-3,4-dichloroaniline;

5-{1-[3,4-bis(methyloxy)phenyl]-1-methylethyl}-2-{[2-(2-chloro-4-fluorophenyl)ethyl]sulfonyl}-1-(4-fluorophenyl)-1H-imidazole;

5-{1-[3,4-bis(methyloxy)phenyl]-1-methylethyl}-2-{[2-(3,4-dichlorophenyl)ethyl]sulfonyl}-1-(4-fluorophenyl)-1H-imidazole;

5-[1-(3,4-dichlorophenyl)-1-methylethyl]-2-{[(3,4-difluorophenyl)methyl]sulfonyl}-1-(4-fluorophenyl)-1H-imidazole;

5-[1-(3,4-dichlorophenyl)-1-methylethyl]-1-(4-fluorophenyl)-2-({[4-fluoro-3-(trifluoromethyl)phenyl]methyl}sulfonyl)-1H-imidazole;

5-[1-(3,4-dichlorophenyl)-1-methylethyl]-2-{[(2,4-dichlorophenyl)methyl]sulfonyl}-1-(4-fluorophenyl)-1H-imidazole;

5-[1-(3,4-dichlorophenyl)-1-methylethyl]-2-{[(2,6-dichlorophenyl)methyl]sulfonyl}-1-(4-fluorophenyl)-1H-imidazole;

5-[1-(3,4-dichlorophenyl)-1-methylethyl]-2-{[(2,5-dichlorophenyl)methyl]sulfonyl}-1-(4-fluorophenyl)-1H-imidazole;

4-{1-[2-{[(2-chloro-6-fluorophenyl)methyl]thio}-1-(4-fluorophenyl)-1H-imidazol-5-yl]-1-methylethyl}benzenesulfonamide;

5-{1-[3,4-bis(methyloxy)phenyl]-1-methylethyl}-2-{[2-(3-chloro-4-fluorophenyl)ethyl]sulfonyl}-1-(4-fluorophenyl)-1H-imidazole;

2-{[(2-chloro-6-fluorophenyl)methyl]sulfonyl}-1-(4-chlorophenyl)-5-[1-(3,4-dichlorophenyl)-1-methylethyl]-1H-imidazole;

2-{[(2-chloro-6-fluorophenyl)methyl]sulfonyl}-1-(3,4-dichlorophenyl)-5-[1-(3,4-dichlorophenyl)-1-methylethyl]-1H-imidazole;

2-{[(2-chloro-4-fluorophenyl)thio]methyl}-5-[1-(3,4-dichlorophenyl)-1-methylethyl]-1-(4-fluorophenyl)-1H-imidazole;

5-[1-(3,4-dichlorophenyl)-1-methylethyl]-2-{[(3,4-dichlorophenyl)thio]methyl}-1-(4-fluorophenyl)-1H-imidazole;

2-{[(2-chloro-6-fluorophenyl)methyl]thio}-1-(4-fluorophenyl)-5-{1-methyl-1-[4-(methylsulfonyl)phenyl]ethyl}-1H-imidazole;

2-{[(2-chloro-6-fluorophenyl)methyl]sulfonyl}-5-[1-(3,4-dichlorophenyl)-1-methylethyl]-1-(2,4-difluorophenyl)-1H-imidazole;

1-(2-chloro-4-fluorophenyl)-2-{[(2-chloro-6-fluorophenyl)methyl]sulfonyl}-5-[1-(3,4-dichlorophenyl)-1-methylethyl]-1H-imidazole;

2-{[(2-chloro-6-fluorophenyl)methyl]thio}-1-(3,4-dichlorophenyl)-5-[1-(3,4-dichlorophenyl)-1-methylethyl]-1H-imidazole;

2-{[(2-chloro-6-fluorophenyl)methyl]thio}-5-[1-(3,4-dichlorophenyl)-1-methylethyl]-1-(2,4-difluorophenyl)-1H-imidazole;

1-(2-chloro-4-fluorophenyl)-2-{[(2-chloro-6-fluorophenyl)methyl]thio}-5-[1-(3,4-dichlorophenyl)-1-methylethyl]-1H-imidazole;

2-{[(2-chloro-4-fluorophenyl)oxy]methyl}-5-[1-(3,4-dichlorophenyl)-1-methylethyl]-1-(4-fluorophenyl)-1H-imidazole;

2-({[(2-chloro-4-fluorophenyl)methyl]oxy}methyl)-5-[1-(3,4-dichlorophenyl)-1-methylethyl]-1-(4-fluorophenyl)-1H-imidazole;

N-(4-{1-[2-{[(2-chloro-6-fluorophenyl)methyl]thio}-1-(4-fluorophenyl)-1H-imidazol-5-yl]-1-methylethyl}phenyl)methanesulfonamide;

5-{1-[3,4-bis(methyloxy)phenyl]-1-methylethyl}-2-{[(2-chloro-6-fluorophenyl)oxy]methyl}-1-(4-fluorophenyl)-1H-imidazole;

1-(3-chloro-4-fluorophenyl)-2-{[(2-chloro-6-fluorophenyl)methyl]thio}-5-[1-(3,4-dichlorophenyl)-1-methylethyl]-1H-imidazole;

2-{[(2-chloro-6-fluorophenyl)methyl]thio}-1-(2,4-dichlorophenyl)-5-[1-(3,4-dichlorophenyl)-1-methylethyl]-1H-imidazole;

2-{[(2-chloro-6-fluorophenyl)methyl]thio}-5-[1-(3,4-dichlorophenyl)-1-methylethyl]-1-[(4-fluorophenyl)methyl]-1H-imidazole;

5-{1-[3,4-bis(methyloxy)phenyl]-1-methylethyl}-N-cyclohexyl-1-(4-fluorophenyl)-1H-imidazole-2-carboxamide;

1-[5-{1-[3,4-bis(methyloxy)phenyl]-1-methylethyl}-1-(4-fluorophenyl)-1H-imidazol-2-yl]-N-[(4-chloro-3-fluorophenyl)methyl]methanamine;

1-(4-chloro-3-fluorophenyl)-2-{[(2-chloro-6-fluorophenyl)methyl]thio}-5-[1-(3,4-dichlorophenyl)-1-methylethyl]-1H-imidazole;

2-{[(2-chloro-6-fluorophenyl)methyl]thio}-5-[1-(3,4-dichlorophenyl)-1-methylethyl]-1-(3,4-difluorophenyl)-1H-imidazole;

1-(4-chloro-2-fluorophenyl)-2-{[(2-chloro-6-fluorophenyl)methyl]thio}-5-[1-(3,4-dichlorophenyl)-1-methylethyl]-1H-imidazole;

5-[1-(4-chloro-3-fluorophenyl)-1-methylethyl]-2-{[(2-chloro-6-fluorophenyl)methyl]thio}-1-(4-fluorophenyl)-1H-imidazole;

2-{[(2-chloro-4-fluorophenyl)methyl]thio}-5-[1-(3,4-dichlorophenyl)-1-methylethyl]-1-(3,4-difluorophenyl)-1H-imidazole;

3-(2-{[(2-chloro-4-fluorophenyl)methyl]thio}-5-[1-(3,4-dichlorophenyl)-1-methylethyl]-1H-imidazol-1-yl)pyridine;

N-[(2-chloro-4-fluorophenyl)methyl]-5-[1-(3,4-dichlorophenyl)-1-methylethyl]-1-(4-fluorophenyl)-1H-imidazole-2-sulfonamide;

N-(2-chloro-4-fluorophenyl)-5-[1-(3,4-dichlorophenyl)-1-methylethyl]-1-(4-fluorophenyl)-1H-imidazole-2-sulfonamide;

4-[4-(2-{[(2-chloro-4-fluorophenyl)methyl]thio}-5-[1-(3,4-dichlorophenyl)-1-methylethyl]-1H-imidazol-1-yl)phenyl]morpholine;

5-{1-[3,4-bis(methyloxy)phenyl]-1-methylethyl}-2-{[(2-chloro-6-fluorophenyl)thio]methyl}-1-(4-fluorophenyl)-1H-imidazole;

2-{[(2-chloro-6-fluorophenyl)methyl]thio}-1-(4-fluorophenyl)-5-{1-methyl-1-[3-(methylsulfonyl)phenyl]ethyl}-1H-imidazole;

2-[({5-[1-(3,4-dichlorophenyl)-1-methylethyl]-1-(4-fluorophenyl)-1H-imidazol-2-yl}thio)methyl]-5-fluorobenzamide;

2-[({5-[1-(3,4-dichlorophenyl)-1-methylethyl]-1-(4-fluorophenyl)-1H-imidazol-2-yl}thio)methyl]-5-fluorobenzonitrile;

5-[({5-[1-(3,4-dichlorophenyl)-1-methylethyl]-1-(4-fluorophenyl)-1H-imidazol-2-yl}thio)methyl]-2-fluorobenzamide;

5-[({5-[1-(3,4-dichlorophenyl)-1-methylethyl]-1-(4-fluorophenyl)-1H-imidazol-2-yl}thio)methyl]-2-fluorobenzonitrile;

2-{[(2-chloro-6-fluorophenyl)methyl]thio}-1-cyclopentyl-5-[1-(3,4-dichlorophenyl)-1-methylethyl]-1H-imidazole;

4-[({5-[1-(3,4-dichlorophenyl)-1-methylethyl]-1-(4-fluorophenyl)-1H-imidazol-2-yl}thio)methyl]-3-fluorobenzoic acid;

4-[({5-[1-(3,4-dichlorophenyl)-1-methylethyl]-1-(4-fluorophenyl)-1H-imidazol-2-yl}thio)methyl]-3-fluorobenzamide;

2-chloro-5-[({5-[1-(3,4-dichlorophenyl)-1-methylethyl]-1-(4-fluorophenyl)-1H-imidazol-2-yl}thio)methyl]benzoic acid;

5-(2-{[(2-chloro-4-fluorophenyl)methyl]thio}-5-[1-(3,4-dichlorophenyl)-1-methylethyl]-1H-imidazol-1-yl)-2-fluorobenzamide;

5-(2-{[(2-chloro-4-fluorophenyl)methyl]thio}-5-[1-(3,4-dichlorophenyl)-1-methylethyl]-1H-imidazol-1-yl)-2-fluorobenzonitrile;

2-{[(2-chloro-4-fluorophenyl)methyl]thio}-5-[1-(3,4-dichlorophenyl)-1-methylethyl]-1-[4-fluoro-3-(trifluoromethyl)phenyl]-1H-imidazole;

2-{[(2-chloro-4-fluorophenyl)methyl]thio}-5-[1-(3,4-dichlorophenyl)-1-methylethyl]-1-[4-fluoro-2-(methyloxy)phenyl]-1H-imidazole;

2-{[(2-chloro-4-fluorophenyl)methyl]thio}-5-[1-(3,4-dichlorophenyl)-1-methylethyl]-1-(3,5-difluorophenyl)-1H-imidazole;

2-[({5-[1-(3,4-dichlorophenyl)-1-methylethyl]-1-(4-fluorophenyl)-1H-imidazol-2-yl}thio)methyl]-5-fluorobenzoic acid;

2-[({5-[1-(3,4-dichlorophenyl)-1-methylethyl]-1-(4-fluorophenyl)-1H-imidazol-2-yl}thio)methyl]-5-fluorobenzenesulfonamide;

5-[({5-[1-(3,4-dichlorophenyl)-1-methylethyl]-1-(4-fluorophenyl)-1H-imidazol-2-yl}thio)methyl]-2-fluorobenzoic acid;

{5-[({5-[1-(3,4-dichlorophenyl)-1-methylethyl]-1-(4-fluorophenyl)-1H-imidazol-2-yl}thio)methyl]-2-fluorophenyl}methanol;

5-[({5-[1-(3,4-dichlorophenyl)-1-methylethyl]-1-(4-fluorophenyl)-1H-imidazol-2-yl}thio)methyl]-2-fluorobenzenesulfonamide;

{2-[({5-[1-(3,4-dichlorophenyl)-1-methylethyl]-1-(4-fluorophenyl)-1H-imidazol-2-yl}thio)methyl]-3-fluorophenyl}methanol;

2-{2-[({5-[1-(3,4-dichlorophenyl)-1-methylethyl]-1-(4-fluorophenyl)-1H-imidazol-2-yl}thio)methyl]-3-fluorophenyl}propan-2-ol;

2-{[(2-chloro-4-fluorophenyl)sulfonyl]methyl}-5-[1-(3,4-dichlorophenyl)-1-methylethyl]-1-(4-fluorophenyl)-1H-imidazole;

4-{1-[2-{[(2-chloro-4-fluorophenyl)methyl]thio}-1-(4-fluorophenyl)-1H-imidazol-5-yl]-1-methylethyl}-N-methylbenzenesulfonamide;

4-{[5-{1-[3,4-bis(methyloxy)phenyl]-1-methylethyl}-1-(4-fluorophenyl)-1H-imidazol-2-yl]carbonyl}morpholine;

5-{1-[3,4-bis(methyloxy)phenyl]-1-methylethyl}-1-(4-fluorophenyl)-2-(pyrrolidin-1-ylcarbonyl)-1H-imidazole;

5-{1-[3,4-bis(methyloxy)phenyl]-1-methylethyl}-N-(3-chloro-4-fluorophenyl)-1-(4-fluorophenyl)-1H-imidazole-2-carboxamide;

5-[1-(3-chloro-4-fluorophenyl)-1-methylethyl]-2-{[(2-chloro-6-fluorophenyl)methyl]thio}-1-(4-fluorophenyl)-1H-imidazole;

2-{[(2-chloro-4-fluorophenyl)methyl]thio}-5-[1-(3,4-dichlorophenyl)-1-methylethyl]-1-[4-fluoro-3-(methyloxy)phenyl]-1H-imidazole;

{2-[({5-[1-(3,4-dichlorophenyl)-1-methylethyl]-1-(4-fluorophenyl)-1H-imidazol-2-yl}thio)methyl]-5-fluorophenyl}methanol;

5-[1-(3,4-dichlorophenyl)-1-methylethyl]-2-({[4-fluoro-2-(methylsulfonyl)phenyl]methyl}thio)-1-(4-fluorophenyl)-1H-imidazole;

5-[1-(3,4-dichlorophenyl)-1-methylethyl]-2-({[4-fluoro-3-(methylsulfonyl)phenyl]methyl}thio)-1-(4-fluorophenyl)-1H-imidazole;

3-chloro-2-[({5-[1-(3,4-dichlorophenyl)-1-methylethyl]-1-(4-fluorophenyl)-1H-imidazol-2-yl}thio)methyl]benzoic acid;

1-[5-{1-[3,4-bis(methyloxy)phenyl]-1-methylethyl}-1-(4-fluorophenyl)-1H-imidazol-2-yl]-N-[(2-chloro-6-fluorophenyl)methyl]methanamine;

5-[1-(3,4-dichlorophenyl)-1-methylethyl]-1-(4-fluorophenyl)-N-[(1S)-2-hydroxy-1-phenylethyl]-1H-imidazole-2-sulfonamide;

5-[1-({5-[1-(3,4-dichlorophenyl)-1-methylethyl]-1-(4-fluorophenyl)-1H-imidazol-2-yl}sulfonyl)piperidin-2-yl]-2-(methyloxy)pyridine;

N-[(2-chloro-6-fluorophenyl)methyl]-5-[1-(3,4-dichlorophenyl)-1-methylethyl]-1-(4-fluorophenyl)-1H-imidazole-2-sulfonamide;

2-{[(2-chloro-4-fluorophenyl)methyl]thio}-5-{1-[3-chloro-4-(methyloxy)phenyl]-1-methylethyl}-1-(4-fluorophenyl)-1H-imidazole;

2-{[(2-chloro-5-fluorophenyl)methyl]thio}-5-{1-[3-chloro-4-(methyloxy)phenyl]-1-methylethyl}-1-(4-fluorophenyl)-1H-imidazole;

2-{[(2-chloro-6-fluorophenyl)methyl]thio}-5-{1[3-chloro-4-(methyloxy)phenyl]-1-methylethyl}-1-(4-fluorophenyl)-1H-imidazole;

2-chloro-5-[({5-[1-(3,4-dichlorophenyl)-1-methylethyl]-1-(4-fluorophenyl)-1H-imidazol-2-yl}thio)methyl]benzamide;

5-{2-chloro-5-[({5-[1-(3,4-dichlorophenyl)-1-methylethyl]-1-(4-fluorophenyl)-1H-imidazol-2-yl}thio)methyl]phenyl}-1H-tetrazole;

2-{[(2-chloro-6-fluorophenyl)methyl]thio}-5-[(3,4-dichlorophenyl)(difluoro)methyl]-1-(4-fluorophenyl)-1H-imidazole;

4-chloro-3-[({5-[1-(3,4-dichlorophenyl)-1-methylethyl]-1-(4-fluorophenyl)-1H-imidazol-2-yl}thio)methyl]benzonitrile;

3-chloro-4-[({5-[1-(3,4-dichlorophenyl)-1-methylethyl]-1-(4-fluorophenyl)-1H-imidazol-2-yl}thio)methyl]benzonitrile;

4-chloro-3-[({5-[1-(3,4-dichlorophenyl)-1-methylethyl]-1-(4-fluorophenyl)-1H-imidazol-2-yl}thio)methyl]benzamide;

5-[1-(4-chloro-2-fluorophenyl)-1-methylethyl]-2-{[(2-chloro-6-fluorophenyl)methyl]thio}-1-(4-fluorophenyl)-1H-imidazole;

2-{[(2-chloro-6-fluorophenyl)methyl]thio}-5-[1-(3,4-dichlorophenyl)-1-methylethyl]-1-[4-fluoro-2-(trifluoromethyl)phenyl]-1H-imidazole;

2-chloro-4-{1-[2-{[(2-chloro-4-fluorophenyl)methyl]thio}-1-(4-fluorophenyl)-1H-imidazol-5-yl]-1-methylethyl}benzenesulfonamide;

[5-(2-{[(2-chloro-4-fluorophenyl)methyl]thio}-5-[1-(3,4-dichlorophenyl)-1-methylethyl]-1H-imidazol-1-yl)-2-fluorophenyl]methanol;

2-{[5-(2-{[(2-chloro-4-fluorophenyl)methyl]thio}-5-[1-(3,4-dichlorophenyl)-1-methylethyl]-1H-imidazol-1-yl)-2-fluorophenyl]oxy}-2-methylpropanoic acid;

{[5-(2-{[(2-chloro-4-fluorophenyl)methyl]thio}-5-[1-(3,4-dichlorophenyl)-1-methylethyl]-1H-imidazol-1-yl)-2-fluorophenyl]oxy}acetic acid;

({5-[({5-[1-(3,4-dichlorophenyl)-1-methylethyl]-1-(4-fluorophenyl)-1H-imidazol-2-yl}thio)methyl]-2-fluorophenyl}oxy)acetic acid;

2-({5-[({5-[1-(3,4-dichlorophenyl)-1-methylethyl]-1-(4-fluorophenyl)-1H-imidazol-2-yl}thio)methyl]-2-fluorophenyl}oxy)-2-methylpropanoic acid;

2-{[(2-chloro-6-fluorophenyl)methyl]thio}-5-[1-(3,4-dichlorophenyl)-1-methylethyl]-1-(4-fluorophenyl)-4-phenyl-1H-imidazole;

5-chloro-2-[({5-[1-(3,4-dichlorophenyl)-1-methylethyl]-1-(4-fluorophenyl)-1H-imidazol-2-yl}thio)methyl] benzoic acid;

4-chloro-3-[({5-[1-(3,4-dichlorophenyl)-1-methylethyl]-1-(4-fluorophenyl)-1H-imidazol-2-yl}thio)methyl] benzoic acid;

4-[({5-[1-(3,4-dichlorophenyl)-1-methylethyl]-1-(4-fluorophenyl)-1H-imidazol-2-yl}thio)methyl]-3-fluoro-N-(2-morpholin-4-ylethyl)benzamide;

4-[({5-[1-(3,4-dichlorophenyl)-1-methylethyl]-1-(4-fluorophenyl)-1H-imidazol-2-yl}thio)methyl]-3-fluoro-N-[2-(methyloxy)ethyl]benzamide ;

2-[({5-[1-(3,4-dichlorophenyl)-1-methylethyl]-1-(4-fluorophenyl)-1H-imidazol-2-yl}thio)methyl]-3-fluorobenzoic acid;

3-chloro-4-[({5-[1-(3,4-dichlorophenyl)-1-methylethyl]-1-(4-fluorophenyl)-1H-imidazol-2-yl}thio)methyl] benzamide;

5-{4-chloro-3-[({5-[1-(3,4-dichlorophenyl)-1-methylethyl]-1-(4-fluorophenyl)-1H-imidazol-2-yl}thio)methyl]phenyl}-1H-tetrazole;

5-{3-chloro-4-[({5-[1-(3,4-dichlorophenyl)-1-methylethyl]-1-(4-fluorophenyl)-1H-imidazol-2-yl}thio)methyl]phenyl}-1H-tetrazole;

5-[1-(3,4-dichlorophenyl)-1-methylethyl]-2-{[(2,6-dichlorophenyl)methyl]thio}-1-(4-fluorophenyl)-1H-imidazole;

5-[1-(3,4-dichlorophenyl)-1-methylethyl]-2-{[(2,6-difluorophenyl)methyl]thio}-1-(4-fluorophenyl)-1H-imidazole;

5-[1-(3,4-dichlorophenyl)-1-methylethyl]-1-(4-fluorophenyl)-2-{[(2,4,6-trifluorophenyl)methyl]thio}-1H-imidazole;

3-chloro-4-[({5-[1-(3,4-dichlorophenyl)-1-methylethyl]-1-(4-fluorophenyl)-1H-imidazol-2-yl}thio)methyl]benzoic acid;

4-({[5-{1-[3-chloro-4-(methyloxy)phenyl]-1-methylethyl}-1-(4-fluorophenyl)-1H-imidazol-2-yl]thio}methyl)-3-fluorobenzoic acid;

5-({[5-{1-[3-chloro-4-(methyloxy)phenyl]-1-methylethyl}-1-(4-fluorophenyl)-1H-imidazol-2-yl]thio}methyl)-2-fluorobenzoic acid;

5-[1-(3,4-dichlorophenyl)-1-methylethyl]-1-(4-fluorophenyl)-N-{[2-fluoro-4-(trifluoromethyl)phenyl]methyl}-1H-imidazole-2-sulfonamide;

2-chloro-4-{1-[2-{[(2-chloro-4-fluorophenyl)methyl]thio}-1-(4-fluorophenyl)-1H-imidazol-5-yl]-1-methylethyl}benzonitrile;

2-{[(2-chloro-4-fluorophenyl)methyl]thio}-5-{1-[4-chloro-3-(methyloxy)phenyl]-1-methylethyl}-1-(4-fluorophenyl)-1H-imidazole;

N-({4-[({5-[1-(3,4-dichlorophenyl)-1-methylethyl]-1-(4-fluorophenyl)-1H-imidazol-2-yl}thio)methyl]-3-fluorophenyl}carbonyl)glycine;

4-[({5-[1-(3,4-dichlorophenyl)-1-methylethyl]-1-(4-fluorophenyl)-1H-imidazol-2-yl}thio)methyl]-3-fluoro-N-(2-hydroxy-2-methylpropyl)benzamide;

4-[({5-[1-(3,4-dichlorophenyl)-1-methylethyl]-1-(4-fluorophenyl)-1H-imidazol-2-yl}thio)methyl]-3-fluoro-N-(2,2,2-trifluoroethyl)benzamide;

N-({5-[({5-[1-(3,4-dichlorophenyl)-1-methylethyl]-1-(4-fluorophenyl)-1H-imidazol-2-yl}thio)methyl]-2-fluorophenyl}carbonyl)glycine;

5-[({5-[1-(3,4-dichlorophenyl)-1-methylethyl]-1-(4-fluorophenyl)-1H-imidazol-2-yl}thio)methyl]-2-fluoro-N-(2-morpholin-4-ylethyl)benzamide;

5-[({5-[1-(3,4-dichlorophenyl)-1-methylethyl]-1-(4-fluorophenyl)-1H-imidazol-2-yl}thio)methyl]-2-fluoro-N-(2-hydroxy-2-methylpropyl)benzamide;

4-({[5-{1-[3,4-bis(methyloxy)phenyl]-1-methylethyl}-1-(4-fluorophenyl)-1H-imidazol-2-yl]thio}methyl)-3-fluorobenzamide;

5-({[5-{1-[3,4-bis(methyloxy)phenyl]-1-methylethyl}-1-(4-fluorophenyl)-1H-imidazol-2-yl]thio}methyl)-2-fluorobenzamide;

5-({[5-{1-[3,4-bis(methyloxy)phenyl]-1-methylethyl}-1-(4-fluorophenyl)-1H-imidazol-2-yl]thio}methyl)-2-fluorobenzenesulfonamide;

2-({[5-{1-[3,4-bis(methyloxy)phenyl]-1-methylethyl}-1-(4-fluorophenyl)-1H-imidazol-2-yl]thio}methyl)-3-fluorobenzoic acid;

3-chloro-4-[({5-[1-(3,4-dichlorophenyl)-1-methylethyl]-1-(4-fluorophenyl)-1H-imidazol-2-yl}thio)methyl] benzenecarboximidamide;

2-chloro-4-[({5-[1-(3,4-dichlorophenyl)-1-methylethyl]-1-(4-fluorophenyl)-1H-imidazol-2-yl}thio)methyl] benzonitrile;

2-chloro-4-[({5-[1-(3,4-dichlorophenyl)-1-methylethyl]-1-(4-fluorophenyl)-1H-imidazol-2-yl}thio)methyl] benzamide;

2-chloro-4-[({5-[1-(3,4-dichlorophenyl)-1-methylethyl]-1-(4-fluorophenyl)-1H-imidazol-2-yl}thio)methyl] benzoic acid;

2-chloro-5-[({5-[1-(3,4-dichlorophenyl)-1-methylethyl]-1-(4-fluorophenyl)-1H-imidazol-2-yl}thio)methyl] benzenecarboximidamide;

4-[({5-[1-(3,4-dichlorophenyl)-1-methylethyl]-1-(4-fluorophenyl)-1H-imidazol-2-yl}thio)methyl]-3,5-difluorobenzonitrile;

1-({5-[1-(3,4-dichlorophenyl)-1-methylethyl]-1-(4-fluorophenyl)-1H-imidazol-2-yl}sulfonyl)-6-fluoro-2-methyl-1,2,3,4-tetrahydroquinoline;

4-[({5-[1-(3,4-difluorophenyl)-1-methylethyl]-1-(4-fluorophenyl)-1H-imidazol-2-yl}thio)methyl]-3-fluorobenzoic acid;

4-chloro-3-[({5-[1-(3,4-difluorophenyl)-1-methylethyl]-1-(4-fluorophenyl)-1H-imidazol-2-yl}thio)methyl] benzoic acid;

5-[({5-[1-(3,4-difluorophenyl)-1-methylethyl]-1-(4-fluorophenyl)-1H-imidazol-2-yl}thio)methyl]-2-fluorobenzoic acid;

4-[({5-[1-(3,4-dichlorophenyl)-1-methylethyl]-1-(4-fluorophenyl)-1H-imidazol-2-yl}thio)methyl]-3,5-difluorobenzoic acid;

5-{1-[3,4-bis(methyloxy)phenyl]-1-methylethyl}-N-(2-chloro-6-fluorophenyl)-1-(4-fluorophenyl)-1H-imidazole-2-carboxamide;

(2-chloro-4-{1-[2-{[(2-chloro-4-fluorophenyl)methyl]thio}-1-(4-fluorophenyl)-1H-imidazol-5-yl]-1-methylethyl}phenyl)methanol;

2-(2-chloro-4-{1-[2-{[(2-chloro-4-fluorophenyl)methyl]thio}-1-(4-fluorophenyl)-1H-imidazol-5-yl]-1-methylethyl}phenyl)propan-2-ol;

({2-[({5-[1-(3,4-dichlorophenyl)-1-methylethyl]-1-(4-fluorophenyl)-1H-imidazol-2-yl}thio)methyl]-5-fluorophenyl}oxy)acetic acid;

5-{5-[({5-[1-(3,4-dichlorophenyl)-1-methylethyl]-1-(4-fluorophenyl)-1H-imidazol-2-yl}thio)methyl]-2-fluorophenyl}-1H-tetrazole;

2-{4-[({5-[1-(3,4-dichlorophenyl)-1-methylethyl]-1-(4-fluorophenyl)-1H-imidazol-2-yl}thio)methyl]-3-fluorophenyl}-2-methylpropanoic acid;
5-[({5-[1-(3,4-dichlorophenyl)-1-methylethyl]-1-(4-fluorophenyl)-1H-imidazol-2-yl}thio)methyl]-2-fluoro-N-[2-(methyloxy)ethyl]benzamide;
5-[({5-[1-(3,4-dichlorophenyl)-1-methylethyl]-1-(4-fluorophenyl)-1H-imidazol-2-yl}thio)methyl]-2-fluoro-N-(2,2,2-trifluoroethyl)benzamide;
2-{[(2-chloro-6-fluorophenyl)methyl]thio}-5-{1[4-chloro-3-(methyloxy)phenyl]-1-methylethyl}-1-(4-fluorophenyl)-1H-imidazole;
5-({[5-{1-[4-chloro-3-(methyloxy)phenyl]-1-methylethyl}-1-(4-fluorophenyl)-1H-imidazol-2-yl]thio}methyl)-2-fluorobenzenesulfonamide;
4-[({5-[1-(3,4-dichlorophenyl)-1-methylethyl]-1-(4-fluorophenyl)-1H-imidazol-2-yl}thio)methyl]-3,5-difluorobenzamide;
4-({[5-{1-[3-chloro-4-(methyloxy)phenyl]-1-methylethyl}-1-(4-fluorophenyl)-1H-imidazol-2-yl]thio}methyl)-3,5-difluorobenzonitrile;
2-chloro-4-[({5-[1-(3,4-dichlorophenyl)-1-methylethyl]-1-(4-fluorophenyl)-1H-imidazol-2-yl}thio)methyl]benzenecarboximidamide;
5-{2-chloro-4-[({5-[1-(3,4-dichlorophenyl)-1-methylethyl]-1-(4-fluorophenyl)-1H-imidazol-2-yl}thio)methyl]phenyl}-1H-tetrazole;
2-{[(2-chloro-6-fluorophenyl)methyl]thio}-5-{1-[3,5-dichloro-4-(methyloxy)phenyl]-1-methylethyl}-1-(4-fluorophenyl)-1H-imidazole;
2-chloro-5-({[5-{1-[3-chloro-4-(methyloxy)phenyl]-1-methylethyl}-1-(4-fluorophenyl)-1H-imidazol-2-yl]thio}methyl)benzoic acid;
4-({[5-{1-[3-chloro-4-(methyloxy)phenyl]-1-methylethyl}-1-(4-fluorophenyl)-1H-imidazol-2-yl]thio}methyl)-3,5-difluorobenzoic acid;
5-({[5-{1-[3-chloro-4-(methyloxy)phenyl]-1-methylethyl}-1-(4-fluorophenyl)-1H-imidazol-2-yl]thio}methyl)-2-fluorobenzenesulfonamide;
3-chloro-4-[({5-[1-(3,4-dichlorophenyl)-1-methylethyl]-1-(4-fluorophenyl)-1H-imidazol-2-yl}thio)methyl]-5-fluorobenzoic acid;
5-{4-[({5-[1-(3,4-dichlorophenyl)-1-methylethyl]-1-(4-fluorophenyl)-1H-imidazol-2-yl}thio)methyl]-3,5-difluorophenyl}-1H-tetrazole;
3-chloro-4-({[5-{1-[3-chloro-4-(methyloxy)phenyl]-1-methylethyl}-1-(4-fluorophenyl)-1H-imidazol-2-yl]thio}methyl)-5-fluorobenzoic acid;
2-{[(2-chloro-4-fluorophenyl)methyl]thio}-5-{1-[3,5-dichloro-4-(methyloxy)phenyl]-1-methylethyl}-1-(4-fluorophenyl)-1H-imidazole;
3-chloro-4-({[5-{1-[3,5-dichloro-4-(methyloxy)phenyl]-1-methylethyl}-1-(4-fluorophenyl)-1H-imidazol-2-yl]thio}methyl)benzenesulfonamide;
3-chloro-4-[({5-[1-(3,4-dichlorophenyl)-1-methylethyl]-1-(4-fluorophenyl)-1H-imidazol-2-yl}thio)methyl]benzenesulfonamide;
4-[({5-[1-(3,4-dichlorophenyl)-1-methylethyl]-1-(4-fluorophenyl)-1H-imidazol-2-yl}thio)methyl]-3-fluorobenzenesulfonamide;
5-[2-chloro-5-({[5-{1-[3-chloro-4-(methyloxy)phenyl]-1-methylethyl}-1-(4-fluorophenyl)-1H-imidazol-2-yl]thio}methyl)phenyl]-1H-tetrazole;
2-{[(2-chloro-4-fluorophenyl)methyl]thio}-5-(1-{3-chloro-4-[(trifluoromethyl)oxy]phenyl}-1-methylethyl)-1-(4-fluorophenyl)-1H-imidazole;
1-[(2-chloro-4-{1-[2-{[(2-chloro-4-fluorophenyl)methyl]thio}-1-(4-fluorophenyl)-1H-imidazol-5-yl]-1-methylethyl}phenyl)oxy]-2-methylpropan-2-ol;
[(2-chloro-4-{1-[2-{[(2-chloro-4-fluorophenyl)methyl]thio}-1-(4-fluorophenyl)-1H-imidazol-5-yl]-1-methylethyl}phenyl)oxy]acetic acid;
2-[(2-chloro-4-{1-[2-{[(2-chloro-4-fluorophenyl)methyl]thio}-1-(4-fluorophenyl)-1H-imidazol-5-yl]-1-methylethyl}phenyl)oxy]-2-methylpropanoic acid;
4-[({5-[1-(3,4-dichlorophenyl)-1-methylethyl]-1-(4-fluorophenyl)-1H-imidazol-2-yl}thio)methyl]-2-fluorobenzoic acid;
2-{5-[({5-[1-(3,4-dichlorophenyl)-1-methylethyl]-1-(4-fluorophenyl)-1H-imidazol-2-yl}thio)methyl]-2-fluorophenyl}-2-methylpropanoic acid;
4-[({5-[1-(3,4-dichlorophenyl)-1-methylethyl]-1-(4-fluorophenyl)-1H-imidazol-2-yl}thio)methyl]-3-fluoro-N-[2-(1H-imidazol-4-yl)ethyl]benzamide;
2-[2-(2-chloro-6-fluorophenyl)ethyl]-5-[1-(3,4-dichlorophenyl)-1-methylethyl]-1-(4-fluorophenyl)-1H-imidazole;
5-{1-[3,4-bis(methyloxy)phenyl]-1-methylethyl}-2-[2-(2-chloro-6-fluorophenyl)ethyl]-1-(4-fluorophenyl)-1H-imidazole;
4-chloro-3-({[5-{1-[4-chloro-3-(methyloxy)phenyl]-1-methylethyl}-1-(4-fluorophenyl)-1H-imidazol-2-yl]thio}methyl)benzoic acid;
4-({[5-{1-[4-chloro-3-(methyloxy)phenyl]-1-methylethyl}-1-(4-fluorophenyl)-1H-imidazol-2-yl]thio}methyl)-3-fluorobenzoic acid;
2-{[(2-chloro-6-fluorophenyl)methyl]thio}-5-[1-(3,4-dichlorophenyl)-1-methylethyl]-1-[4-fluoro-3-(methyloxy)phenyl]-1H-imidazole;
2-chloro-4-[({5-[1-(3,4-dichlorophenyl)-1-methylethyl]-1-(4-fluorophenyl)-1H-imidazol-2-yl}methyl)oxy]benzamide;
4-({[5-{1-[3,5-dichloro-4-(methyloxy)phenyl]-1-methylethyl}-1-(4-fluorophenyl)-1H-imidazol-2-yl]thio}methyl)-3-fluorobenzenesulfonamide;
5-({[5-{1-[3,5-dichloro-4-(methyloxy)phenyl]-1-methylethyl}-1-(4-fluorophenyl)-1H-imidazol-2-yl]thio}methyl)-2-fluorobenzenesulfonamide;
2-chloro-5-[({5-[1-(3,4-dichlorophenyl)-1-methylethyl]-1-(4-fluorophenyl)-1H-imidazol-2-yl}thio)methyl]benzenesulfonamide;
4-[({5-[1-(3,4-dichlorophenyl)-1-methylethyl]-1-(4-fluorophenyl)-1H-imidazol-2-yl}thio)methyl]-2-fluorobenzenesulfonamide;
2,4-dichloro-5-[({5-[1-(3,4-dichlorophenyl)-1-methylethyl]-1-(4-fluorophenyl)-1H-imidazol-2-yl}thio)methyl]benzenesulfonamide;
5-{1-[3,4-bis(methyloxy)phenyl]-1-methylethyl}-N-(2-chloro-4-fluorophenyl)-1-(4-fluorophenyl)-1H-imidazole-2-carboxamide;
1-({2-[({5-[1-(3,4-dichlorophenyl)-1-methylethyl]-1-(4-fluorophenyl)-1H-imidazol-2-yl}thio)methyl]-5-fluorophenyl}oxy)-2-methylpropan-2-ol;
2-({2-[({5-[1-(3,4-dichlorophenyl)-1-methylethyl]-1-(4-fluorophenyl)-1H-imidazol-2-yl}thio)methyl]-5-fluorophenyl}oxy)-2-methylpropanoic acid;
4-[({5-[1-(3,4-dichlorophenyl)-1-methylethyl]-1-(4-fluorophenyl)-1H-imidazol-2-yl}thio)methyl]-2-fluorobenzamide;
5-[({5-[1-(3,4-dichlorophenyl)-1-methylethyl]-1-(4-fluorophenyl)-1H-imidazol-2-yl}thio)methyl]-2-fluoro-N-[2-(1H-imidazol-4-yl)ethyl]benzamide;

2-{2-chloro-5-[({5-[1-(3,4-dichlorophenyl)-1-methylethyl]-1-(4-fluorophenyl)-1H-imidazol-2-yl}thio)methyl]phenyl}propan-2-ol;
4-({[5-{1-[4-chloro-3-(methyloxy)phenyl]-1-methylethyl}-1-(4-fluorophenyl)-1H-imidazol-2-yl]thio}methyl)-2-fluorobenzoic acid;
2-chloro-4-{1-[2-{[(2-chloro-4-fluorophenyl)methyl]thio}-1-(4-fluorophenyl)-1H-imidazol-5-yl]-1-methylethyl}benzamide;
5-{4-[({5-[1-(3,4-dichlorophenyl)-1-methylethyl]-1-(4-fluorophenyl)-1H-imidazol-2-yl}thio)methyl]-3-fluorophenyl}-1H-tetrazole;
5-{4-[({5-[1-(3,4-dichlorophenyl)-1-methylethyl]-1-(4-fluorophenyl)-1H-imidazol-2-yl}thio)methyl]-2-fluorophenyl}-1H-tetrazole;
5-[2,4-dichloro-5-({[5-{1-[3-chloro-4-(methyloxy)phenyl]-1-methylethyl}-1-(4-fluorophenyl)-1H-imidazol-2-yl]thio}methyl)phenyl]-1H-tetrazole;
4-chloro-3-[({5-[1-(3,4-dichlorophenyl)-1-methylethyl]-1-(4-fluorophenyl)-1H-imidazol-2-yl}thio)methyl]benzenesulfonamide;
3-chloro-4-[({5-[1-(3,4-dichlorophenyl)-1-methylethyl]-1-(4-fluorophenyl)-1H-imidazol-2-yl}methyl)oxy]benzoic acid;
5-{3-chloro-4-[({5-[1-(3,4-dichlorophenyl)-1-methylethyl]-1-(4-fluorophenyl)-1H-imidazol-2-yl}methyl)oxy]phenyl}-2H-tetrazole;
5-{1-[3,4-bis(methyloxy)phenyl]-1-methylethyl}-N-(3,4-dichlorophenyl)-1-(4-fluorophenyl)-1H-imidazole-2-carboxamide;
5-{1-[3,4-bis(methyloxy)phenyl]-1-methylethyl}-N-[(4-chloro-3-fluorophenyl)methyl]-1-(4-fluorophenyl)-1H-imidazole-2-carboxamide;
1-({5-[({5-[1-(3,4-dichlorophenyl)-1-methylethyl]-1-(4-fluorophenyl)-1H-imidazol-2-yl}thio)methyl]-2-fluorophenyl}oxy)-2-methylpropan-2-ol;
2-{3-[({5-[1-(3,4-dichlorophenyl)-1-methylethyl]-1-(4-fluorophenyl)-1H-imidazol-2-yl}thio)methyl]-4-fluorophenyl}-2-methylpropanoic acid;
2-{4-[({5-[1-(3,4-dichlorophenyl)-1-methylethyl]-1-(4-fluorophenyl)-1H-imidazol-2-yl}thio)methyl]-3-fluorophenyl}propan-2-ol;
2-{3-chloro-4-[({5-[1-(3,4-dichlorophenyl)-1-methylethyl]-1-(4-fluorophenyl)-1H-imidazol-2-yl}thio)methyl]phenyl}propan-2-ol;
2-{5-[({5-[1-(3,4-dichlorophenyl)-1-methylethyl]-1-(4-fluorophenyl)-1H-imidazol-2-yl}thio)methyl]-2-fluorophenyl}propan-2-ol;
3-chloro-4-({[5-{1-[4-chloro-3-(methyloxy)phenyl]-1-methylethyl}-1-(4-fluorophenyl)-1H-imidazol-2-yl]thio}methyl)-5-fluorobenzoic acid;
5-[4-({[5-{1-[3-chloro-4-(methyloxy)phenyl]-1-methylethyl}-1-(4-fluorophenyl)-1H-imidazol-2-yl]thio}methyl)-3,5-difluorophenyl]-1H-tetrazole;
1-[(2-chloro-5-{1-[2-{[(2-chloro-6-fluorophenyl)methyl]thio}-1-(4-fluorophenyl)-1H-imidazol-5-yl]-1-methylethyl}phenyl)oxy]-2-methylpropan-2-ol;
4-{3-[(2-chloro-5-{1-[2-{[(2-chloro-6-fluorophenyl)methyl]thio}-1-(4-fluorophenyl)-1H-imidazol-5-yl]-1-methylethyl}phenyl)oxy]propyl}morpholine;
1-{5-[({5-[1-(3,4-dichlorophenyl)-1-methylethyl]-1-(4-fluorophenyl)-1H-imidazol-2-yl}thio)methyl]-2-fluorophenyl}-4-methylpiperazine;
4-[({5-[1-(3,4-dichlorophenyl)-1-methylethyl]-1-(4-fluorophenyl)-1H-imidazol-2-yl}thio)methyl]piperidine;
5-[2-chloro-5-({[5-{1-[4-chloro-3-(methyloxy)phenyl]-1-methylethyl}-1-(4-fluorophenyl)-1H-imidazol-2-yl]thio}methyl)phenyl]-1H-tetrazole;
4-[({5-[1-(3,4-dichlorophenyl)-1-methylethyl]-1-(4-fluorophenyl)-1H-imidazol-2-yl}thio)methyl]-1-(methylsulfonyl)piperidine;
2-chloro-5-{1-[2-{[(2-chloro-6-fluorophenyl)methyl]thio}-1-(4-fluorophenyl)-1H-imidazol-5-yl]-1-methylethyl}phenol;
2-[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]propan-2-ol;
4-({[5-{1-[4-chloro-3-(methyloxy)phenyl]-1-methylethyl}-1-(4-fluorophenyl)-1H-imidazol-2-yl]thio}methyl)-3,5-difluorobenzoic acid;
4-[({5-[1-(4-chloro-3-hydroxyphenyl)-1-methylethyl]-1-(4-fluorophenyl)-1H-imidazol-2-yl}thio)methyl]-3,5-difluorobenzoic acid;
5-[4-({[5-{1-[4-chloro-3-(methyloxy)phenyl]-1-methylethyl}-1-(4-fluorophenyl)-1H-imidazol-2-yl]thio}methyl)-3,5-difluorophenyl]-1H-tetrazole;
3-chloro-4-[({5-[1-(3,4-difluorophenyl)-1-methylethyl]-1-(4-fluorophenyl)-1H-imidazol-2-yl}thio)methyl]-5-fluorobenzoic acid;
2-[(2-chloro-5-{1-[2-{[(2-chloro-6-fluorophenyl)methyl]thio}-1-(4-fluorophenyl)-1H-imidazol-5-yl]-1-methylethyl}phenyl)oxy]-N,N-diethylethanamine;
4-[({5-[1-(3,4-difluorophenyl)-1-methylethyl]-1-(4-fluorophenyl)-1H-imidazol-2-yl}thio)methyl]-3,5-difluorobenzoic acid;
1,1-dimethylethyl 4-[({5-[1-(3,4-difluorophenyl)-1-methylethyl]-1-(4-fluorophenyl)-1H-imidazol-2-yl}thio)methyl]piperidine-1-carboxylate;
4-{2-[(2-chloro-5-{1-[2-{[(2-chloro-6-fluorophenyl)methyl]thio}-1-(4-fluorophenyl)-1H-imidazol-5-yl]-1-methylethyl}phenyl)oxy]ethyl}morpholine;
5-{1[3,4-bis(methyloxy)phenyl]-1-methylethyl}-N-(2-chloro-6-fluorophenyl)-1-(4-fluorophenyl)-N-methyl-1H-imidazole-2-carboxamide;
N-{5-{1-[3,4-bis(methyloxy)phenyl]-1-methylethyl}-1-(4-fluorophenyl)-1H-imidazol-2-yl]methyl}-2-chloro-6-fluoro-N-methylaniline;
5-(2-chloro-5-{[(5-{1-[4-chloro-3-(methyloxy)phenyl]-1-methylethyl}-1-[4-fluoro-3-(methyloxy)phenyl]-1H-imidazol-2-yl)thio]methyl}phenyl)-1H-tetrazole;
4-({[5-{1-[4-chloro-3-(methyloxy)phenyl]-1-methylethyl}-1-(4-fluorophenyl)-1H-imidazol-2-yl]thio}methyl)-1-(methylsulfonyl)piperidine;
3-chloro-4-({[5-{1-[4-chloro-3-(methyloxy)phenyl]-1-methylethyl}-1-(4-fluorophenyl)-1H-imidazol-2-yl]methyl}oxy)-5-fluorobenzoic acid;
2-chloro-5-{1-[2-{[(2-chloro-4-fluorophenyl)methyl]thio}-1-(4-fluorophenyl)-1H-imidazol-5-yl]-1-methylethyl}benzenesulfonamide;
1-{2-chloro-4-[({5-[1-(3,4-dichlorophenyl)-1-methylethyl]-1-(4-fluorophenyl)-1H-imidazol-2-yl}thio)methyl]phenyl}-4-methylpiperazine;
1-{4-[({5-[1-(3,4-dichlorophenyl)-1-methylethyl]-1-(4-fluorophenyl)-1H-imidazol-2-yl}thio)methyl]-2-fluorophenyl}-4-methylpiperazine;
4-[({5-[1-(3,4-difluorophenyl)-1-methylethyl]-1-(4-fluorophenyl)-1H-imidazol-2-yl}thio)methyl]-1-(methylsulfonyl)piperidine;
3-[(2-chloro-5-{1-[2-{[(2-chloro-6-fluorophenyl)methyl]thio}-1-(4-fluorophenyl)-1H-imidazol-5-yl]-1-methylethyl}phenyl)oxy]propan-1-ol;

5-[5-({[5-{1-[4-chloro-3-(methyloxy)phenyl]-1-methylethyl}-1-(4-fluorophenyl)-1H-imidazol-2-yl]thio}methyl)-2-fluorophenyl]-1H-tetrazole;

3-chloro-4-({[5-(1-{4-chloro-3-[(3-morpholin-4-ylpropyl)oxy]phenyl}-1-methylethyl)-1-(4-fluorophenyl)-1H-imidazol-2-yl]thio}methyl)-5-fluorobenzoic acid;

3-{4-[({5-[1-(3,4-difluorophenyl)-1-methylethyl]-1-(4-fluorophenyl)-1H-imidazol-2-yl}thio)methyl]piperidin-1-yl}propane-1,2-diol;

2-[4-({[5-{1-[4-chloro-3-(methyloxy)phenyl]-1-methylethyl}-1-(4-fluorophenyl)-1H-imidazol-2-yl]thio}methyl)piperidin-1-yl]ethanol;

[4-({[5-{1-[4-chloro-3-(methyloxy)phenyl]-1-methylethyl}-1-(4-fluorophenyl)-1H-imidazol-2-yl]thio}methyl)piperidin-1-yl]acetic acid;

3-chloro-4-[({5-[1-(3,4-dichlorophenyl)-1-methylethyl]-1-[4-fluoro-3-(methyloxy)phenyl]-1H-imidazol-2-yl}thio)methyl]-5-fluorobenzoic acid;

methyl 3-chloro-4-[({5-[1-(3,4-dichlorophenyl)-1-methylethyl]-1-(4-fluorophenyl)-1H-imidazol-2-yl}methyl)oxy]-5-fluorobenzoate;

3-chloro-4-[({5-[1-(3,4-dichlorophenyl)-1-methylethyl]-1-(3-{[2-(diethylamino)ethyl]oxy}-4-fluorophenyl)-1H-imidazol-2-yl}thio)methyl]-5-fluorobenzoic acid;

4-({[5-{1-[4-chloro-3-(methyloxy)phenyl]-1-methylethyl}-1-(4-fluorophenyl)-1H-imidazol-2-yl]sulfonyl}methyl)-1-(methylsulfonyl)piperidine;

2-chloro-4-{1-[2-({[4-chloro-3-(1H-tetrazol-5-yl)phenyl]methyl}thio)-1-(4-fluorophenyl)-1H-imidazol-5-yl]-1-methylethyl}benzenesulfonamide;

4-({[5-{1-[4-(aminosulfonyl)-3-chlorophenyl]-1-methylethyl}-1-(4-fluorophenyl)-1H-imidazol-2-yl]thio}methyl)-3-chloro-5-fluorobenzoic acid;

4-({[5-{1-[3-(aminosulfonyl)-4-chlorophenyl]-1-methylethyl}-1-(4-fluorophenyl)-1H-imidazol-2-yl]thio}methyl)-3-chloro-5-fluorobenzoic acid;

2-chloro-5-{1-[2-({[4-chloro-3-(1H-tetrazol-5-yl)phenyl]methyl}thio)-1-(4-fluorophenyl)-1H-imidazol-5-yl]-1-methylethyl}benzenesulfonamide;

2-({[4-({[5-{1-[4-chloro-3-(methyloxy)phenyl]-1-methylethyl}-1-(4-fluorophenyl)-1H-imidazol-2-yl]thio}methyl)-3-fluorophenyl]carbonyl}amino)ethanesulfonic acid;

3-chloro-4-{[(5-[1-(3,4-dichlorophenyl)-1-methylethyl]-1-{4-fluoro-3-[(3-hydroxypropyl)oxy]phenyl}-1H-imidazol-2-yl)thio]methyl}-5-fluorobenzoic acid;

5-[2-chloro-5-({[5-{1-[4-chloro-3-(methyloxy)phenyl]-1-methylethyl}-1-(4-fluorophenyl)-1H-imidazol-2-yl]methyl}oxy)phenyl]-1H-tetrazole;

3-chloro-4-[({5-[1-(3,4-dichlorophenyl)-1-methylethyl]-1-(4-fluorophenyl)-1H-imidazol-2-yl}methyl)oxy]-5-fluorobenzoic acid;

2-({4-[({5-[1-(3,4-dichlorophenyl)-1-methylethyl]-1-(4-fluorophenyl)-1H-imidazol-2-yl}thio)methyl]-2-(1H-tetrazol-5-yl)phenyl}oxy)-N,N-diethylethanamine;

4-[({5-[1-(3,4-dichlorophenyl)-1-methylethyl]-1-[4-fluoro-3-(methyloxy)phenyl]-1H-imidazol-2-yl}thio)methyl]-3,5-difluorobenzoic acid;

4-[({5-[1-(3,4-dichlorophenyl)-1-methylethyl]-1-(4-fluorophenyl)-1H-imidazol-2-yl}thio)methyl]-1-(4-fluorophenyl)piperidine;

2-({4-[({5-[1-(3,4-dichlorophenyl)-1-methylethyl]-1-(4-fluorophenyl)-1H-imidazol-2-yl}thio)methyl]piperidin-1-yl}sulfonyl)-N,N-diethylethanamine;

4-[({5-[1-(3,4-dichlorophenyl)-1-methylethyl]-1-(4-fluorophenyl)-1H-imidazol-2-yl}thio)methyl]-1-(1H-tetrazol-5-yl)piperidine;

1-acetyl-4-[({5-[1-(3,4-dichlorophenyl)-1-methylethyl]-1-(4-fluorophenyl)-1H-imidazol-2-yl}thio)methyl]piperidine;

5-[({5-[1-(3,4-dichlorophenyl)-1-methylethyl]-1-(4-fluorophenyl)-1H-imidazol-2-yl}thio)methyl]-2-[(3-hydroxypropyl)oxy]benzonitrile;

2-chloro-5-[({5-[1-(3,4-dichlorophenyl)-1-methylethyl]-1-(4-fluorophenyl)-1H-imidazol-2-yl}methyl)oxy]benzenesulfonamide;

4-({[5-{1-[4-(aminosulfonyl)-3-chlorophenyl]-1-methylethyl}-1-(4-fluorophenyl)-1H-imidazol-2-yl]thio}methyl)-3,5-difluorobenzoic acid;

4-({[5-{1-[3-(aminosulfonyl)-4-chlorophenyl]-1-methylethyl}-1-(4-fluorophenyl)-1H-imidazol-2-yl]thio}methyl)-3,5-difluorobenzoic acid;

3,5-difluoro-4-({[1-(4-fluorophenyl)-5-(1-methyl-1-naphthalen-2-ylethyl)-1H-imidazol-2-yl]thio}methyl)benzoic acid;

6-[({5-[1-(3,4-dichlorophenyl)-1-methylethyl]-1-(4-fluorophenyl)-1H-imidazol-2-yl}methyl)oxy]pyridine-3-carbonitrile;

6-[({5-[1-(3,4-dichlorophenyl)-1-methylethyl]-1-(4-fluorophenyl)-1H-imidazol-2-yl}methyl)oxy]pyridine-3-carboxamide;

1-{5-[({5-[1-(3,4-dichlorophenyl)-1-methylethyl]-1-(4-fluorophenyl)-1H-imidazol-2-yl}thio)methyl]-2-fluorophenyl}guanidine;

N-({5-[1-(3,4-dichlorophenyl)-1-methylethyl]-1-(4-fluorophenyl)-1H-imidazol-2-yl}methyl)-1-(methylsulfonyl)piperidin-4-amine;

4-[({5-[1-(3,4-dichlorophenyl)-1-methylethyl]-1-(4-fluorophenyl)-1H-imidazol-2-yl}methyl)oxy]-1-(methylsulfonyl)piperidine;

3-[({5-[1-(3,4-dichlorophenyl)-1-methylethyl]-1-(4-fluorophenyl)-1H-imidazol-2-yl}thio)methyl]-1-(1H-tetrazol-5-yl)piperidine;

4-({[5-{1-[4-chloro-3-(methyloxy)phenyl]-1-methylethyl}-1-(4-fluorophenyl)-1H-imidazol-2-yl]thio}methyl)-1-(1H-tetrazol-5-yl)piperidine;

1,1-dimethylethyl 4-[({5-[1-(3,4-dichlorophenyl)-1-methylethyl]-1-(4-fluorophenyl)-1H-imidazol-2-yl}methyl)oxy]piperidine-1-carboxylate;

2-{[(2-chloro-6-fluorophenyl)methyl]thio}-5-{1-[4-chloro-3-(methyloxy)phenyl]-1-methylethyl}-1-(4-fluorophenyl)-4-methyl-1H-imidazole;

ethyl 3-chloro-4-({[5-{1-[4-chloro-3-(methyloxy)phenyl]-1-methylethyl}-1-(4-fluorophenyl)-4-methyl-1H-imidazol-2-yl]thio}methyl)-5-fluorobenzoate;

3-chloro-4-({[5-{1-[4-chloro-3-(methyloxy)phenyl]-1-methylethyl}-1-(4-fluorophenyl)-4-methyl-1H-imidazol-2-yl]thio}methyl)-5-fluorobenzoic acid;

3-chloro-4-{[(5-{1-[4-chloro-3-(methyloxy)phenyl]-1-methylethyl}-1-pyridin-3-yl-1H-imidazol-2-yl)thio]methyl}-5-fluorobenzoic acid;

3-(2-{[(2-chloro-6-fluorophenyl)methyl]thio}-5-{1-[4-chloro-3-(methyloxy)phenyl]-1-methylethyl}-1H-imidazol-1-yl)pyridine;

3-chloro-4-({[5-{1-[4-chloro-3-(methyloxy)phenyl]-1-methylethyl}-1-(5-fluoropyridin-2-yl)-1H-imidazol-2-yl]thio}methyl)-5-fluorobenzoic acid;

({2-(aminosulfonyl)-4-[({5-[1-(3,4-dichlorophenyl)-1-methylethyl]-1-(4-fluorophenyl)-1H-imidazol-2-yl}thio)methyl]phenyl}oxy)acetic acid;

2-chloro-N-({5-[1-(3,4-dichlorophenyl)-1-methylethyl]-1-(4-fluorophenyl)-1H-imidazol-2-yl}methyl)-6-fluoro-N-methylaniline;

4-[({4-chloro-5-[1-(3,4-dichlorophenyl)-1-methylethyl]-1-(4-fluorophenyl)-1H-imidazol-2-yl}thio)methyl]-3,5-difluorobenzoic acid;

3-[({5-[1-(3,4-dichlorophenyl)-1-methylethyl]-1-(4-fluorophenyl)-1H-imidazol-2-yl}thio)methyl]-1-(methylsulfonyl)piperidine;

1,1-dimethylethyl 3-[({5-[1-(3,4-dichlorophenyl)-1-methylethyl]-1-(4-fluorophenyl)-1H-imidazol-2-yl}thio)methyl]pyrrolidine-1-carboxylate;

5-[({5-[1-(3,4-dichlorophenyl)-1-methylethyl]-1-(4-fluorophenyl)-1H-imidazol-2-yl}thio)methyl]-2-{[2-(diethylamino)ethyl]oxy}benzenesulfonamide;

4-[({5-[1-(3,4-dichlorophenyl)-1-methylethyl]-1-(4-fluorophenyl)-1H-imidazol-2-yl}thio)methyl]-3,5-difluoro-N-hydroxybenzamide;

4-[({5-[1-(3-cyano-4-fluorophenyl)-1-methylethyl]-1-(4-fluorophenyl)-1H-imidazol-2-yl}thio)methyl]-3,5-difluorobenzoic acid;

5-chloro-2-[({5-[1-(3,4-dichlorophenyl)-1-methylethyl]-1-(4-fluorophenyl)-1H-imidazol-2-yl}methyl)oxy]pyridine;

6-[({5-[1-(3,4-dichlorophenyl)-1-methylethyl]-1-(4-fluorophenyl)-1H-imidazol-2-yl}methyl)oxy]pyridine-3-carboxylic acid;

2-[({4-[({5-[1-(3,4-dichlorophenyl)-1-methylethyl]-1-(4-fluorophenyl)-1H-imidazol-2-yl}thio)methyl]-3-fluorophenyl}carbonyl)amino]ethanesulfonic acid-sodium (1:1);

3,5-difluoro-4-{[(1-[4-fluoro-3-(methyloxy)phenyl]-5-{1-methyl-1-[3-(methylsulfonyl)phenyl]ethyl}-1H-imidazol-2-yl)thio]methyl}benzoic acid;

3-chloro-4-[({5-[1-(3,4-dichlorophenyl)-1-methylethyl]-1-(4-fluorophenyl)-1H-imidazol-2-yl}thio)methyl]-N-{[(1-methylethyl)amino]carbonyl}benzenesulfonamide;

5-[({5-[1-(3,4-dichlorophenyl)-1-methylethyl]-1-(4-fluorophenyl)-1H-imidazol-2-yl}thio)methyl]-2-fluoro-N-{[(1-methylethyl)amino]carbonyl}benzenesulfonamide;

N-({3-chloro-4-[({5-[1-(3,4-dichlorophenyl)-1-methylethyl]-1-(4-fluorophenyl)-1H-imidazol-2-yl}thio)methyl]phenyl}sulfonyl)acetamide;

5-[1-(3,4-dichlorophenyl)-1-methylethyl]-1,2-bis(4-fluorophenyl)-1H-imidazole;

2-{[(2-chloro-6-fluorophenyl)oxy]methyl}-5-[1-(3,4-dichlorophenyl)-1-methylethyl]-1-(4-fluorophenyl)-1H-imidazole;

5-[1-(3,4-dichlorophenyl)-1-methylethyl]-1-(4-fluorophenyl)-2-[{[1-(methylsulfonyl)pyrrolidin-3-yl]methyl}thio)-1H-imidazole;

5-{3-[({5-[1-(3,4-dichlorophenyl)-1-methylethyl]-1-(4-fluorophenyl)-1H-imidazol-2-yl}thio)methyl]pyrrolidin-1-yl}-1H-tetrazole;

4-[({5-[1-(3,4-dichlorophenyl)-1-methylethyl]-1-[4-fluoro-3-(methyloxy)phenyl]-1H-imidazol-2-yl}thio)methyl]-N-(1-methylethyl)piperidine-1-carboxamide;

N-[(4-chloro-2-fluorophenyl)methyl]-5-{1-[4-chloro-3-(methyloxy)phenyl]-1-methylethyl}-1-(4-fluorophenyl)-1H-imidazol-2-amine;

3-chloro-4-[({5-[1-(3,4-dichlorophenyl)-1-methylethyl]-1-(4-fluorophenyl)-1H-imidazol-2-yl}thio)methyl]-N-[(pyrrolidin-1-ylamino)carbonyl]benzenesulfonamide;

4-[({5-[1-(3,4-dichlorophenyl)cyclopropyl]-1-(4-fluorophenyl)-1H-imidazol-2-yl}thio)methyl]-3,5-difluorobenzoic acid;

3-chloro-2-[({5-[1-(3,4-dichlorophenyl)-1-methylethyl]-1-(4-fluorophenyl)-1H-imidazol-2-yl}methyl)oxy]-5-(trifluoromethyl)pyridine;

3,5-difluoro-4-{[(1-[4-fluoro-3-(methyloxy)phenyl]-5-{1-methyl-1-[4-(methylsulfonyl)phenyl]ethyl}-1H-imidazol-2-yl)thio]methyl}benzoic acid;

4-{[(5-{1-[4-(aminosulfonyl)phenyl]-1-methylethyl}-1-[4-fluoro-3-(methyloxy)phenyl]-1H-imidazol-2-yl)thio]methyl}-3,5-difluorobenzoic acid;

2-{1-[(2-chloro-4-fluorophenyl)thio]ethyl}-5-[1-(3,4-dichlorophenyl)-1-methylethyl]-1-(4-fluorophenyl)-1H-imidazole;

2-{1-[(2-chloro-4-fluorophenyl)sulfonyl]ethyl}-5-[1-(3,4-dichlorophenyl)-1-methylethyl]-1-(4-fluorophenyl)-1H-imidazole;

4-{5-[1-(3,4-dichlorophenyl)-1-methylethyl]-1-(4-fluorophenyl)-1H-imidazol-2-yl}-1-(methylsulfonyl)-1,2,3,6-tetrahydropyridine;

4-({[4-chloro-5-{1-[4-chloro-3-(methyloxy)phenyl]-1-methylethyl}-1-(4-fluorophenyl)-1H-imidazol-2-yl]thio}methyl)-1-(methylsulfonyl)piperidine;

4-[({5-[1-(3,4-dichlorophenyl)-1-methylethyl]-1-[4-fluoro-3-(methyloxy)phenyl]-1H-imidazol-2-yl}thio)methyl]-1-(1H-tetrazol-5-yl)piperidine;

3-chloro-4-({[5-{1-[4-chloro-3-(methyloxy)phenyl]-1-methylethyl}-1-(4-fluorophenyl)-1H-imidazol-2-yl]thio}methyl)-N-{[(1-methylethyl)amino]carbonyl}benzenesulfonamide;

4-(2-{5-[1-(3,4-dichlorophenyl)-1-methylethyl]-1-(4-fluorophenyl)-1H-imidazol-2-yl}-2-fluoroethyl)-1-(methylsulfonyl)piperidine;

5-[1-(3,4-dichlorophenyl)-1-methylethyl]-2-{1-[(3,4-dichlorophenyl)oxy]ethyl}-1-(4-fluorophenyl)-1H-imidazole;

2-chloro-5-[({5-[1-(3,4-dichlorophenyl)-1-methylethyl]-1-(4-fluorophenyl)-1H-imidazol-2-yl}thio)methyl]-N-{[(1-methylethyl)amino]carbonyl}benzenesulfonamide 4-{5-[1-(3,4-dichlorophenyl)-1-methylethyl]-1-(4-fluorophenyl)-1H-imidazol-2-yl}-1-(methylsulfonyl)piperidine;

4-({[4-chloro-5-{1-[4-chloro-3-(methyloxy)phenyl]-1-methylethyl}-1-(4-fluorophenyl)-1H-imidazol-2-yl]thio}methyl)-1-(1H-tetrazol-5-yl)piperidine;

3-chloro-4-({[5-{1-[4-chloro-3-(methyloxy)phenyl]-1-methylethyl}-1-(4-fluorophenyl)-1H-imidazol-2-yl]thio}methyl)-N-[(pyrrolidin-1-ylamino)carbonyl]benzenesulfonamide;

4-[({5-[1-(3,4-dichlorophenyl)-1-methylethyl]-1-(4-fluorophenyl)-1H-imidazol-2-yl}oxy)methyl]-1-(1H-tetrazol-5-yl)piperidine;

4-[({5-[1-(3,4-difluorophenyl)-1-methylethyl]-1-(4-fluorophenyl)-1H-imidazol-2-yl}thio)methyl]-N-pyrrolidin-1-ylpiperidine-1-carboxamide;

5-[({5-[1-(3,4-dichlorophenyl)-1-methylethyl]-1-(4-fluorophenyl)-1H-imidazol-2-yl}thio)methyl]-2-[(2-hydroxy-2-methylpropyl)oxy]benzenesulfonamide;

5-[({5-[1-(3,4-dichlorophenyl)-1-methylethyl]-1-(4-fluorophenyl)-1H-imidazol-2-yl}thio)methyl]-2-[(2-oxopropyl)oxy]benzenesulfonamide;

6-[({5-[1-(3,4-dichlorophenyl)-1-methylethyl]-1-(4-fluorophenyl)-1H-imidazol-2-yl}methyl)oxy]quinoline;

4-[({5-[1-(3,4-dichlorophenyl)-1-methylethyl]-1-(4-fluorophenyl)-1H-imidazol-2-yl}methyl)oxy]quinoline;

1-{3-chloro-4-[({5-[1-(3,4-dichlorophenyl)-1-methylethyl]-1-(4-fluorophenyl)-1H-imidazol-2-yl}methyl)oxy]phenyl}ethanone;

4-({[5-{1-[4-chloro-3-(methyloxy)phenyl]-1-methylethyl}-1-(4-fluorophenyl)-1H-imidazol-2-yl]thio}methyl)-3,5-difluoro-N-hydroxybenzamide;

ethyl{[3-chloro-4-({[5-{1-[4-chloro-3-(methyloxy)phenyl]-1-methylethyl}-1-(4-fluorophenyl)-1H-imidazol-2-yl]thio}methyl)phenyl]sulfonyl}carbamate;

3-chloro-4-({[5-{1-[4-chloro-3-(methyloxy)phenyl]-1-methylethyl}-1-(4-fluorophenyl)-1H-imidazol-2-yl]thio}methyl)-N-[(propylamino)carbonyl]benzenesulfonamide;

4-[({5-[1-(3,4-difluorophenyl)-1-methylethyl]-1-(4-fluorophenyl)-1H-imidazol-2-yl}thio)methyl]-N-(1-methylethyl)piperidine-1-carboxamide;

3-chloro-4-({[5-{1-[4-chloro-3-(methyloxy)phenyl]-1-methylethyl}-1-(4-fluorophenyl)-1H-imidazol-2-yl]thio}methyl)-N-[(morpholin-4-ylamino)carbonyl]benzenesulfonamide;

3-chloro-4-[({5-[1-(3,4-difluorophenyl)-1-methylethyl]-1-(4-fluorophenyl)-1H-imidazol-2-yl}thio)methyl]benzenesulfonamide;

3-chloro-4-[({5-[1-(3,4-difluorophenyl)-1-methylethyl]-1-(4-fluorophenyl)-1H-imidazol-2-yl}thio)methyl]-N-[(pyrrolidin-1-ylamino)carbonyl]benzenesulfonamide;

ethyl ({3-chloro-4-[({5-[1-(3,4-dichlorophenyl)-1-methylethyl]-1-[4-fluoro-3-(methyloxy)phenyl]-1H-imidazol-2-yl}thio)methyl]phenyl}sulfonyl)carbamate;

3-chloro-4-[({5-[1-(3,4-difluorophenyl)-1-methylethyl]-1-(4-fluorophenyl)-1H-imidazol-2-yl}thio)methyl]-N-{[(1-methylethyl)amino]carbonyl}benzenesulfonamide;

5-{2-chloro-5-[({1-(3-chlorophenyl)-5-[1-(3,4-dichlorophenyl)-1-methylethyl]-1H-imidazol-2-yl}thio)methyl]phenyl}-1H-tetrazole;

5-{2-chloro-4-[({4-chloro-5-[1-(3,4-dichlorophenyl)-1-methylethyl]-1-(4-fluorophenyl)-1H-imidazol-2-yl}thio)methyl]phenyl}-1H-tetrazole;

4-[({5-[1-(3,4-dichlorophenyl)-1-methylethyl]-1-(4-fluoro-3-methylphenyl)-1H-imidazol-2-yl}thio)methyl]-3,5-difluorobenzoic acid;

4-[({5-[1(3,4-dichlorophenyl)-1-methylethyl]-1-[3-(difluoromethyl)-4-fluorophenyl]-1H-imidazol-2-yl}thio)methyl]-3,5-difluorobenzoic acid;

4-[({5-[1-(3,4-dichlorophenyl)-1-methylethyl]-1-[4-fluoro-3-(methyloxy)phenyl]-1H-imidazol-2-yl}thio)methyl]-3,5-difluoro-N-hydroxybenzamide;

4-[({5-[1-(3-cyano-4-fluorophenyl)-1-methylethyl]-1-[4-fluoro-3-(methyloxy)phenyl]-1H-imidazol-2-yl}thio)methyl]-3,5-difluorobenzoic acid;

4-[({5-[1-(3-amino-1,2-benzisoxazol-5-yl)-1-methylethyl]-1-[4-fluoro-3-(methyloxy)phenyl]-1H-imidazol-2-yl}thio)methyl]-3,5-difluorobenzoic acid;

4-[({5-[1-(3,4-dichlorophenyl)-1-methylethyl]-1-(3,4-difluorophenyl)-1H-imidazol-2-yl}thio)methyl]-1-(1H-tetrazol-5-yl)piperidine;

4-[({5-[1-(3,4-dichlorophenyl)-1-methylethyl]-1-(3,4-difluorophenyl)-1H-imidazol-2-yl}thio)methyl]-1-(methylsulfonyl)piperidine;

5-{2-chloro-5-[({5-[1-(3,4-dichlorophenyl)-1-methylethyl]-1-(3-fluorophenyl)-1H-imidazol-2-yl}thio)methyl]phenyl}-1H-tetrazole;

4-[({1-(3-chloro-4-fluorophenyl)-5-[1-(3,4-dichlorophenyl)-1-methylethyl]-1H-imidazol-2-yl}thio)methyl]-1-(methylsulfonyl)piperidine;

ethyl {[4-({[5-{1-[4-chloro-3-(methyloxy)phenyl]-1-methylethyl}-1-(4-fluorophenyl)-1H-imidazol-2-yl]thio}methyl)-3-fluorophenyl]sulfonyl}carbamate;

ethyl {[4-({[5-{1-[4-chloro-3-(methyloxy)phenyl]-1-methylethyl}-1-(4-fluorophenyl)-1H-imidazol-2-yl]thio}methyl)-2-fluorophenyl]sulfonyl}carbamate;

3-chloro-4-({[5-{1-[3-chloro-4-(methyloxy)phenyl]-1-methylethyl}-1-(4-fluorophenyl)-1H-imidazol-2-yl]thio}methyl)benzenesulfonamide;

3-chloro-4-({[5-{1-[3-chloro-4-(methyloxy)phenyl]-1-methylethyl}-1-(4-fluorophenyl)-1H-imidazol-2-yl]thio}methyl)-N-[(pyrrolidin-1-ylamino)carbonyl]benzenesulfonamide;

ethyl {[3-chloro-4-({[5-{1-[3-chloro-4-(methyloxy)phenyl]-1-methylethyl}-1-(4-fluorophenyl)-1H-imidazol-2-yl]thio}methyl)phenyl]sulfonyl}carbamate;

3-chloro-4-(2-{5-[1-(3,4-dichlorophenyl)-1-methylethyl]-1-(4-fluorophenyl)-1H-imidazol-2-yl}ethyl)benzenesulfonamide;

4-[({1-(3-chloro-4-fluorophenyl)-5-[1-(3,4-dichlorophenyl)-1-methylethyl]-1H-imidazol-2-yl}thio)methyl]-1-(1H-tetrazol-5-yl)piperidine;

3-chloro-4-[({5-[1-(3,4-dichlorophenyl)-1-methylethyl]-1-[4-fluoro-3-(methyloxy)phenyl]-1H-imidazol-2-yl}thio)methyl]-N-[(pyrrolidin-1-ylamino)carbonyl]benzenesulfonamide;

4-({[5-{1-[4-(aminosulfonyl)-3-chlorophenyl]-1-methylethyl}-1-(4-fluorophenyl)-1H-imidazol-2-yl]thio}methyl)-3-chloro-N-[(pyrrolidin-1-ylamino)carbonyl]benzenesulfonamide;

3-chloro-4-({[5-{1-[3-chloro-4-(methyloxy)phenyl]-1-methylethyl}-1-(4-fluorophenyl)-1H-imidazol-2-yl]thio}methyl)-N-{[(1-methylethyl)amino]carbonyl}benzenesulfonamide;

3-chloro-4-(2-{5-[1-(3,4-dichlorophenyl)-1-methylethyl]-1-(4-fluorophenyl)-1H-imidazol-2-yl}ethyl)-N-[(pyrrolidin-1-ylamino)carbonyl]benzenesulfonamide;

ethyl [(4-{[(5-{1-[4-(aminosulfonyl)-3-chlorophenyl]-1-methylethyl}-1-[4-fluoro-3-(methyloxy)phenyl]-1H-imidazol-2-yl)thio]methyl}-3-chlorophenyl)sulfonyl]carbamate;

({[4-({[5-{1-[4-chloro-3-(methyloxy)phenyl]-1-methylethyl}-1-(4-fluorophenyl)-1H-imidazol-2-yl]thio}methyl)-3-fluorophenyl]carbonyl}amino)methanesulfonic acid;

N-{[4-({[5-{1-[4-chloro-3-(methyloxy)phenyl]-1-methylethyl}-1-(4-fluorophenyl)-1H-imidazol-2-yl]thio}methyl)-3-fluorophenyl]carbonyl}-beta-alanine;

4-{5-[1-(3,4-dichlorophenyl)-1-methylethyl]-1-(4-fluorophenyl)-1H-imidazol-2-yl}-N-pyrrolidin-1-ylpiperidine-1-carboxamide;

5-[({5-[1-(3,4-dichlorophenyl)-1-methylethyl]-1-(4-fluorophenyl)-1H-imidazol-2-yl}thio)methyl]-2-[(2-hydroxyethyl)oxy]benzenesulfonamide;

4-[({5-[1-(3-amino-1,2-benzisoxazol-5-yl)-1-methylethyl]-1-(4-fluorophenyl)-1H-imidazol-2-yl}thio)methyl]-3,5-difluorobenzoic acid;

4-{[(5-{1-[4-(aminosulfonyl)-3-chlorophenyl]-1-methylethyl}-1-[4-fluoro-3-(methyloxy)phenyl]-1H-imidazol-2-yl)thio]methyl}-3,5-difluorobenzoic acid;

3,5-difluoro-4-({[1-(4-fluorophenyl)-5-{1-methyl-1-[4-(methylsulfonyl)phenyl]ethyl}-1H-imidazol-2-yl]thio}methyl)benzoic acid;

2-chloro-4-(1-{2-({[4-chloro-3-(1H-tetrazol-5-yl)phenyl]methyl}thio)-1-[4-fluoro-3-(methyloxy)phenyl]-1H-imidazol-2-yl}-1-methylethyl)benzenesulfonamide;

ethyl {[4-({[5-{1-[4-(aminosulfonyl)-3-chlorophenyl]-1-methylethyl}-1-(4-fluorophenyl)-1H-imidazol-2-yl]thio}methyl)-3-chlorophenyl]sulfonyl}carbamate;

3-chloro-4-({[5-{1-[4-chloro-3-(methyloxy)phenyl]-1-methylethyl}-1-(4-fluorophenyl)-1H-imidazol-2-yl]thio}methyl)-N-[(ethylamino)carbonyl]benzenesulfonamide;

3-chloro-4-({[5-{1-[4-chloro-3-(methyloxy)phenyl]-1-methylethyl}-1-(4-fluorophenyl)-1H-imidazol-2-yl]thio}methyl)-N-{[(2-hydroxy-2-methylpropyl)amino]carbonyl}benzenesulfonamide;

[({4-[({5-[1-(3,4-dichlorophenyl)-1-methylethyl]-1-[4-fluoro-3-(methyloxy)phenyl]-1H-imidazol-2-yl}thio)methyl]-3,5-difluorophenyl}carbonyl)amino]methanesulfonic acid;

4-({[5-{1-[4-chloro-3-(methyloxy)phenyl]-1-methylethyl}-1-(4-fluorophenyl)-1H-imidazol-2-yl]thio}methyl)-3-fluoro-N-[(pyrrolidin-1-ylamino)carbonyl]benzenesulfonamide;

3-chloro-4-(2-{5-[1-(3,4-dichlorophenyl)-1-methylethyl]-1-(4-fluorophenyl)-1H-imidazol-2-yl}ethyl)-5-fluorobenzoic acid;

3-chloro-4-{[(5-{1-[4-chloro-3-(methyloxy)phenyl]-1-methylethyl}-1-[4-fluoro-3-(methyloxy)phenyl]-1H-imidazol-2-yl)thio]methyl}benzenesulfonamide;

N-{[3-chloro-4-({[5-{1-[4-chloro-3-(methyloxy)phenyl]-1-methylethyl}-1-(4-fluorophenyl)-1H-imidazol-2-yl]thio}methyl)phenyl]sulfonyl}pyrrolidine-1-carboxamide;

3-chloro-4-{[(5-{1-[4-chloro-3-(methyloxy)phenyl]-1-methylethyl}-1-[4-fluoro-3-(methyloxy)phenyl]-1H-imidazol-2-yl)thio]methyl}-N-[(pyrrolidin-1-ylamino)carbonyl]benzenesulfonamide;

4-[({5-[1-(3,4-dichlorophenyl)-1-methylethyl]-1-[4-fluoro-3-(hydroxymethyl)phenyl]-1H-imidazol-2-yl}thio)methyl]-3,5-difluorobenzoic acid;

4-({[1-(3,4-difluorophenyl)-5-{1-methyl-1-[4-(methylsulfonyl)phenyl]ethyl}-1H-imidazol-2-yl]thio}methyl)-3,5-difluorobenzoic acid;

3-chloro-4-({[5-{1-[4-chloro-3-(methyloxy)phenyl]-1-methylethyl}-1-(4-fluorophenyl)-1H-imidazol-2-yl]thio}methyl)-N-[(cyclopropylamino)carbonyl]benzenesulfonamide;

3-chloro-4-({[5-{1-[4-chloro-3-(methyloxy)phenyl]-1-methylethyl}-1-(4-fluorophenyl)-1H-imidazol-2-yl]thio}methyl)-N-[(cyclopentylamino)carbonyl]benzenesulfonamide;

3-chloro-4-[({1-(3,4-difluorophenyl)-5-[1-(3,4-difluorophenyl)-1-methylethyl]-1H-imidazol-2-yl}thio)methyl]-N-[(pyrrolidin-1-ylamino)carbonyl]benzenesulfonamide;

3-chloro-4-[({1-(3-chloro-4-fluorophenyl)-5-[1-(3,4-difluorophenyl)-1-methylethyl]-1H-imidazol-2-yl}thio)methyl]-N-[(pyrrolidin-1-ylamino)carbonyl]benzenesulfonamide;

3-chloro-4-[({5-[1-(3,4-dichlorophenyl)-1-methylethyl]-1-[4-fluoro-3-(methyloxy)phenyl]-1H-imidazol-2-yl}thio)methyl]-N-[(morpholin-4-ylamino)carbonyl]benzenesulfonamide;

2-[({4-[({5-[1-(3,4-dichlorophenyl)-1-methylethyl]-1-[4-fluoro-3-(methyloxy)phenyl]-1H-imidazol-2-yl}thio)methyl]-3,5-difluorophenyl}carbonyl)amino]ethanesulfonic acid;

4-({[5-{1-[4-chloro-3-(methyloxy)phenyl]-1-methylethyl}-1-(4-fluorophenyl)-1H-imidazol-2-yl]thio}methyl)-3,5-difluoro-N-[(pyrrolidin-1-ylamino)carbonyl]benzenesulfonamide;

3-chloro-4-({[1-(3-chloro-4-fluorophenyl)-5-{1-[4-chloro-3-(methyloxy)phenyl]-1-methylethyl}-1H-imidazol-2-yl]thio}methyl)-N-[(pyrrolidin-1-ylamino)carbonyl]benzenesulfonamide;

3-chloro-4-({[5-{1-[4-chloro-3-(methyloxy)phenyl]-1-methylethyl}-1-(3,4-difluorophenyl)-1H-imidazol-2-yl]thio}methyl)-N-[(pyrrolidin-1-ylamino)carbonyl]benzenesulfonamide;

N-({4-[({5-[1-(3,4-dichlorophenyl)-1-methylethyl]-1-[4-fluoro-3-(methyloxy)phenyl]-1H-imidazol-2-yl}thio)methyl]-3,5-difluorophenyl}carbonyl)-beta-alanine;

N-[({[3-chloro-4-({[5-{1-[4-chloro-3-(methyloxy)phenyl]-1-methylethyl}-1-(4-fluorophenyl)-1H-imidazol-2-yl]thio}methyl)phenyl]sulfonyl}amino)carbonyl]-beta-alanine;

3-chloro-4-[({1-[4-fluoro-3-(methyloxy)phenyl]-5-[1-(4-fluorophenyl)-1-methylethyl]-1H-imidazol-2-yl}thio)methyl]-N-[(pyrrolidin-1-ylamino)carbonyl]benzenesulfonamide;

4-(1-{2-({[4-(aminosulfonyl)-2-chlorophenyl]methyl}thio)-1-[4-fluoro-3-(methyloxy)phenyl]-1H-imidazol-5-yl}-1-methylethyl)-2-chlorobenzenesulfonamide;

4-{[(5-{1-[4-(aminosulfonyl)-3-chlorophenyl]-1-methylethyl}-1-[4-fluoro-3-(methyloxy)phenyl]-1H-imidazol-2-yl)thio]methyl}-3-chloro-N-[(morpholin-4-ylamino)carbonyl]benzenesulfonamide;

4-({[5-{1-[4-(aminosulfonyl)-3-chlorophenyl]-1-methylethyl}-1-(3,4-difluorophenyl)-1H-imidazol-2-yl]thio}methyl)-3-chloro-N-[(morpholin-4-ylamino)carbonyl]benzenesulfonamide;

3-chloro-4-[({5-[1-(3,4-difluorophenyl)-1-methylethyl]-1-[4-fluoro-3-(methyloxy)phenyl]-1H-imidazol-2-yl}thio)methyl]-N-[(pyrrolidin-1-ylamino)carbonyl]benzenesulfonamide;

3-chloro-4-({[5-{1-[4-chloro-3-(methyloxy)phenyl]-1-methylethyl}-1-(5-fluoropyridin-2-yl)-1H-imidazol-2-yl]thio}methyl)-N-[(pyrrolidin-1-ylamino)carbonyl]benzenesulfonamide;

4-({[5-{1-[4-chloro-3-(methyloxy)phenyl]-1-methylethyl}-1-(4-fluorophenyl)-1H-imidazol-2-yl]thio}methyl)-3,5-difluoro-N-[(morpholin-4-ylamino)carbonyl]benzenesulfonamide;

3-chloro-4-[({5-[1-(3,4-dichlorophenyl)-1-methylethyl]-1-(5-fluoropyridin-2-yl)-1H-imidazol-2-yl}thio)methyl]-N-[(pyrrolidin-1-ylamino)carbonyl]benzenesulfonamide;

3-chloro-4-({[5-{1-[4-chloro-3-(methyloxy)phenyl]-1-methylethyl}-1-(4-fluoro-3-methylphenyl)-1H-imidazol-2-yl]thio}methyl)-N-[(pyrrolidin-1-ylamino)carbonyl]benzenesulfonamide;

3-chloro-4-({[1-(4-fluoro-3-methylphenyl)-5-{1-methyl-1-[4-(methylsulfonyl)phenyl]ethyl}-1H-imidazol-2-yl]thio}methyl)-N-[(pyrrolidin-1-ylamino)carbonyl]benzenesulfonamide;

3-chloro-4-{[(1-[4-fluoro-3-(methyloxy)phenyl]-5-{1-methyl-1-[4-(methylsulfonyl)phenyl]ethyl}-1H-imidazol-2-yl)thio]methyl}-N-[(pyrrolidin-1-ylamino)carbonyl]benzenesulfonamide;

3-chloro-4-({[1-(5-fluoropyridin-2-yl)-5-{1-methyl-1-[4-(methylsulfonyl)phenyl]ethyl}-1H-imidazol-2-yl]thio}methyl)-N-[(pyrrolidin-1-ylamino)carbonyl]benzenesulfonamide;

3-chloro-4-({[5-{1-[4-chloro-3-(methyloxy)phenyl]-1-methylethyl}-1-(2,4-difluorophenyl)-1H-imidazol-2-yl]thio}methyl)-N-[(pyrrolidin-1-ylamino)carbonyl]benzenesulfonamide;

3-chloro-4-[({1-(3,4-difluorophenyl)-5-[1-(4-fluorophenyl)-1-methylethyl]-1H-imidazol-2-yl}thio)methyl]-N-[(pyrrolidin-1-ylamino)carbonyl]benzenesulfonamide;

3-chloro-4-({[1-(4-fluorophenyl)-5-{1-methyl-1[4-(methylsulfonyl)phenyl]ethyl}-1H-imidazol-2-yl]thio}methyl)-N-[(pyrrolidin-1-ylamino)carbonyl]benzenesulfonamide;

3-chloro-4-[({1-(3-chloro-4-fluorophenyl)-5-[1-(4-fluorophenyl)-1-methylethyl]-1H-imidazol-2-yl}thio)methyl]-N-[(pyrrolidin-1-ylamino)carbonyl]benzenesulfonamide;

4-({[5-{1-[4-(aminosulfonyl)-3-chlorophenyl]-1-methylethyl}-1-(3,4-difluorophenyl)-1H-imidazol-2-yl]thio}methyl)-3,5-difluorobenzoic acid;

2-chloro-4-{1-[2-({[4-chloro-3-(1H-tetrazol-5-yl)phenyl]methyl}thio)-1-(3,4-difluorophenyl)-1H-imidazol-5-yl]-1-methylethyl}benzenesulfonamide;

5-[2-chloro-5-({[1-(4-fluorophenyl)-5-{1-methyl-1-[4-(methylsulfonyl)phenyl]ethyl}-1H-imidazol-2-yl]thio}methyl)phenyl]-1H-tetrazole;

2-({[3-chloro-4-(2-{5-[1-(3,4-dichlorophenyl)-1-methylethyl]-1-(4-fluorophenyl)-1H-imidazol-2-yl}ethyl)-5-fluorophenyl]carbonyl}amino)ethanesulfonic acid;

3-chloro-4-({[1-(3,4-difluorophenyl)-5-{1-methyl-1-[4-(methylsulfonyl)phenyl]ethyl}-1H-imidazol-2-yl]thio}methyl)-N-[(pyrrolidin-1-ylamino)carbonyl]benzenesulfonamide;

3-chloro-4-[({5-[1-(4-chlorophenyl)-1-methylethyl]-1-(2,4-difluorophenyl)-1H-imidazol-2-yl}thio)methyl]-N-[(pyrrolidin-1-ylamino)carbonyl]benzenesulfonamide;

3-chloro-4-[({5-[1-(3,4-difluorophenyl)-1-methylethyl]-1-(4-fluoro-3-methylphenyl)-1H-imidazol-2-yl}thio)methyl]-N-[(pyrrolidin-1-ylamino)carbonyl]benzenesulfonamide;

4-({[5-{1-[4-(aminosulfonyl)-3-chlorophenyl]-1-methylethyl}-1-(3-chloro-4-fluorophenyl)-1H-imidazol-2-yl]thio}methyl)-3-chloro-N-[(morpholin-4-ylamino)carbonyl]benzenesulfonamide;

4-{[(5-{1-[4-(aminosulfonyl)-3-chlorophenyl]-1-methylethyl}-1-[4-fluoro-3-(methyloxy)phenyl]-1H-imidazol-2-yl)thio]methyl}-3,5-difluoro-N-[(morpholin-4-ylamino)carbonyl]benzenesulfonamide;

4-({[5-{1-[4-chloro-3-(methyloxy)phenyl]-1-methylethyl}-1-(5-fluoropyridin-2-yl)-1H-imidazol-2-yl]thio}methyl)-3,5-difluoro-N-[(morpholin-4-ylamino)carbonyl]benzenesulfonamide;

3-chloro-4-({[5-{1-[3-chloro-4-(methyloxy)phenyl]-1-methylethyl}-1-(4-fluoro-3-methylphenyl)-1H-imidazol-2-yl]thio}methyl)-N-[(pyrrolidin-1-ylamino)carbonyl]benzenesulfonamide;

3-chloro-4-({[5-{1-[4-chloro-3-(methyloxy)phenyl]-1-methylethyl}-1-(3,5-difluoropyridin-2-yl)-1H-imidazol-2-yl]thio}methyl)-N-[(pyrrolidin-1-ylamino)carbonyl]benzenesulfonamide;

3-chloro-4-[({5-[1-(3,4-dichlorophenyl)-1-methylethyl]-1-(3,5-difluoropyridin-2-yl)-1H-imidazol-2-yl}thio)methyl]-N-[(pyrrolidin-1-ylamino)carbonyl]benzenesulfonamide;

3-chloro-4-[({5-[1-(3,4-dichlorophenyl)-1-methylethyl]-1-(4-fluorophenyl)-1H-imidazol-2-yl}thio)methyl]benzenesulfonic acid;

4-({[5-{1-[4-(aminosulfonyl)phenyl]-1-methylethyl}-1-(3,4-difluorophenyl)-1H-imidazol-2-yl]thio}methyl)-3-chloro-N-[(morpholin-4-ylamino)carbonyl]benzenesulfonamide;

3-chloro-4-[({1-(2,4-difluorophenyl)-5-[1-(3,4-difluorophenyl)-1-methylethyl]-1H-imidazol-2-yl}thio)methyl]-N-[(pyrrolidin-1-ylamino)carbonyl]benzenesulfonamide;

4-({[5-{1-[4-(aminosulfonyl)phenyl]-1-methylethyl}-1-(3-chloro-4-fluorophenyl)-1H-imidazol-2-yl]thio}methyl)-3-chloro-N-[(morpholin-4-ylamino)carbonyl]benzenesulfonamide;

3-chloro-4-({[5-{1-[3-(difluoromethyl)-4-fluorophenyl]-1-methylethyl}-1-(4-fluorophenyl)-1H-imidazol-2-yl]thio}methyl)-N-{[(1-methylethyl)amino]carbonyl}benzenesulfonamide;

3-chloro-4-({[5-{1-[4-(difluoromethyl)-3-fluorophenyl]-1-methylethyl}-1-(4-fluorophenyl)-1H-imidazol-2-yl]thio}methyl)-N-{[(1-methylethyl)amino]carbonyl}benzenesulfonamide;

4-({[5-{1-[4-(aminosulfonyl)-3-chlorophenyl]-1-methylethyl}-1-(5-fluoropyridin-2-yl)-1H-imidazol-2-yl]thio}methyl)-3,5-difluorobenzoic acid;

3,5-difluoro-4-({[1-(5-fluoropyridin-2-yl)-5-{1-methyl-1-[4-(methylsulfonyl)phenyl]ethyl}-1H-imidazol-2-yl]thio}methyl)benzoic acid;

5-(2-chloro-5-{[((1-[4-fluoro-3-(methyloxy)phenyl]-5-{1-methyl-1-[4-(methylsulfonyl)phenyl]ethyl}-1H-imidazol-2-yl)thio]methyl}phenyl)-1H-tetrazole;

5-[2-chloro-5-({[1-(3,4-difluorophenyl)-5-{1-methyl-1-[4-(methylsulfonyl)phenyl]ethyl}-1H-imidazol-2-yl]thio}methyl)phenyl]-1H-tetrazole;

3-chloro-4-[({5-[1-(3,4-dichlorophenyl)-1-methylethyl]-1-(4-fluoro-3-methylphenyl)-1H-imidazol-2-yl}thio)methyl]-N-[(pyrrolidin-1-ylamino)carbonyl]benzenesulfonamide;

3-chloro-4-({[5-{1-[4-chloro-3-(methyloxy)phenyl]-1-methylethyl}-1-(4-fluorophenyl)-1H-imidazol-2-yl]thio}methyl)-N-[(1H-pyrrol-1-ylamino)carbonyl]benzenesulfonamide;

3-chloro-4-({[5-{1-[4-chloro-3-(methyloxy)phenyl]-1-methylethyl}-1-(4-fluorophenyl)-1H-imidazol-2-yl]thio}methyl)-N-[({(2R)-2-[(methyloxy)methyl]pyrrolidin-1-yl}amino)carbonyl]benzenesulfonamide;

N-2-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}-L-arginine;

3-chloro-4-({[5-{1-[4-chloro-3-(methyloxy)phenyl]-1-methylethyl}-1-(5-chloro-4-methylpyridin-2-yl)-1H-imidazol-2-yl]thio}methyl)-N-[(pyrrolidin-1-ylamino)carbonyl]benzenesulfonamide;

3-chloro-4-{[(5-{1-[4-chloro-3-(methyloxy)phenyl]-1-methylethyl}-1-[4-fluoro-3-(hydroxymethyl)phenyl]-1H-imidazol-2-yl)thio]methyl}-N-[(pyrrolidin-1-ylamino)carbonyl]benzenesulfonamide;

({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}amino)methanesulfonic acid;

3-chloro-4-[({1-(4-fluoro-3-methylphenyl)-5-[1-(4-fluorophenyl)-1-methylethyl]-1H-imidazol-2-yl}thio)methyl]-N-[(pyrrolidin-1-ylamino)carbonyl]benzenesulfonamide;

N-[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]-L-alpha-asparagine;

3-chloro-4-({[5-{1-[4-chloro-3-(methyloxy)phenyl]-1-methylethyl}-1-(4-fluorophenyl)-1H-imidazol-2-yl]thio}methyl)-N-{[(4-methylpiperazin-1-yl)amino]carbonyl}benzenesulfonamide;

2-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}amino)ethanesulfonic acid;

4-{[(5-{1-[4-(aminosulfonyl)-3-chlorophenyl]-1-methylethyl}-1-[4-fluoro-3-(methyloxy)phenyl]-1H-imidazol-2-yl)thio]methyl}-3-chloro-N-[(piperidin-1-ylamino)carbonyl]benzenesulfonamide;

3-chloro-4-({[5-{1-[4-chloro-3-(methyloxy)phenyl]-1-methylethyl}-1-(4-fluorophenyl)-1H-imidazol-2-yl]thio}methyl)-N-[({(2S)-2-[(methyloxy)methyl]pyrrolidin-1-yl}amino)carbonyl]benzenesulfonamide;

N-[(4-{[(5-{1-[4-(aminosulfonyl)-3-chlorophenyl]-1-methylethyl}-1-[4-fluoro-3-(methyloxy)phenyl]-1H-imidazol-2-yl)thio]methyl}-3,5-difluorophenyl)carbonyl]-beta-alanine;

N-[(4-{[(5-{1-[4-(aminosulfonyl)-3-chlorophenyl]-1-methylethyl}-1-[4-fluoro-3-(methyloxy)phenyl]-1H-imidazol-2-yl)thio]methyl}-3-fluorophenyl)carbonyl]-beta-alanine;

2-({[4-({[5-{1-[4-chloro-3-(methyloxy)phenyl]-1-methylethyl}-1-(4-fluorophenyl)-1H-imidazol-2-yl]thio}methyl)-3,5-difluorophenyl]carbonyl}amino)ethanesulfonic acid;

[({4-[({1-(3-chloro-4-fluorophenyl)-5-[1-(3,4-dichlorophenyl)-1-methylethyl]-1H-imidazol-2-yl}thio)methyl]-3,5-difluorophenyl}carbonyl)amino]methanesulfonic acid;

2-[({4-[({1-(3-chloro-4-fluorophenyl)-5-[1-(3,4-dichlorophenyl)-1-methylethyl]-1H-imidazol-2-yl}thio)methyl]-3,5-difluorophenyl}carbonyl)amino]ethanesulfonic acid;

({[4-({[5-{1-[4-chloro-3-(methyloxy)phenyl]-1-methylethyl}-1-(4-fluorophenyl)-1H-imidazol-2-yl]thio}methyl)-3,5-difluorophenyl]carbonyl}amino)methanesulfonic acid;

N-5-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}-L-ornithine;

2-{[(4-{[(5-{1-[4-(aminosulfonyl)-3-chlorophenyl]-1-methylethyl}-1-[4-fluoro-3-(methyloxy)phenyl]-1H-imidazol-2-yl)thio]methyl}-3,5-difluorophenyl)carbonyl]amino}ethanesulfonic acid;

2-{[(4-{[(5-{1-[4-(aminosulfonyl)-3-chlorophenyl]-1-methylethyl}-1-[4-fluoro-3-(methyloxy)phenyl]-1H-imidazol-2-yl)thio]methyl}-3-fluorophenyl)carbonyl]amino}ethanesulfonic acid;

N-2-{[3-chloro-4-(2-{5-[1-(3,4-dichlorophenyl)-1-methylethyl]-1-(4-fluorophenyl)-1H-imidazol-2-yl}ethyl)-5-fluorophenyl]carbonyl}-L-arginine;

3-chloro-4-({[5-{1-[4-chloro-3-(methyloxy)phenyl]-1-methylethyl}-1-(4-fluorophenyl)-1H-imidazol-2-yl]thio}methyl)-N-[(1,3-thiazol-2-ylamino)carbonyl]benzenesulfonamide;

N-{[3-chloro-4-({[5-{1-[4-chloro-3-(methyloxy)phenyl]-1-methylethyl}-1-(4-fluorophenyl)-1H-imidazol-2-yl]thio}methyl)phenyl]sulfonyl}-3-hydroxypyrrolidine-1-carboxamide;

3-chloro-4-({[5-{1-[4-chloro-3-(methyloxy)phenyl]-1-methylethyl}-1-(4-fluorophenyl)-1H-imidazol-2-yl]thio}methyl)-5-fluoroaniline;

N-[({[3-chloro-4-({[5-{1-[4-chloro-3-(methyloxy)phenyl]-1-methylethyl}-1-(4-fluorophenyl)-1H-imidazol-2-yl]thio}methyl)phenyl]sulfonyl}amino)carbonyl]glycine;

3-chloro-4-({[5-{1-[3-(difluoromethyl)-4-fluorophenyl]-1-methylethyl}-1-(4-fluorophenyl)-1H-imidazol-2-yl]thio}methyl)-N-[(pyrrolidin-1-ylamino)carbonyl]benzenesulfonamide;

3-chloro-4-({[5-{1-[4-(difluoromethyl)-3-chlorophenyl]-1-methylethyl}-1-(4-fluorophenyl)-1H-imidazol-2-yl]thio}methyl)-N-[(pyrrolidin-1-ylamino)carbonyl]benzenesulfonamide;

2-chloro-4-{1-[2-({[2-chloro-4-({[(pyrrolidin-1-ylamino)carbonyl]amino}sulfonyl)phenyl]methyl}thio)-1-(4-fluorophenyl)-1H-imidazol-5-yl]-1-methylethyl}-N-methylbenzenesulfonamide;

N-2-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}-L-ornithine;

3-chloro-4-({[5-{1-[4-chloro-3-(methyloxy)phenyl]-1-methylethyl}-1-(5-fluoro-4-methylpyridin-2-yl)-1H-imidazol-2-yl]thio}methyl)-N-[(pyrrolidin-1-ylamino)carbonyl]benzenesulfonamide;

N-2-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}-D-arginine;

3-chloro-4-[({5-[1-(3-cyano-4-fluorophenyl)-1-methylethyl]-1-(4-fluorophenyl)-1H-imidazol-2-yl}thio)methyl]-N-[(pyrrolidin-1-ylamino)carbonyl]benzenesulfonamide;

3-chloro-4-[({5-[1-(3-cyano-4-fluorophenyl)-1-methylethyl]-1-[4-fluoro-3-(methyloxy)phenyl]-1H-imidazol-2-yl}thio)methyl]-N-[(pyrrolidin-1-ylamino)carbonyl]benzenesulfonamide;

3-chloro-4-{[(5-{1-[3-chloro-4-(methylsulfonyl)phenyl]-1-methylethyl}-1-[4-fluoro-3-(methyloxy)phenyl]-1H-imidazol-2-yl)thio]methyl}-N-[(pyrrolidin-1-ylamino)carbonyl]benzenesulfonamide;

methyl 2-(3-{[amino(imino)methyl]amino}prop-1-yn-1-yl)-5-[({5-[1-(3,4-dichlorophenyl)-1-methylethyl]-1-[4-fluoro-3-(methyloxy)phenyl]-1H-imidazol-2-yl}thio)methyl]benzoate;

N-2-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]amino}carbonyl)-L-arginine;

2-(3-{[amino(imino)methyl]amino}prop-1-yn-1-yl)-5-[({5-[1-(3,4-dichlorophenyl)-1-methylethyl]-1-[4-fluoro-3-(methyloxy)phenyl]-1H-imidazol-2-yl}thio)methyl]benzoic acid;

2-(3-{[amino(imino)methyl]amino}propyl)-5-[({5-[1-(3,4-dichlorophenyl)-1-methylethyl]-1-[4-fluoro-3-(methyloxy)phenyl]-1H-imidazol-2-yl}thio)methyl]benzoic acid;

N-6-[amino(imino)methyl]-N-2-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}-L-lysine;

3-chloro-4-[({5-[1-(3-cyano-4-fluorophenyl)-1-methylethyl]-1-(4-fluorophenyl)-1H-imidazol-2-yl}thio)methyl]-N-{[(1-methylethyl)amino]carbonyl}benzenesulfonamide;

3-chloro-4-[({5-[1-(3-cyano-4-fluorophenyl)-1-methylethyl]-1-[4-fluoro-3-(methyloxy)phenyl]-1H-imidazol-2-yl}thio)methyl]-N-{[(1-methylethyl)amino]carbonyl}benzenesulfonamide;

3-chloro-4-[({5-[1-(3-chloro-4-fluorophenyl)-1-methylethyl]-1-(4-fluorophenyl)-1H-imidazol-2-yl}thio)methyl]-N-[(pyrrolidin-1-ylamino)carbonyl]benzenesulfonamide;

3-chloro-4-({[5-{1-[4-fluoro-3-(methyloxy)phenyl]-1-methylethyl}-1-(4-fluorophenyl)-1H-imidazol-2-yl]thio}methyl)-N-[(pyrrolidin-1-ylamino)carbonyl]benzenesulfonamide;

N-2-[amino(imino)methyl]-N-5-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}-L-ornithine;

1-{3-[4-({[5-{1-[4-chloro-3-(methyloxy)phenyl]-1-methylethyl}-1-(4-fluorophenyl)-1H-imidazol-2-yl]thio}methyl)-3,5-difluorophenyl]prop-2-yn-1-yl}guanidine;

2-(3-{[amino(imino)methyl]amino}propyl)-5-({[5-{1-[4-chloro-3-(methyloxy)phenyl]-1-methylethyl}-1-(4-fluorophenyl)-1H-imidazol-2-yl]thio}methyl)benzoic acid;

1-{3-[4-({[5-{1-[4-chloro-3-(methyloxy)phenyl]-1-methylethyl}-1-(4-fluorophenyl)-1H-imidazol-2-yl]thio}methyl)-3,5-difluorophenyl]propyl}guanidine;

2-(3-{[amino(imino)methyl]amino}prop-1-yn-1-yl)-5-({[5-{1-[4-chloro-3-(methyloxy)phenyl]-1-methylethyl}-1-(4-fluorophenyl)-1H-imidazol-2-yl]thio}methyl)benzoic acid;

3-chloro-4-({[1-(4-fluorophenyl)-5-{1-methyl-1-[3-(methyloxy)-4-(methylsulfonyl)phenyl]ethyl}-1H-imidazol-2-yl]thio}methyl)-N-[(pyrrolidin-1-ylamino)carbonyl]benzenesulfonamide;

4-({[5-{1-[4-(aminosulfonyl)-3-(methyloxy)phenyl]-1-methylethyl}-1-(4-fluorophenyl)-1H-imidazol-2-yl]thio}methyl)-3-chloro-N-[(pyrrolidin-1-ylamino)carbonyl]benzenesulfonamide;

4-{1-[2-({[2-chloro-4-({[(pyrrolidin-1-ylamino)carbonyl]amino}sulfonyl)phenyl]methyl}thio)-1-(4-fluorophenyl)-1H-imidazol-5-yl]-1-methylethyl}-N-methyl-2-(methyloxy)benzenesulfonamide;

1-{4-[4-({[5-{1-[4-chloro-3-(methyloxy)phenyl]-1-methylethyl}-1-(4-fluorophenyl)-1H-imidazol-2-yl]thio}methyl)-3,5-difluorophenyl]butyl}guanidine;

1-{5-[4-({[5-{1-[4-chloro-3-(methyloxy)phenyl]-1-methylethyl}-1-(4-fluorophenyl)-1H-imidazol-2-yl]thio}methyl)-3,5-difluorophenyl]pentyl}guanidine;

4-({[5-{1-[4-chloro-3-(methyloxy)phenyl]-1-methylethyl}-1-(4-fluorophenyl)-1H-imidazol-2-yl]thio}methyl)-3,5-difluorobenzenesulfonamide;

N-(3-{[amino(imino)methyl]amino}propyl)-4-({[5-{1-[4-chloro-3-(methyloxy)phenyl]-1-methylethyl}-1-(4-fluorophenyl)-1H-imidazol-2-yl]thio}methyl)-3,5-difluorobenzenesulfonamide;

3-chloro-4-({[5-{1-[4-chloro-3-(methyloxy)phenyl]-1-methylethyl}-1-(4-fluorophenyl)-1H-imidazol-2-yl]thio}methyl)-5-fluoro-N-[1-(1H-tetrazol-5-yl)piperidin-4-yl]benzamide;

N-(3-{[amino(imino)methyl]amino}propyl)-3-chloro-4-({[5-{1-[4-chloro-3-(methyloxy)phenyl]-1-methylethyl}-1-(4-fluorophenyl)-1H-imidazol-2-yl]thio}methyl)-5-fluorobenzamide;

3-chloro-4-({[5-{1-[4-chloro-3-(methyloxy)phenyl]-1-methylethyl}-1-(4-fluorophenyl)-1H-imidazol-2-yl]thio}methyl)-5-fluoro-N-1H-tetrazol-5-ylbenzamide;

N-2-{[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]carbonyl}-D-arginine;

4-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]carbonyl}amino)butanoic acid;

3-chloro-4-({[5-{1-[4-chloro-3-(methyloxy)phenyl]-1-methylethyl}-1-(4-fluorophenyl)-1H-imidazol-2-yl]thio}methyl)-N-[(1H-tetrazol-5-ylamino)carbonyl]benzenesulfonamide;

1-(2-{[4-({[5-{1-[4-chloro-3-(methyloxy)phenyl]-1-methylethyl}-1-(4-fluorophenyl)-1H-imidazol-2-yl]thio}methyl)-3,5-difluorophenyl]oxy}ethyl)guanidine;

4-({[5-{1-[4-chloro-3-(methyloxy)phenyl]-1-methylethyl}-1-(4-fluorophenyl)-1H-imidazol-2-yl]thio}methyl)pyridin-2-amine;

5-[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]-1,3,4-oxadiazol-2(3H)-one;

N-2-({4-[({5-[1-(3-amino-1,2-benzisoxazol-5-yl)-1-methylethyl]-1-(4-fluorophenyl)-1H-imidazol-2-yl}thio)methyl]-3-chloro-5-fluorophenyl}carbonyl)-D-arginine;

3-[4-({[5-{1-[4-chloro-3-(methyloxy)phenyl]-1-methylethyl}-1-(4-fluorophenyl)-1H-imidazol-2-yl]thio}methyl)-3,5-difluorophenyl]-1,2,4-oxadiazol-5(4H)-one;

5-({[4-({[5-{1-[4-chloro-3-(methyloxy)phenyl]-1-methylethyl}-1-(4-fluorophenyl)-1H-imidazol-2-yl]thio}methyl)-3,5-difluorophenyl]oxy}methyl)-1H-tetrazole;

N-2-[(4-{[(5-{1-[4-(aminosulfonyl)-3-chlorophenyl]-1-methylethyl}-1-[4-fluoro-3-(methyloxy)phenyl]-1H-imidazol-2-yl)thio]methyl}-3-chloro-5-fluorophenyl)carbonyl]-D-arginine N-2-({4-[({5-[1-(3-amino-1,2-benzisoxazol-5-yl)-1-methylethyl]-1-[4-fluoro-3-(methyloxy)phenyl]-1H-imidazol-2-yl}thio)methyl]-3-chloro-5-fluorophenyl}carbonyl)-D-arginine;

3-chloro-4-({[5-{1-[4-chloro-3-(methyloxy)phenyl]-1-methylethyl}-1-(4-fluorophenyl)-1H-imidazol-2-yl]thio}methyl)-5-fluorobenzenesulfonic acid;

3-{4-[({5-[1-(3-chloro-4-fluorophenyl)-1-methylethyl]-1-[4-fluoro-3-(methyloxy)phenyl]-1H-imidazol-2-yl}thio)methyl]-3,5-difluorophenyl}-N,N-dimethylpropan-1-amine;

2-chloro-5-({[5-{1-[4-chloro-3-(methyloxy)phenyl]-1-methylethyl}-1-(4-fluorophenyl)-1H-imidazol-2-yl]thio}methyl)benzenesulfonamide;

2-({[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]sulfonyl}amino)ethanesulfonic acid;

2-({[4-({[5-{1-[4-chloro-3-(methyloxy)phenyl]-1-methylethyl}-1-(4-fluorophenyl)-1H-imidazol-2-yl]thio}methyl)-3,5-difluorophenyl]sulfonyl}amino)ethanesulfonic acid;

1-(3-{[4-({[5-{1-[4-chloro-3-(methyloxy)phenyl]-1-methylethyl}-1-(4-fluorophenyl)-1H-imidazol-2-yl]thio}methyl)-3,5-difluorophenyl]oxy}propyl)guanidine;

1-(2-{[3,5-difluoro-4-({[5-{1-[4-fluoro-3-(methyloxy)phenyl]-1-methylethyl}-1-(4-fluorophenyl)-1H-imidazol-2-yl]thio}methyl)phenyl]oxy}ethyl)guanidine;

4-chloro-5-({[5-{1-[4-chloro-3-(methyloxy)phenyl]-1-methylethyl}-1-(4-fluorophenyl)-1H-imidazol-2-yl]thio}methyl)-2-fluorobenzenesulfonamide;

1-(3-{[3,5-difluoro-4-({[5-{1-[4-fluoro-3-(methyloxy)phenyl]-1-methylethyl}-1-(4-fluorophenyl)-1H-imidazol-2-yl]thio}methyl)phenyl]oxy}propyl)guanidine;

2-chloro-5-({[5-{1-[4-chloro-3-(methyloxy)phenyl]-1-methylethyl}-1-(4-fluorophenyl)-1H-imidazol-2-yl]thio}methyl)-4-fluorobenzenesulfonamide;

1-(2-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]oxy}ethyl)guanidine;

1-(2-{[2-chloro-5-({[5-{1-[4-chloro-3-(methyloxy)phenyl]-1-methylethyl}-1-(4-fluorophenyl)-1H-imidazol-2-yl]thio}methyl)-4-fluorophenyl]oxy}ethyl)guanidine;

3-({[5-{1-[4-chloro-3-(methyloxy)phenyl]-1-methylethyl}-1-(4-fluorophenyl)-1H-imidazol-2-yl]thio}methyl)-2,4-difluorobenzenesulfonamide;

1-[2-({4-[({5-[1-(3-chloro-4-fluorophenyl)-1-methylethyl]-1-[4-fluoro-3-(methyloxy)phenyl]-1H-imidazol-2-yl}thio)methyl]-3,5-difluorophenyl}oxy)ethyl]guanidine;

(2E)-2-(3-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]oxy}propylidene)hydrazinecarboximidamide;

1-(2-{[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]oxy}ethyl)guanidine;

1-(3-{[3-chloro-4-({[5-{1-[4-chloro-3-(methyloxy)phenyl]-1-methylethyl}-1-(4-fluorophenyl)-1H-imidazol-2-yl]thio}methyl)-5-fluorophenyl]oxy}propyl)guanidine;

1-(3-{[3-chloro-5-fluoro-4-({[5-{1-[4-fluoro-3-(methyloxy)phenyl]-1-methylethyl}-1-(4-fluorophenyl)-1H-imidazol-2-yl]thio}methyl)phenyl]oxy}propyl)guanidine;

3-chloro-4-({[5-{1-[4-chloro-3-(methyloxy)phenyl]-1-methylethyl}-1-(4-fluorophenyl)-1H-imidazol-2-yl]thio}methyl)-5-fluoro-N-3,6,9,12,15,18,21,24,27,30,33,36,39,42-tetradecaoxatritetracont-1-ylbenzenesulfonamide;

N-(2-{[4-({[5-{1-[4-chloro-3-(methyloxy)phenyl]-1-methylethyl}-1-(4-fluorophenyl)-1H-imidazol-2-yl]thio}methyl)-3,5-difluorophenyl]oxy}ethyl)imidodicarbonimidic diamide; and 1-(3-{[2-chloro-4-fluoro-3-({[5-{1-[4-fluoro-3-(methyloxy)phenyl]-1-methylethyl}-1-(4-fluorophenyl)-1H-imidazol-2-yl]thio}methyl)phenyl]oxy}propyl)guanidine, or a pharmaceutically acceptable salt of any of the above compounds.

11. A composition comprising a compound according to claim 1 and a pharmaceutically acceptable diluent, excipient, or carrier.

12. A method for treating obesity, hyperlipidemia, atherosclerosis or type II diabetes, or for lowering blood glucose or enhancing insuling secretion, in a subject in need of such treatment, comprising administering to the subject an effective amount of a compound of claim 1.

13. A method for treating obesity or type II diabetes in a subject in need of such treatment comprising co-administering to the subject, simultaneously or sequentially, an effective amount of a compound according to claim 1 and a second anti-diabetic drug.

14. A method for inducing increased GLP-1 secretion in cell, in vitro, comprising contacting the cell with an inducing effective amount of a compound of claim 1.

* * * * *